(12) United States Patent
Rahman et al.

(10) Patent No.: US 11,746,116 B2
(45) Date of Patent: Sep. 5, 2023

(54) ANTIBIOTIC RESISTANCE BREAKERS

(71) Applicants: KING'S COLLEGE LONDON, London (GB); Secretary of State for Health and Social Care, London (GB)

(72) Inventors: Khondaker Mirazur Rahman, London (GB); Shirin Jamshidi, London (GB); Mark Benjamin Laws, London (GB); Kazi Nahar, London (GB); John Mark Sutton, Salisbury (GB); Charlotte Hind, Salisbury (GB)

(73) Assignees: King's College London, London (GB); Secretary of State for Health and Social Care, London (GB)

( * ) Notice: Subject to any disclaimer, the term of this patent is extended or adjusted under 35 U.S.C. 154(b) by 0 days.

(21) Appl. No.: 16/616,697

(22) PCT Filed: May 30, 2018

(86) PCT No.: PCT/GB2018/051468
§ 371 (c)(1),
(2) Date: Nov. 25, 2019

(87) PCT Pub. No.: WO2018/220365
PCT Pub. Date: Dec. 6, 2018

(65) Prior Publication Data
US 2021/0261570 A1    Aug. 26, 2021

(30) Foreign Application Priority Data
May 30, 2017   (GB) .................... 1708606

(51) Int. Cl.
*C07D 498/06*   (2006.01)
*A61P 31/04*    (2006.01)
*A61K 45/06*    (2006.01)

(52) U.S. Cl.
CPC ............ *C07D 498/06* (2013.01); *A61K 45/06* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 4,382,892 A | 5/1983 | Hayakawa et al. | |
| 5,221,676 A | 6/1993 | Laborde et al. | |
| 5,342,846 A * | 8/1994 | Singh ................... | C07D 231/12 546/156 |
| 2002/0177559 A1 | 11/2002 | de Souza et al. | |
| 2003/0130302 A1 | 7/2003 | Park et al. | |

FOREIGN PATENT DOCUMENTS

| | | |
|---|---|---|
| CA | 2478763 A1 | 9/2003 |
| EP | 0047005 | 3/1982 |
| EP | 0195316 | 9/1986 |
| EP | 0302372 | 2/1989 |
| EP | 0561850 | 9/1993 |
| JP | 03078439 A1 | 9/2003 |
| KR | 1020160044768 A1 | 4/2016 |
| WO | 1992010492 A1 | 6/1992 |
| WO | WO92/10492 * | 6/1992 |
| WO | 1993024481 | 12/1993 |
| WO | 03002560 | 1/2003 |

OTHER PUBLICATIONS

Grant & Hackh's Chemical Dictionary (5th Ed. 1987) at p. 148.*
Kawakami et al., Antimycobacterial Activities of Novel Levofloxacin Analogues. Antimicrobial Agents and Chemotherapy, 2000, 44, 2126-2129.*
Seelmann, Ingo, Written Opinion of Int'l Search Authority (PCT/GB2018/051468) dated Sep. 4, 2018.
Tran, et al., "Anthelmintic Closantel Enhances Bacterial Killing of Polymyxin B against Multidrug-Resistant Acinetobacter Baumannii," The Journal of Antibiotics, 2016, pp. 415-421, vol. 69.
JP Patent Application No. 2019565892 Office Action dated May 9, 2022.
CN Patent Application No. 201880035533.X Office Action dated Dec. 24, 2021.
Reddy, et al., "Microwave assisted amination of quinolone carboxylic acids: an expeditious synthesis of fluoroquinolone antibacterials," Department of Chemistry, Indian Institute of Technology, pp. 6775-6777, 2001.
Minovski, et al., "Investigation of 6-fluoroquinolones activity against *Mycobacterium tuberculosis* using theoretical molecular descriptors: a case study," Central European Journal of Chemistry, 2011, pp. 855-866, vol. 9, No. 5.

* cited by examiner

*Primary Examiner* — Po-Chih Chen
(74) *Attorney, Agent, or Firm* — Nicholas J. Landau; Maynard Nexsen PC

(57) ABSTRACT

The invention relates to antibiotic compounds of formula (A1) and pharmaceutically acceptable salts, solvates, tautomers and combinations thereof, wherein X and L are optional linkers and one of $R_A$ or $R_1$ comprises $Ar_1$, wherein $Ar_1$ is an antibiotic resistance breaker moiety which comprises an optionally substituted $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, —C(=NR')—NR'R" or —CH$_2$—CH=CH$_2$ group; wherein after administration of the compound to a bacterial infection this moiety reduces or prevents efflux. The invention also discloses pharmaceutical compositions comprising compounds of formula (A1) and the use of such compounds as medicaments, in particular, to treat bacterial infections, such as drug-resistant bacterial infections.

17 Claims, 42 Drawing Sheets

*Acinetobacter baumannii* AdeB 2D model of the ligand binding pocket 3D model of the ligand binding pocket

*Acinetobacter baumannii* NorM 2D model of the ligand binding pocket 3D model of the ligand binding pocket

*Escherichia coli* MdtK 2D model of the ligand binding pocket 3D model of the ligand binding pocket

*Escherichia coli* AcrB 2D model of the ligand binding pocket 3D model of the ligand binding pocket

*Enterococcus faecium (Streptococcus faecium)* EfmE 2D model of the ligand binding pocket 3D model of the ligand binding pocket

*Enterococcus faecalis (Streptococcus faecalis)* OqxD 2D model of the ligand binding pocket 3D model of the ligand binding pocket

*Klebsiella pneumoniae* AcrB 2D model of the ligand binding pocket 3D model of the ligand binding pocket

*Klebsiella pneumoniae* MdtK 2D model of the ligand binding pocket 3D model of the ligand binding pocket

*Pseudomonas aeruginosa* MexF 2D model of the ligand binding pocket 3D model of the ligand binding pocket

*Pseudomonas aeruginosa* PmpM 2D model of the ligand binding pocket 3D model of the ligand binding pocket

*Pseudomonas aeruginosa PAO1* MexB 2D model of the ligand binding pocket 3D model of the ligand binding pocket

*Staphylococcus aureus N315 MepA*

2D model of the ligand binding pocket 3D model of the ligand binding pocket

*Staphylococcus aureus* NorA 2D model of the ligand binding pocket 3D model of the ligand binding pocket

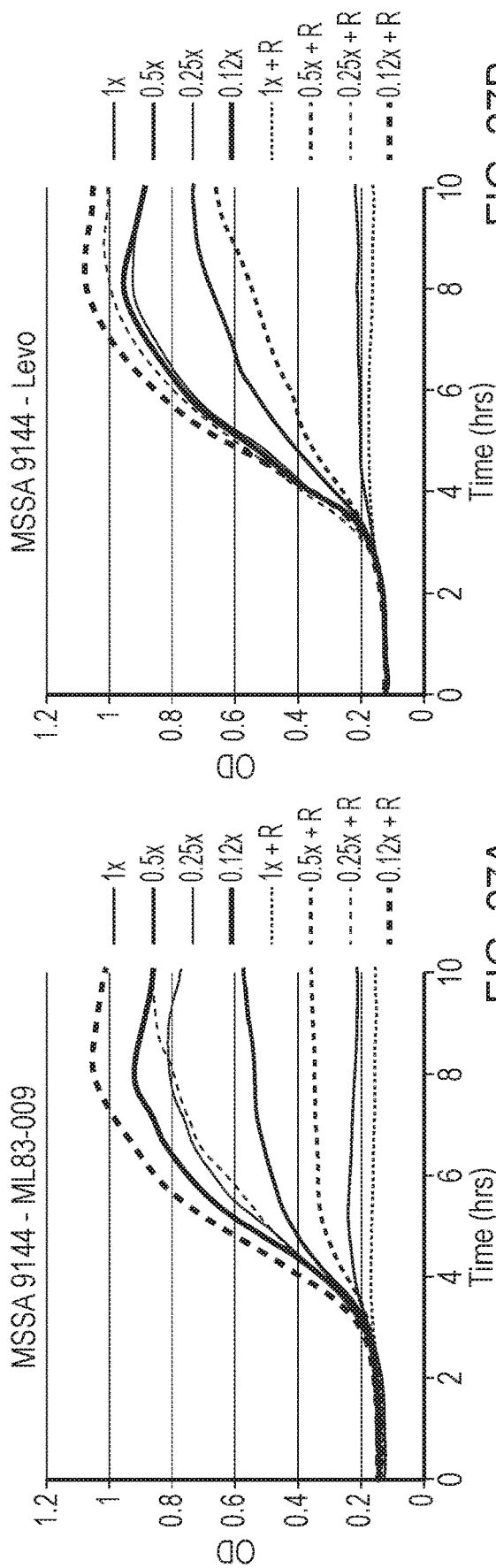
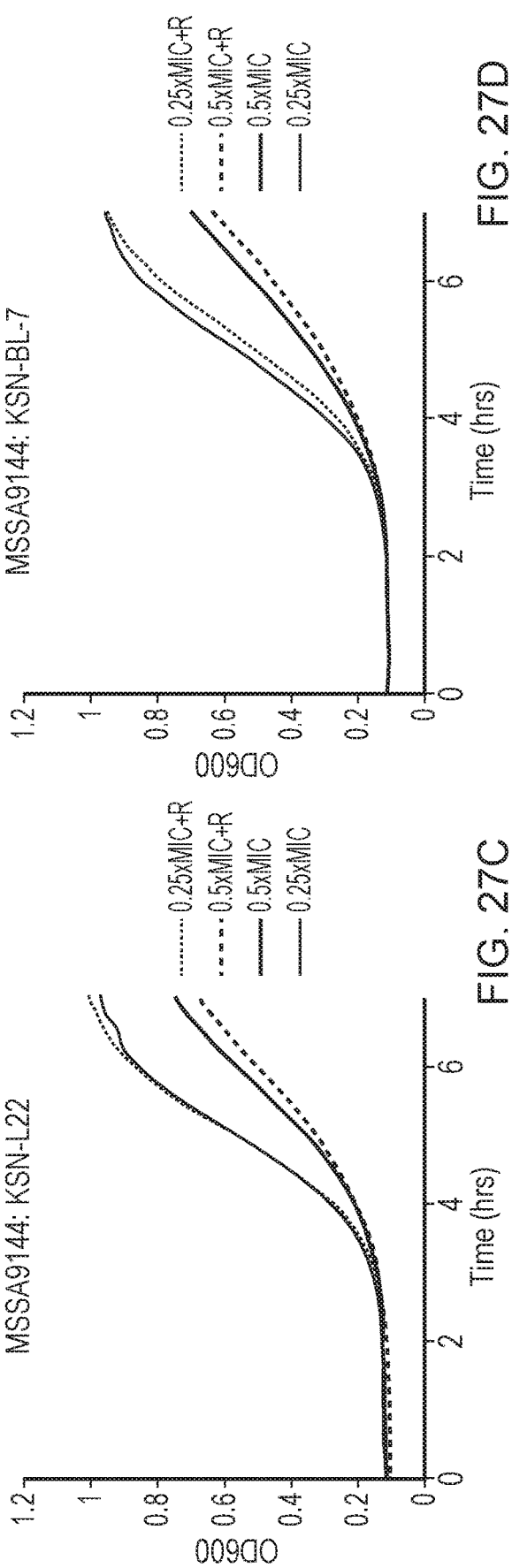
FIG. 27A, FIG. 27B, FIG. 27C, FIG. 27D

ANTIBIOTIC RESISTANCE BREAKERS

CROSS-REFERENCE TO RELATED APPLICATIONS

This application is a national stage under 35 U.S.C. 371 of International Application No. PCT/GB2018/051468, filed May 20, 2018 (currently published). International Application No. PCT/GB2018/051468 cites the priority of GB 1708606.7, filed May 30, 2017 (expired).

FIELD OF THE INVENTION

The invention relates to antibiotic compounds, pharmaceutical compositions and the use of such compounds to treat bacterial infections, such as drug-resistant bacterial infections. The antibiotic compounds comprise an antibacterial drug moiety, a linker and an antibiotic resistance breaker moiety that reduces or prevents efflux after administration of the compound to a bacterial infection.

BACKGROUND

Antimicrobial resistance represents a significant challenge to future healthcare provision. While appropriate use of antibiotics will inevitably encourage the onset of Antimicrobial resistance, the emergence of strains of multidrug-resistant micro-organisms is undoubtedly due, in part, to the overuse and misuse of antibiotics (1). With Antimicrobial resistance continually growing in prevalence across the globe, there is a need for novel antimicrobials to be developed to avoid an unwelcome reversion to the pre-penicillin era of medicine. However, for the last 50 years the scientific community has been unable to keep pace with the emergence of resistance; of note is the dearth of new classes of antimicrobial compounds reaching the market after the 1960s. The intervening years have primarily yielded variations of known classes, with optimised toxicities, dosing regimens and spectra of activity, rather than novel antibiotic scaffolds. This so-called 'discovery void' is not due to a lack of innovation on the part of the scientific community, but rather the increasingly 'high risk, no reward' nature of high-throughput pipelines used to bring new antibiotics to market. This high attrition rate for anti-infective agents, especially through clinical trials, has cause a reduction in private sector funding and the withdrawal of big pharmaceutical companies from the area (2).

The prokaryotic organisms are recognised as major threats in this regard include *Enterococcus faecalis, Staphylococcus aureus, Klesiella pneumoniae, Acinetobacter baumannii, Pseudomonas aeruginosa, Enterobacter* spp and *Escherichia coli* (collectively referred to as the "ESKAPEE" pathogens) although a number of other organisms are equally challenging to treat in the clinic (3-8). It is likely to take considerable time and effort to develop new classes of antibacterials and it is urgent to extend the life-span current antibiotics so that a possible "antibiotic apocalypse" can be delayed (9).

Bacteria can acquire resistance to an antibiotic compound either endogenously through vertical evolution, a spontaneous mutation in the bacterial genome that confers increased resistance to the compound on the bacterium and its progeny, or exogenously through horizontal evolution, transfer of a resistance gene from a resistant bacterium to a susceptible bacterium. Resistance can be achieved via a number of mechanisms, including destruction or alteration of the antibiotic, modification of the antibiotic target, indirect protection of the target, barrier mechanisms and efflux pumps (2).

Four major categories of resistance include; efflux-mediated, target-mediated, plasmid-mediated and chromosome-mediated resistance. It has recently been demonstrated that efflux-mediated resistance acts as the initiator for other resistance mechanisms. In other words, every resistant microorganism proceeds through an efflux mutant version. Therefore, an antibiotic resistance breaker capable of reversing or negating efflux can significantly reduce the chances of resistance emerging.

The ability to reverse or negate efflux is particularly important when dealing with multidrug-resistant (MDR) pathogens. MDR pathogens have emerged as a major concern for public health, and there are particular concerns about the emergence of a number of Gram-negative pathogens, for which there are dwindling treatment options and few compounds are in the development stage. These pathogens are characterised by the ability to rapidly develop and/or acquire resistance mechanisms in response to exposure to different antimicrobial agents. A key part of the armoury of these pathogens are a series of efflux pumps, which effectively exclude or reduce the intracellular concentration of a large number of antibiotics, making the pathogens significantly more resistant. It has been demonstrated that efflux is a key mediator of resistance, and the efflux mutant strains eventually develop multiple target mutations, leading to multidrug-resistance.

Efflux-mediated resistance: Efflux as a mechanism of antibiotic resistance was first reported in the early 1980s, for tetracycline, by two groups of researchers (9). Since then, efflux-mediated resistance to several antimicrobial agents, including quinolones, has been reported in a variety of bacterial species, and a number of efflux determinants have been cloned and sequenced. Quinolones, in particular fluoroquinolones, are one of the most frequently prescribed family of antimicrobial agents. Bacterial antimicrobial efflux transporters have generally been grouped into four superfamilies, primarily on the basis of amino acid sequence homology. These include the major facilitator superfamily (MFS), the ATP-binding cassette family (ABC), the resistance-nodulation-division (RND) family, and the small multidrug-resistance protein (SMR) family. Recently, a fifth family, referred to as the multidrug and toxic compound extrusion (MATE) family, has been identified (10). Antibiotic efflux pumps fall into the RND, MFS, and MATE groups, with the RND and MATE families so far being unique to Gram-negative bacteria. Thus, MFS-type transporters predominate with regard to the efflux of antimicrobial agents in Gram-positive organisms.

Fluoroquinolone resistance attributable to efflux has been reported in a number of Gram-positive and Gram-negative organisms including *Staphylococcus aureus, Enterococcus* spp., *Streptococcus pneumoniae, Burkholderia cepacia/cenocepacia, Escherichia coli, Klebsiella pneumoniae* and *Pseudomonas aeruginosa*. Efflux-mediated resistance in Gram-positive bacteria is generally mediated by MFS-type efflux pumps and provides clinically significant resistance to fluoroquinolones.

Current research into combatting these efflux systems involves the development of efflux pump inhibitors (EPIs). A number of EPIs have been developed from both natural and synthetic sources. Naturally-derived classes of EPI include the plant alkaloids (e.g. reserpine (ii)), phenolic metabolites (including the flavolignans (12), methoxylated flavones and isoflavones (13). Synthetic classes of EPI include peptidomimetics (e.g. PaβN (14)), G-918, biricodar and timcodar (15), phenothiazine and thioxanthene derivatives (e.g. chlorpromazine (16)) and quinoline derivatives (17).

Understanding how the transport process operates requires information on the organization and interaction of the subunits within a full tripartite assembly. Reconstituting tripartite assemblies for experimental structural elucidation has been a technical challenge, and simply mixing the components together does not yield the assembled complex in sufficient yield or purity to enable analysis (18).

So far, efflux pump inhibitors have been developed using random screening of synthetic chemical agents or plant metabolites (19). Use of advanced 3D structure resolution, molecular modelling and molecular dynamics simulation can help the researchers to identify the pharmacophores of a putative inhibitor that recognise the specific binding site of an efflux pump (19).

The traditonal approach of reversing efflux mediated resistance using a combination of efflux pump inhibitors (EPI) and antibiotics have failed to date, as the unmodified antibiotic gets effluxed when picked up by the pump, and a very high concentration of EPIs are required to reduce the probability, which is too toxic for therapeutic use. The design of effective EPIs has been hampered by the lack of structural information and molecular mechanisms of action, due to the large complex nature of efflux pumps and the transmemberane nature of the transporters.

There remains a need for new and improved methods for combating antibiotic resistance, in particular, to reduce or prevent efflux-mediated resistance. We have used a combination of homology modeling and available X-ray structures to develop moelcular models of efflux pumps, and used these molecular models to unravel the molecular mechanism of efflux of antibiotics, and the differences in the interaction of EPIs and antibiotic substrates. Using this detailed structural information of bacterial efflux pumps, we have developed unique antibiotic resistance breaker technology. We have been able to demonstrate that the incorporation of small chemical fragments that strongly interact with the binding pocket of bacterial efflux pumps can act as antibiotic resistance breakers (ARB s). Chemically linking these ARB s to existing antibacterial chemical scaffolds (key pharmacophore or intermediate with antibacterial activity) can resensitize MDR bacteria to these ARB-modified antibacterial agents, while retaining the activity of the antibiotic against its target. This ARB-modified antibiotics work as substrate inhibitors, and block the efflux pumps, resulting in high intracellular concentrations of ARB-antibiotics within the bacterial cell. This increased concentration of ARB-antibiotics results in bacterial death, even in the presence of multiple target mutations, which has been demonstrated by us. The mechanism of action of ARB-antibiotics, and their key differences with standard antibiotics, is outlined in FIG. 1.

The experimental approach for identifying a suitable ARB fragment, covalently linking them to core antibiotic chemical scaffold, developing ARB-linked antibiotic and validation of the concept is shown in FIG. 34.

Briefly, using available crystal structures or homology models built with related efflux pumps, the binding of the antibiotic core scaffold within the target identifies key residues that can be targeted to develop the novel ARB-modified antibiotics. This is followed by in silico screening of small-molecule fragment libraries to assess available scaffolds that are compatible with developing ARB s for that antibiotic class. Molecular dynamics simulations are carried out on fragment-linked lead molecules to confirm their interaction with the efflux pumps and ability to maintain interactions with the antibiotic target (e.g. gyrase, topoisomerase, etc.). Top-ranked ARB fragment-linked antibiotics are synthesized and tested for their ability to reverse efflux mediated resistance.

Surprisingly, it has been found (e.g. see Table 12) that ARB compounds that use a 5-membered ring, such as a pyrrolodine ring, significantly reduce the bacterial load and reduce efflux as compared to compounds containing a 6-membered piperazine ring (as commonly used in fluoroquinolone antibiotics).

The antibiotic resistance breakers as disclosed herein work by chemical modification of the efflux substrate antibiotic unlike the traditional co-administration approach.

The present invention seeks to alleviate these problems associated with the prior art.

SUMMARY

In a first aspect there is provided an antibiotic compound of formula (A1):

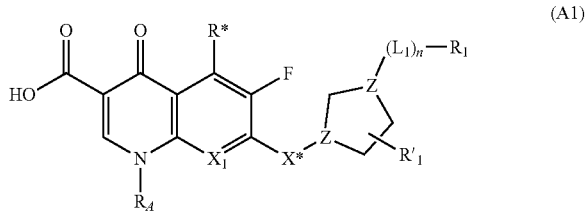

and pharmaceutically acceptable salts, solvates, tautomers and combinations thereof, wherein:
$X_1$ is selected from N, C—H and C—$R_B$;
$R_A$ is selected from methyl, ethyl, allyl, vinyl, cyclopropyl and —$(CH_2)_k$—$Ar_1$;
$R_B$ is selected from halo and $OCH_3$;
or $X_1$ is C—$R_B$, and $R_A$ and $R_B$ together with the atoms to which they are attached form a 6-membered ring wherein from $R_A$ to $R_B$ is a —$CH(CH_3)$—$CH_2$—O— linking group;
$R^*$ is selected from H or $NH_2$;
either $Z_1$ is CH and $X^*$ is —NR'—; or $Z_1$ is N and $X^*$ is absent;
$L_1$ is —$(CH_2)_m$—, —NR'—$(CH_2)_s$—, —O—$(CH_2)_s$—, —NR'—C(=O)—NR''—, —NR'—C(=O)— or —N=CH—;
n is 0 or 1;
m is 1, 2, 3, 4 or 5;
each k or s is independently 0, 1, 2, 3, 4 or 5;
Z is N or C—H;
$R'_1$ is H, $C_{1-6}$ alkyl or —$(CH_2)_t$—C(=O)—OR';
$R_1$ is H, $Ar_1$, $C_{1-6}$ alkyl or $C_{2-12}$ alkenyl;
$Ar_1$ is selected from $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, —C(=NR')—NR'R'' and —$CH_2$—CH=$CH_2$; and the $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl or $C_{4-13}$ carbocyclalkyl group is optionally substituted with a phenyl, a $C_{5-10}$ heteroaryl, a $C_{6-13}$ heterocyclalkyl or a $C_{5-10}$ heterocyclyl group; and the $Ar_1$ group may be optionally substituted with 1, 2 or 3 optional substituents selected from —$C_{1-6}$ alkyl, -halo, —(CH$_2$)$_t$—OR', —(CH$_2$)$_t$—C(=O)—OR', oxo, —(CH$_2$)$_t$—NR'R", —NO$_2$, —NR'-(cyclopropyl), -(cyclopropyl), —NR'—(CH$_2$)$_t$—NR'R", —C(=NR')—NR'R", —(CH$_2$)$_t$—NR'—C(=NR')—NR'R", —CH$_2$—CH=CH$_2$, —CH=CH—(C$_{1-6}$ alkyl), —CH=CH—CN, —SO$_2$—NR'R" and —SO$_2$NR'—(CH$_2$)$_t$—Ar$_2$;

each t is independently 0, 1, 2, 3, 4 or 5;
each Ar$_2$ is independently selected from C$_{5-9}$ heteroaryl;
each R' and R" is independently selected from H and C$_{1-6}$ alkyl; and
provided that one of R$_A$ or R$_1$ comprises Ar$_1$, and (i) when R$_A$ comprises Ar$_1$ then R$_1$ is H, C$_{1-6}$alkyl or C$_{2-12}$ alkenyl; and (ii) when R$_1$ comprises Ar$_1$ then R$_A$ is selected from methyl, ethyl, allyl, vinyl and cyclopropyl; or X$_1$ is C—R$_B$, and R$_A$ and R$_B$ together with the atoms to which they are attached form a 6-membered ring wherein from R$_A$ to R$_B$ is a —CH(CH$_3$)—CH$_2$—O— linking group.

In a further aspect, the antibiotic compound of formula (A1), is selected from formula (II):

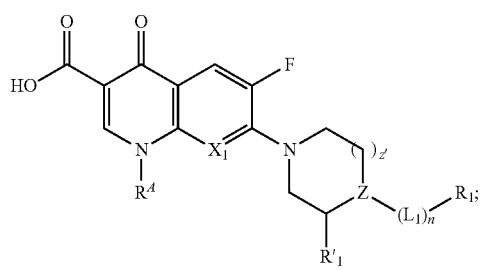

(II)

and pharmaceutically acceptable salts, solvates, tautomers and combinations thereof, wherein:
X$_1$ is selected from N, C—H and C—R$_B$;
R$_A$ is selected from methyl, ethyl, allyl, vinyl, cyclopropyl and —(CH$_2$)$_k$—Ar$_1$;
R$_B$ is selected from halo and OCH$_3$;
or R$_A$ and R$_B$ together with the atoms to which they are attached form a 6-membered ring wherein from R$_A$ to R$_B$ is a —CH(CH$_3$)—CH$_2$—O— linking group;
L$_1$ is —(CH$_2$)$_m$—, —NR'—(CH$_2$)$_s$— and —O—(CH$_2$)$_s$—;
n is 0 or 1;
m is independently 1, 2, 3 or 5;
each k or s is independently 0, 1, 2, 3, 4 or 5;
z' is 0;
Z is N or C—H;
R'$_1$ is H or C$_{1-6}$ alkyl;
R$_1$ is H or Ar$_1$;
Ar$_1$ comprises an optionally substituted C$_{6-10}$ aryl, C$_{7-13}$ aralkyl, C$_{5-10}$ heteroaryl, C$_{6-13}$ heteroaralkyl, C$_{5-10}$ heterocyclyl, C$_{6-13}$ heterocyclalkyl, C$_{3-10}$ carbocyclyl, C$_{4-13}$ carbocyclalkyl, —C(=NR')—NR'R", and —CH$_2$—CH=CH$_2$ group; and the C$_{6-10}$ aryl, C$_{7-13}$ aralkyl, C$_{5-10}$ heteroaryl, C$_{6-13}$ heteroaralkyl, C$_{5-10}$ heterocyclyl, C$_{6-13}$ heterocyclalkyl, C$_{3-10}$ carbocyclyl or C$_{4-13}$ carbocyclalkyl group is optionally substituted with a substituent group —Y$_6$—(Y$_7$)$_{0-1}$—(Y$_8$)$_{0-1}$, wherein:
each Y$_6$, Y$_7$ and Y$_8$ is independently selected from C$_{6-10}$ aryl, C$_{7-13}$ aralkyl, C$_{5-10}$ heteroaryl, C$_{6-13}$ heteroaralkyl, C$_{5-10}$ heterocyclyl, C$_{6-13}$ heterocyclalkyl, C$_{3-10}$ carbocyclyl and C$_{4-13}$ carbocyclalkyl;

the Ar$_1$ group may be optionally substituted with 1, 2, 3, 4, 5 or 6 optional substituents selected from —C$_{1-6}$ alkyl, -halo, —(CH$_2$)$_t$—OR', —(CH$_2$)$_t$—C(=O)—OR', —(CH$_2$)$_t$—NR'R", —NR'—(CH$_2$)$_t$—NR'R", —C(=NR')—NR'R", —(CH$_2$)$_t$—NR'—C(=NR')—NR'R", —CH$_2$—CH=CH$_2$, —SO$_2$—NR'R", —SO$_2$NR'—(CH$_2$)$_t$—Ar$_2$ and oxo;
each t is independently 0, 1, 2, 3, 4 or 5;
each Ar$_2$ is independently selected from C$_{5-10}$ heteroaryl;
with the proviso that one of R$_A$ or R$_1$ comprises Ar$_1$, and
(i) when R$_A$ comprises Ar$_1$ then R$_1$ is H; and (ii) when R$_1$ comprises Ar$_1$ then R$_A$ is selected from methyl, ethyl, allyl, vinyl and cyclopropyl; or R$_A$ and R$_B$ together with the atoms to which they are attached form a 6-membered ring wherein from R$_A$ to R$_B$ is a —CH(CH$_3$)—CH$_2$—O— linking group; and
each R' and R" is independently selected from H and C$_{1-6}$ alkyl.

In a further aspect there is provided a pharmaceutical composition comprising a compound of formula (I) and/or (A1) and pharmaceutically acceptable salts, solvates, tautomers and combinations thereof, and a pharmaceutically acceptable carrier or diluent.

In a further aspect there is provided a compound of formula (I) and/or formula (A1) and pharmaceutically acceptable salts, solvates, tautomers and combinations thereof, for use as a medicament.

In a further aspect there is provided a compound of formula (I) and/or formula (A1) and pharmaceutically acceptable salts, solvates, tautomers and combinations thereof, for use in the treatment of a bacterial infection in a subject.

In a further aspect there is provided a compound of formula (I) and/or formula (A1) and pharmaceutically acceptable salts, solvates, tautomers and combinations thereof, for use in the treatment of a multidrug-resistant bacterial infection in a subject.

In a further aspect, there is provided a compound of formula (I) and/or formula (A1) and salts and solvates thereof, for use in treating anthrax, bronchitis, pneumonia, prostatitis, pyelonephritis, sinusitis, skin and skin structure infections, sexually transmitted disease or urinary tract infections.

In a further aspect, the present invention provides a method of treating a multidrug-resistant bacterial infection in a patient comprising administering to a patient in need thereof a therapeutically effective amount of a compound of formula (I) and/or formula (A1) and pharmaceutically acceptable salts, solvates, tautomers and combinations thereof, or a pharmaceutical composition comprising a compound of formula (I) and/or formula (A1) and pharmaceutically acceptable salts, solvates, tautomers and combinations thereof.

In a further aspect, the present invention provides a method of inhibiting a bacterium, the method comprising the step of contacting the bacteria with a compound of formula (I) and/or formula (A1) and pharmaceutically acceptable salts, solvates, tautomers and combinations thereof, or a pharmaceutical composition of the present invention.

In a further aspect, the compound of formula (I) and/or formula (A1) and pharmaceutically acceptable salts, solvates, tautomers and combinations thereof, may be administered alone or in combination with other treatments, separately, simultaneously or sequentially depending upon the condition to be treated. Such treatments may comprise one or more other antibiotic drugs.

The pharmaceutical composition of the present invention may further comprise one or more (e.g. two, three or four) further active agents. Such active agents may be other antibacterial drugs.

There is also described an antibiotic compound of formula (I):

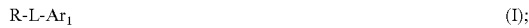   (I);

and pharmaceutically acceptable salts, solvates, tautomers and combinations thereof, wherein R is an antibacterial drug moiety;

L is an optional linker;

m is 0, 1 or 2;

$Ar_1$ is an antibiotic resistance breaker moiety.

There is also described an antibiotic compound of formula (I):

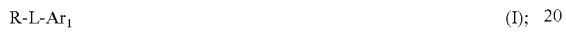   (I);

and pharmaceutically acceptable salts, solvates, tautomers and combinations thereof, wherein R is an antibacterial drug moiety;

L is an optional linker selected from $—(CH_2)_m—$, $—NR'—(CH_2)_s—$ or $—O—(CH_2)_s$ optionally substituted with a $C_{5-10}$ heterocyclylene or a $C_{3-10}$ carbocyclylene group these carbocyclylene or hetercyclylene groups may be optionally substituted with 1, 2 or 3 groups independently selected from $C_{1-6}$ alkyl groups;

m or s is 0, 1, 2, 3, 4 or 5; and $Ar_1$ is an antibiotic resistance breaker moiety which comprises an optionally substituted $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, $—C(=NR')—NR'R''$ or $—CH_2—CH=CH_2$ group; wherein after administration of the compound to a bacterial infection this moiety reduces or prevents efflux.

There is also described an antibiotic compound of formula (I), wherein the compound is selected from formula (II), (III), (IV):

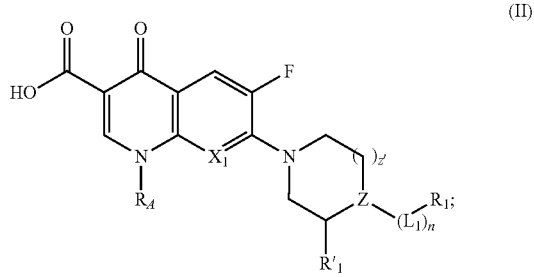

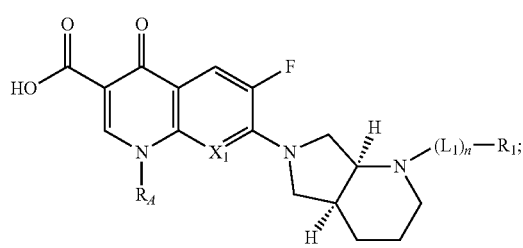

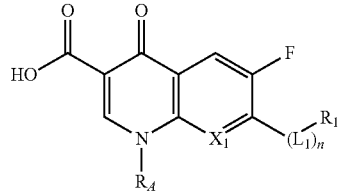

and pharmaceutically acceptable salts, solvates, tautomers and combinations thereof, wherein:

$X_1$ is selected from N, C—H and C—$R_B$;

$R_A$ is selected from methyl, ethyl, allyl, vinyl, cyclopropyl and $—(CH_2)_k—Ar_1$;

$R_B$ is selected from halo and $OCH_3$;

or $R_A$ and $R_B$ together with the atoms to which they are attached form a 6-membered ring wherein from $R_A$ to $R_B$ is a $—CH(CH_3)—CH_2—O—$ linking group;

$L_1$ is $—(CH_2)_m—$, $—NR'—(CH_2)_s—$ and $—O—(CH_2)_s—$, n is 0 or 1;

m is independently 1, 2, 3 or 5;

each k or s is independently 0, 1, 2, 3, 4 or 5;

z' is 0, 1 or 2;

Z is N or C—H;

$R'_1$ is H or $C_{1-6}$ alkyl;

$R_1$ is H or $Ar_1$;

$Ar_1$ comprises an optionally substituted $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, $—C(=NR')—NR'R''$, and $—CH_2—CH=CH_2$ group; and the $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl or $C_{4-13}$ carbocyclalkyl group is optionally substituted with a substituent group $—Y_6—(Y_7)_{0-1}—(Y_8)_{0-1}$, wherein:

each $Y_6$, $Y_7$ and $Y_8$ is independently selected from $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl and $C_{4-13}$ carbocyclalkyl;

the $Ar_1$ group may be optionally substituted with 1, 2, 3, 4, 5 or 6 optional substituents selected from $—C_{1-6}$ alkyl, -halo, $—(CH_2)_t—OR'$, $—(CH_2)_t—C(=O)—OR'$, $—(CH_2)_t—NR'R''$, $—NR'—(CH_2)_t—NR'R''$, $—C(=NR')—NR'R''$, $—(CH_2)_t—NR'—C(=NR')—NR'R''$, $—CH_2—CH=CH_2$, $—SO_2—NR'R''$, $—SO_2NR'—(CH_2)_t—Ar_2$ and oxo;

each t is independently 0, 1, 2, 3, 4 or 5;

each $Ar_2$ is independently selected from $C_{5-10}$ heteroaryl;

with the proviso that one of $R_A$ or $R_1$ comprises $Ar_1$, and (i) when $R_A$ comprises $Ar_1$ then $R_1$ is H; and (ii) when $R_1$ comprises $Ar_1$ then $R_A$ is selected from methyl, ethyl, allyl, vinyl and cyclopropyl; or $R_A$ and $R_B$ together with the atoms to which they are attached form a 6-membered ring wherein from $R_A$ to $R_B$ is a $—CH(CH_3)—CH_2—O—$ linking group; and each R' and R'' is independently selected from H and $C_{1-6}$ alkyl.

There is also described an antibiotic compound of formula (I), wherein the compound is selected from formula (II), (III), (IV):

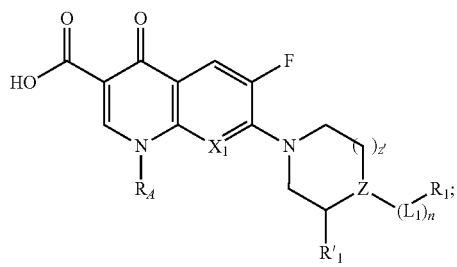

(II)

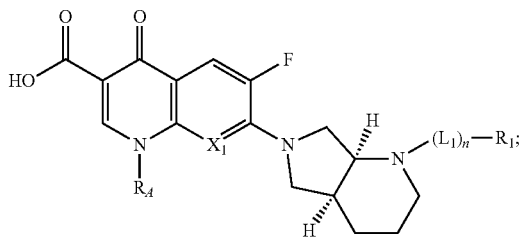

(III)

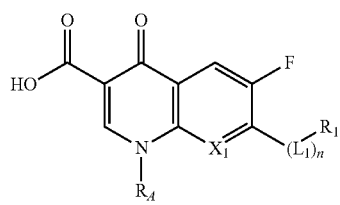

(IV)

and pharmaceutically acceptable salts, solvates, tautomers and combinations thereof, wherein:

$X_1$ is selected from N, C—H and C—$R_B$;
$R_A$ is selected from methyl, ethyl, allyl, vinyl, cyclopropyl and —$(CH_2)_k$—$Ar_1$;
$R_B$ is selected from halo and $OCH_3$;
or $R_A$ and $R_B$ together with the atoms to which they are attached form a 6-membered ring wherein from $R_A$ to $R_B$ is a —$CH(CH_3)$—$CH_2$—O— linking group;
$L_1$ is —$(CH_2)_m$—, —NR'—$(CH_2)_s$— and —O—$(CH_2)_s$—;
n is 0 or 1;
m is independently 1, 2, 3 or 5;
each k or s is independently 0, 1, 2, 3, 4 or 5;
z' is 0, 1 or 2;
Z is N or C—H;
$R'_1$ is H or $C_{1-6}$ alkyl;
$R_1$ is H or $Ar_1$;
$Ar_1$ is selected from $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, —C(=NR')—NR'R" and —$CH_2$—CH=$CH_2$ group; and the $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl or $C_{4-13}$ carbocyclalkyl group is optionally substituted with a phenyl, a heteroaryl, a $C_{6-13}$ heteroaralkyl or a $C_{5-10}$ heterocyclyl group; and the $Ar_1$ group may be optionally substituted with 1, 2 or 3 optional substituents selected from —$C_{1-6}$ alkyl, -halo, —$(CH_2)_t$—OR', —$(CH_2)_t$—C(=O)—OR', oxo, —$(CH_2)_t$—NR'R", —NR'—$(CH_2)_t$—NR'R", —C(=NR')—NR'R", —$(CH_2)_t$—NR'—C(=NR')—NR'R", —$CH_2$—CH=$CH_2$, —$SO_2$—NR'R" and —$SO_2$NR'—$(CH_2)_t$—$Ar_2$;
each t is independently 0, 1, 2, 3, 4 or 5;
each $Ar_2$ is independently selected from $C_{5-10}$ heteroaryl;
with the proviso that one of $R_A$ or $R_1$ comprises $Ar_1$, and (i) when $R_A$ comprises $Ar_1$ then $R_1$ is H; and (ii) when $R_1$ comprises $Ar_1$ then $R_A$ is selected from methyl, ethyl, allyl, vinyl and cyclopropyl; or $R_A$ and $R_B$ together with the atoms to which they are attached form a 6-membered ring wherein from $R_A$ to $R_B$ is a —CH(CH_3)—CH_2—O— linking group; and
each R' and R" is independently selected from H and $C_{1-6}$ alkyl.

There is also described an antibiotic compound of formula (I), wherein the compound is selected from formula (V):

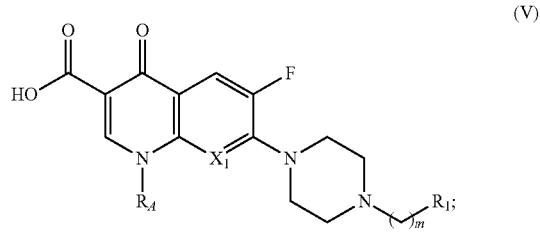

(V)

and pharmaceutically acceptable salts, solvates, tautomers and combinations thereof, wherein:

$X_1$ is selected from N, C—H and C—$R_B$;
$R_A$ is selected from methyl, ethyl, allyl, vinyl, cyclopropyl and —$(CH_2)_k$—$Ar_1$;
$R_B$ is selected from H, halo, $OCH_3$;
or $R_A$ and $R_B$ together with the atoms to which they are attached form a 6-membered ring wherein from $R_A$ to $R_B$ is a —$CH(CH_3)$—$CH_2$—O— linking group;
m is 0, 1 or 2;
k is 0, 1, 2, 3, 4 or 5;
$R_1$ is H or $Ar_1$;
$Ar_1$ comprises an aryl or heteroaryl group selected from phenyl, pyrimidinyl, naphthalenyl, 5,6-dihydronaphthalenyl, 7,8-dihydronaphthalenyl, 5,6,7,8-tetrahydronaphthalenyl and benzothiophenyl; and the aryl or heteroaryl group is optionally substituted with a phenyl or a 5-membered heteroaryl group; and the $Ar_1$ group may be optionally substituted with 1, 2 or 3 optional substituents selected from $C_{1-6}$ alkyl, halo and NR'R";
with the proviso that one of $R_A$ or $R_1$ comprises $Ar_1$, and (i) when $R_A$ comprises $Ar_1$ then $R_1$ is H; and (ii) when $R_1$ comprises $Ar_1$ then $R_A$ is selected from methyl, ethyl, allyl, vinyl and cyclopropyl; or $R_A$ and $R_B$ together with the atoms to which they are attached form a 6-membered ring wherein from $R_A$ to $R_B$ is a —CH(CH_3)—CH_2—O— linking group; and
each R' and R" is independently selected from H and $C_{1-6}$ alkyl.

Further particular and preferred aspects are set out in the accompanying independent and dependent claims. Features of the dependent claims may be combined with features of the independent claims as appropriate, and in combinations other than those explicitly set out in the claims.

Definitions

The following abbreviations are used throughout the specification: Ac acetyl; Bn benzyl; Boc tert-butoxycarbonyl; DBU 1,8-diazabicyclo[5.4.0]undec-7-ene; DCM dichloro-methane; DMF dimethylformamide; DMSO dimethyl sulfoxide; EtOAc ethyl acetate; Me methyl; MIC minimum inhibitory concentration; Ph phenyl; rt room temperature; TLC thin layer chromatography; and TFA trifluoroacetic acid.

$C_{1-6}$ alkyl: refers to straight chain and branched saturated hydrocarbon groups, generally having from 1 to 6 carbon atoms; more suitably $C_{1-5}$ alkyl; more suitably $C_{1-4}$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like.

$C_{2-12}$ alkenyl: refers to a hydrocarbon radical having from 2 to 12 carbon atoms and at least one double bond including, but not limited to, ethenyl, i-propenyl, 2-propenyl, isopropenyl, i-butenyl, 2-butenyl, 3-butenyl, pentenyl and hexenyl and the like. More suitably, a $C_{2-11}$ alkenyl; a $C_{2-10}$ alkenyl; a $C_{2-9}$ alkenyl; $C_{2-8}$ alkenyl; a $C_{2-7}$ alkenyl; $C_{2-6}$ alkenyl; a $C_{2-5}$ alkenyl; $C_{2-4}$ alkenyl; a $C_{2-3}$ alkenyl; or a $C_2$ alkenyl.

"Antibacterial drug moiety" refers to a moiety derived from an antibacterial drug wherein a substituent, such as a hydrogen, in the antibacterial drug is replaced with a bond to the rest of the compound of formula (I) or formula (A1), i.e. to the linker or, if the linker is not present, to the antibiotic resistance breaker moiety. The moiety may be derived by replacing a group (such as a substituted or unsubstituted piperidinyl, piperazinyl or pyrrolidinyl group) with a bond to the rest of the compound of formula (I) and/or (A1). Where a group such as a piperidinyl, piperazinyl or pyrrolidinyl group is replaced, the antibacterial drug moiety may be considered as a fragment of the parent antibacterial drug. Such framents will include the major part of the parent antibacterial agent, such as the major fused ring moiety of tetracycline or quinolone antibacterial agents.

"Aryl": refers to fully unsaturated monocyclic, bicyclic and polycyclic aromatic hydrocarbons having at least one aromatic ring. Suitably, an aryl group is a $C_{6-10}$ awl and having a specified number of carbon atoms that comprise their ring members (e.g., 6 to 10 carbon atoms as their ring members). The awl group may comprise fused rings, at least one of which is a fully unsaturated ring, for example indanyl and 5,6,7,8-tetrahydronaphthalenyl. The aryl group may be attached to a parent group or to a substrate at any ring atom and may include one or more non-hydrogen substituents unless such attachment or substitution would violate valence requirements. Examples of awl groups include phenyl, biphenyl, indanyl, indenyl, naphthalenyl, 5,6-dihydronaphthalenyl, 7,8-dihydronaphthalenyl and 5,6,7,8-tetrahydronaphthalenyl.

"$C_{7-13}$ aralkyl, $C_{6-13}$ heteroaralkyl, $C_{6-13}$ heterocyclalkyl and $C_{4-13}$ carbocyclalkyl" represent alkyl substitutents that are substituted with the named ring structure. For example, an aralkyl group comprises an alkyl group substituted with an awl group. Suitably, $C_{7-13}$ aralkyl, $C_{6-13}$ heteroaralkyl, $C_{6-13}$ heterocyclalkyl and $C_{4-13}$ carbocyclalkyl groups comprise a $C_{1-3}$ alkyl group substituted with a $C_{6-10}$ aryl, $C_{5-10}$ heteroaryl, $C_{5-10}$ heterocyclyl or $C_{3-10}$ carbocyclyl group respectively. Suitably, the alkyl group in $C_{7-13}$ aralkyl, $C_{6-13}$ heteroaralkyl, $C_{6-13}$ heterocyclalkyl and $C_{4-13}$ carbocyclalkyl is a $C_1$ or $C_2$ alkyl group; more suitably, a $C_1$ alkyl group.

"Bacterial infection" includes infections caused by one or more species of Gram-negative, Gram-positive, or atypical bacteria. The term "bacterial infection" pertains to the invasion of body tissues by bacteria, their multiplication and the reaction of body tissues to the bacteria and the toxins that they produce.

"$C_3$-$C_{10}$ carbocyclyl" by itself or as part of another term, is a 3-, 4-, 5-, 6-, 7-, 8-, 9- or 10-membered monovalent, substituted or unsubstituted, saturated or unsaturated non-aromatic monocyclic or bicyclic carbocyclic ring derived by the removal of one hydrogen atom from a ring atom of a parent ring system. Representative $C_3$-$C_{10}$ carbocyclyl groups include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.)pentane, and bicyclo(2.2.2.)octane. A $C_3$-$C_8$ carbocyclyl group can be optionally substituted.

"$C_3$-$C_{10}$ carbocyclylene" refers to a divalent radical derived from a $C_3$-$C_{10}$ carbocyclyl, e.g. such as a cyclohexylene —$C_6H_{10}$— group.

As used herein the term "comprising" means "including at least in part of" and is meant to be inclusive or open ended. When interpreting each statement in this specification that includes the term "comprising", features, elements and/or steps other than that or those prefaced by the term may also be present. Related terms such as "comprise" and "comprises" are to be interpreted in the same manner.

The term "consisting essentially of" limits the scope of a claim to the specified materials or steps "and those that do not materially affect the basic and novel characteristic(s)" of the claimed invention. When the phrase "consisting essentially of" appears in a clause of the body of a claim, rather than immediately following the preamble, it limits only the element set forth in that clause.

The term "consisting of" excludes any element, step, or ingredient not specified in the claim; "consisting of" defined as "closing the claim to the inclusion of" materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

It should be understood that while various embodiments in the specification are presented using "comprising" language, under various circumstances, a related embodiment is also be described using "consisting of" or "consisting essentially of" language.

"Drug", "drug substance", "active pharmaceutical ingredient", and the like, refer to a compound (e.g., compounds of Formula (I) and/or (A1) and compounds specifically named above) that may be used for treating a subject in need of treatment.

"Excipient" refers to any substance that may influence the bioavailability of a drug, but is otherwise pharmacologically inactive.

"Halogen" or "halo" refers to a halogen selected from fluoro, chloro, bromo, and iodo. Suitably the halogen may be selected from fluoro, chloro and iodo.

"$C_{5-10}$ heteroaryl": refers to unsaturated monocyclic or bicyclic aromatic groups comprising from 5 to 10 ring atoms, whether carbon or heteroatoms, of which from 1 to 5 are ring heteroatoms. Suitably, the heteroaryl group is a 5- to 10-membered ring heteroaryl comprising 5 to 10 ring atoms, whether carbon or heteroatoms, of which from 1 to 5 are ring heteroatoms. Suitably, any monocyclic heteroaryl ring has from 5 to 6 ring atoms including from 1 to 3 ring heteroatoms. Suitably each ring heteroatom is independently selected from nitrogen, oxygen, and sulfur. The bicyclic rings include fused ring systems and, in particular, include bicyclic groups in which a monocyclic heterocycle comprising 5 ring atoms is fused to a benzene ring. The heteroaryl group may be attached to a parent group or to a substrate at any ring atom and may include one or more non-hydrogen substituents unless such attachment or substitution would violate valence requirements or result in a chemically unstable compound.

Examples of monocyclic heteroaryl groups include, but are not limited to, those derived from:
$N_1$: pyrrole, pyridine;
$O_1$: furan;
$S_1$: thiophene isoxazole, isoxazine;
$N_1O_1$: oxazole, isoxazole;
$N_2O_1$: oxadiazole (e.g. 1-oxa-2,3-diazolyl, 1-oxa-2,4-diazolyl, 1-oxa-2,5-diazolyl, 1-oxa-3,4-diazolyl);
$N_3O_1$: oxatriazole;
$N_1S_1$: thiazole, isothiazole;
$N_2S_1$: thiadiazole (e.g. 1,3,4-thiadiazole);
$N_2$: imidazole, pyrazole, pyridazine, pyrimidine, pyrazine;
$N_3$: triazole, triazine; and,
$N_4$: tetrazole.

Examples of heteroaryl which comprise fused rings, include, but are not limited to, those derived from:
$O_1$: benzofuran, isobenzofuran;
$N_1$: indole, isoindole, indolizine, isoindoline;
$S_1$: benzothiofuran;
$N_1O_1$: benzoxazole, benzisoxazole;
$N_1S_1$: benzothiazole;
$N_2$: benzimidazole, indazole; quinoxaline; quinazoline;
$O_2$: benzodioxole;
$N_2O_1$: benzofurazan;
$N_2S_1$: benzothiadiazole;
$N_3$: benzotriazole; and
$N_4$: purine (e.g., adenine, guanine).

"$C_{3-10}$ heterocyclyl" or "heterocyclo": refers to saturated or partially unsaturated monocyclic, bicyclic or polycyclic groups having ring atoms composed of 3 to 10 ring atoms, whether carbon atoms or heteroatoms, of which from 1 to 10 are ring heteroatoms. Suitably, each ring has from 3 to 7 ring atoms and from 1 to 4 ring heteroatoms (e.g., suitably $C_{3-5}$ heterocyclyl refers to a heterocyclyl group having 3 to 5 ring atoms and 1 to 4 heteroatoms as ring members). The ring heteroatoms are independently selected from nitrogen, oxygen, and sulphur.

As with bicyclic cycloalkyl groups, bicyclic heterocyclyl groups may include isolated rings, Spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound.

Examples of monocyclic heterocyclyl groups include, but are not limited to, those derived from:
$N_1$: aziridine, azetidine, pyrrolidine, pyrroline, 2H-pyrrole or 3H-pyrrole, piperidine, dihydropyridine, tetrahydropyridine, azepine;
$O_1$: oxirane, oxetane, tetrahydrofuran, dihydrofuran, tetrahydropyran, dihydropyran, pyran, oxepin;
$S_1$: thiirane, thietane, tetrahydrothiophene, tetrahydrothiopyran, thiepane;
$O_2$: dioxoiane, dioxane, and dioxepane;
$O_3$: trioxane;
$N_2$: imidazoiidine, pyrazolidine, imidazoline, pyrazoline, piperazine:
$N_1O_1$: tetrahydrooxazole, dihydrooxazole, tetrahydroisoxazole, dihydroisoxazole, morpholine, tetrahydrooxazine, dihydrooxazine, oxazine;
$N_1S_1$: thiazoline, thiazolidine, thiomorpholine;
$N_2O_1$: oxadiazine;
$O_1S_1$: oxathiole and oxathiane (thioxane); and
$N_1O_1S_1$: oxathiazine.

Examples of substituted monocyclic heterocyclyl groups include those derived from saccharides, in cyclic form, for example, furanoses, such as arabinofuranose, lyxofuranose, ribofuranose, and xylofuranse, and pyranoses, such as aliopyranose, altropyranose, glucopyranose, mannopyranose, gulopyranose, idopyranose, galactopyranose, and talopyranose.

"$C_{3-10}$ heterocyclylene" refers to a divalent radical derived from a $C_3$-$C_{10}$ heterocyclyl group, e.g. such as a pieridinylene —$O_5H_9N$— group.

"Independently selected" is used in the context of statement that, for example, "each R' and R" is independently selected from H and $C_{1-6}$ alkyl" and means that each instance of the functional group, e.g. R', is selected from the listed options independently of any other instance of R; or R" in the compound. Hence, for example, the first instance of the group R' may be selected as $CH_3$, whereas for the second instance of the R' may be selected as H; and the first instance of R" may be selected as and R" as $CH_2CH_3$.

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-10-risk ratio, and effective for their intended use.

"Pharmaceutically acceptable salts, solvates, tautomers and combinations thereof" means that the compound may be a combination of these options such as being both a tautomer and a pharmaceutically acceptable salt.

"Pharmaceutical composition" refers to the combination of one or more drug substances and one or more excipients.

"Substituted", when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"Optionally substituted" refers to a parent group which may be unsubstituted or which may be substituted with one or more substituents. The statement that an "aryl or heteroaryl group is optionally substituted" indicates that any of the aryl or heteroaryl groups may be optionally substituted with the optional substituents, e.g. a phenyl group may be selected and it may be optionally substituted. Where the parent group contains a heteroatom and is optionally substituted, then the parent group may be optionally substituted on either a carbon atom or a heteroatom provide that the valence requirements are met. Suitably, unless otherwise specified, when optional substituents are present the optional substituted parent group comprises from one to three optional substituents, i.e. 0, 1, 2 or 3 optional substituents may be present. If not otherwise specified, suitably, the optional substituents may be selected from $C_{1-6}$ alkyl, halo and NR'R". In some embodiments, the optional substituents may comprise a —$Y_6$—$(Y_7)_{0-1}$—$(Y_8)_{0-1}$ substituent group.

"Therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things. The "effective amount" includes an amount of the compound of formula (I) and/or (A1) that will elicit a biological or medical response of a subject, for example, the reduction or inhibition of enzyme or protein activity related to a bacterial infection, amelioration of symptoms of a bacterial infection, or the slowing or delaying of progression of a bacterial infection. In some embodiments, the language "effective amount" includes the amount of a compound of formula (I) and/or (A1), that when administered to a subject, is effective to at least partially alleviate, inhibit, and/or ameliorate a bacterial infection and/or reduce or inhibit the bacterial growth, replication or bacterial load of a bacteria in a subject.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

Antibacterial Drug Moiety R

Suitably, the antibacterial drug moiety R is a quinolone antibacterial drug moiety or a tetracycline antibacterial drug moiety.

Repersentative examples of quinolone and tetracycline bacterial drugs are ciprofloxacin and tetracycline shown below. The antibacterial drug moiety may be derived by replacing a group (e.g. such as an H, or a piperazinyl group) with a bond to the rest of the compound of formula (I). The antibacterial drug moiety will include the major fused ring portion of the quinolone or tetracycline drug (i.e. the bicyclic or tetracycli ring structure).

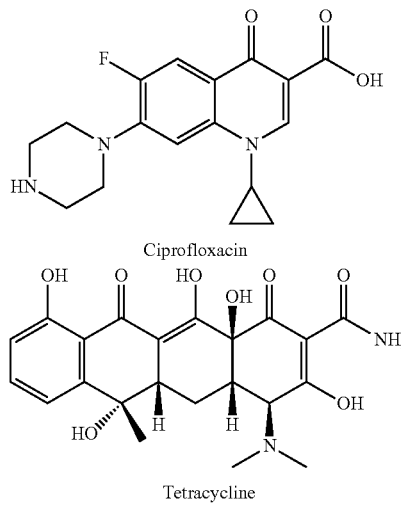

Ciprofloxacin

Tetracycline

Suitably, the antibacterial drug moiety R is a DNA synthesis inhibitor antibacterial drug moiety.

Suitably, the antibacterial drug moiety R is a fluoroquinolone antibacterial drug moiety.

Suitably, the antibacterial drug moiety R is selected from balofloxacin, cinoxacin, ciprofloxacin, clinafloxacin, enoxacin, fleroxacin, gemifloxacin, levofloxacin, lomefloxacin, moxifloxacin, nadifloxacin, nalidixic acid, norfloxacin, ofloxacin, oxolinic acid, pazufloxacin, pefloxacin, pipemidic acid, piromidic acid, prulifloxacin, rosoxacin, rufloxacin, sitafloxacin, sparfloxacin, tosufloxacin, chlortetracycline, demeclocycline, doxycycline, lymecycline, meclocycline, methacycline, minocycline, omadacycline, oxytetracycline, rolitetracycline, sarecycline, tetracycline and tigecycline drug moieties.

More suitably, the antibacterial drug moiety R is a quinolone antibacterial drug moiety selected from balofloxacin, cinoxacin, ciprofloxacin, clinafloxacin, enoxacin, fleroxacin, gemifloxacin, levofloxacin, lomefloxacin, moxifloxacin, nadifloxacin, nalidixic acid, norfloxacin, ofloxacin, oxolinic acid, pazufloxacin, pefloxacin, pipemidic acid, piromidic acid, prulifloxacin, rosoxacin, rufloxacin, sitafloxacin, sparfloxacin and tosufloxacin drug moieties.

These antibacterial drugs have the following structures:

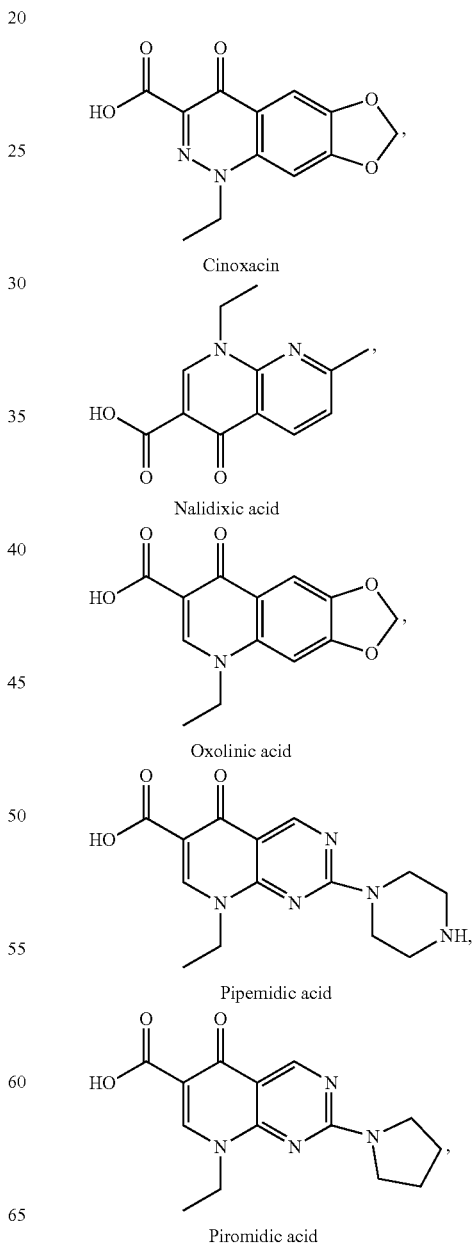

Cinoxacin

Nalidixic acid

Oxolinic acid

Pipemidic acid

Piromidic acid

-continued
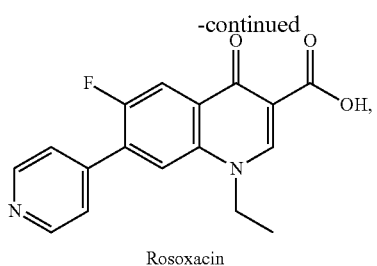
Rosoxacin
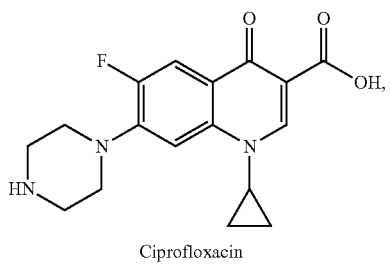
Ciprofloxacin
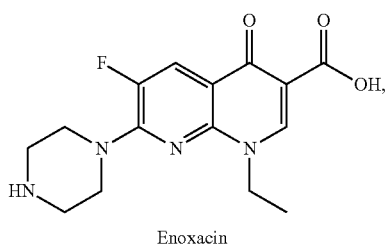
Enoxacin
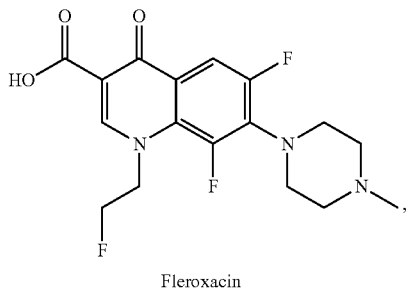
Fleroxacin
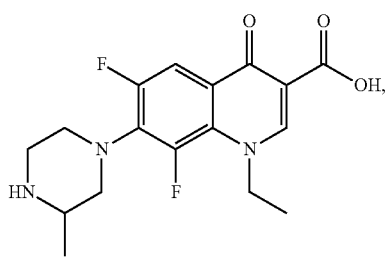
Lomefloxacin
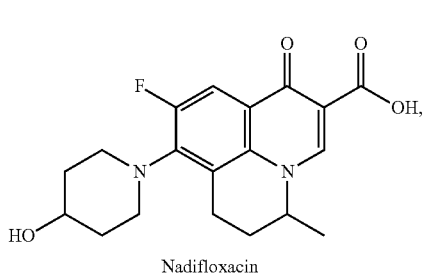
Nadifloxacin
-continued
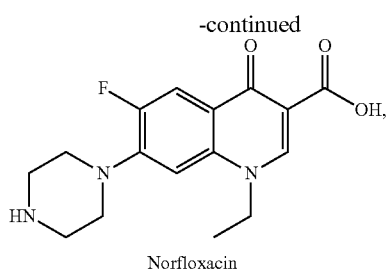
Norfloxacin
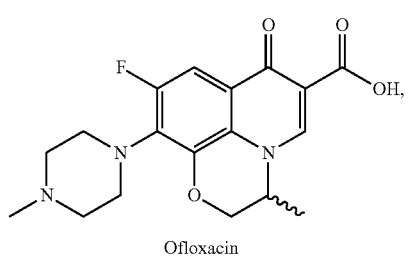
Ofloxacin
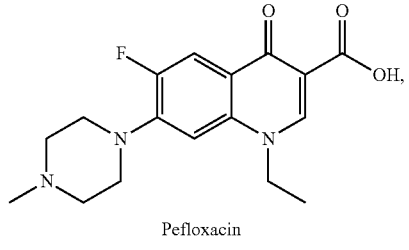
Pefloxacin
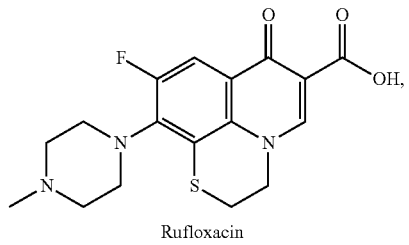
Rufloxacin
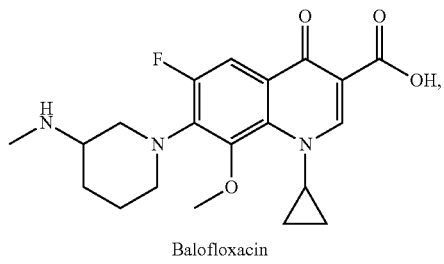
Balofloxacin
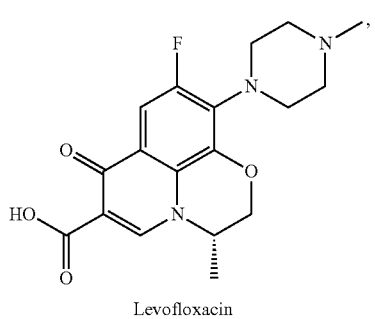
Levofloxacin 19
-continued
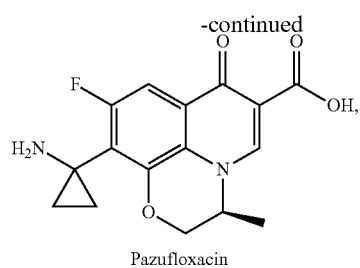
Pazufloxacin
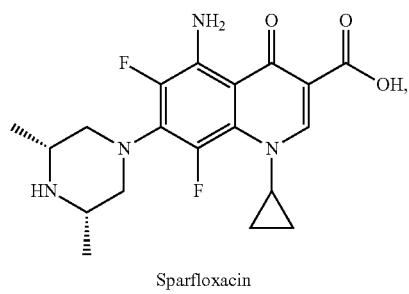
Sparfloxacin
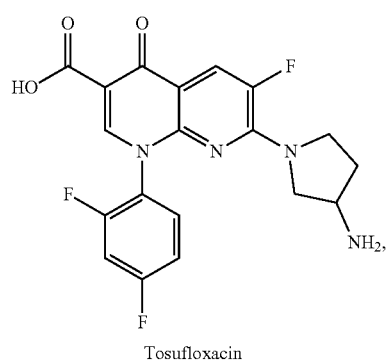
Tosufloxacin
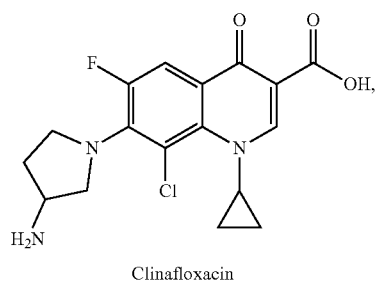
Clinafloxacin
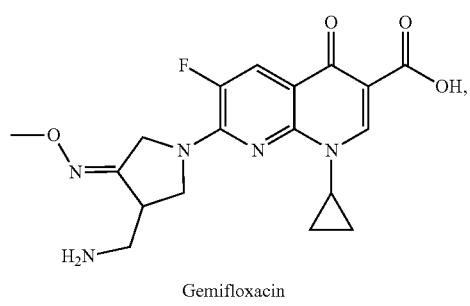
Gemifloxacin
20
-continued
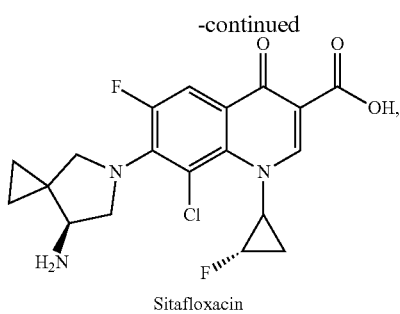
Sitafloxacin
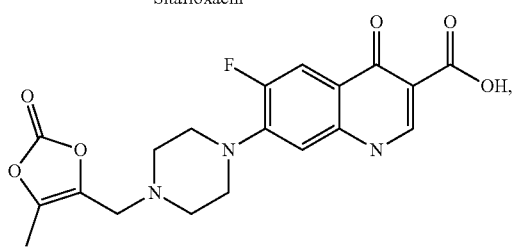
Prulifloxacin
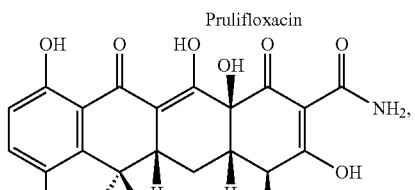
Chlorotetracycline
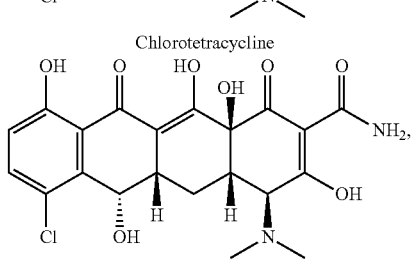
Demeclocycline
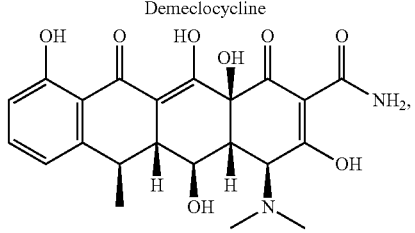
Doxycycline
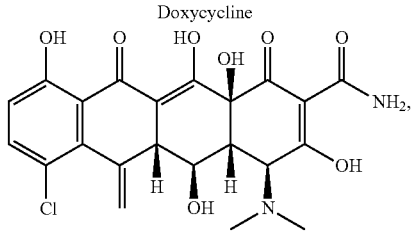
Meclocycline
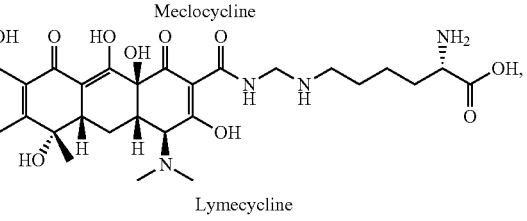
Lymecycline

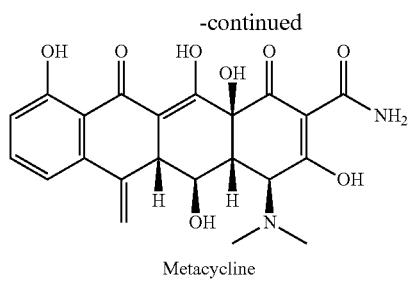
Metacycline

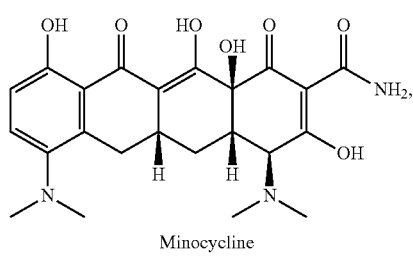
Minocycline

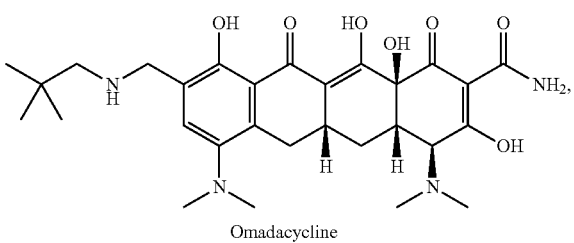
Omadacycline

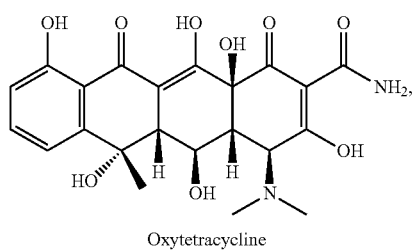
Oxytetracycline

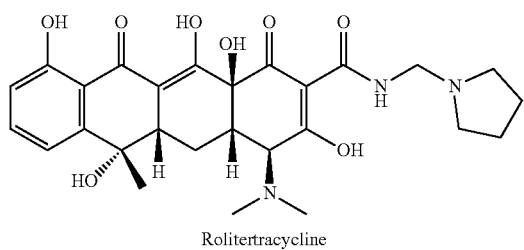
Rolitertracycline

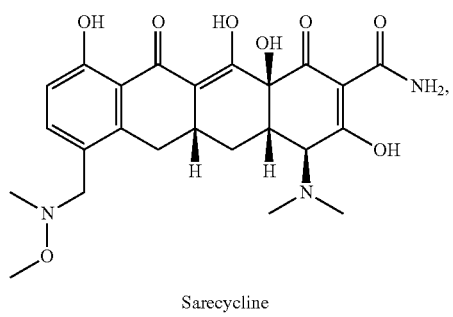
Sarecycline

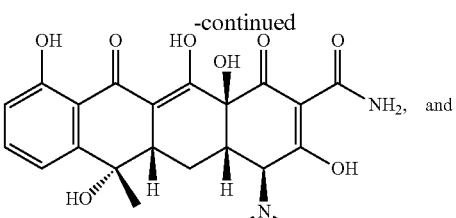
Tetacycline

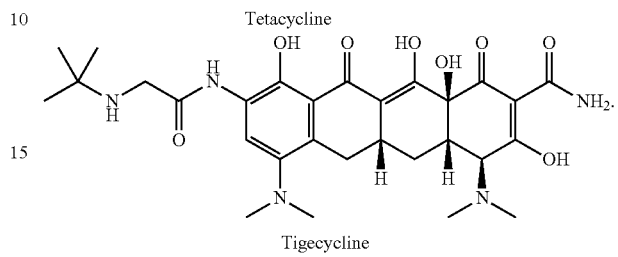
Tigecycline

Suitably, the antibacterial drug moiety R is a fluoroquinolone antibiotic drug moiety selected from balofloxacin, ciprofloxacin, clinafloxacin, enoxacin, fleroxacin, gemifloxacin, levofloxacin, lomefloxacin, moxifloxacin, nadifloxacin, norfloxacin, ofloxacin, pazufloxacin, pefloxacin, prulifloxacin, rufloxacin, sitafloxacin, sparfloxacin and tosufloxacin drug moieties.

More suitably, the antibacterial drug moiety R is a fluoroquinolone antibacterial drug moiety selected from ciprofloxacin, enoxacin, levofloxacin and norfloxacin drug moieties.

Suitably the antibacterial drug moiety comprises an antibacterial drug wherein a hydrogen, a methyl, a halo, a substituted or unsubstituted piperidinyl, a substituted or unsubstituted piperazinyl or a substituted or unsubstituted pyrrolidinyl group has been replaced with a bond to the rest of the compound of formula (I).

Suitably the antibacterial drug moiety comprises a quinolone antibacterial drug wherein a hydrogen, a methyl, a halo, a substituted or unsubstituted piperidinyl, a substituted or unsubstituted piperazinyl, a substituted or unsubstituted pyrrolidinyl group or the substituent on the N-1 nitrogen of the quinolone has been replaced with a bond to the rest of the compound of formula (I).

Thus, for example, for the drug norfloxacin (see below) the N-1 nitrogen has an ethyl group which in the compound of formula (I) may be replaced by a bond to -L-Ar$_1$.

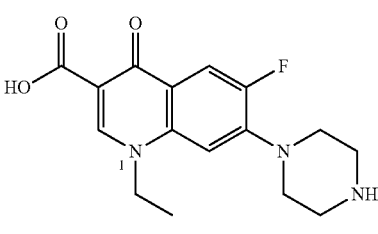
Norfloxacin

Suitably, the antibacterial drug moiety comprises a quinolone antibacterial drug wherein a hydrogen of an amine group, a methyl, a halo, a substituted or unsubstituted piperidinyl, a substituted or unsubstituted piperazinyl, a substituted or unsubstituted pyrrolidinyl group or the substituent on the N-1 nitrogen of the quinolone has been replaced with a bond to the rest of the compound of formula (I).

More suitably, the antibacterial drug moiety comprises a quinolone antibacterial drug wherein a hydrogen or a methyl of an amine group has been replaced with a bond to the rest of the compound of formula (I).

Suitably, the antibacterial drug moiety R has the structure (XI):

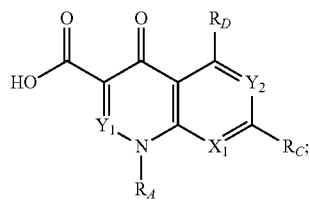

(XI)

wherein $Y_1$ is N or C—H;
  $R_A$ is selected from methyl, ethyl, —CH$_2$—CH$_2$—F, 2,4-difluorophenyl, allyl, vinyl cyclopropyl and flurocyclopropyl, or is a bond to -L-Ar$_1$;
  $X_1$ is selected from N and C—$R_B$;
  $R_B$ is H, halo, OCH$_3$ or a bond to -L-Ar$_1$;
  $Y_1$ is CH or N;
  or either $R_A$ and $R_B$ together with the atoms to which they are attached form a 6-membered ring wherein from $R_A$ to $R_B$ is a —CH(CH$_3$)—CH$_2$—O—, —CH(CH$_3$)—CH$_2$—CH$_2$— or —CH$_2$—CH$_2$—S—, a linking group;
  or $R_A$ to $Y_1$ together with the nitrogen to which they are attached form a 4-membered ring wherein from $R_A$ to $Y_1$ is —CH(CH$_3$)—S—CH$_2$—;
$R_C$ is selected from methyl,

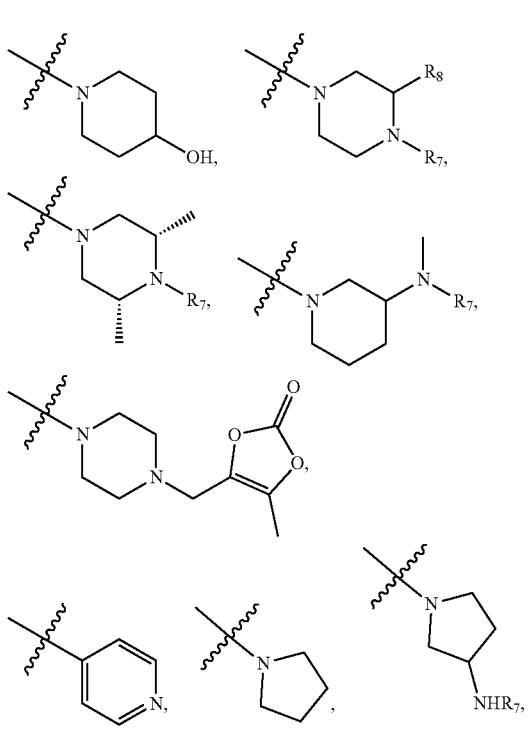

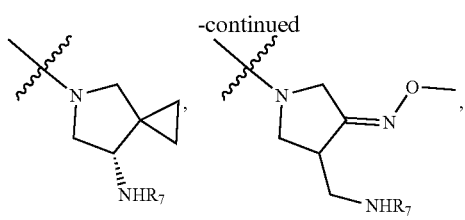

and

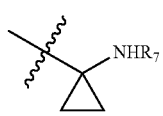

$Y_2$ is selected from N, C—H, and C—F;
$R_D$ is H or NH$_2$;
  or $R_C$ to $Y_2$ together with the carbon to which they are attached form a 5-membered ring wherein from $R_C$ to $Y_2$ is —O—CH$_2$—O—;
$R_7$ is H, CH$_3$ or is a bond to -L-Ar$_1$; and
$R_8$ is selected from H and CH$_3$;
with the proviso that structure (XI) comprises only one bond to -L-Ar$_1$.

The zig-zag line indicates the bond that attaches the $R_C$ fragment to the rest of the compound of formula (XI).

Suitably, the antibacterial drug moiety R has the structure (XII):

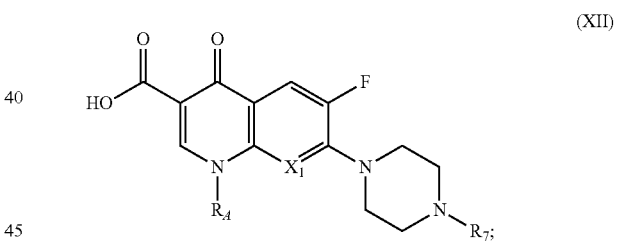

(XII)

$R_A$ is selected from methyl, ethyl, allyl, vinyl, cyclopropyl and a bond to -L-Ar$_1$;
$R_B$ is selected from H, halo, OCH$_3$;
  or $R_A$ and $R_B$ together with the atoms to which they are attached form a 6-membered ring wherein from $R_A$ to $R_B$ is a —CH(CH$_3$)—CH$_2$—O— linking group;
$M_1$ is 0, 1 or 2;
$R_7$ is H, CH$_3$ or a bond to -L-Ar$_1$;
with the proviso that one of $R_A$ or $R_7$ comprises a bond to -L-Ar$_1$, and when $R_A$ is a bond to -L-Ar$_1$ then $R_7$ is H or CH$_3$; and when $R_1$ a bond to -L-Ar$_1$ then $R_A$ is selected from methyl, ethyl, allyl, vinyl and cyclopropyl.

Suitably for (XII) $R_7$ comprises a bond to -L-Ar$_1$, and $R_1$ a bond to -L-Ar$_1$ then $R_A$ is selected from methyl, ethyl, allyl, vinyl and cyclopropyl.

More suitably the antibacterial drug moiety R is selected from;

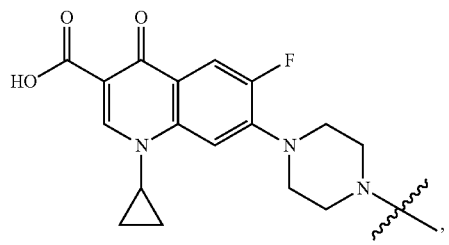
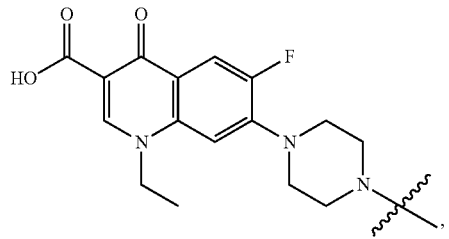
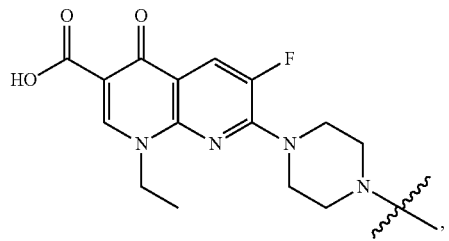
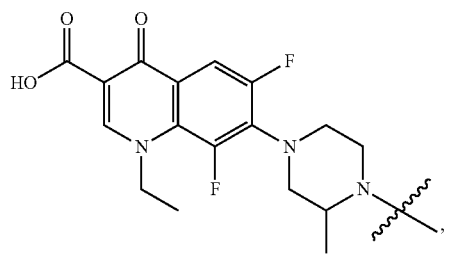
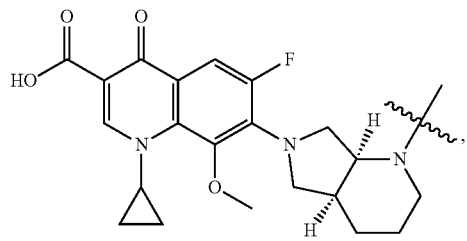
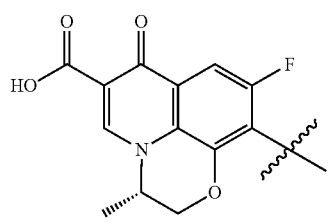
and
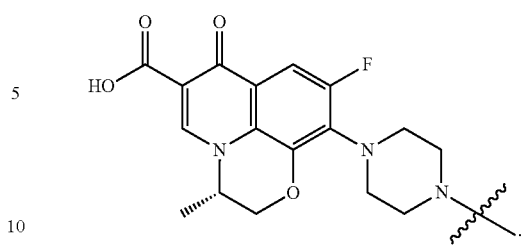
The zig-zag line represents the bond that attached the R group to -L-Ar$_1$ in the compounds of formula (I).
Fluoroquinolone Moiety
The antibiotic compound of formula (A1) and pharmaceutically acceptable salts, solvates, tautomers and combinations thereof, comprises a fluoroquinolone moiety:
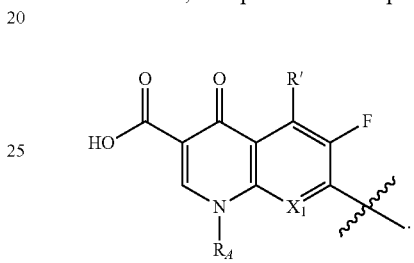
Suitably, the fluoroquinolone moiety is selected from:
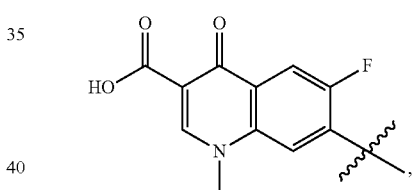
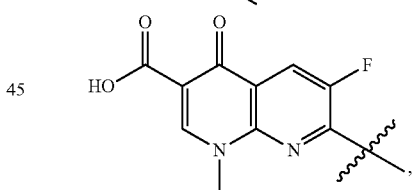
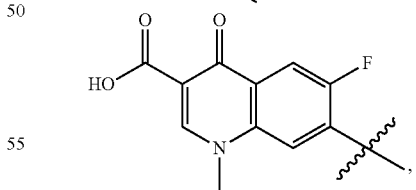
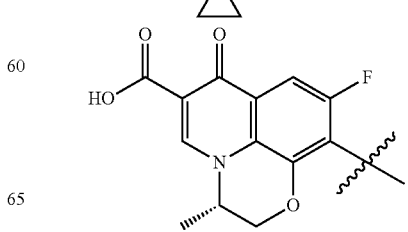

-continued

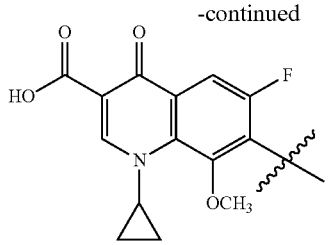

and and

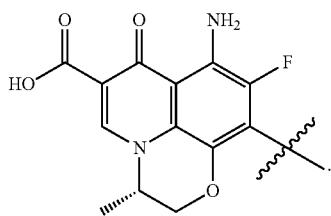 [SMILES: *c1c(F)c(N)c2c(=O)c(C(=O)O)cn3c2c1OC[C@@H]3C]

More suitably, the fluoroquinolone moiety is selected from:

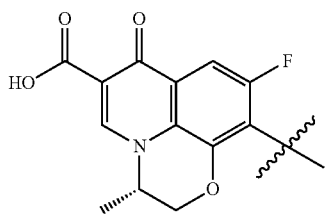 [SMILES: *c1c(F)cc2c(=O)c(C(=O)O)cn3c2c1OC[C@@H]3C]

and

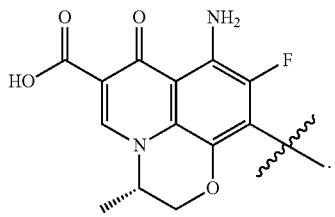 [SMILES: *c1c(F)c(N)c2c(=O)c(C(=O)O)cn3c2c1OC[C@@H]3C]

L

L is an optional linker and in some emboidments is absent.

Where the linker L is unsymmetric, it may be attached in either direction. Hence, the linker —NR'—CH$_2$— may be attached as R—NR'—CH$_2$—Ar$_1$ or as R—CH$_2$—NR'—Ar$_1$.

L is an optional linker selected from —(CH$_2$)$_m$—, —NR'—(CH$_2$)$_x$— or —O—(CH$_2$)$_s$ optionally substituted with a C$_{5-10}$ heterocyclylene or a C$_{3-10}$ carbocyclylene group these carbocyclylene or hetercyclylene groups may be optionally substituted with 1, 2 or 3 groups independently selected from C$_{1-6}$ alkyl groups. Hence, L may be selected as —(CH$_2$)$_m$— optionally substituted with, for example, a C$_6$ piperidinylene group to give -piperidinylene-(CH$_2$)$_m$—. For this group, where m is greater than 1, e.g. 2, then the piperinylene may be substituted either at one end of the alkylene group or within the alkylene group, i.e. —CH$_2$—CH$_2$-piperidinylene- or —CH$_2$-piperidinyl-CH$_2$—. In addition, where the as —(CH$_2$)$_m$— is substituted with a C$_{5-10}$ heterocyclylene or a C$_{3-10}$ carbo-cyclylene group, e.g. a C$_7$ diazepanylene group, and m is selected as 0, then L will consist of the C$_{5-10}$ heterocyclylene or a C$_{3-10}$ carbocyclylene group alone, e.g. L is -diazepanylene-.

Suitably, L is —(CH$_2$)$_m$—, —NR'—(CH$_2$)$_s$— or —O—(CH$_2$)$_s$ optionally substituted with a C$_{5-7}$ heterocyclyl or a C$_{3-10}$ carbocyclyl group these carbocyclyl or hetercyclyl groups may be optionally substituted with 1, 2 or 3 groups independently selected from C$_{1-6}$ alkyl groups.

Suitably, L is —(CH$_2$)$_m$—, —NR'—(CH$_2$)$_s$— or —O—(CH$_2$)$_s$ optionally substituted with a pyrrolidinylene, piperidinylene, piperazinylene, morpholinylene or a dazepanylene group which group may be optionally substituted with 1, 2 or 3 groups independently selected from C$_{1-6}$ alkyl groups.

Suitably, L is-CH$_2$—CH$_2$—CH$_2$—, —CH$_2$—CH$_2$—, —CH$_2$—, —NR'—CH$_2$—CH$_2$—CH$_2$—, —NR'—CH$_2$—CH$_2$—, —NR'—CH$_2$—, —NR'—, —O—CH$_2$—CH$_2$—CH$_2$—, —O—CH$_2$—CH$_2$—, —O—CH$_2$— or —O—, optionally substituted with a pyrrolidinylene, piperidinylene, piperazinylene, morpholinylene or a dazepanylene group which group may be optionally substituted with 1, 2 or 3 groups independently selected from C$_{1-6}$ alkyl groups.

Suitably, L is -(L$_1$)$_n$-.

Suitably, L$_1$ is —(CH$_2$)$_m$—, —NR'—(CH$_2$)$_s$— or —O—(CH$_2$)$_1$— where n is 0 or 1; m is independently 1, 2, 3 or 5; and s is 0, 1, 2, 3, 4 or 5.

More suitably L is a —(CH$_2$)$_m$-linker; wherein m is 0, 1 or 2. Hence, L is selected from a bond attaching R to Ar$_1$, —CH$_2$— and —CH$_2$—CH$_2$—.

More suitably, L is a bond or —CH$_2$—. Most suitably, L is —CH$_2$—.

L$_1$

L$_1$ is —(CH$_2$)$_m$—, —NR'—(CH$_2$)$_s$—, —O—(CH$_2$)$_s$—, —NR'—C(=O)—NR''—, —NR'—C(=O)— or —N=CH—.

Suitably, L$_1$ is —(CH$_2$)$_m$—, —NR'—(CH$_2$)$_s$—, —O—(CH$_2$)$_s$—, —NH—C(=O)—NH—, —NH—C(=O)— or —N=CH—.

More suitably, L$_1$ is —CH$_2$—, —NH—, N(CH$_3$)—, —NH—CH$_2$—, —N(CH$_3$)—CH$_2$—, —O—CH$_2$—, —O—CH$_2$—CH$_2$—, —NH—C(=O)—NH—, —NH—C(=O)— or —N=CH—.

More suitably, L$_1$ is —CH$_2$—, —NH—, N(CH$_3$)—, —NH—CH$_2$—, —NH—C(=O)—NH—, —NH—C(=O)— or —N=CH—.

m

Suitably, m is 1, 2, 3 or 5;

Suitably, m is 0, 1, 2 or 3.

More suitably, m is 0 or 1. Most suitably m is 1.

n

In some embodiments, n is 0. In alternative embodiments, n is 1.

n'

In some embodiments, n' is 0. In alternative embodiments, n' is 1.

k and s

Suitably, each k or s is independently selected from 0, 1, 2 or 3.

Suitably, each k or s is independently selected from 0 or 1.

t

Suitably, each t is independently selected from 0, 1, 2 or 3.

Suitably, each t is independently selected from 0 or 1.

Antibiotic resistance breaker moiety Ar$_1$

The antibiotic resistance breaker moiety $Ar_1$ is an optionally substituted $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, —C(=NR')—NR'R" or —CH$_2$—CH=CH$_2$ group, which means that any of the listed groups, i.e. $C_{6-10}$ aryl, $C_{7-13}$ aralkyl, $C_{5-10}$ heteroaryl, etc. may be optionally substituted.

Suitably, the antibiotic resistance breaker moiety $Ar_1$ comprises an optionally substituted $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, —C(=NR')—NR'R", and —CH$_2$—CH=CH$_2$ group; and the $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl or $C_{4-13}$ carbocyclalkyl is optionally substituted with a substituent group —Y$_6$—(Y$_7$)$_{0-1}$—(Y$_8$)$_{0-1}$, wherein:

each $Y_6$, $Y_7$ and $Y_8$ is independently selected from $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl and $C_{4-13}$ carbocyclalkyl;

the $Ar_1$ group may be optionally substituted with 1, 2, 3, 4, 5 or 6 optional substituents selected from —$C_{1-6}$ alkyl, -halo, —(CH$_2$)$_t$—OR', —(CH$_2$)$_t$—C(=O)—OR', —(CH$_2$)$_t$—NR'R", —NO$_2$, —NR'-(cyclopropyl), -(cyclopropyl), —NR'—(CH$_2$)$_t$—NR'R", —C(=NR')—NR'R", —(CH$_2$)$_t$—NR'—C(=NR')—NR'R", —CH$_2$—CH=CH$_2$, —CH=CH—(C$_{1-6}$ alkyl), —CH=CH—CN, —SO$_2$—NR'R", —SO$_2$NR'—(CH$_2$)$_t$—Ar$_2$ and oxo;

each t is independently 0, 1, 2, 3, 4 or 5;

each $Ar_2$ is independently selected from $C_{5-9}$ heteroaryl; and each R' and R" is independently selected from H and $C_{1-6}$ alkyl.

Hence, the substitutent group —Y$_6$—(Y$_7$)$_{0-1}$—(Y$_8$)$_{0-1}$ may comprise 1, 2 or 3 ring containing units as $Y_7$ and/or $Y_8$ may be present or absent depending on whether the integer 0 or 1 is selected for (Y$_7$)$_{0-1}$ and for —(Y$_8$)$_{0-1}$. Suitably, the substituent groups is —Y$_6$—(Y$_7$)$_{0-1}$.

Suitably, $Ar_1$ is an antibiotic resistance breaker moiety which comprises an optionally substituted $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, —C(=NR')—NR'R", and —CH$_2$—CH=CH$_2$ group; and the $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl or $C_{4-13}$ carbocyclalkyl is optionally substituted with a $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl or a $C_{4-13}$ carbocyclalkyl group; and the $Ar_1$ group may be optionally substituted with 1, 2 or 3 optional substituents selected from —$C_{1-6}$ alkyl, -halo, —(CH$_2$)$_t$—OR', —(CH$_2$)$_t$—C(=O)—OR', —(CH$_2$)$_t$—NR'R", —NR'—(CH$_2$)$_t$—NR'R", —C(=NR')—NR'R", —(CH$_2$)$_t$—NR'—C(=NR')—NR'R", —CH$_2$—CH=CH$_2$, —SO$_2$—NR'R", —SO$_2$NR'—(CH$_2$)$_t$—Ar$_2$ and oxo.

Suitably, $Ar_1$ is an antibiotic resistance breaker moiety which comprises an optionally substituted $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl, $C_{4-13}$ carbocyclalkyl, —C(=NR')—NR'R", and —CH$_2$—CH=CH$_2$; and the $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, $C_{3-10}$ carbocyclyl or $C_{4-13}$ carbocyclalkyl is optionally substituted with a phenyl, a $C_{5-10}$ heteroaryl, a $C_{6-13}$ heteroaralkyl or a $C_{5-10}$ heterocyclyl group; and the $Ar_1$ group may be optionally substituted with 1, 2 or 3 optional substituents selected from —$C_{1-6}$ alkyl, -halo, —(CH$_2$)$_t$—OR', —(CH$_2$)$_t$—C(=O)—OR', —(CH$_2$)$_t$—NR'R", —NR'—(CH$_2$)$_t$—NR'R", —C(=NR')—NR'R", —(CH$_2$)$_t$—NR'—C(=NR')—NR'R", —CH$_2$—CH=CH$_2$, —SO$_2$—NR'R", —SO$_2$NR'—(CH$_2$)$_t$—Ar$_2$ and oxo.

Suitably, the antibiotic resistance breaker moiety $Ar_1$ is selected from a ring structure, —C(=NR')—NR'R" and —CH$_2$—CH=CH$_2$ groups; and the ring structure is selected from 7-azaindolyl; 1,3-benzodioxolyl; benzimidazolyl; benzothiophenyl; cyclopropyl; cyclohexyl; decahydronaphthalenyl; diazepanyl; furanyl, imidazolyl; indolyl; morpholinyl; naphthalenyl; 5,6-dihydronaphthalenyl; 7,8-dihydronaphthalenyl; 5,6,7,8-tetrahydro-naphthalenyl; naphthalenyl; oxadiazolyl; phenyl; piperazinyl; piperidinyl; purinyl; pyrazinyl; pyrazolyl; pyridinyl; pyrimidinyl; pyrimidinonlyl; 6,7-dihydro-5H-pyrrolo[3,4-d]pyrimidin-4-onlyl; pyrrolidinyl; pyrrolyl; quinoxalinyl; quinazolinyl; quinolinyl; quinolinonyl; thiadiazolyl; thiazolyl; thiomorpholinyl; triazabicyclodecenyl; triazinyl; triazoyl; and the ring structure is optionally substituted with a phenyl, a $C_{5-10}$ heteroaryl, a $C_{6-13}$ heteroaralkyl or a $C_{5-10}$ heterocyclyl group; and the $Ar_1$ group may be optionally substituted with 1, 2 or 3 optional substituents selected from —$C_{1-6}$ alkyl, -halo, —(CH$_2$)$_t$—OR', —(CH$_2$)$_t$—C(=O)—OR', —(CH$_2$)$_t$—NR'R", —NO$_2$, —NR'-(cyclopropyl), -(cyclopropyl), —NR'—(CH$_2$)$_t$—NR'R", —C(=NR')—NR'R", —(CH$_2$)$_t$—NR'—C(=NR')—NR'R", —CH$_2$—CH=CH$_2$, —CH=CH—(C$_{1-6}$ alkyl), —CH=CH—CN, —SO$_2$—NR'R", —SO$_2$NR'—(CH$_2$)$_t$—Ar$_2$ and oxo.

The substituents 7-azaindolyl; 6,7-dihydro-5H-pyrrolo[3,4-d]pyrimidin-4-onlyl; and triazabicyclodecenyl have the following structures respectively:

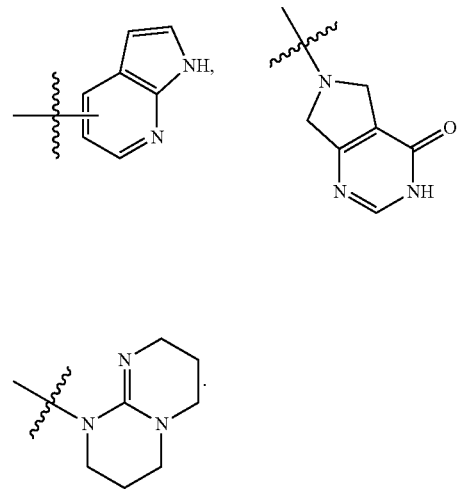

and

The phrase "optionally substituted with a phenyl, a $C_{5-10}$ heteroaryl, a $C_{6-13}$ heteroaralkyl or a $C_{5-10}$ heterocyclyl group" applies to all of the options in the preceding list. Hence, if a 7-azaindolyl group is selected it may be optionally substituted with a phenyl, a $C_{5-10}$ heteroaryl, a $C_{6-13}$ heteroaralkyl, or a $C_{5-10}$ heterocyclyl group. In addition, the feature that "the Art group may be optionally substituted with 1, 2 or 3 optional substituents selected from —$C_{t-6}$ alkyl, -halo, —(CH$_2$)$_t$—OR', —(CH$_2$)$_t$—C(=O)—OR', —(CH$_2$)$_t$—NR'R", —NO$_2$, —NR'-(cyclopropyl), -(cyclopropyl), —NR'—(CH$_2$)$_t$—NR'R", —C(=NR')—NR'R", —(CH$_2$)$_t$—NR'—C(=NR')—NR'R", —CH$_2$—CH=CH$_2$, —CH=CH—(C$_{1-6}$ alkyl), —CH=CH—CN, —SO$_2$—

NR'R", —SO$_2$NR'—(CH$_2$)$_t$—Ar$_2$ and oxo" means that any part of the Ar$_1$ group may be substituted with these optional substituents. For example, if Ar$_1$ comprises a phenyl that is substituted with a C$_5$ heteroaryl pyrrolyl group then the phenyl and/or the pyrrolyl may be optionally substituted with 1, 2 or 3 of the listed optional substitutents. Hence, there may be optional substituents on, e.g. both the phenyl and the pyrrolyl.

Suitably, the antibiotic resistance breaker moiety Ar$_1$ is selected from 7-azaindolyl; 1,3-benzodioxolyl; benzimidazolyl; benzothiophenyl; cyclopropyl; cyclohexyl; decahydronaphthalenyl; diazepanyl; furanyl, indolyl; morpholinyl; naphthalenyl; 5,6,7,8-tetrahydronaphthalenyl; naphthalenyl; phenyl; piperazinyl; piperidinyl; purinyl; pyridinyl; pyrimidinyl; pyrimidinonlyl; 6,7-dihydro-5H-pyrrolo[3,4-d]pyrimidin-4-onlyl; pyrrolidinyl; pyrrolyl; quinoxalinyl; quinazolinyl; quinolinyl; quinolinonyl; thiomorpholinyl; triazabicyclodecenyl; triazinyl; —C(=NR')—NR'R" and —CH$_2$—CH=CH$_2$ groups optionally substituted with a furanyl, phenyl, piperazinyl, pyrrolyl, imidazolyl, naphthalenyl, oxazoyl, oxadiazolyl, pyrazinyl, pyrazolyl, pyrimidinyl, pyrazolyl, pyridinyl, quinoxalinyl, quinazolinyl, thiadiazolyl, thiazolyl, morpholinyl, piperazinyl, piperidinyl, thiomorpholinyl, triazoyl or a triazinyl; and the Ar$_1$ group may be optionally substituted with 1, 2 or 3 optional substituents selected from —C$_{1-6}$ alkyl, -halo, —(CH$_2$)$_t$—OR', —(CH$_2$)$_t$—C(=O)—OR', —(CH$_2$)$_t$—NR'R", —NO$_2$, —NR'-(cyclopropyl), -(cyclopropyl), —NR'—(CH$_2$)$_t$—NR'R", —C(=NR')—NR'R", —(CH$_2$)$_t$—NR'—C(=NR')—NR'R", —CH$_2$—CH=CH$_2$, —CH=CH—(C$_{1-6}$ alkyl), —CH=CH—CN, —SO$_2$—NR'R", —SO$_2$NR'—(CH$_2$)$_t$—Ar$_2$ and oxo.

Suitably, the antibiotic resistance breaker moiety Ar$_1$ is selected from 7-azaindolyl; 1,3-benzodioxolyl; benzimidazolyl; benzothiophenyl; cyclopropyl; cyclohexyl; decahydronaphthalenyl; diazepanyl; imidazolyl; indolyl; morpholinyl; naphthalenyl; 5,6-dihydronaphthalenyl; 7,8-dihydronaphthalenyl; 5,6,7,8-tetrahydro-naphthalenyl; naphthalenyl; oxadiazolyl; phenyl; piperazinyl; piperidinyl; purinyl; pyrazinyl; pyrazolyl; pyridinyl; pyrimidinyl; pyrimidinonlyl; 6,7-dihydro-5H-pyrrolo[3,4-d]pyrimidin-4-onlyl; pyrrolidinyl; pyrrolyl; quinolinyl; quinolinonyl; thiadiazolyl; thiazolyl; thiomorpholinyl; triazabicyclodecenyl and triazinyl groups optionally substituted with a phenyl, a C$_{5-10}$ heteroaryl or a C$_{5-10}$ heterocyclyl group; and the Ar$_1$ group may be optionally substituted with 1, 2 or 3 optional substituents selected from —C$_{1-6}$ alkyl, -halo, —(CH$_2$)$_t$—OR', —(CH$_2$)$_t$—C(=O)—OR', —(CH$_2$)$_t$—NR'R", —NR'—(CH$_2$)$_t$—NR'R", —C(=NR')—NR'R", —(CH$_2$)$_t$—NR'—C(=NR')—NR'R", —CH$_2$—CH=CH$_2$, —SO$_2$—NR'R", —SO$_2$NR'—(CH$_2$)$_t$—Ar$_2$ and oxo.

Suitably, the antibiotic resistance breaker moiety Ar$_1$ is selected from 7-azaindolyl; 1,3-benzodioxolyl; benzimidazolyl; benzothiophenyl; cyclopropyl; cyclohexyl; decahydronaphthalenyl; diazepanyl; imidazolyl; indolyl; morpholinyl; naphthalenyl; 5,6-dihydronaphthalenyl; 7,8-dihydronaphthalenyl; 5,6,7,8-tetrahydro-naphthalenyl; naphthalenyl; oxadiazolyl; phenyl; piperazinyl; piperidinyl; purinyl; pyrazinyl; pyrazolyl; pyridinyl; pyrimidinyl; pyrimidinonlyl; 6,7-dihydro-5H-pyrrolo[3,4-d]pyrimidin-4-onlyl; pyrrolidinyl; pyrrolyl; quinolinyl; quinolinonyl; thiadiazolyl; thiazolyl; thiomorpholinyl; triazabicyclodecenyl and triazinyl groups optionally substituted with a phenyl, a C$_{5-10}$ heteroaryl or a C$_{5-10}$ heterocyclyl group; and the Ar$_1$ group may be optionally substituted with 1, 2 or 3 optional substituents selected from —C$_{1-6}$ alkyl, -halo, —(CH$_2$)$_t$—OR', —(CH$_2$)$_t$—C(=O)—OR', —(CH$_2$)$_t$—NR'R", —NR'—(CH$_2$)$_t$—NR'R", —C(=NR')—NR'R", —(CH$_2$)$_t$—NR'—C(=NR')—NR'R", —CH$_2$—CH=CH$_2$, —SO$_2$—NR'R", —SO$_2$NR'—(CH$_2$)$_t$—Ar$_2$ and oxo.

More suitably, the antibiotic resistance breaker moiety Ar$_1$ is selected from diazepanyl; naphthalenyl; phenyl; piperazinyl; piperidinyl; pyrimidinyl; pyrimidinonlyl; pyrrolidinyl; quinolinyl and quinolinonyl groups optionally substituted with a phenyl, pyrrolyl, imidazolyl, oxadiazolyl, pyrazinyl, pyrazolyl, thiadiazolyl, thiazolyl, morpholinyl, piperazinyl, piperidinyl or a thiomorpholinyl; and the Ar$_1$ group may be optionally substituted with 1, 2 or 3 optional substituents selected from —C$_{1-6}$ alkyl, -halo, —(CH$_2$)$_t$—OR', —(CH$_2$)$_t$—C(=O)—OR', —(CH$_2$)$_t$—NR'R", —NR'—(CH$_2$)$_t$—NR'R", —C(=NR')—NR'R", —(CH$_2$)$_t$—NR'—C(=NR')—NR'R", —CH$_2$—CH=CH$_2$, —SO$_2$—NR'R", —SO$_2$NR'—(CH$_2$)$_t$—Ar$_2$ and oxo.

In some embodiments, more suitably, the antibiotic resistance breaker moiety Ar$_1$ is a ring structure selected from cyclopropyl; furanyl, imidazolyl; morpholinyl; naphthalenyl; oxazoyl; oxadiazolyl; piperazinyl; pyrazinyl; pyrazolyl; pyridinyl; pyrimidinyl; pyrrolyl; quinoxalinyl; quinazolinyl; thiadiazolyl; thiazolyl; thiomorpholinyl; triazinyl; triazoyl; and the ring structure is optionally substituted with 1, 2 or 3 optional substituents selected from —C$_{1-6}$ alkyl, -halo, —(CH$_2$)$_t$—OR', —(CH$_2$)$_t$—C(=O)—OR', —(CH$_2$)$_t$—NR'R", —NO$_2$, —NR'-(cyclopropyl), -(cyclopropyl), —NR—(CH$_2$)$_t$—NR'R", —C(=NR')—NR'R", —(CH$_2$)$_t$—NR'—C(=NR')—NR'R", —CH$_2$—CH=CH$_2$, —CH=CH—(C$_{1-6}$ alkyl), —CH=CH—CN, —SO$_2$—NR'R", —SO$_2$NR'—(CH$_2$)$_t$—Ar$_2$ and oxo.

In some embodiments, more suitably, the antibiotic resistance breaker moiety Ar$_1$ is a ring structure selected from cyclopropyl; furanyl, imidazolyl; morpholinyl; naphthalenyl; oxazoyl; oxadiazolyl; piperazinyl; pyrazinyl; pyrazolyl; pyridinyl; pyrimidinyl; pyrrolyl; quinoxalinyl; quinazolinyl; thiadiazolyl; thiazolyl; thiomorpholinyl; triazinyl; triazoyl; and the ring structure is optionally substituted with 1, 2 or 3 optional substituents selected from —C$_{1-6}$ alkyl, -halo, —(CH$_2$)$_t$—OR', —(CH$_2$)$_t$—C(=O)—OR', oxo, —(CH$_2$)$_t$—NR'R", —NO$_2$, —NR'-(cyclopropyl), -(cyclopropyl), —NR'—(CH$_2$)$_t$—NR'R", —C(=NR')—NR'R", —(CH$_2$)$_t$NR'—C(=NR')—NR'R", —CH$_2$—CH=CH$_2$, —CH=CH—C$_{1-6}$ alkyl, —CH=CH—CN, —SO$_2$—NR'R" and —SO$_2$NR'—(CH$_2$)$_t$—Ar$_2$.

In some embodiments, suitably, the antibiotic resistance breaker moiety Ar$_1$ comprises an optionally substituted aryl or heteroaryl group.

Suitably, after administration of the compound of formula (I) and/or (A1) and pharmaceutically acceptable salts, solvates, tautomers and combinations thereof to a bacterial infection the antibiotic resistance breaker moiety reduces or prevents efflux. Hence, the antibiotic resistance breaker moiety reduces or prevents efflux of the compound of formula (I) and/or (A1) as compared to the parent antibacterial drug that is used as the antibacterial drug moiety.

Antibiotic resistance breaker moieties have been identified which when covalent linked, directly or indirectly to an antibacterial drug moiety interact with the molecular machinery of the efflux pumps to reduce or prevent the efflux from the resistant bacteria, making the pathogen susceptible to the antibiotic.

Suitably, after administration of the compound of formula (I) and/or (A1) and pharmaceutically acceptable salts, solvates, tautomers and combinations thereof to a bacterial infection the antibiotic resistance breaker moiety interacts with residues of a bacterial efflux pump to reduce or prevent efflux.

Suitably, after administration of the compound of formula (I) and/or (A1) and pharmaceutically acceptable salts, solvates, tautomers and combinations thereof to a bacterial infection the antibiotic resistance breaker moiety interacts with the efflux pump inhibitor domain of a bacterial efflux pump to reduce or prevent efflux.

Suitably, after administration of the compound of formula (I) and/or (A1) and pharmaceutically acceptable salts, solvates, tautomers and combinations thereof to a bacterial infection the antibiotic resistance breaker moiety interacts with residues of a major facilitator superfamily (MFS) bacterial efflux pump, or with residues of a resistance-nodulation-division (RND) superfamily bacterial efflux pump, to reduce or prevent efflux.

Suitably, after administration of the compound of formula (I) and/or (A1) and pharmaceutically acceptable salts, solvates, tautomers and combinations thereof to a bacterial infection the antibiotic resistance breaker moiety interacts with the efflux pump inhibitor domain of a major facilitator superfamily (MFS) bacterial efflux pump, or with the efflux pump inhibitor domain of a resistance-nodulation-division (RND) superfamily bacterial efflux pump, to reduce or prevent efflux.

Suitably, after administration of the compound of formula (I) and/or (A1) and pharmaceutically acceptable salts, solvates, tautomers and combinations thereof to a bacterial infection the antibiotic resistance breaker moiety interacts with the efflux pump inhibitor domain of a bacterial efflux pump selected from NorA, AdeB and MexB efflux pumps to reduce or prevent efflux.

Suitably, the antibiotic resistance breaker moiety $Ar_1$ has a molecular weight of 200 or less.

Suitably, the antibiotic resistance breaker moiety $Ar_1$ has a molecular weight of from 75 to 200. Suitably, the antibiotic resistance breaker moiety $Ar_1$ has a molecular weight of from 75 to 190; has a molecular weight of from 75 to 180; has a molecular weight of from 75 to 170; has a molecular weight of from 75 to 165.

Suitably, the antibiotic resistance breaker moiety $Ar_1$ is a hydrophobic moiety.

Suitably, the antibiotic resistance breaker moiety $Ar_1$ is non-toxic.

Suitably, the antibiotic resistance breaker moiety $Ar_1$ comprises an optionally substituted aryl or heteroaryl group.

Suitably, the antibiotic resistance breaker moiety $Ar_1$ comprises an optionally substituted $C_{6-10}$ aryl or a $C_{5-10}$ ring heteroaryl group.

In some embodiments, suitably, the antibiotic resistance breaker moiety $Ar_1$ is selected from phenyl, pyrimidinyl, naphthalenyl, 5,6-dihydronaphthalenyl, 7,8-dihydronaphthalenyl, 5,6,7,8-tetrahydro-naphthalenyl and benzothiophenyl; and these groups are optionally substituted with a phenyl or a $C_5$ heteroaryl group; and the $Ar_1$ group may be optionally substituted with 1, 2 or 3 optional substituents selected from $C_{1-6}$ alkyl, halo and NR'R"; and each R' and R" is independently selected from H and $C_{1-6}$ alkyl.

Suitably, the $C_5$ heteroaryl group may be selected from optionally substituted pyrrolyl, pyrazolyl, 1,2,3-thiazolyl and 1,2,4-oxazolyl. More suitably, the $C_5$ heteroaryl group may be selected from optionally substituted pyrrolyl and 1,2,3-thiazolyl.

In some embodiments, suitably, the antibiotic resistance breaker moiety $Ar_1$ is selected from phenyl, pyrimidinyl, naphthalenyl, 5,6,7,8-tetrahydronaphthalenyl and benzothiophenyl; and these groups are optionally substituted with a phenyl or a $C_5$ heteroaryl group; and the $Ar_1$ group may be optionally substituted with 1, 2 or 3 optional substituents selected from $C_{1-6}$ alkyl, halo, $-(CH_2)_t-OR'$ and $-(CH_2)_t-NR'R"$; and each R' and R" is independently selected from H and $C_{1-6}$ alkyl.

In some embodiments, suitably, the antibiotic resistance breaker moiety $Ar_1$ is an optionally substituted phenyl, biphenyl, pyrimidinyl, naphthalenyl and 5,6,7,8-tetrahydronaphthalenyl; and the Ar1 group may be optionally substituted with 1, 2 or 3 optional substituents selected from $C_{1-6}$ alkyl, halo and NR'R"; and each R' and R" is independently selected from H and $C_{1-6}$ alkyl.

Suitably, the antibiotic resistance breaker moiety Ar1 group comprises 0, 1, 2 or 3 optional substituents selected from $-CH_3$, $-CH_2-CH_3$, $-CH_2-CH_2-CH_3$, $-CH_2-C(CH_3)_2$, F, Br, Cl, I, $-OH$, $-O-CH_3$, $-O-CH_2-CH_3$, $-CH_2-OH$, $-CH_2-O-CH_3$, $-CH_2-CH_2-OH$, $-CH_2-CH_2-O-CH_3$, $-NH_2$, $-NH(CH_3)$, $-N(CH_3)_2$, $-CH_2-NH_2$, $-CH_2-N(CH_3)_2$, $-SO_2-NH_2$, $-SO_2-N(CH_3)_2$, $-NH-CH_2-CH_2-NH_2$, $-NH-CH_2-CH_2-N(CH_3)_2$, oxo, $-SO_2-N(CH_3)_2$, $-SO_2-N(CH_2CH_3)_2$ and

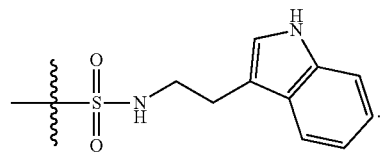 [SMILES: *S(=O)(=O)NCCc1c[nH]c2ccccc12]

Suitably, the antibiotic resistance breaker moiety $Ar_1$ comprises 0, 1 or 2 optional substituents selected from $C_{1-6}$ alkyl, halo, $-(CH_2)_t-OR'$, $-NO_2$ and $-(CH_2)_t-NR'R"$.

In one embodiment, more suitably, the antibiotic resistance breaker moiety $Ar_1$ consists of no optional substituents'.

More suitably, $Ar_1$ is selected from:

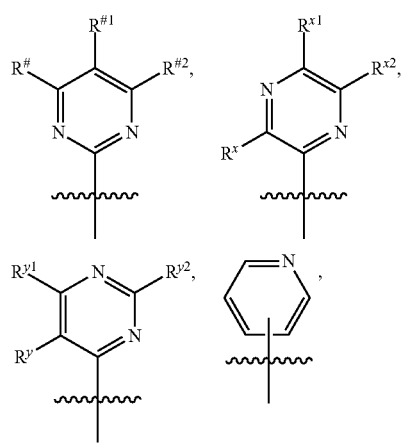

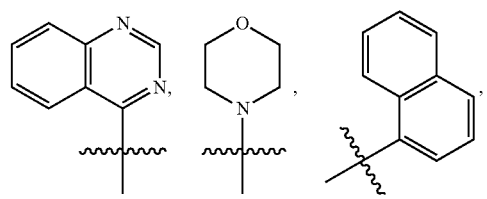

-continued
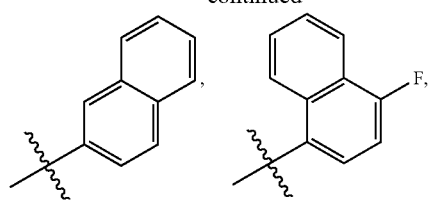
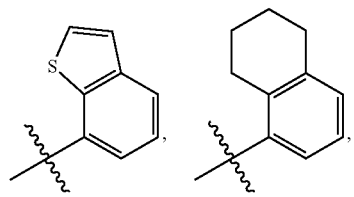
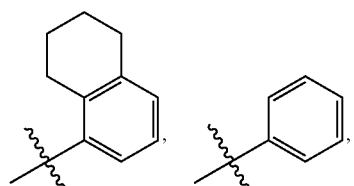
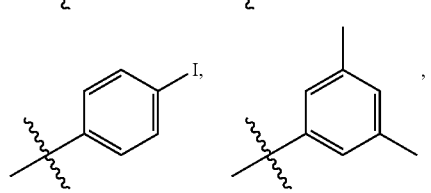
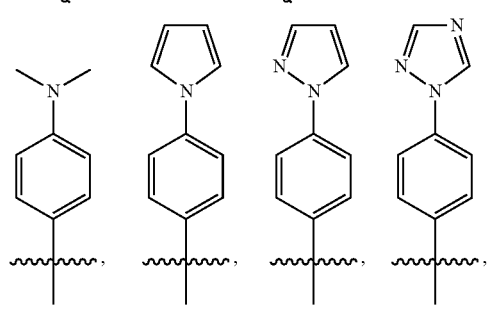
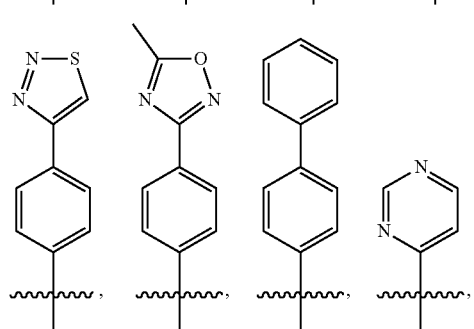
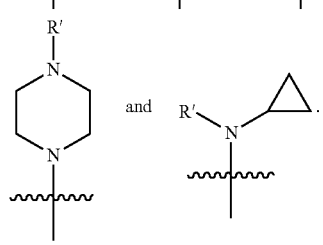
In some aspects, more suitably, Ar$_1$ is selected from:
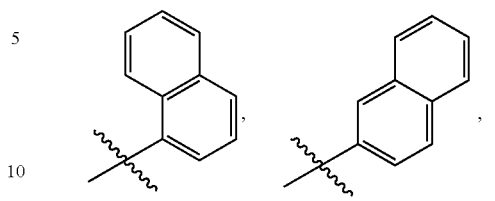
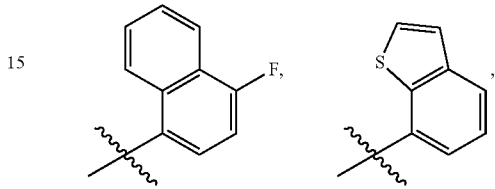
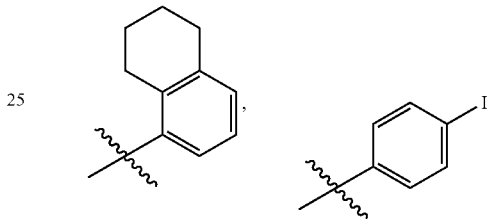
and
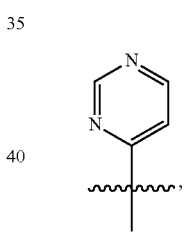
In some aspect, more suitably, Ar$_1$ is selected from:
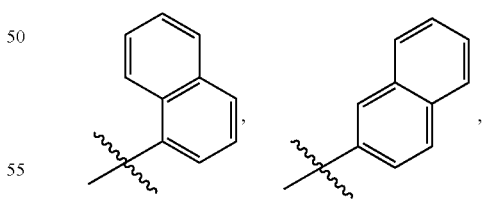
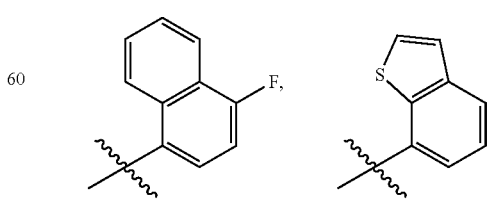
and

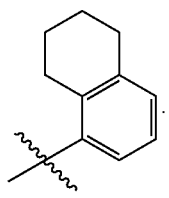
In some aspect, more suitably, Ar₁ is selected from:
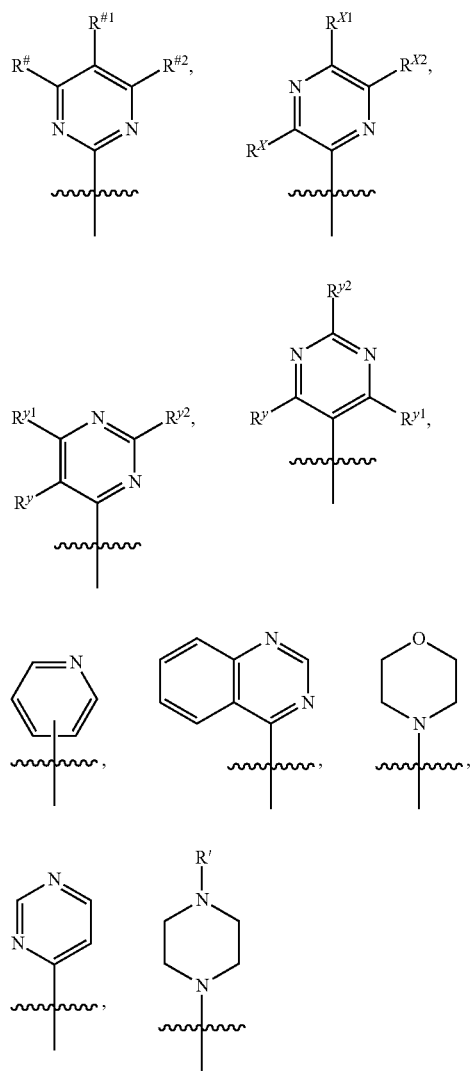
and
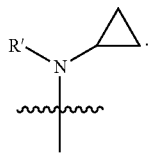
-L-Ar₁
Suitably, the -L-Ar₁ group is selected from
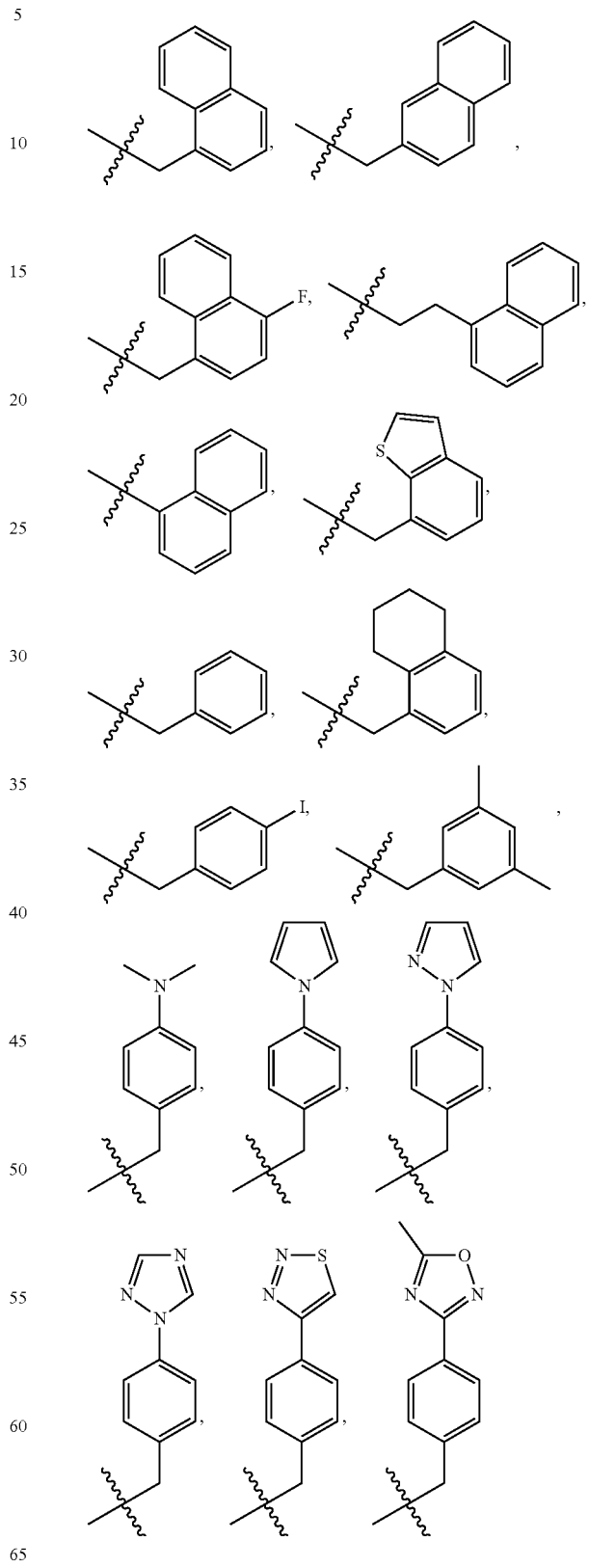
and

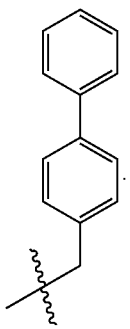 [SMILES: *Cc1ccc(-c2ccccc2)cc1]

Suitable Structures

In some aspects for the antibiotic compound of formula (A1), $Z_1$ is N and X* is absent; R* is H; $Z_1$ is N and X* is absent; $L_1$ is —(CH$_2$)$_m$—, —NR'—(CH$_2$)$_s$— or —O—(CH$_2$)$_1$—; R'$_1$ is H or C$_{1-6}$ alkyl; and the Ar$_1$ group is optionally substituted with 1, 2 or 3 optional substituents selected from —C$_{1-6}$ alkyl, -halo, —(CH$_2$)$_t$—OR', —(CH$_2$)$_t$—C(=O)—OR', oxo, —(CH$_2$)$_t$—NR'R", —NR'—(CH$_2$)$_t$—NR'R", —C(=NR')—NR'R", —(CH$_2$)$_t$—NR'—C(=NR')—NR'R", —CH$_2$—CH=CH$_2$, —SO$_2$—NR'R" and —SO$_2$NR'—(CH$_2$)$_t$—Ar$_2$.

Suitably, the antibiotic compound of formula (A1), is selected from a compound of formula (A2):

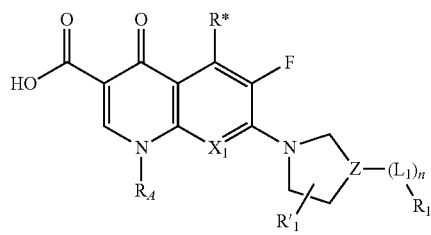

(A2)

and pharmaceutically acceptable salts, solvates, tautomers and combinations thereof.

Suitably, the antibiotic compound of formula (A1), is selected from a compound of formula (A3):

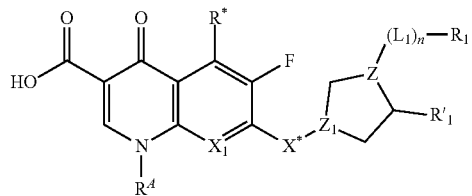

(A3)

and pharmaceutically acceptable salts, solvates, tautomers and combinations thereof.

More suitably, the antibiotic compound of formula (A1), is selected from a compound of formula (A4):

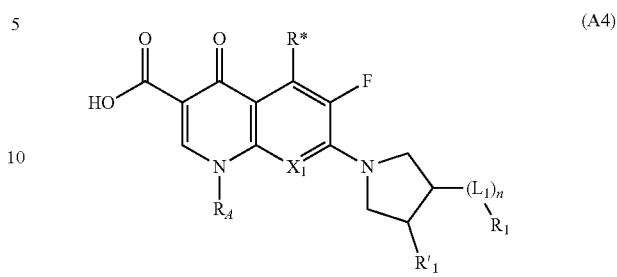

(A4)

and pharmaceutically acceptable salts, solvates, tautomers and combinations thereof.

The compound of formula (A4) may also be drawn as a compound of formula (II)

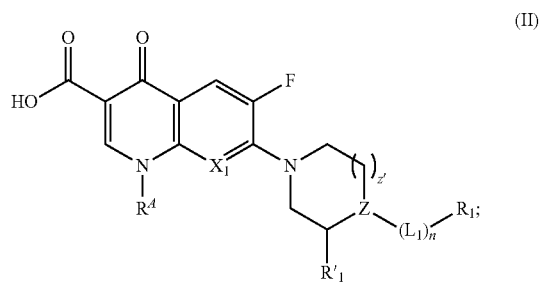

(II)

and pharmaceutically acceptable salts, solvates, tautomers and combinations thereof, wherein Z' is 0 and R* is H.

More suitably, the antibiotic compound of formula (A1), is selected from a compound of formula (A5) or formula (A6):

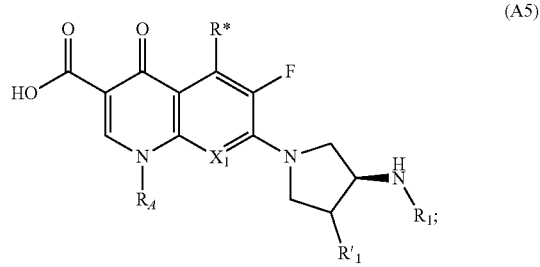

(A5)

or

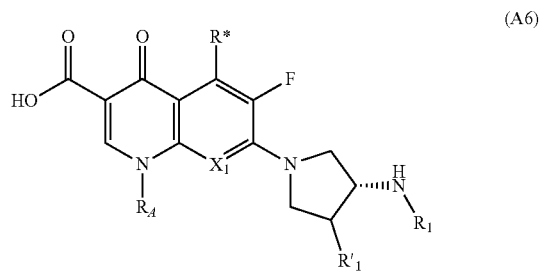

(A6)

and pharmaceutically acceptable salts, solvates, tautomers and combinations thereof.

Suitably, the antibiotic compound of formula (A1), is selected from a compound of formula (A7):
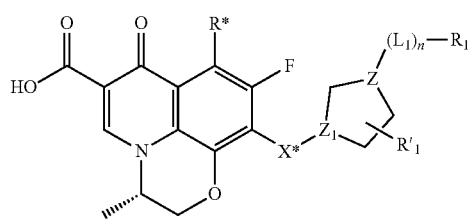
(A7)
and pharmaceutically acceptable salts, solvates, tautomers and combinations thereof.
More suitably, the antibiotic compound of formula (A1) is selected from:
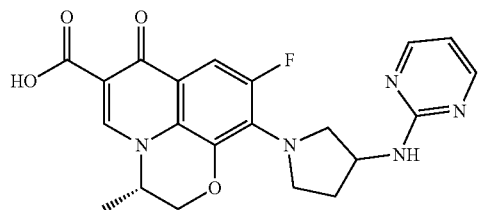,
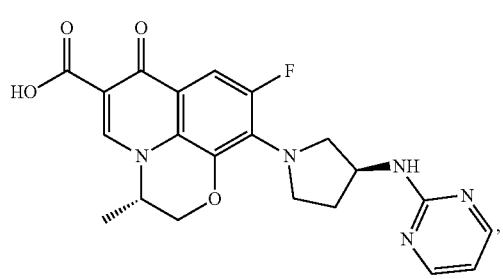,
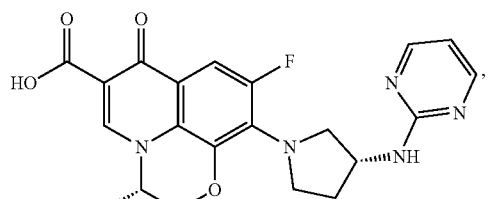,
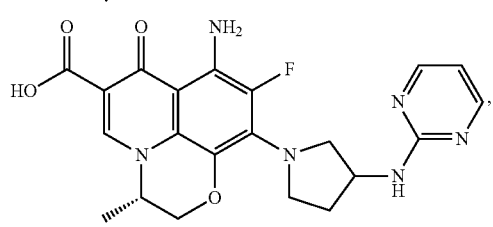,
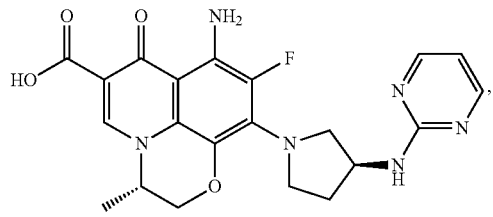,
-continued
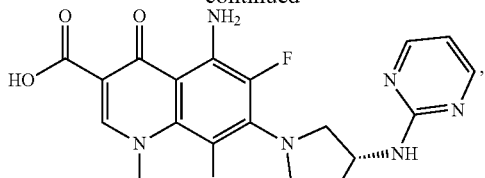,
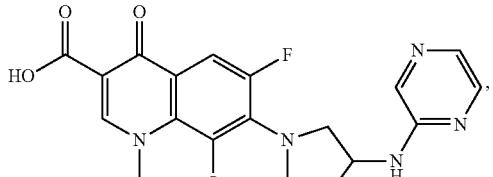,
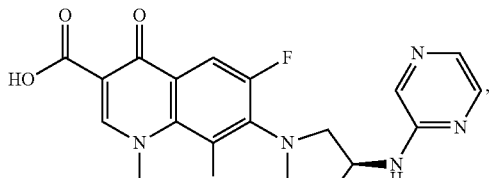,
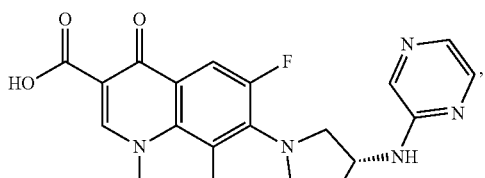,
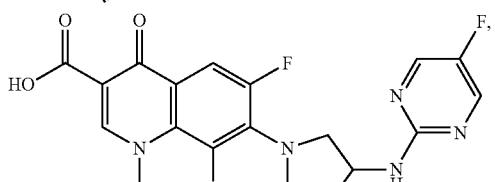,
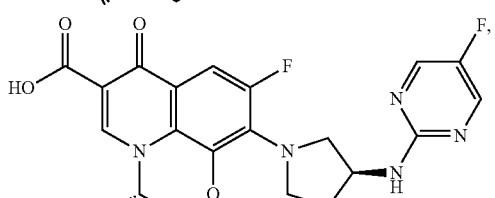,
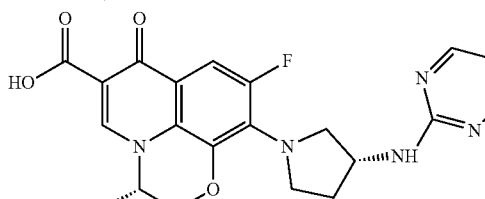,
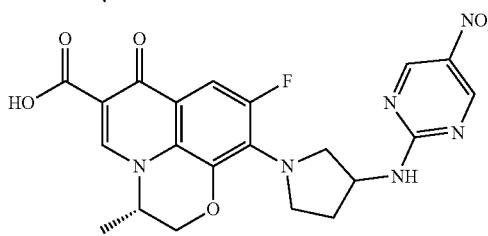,

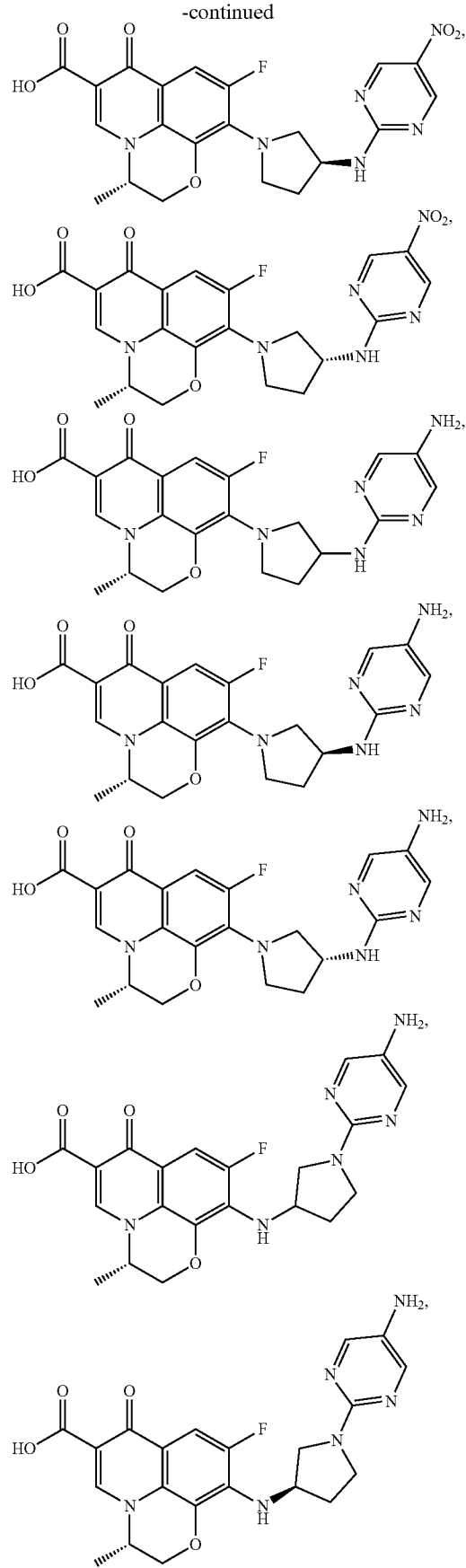
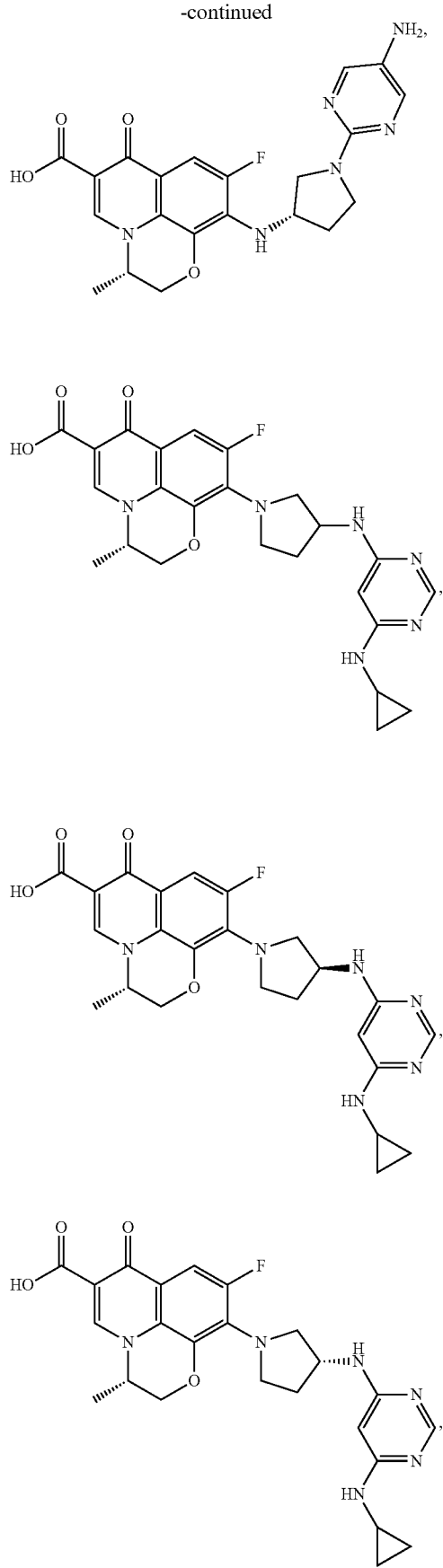

45
-continued
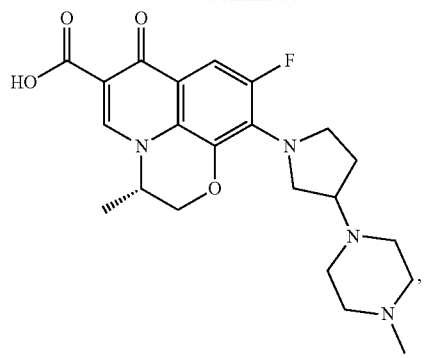
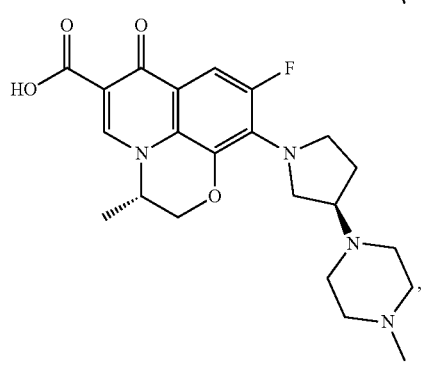
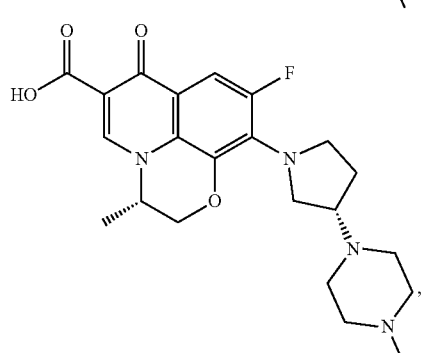
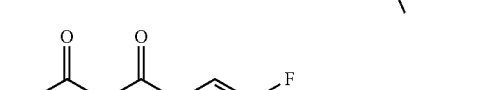
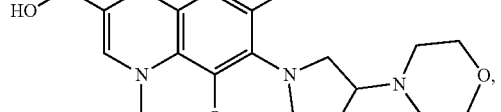
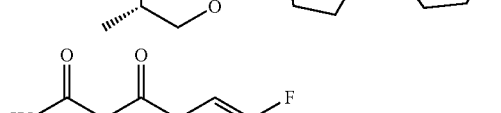
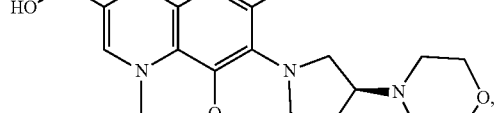
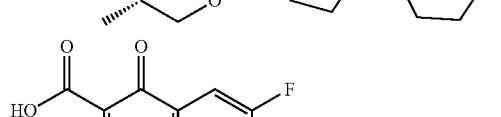
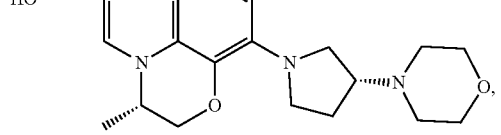
46
-continued
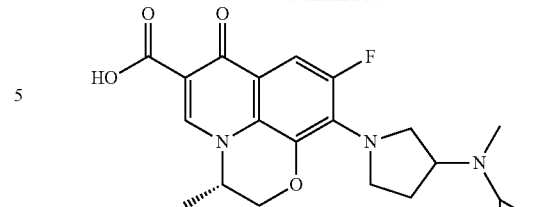
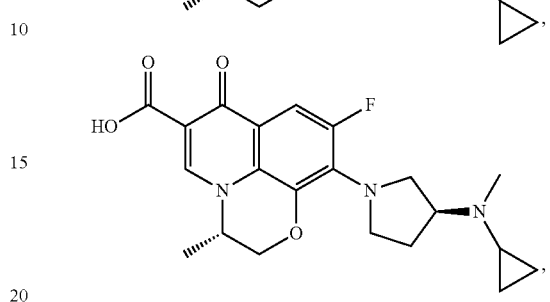
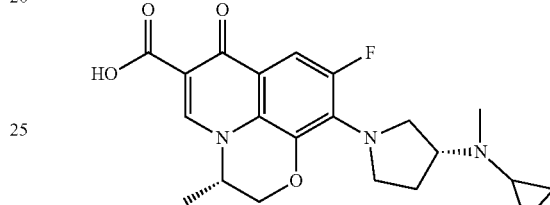
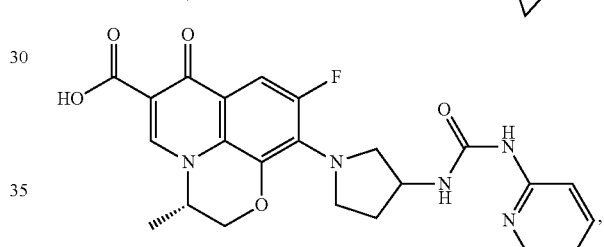
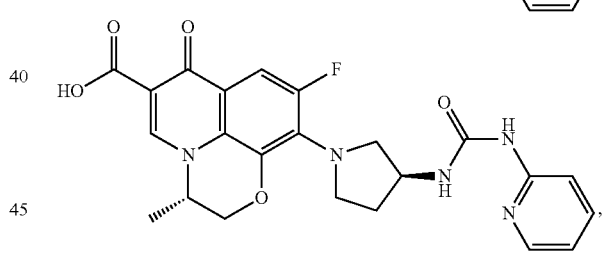
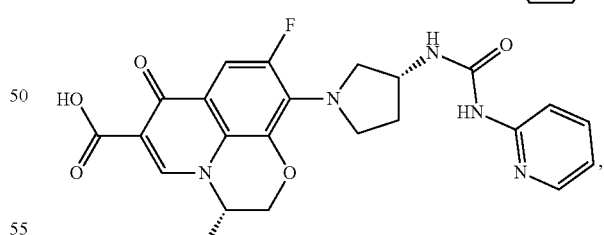
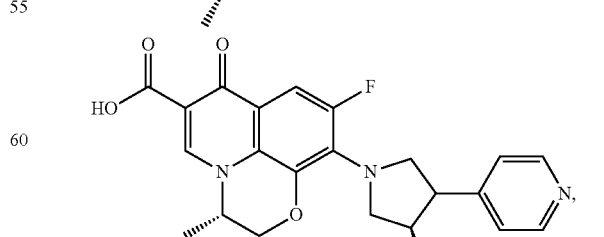

47
-continued
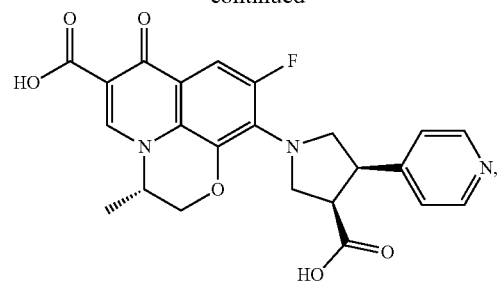
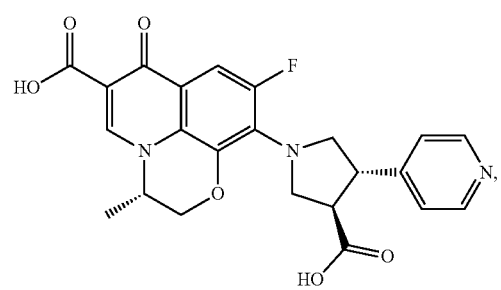
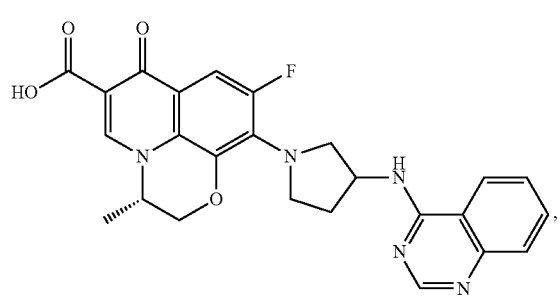
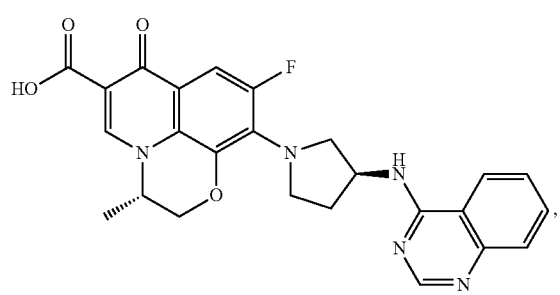
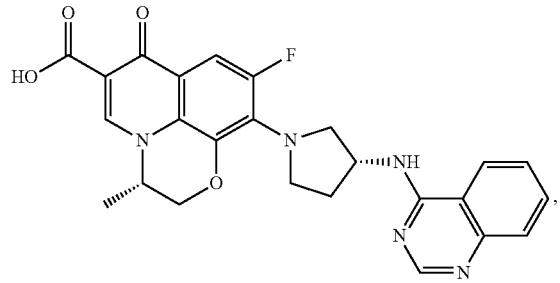
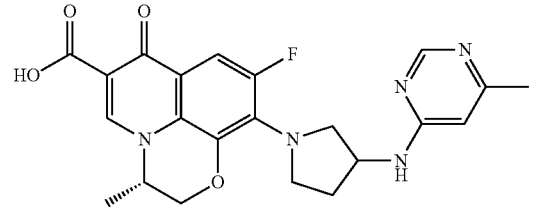
48
-continued
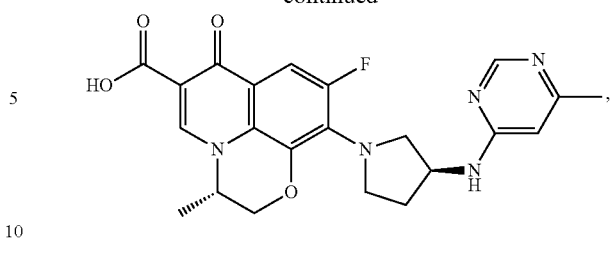
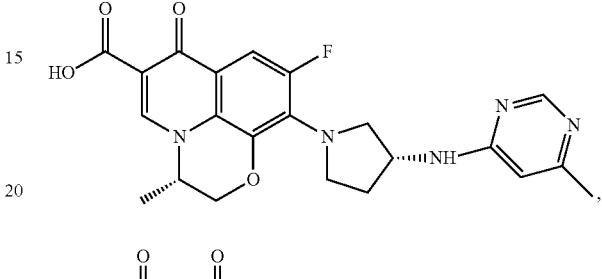
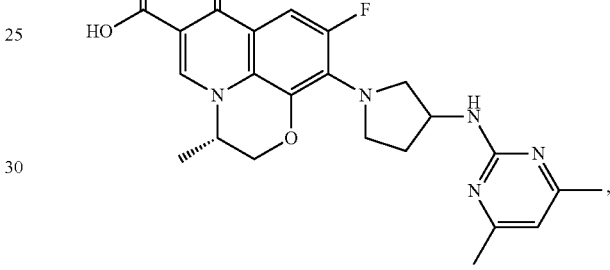
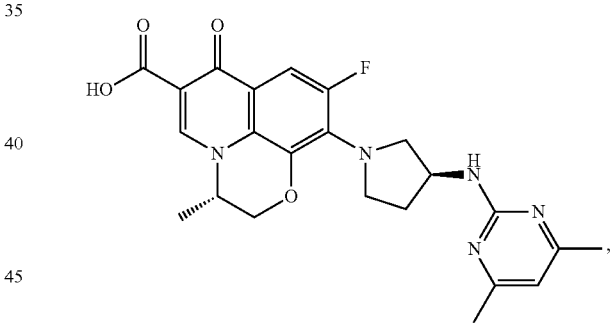
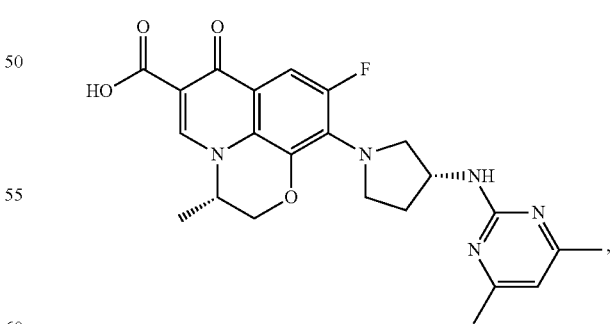
and pharmaceutically acceptable salts, solvates, tautomers and combinations thereof.
Suitably, the compound of formula (I) and pharmaceutically acceptable salts, solvates, tautomers and combinations thereof, is an antibiotic compound of formula (V):

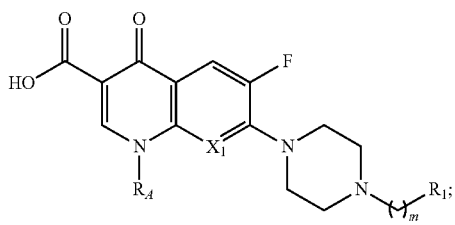

(V)

and pharmaceutically acceptable salts, solvates, tautomers and combinations thereof, wherein:

$X_1$ is selected from N, C—H and C—$R_B$;

$R_A$ is selected from methyl, ethyl, allyl, vinyl, cyclopropyl and —$(CH_2)_k$—$Ar_1$;

$R_B$ is H;

or $R_A$ and $R_B$ together with the atoms to which they are attached form a 6-membered ring wherein from $R_A$ to $R_B$ is a —CH(CH$_3$)—CH$_2$—O— linking group;

m is 0, 1 or 2;

k is 0, 1, 2, 3, 4 or 5;

$R_1$ is H or $Ar_1$;

$Ar_1$ comprises an aryl or heteroaryl group selected from phenyl, pyrimidinyl, naphthalenyl, 5,6-dihydronaphthalenyl, 7,8-dihydronaphthalenyl, 5,6,7,8-tetrahydronaphthalenyl and benzothiophenyl; and the aryl or heteroaryl group is optionally substituted with a phenyl or a 5-membered heteroaryl group; and the $Ar_1$ group may be optionally substituted with 1, 2 or 3 optional substituents selected from $C_{1-6}$ alkyl, halo and NR'R";

with the proviso that one of $R_A$ or $R_1$ comprises $Ar_1$, and when $R_A$ comprises $Ar_1$ then $R_1$ is H; and when $R_1$ comprises $Ar_1$ then $R_A$ is selected from methyl, ethyl, allyl, vinyl and cyclopropy; and each R' and R" is independently selected from H and $C_{1-6}$alkyl.

In some embodiments of the antibiotic compound of formula (V), suitably $R_A$ and $R_B$ together with the atoms to which they are attached form a 6-membered ring wherein from $R_A$ to $R_B$ is a —CH(CH$_3$)—CH$_2$—O— linking group, having the structure (VI):

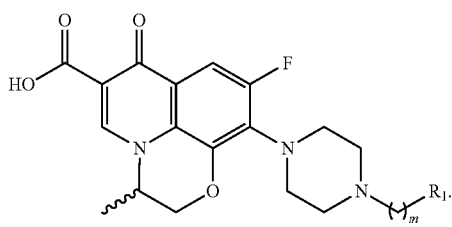

(VI)

More suitably, in embodiments of the antibiotic compound of formula (V), where $R_A$ and $R_B$ together with the atoms to which they are attached form a 6-membered ring wherein from $R_A$ to $R_B$ is a —CH(CH$_3$)—CH$_2$—O— linking group, the compound has a defined stereochemistry of structure (VI):

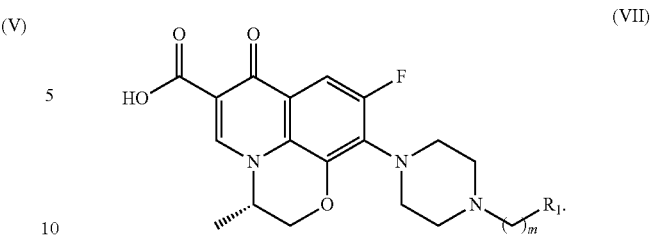

(VII)

Suitably, the compound of formula (I) and pharmaceutically acceptable salts, solvates, tautomers and combinations thereof, has the formula (VIII):

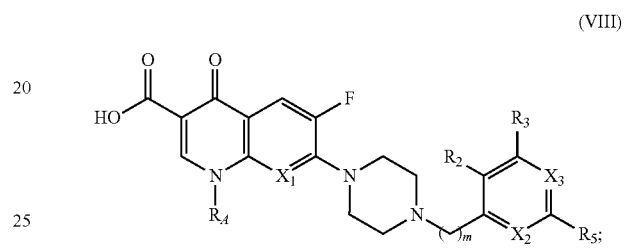

(VIII)

and pharmaceutically acceptable salts, solvates, tautomers and combinations thereof, wherein $R_2$ is selected from H, $C_{1-6}$ alkyl, halo and NR'R";

$R_3$ is selected from H, $C_{1-6}$ alkyl, halo and NR'R";

$X_3$ is N or C—$R_4$;

$R_4$ is selected from H, $C_{1-6}$ alkyl, halo, NR'R", phenyl, 5-membered heteroaryl group; and the phenyl or 5-membered heteroaryl group may be optionally substituted with 1, 2 or 3 optional substituents selected from $C_{1-6}$ alkyl, halo and NR'R";

or one of $R_2$ and $R_3$ or $R_3$ and $R_4$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R";

$R_5$ is selected from H, $C_{1-6}$ alkyl, halo and NR'R";

$X_2$ is N or C—$R_6$; and $R_6$ is selected from H, $C_{1-6}$ alkyl, halo and NR'R".

In some embodiments of the antibiotic compound of formula (VIII), suitably $R_A$ and $R_B$ together with the atoms to which they are attached form a 6-membered ring wherein from $R_A$ to $R_B$ is a —CH(CH$_3$)—CH$_2$—O— linking group, having the structure (IX):

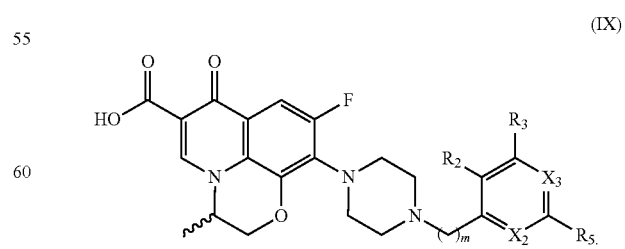

(IX)

More suitably, in embodiments of the antibiotic compound of formula (VIII), where $R_A$ and $R_B$ together with the atoms to which they are attached form a 6-membered ring wherein from $R_A$ to $R_B$ is a —CH(CH$_3$)—CH$_2$—O— linking group, the compound has a defined stereochemistry of structure (IX):
(X)
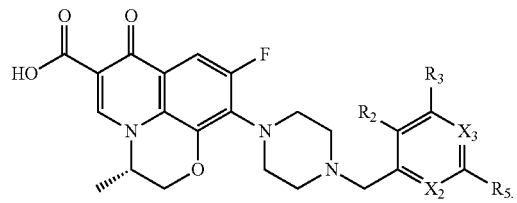
Suitably, the compound of formula (I) is selected from:
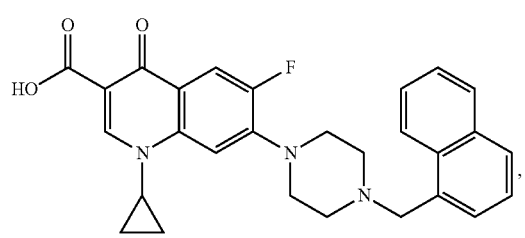
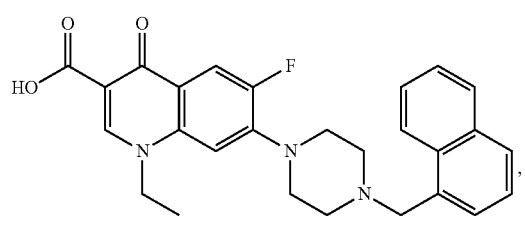
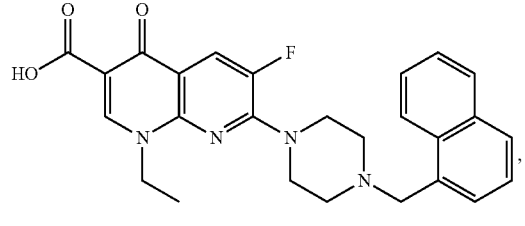
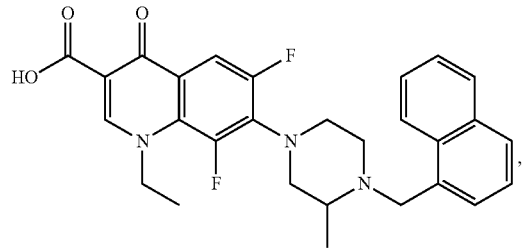
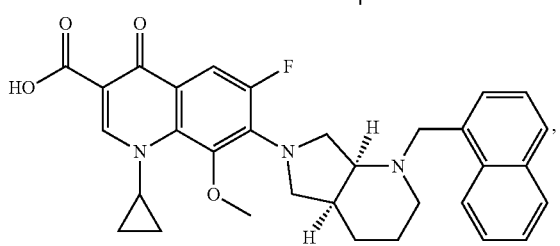
-continued
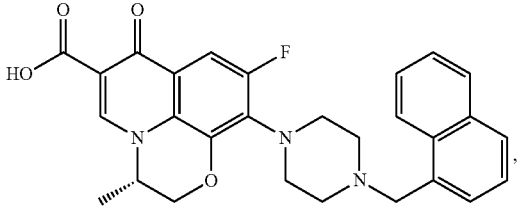
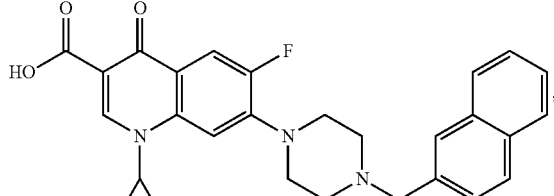
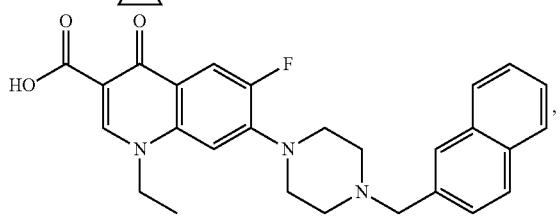
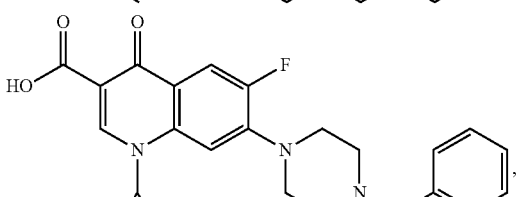
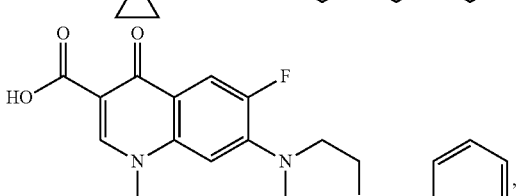
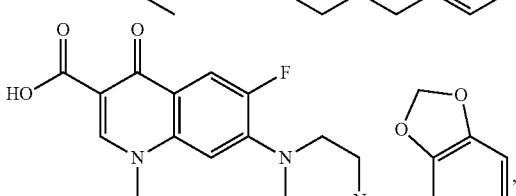
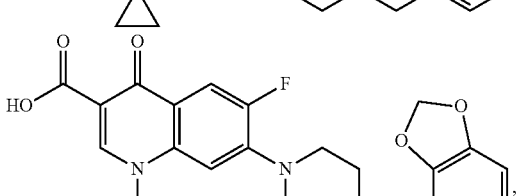
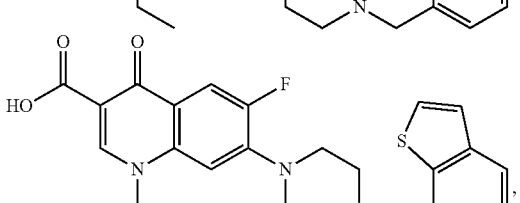

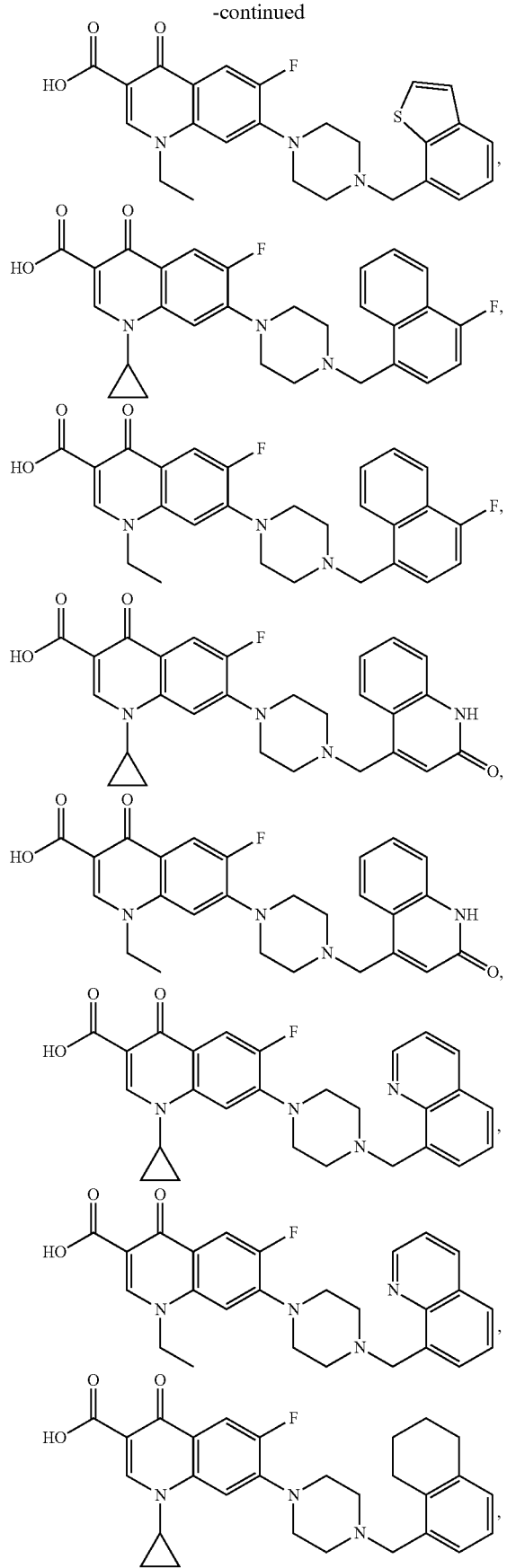
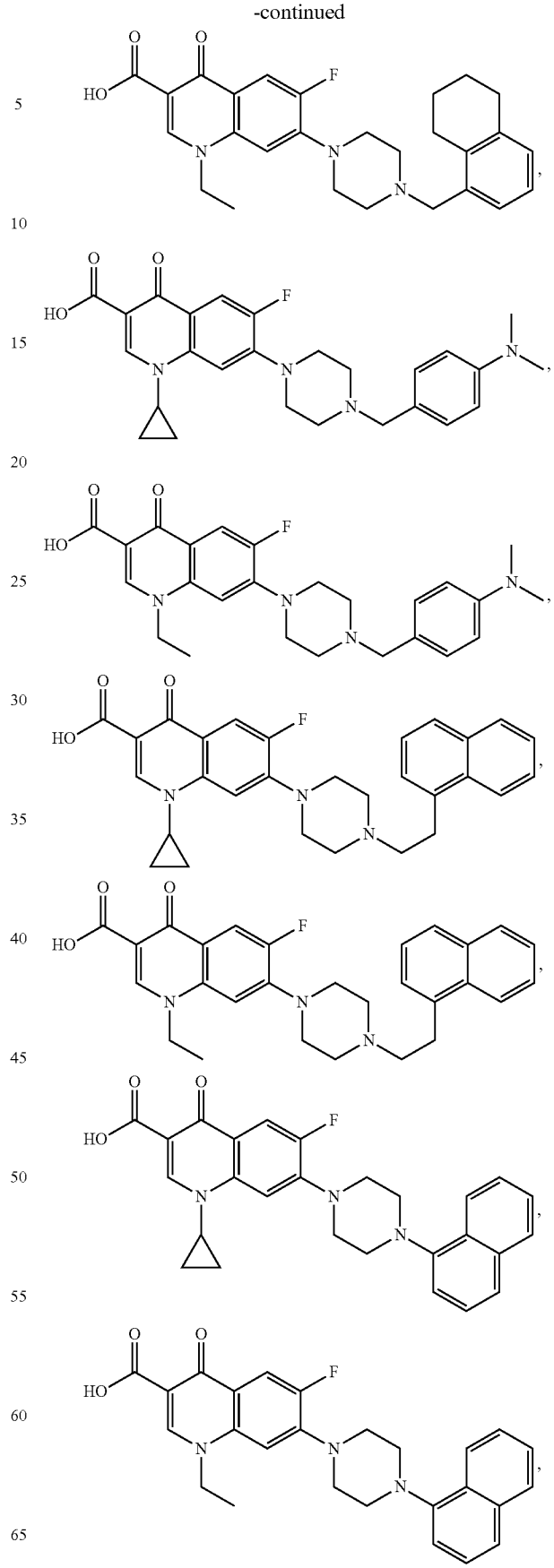

-continued
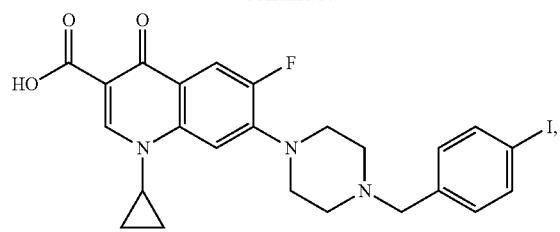

-continued
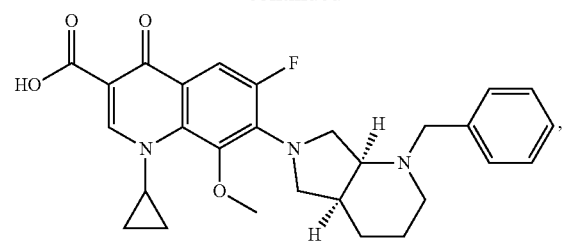
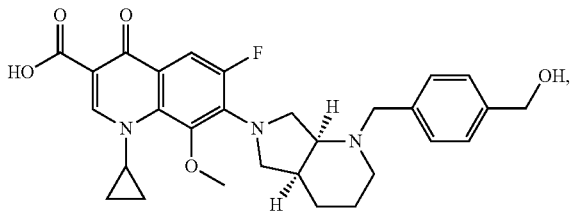
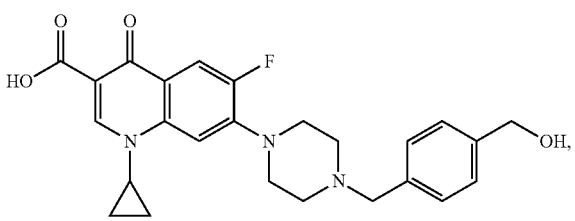
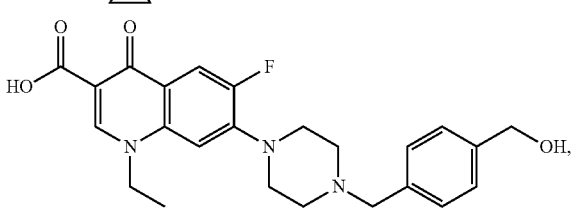
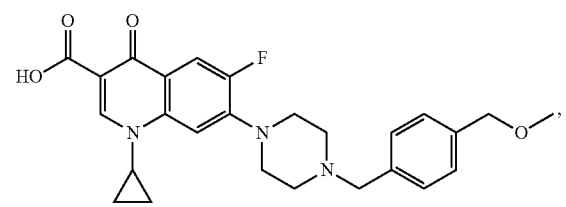
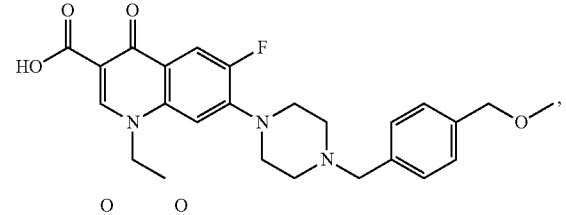
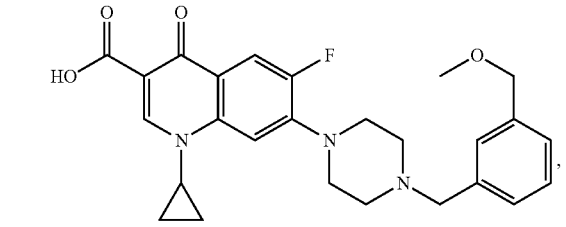
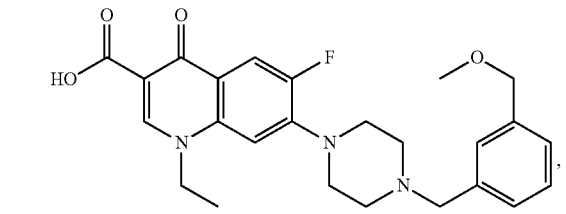
-continued
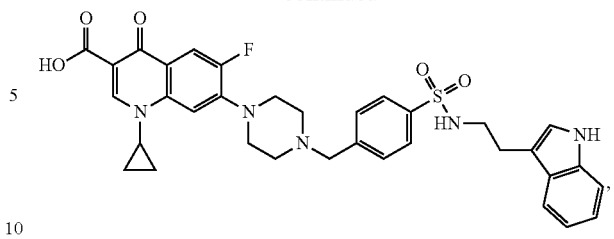
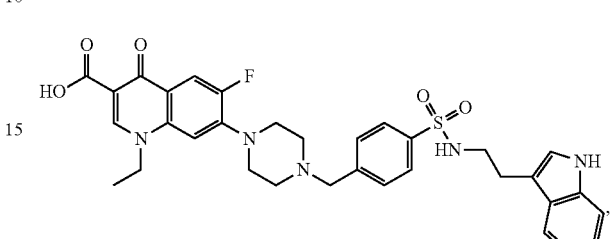

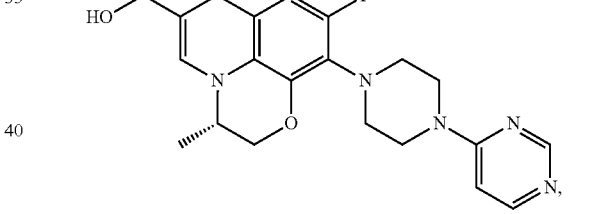
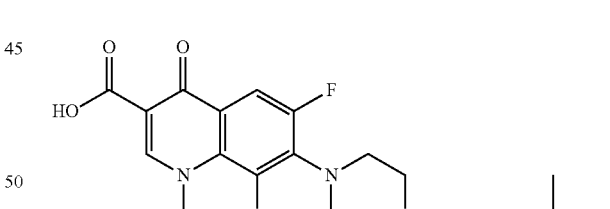
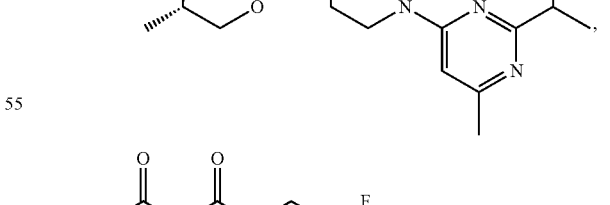
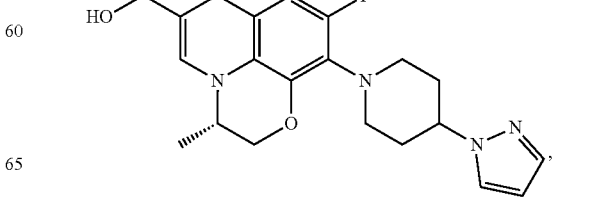

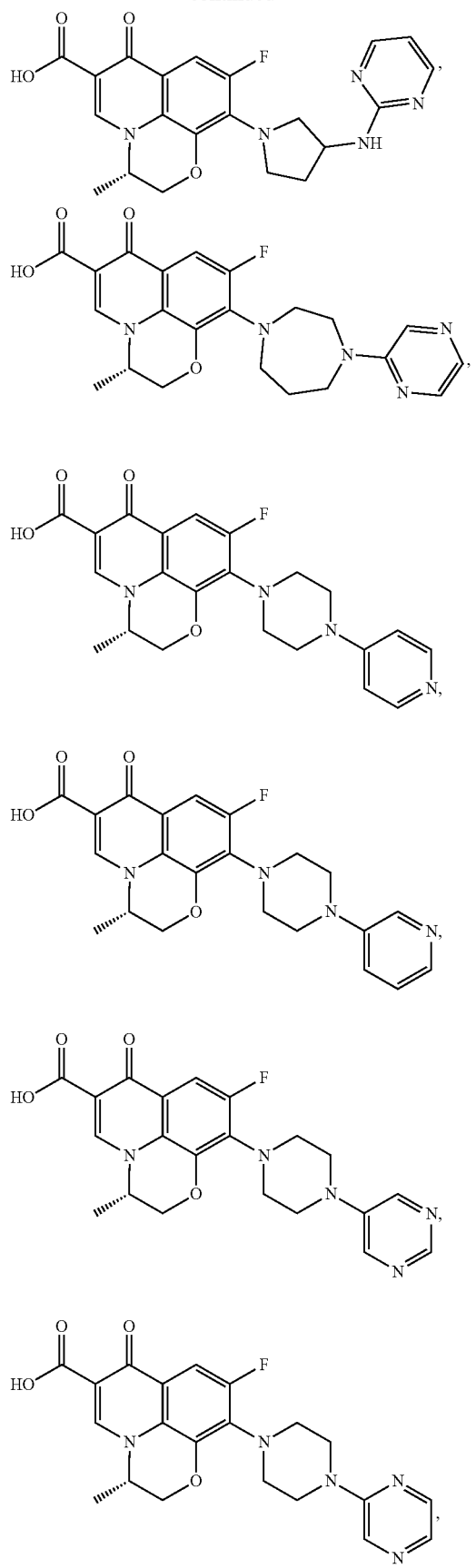
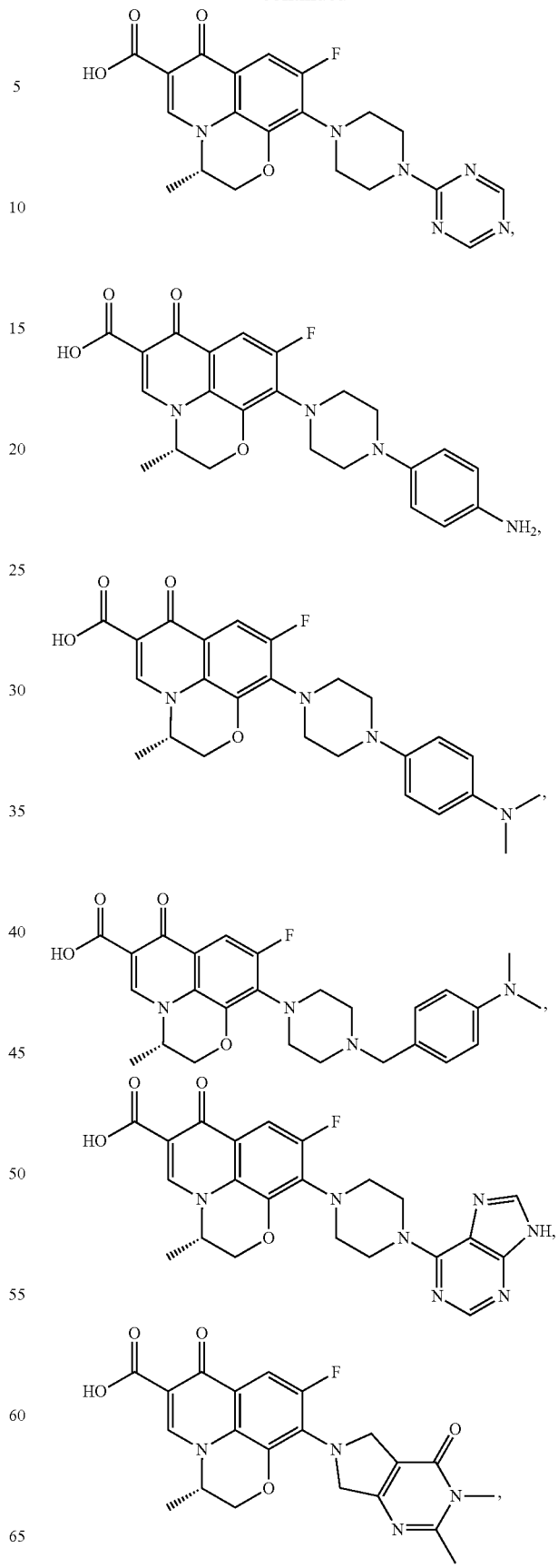

61
-continued
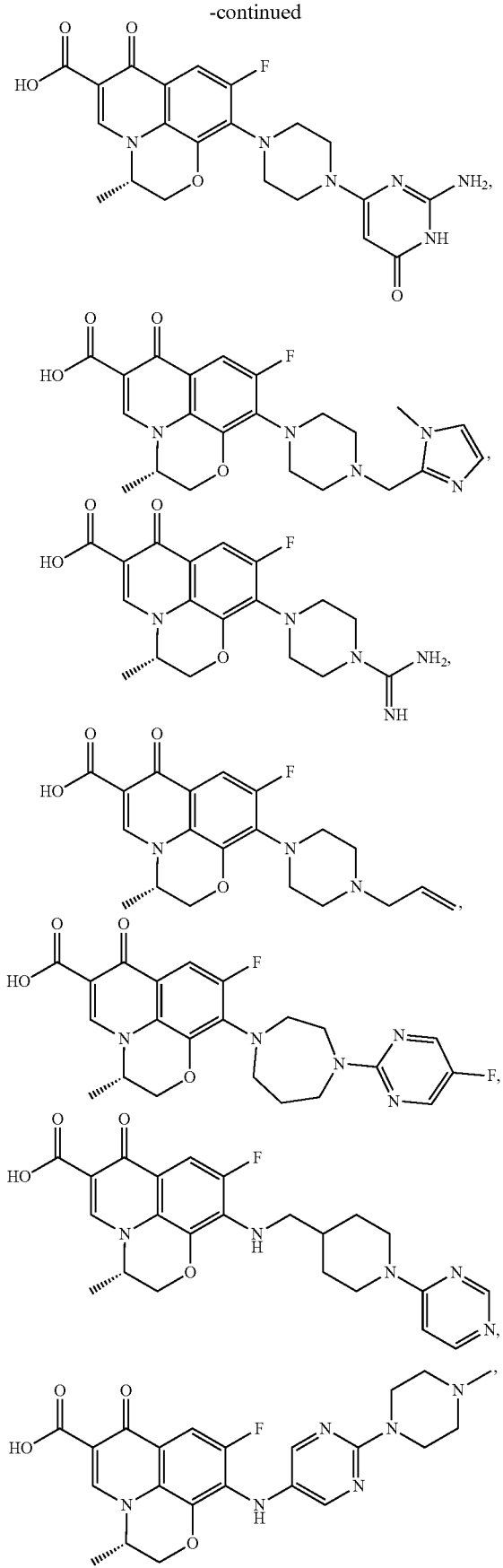
62
-continued
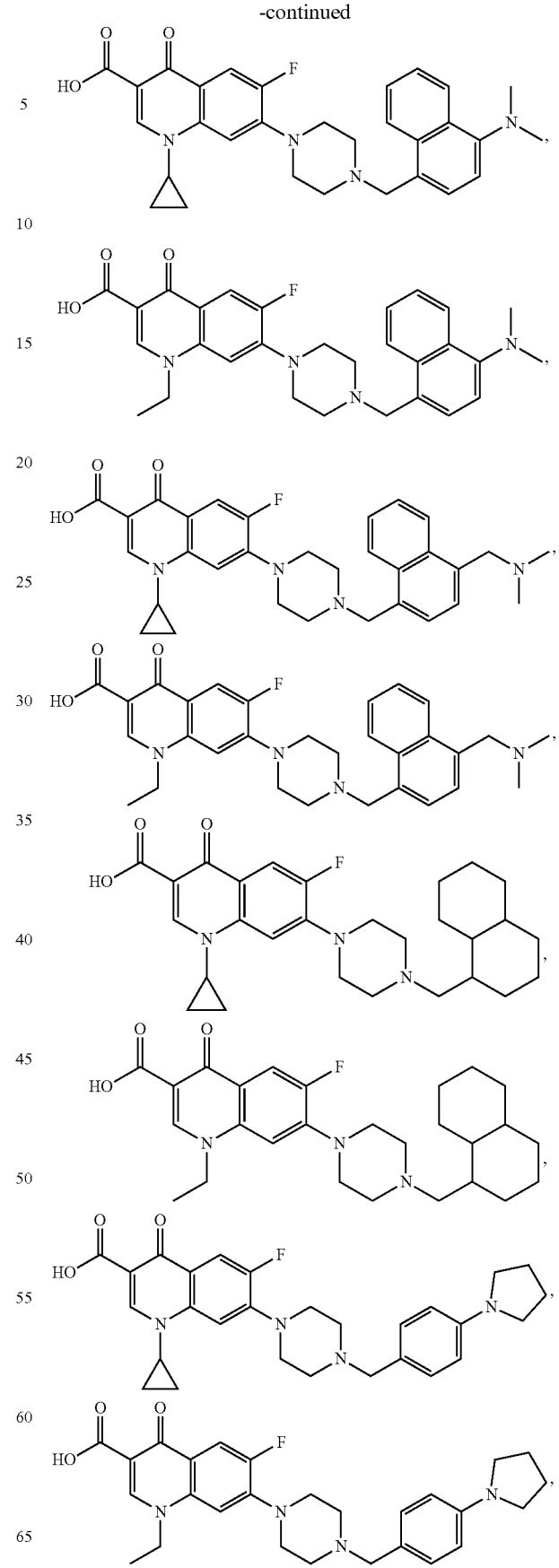

63
-continued
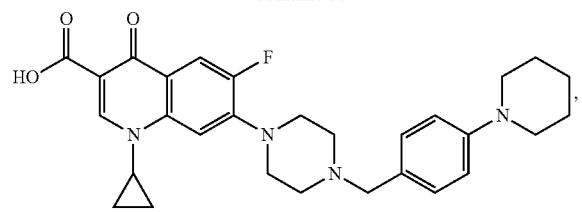
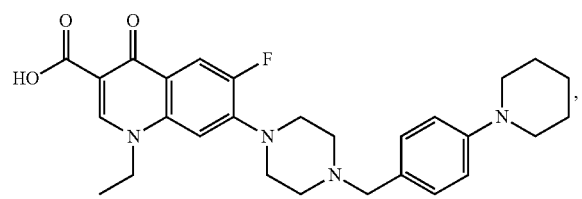
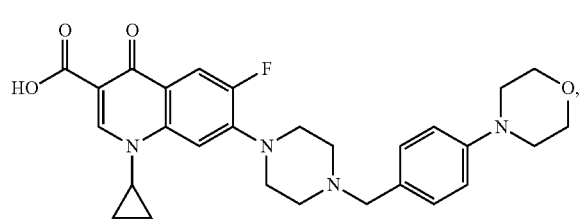
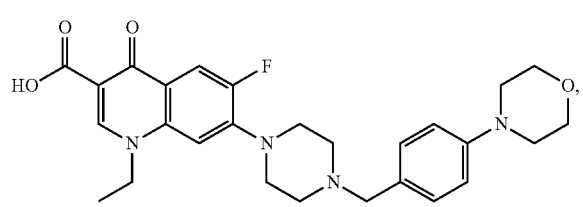
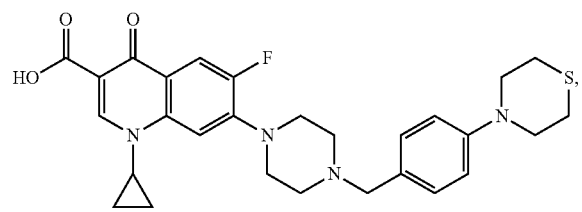
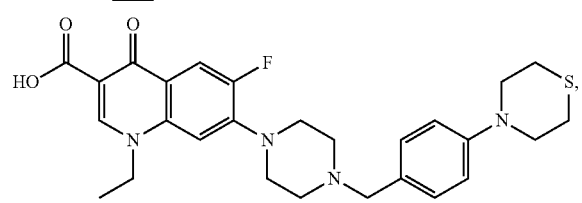
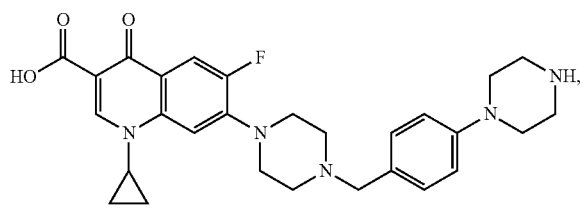
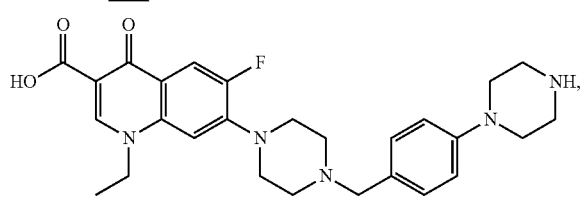
64
-continued
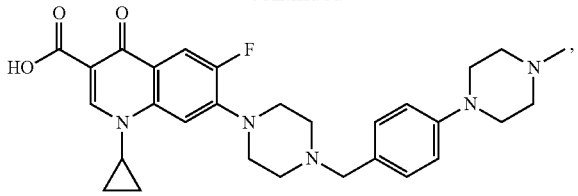
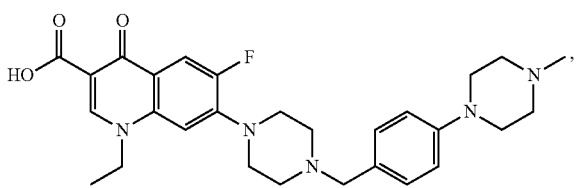
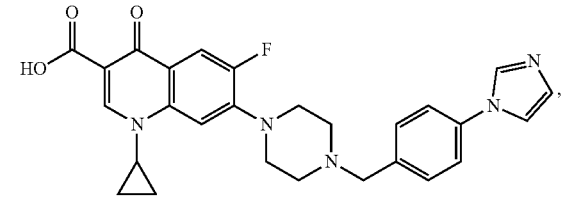
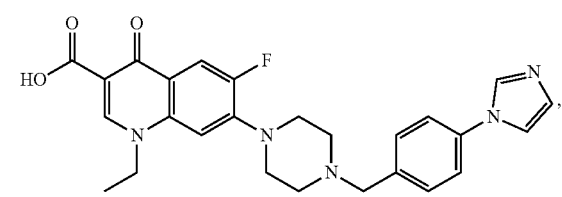
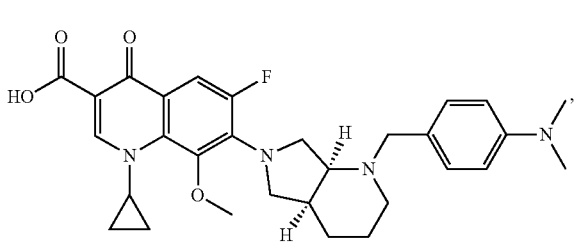
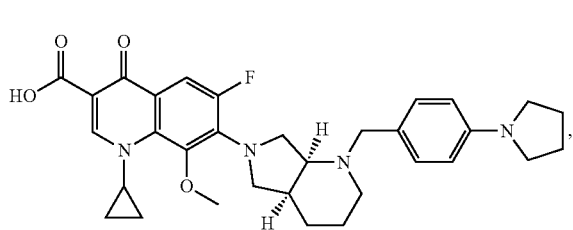
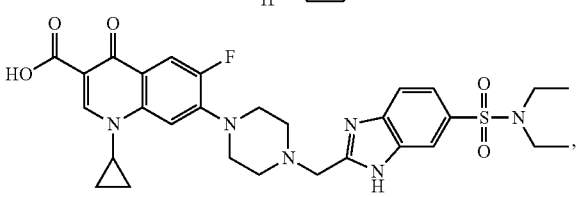
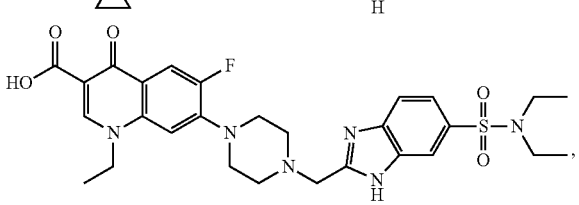

65
-continued
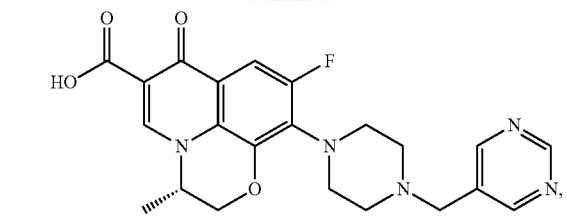
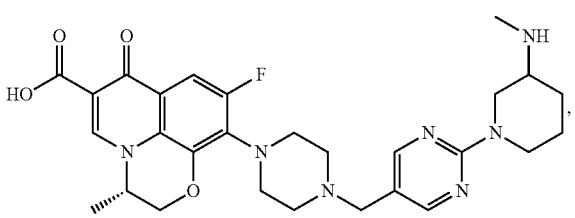
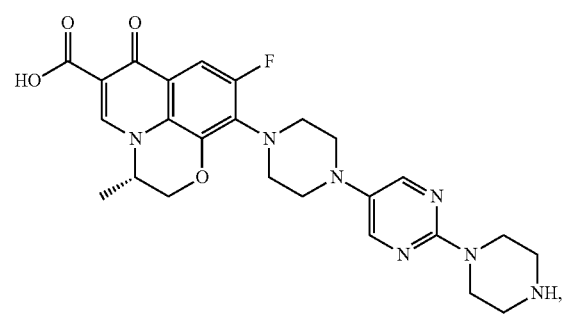
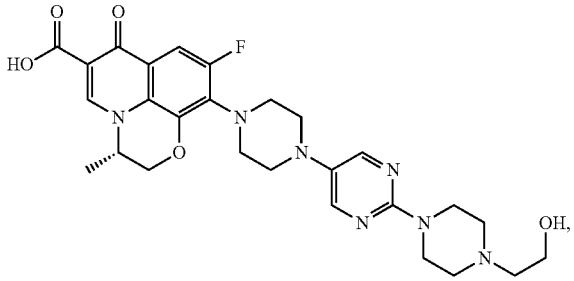
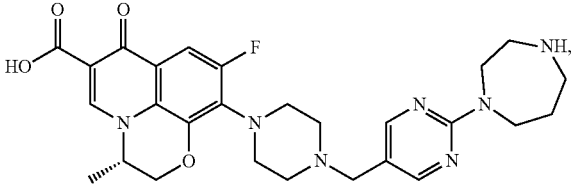
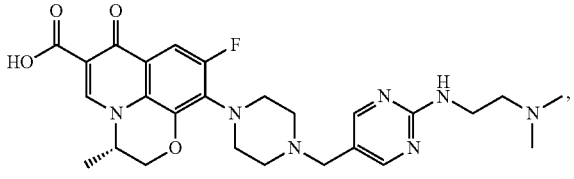
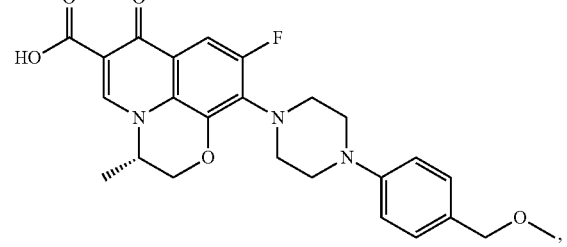
66
-continued
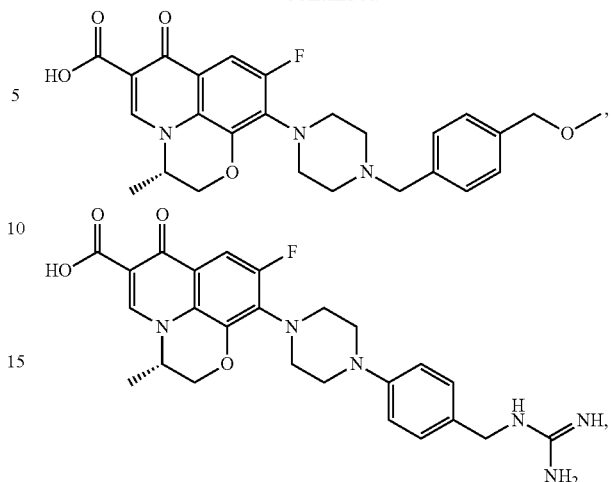
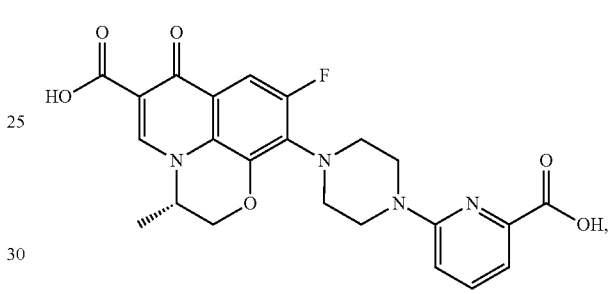
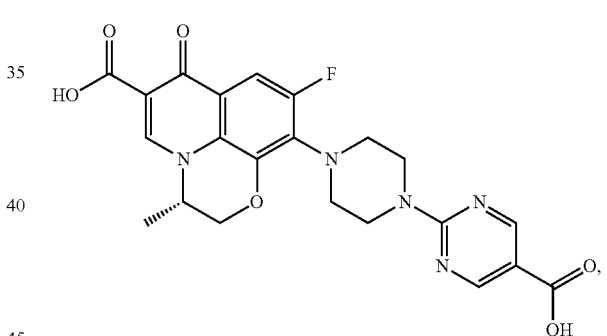
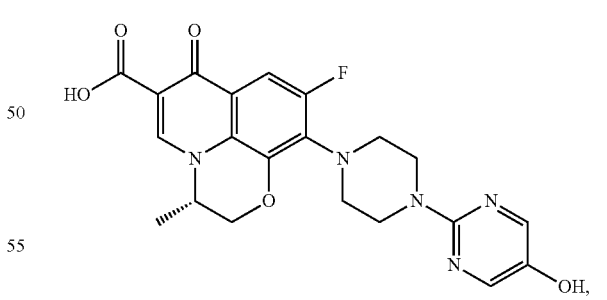
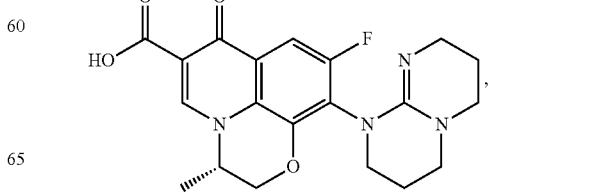

67
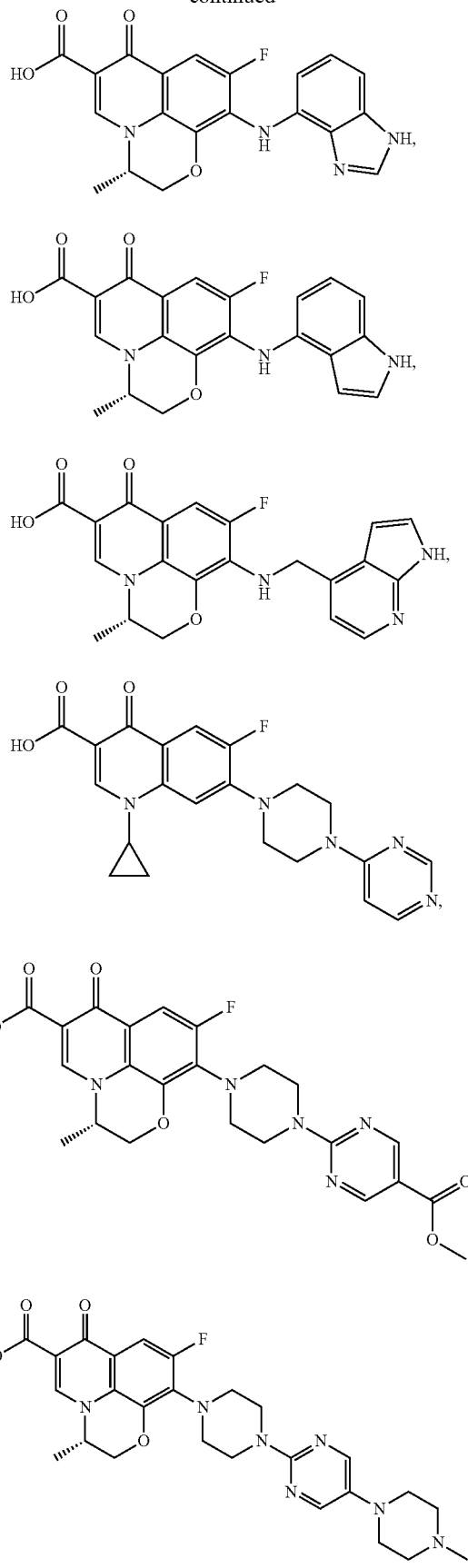
68
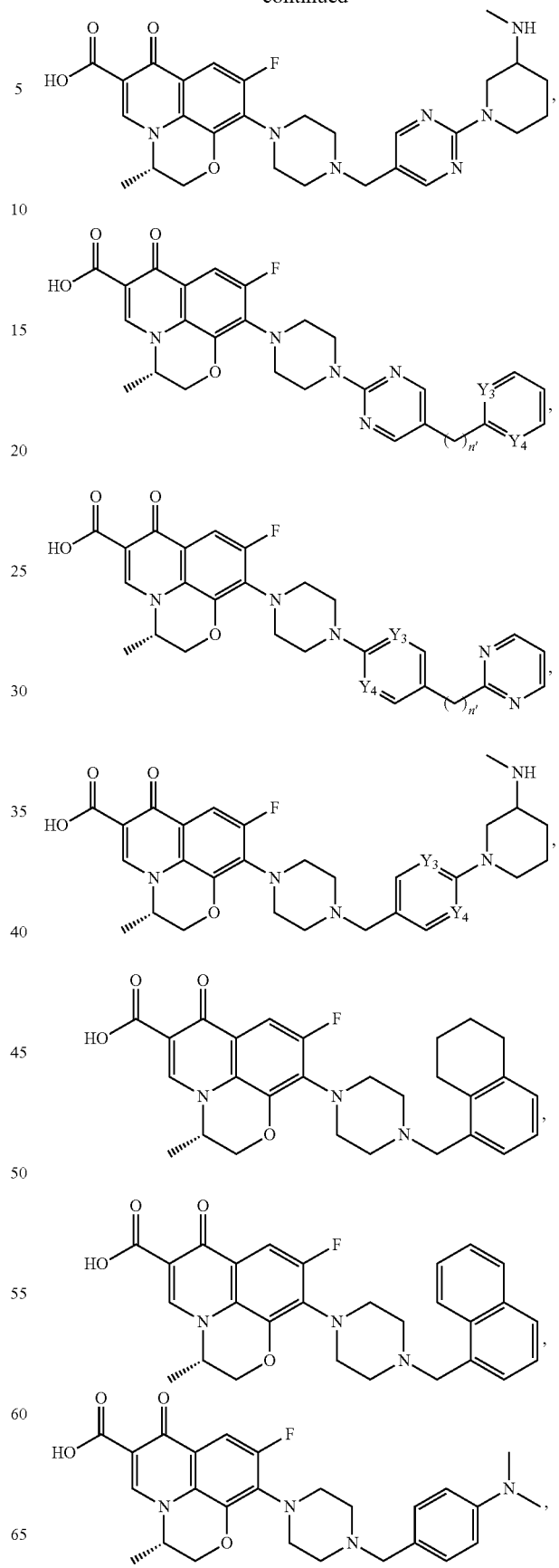

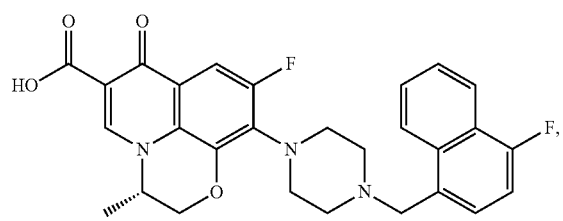
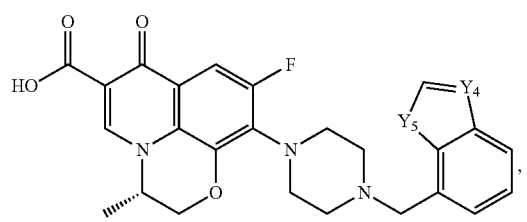
and pharmaceutically acceptable salts, solvates, tautomers and combinations thereof, wherein each $Y_3$ is independently C or N; each $Y_4$ is independently C or N; each $Y_5$ is independently O, N or S; and each n' is independently 0 or 1.
Suitably, the compound of formula (I) is selected from:
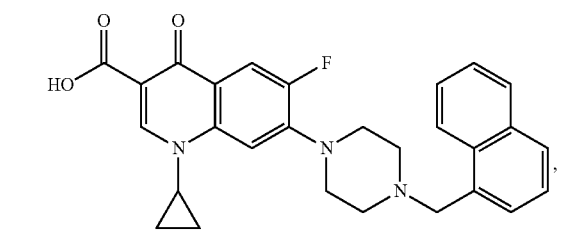
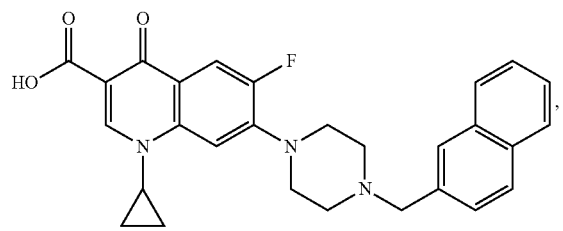
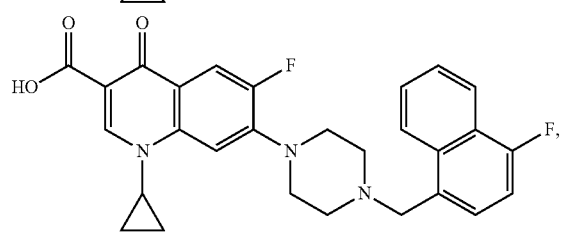
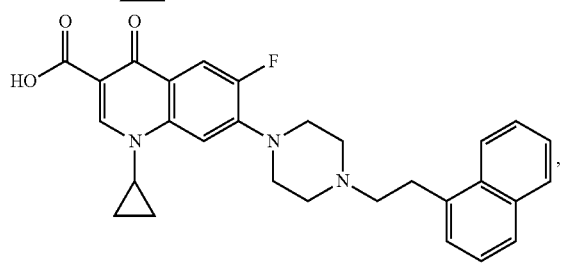
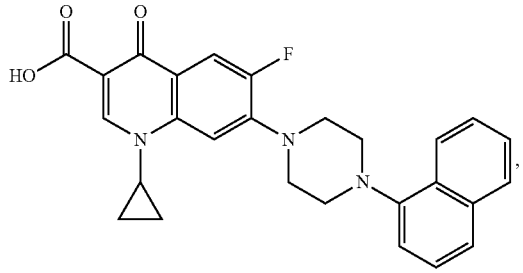
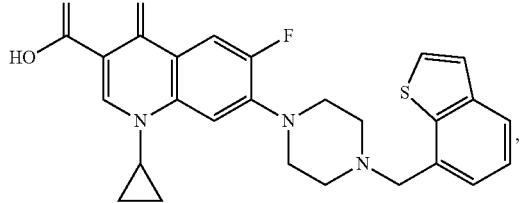
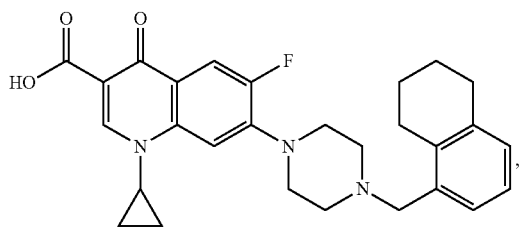
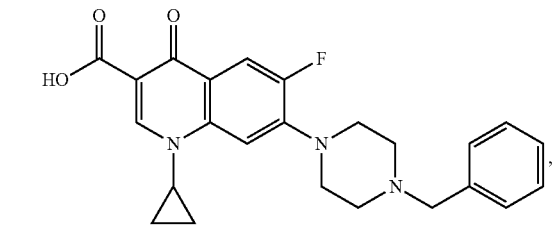
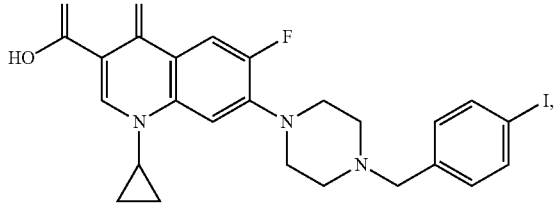
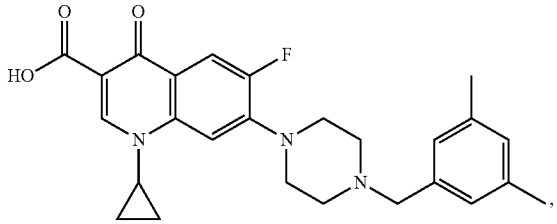
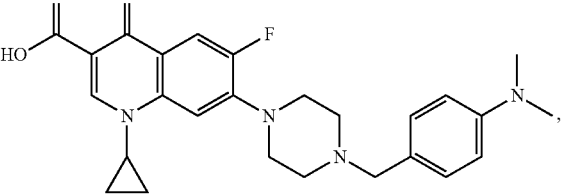

71
-continued
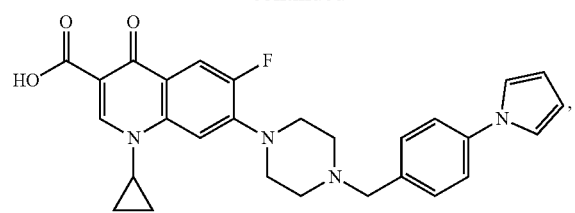
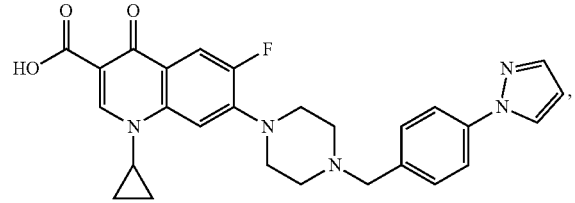
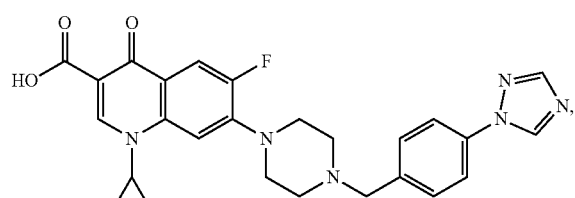
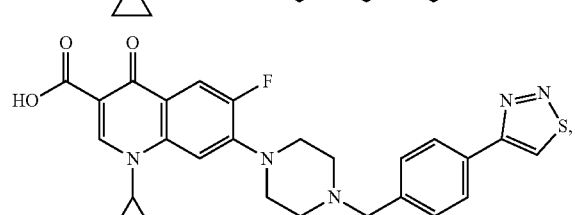
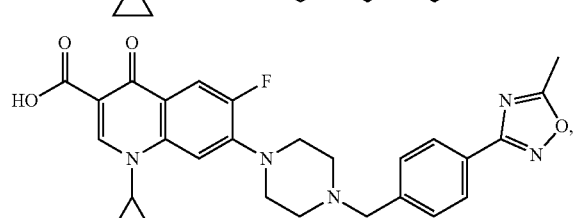
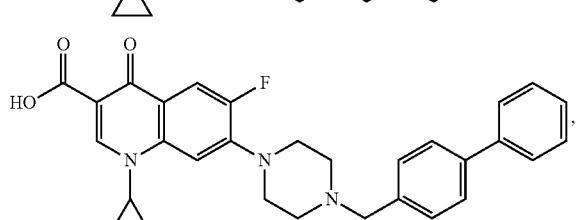
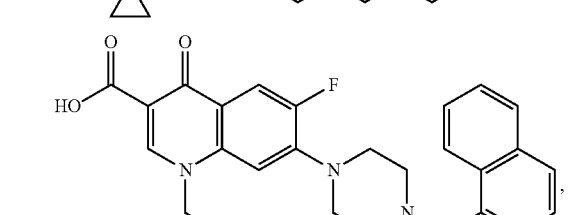
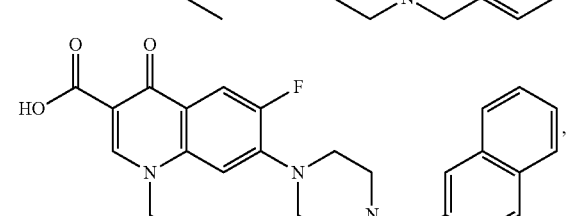
72
-continued
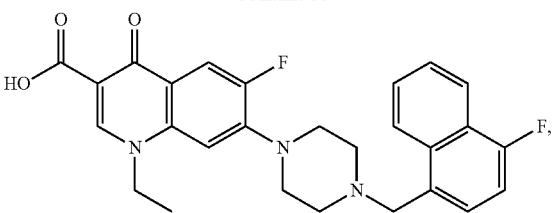
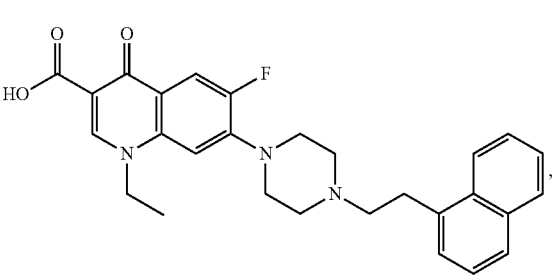
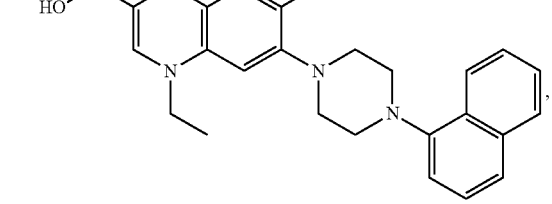
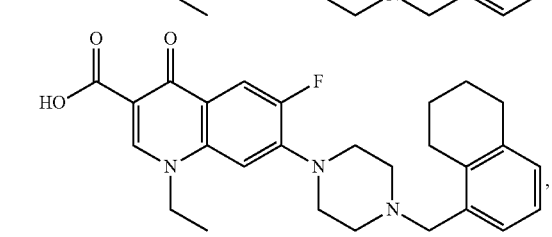
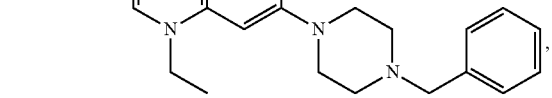

73
-continued
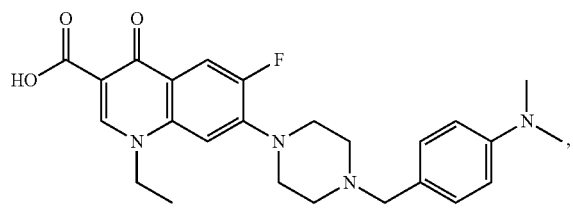
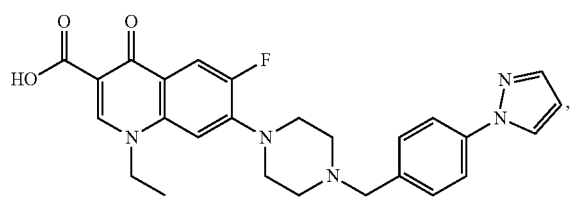
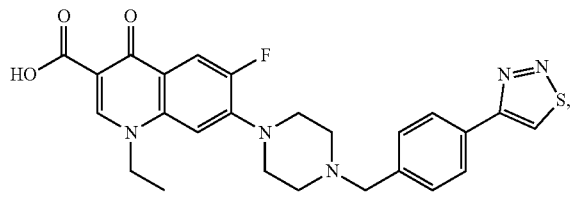
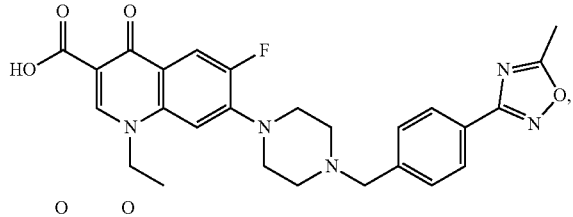
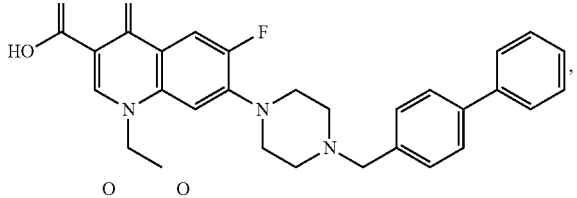
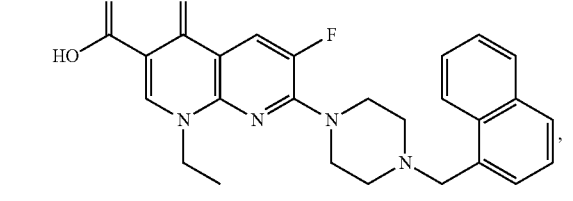
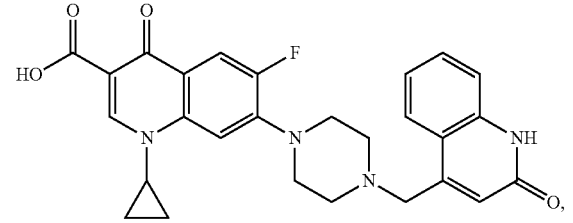
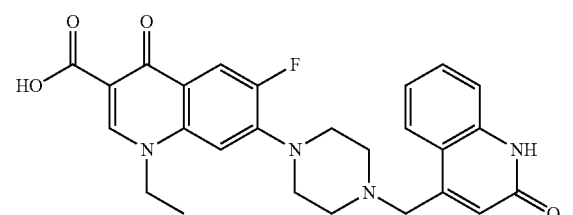
74
-continued
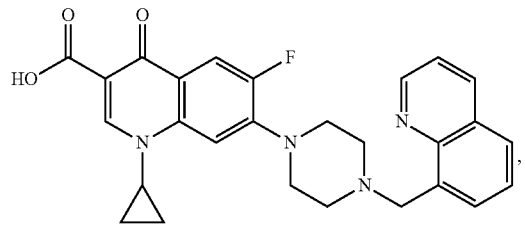
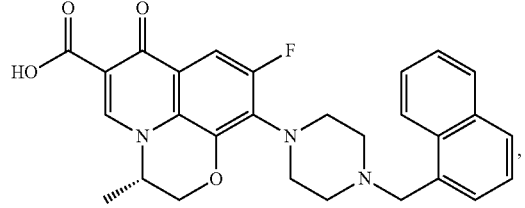
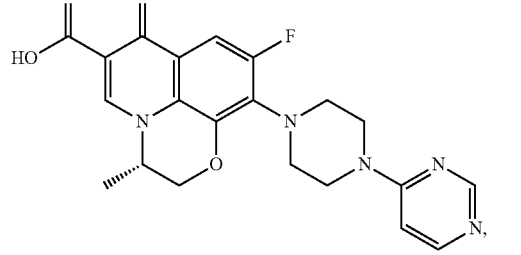
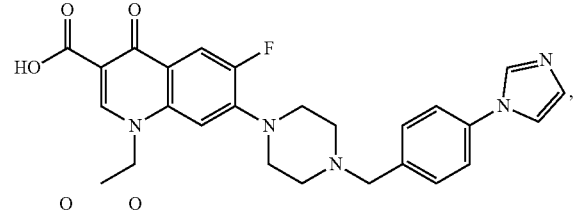
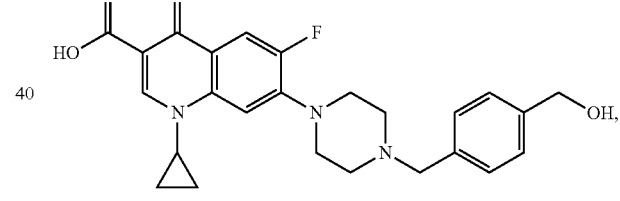
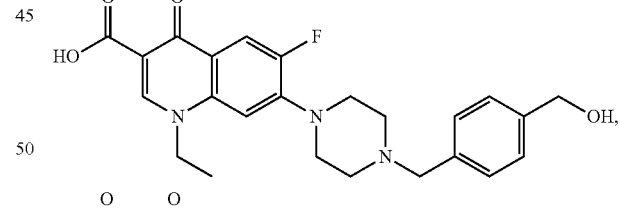
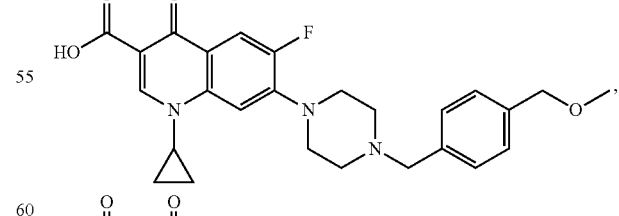
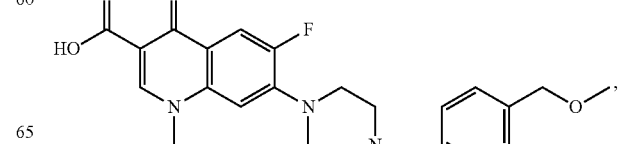

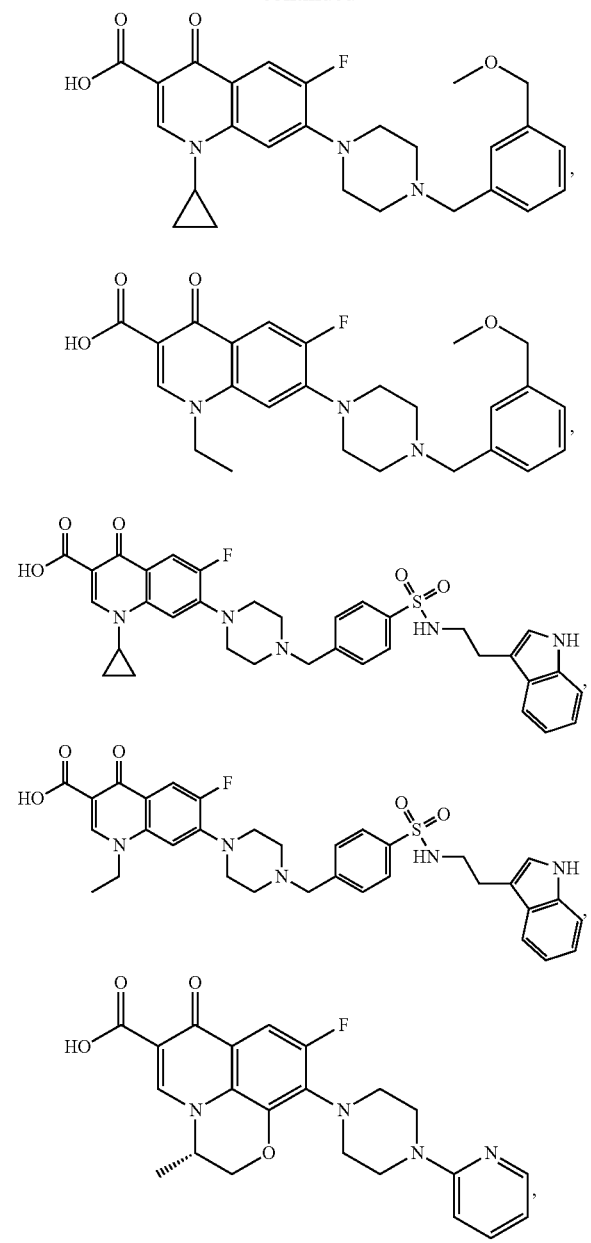
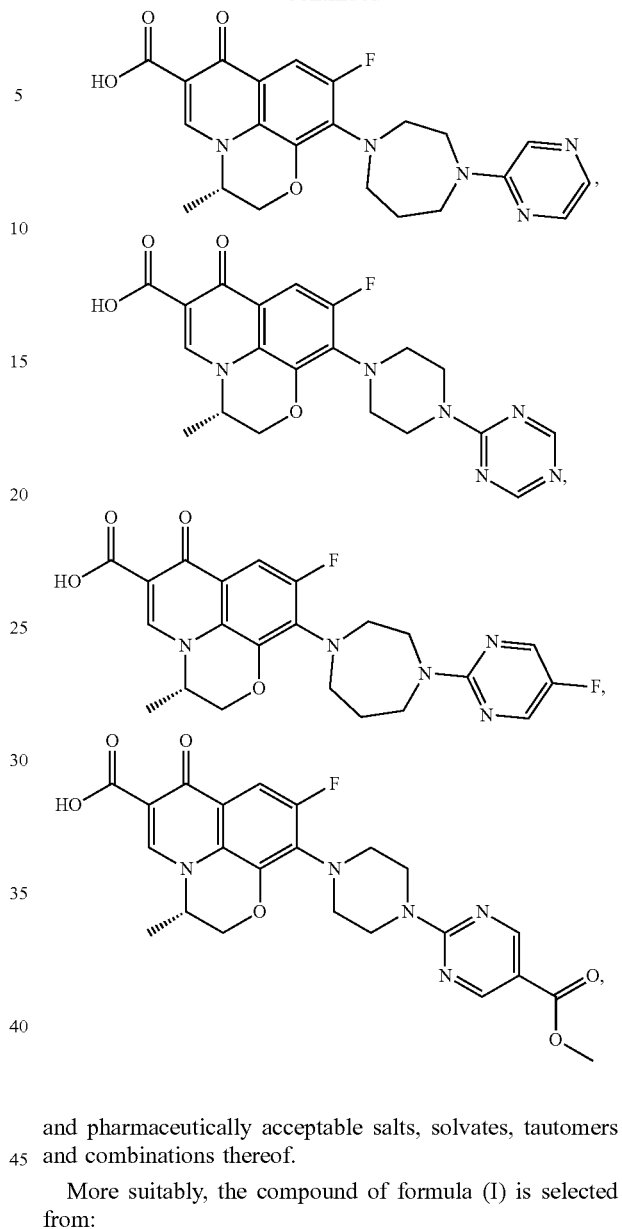
and pharmaceutically acceptable salts, solvates, tautomers and combinations thereof.
More suitably, the compound of formula (I) is selected from:
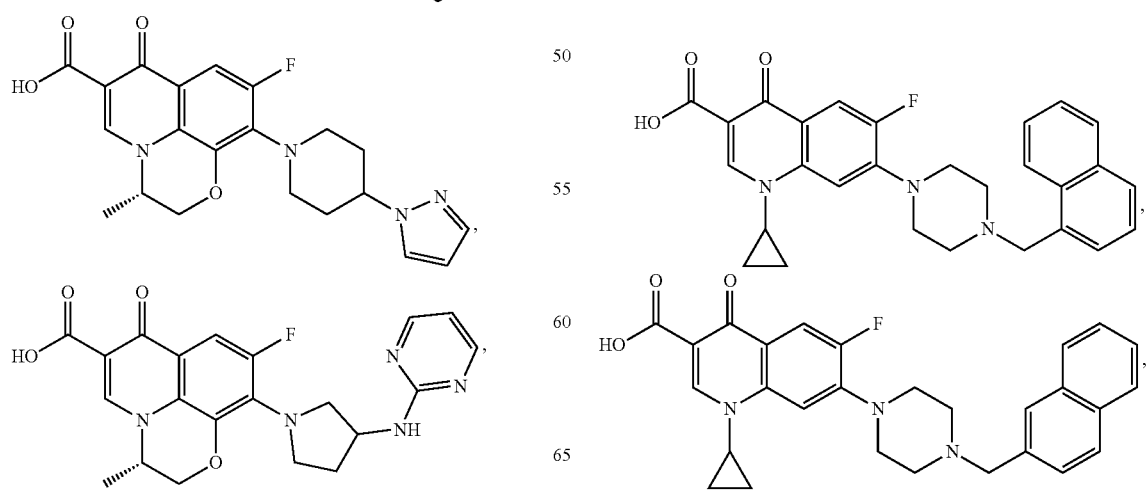

77
-continued
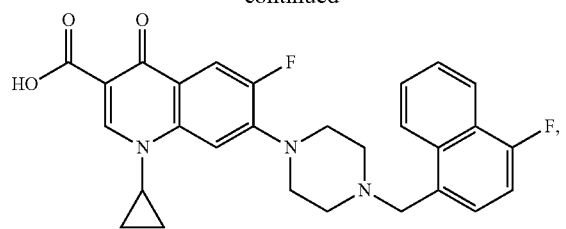
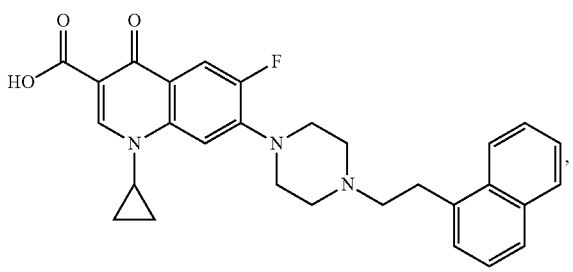
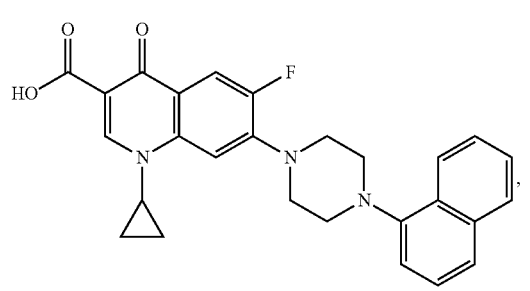
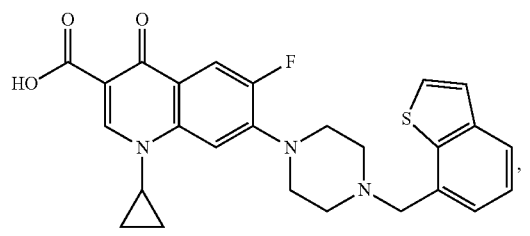
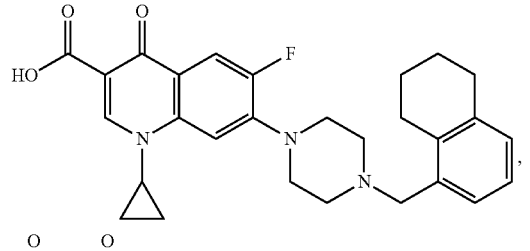
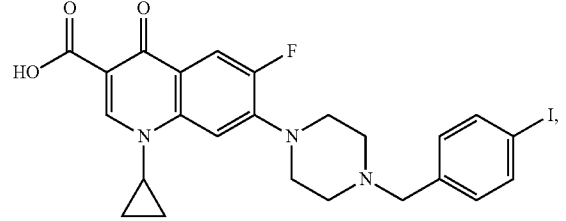
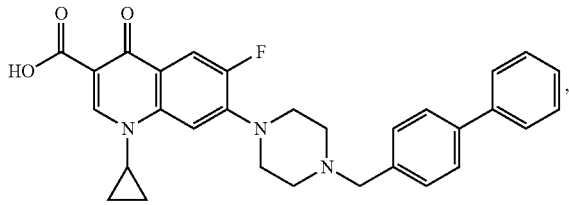
78
-continued
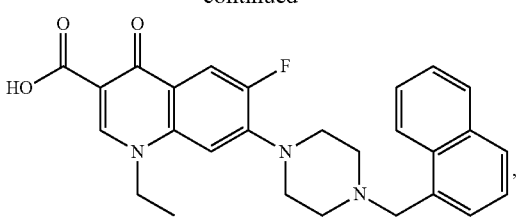
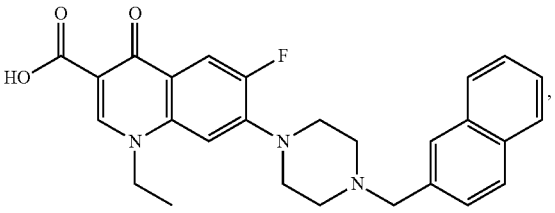
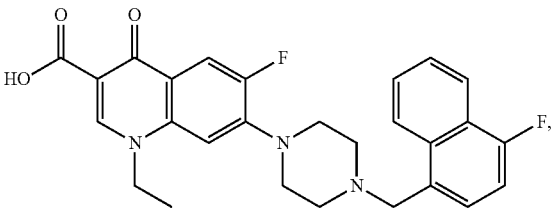
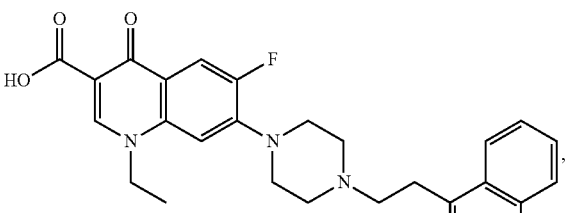
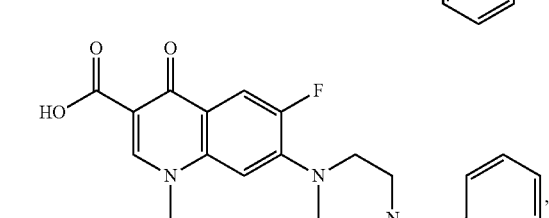
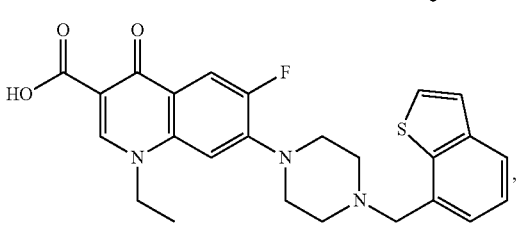
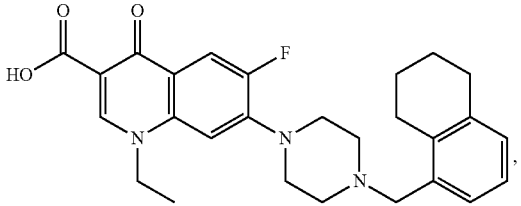

-continued

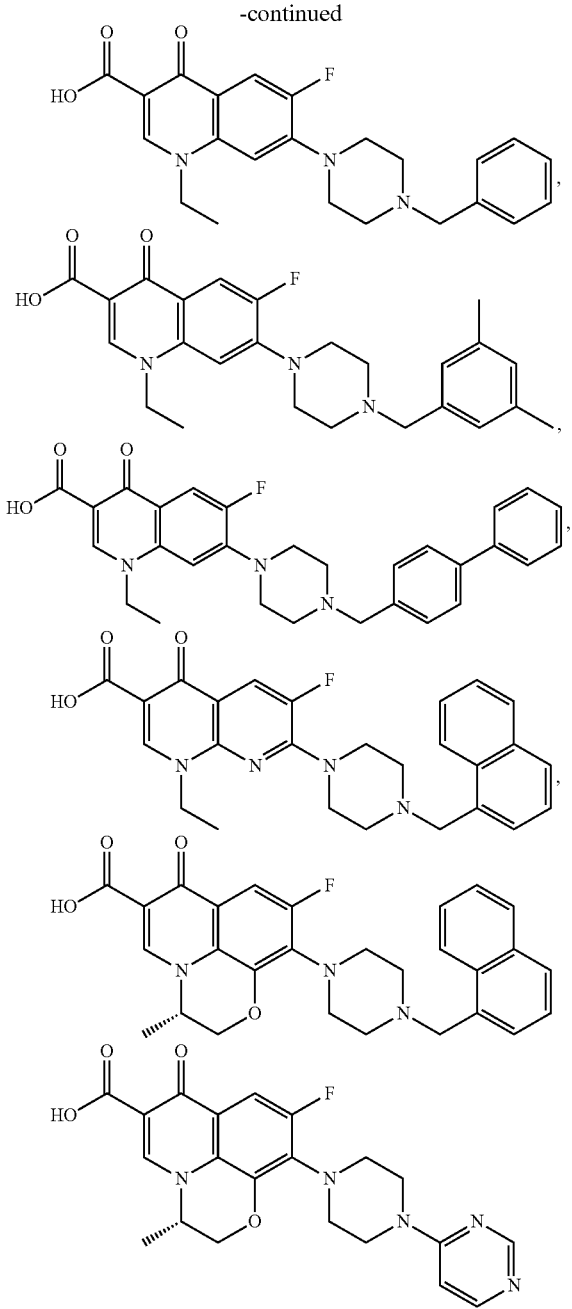

and pharmaceutically acceptable salts, solvates, tautomers and combinations thereof.

$Y_1$

In one aspect, $Y_1$ is N. In a more suitable aspect, $Y_1$ is C—H.

$Y_2$

Suitably, $Y_2$ is selected from C—H, and C—F. More suitably, $Y_2$ is C—F.

$Y_3$

In some embodiments, each $Y_3$ is C. In other embodiments, each $Y_3$ is N.

$Y_4$

In some embodiments, each $Y_4$ is C. In other embodiments, each $Y_4$ is N.

$Y_5$

In some embodiments, each $Y_5$ is O. In other embodiments, each $Y_3$ is N. In other embodiments, each $Y_5$ is S.

$Y_6$

Suitably, $Y_6$ is selected from $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, cyclopentyl and cyclohexyl.

Suitably, $Y_6$ is selected from phenyl, naphthalenyl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, cyclopentyl and cyclohexyl.

Suitably, $Y_6$ is selected from 7-azaindolyl; 1,3-benzodioxolyl; benzimidazolyl; benzothiophenyl; cyclopropyl; cyclohexyl; decahydronaphthalenyl; diazepanyl; imidazolyl; indolyl; morpholinyl; naphthalenyl; 5,6,7,8-tetrahydronaphthalenyl; naphthalenyl; oxadiazolyl; phenyl; piperazinyl; piperidinyl; purinyl; pyridinyl; pyrimidinyl; pyrimidinonlyl; 6,7-dihydro-5H-pyrrolo[3,4-d]pyrimidin-4-onlyl; pyrrolidinyl; pyrrolyl; pyrazinyl; pyrazolyl; quinolinyl; quinolinonyl; thiadiazolyl; thiazolyl; thiomorpholinyl; triazabicyclodecenyl and triazinyl.

Suitably, $Y_7$ is selected from $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, cyclopentyl and cyclohexyl.

Suitably, $Y_7$ is selected from phenyl, naphthalenyl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, cyclopentyl and cyclohexyl.

Suitably, $Y_7$ is selected from 7-azaindolyl; 1,3-benzodioxolyl; benzimidazolyl; benzothiophenyl; cyclopropyl; cyclohexyl; decahydronaphthalenyl; diazepanyl; imidazolyl;

indolyl; morpholinyl; naphthalenyl; 5,6,7,8-tetrahydronaphthalenyl; naphthalenyl;

oxadiazolyl; phenyl; piperazinyl; piperidinyl; purinyl; pyridinyl; pyrimidinyl; pyrimidinonlyl; 6,7-dihydro-5H-pyrrolo[3,4-d]pyrimidin-4-onlyl; pyrrolidinyl; pyrrolyl; pyrazinyl; pyrazolyl; quinolinyl; quinolinonyl; thiadiazolyl; thiazolyl; thiomorpholinyl; triazabicyclodecenyl and triazinyl.

$Y_8$

Suitably, $Y_8$ is selected from $C_{6-10}$ aryl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, cyclopentyl and cyclohexyl.

Suitably, $Y_8$ is selected from phenyl, naphthalenyl, $C_{7-13}$ aralkyl, $C_{5-10}$ heteroaryl, $C_{6-13}$ heteroaralkyl, $C_{5-10}$ heterocyclyl, $C_{6-13}$ heterocyclalkyl, cyclopentyl and cyclohexyl.

Suitably, $Y_8$ is selected from 7-azaindolyl; 1,3-benzodioxolyl; benzimidazolyl; benzothiophenyl; cyclopropyl; cyclohexyl; decahydronaphthalenyl; diazepanyl; imidazolyl; indolyl; morpholinyl; naphthalenyl; 5,6,7,8-tetrahydronaphthalenyl; naphthalenyl; oxadiazolyl; phenyl; piperazinyl; piperidinyl; purinyl; pyridinyl; pyrimidinyl; pyrimidinonlyl; 6,7-dihydro-5H-pyrrolo[3,4-d]pyrimidin-4-onlyl; pyrrolidinyl; pyrrolyl; pyrazinyl; pyrazolyl; quinolinyl; quinolinonyl; thiadiazolyl; thiazolyl; thiomorpholinyl; triazabicyclodecenyl and triazinyl.)

$X_1$

In one aspect, $X_1$ is N. In a more suitable aspect, $X_1$ is CH or C—$R_B$.

$X_2$

In one aspect, $X_2$ is N. In a more suitable aspect, $X_2$ is C—$R_6$.

$X_3$

In one aspect, $X_3$ is N. In a more suitable aspect, $X_2$ is C—$R_4$.

R' Suitably, each R' is independently selected from H, methyl, ethyl and propyl.

In one aspect, more suitably, each R' is selected from methyl, ethyl and propyl. More suitably, each R' is selected from methyl and ethyl. Most suitably, each R' is methyl.

R" Suitably, each R" is independently selected from H, methyl, ethyl and propyl.

In one aspect, more suitably, each R" is selected from methyl, ethyl and propyl. More suitably, each R" is selected from methyl and ethyl. Most suitably, each R" is methyl.

$R_A$ and $R_1$

One of $R_A$ or $R_1$ comprises $Ar_1$, and (i) when $R_A$ comprises $Ar_1$ then $R_1$ is H, $C_{1-6}$ alkyl or $C_{2-12}$ alkenyl; and (ii) when $R_1$ comprises $Ar_1$ then $R_A$ is selected from methyl, ethyl, allyl, vinyl and cyclopropyl; or $X_1$ is C—$R_B$, and $R_A$ and $R_B$ together with the atoms to which they are attached form a 6-membered ring wherein from $R_A$ to $R_B$ is a —CH(CH$_3$)—CH$_2$—O— linking group.

Suitably, one of $R_A$ or $R_1$ comprises $Ar_1$, and when $R_A$ comprises $Ar_1$ then $R_1$ is H; and when $R_1$ comprises $Ar_1$ then $R_A$ is selected from methyl, ethyl, allyl, vinyl and cyclopropyl.

In some aspects, (i) $R_A$ comprises $Ar_1$ and $R_1$ is H.

More suitably, (ii) $R_1$ is $Ar_1$ and $R_A$ is selected from methyl, ethyl, allyl, vinyl and cyclopropyl; or $X_1$ is C—$R_B$, and $R_A$ and $R_B$ together with the atoms to which they are attached form a 6-membered ring wherein from $R_A$ to $R_B$ is a —CH(CH$_3$)—CH$_2$—O— linking group.

More suitably, (ii) $R_1$ is $Ar_1$ and $R_A$ and $R_B$ together with the atoms to which they are attached form a 6-membered ring wherein from $R_A$ to $R_B$ is a —CH(CH$_3$)—CH$_2$—O— linking group.

$R_A$

Suitably, $R_A$ is selected from methyl, ethyl and cyclopropyl, or is a bond to -L-$Ar_1$;

or $R_A$ and $R_B$ together with the atoms to which they are attached form a 6-membered ring wherein from $R_A$ to $R_B$ is a —CH(CH$_3$)—CH$_2$—O— linking group.

Suitably, $R_A$ is selected from ethyl and cyclopropyl, or is a bond to -L-$Ar_1$;

or $R_A$ and $R_B$ together with the atoms to which they are attached form a 6-membered ring wherein from $R_A$ to $R_B$ is a

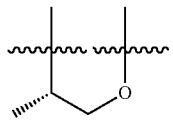

linking group.

When $R_A$ and $R_B$ together with the atoms to which they are attached form a 6-membered ring wherein from $R_A$ to $R_B$ is a

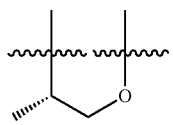

linking group, then $X_1$ is C—$R_B$, and the fluoroquinolone moiety of the compound may be shown as:

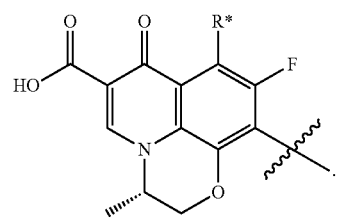

More suitably, $R_A$ is selected from ethyl and cyclopropyl, or $R_A$ and $R_B$ together with the atoms to which they are attached form a 6-membered ring wherein from $R_A$ to $R_B$ is a

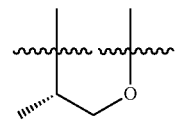

linking group.

$R_B$

Suitably, $R_B$ is selected from H, halo and OCH$_3$;

or $R_A$ and $R_B$ together with the atoms to which they are attached form a 6-membered ring wherein from $R_A$ to $R_B$ is a —CH(CH$_3$)—CH$_2$—O— linking group.

More suitably, $R_B$ is H, F, Cl and OCH$_3$;

or $R_A$ and $R_B$ together with the atoms to which they are attached form a 6-membered ring wherein from $R_A$ to $R_B$ is a —CH(CH$_3$)—CH$_2$—O— linking group.

More suitably, $R_5$ is H;

or $R_A$ and $R_B$ together with the atoms to which they are attached form a 6-membered ring wherein from $R_A$ to $R_B$ is a

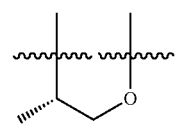 [SMILES: *OC[C@@H](*)C]

linking group.

$R_C$

Suitably, $R_C$ is selected from methyl,

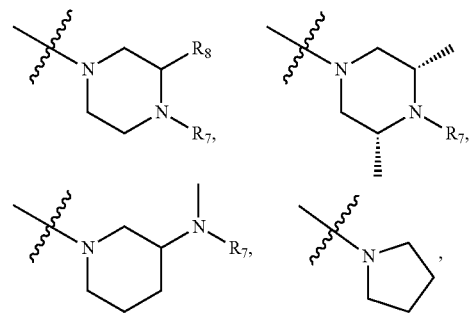

and

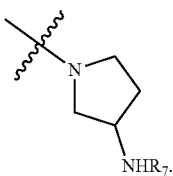

More suitably, R_C is selected from

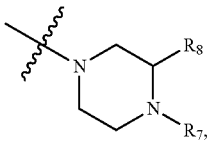 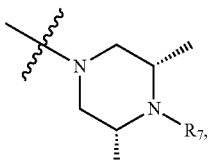

and

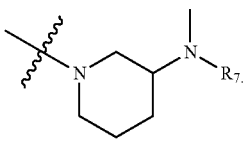

More suitably, R_C is:

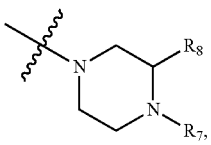

R_D

In one aspect, R_D is NH_2. In a more suitable aspect, R_D is H.

$R^\#$, $R^{\#1}$ and $R^{\#2}$.

$R^\#$, $R^{\#1}$ and $R^{\#2}$ are independently selected from H, —$C_{1-6}$ alkyl, -halo, —(CH_2)_t—OR', —(CH_2)_t—C(=O)—OR', —(CH_2)_t—NR'R", —NO_2, —NR'-(cyclopropyl), -(cyclopropyl), —NR'—(CH_2)_t—NR'R", —C(=NR')—NR'R", —(CH_2)_t—NR'—C(=NR')—NR'R", —CH_2—CH=CH_2, —CH=CH—(C_{1-6} alkyl), —CH=CH—CN, —SO_2—NR'R" and —SO_2NR'—(CH_2)_t—Ar_2.

More suitably, $R^\#$, $R^{\#1}$ and $R^{\#2}$ are independently selected from H, —$C_{1-6}$ alkyl, F Cl, Br, —(CH_2)_t—OH, —(CH_2)_t—OCH_3, —(CH_2)_t—C(=O)—OH, —(CH_2)_t—C(=O)—OCH_3, —NH_2, (CH_2)_t—NR'R", —NO_2, —NR'-(cyclopropyl), -(cyclopropyl), —CH_2—CH=CH_2, —CH=CH—(C_{1-6} alkyl) and —CH=CH—CN.

Suitably, at least one of $R^\#$, $R^{\#1}$ and $R^{\#2}$ is H; suitably, at least two of $R^\#$1 and $R^{\#2}$ are H; suitably, $R^\#$, $R^{\#1}$ and $R^{\#2}$ are H.

Suitably, $R^{\#1}$ is H.

Suitably, $R^\#$ and $R^{\#2}$ are H;

In some aspects, suitably, $R^\#1$ is H; and $R^\#$ and $R^{\#2}$ are independently selected from —CH_3, —CH_2CH_3, —CH(CH_3)_2, —C(CH_3)_3.

In some aspects, suitably $R^\#$ and $R^{\#2}$ are H; and $R^{\#1}$ is —$C_{1-6}$ alkyl, F Cl, Br, —(CH_2)_t—OH, —(CH_2)_t—OCH_3, —(CH_2)_t—C(=O)—OH, —(CH_2)_t—C(=O)—OCH_3, —NH_2, (CH_2)_t—NR'R", —NO_2, —NR'-(cyclopropyl), -(cyclopropyl), —CH_2—CH=CH_2, —CH=CH—(C_{1-6} alkyl) and —CH=CH—CN.

$R^x$, $R^{x1}$ and $R^{x2}$ $R^x$, $R^{x1}$ and $R^{x2}$ are independently selected from H, —$C_{1-6}$ alkyl, -halo, —(CH_2)_t—OR', —(CH_2)_t—C(=O)—OR', —(CH_2)_t—NR'R", —NO_2, —NR'-(cyclopropyl), -(cyclopropyl), —NR'—(CH_2)_t—NR'R", —C(=NR')—NR'R", —(CH_2)_t—NR'—C(=NR')—NR'R", —CH_2—CH=CH_2, —CH=CH—(C_{1-6} alkyl), —CH=CH—CN, —SO_2—NR'R" and —SO_2NR'—(CH_2)_t—Ar_2.

More suitably, $R^x$, $R^{x1}$ and $R^{x2}$ are independently selected from H, —$C_{1-6}$ alkyl, F Cl, Br, —(CH_2)_t—OH, —(CH_2)_t—OCH_3, —(CH_2)_t—C(=O)—OH, —(CH_2)_t—C(=O)—OCH_3, —NH_2, (CH_2)_t—NR'R", —NO_2, —NR'-(cyclopropyl), -(cyclopropyl), —CH_2—CH=CH_2, —CH=CH—(C_{1-6} alkyl) and —CH=CH—CN.

Suitably, at least one of $R^x$, $R^{x1}$ and $R^{x2}$ is H; suitably, at least two of $R^x$, $R^{x1}$ and $R^{x2}$ are H; suitably, $R^x$, $R^{x1}$ and $R^{x2}$ are H.

$R^y$, $R^{y1}$ and $R^{y2}$ $R^y$, $R^{y1}$ and $R^{y2}$ are independently selected from H, —$C_{1-6}$ alkyl, -halo, —(CH_2)_t—OR', —(CH_2)_t—C(=O)—OR', —(CH_2)_t—NR'R", —NO_2, —NR'-(cyclopropyl), -(cyclopropyl), —NR'—(CH_2)_t—NR'R", —C(=NR')—NR'R", —(CH_2)_t—NR'—C(=NR')—NR'R", —CH_2—CH=CH_2, —CH=CH—(C_{1-6} alkyl), —CH=CH—CN, —SO_2—NR'R" and —SO_2NR'—(CH_2)_t—Ar_2.

More suitably, $R^y$, $R^{y1}$ and $R^{y2}$ are independently selected from H, —$C_{1-6}$ alkyl, F Cl, Br, —(CH_2)_t—OH, —(CH_2)_t—OCH_3, —(CH_2)_t—C(=O)—OH, —(CH_2)_t—C(=O)—OCH_3, —NH_2, (CH_2)_t—NR'R", —NO_2, —NR'-(cyclopropyl), -(cyclopropyl), —CH_2—CH=CH_2, —CH=CH—(C_{1-6} alkyl) and —CH=CH—CN.

Suitably, at least one of $R^y$, $R^{y1}$ and $R^{y2}$ is H; suitably, at least two of $R^y$, $R^{y1}$ and $R^{y2}$ are H; suitably, $R^y$, $R^{y1}$ and $R^{y2}$ are H.

$R_1$

In one aspect, $R_1$ is H. In a more suitable aspect, $R_1$ is $Ar_1$.

$R_2$

Suitably, $R_2$ is selected from H, methyl, ethyl, propyl, F, Cl, I and NR'R";

or $R_2$ and $R_3$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

Suitably, $R_2$ is selected from H, methyl, F, I and $N(CH_3)_2$;

or $R_2$ and $R_3$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

More suitably, $R_2$ is H;

or $R_2$ and $R_3$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

$R_3$

Suitably, $R_3$ is selected from H, methyl, ethyl, propyl, F, Cl, I and NR'R";

or $R_2$ and $R_3$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

Suitably, $R_3$ is selected from H, methyl, F, I and $N(CH_3)_2$;

or $R_2$ and $R_3$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

More suitably, $R_3$ is H;

or $R_2$ and $R_3$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

$R_4$

Suitably, $R_4$ is selected from H, methyl, ethyl, propyl, F, Cl, I, NR'R", phenyl, 5-membered heteroaryl group; and the phenyl or 5-membered heteroaryl group may be optionally substituted with 1, 2 or 3 optional substituents selected from $C_{1-6}$ alkyl, halo and NR'R";

or $R_3$ and $R_4$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

Suitably, $R_4$ is selected from H, methyl, F, I, $N(CH_3)_2$, phenyl, pyrrolyl, pyrazolyl, 1,2,3-thiazolyl and 1,2,4-oxazolyl; and the phenyl, pyrrolyl, pyrazolyl, 1,2,3-thiazolyl and 1,2,4-oxazolyl groups may be optionally substituted with 1, 2 or 3 optional substituents selected from $C_{1-6}$ alkyl, halo and NR'R";

or $R_3$ and $R_4$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

Suitably, $R_4$ is selected from H, methyl, F, I, $N(CH_3)_2$, phenyl, pyrrolyl and 1,2,3-thiazolyl; and the phenyl, pyrrolyl and 1,2,3-thiazolyl groups may be optionally substituted with 1, 2 or 3 optional substituents selected from $C_{1-6}$ alkyl, halo and NR'R";

or $R_3$ and $R_4$ together with the atoms to which they are attached form a 6-membered aryl ring, a 6-membered carbocylic ring, or a thiophenyl ring and these rings are optionally substituted with 1, 2 or 3 optional substituents selected from $C_{1-6}$ alkyl, halo and NR'R".

Suitably, $R_4$ comprises 0, 1 or 2 optional substituents selected from methyl, ethyl, propyl, F, Cl, I and $N(CH_3)_2$. More suitably, $R_4$ comprises 0 or 1 optional substituents selected from methyl, F, I and $N(CH_3)_2$. Most suitably, $R_4$ comprises no optional substituents.

$R_5$

Suitably, $R_5$ is selected from H, methyl, ethyl, propyl, F, Cl, I and NR'R".

More suitably, $R_5$ is selected from H, methyl, F, I and $N(CH_3)_2$.

Most suitably, $R_5$ is H.

$R_6$

Suitably, $R_6$ is selected from H, methyl, ethyl, propyl, F, Cl, I and NR'R".

More suitably, $R_6$ is selected from H, methyl, F, I and $N(CH_3)_2$.

Most suitably, $R_6$ is H.

$R_7$

Suitably, $R_1$ is H or a bond to -L-$Ar_1$.

More suitably, $R_7$ is a bond to -L-$Ar_1$.

$R_8$

In one aspect, $R_8$ is $CH_3$. In a more suitable aspect, $R_8$ is H.

$Ar_2$

Suitably, each $Ar_2$ is independently selected from benzodioxolyl, benzimidazolyl, benzothiophenyl, pyrrolyl, pyrimidinyl, imidazolyl, indolyl, oxadiazolyl, pyrazolyl, thiadiazolyl and thiazolyl.

More suitably each $Ar_2$ is independently selected from benzodioxolyl, benzimidazolyl, benzothiophenyl and indolyl.

Applications

The invention finds application in the treatment of a bacterial infection in a subject In one aspect, the invention provides a compound of formula (I) and/or (A1) and salts and solvates thereof, for use in the treatment of a bacterial infection in a subject.

In another aspect, the invention provides a pharmaceutical composition comprising a compound of formula (I) and/or (A1) and salts and solvates thereof, for use in the treatment of a bacterial infection in a subject.

Suitably, the bacterial infection may be a multidrug-resistant bacterial infection in a subject, but the bacterial infection is not necessarily limited to multidrug-resistant bacterial infections.

In some aspects, the compounds of formula (I) and/or (A1) and pharmaceutically acceptable salts, solvates, tautomers and combinations thereof, are broad spectrum agents capable of treating a bacterial infection caused by Gram-positive bacteria and/or Gram-negative bacteria and/or atypical bacteria.

Suitably the bacterial infection is caused by at least one bacterium selected from the genera *Acinetobacter, Bacillus, Brucella, Burkholderia, Campylobacter, Coxiella, Enterococcus, Enterobacter, Escherichia, Francisella, Klebsiella, Neisseria, Pseudomonas, Staphylococcus, Streptococcus* and *Yersina*.

Suitably the bacterial infection is caused by at least one bacterium selected from the genera *Enterococcus, Staphylococcus, Klebsiella, Acinetobacter, Pseudomonas, Enterobacter* and *Escherichia*.

More suitably, the bacterial infection is caused by at least one bacterium selected from the genera *Enterococcus, Staphylococcus*, and *Acinetobacter*.

Suitably the bacterial infection is caused by at least one bacterium selected from *Enterococcus faecalis, Enterococcus faecium*, Vanomycin Resistant *Enterococcus, Staphylococcus aureus, Staphylococcus epidermidis, Streptococcus pyogenes, Streptococcus pneumoniae, Streptococcus agalactiae, Bacillus anthracis, Bacillus cereus, Bacillus subtilis, Haemophilus influenzae, Acinetobacter baumannii, Acinetobacter calcoaceticus, Acinetobacter lwoffii, Acinetobacter johnsonii, Burkholderia multivorans, Burkholderia cenocepacia, Burkholderia cepacia, Burkholderia mallei, Burkholderia pseudomallei, Coxiella burnetii, Brucella melitensis, Citrobacter freundii, Escherichia coli, Enterobacter cloacae, Enterobacter aerogenes, Francisella tularensis, Yersina pestis, Klebsiella pneumoniae, Serratia marcesens, Salmonella typhi, Salmonella typhimurum, Stenotrophomonas maltophilia, Pseudomonas aeruginosa, Stenotrophomonas maltophilia, Proteus mirabilis, Campylobacter jejuni, Chlamydia trachomatis, Legionella pneumophilia, Mycobacterium tuberculosis* and *Neisseria gonorrhoeae*.

Suitably, the bacterial infection is a caused by at least one bacterium selected from *Campylobacter jejuni, Neisseria gonorrhoea, Enterococcus faecalis, Enterococcus faecium,*

*Staphylococcus aureus, Staphylococcus epidermidis, Streptococcus pneumoniae, Klebsiella pneumoniae, Acinetobacter baumannii, Pseudomonas aeruginosa, Enterobacter cloacae* and *Escherichia coli*; or at least one bacterium selected from *Bacillus anthracis, Burkholderia mallei, Burkholderia pseudomallei, Brucella melitensis, Coxiella burnettii, Francisella tularensis, Proteus mirabilis* and *Yersinia pestis*

Suitably, the bacterial infection is a caused by at least one bacterium selected from *Campylobacter jejuni, Neisseria gonorrhoea, Enterococcus faecalis, Enterococcus faecium, Staphylococcus aureus, Staphylococcus epidermidis, Streptoccus pneumoniae, Klebsiella pneumoniae, Acinetobacter baumannii, Pseudomonas aeruginosa, Enterobacter cloacae* and *Escherichia coli*.

More suitably, the bacterial infection is caused by at least one bacterium selected from *Enterococcus faecalis, Enterococcus faecium, Escherichia coli, Staphylococcus aureus, Staphylococcus epidermidis, Streptoccus pneumoniae, Klebsiella pneumoniae* and *Acinetobacter baumannii*.

More suitably, the bacterial infection is caused by at least one bacterium selected from *Enterococcus faecalis, Enterococcus faecium, Staphylococcus aureus, Staphylococcus epidermidis, Pseudomonas aeruginosa* and *Acinetobacter baumannii*.

In some embodiments, the bacterial infection is caused by intracellular pathogens.

In some embodiments, the bacterial infection is a caused by at least one bacterium selected from *Bacillus anthracis, Burkholderia mallei, Burkholderia pseudomallei, Brucella melitensis, Coxiella burnettii, Francisella tularensis, Proteus mirabilis* and *Yersinia pestis*.

In some embodiments, the bacterial infection is caused by Gram-positive bacteria selected from *Enterococcus faecalis, Enterococcus faecium, Staphylococcus aureus, Streptococcus pyogenes, Streptococcus pneumoniae, Streptococcus agalactiae, Bacillus anthracis, Bacillus cereus* and *Bacillus subtilis*.

In some embodiments, the infection is caused by Gram-negative bacteria, such as *Haemophilus influenzae, Acinetobacter baumannii, Acinetobacter calcoaceticus, Acinetobacter lwoffii, Acinetobacter johnsonii, Burkholderia multivorans, Burkholderia cenocepacia, Burkholderia cepacia, Burkholderia mallei, Burkholderia pseudomallei, Coxiella burnetii, Citrobacter freundii, Escherichia coli, Enterobacter cloacae, Enterobacter aerogenes, Francisella tularensis, Yersina pestis, Klebsiella pneumoniae, Pseudomonas aeruginosa, Stenotrophomonas maltophilia, Proteus mirabilis, Campylobacter jejuni, Chlamydia trachomatis* and *Neisseria gonorrhoeae*.

In some embodiments, the bacterial infection is caused by drug-resistant bacteria. Such drug-resistant bacteria are bacteria that are resistant to one or more antibacterials other than the compounds of formula (I) and/or (A1) described herein. The language "resistance" and "antibacterial resistance" "drug-resistant" refers to bacteria that are able to survive exposure to one or more antibacterial drugs. In some embodiments, the drug-resistant bacteria include *Enterococcus faecalis, Enterococcus faecium, Streptococcus pyogenes, Streptococcus agalactiae, Streptococcus pneumoniae* (including penicillin-resistant *Streptococcus pneumoniae*), *Staphylococcus aureus* (including vancomycin-resistant *Staphylococcus aureus* (VRSA)), methicillin-resistant *Staphylococcus aureus* (MRSA) (including hospital-acquired MRSA, community acquired MRSA and coagulase negative staphylocci), *Acinetobacter baumannii, Burkholderia multivorans, Burkholderia cenocepacia, Burkholderia cepacia, Klebsiella pneumoniae Pseudomonas aeruginosa, Escherichia coli, Enterobacter cloacae, Enterobacter aerogenes* and *Neisseria gonorrhoeae* (including penicillin-resistant *Neisseria gonorrhoeae*).

In some embodiments, the drug-resistant bacteria is a multidrug-resistant bacteria (or multiple drug-resistant bacteria). The language "multidrug-resistant bacteria" refers to bacteria that is resistant to two or more of antibiotics from different categories of antibiotics typically used for the treatment of such bacterial infections, for example, tetracycline, penicillin, cephalosporins (e.g., ceftriazone or cefixime), glycopeptides (e.g. vancomycin), quinolones (e.g., norfloxacin, ciprofloxacin or ofloxacin), co-trimoxazole, sulfonamides, aminoglycosides (e.g., kanamycin or gentamicin) and macrolides (e.g., azithromycin).

In one aspect, the invention provides a method for treating anthrax, bronchitis, pneumonia, prostatitis, pyelonephritis, sinusitis, skin and skin structure infections, sexually transmitted disease or urinary tract infections in a subject in need thereof comprising administering an effective amount of a compound of formula (I) and/or (A1) and salts and solvates thereof.

Suitably, the invention provides a method for treating anthrax [suitably, inhalational anthrax (post exposure)], bronchitis (suitably, acute bacterial exacerbation of chronic bronchitis), pneumonia (suitably, nosocomial pneumonia and/or community-acquired pneumonia), prostatitis (suitably chronic bacterial prostatitis), pyelonephritis [suitably, acute pyelonephritis (mild to moderate)], sinusitis (suitably, acute bacterial sinusitis), skin and skin structure infections (suitably, uncomplicated skin and skin structure infections (mild to moderate) or complicated skin and skin structure infections), sexually transmitted disease or urinary tract infections [suitably, uncomplicated urinary tract infections (mild to moderate) or complicated urinary tract infections (mild to moderate)] in a subject in need thereof comprising administering an effective amount of a compound of formula (I) and/or (A1) and salts and solvates thereof.

In one aspect, the invention provides a compound of formula (I) and/or (A1) and salts and solvates thereof, for use in treating anthrax, bronchitis, pneumonia, prostatitis, pyelonephritis, sinusitis, skin and skin structure infections, sexually transmitted disease or urinary tract infections.

Suitably, the invention provides a compound of formula (I) and/or (A1) and salts and solvates thereof, for use in treating anthrax [suitably, inhalational anthrax (post exposure)], bronchitis (suitably, acute bacterial exacerbation of chronic bronchitis), pneumonia (suitably, nosocomial pneumonia and/or community-acquired pneumonia), prostatitis (suitably chronic bacterial prostatitis), pyelonephritis [suitably, acute pyelonephritis (mild to moderate)], sinusitis (suitably, acute bacterial sinusitis), skin and skin structure infections (suitably, uncomplicated skin and skin structure infections (mild to moderate) or complicated skin and skin structure infections), sexually transmitted disease or urinary tract infections [suitably, uncomplicated urinary tract infections (mild to moderate) or complicated urinary tract infections (mild to moderate)].

In one aspect, the invention provides a pharmaceutical composition comprising a compound of formula (I) and/or (A1) and salts and solvates thereof, for use in treating anthrax, bronchitis, pneumonia, prostatitis, pyelonephritis, sinusitis, skin and skin structure infections, sexually transmitted disease or urinary tract infections.

Suitably, the invention provides a pharmaceutical composition comprising a compound of formula (I) and/or (A1) and salts and solvates thereof, for use in treating anthrax

[suitably, inhalational anthrax (post exposure)], bronchitis (suitably, acute bacterial exacerbation of chronic bronchitis), pneumonia (suitably, nosocomial pneumonia and/or community-acquired pneumonia), prostatitis (suitably chronic bacterial prostatitis), pyelonephritis [suitably, acute pyelonephritis (mild to moderate)], sinusitis (suitably, acute bacterial sinusitis), skin and skin structure infections (suitably, uncomplicated skin and skin structure infections (mild to moderate) or complicated skin and skin structure infections), sexually transmitted disease or urinary tract infections [suitably, uncomplicated urinary tract infections (mild to moderate) or complicated urinary tract infections (mild to moderate)].

One of ordinary skill in the art is readily able to determine whether or not a candidate compound treats a bacterial infection by, for example, assays (such as those described in the examples) which may be used to determine the activity of a particular compound.

Suitably, subjects are human or non-human mammals. Examples of non-human mammals include livestock animals such as sheep, horses, cows, pigs, goats, rabbits and deer; and companion animals such as cats, dogs, rodents, and horses.

More suitably subjects are human.

Formulation and Compositions

In some aspects, the present invention provides a pharmaceutical composition comprising a compound of formula (I) and/or (A1) and a pharmaceutically acceptable carrier or diluent.

Suitably the pharmaceutical composition further comprises an efflux pump inhibitor that reduces the ability of bacterial cells to pump the therapeutic compounds of the invention out of the cell. In some aspects, the pharmaceutical composition further comprise an efflux pump inhibitor and an agent for increasing the permeability of bacterial membranes.

In one aspect, suitably the pharmaceutical composition further comprises an agent for increasing the permeability of bacterial membranes.

In one aspect, the present invention provides a kit comprising: (i) a compound of formula (I) and/or (A1) and salts and solvates thereof; (ii) an agent for increasing the permeability of bacterial membranes; and/or (iii) an efflux pump inhibitor. Thus, this kit may comprise components (i) and (ii); components (i) and (iii); or components (i), (ii) and (iii). The components of the kit may be administered separately, simultaneously or sequentially in any order.

Suitably the efflux pump inhibitor in the pharmaceutical composition or in the kit is selected from a group of compounds which inhibits the action of one or more type of efflux pump, namely the major facilitator superfamily (MFS), small multidrug resistance (SMR), resistance nodulation cell division (RND), multidrug and toxic agents extrusion (MATE) and the ATP-binding cassette (ABC) families. More suitably the efflux pump inhibitor is selected from 3-chlorophenylhydrazone, chlorpromazine, 1-(1-Naphthylmethyl)-Piperazine, Pyridopyrimidinone Analogs, Pyranopyridines, phenylalanine-arginine β-naphthylamide and combinations thereof.

Suitably, the agent for increasing the permeability of bacterial membranes in the pharmaceutical composition or in the kit is selected from polymyxins, lipopeptides (e.g. daptomycin), antimicrobial peptides (e.g. morian and melittin), polycationic compounds (e.g. bis-guanidines [e.g. chlorhexidine digluconate]); quaternary ammonium compounds ([e.g. benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide]; and polyhexanide), zeamines (38) (e.g. zeamine, zeamine I and zeamine II) and phage endolysins (39-42).

More suitably, the agent for increasing the permeability of bacterial membranes in the pharmaceutical composition or in the kit is a polymyxin. More suitably, the polymyxin is selected from a polymixin B, polymyxin C and bacitracin. More suitably the polymyxin is polymyxin B nonapeptide.

Administration & Dose

Compounds of formula (I) and/or (A1) may be administered alone or in combination with one or another or with one or more pharmacologically active compounds which are different from the compounds of formula (I), and/or (A1)

Compounds of the invention may suitably be combined with various components to produce compositions of the invention. Suitably the compositions are combined with a pharmaceutically acceptable carrier or diluent to produce a pharmaceutical composition (which may be for human or animal use). Suitable carriers and diluents include isotonic saline solutions, for example phosphate-buffered saline. Useful pharmaceutical compositions and methods for their preparation may be found in standard pharmaceutical texts. See, for example, *Handbook for Pharmaceutical Additives*, 3rd Edition (eds. M. Ash and I. Ash), 2007 (Synapse Information Resources, Inc., Endicott, New York, USA) and *Remington: The Science and Practice of Pharmacy*, 21st Edition (ed. D. B. Troy) 2006 (Lippincott, Williams and Wilkins, Philadelphia, USA) which are incorporated herein by reference.

The compounds of the invention may be administered by any suitable route. Suitably the compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form.

The compounds of the invention, their pharmaceutically acceptable salts, and pharmaceutically acceptable solvates can be administered alone but will generally be administered in admixture with a suitable pharmaceutical excipient diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and combinations thereof. Modified release and pulsatile release dosage forms may contain one or a combination of release rate modifying excipients. Release rate modifying excipients may be present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intravenously, intra-arterially, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Suitably formulation of the invention is optimised for the route of administration e.g. oral, intravenously, etc.

Administration may be in one dose, continuously or intermittently (e.g. in divided doses at appropriate intervals) during the course of treatment. Methods of determining the most effective means and dosage are well known to a skilled person and will vary with the formulation used for therapy, the purpose of the therapy, the target cell(s) being treated, and the subject being treated. Single or multiple administrations can be carried out with the dose level and the dose regimen being selected by the treating physician, veterinarian, or clinician.

Depending upon the disorder and patient to be treated, as well as the route of administration, the compositions may be administered at varying doses. For example, a typical dosage for an adult human may be 100 ng to 25 mg (suitably about 1 micro g to about 10 mg) per kg body weight of the subject per day.

Suitably guidance may be taken from studies in test animals when estimating an initial dose for human subjects. For example when a particular dose is identified for mice, suitably an initial test dose for humans may be approx. 0.5× to 2× the mg/Kg value given to mice.

The compound of formula (I) and/or (A1) may be administered once, twice, three times a day or as many times in a 24 hour period as medically necessary. One of skill in the art would readily be able to determine the amount of each individual dose based on the subject. In some embodiments, the compound of formula (I) and/or (A1) is administered in one dosage form. In some embodiments, the compound of formula (I) and/or (A1) is administered in multiple dosage forms.

Doses are mg/Kg/day for humans unless otherwise stated.

The amount of active ingredient that is combined with one or more excipients to produce a single dosage form will necessarily vary depending upon the host treated and the particular route of administration. Further information on formulation, on routes of administration and on dosage regimes may be found in Chapter 25.2 and 25.3 in Volume 5 of Comprehensive Medicinal Chemistry (Corwin Hansch; Chairman of Editorial Board), Pergamon Press 1990.

Other Forms Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N+HR'R''), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (—) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH.

A reference to a class of structures may well include structurally isomeric forms falling within that class (e.g. C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Some of the compounds of formula (I) and/or (A1) exist in an equilibrium of tautomeric forms, such as for example, the keto-enol tautomers of compound ML-77-058 as prepared in synthesis of compound 2.14. The tautomeric forms may be shown as follows:

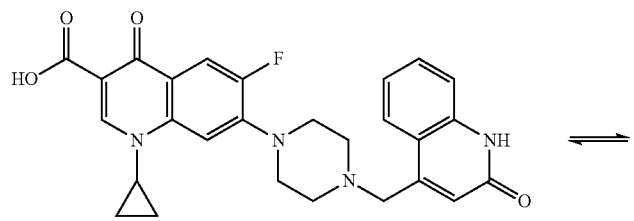 ⇌ 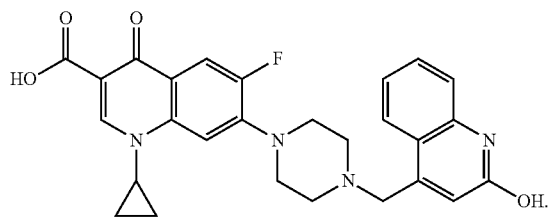

For convenience, this compounds is shown in the single keto form in this specification. However, claims covering such compounds cover all the tautomeric forms for such compounds.

Note that specifically included in the term "isomer" are compounds with one or more isotopic substitutions. For example, H may be in any isotopic form, including 1H, 2H (D), and 3H (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other combinations thereof.

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

Compounds of Formula (I) and/or (A1), which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —$NH_2$ may be —$NH_3^+$), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —$COO^-$), then a base salt may be formed with a suitable cation.

Examples of suitable inorganic cations include, but are not limited to, metal cations, such as an alkali or alkaline earth metal cation, ammonium and substituted ammonium cations, as well as amines. Examples of suitable metal cations include sodium ($Na^+$) potassium ($K^+$), magnesium ($Mg^{2+}$), calcium ($Ca^{2+}$), zinc ($Zn^{2+}$), and aluminum ($Al^{3+}$). Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$. Examples of suitable amines include arginine, N,N'-dibenzylethylene-diamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011)

Pharmaceutically acceptable salts may be prepared using various methods. For example, one may react a compound of Formula (I) and/or (A1) with an appropriate acid or base to give the desired salt. One may also react a precursor of the compound of Formula (I) and/or (A1) with an acid or base to remove an acid- or base-labile protecting group or to open a lactone or lactam group of the precursor. Additionally, one may convert a salt of the compound of Formula (I) and/or (A1) to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

These compounds may be isolated in solid form, for example, by lyophilisation.

Further particular and preferred aspects are set out in the accompanying independent and dependent claims. Features of the dependent claims may be combined with features of the independent claims as appropriate, and in combinations other than those explicitly set out in the claims.

BRIEF DESCRIPTION OF THE DRAWINGS

Embodiments of the present invention will now be described further, with reference to the accompanying drawings, in which:

FIG. 27A-27G show reserpine growth assay in several multidrug resistant strains for various 5-membered pyrrolidine ring with exocyclic amine containing ARB fragment compounds (FIGS. 27C, 27D, 27F & 27G) and for 6-membered piperizine ring containing compounds ML-83-009 (FIG. 27A) and Levofloxacin (FIGS. 27B & 27E).

EXPERIMENTAL

Figure 1:
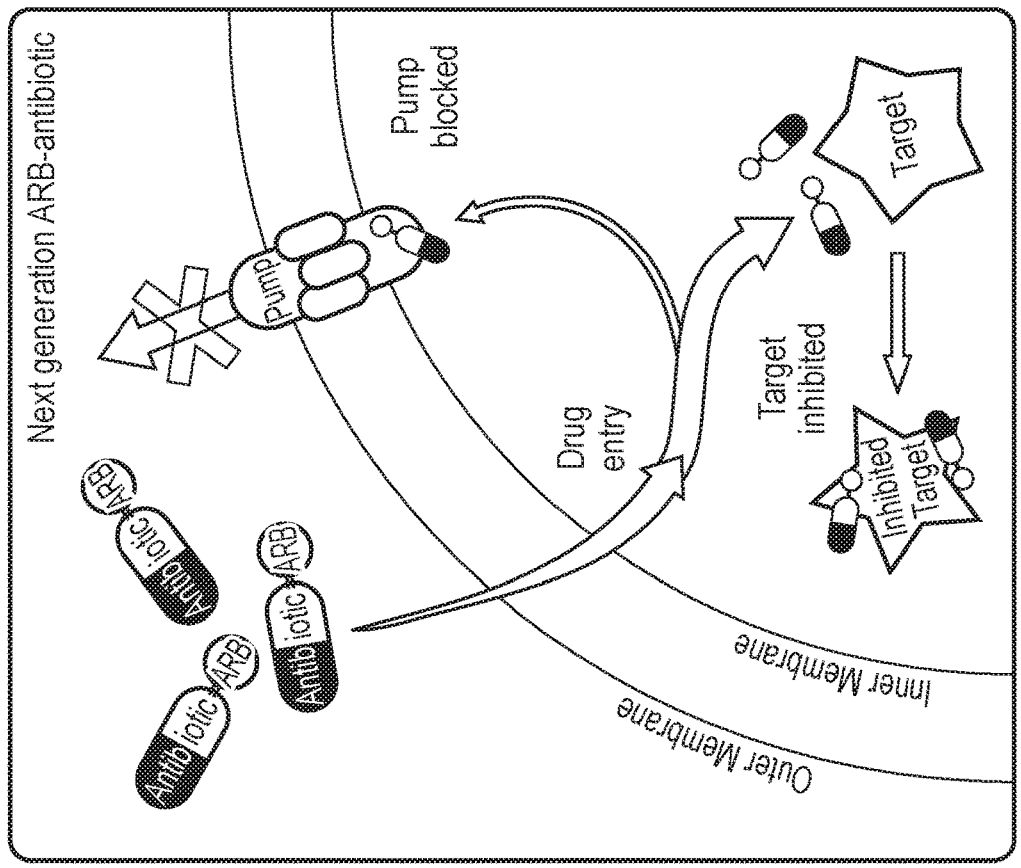
FIG. 1 shows the next generartion ARB-antibiotic approach reduces pump-mediated drug efflux and increases on-target antibacterial efficacy.
Figure 1:
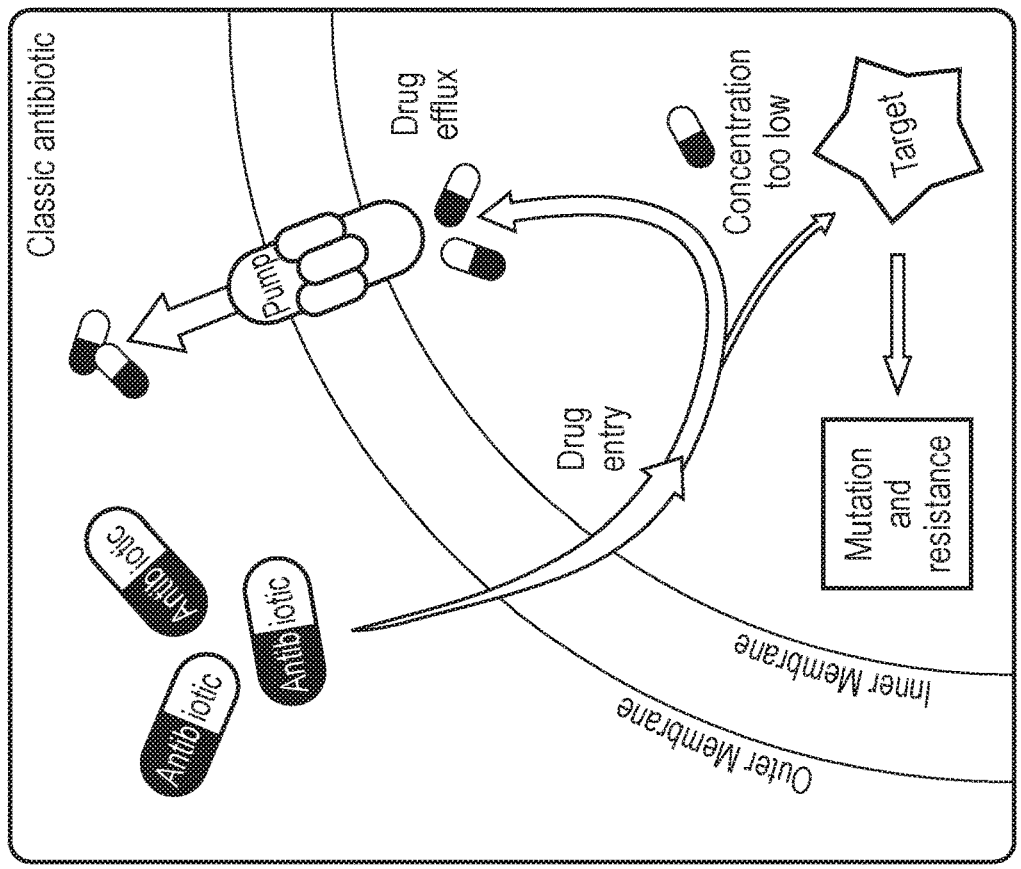

Methods and Materials
Reagent Sources

Synthetic building blocks and reagents were purchased from a number of suppliers including Sigma-Aldrich (Merck KGaA, USA), Thermo Fisher Scientific (UK, including Acros Organics, Maybridge and Alfa Aesar), Fluorochem (USA), Insight Biotechnology (UK), Activate Scientific (UK), Enamine (Ukraine), VWR International (USA), Oxchem (USA), Apollo Scientific (UK), Combi-Blocks (USA) and Ark Pharm Inc (USA). Solvents were purchased from Sigma-Aldrich and Thermo Fisher Scientific. SCX-2 solid phase extraction cartridges were purchased from Biotage (Sweden).

Microwave Reactions

Microwave reactions were performed in a Biotage Initiator+Microwave Synthesiser fitted with a pressurised air supply for cooling. Vessels were stirred at 600 RPM and cooled to below 40° C. before finishing a reaction.

Bacterial Strains

The bacterial strains used in the biological tests were obtained from type culture collections, in particular, ATCC, the National Collection of Culture Types (NCTC) and the Belgium Coordinated Collection of Microorganisms. In some cases the strains have been previously described 25-27).

Thin Layer Chromatography (TLC)

Thin-layer chromatography (TLC) analysis was performed using silica gel plates (Merck silica gel 60 $F_{254}$ plates) and visualised using ultraviolet (UV) light (254 nm wavelength) and/or staining with potassium permanganate solution.

Flash Column Chromatography

Manual flash column chromatography was performed using silica gel (Merck 9385, 230-400 mesh ASTM, 40-63 μM) as the stationary phase. TLC was employed to discern solvent systems (mobile phases) with appropriate separation profiles and were comprised of hexanes, ethyl acetate, dichloromethane and methanol. Purification of tertiary amine-containing compounds was expedited through pre-neutralisation of the stationary phase via the addition of 3% triethylamine to the initial non-polar solvent wash, i.e. in the non-polar mobile phase component prior to running the column.

Automated flash column chromatography is an air pressure-driven hybrid of medium pressure and short column chromatography, optimized for rapid separations on the basis of UV and ELSD detection. It was performed using a Reveleris® X2 Flash Chromatography System. Normal phase separations were carried out on Grace™ Reveleris™ Silica Flash Cartridges. Reverse phase separations were carried out on Biotage® SNAP Ultra C18 Cartridges. This technique was employed for the separation of particularly difficult mixtures of compounds with similar Rf values. This technique was employed for the separation of particularly difficult mixtures of compounds, such as tertiary amine-containing compounds, with similar Rf values.

Mass-Directed Reverse-Phase High Performance Liquid Chromatography (HPLC)

Mass-Directed Reverse-Phase High Performance Liquid Chromatography (HPLC) was performed on an Agilent 1290 Infinity II Preparative LC/MSD System fitted with the following subunits; 1290 MS Flow Modulator, 1290 Prep Fraction Collector, 1290 Prep Column Compartment, 1290 Prep Bin Pump, 1260 Prep Autosampler, 1260 DAD WR, 1260 Quat Pump and InfinityLab LC/MSD. The column used was a Phenomenex Luna® 5 μm C18(2) 100 Å LC column, 100×21.2 mm. Mobile phases were water (A) and acetonitrile (B); formic acid (0.1%) was added through a separate channel to ensure acidic conditions throughout the purification method. The following methods were employed for compound purification;

Method 1 (10 min): Flow rate 20 mL/min.
i) 95% A/5% B for one minute;
ii) from 95% A/5% B to 70% A/30% B over a further minute;
iii) from 70% A/30% B to 50% A/50% B over 3.5 minutes;
iv) from 50% A/50% B to 10% A/90% B over 1.5 minutes;
v) from 10% A/90% B to 80% A/20% B over 30 seconds;
vi) held constant at 80% A/20% B for a further minute.

Purification Via Recrystallisation

Purification of compounds via recrystallisation was achieved by dissolving the crude compound in the minimum volume of a hot solvent of choice, then covering the container and leaving it to cool to room temperature gradually until crystal formation was observed. Any insoluble contaminants or byproducts were removed by employing a hot filtration step prior to cooling. Slow crystallisations were further cooled to −20° C. from room temperature to expedite crystal formation.

Liquid Chromatography-Mass Spectrometry (LC-MS)

Liquid chromatography-mass spectrometry (LC-MS) was employed to monitor reaction progression and compound identification. All LC-MS analysis was performed on a Waters Alliance 2695 with water (A) and acetonitrile (B) comprising the mobile phases. Formic acid (0.1%) was added to both acetonitrile and water to ensure acidic conditions throughout the analysis. Function type: Diode array (535 scans). Column type: Monolithic C18 50×4.60 mm. Mass spectrometry data (both ESI+ and ESI− modes) were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; De-solvation Temperature (° C.), 200; Cone flow rate (L/h), 50; De-solvation flow rate (L/h), 250. LC-MS gradient conditions are described as follows;

Method A (5 min): (i) from 95% A/5% B to 50% A/50% B over 3 min. (ii) Then from 50% A/50% B to 20% A/80% B over 2 min. (iii) Then from 20% A/80% B to 5% A/95% B over 1.5 min and (iv) held constant at 5% A/95% B for 1.5 min. (v) This was then reduced from 5% A/95% B to 95% A/5% B over 0.2 min and (iv) maintained to 95% A/5% B for 1.8 min. The flow rate was 0.5 mL/min, 200 μL was split via a zero dead volume T piece which passed into the mass spectrometer. The wavelength range of the UV detector was 220-400 nm.

Method B (5 min): (i) from 95% A/5% B to 10% A/90% B over 3 min. (ii) Then from 10% A/90% B to 5% A/95% B over 0.5 min and (ii) held constant at 5% A/95% B for 1 min. (iv) This was then reduced from 5% A/95% B to 95% A/5% B over 0.5 min. The flow rate was 1.0 mL/min, 100

μL was split via a zero dead volume T piece which passed into the mass spectrometer. The wavelength range of the UV detector was 220-500 nm.

High Resolution Mass Spectrometry (HRMS)

High resolution mass spectra (HRMS) were obtained on a Thermo Navigator mass spectrometer coupled with liquid chromatography (LC) using electrospray ionisation (ES) and time-of-flight (TOF) mass spectrometry.

Infrared Spectroscopy (IR)

Infrared spectra (IR) were recorded on a Perkin Elmer spectrum 1000 instrument. Compounds were analysed in solid form.

Nuclear Magnetic Resonance Spectroscopy (NMR)

All NMR spectra were obtained at room temperature using a Bruker DPX400 spectrometer. Chemical shifts (δ H) are expressed in parts per million (ppm) relative to deuterated chloroform (CDCl$_3$ or CHLOROFORM-d, residual signal $^1$H δ=7.26, $^{13}$C δ=77.2) or deuterated dimethyl sulfoxide (DMSO-d$_6$, residual signal $^1$H δ=2.54, $^{13}$C δ=40.45) or deuterated methanol (METHANOL-d$_4$, residual signal $^1$H δ=3.31, $^{13}$C δ=49.0). Coupling constants are expressed in Hz. Multiplicities in $^1$H NMR spectra are quoted as s=singlet, d=doublet, t=triplet q=quartet, m=multiplet, dd=doublet of doublets, ddd=doublet of doublet of doublets, dt=doublet of triplets, td=triplet of doublets, spt=septet and br=broad. The code (o) in $^{13}$C NMR spectra denotes the presence of a quaternary carbon.

Solid Phase Extraction

SCX-2 resin cartridges, purchased from Biotage (Uppsala, Sweden), contain propylsulfonic acid-functionalised silica, a strong cation exchange sorbent primarily used for basic drug extraction. Cartridges (1 g, 2 g, 10 g) were selected based on reaction scale; sorbent mass should be 10 times that of the calculated mass of the product. Cartridges were first activated by an initial wash with 2 column volumes of dichloromethane and 4 column volumes of methanol. The reaction mixtures were then poured onto the cartridge and the solvent allowed to pass through the cartridges under gravity. The cartridges were then washed with dichloromethane (3 times), dimethylformamide (3 times) and methanol (1 time) and this cycle was repeated three times under vacuum to remove impurities. Products were eluted using 2M ammonia solution in methanol and concentrated in vacuo.

Purification Via Trituration

Trituration is the process of purifying a compound from a mixture based on the different solubility profiles of the mixture's constituents. A solvent (either polar or non-polar) was selected in which the desired product was poorly soluble and the unwanted by-products were highly soluble. The crude material was suspended in the solvent, filtered and washed again, leaving the purified product in solid form and any impurities in solution.

Lyophilisation

Lyophilisation (freeze-drying, cryodesiccation) was carried out on a Frozen in Time Lablyo bench top freeze drier connected to an Edwards RV vacuum pump. Samples, dissolved in water or mixtures of water and acetonitrile, were frozen solid in a dewar of dry ice before being connected to the lyophiliser unit Organic Synthesis Synthesis of Levofloxacin Based Fluoroquinolone Core for ARB Fragment Attachment Synthesis of ethyl (R,Z)-3-((1-hydroxypropan-2-yl)amino)-2-(2,3,4,5-tetrafluorobenzoyl) acrylate (A1.2)

Ethyl 2,3,4,5-tetrafluorobenzoylacetate (A1.1; 5 g, 18.9 mmol, 1 eq) was dissolved in triethyl orthoformate (6.30 mL, 37.9 mmol, 2 eq) and heated at 140° C. for 30 minutes. Acetic anhydride (5.37 mL, 56.8 mmol, 3 eq) was then added and the mixture refluxed at 140° C. for another 40 hours and monitored by TLC (10% ethyl acetate/90% hexanes). Upon completion, the reaction was cooled to room temperature, dichloromethane (15 mL) was added and the mixture stirred at room temperature for 5 minutes. Then L-alaninol (3.01 mL, 37.9 mmol, 2 eq) was added and the reaction was stirred for 48 hours at room temperature. Then a further 2 eq. of L-alaninol was added, and the reaction stirred for a further 48 hours. The crude was concentrated in vacuo and purified by flash column chromatography (1:1 ethyl acetate/hexanes rising to 3:1 ethyl acetate/hexanes) to give A1.2 (5.768 g, 87.3% yield) as a yellow oil.

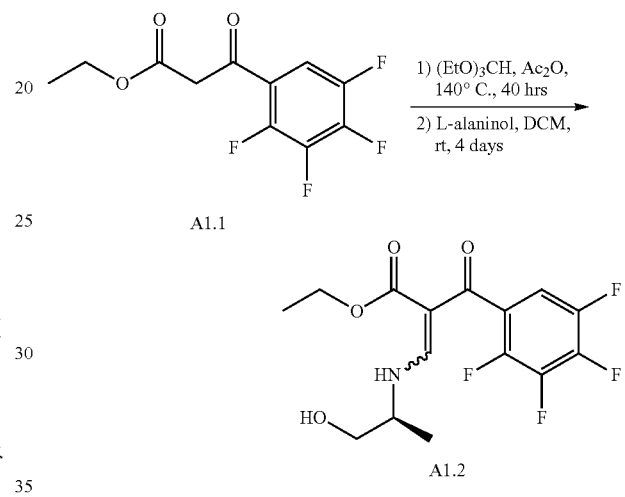

$^1$H NMR (400 MHz, CHLOROFORM-d) δ 10.93 (br. s., 0.75H, H5), 9.58 (br. s., 0.25H, H5), 8.21 (d, J=14.21 Hz, 1H, H1), 7.10 (br. s., 0.25H, H4), 6.98 (br. s., 0.75H, H4), 3.93-4.19 (m, 2H, H2), 3.73-3.85 (m, 1H, H6), 3.56-3.72 (m, 2H, H8), 2.44 (br. s., 1H, H9), 1.31-1.42 (m, 3H, H7), 1.10 (t, J=7.06 Hz, 2.25H, H3), 0.98 (t, J=6.24 Hz, 0.75H, H3); $^{13}$C NMR (100 MHz, CHLOROFORM-d) δ 186.9, 185.1, 168.3, 166.6, 159.9, 159.4, 148.4, 145.6, 145.5, 142.9, 141.4, 138.8, 127.2, 127.1, 110.7, 110.5, 109.9, 109.7, 101.0, 66.1, 60.0, 59.7, 57.9, 57.4, 17.0, 14.0, 13.6; LC-MS (Method B) Retention time 3.35 minutes, purity=100%, Found 350.1 [M+H]$^+$; calculated for C$_{15}$H$_{15}$F$_4$NO$_4$ 350.29 [M+H]$^+$; R$_f$ 0.81 (100% ethyl acetate).

Synthesis of ethyl (S)-9,10-difluoro-3-methyl-7-oxo-2,3-dihydro-7H-[1,4]oxazino[2,3,4-ij]quinoline-6-carboxylate (A1.3)

Compound A1.2 (5.933 g, 16.99 mmol, 1 eq) was dissolved in dimethyl acetamide (40 mL) and stirred for 5 mins to dissolve. The solution was then divided evenly into two 20 mL capacity microwave vessels fitted with magnetic stirrer bars and potassium carbonate (7.043 g, 50.96 mmol, 3 eq.) was divided evenly and added to the two vessels. Each microwave vessel was then, in turn, microwaved at 160° C. for 20 minutes. Upon cooling, the contents of each vessel was added to dichloromethane (200 mL) and washed with distilled water (300 mL). The organic layers were combined and washed two further times with distilled water (2×100 mL). The organics were dried over Na$_2$SO$_4$, decanted and concentrated in vacuo to afford crude A1.3 (4.651 g, 88.5% yield) as an off white solid. This material was used in subsequent reactions without further purification.

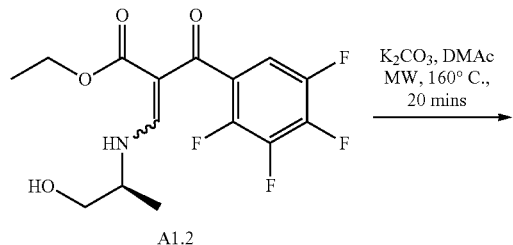

A1.2

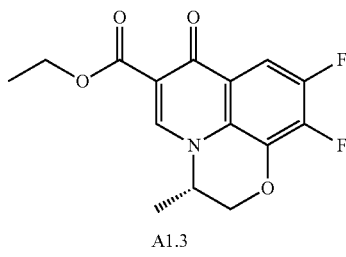

A1.3

$^1$H NMR (400 MHz, CHLOROFORM-d) δ 8.36 (s, 1H, H4), 7.76 (dd, J=8.07, 10.18 Hz, 1H, H1), 4.40-4.52 (m, 3H, H5+6), 4.36 (q, J=7.00 Hz, 2H, H2), 1.60 (d, J=6.51 Hz, 3H, H7), 1.39 (t, J=7.02 Hz, 3H, H3); $^{13}$C NMR (100 MHz, DMSO-d$_6$) δ 171.1, 164.2, 149.7, 149.4, 149.3, 149.1, 146.6, 135.4, 135.2, 124.4, 124.4, 123.7, 123.7, 109.8, 103.8, 103.6, 68.8, 59.9, 53.8, 17.6, 14.3; 19F NMR (400 MHz, CHLOROFORM-d) δ −136.4 (d, J=21.46 Hz, 1F), −151.3 (d, J=21.45 Hz, 1F); LC-MS (Method B) Retention time 2.85 minutes, purity=75%, Found 310.1 [M+H]$^+$; calculated for C$_{15}$H$_{13}$F$_2$NO$_4$ 310.28 [M+H]$^+$; [α]$^{25.3}$D, −43° (c=0.117, CH$_2$Cl$_2$)

Synthesis of (S)-9,10-difluoro-3-methyl-7-oxo-2,3-dihydro-7H-[1,4]oxazino[2,3,4-ij]quinoline-6-carboxylic acid (A1.4)

To compound A1.3 (2.018 g, 6.53 mmol, 1 eq) was added ethanol (20 mL) and a 15% w/v aqueous solution of sodium hydroxide (20 mL) and the suspension stirred at room temperature for one hour. The mixture was then acidified to pH 3 using a 1M hydrochloric acid and a few drops of 37% hydrochloric acid, vacuum filtered and washed with distilled water (3×100 mL). Powder was collected and dried for 1 hour more on a Schlenk line to afford the crude A1.4 (1.599 g, 87.2% yield) as an off white solid. This material was used in subsequent reactions without further purification.

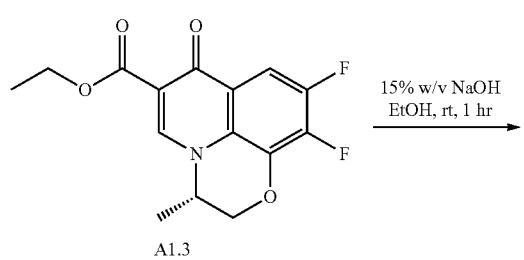

A1.3

-continued

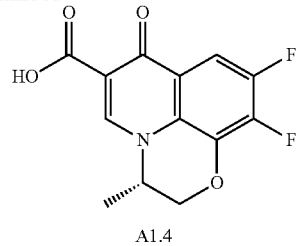

A1.4

$^1$H NMR (400 MHz, DMSO-d$_6$) δ 14.80 (s, 1H, H2), 9.09 (s, 1H, H3), 7.80 (dd, J=7.79, 10.36 Hz, 1H, H1), 5.02 (q, J=6.48 Hz, 1H, H5), 4.64-4.73 (m, 1H, H4), 4.44-4.55 (m, 1H, H4), 1.47 (d, J=6.79 Hz, 3H, H6); $^{13}$C NMR (100 MHz, DMSO-d$_6$) δ 176.4, 176.4, 165.6, 150.2, 150.1, 147.7, 147.6, 147.1, 143.0, 142.8, 140.5, 140.3, 136.0, 135.9, 135.9, 135.8, 125.3, 125.3, 121.4, 121.4, 121.3, 121.3, 107.7, 103.6, 103.4, 68.9, 55.0, 17.8; $^{19}$F NMR (400 MHz, DMSO-d$_6$) δ−135.9 (d, J=22.47 Hz, 1F), −151.0 (d, J=22.48 Hz, 1F); LC-MS (Method B) Retention time 3.11 minutes, purity=81%, Found 282.1 [M+H]$^+$; calculated for C$_{13}$H$_9$F$_2$NO$_4$ 282.22 [M+H]$^+$; R$_f$ 0.30, streaks (100% acetone); [α]$^{25.9}$D, −20° (c=0.088, CH$_2$Cl$_2$)

Compound 1.4 was used in the synthesis of all of the ARB-linked fluoroquinolones.

Synthesis of (S)-9,10-difluoro-3-methyl-8-nitro-7-oxo-2,3-dihydro-7H-[1,4]oxazino[2,3,4-ij]quinoline-6-carboxylic acid (A1.5)

Compound A1.4 (818.9 mg, 2.91 mmol, 1 eq) was dissolved in 96% sulphuric acid (5 mL) and cooled to 0° C. over 10 minutes. Then potassium nitrate (589 mg, 5.82 mmol, 2 eq) was added in small portions with stirring over 15 minutes. The reaction was subsequently allowed to warm to room temperature over 15 more minutes. The reaction was quenched over 200 mL of ice/water slurry, then extracted with dichloromethane (3×30 mL washes). Organic layers were combined, dried over MgSO$_4$, filtered and concentrated in vacuo to afford the crude A1.5 (760.7 mg, 80.1% yield) as a pink solid. This material was used in subsequent reactions without further purification.

¹H NMR (400 MHz, DMSO-d₆) δ 13.80 (br. s., 1H, H1), 9.16 (s, 1H, H2), 5.09 (q, J=6.66 Hz, 1H, H4), 4.77 (dd, J=1.33, 11.42 Hz, 1H, H3), 4.52 (dd, J=2.06, 11.42 Hz, 1H, H3), 1.47 (d, J=6.79 Hz, 3H, H5); ¹³C NMR (100 MHz, DMSO-d₆) δ 173.8, 173.8, 164.6, 148.1, 143.3, 143.2, 142.1, 142.0, 140.8, 140.7, 139.6, 139.4, 137.8, 137.7, 137.6, 137.6, 128.9, 128.8, 125.2, 125.1, 113.1, 113.1, 109.2, 69.1, 55.4, 17.8; ¹⁹F NMR (400 MHz, DMSO-d₆) δ −148.1 (d, J=23.16 Hz, 1F), −149.7 (d, J=22.82 Hz, 1F); LC-MS (Method B) Retention time 3.27 minutes, purity=97%, Found 326.9 [M+H]⁺; calculated for C₁₃H₈F₂N₂O₆ 327.22 [M+H]⁺

Synthesis of (S)-8-amino-9,10-difluoro-3-methyl-7-oxo-2,3-dihydro-7H-[1,4]oxazino[2,3,4-ij]quinoline-6-carboxylic acid (A1.6)

Compound A1.5 (711.6 mg, 2.18 mmol, 1 eq) was dissolved in N,N-dimethylformamide (12 mL) and added to a hydrogenation vessel. Palladium on carbon (233 mg, 0.22 mmol, 0.1 eq) was subsequently added to the vessel in N,N-dimethylformamide (1 mL). The mixture was then hydrogenated at 30 psi for 2 hours, whereupon the pressure stabilized, indicating reaction completion. The mixture was vacuum filtered through two successive celite plugs, washing each time with dichloromethane (3×20 mL per plug). The combined filtrate was concentrated in vacuo to afford crude A1.6 (250.9 mg, 38.8% yield) as a yellow solid. This material was used in subsequent reactions without further purification.

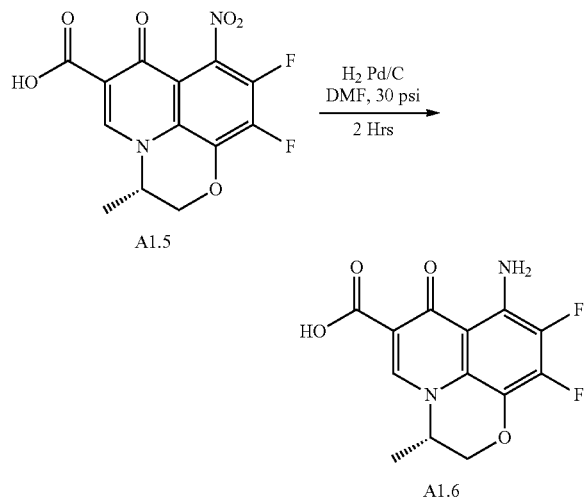

¹H NMR (400 MHz, DMSO-d₆) δ 14.70 (br. s., 1H, H2), 8.89 (s, 1H, H3), 7.26 (br. s., 2H, H1), 4.79-4.97 (m, 1H, H5), 4.48 (d, J=11.19 Hz, 1H, H4), 4.22 (d, J=11.37 Hz, 1H, H4), 1.41 (d, J=6.60 Hz, 3H, H6); ¹³C NMR (100 MHz, DMSO-d₆) δ 180.4, 180.3, 165.6, 147.2, 144.2, 144.1, 141.7, 141.6, 136.3, 136.1, 134.2, 134.2, 134.1, 134.1, 133.9, 133.8, 124.5, 124.5, 124.5, 124.5, 122.7, 122.6, 122.5, 107.0, 107.0, 106.9, 106.3, 67.4, 55.6, 17.8; ¹⁹F NMR (400 MHz, DMSO-d₆) δ −149.8 (d, J=21.80 Hz, 1F), −162.8 (d, J=21.80 Hz, 1F); LC-MS (Method B) Retention time 3.08 minutes, purity=97%, Found 297.0 [M+H]⁺; calculated for C₁₃H₁₀F₂N₂O₄ 297.24 [M+H]⁺.

Synthesis of (S)-9-fluoro-3-methyl-7-oxo-10-(4-(pyrimidin-4-yl)piperazin-1-yl)-2,3-dihydro-7H-[1,4]oxazino[2,3,4-ij]quinoline-6-carboxylic acid (A1.7)

Compound A1.4 (1.37 g, 4.87 mmol, 1 eq) was dissolved in N,N-dimethylformamide (20 mL) with 4-(piperazin-1-yl)pyrimidine (1.00 g, 6.09 mmol, 1.25 eq) and stirred at 140° C. for 90 hours. Upon cooling, the mixture was added to 50 mL dichloromethane and washed with 100 mL brine (back extracted with 50 mL more dichloromethane) and 100 mL distilled water. Organic layers were combined, dried over MgSO₄, filtered and concentrated in vacuo to yield the crude product. Purification was achieved via flash column chromatography (100% dichloromethane to 100% acetonitrile to 1% water/acetonitrile; product subsequently eluted with 2M ammonia in methanol). Pure fractions were concentrated in vacuo, re-dissolved in dichloromethane, filtered and concentrated again to afford A1.7 (234.4 mg, 18.1% yield) as an orange solid.

¹H NMR (400 MHz, CHLOROFORM-d) δ 14.92 (br. s., 1H, H2), 8.66 (s, 1H, H3), 8.62 (s, 1H, H13), 8.24 (d, J=6.29 Hz, 1H, H11), 7.71 (d, J=12.09 Hz, 1H, H1), 6.56 (d, J=6.29 Hz, 1H, H12), 4.53-4.64 (m, 1H, H5), 4.49 (d, J=11.33 Hz, 1H, H4), 4.41 (d, J=11.33 Hz, 1H, H4), 3.75-3.89 (m, 4H, H7+8), 3.36-3.50 (m, 4H, H9+10), 1.63 (d, J=6.80 Hz, 3H, H6); ¹⁹F NMR (400 MHz, CHLOROFORM-d) δ −119.1 (s, 1F); LC-MS (Method B) Retention time 2.70 minutes, purity=100%, Found 426.0 [M+H]⁺; calculated for C₂₁H₂₀FN₅O₄ 426.43 [M+H]⁺; R_f 0.31 (5% methanol in dichloromethane)

Synthesis of (S)-9-fluoro-10-(4-(2-isopropyl-6-methylpyrimidin-4-yl)piperazin-1-yl)-3-methyl-7-oxo-2,3-dihydro-7H-[1,4]oxazino[2,3,4-ij]quinoline-6-carboxylic acid (A1.8)

(S)-9,10-difluoro-3-methyl-7-oxo-2,3-dihydro-7H-[1,4]oxazino[2,3,4-ij]quinolone-6-carboxylic acid (A1.4; 128 mg, 0.45 mmol, 1 eq) and 2-isopropyl-4-methyl-6-(piperazin-1-yl)pyrimidine (100 mg, 0.45 mmol, 1 eq) were added to DMF (3 mL) and stirred at 140° C. for 1.5 hours. The mixture was allowed to cool and the crude concentrated in vacuo, then re-suspended in 3:1 distilled water:MeOH (20 mL) and filtered hot. Purification was achieved via automated flash column chromatography of the crude solid (see Flash Column Chromatography; 0%-50%-100% DCM/Acetone) to afford A1.8 (22.0 mg, 10.0%) as a light brown solid.

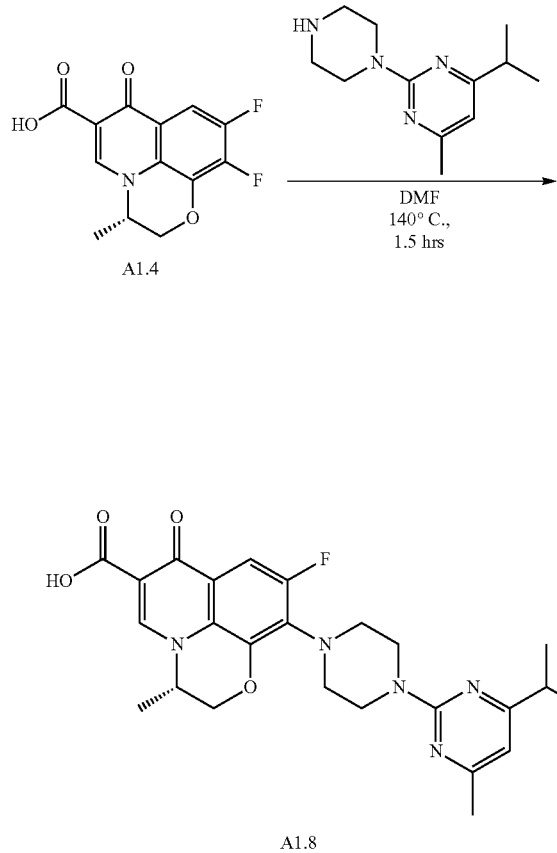

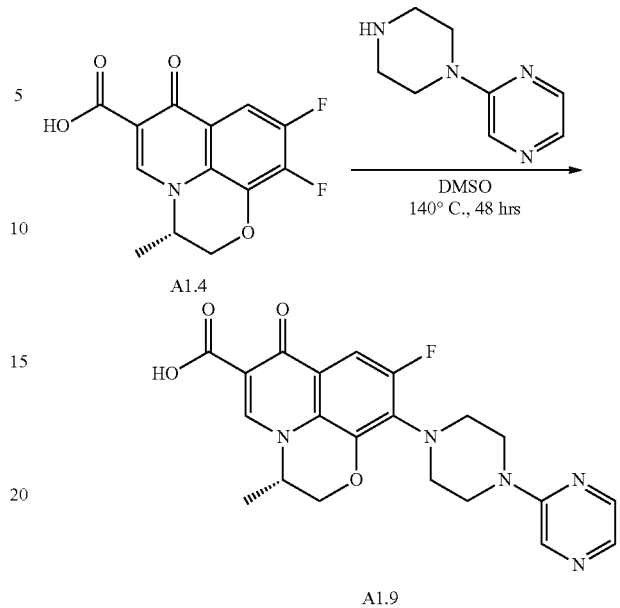

¹H NMR (400 MHz, CHLOROFORM-d) δ 14.92 (br. s., 1H, H2), 8.64 (s, 1H, H3), 7.76 (d, J=12.09 Hz, 1H, H1), 6.26 (s, 1H, H11), 4.44-4.58 (m, 2H, H4+5), 4.36-4.43 (m, 1H, H4), 3.85 (m, 4H, H7+8), 3.45 (td, J=5.07, 9.76 Hz, 4H, H9+10), 3.04-3.13 (m, 1H, H14), 2.41 (s, 3H, H12), 1.64 (d, J=6.55 Hz, 3H, H6), 1.29 (d, J=7.05 Hz, 6H, H13+15); ¹⁹F NMR (400 MHz, CHLOROFORM-d) δ −119.2 (s, 1F); LC-MS (Method B) Retention time 30.07 minutes, purity=100%, Found 482.0 [M+H]⁺; calculated for $C_{25}H_{28}FN_5O_4$ 482.53 [M+H]⁺

Synthesis of (S)-9-fluoro-3-methyl-7-oxo-10-(4-(pyrazin-2-yl)piperazin-1-yl)-2,3-dihydro-7H-[1,4]oxazino[2,3,4-ij]quinoline-6-carboxylic acid (A1.9)

Compound A1.4 (100.4 mg, 0.36 mmol, 1 eq) was dissolved in dimethyl sulfoxide (3 mL) with 2-(piperazin-1-yl)pyrazine (175.9 mg, 1.07 mmol, 3 eq) and stirred at 140° C. for 48 hours. Upon cooling, the mixture concentrated in vacuo before being purified via automated flash column chromatography (see Flash Column Chromatography; 5%-95% acetonitrile in water) to afford A1.9 as an orange solid.

¹H NMR (400 MHz, CHLOROFORM-d) δ 14.92 (br. s., 1H, H2), 8.64 (s, 1H, H3), 8.21 (d, J=1.10 Hz, 1H, H11), 8.07-8.14 (m, 1H, H12), 7.90 (d, J=2.57 Hz, 1H, H13), 7.76 (d, J=12.10 Hz, 1H, H1), 4.44-4.58 (m, 2H, H4+5), 4.36-4.44 (m, 1H, H4), 3.69-3.84 (m, 4H, H7+8), 3.41-3.58 (m, 4H, H9+10), 1.64 (d, J=6.60 Hz, 3H, H6); ¹⁹F NMR (400 MHz, CHLOROFORM-d) δ −119.10 (s, 1F); LC-MS (Method B) Retention time 30.23 minutes, purity=95%, Found 426.1 [M+H]⁺; calculated for $C_{21}H_{20}FN_5O_4$ 426.43 [M+H]⁺

Synthesis of (S)-9-fluoro-3-methyl-7-oxo-10-(4-(pyrimidin-2-yl)piperazin-1-yl)-2,3-dihydro-7H-[1,4]oxazino[2,3,4-ij]quinoline-6-carboxylic acid (A1.10)

Compound A1.4 (100 mg, 0.36 mmol, 1 eq) was dissolved in dimethyl sulfoxide (2 mL) with 2-(piperazin-1-yl)pyrimidine (146 mg, 0.89 mmol, 2.5 eq) in a 5 mL capacity microwave vessel fitted with a magnetic stirrer bar and microwaved at 200° C. for 20 minutes. Upon cooling, the mixture was filtered through a Mini-UniPrep™ polypropylene filter (0.45 μm pore size). Recrystallisation occurred upon leaving overnight; crystals were vacuum filtered and further concentrated in vacuo to afford A1.10 (37.2 mg, 24.6% yield) as an orange solid.

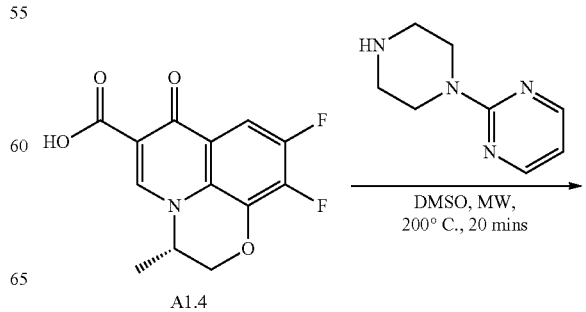

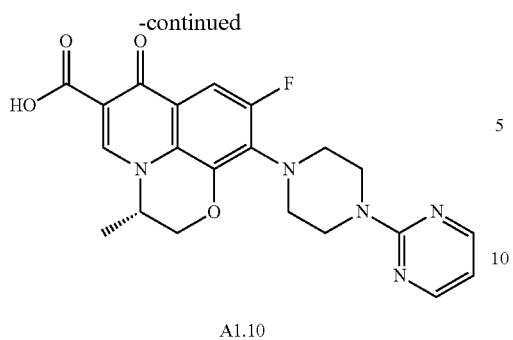

A1.10

$^1$H NMR (400 MHz, DMSO-d$_6$) δ 15.11 (br. s., 1H, H2), 8.97 (s, 1H, H3), 8.39 (d, J=4.68 Hz, 2H, H11+13), 7.58 (d, J=12.20 Hz, 1H, H1), 6.65 (t, J=4.72 Hz, 1H, H12), 4.93 (q, J=6.63 Hz, 1H, H5), 4.56-4.63 (m, 1H, H4), 4.35-4.44 (m, 1H, H4), 3.81-3.95 (m, 4H, H7+8), 3.33-3.41 (m, 4H, H9+10), 1.46 (d, J=6.69 Hz, 3H, H6); $^{19}$F NMR (400 MHz, DMSO-d$_6$) δ −120.70 (s, 1F);); LC-MS (Method A) Retention time 7.30 minutes, purity=100%, Found 426.1 [M+H]$^+$; calculated for C$_{21}$H$_{20}$FN$_6$O$_4$ 426.43 [M+H]$^+$; LC-MS (Method B) Retention time 3.34 minutes, purity=100%, Found 426.1 [M+H]$^+$; calculated for C$_{21}$H$_{20}$FN$_5$O$_4$ 426.43 [M+H]$^+$ Synthesis of (S)-9-fluoro-10-(4-(5-fluoropyrimidin-2-yl)piperazin-1-yl) methyl-7-oxo-2,3-dihydro-7H-[1,4]oxazino[2,3,4-ij]quinoline-6-carboxylic acid (A1.11)

Compound A1.4 (71 mg, 0.25 mmol, 1 eq) was dissolved in dimethyl sulfoxide (2 mL) with 5-fluoro-2-(piperazin-1-yl)pyrimidine (100 mg, 0.50 mmol, 2 eq) in a 5 mL capacity microwave vessel fitted with a magnetic stirrer bar and microwaved at 160° C. for 1.5 hours. Upon cooling, methanol (10 mL) was added and the mixture filtered. The crude solid was recrystallized from hot methanol to afford A1.11 (69.6 mg, 62.13% yield) as an orange solid.

1H NMR (400 MHz, DMSO-d$_6$) δ 8.98 (s, 1H, H3), 8.49 (s, 2H, H11+12), 7.62 (d, J=12.10 Hz, 1H, H1), 4.89-4.98 (m, 1H, H5), 4.60 (d, J=11.37 Hz, 1H, H4), 4.39 (d, J=11.19 Hz, 1H, H4), 3.84 (t, J=5.23 Hz, 2H, H7+8), 3.73-3.80 (m, 2H, H7+8), 3.34-3.41 (m, 2H, H9+10), 2.95-3.02 (m, 2H, H9-1-10), 1.46 (d, J=6.60 Hz, 3H, H6); LC-MS (Method B) Retention time 3.57 minutes, purity=98%, Found 444.1 [M+H]$^+$; calculated for C$_{21}$H$_{19}$F$_2$N$_5$O$_4$ 444.42 [M+H]$^+$ Synthesis of (S)-10-(4-(4,6-dimethylpyrimidin-2-yl)piperazin-1-yl)-9-fluoro-3-methyl-7-oxo-2,3-dihydro-7H-[1,4]oxazino[2,3,4-ij]quinoline-6-carboxylic acid (A1.12)

Compound A1.4 (71 mg, 0.25 mmol, 1 eq) was dissolved in dimethyl sulfoxide (2 mL) with 4,6-dimethyl-2-(piperazin-1-yl)pyrimidine (91.8 mg, 0.50 mmol, 2 eq) in a 5 mL capacity microwave vessel fitted with a magnetic stirrer bar and microwaved at 160° C. for 1.5 hours. Upon cooling, methanol (10 mL) was added and the mixture filtered. The crude solid was recrystallized from hot methanol to afford A1.12 as a yellow solid,

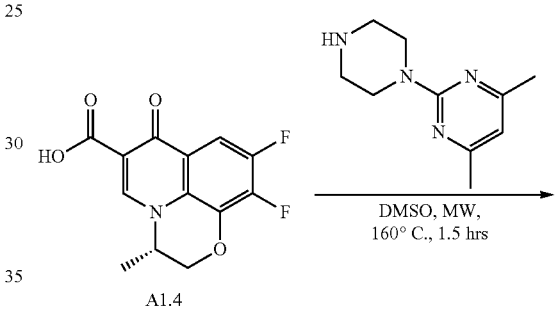

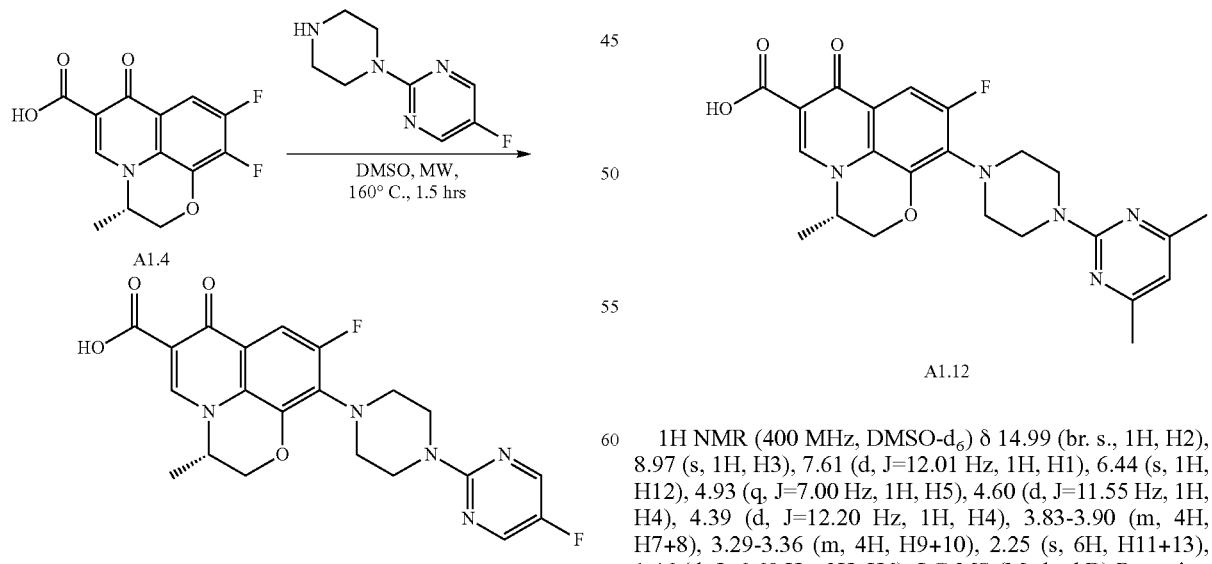

1H NMR (400 MHz, DMSO-d$_6$) δ 14.99 (br. s., 1H, H2), 8.97 (s, 1H, H3), 7.61 (d, J=12.01 Hz, 1H, H1), 6.44 (s, 1H, H12), 4.93 (q, J=7.00 Hz, 1H, H5), 4.60 (d, J=11.55 Hz, 1H, H4), 4.39 (d, J=12.20 Hz, 1H, H4), 3.83-3.90 (m, 4H, H7+8), 3.29-3.36 (m, 4H, H9+10), 2.25 (s, 6H, H11+13), 1.46 (d, J=6.60 Hz, 3H, H6); LC-MS (Method B) Retention time 3.34 minutes, purity=84%, Found 454.1 [M+H]$^+$; calculated for C$_{23}$H$_{24}$FN$_5$O$_4$ 454.48 [M+H]$^+$ Synthesis of ARB-Antibiotics with ARB Fragment Containing 5-Membered Pyrrolidine with Exocyclic Nitrogen Linked to a Pyrimidine Ring or Substituted Pyrimidine Rings Synthesis of (3S)-9-fluoro-3-methyl-7-oxo-10-(3-(pyrimidin-2-ylamino)pyrrolidin-1-yl)-2,3-dihydro-7H-[1,4]oxazino[2,3,4-ij]quinoline-6-carboxylic acid (A1.13, KSN-82-L7)

Compound A1.4 (80 mg, 0.284 mmol, 1 eq) was dissolved in dimethyl sulfoxide (2 mL) with N-(pyrrolidin-3-yl)pyrimidin-2-amine (93.43 mg, 0.568 mmol, 2 eq) in a 5 mL capacity microwave vessel fitted with a magnetic stirrer bar and microwaved at 160° C. for 1.5 hours. The DMSO was evaporated and the compound was crystalized using hot ethanol to afford compound A1.13.

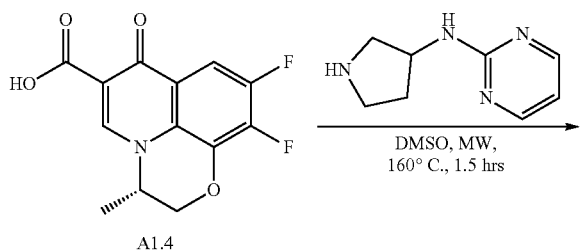

A1.4

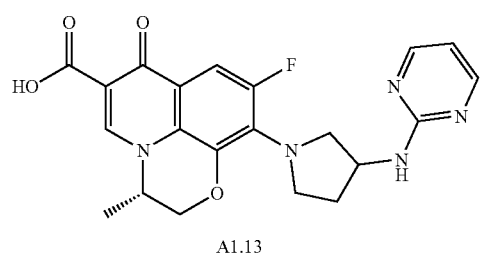

A1.13

$^1$H NMR (400 MHz, DMSO-d$_6$) δ 8.89 (br. s., 1H), 8.30 (d, J=4.65 Hz, 2H), 7.54 (d, J=14.43 Hz, 1H), 7.45 (d, J=5.62 Hz, 1H), 6.61 (t, J=4.52 Hz, 1H), 4.86 (br. s., 1H), 4.52 (d, J=11.25 Hz, 1H), 4.44-4.40 (m, 1H), 4.28 (d, J=11.25 Hz, 1H), 4.00 (br. s., 1H), 4.04-3.87 (m, 2H), 3.82-3.60 (m, 2H), 2.19-1.94 (m, 2H), 1.45 (d, J=6.36 Hz, 3H); Formula C$_{21}$H$_{20}$FN$_5$O$_4$;

LC-MC Retention time 2.946 min, Found 426.1 [M–H]$^+$

Synthesis of (S)-9-fluoro-3-methyl-7-oxo-10-((S)-3-(pyrimidin ylamino)pyrrolidin-1-yl)-2,3-dihydro-7H-[1,4]oxazino[2,3,4-ij]quinoline carboxylic acid (A1.14/KSN-82-L19)

Compound A1.4 (50 mg, 0.177 mmol, 1 eq) was dissolved in dimethyl sulfoxide (2 mL) with (S)—N-(pyrrolidin-3-yl)pyrimidin-2-amine (58.39 mg, 0.355 mmol, 2 eq) in a 5 mL capacity microwaveA vessel fitted with a magnetic stirrer bar and microwaved at 160° C. for 1.5 hours. The DMSO was evaporated the compound was crystalized using hot ethanol to afford compound A1.14.

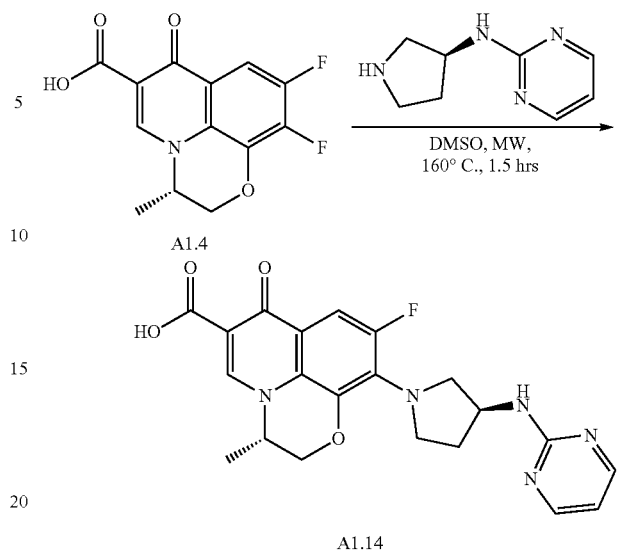

$^1$H NMR (400 MHz, DMSO-d$_6$) δ 8.89 (s, 1H), 8.33 (d, J=4.65 Hz, 2H), 7.54 (d, J=14.43 Hz, 1H), 6.65-6.63 (m, 1H), 4.87 (d, J=6.36 Hz, 1H), 4.52 (d, J=10.76 Hz, 1H), 4.43 (br. s., 1H), 4.28 (d, J=10.03 Hz, 1H), 4.04-3.90 (m, 2H), 3.77-3.63 (m, 3H), 2.20-1.96 (m, 2H), 1.45 (d, J=6.60 Hz, 3H); Formula C$_{21}$H$_2$OFN$_5$O; LC-MC Retention time 2.945 min, Found 426.1 [M+H]$^+$ Synthesis of (S)-10-((S)-3-((6-(cyclopropylamino)pyrimidin-4-yl)amino)pyrrolidin-1-yl)-9-fluoro-3-methyl-7-oxo-2,3-dihydro-7H-[1,4]oxazino[2,3,4-ij]quinoline-6-carboxylic acid (KSN-L21/A1.15)

Compound A1.4 (50 mg, 0.177 mmol, 1 eq) was dissolved in dimethyl sulfoxide (2 mL) (S)—N4-cyclopropyl-N6-(pyrrolidin-3-yl)pyrimidine-4,6-diamine (77.98 mg, 0.355 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.15.

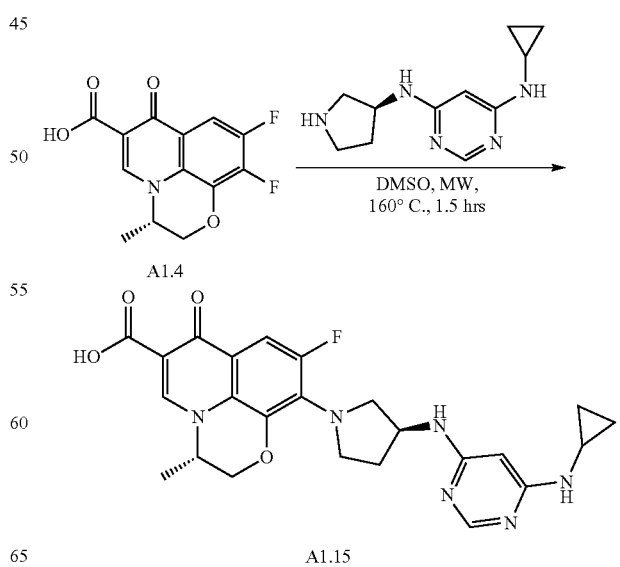

¹H NMR (400 MHz, DMSO-d₆) δ 15.42 (br. s., 1H), 8.89 (s, 1H), 7.92 (s, 1H), 7.54 (d, J=13.94 Hz, 1H), 7.03 (d, J=4.65 Hz, 1H), 6.83 (br. s., 1H), 5.64 (s, 1H), 4.88 (d, J=7.09 Hz, 1H), 4.53 (d, J=10.76 Hz, 1H), 4.41 (br. s., 1H), 4.28 (d, J=10.03 Hz, 1H), 4.03-3.90 (m, 2H), 3.77-3.55 (m, 2H), 2.38 (br. s., 1H), 2.17-1.90 (m, 2H), 1.45 (d, J=6.60 Hz, 3H), 0.66 (d, J=4.65 Hz, 2H), 0.43 (br. s., 2H); Formula C₂₄H₂₅FN₆O₄; LC-MC Retention time 2.453 min, Found 481.2 [M+H]⁺

Synthesis of (S)-9-fluoro-3-methyl-7-oxo-10-aR)-3-(pyrimidin ylamino)pyrrolidin-1-yl)-2,3-dihydro-7H-[1,4]oxazino[2,3,4-ij]quinoline-6-carboxylic acid (KSN-82-L22/A1.16)

Compound A1.4 (50 mg, 0.177 mmol, 1 eq) was dissolved in dimethyl sulfoxide (2 mL) with (R)—N-(pyrrolidin-3-yl)pyrimidin-2-amine (58.39 mg, 0.355 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.16.

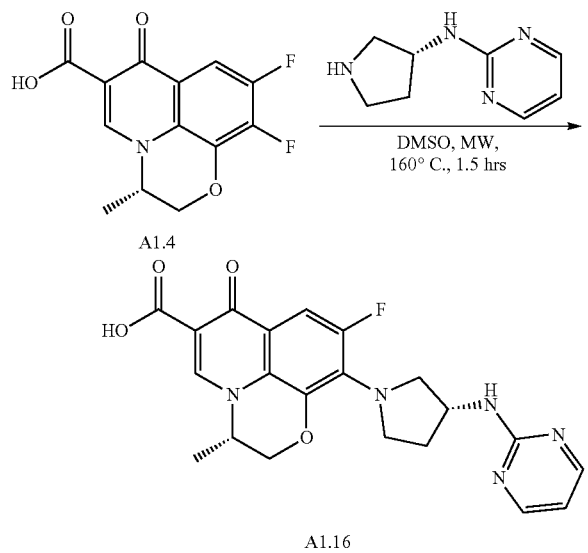

¹H NMR (400 MHz, DMSO-d₆) δ 15.41 (br. s., 1H), 8.89 (s, 1H), 8.30 (d, J=4.58 Hz, 2H), 7.54 (d, J=14.12 Hz, 1H), 7.47 (d, J=6.24 Hz, 1H), 6.61 (t, J=4.77 Hz, 1H), 4.87 (d, J=6.42 Hz, 1H), 4.52 (d, J=11.55 Hz, 1H), 4.44-4.40 (m, 1H), 4.28 (d, J=10.82 Hz, 1H), 4.0-3.86 (m, 2H), 3.84-3.61 (m, 2H), 2.19-1.96 (m, 2H), 1.45 (d, J=6.60 Hz, 3H); Formula C₂₁H₂OFN₅O₄; LC-MC Retention time 2.932 min, Found 426.2 [M+H]⁺

Synthesis of (3S)-9-fluoro-3-methyl-10-(3-(4-methylpiperazin-1-yl)pyrrolidin-1-yl)-7-oxo-2,3-dihydro-7H-[1,4]oxazino[2,3,4-ij]quinoline-6-carboxylic acid (KSN-82-L31/A1.17)

Compound A1.4 (50 mg, 0.177 mmol, 1 eq) was dissolved in dimethyl sulfoxide (2 mL) 1-methyl-4-(pyrrolidin-3-yl)piperazine (60.19 mg, 0.355 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.17.

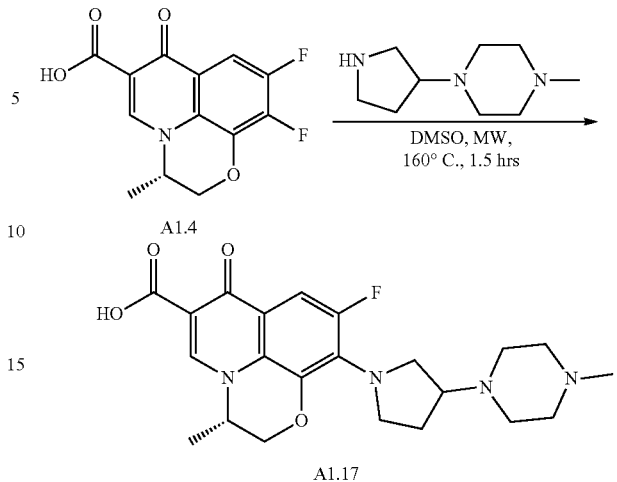

¹H NMR (400 MHz, Chloroform-d) δ 15.04 (br. s., 1H), 8.58 (s, 1H), 7.67 (d, J=4.58 Hz, 2H), 4.49 (dd, J=2.29, 6.69 Hz, 1H), 4.37-4.45 (m, 1H), 4.26-4.35 (m, 1H), 4.07-3.95 (m, 1H), 3.89-3.67 (m, 8H), 2.94-2.88 (m, 1H), 2.58-2.67 (m, 4H), 2.22-2.16 (m, 1H), 1.92-1.77 (m, 2H), 1.62 (d, J=6.60 Hz, 3H); Formula C₂₂H₂₇FN₄O₄; LC-MC Retention time 2.031 min, Found 431.1 [M−H]⁺

Synthesis of (3S)-9-fluoro-3-methyl-10-(3-morpholinopyrrolidin-1-yl)-7-oxo-2,3-dihydro-7H-[1,4]oxazino[2,3,4-ij]quinoline-6-carboxylic acid (KSN-82-L33/A1.18)

Compound 1.4 (50 mg, 0.177 mmol, 1 eq) was dissolved in dimethyl sulfoxide (2 mL) with 4-(pyrrolidin-3-yl)morpholine (55.56 mg, 0.355 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.18.

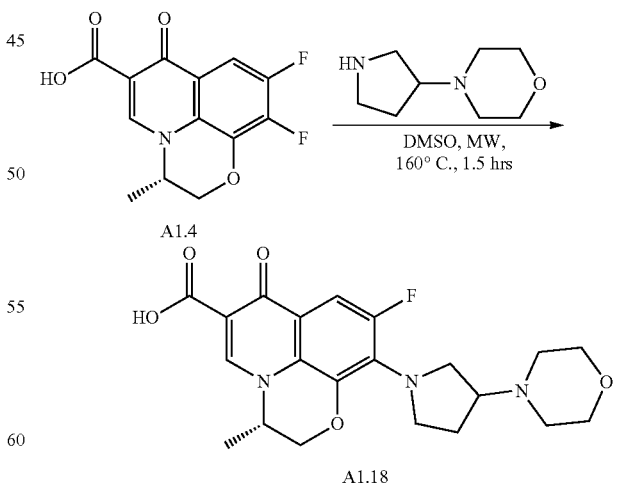

¹H NMR (400 MHz, DMSO-d₆) δ 8.90 (s, 1H), 7.54 (d, J=14.12 Hz, 1H), 4.87 (t, J=6.88 Hz, 1H), 4.57-4.51 (m, 1H), 4.32-4.24 (m, 1H), 3.92-3.84 (m, 1H), 3.69 (dd, J=2.66, 7.61 Hz, 2H), 3.67-3.55 (m, 5H), 2.86-2.76 (m, 1H), 2.49-2.35

(m, 4H), 2.16-2.07 (m, 1H), 1.78-1.67 (m, 1H), 1.45 (dd, J=4.86, 6.51 Hz, 3H); Formula $C_{21}H_{24}FN_3O_5$; LC-MC Retention time 2.032 min, Found 418.2 $[M-H]^+$

Synthesis of (S)-9-fluoro-10-((R)-3-((5-fluoropyrimidin-2-yl)amino)pyrrolidin-1-yl)-3-methyl-7-oxo-2,3-dihydro-7H-[1,4]oxazino[2,3,4-ij]quinoline-6-carboxylic acid (KSN-82-L34/A1.19)

Compound A1.4 (48 mg, 0.170 mmol, 1 eq) was dissolved in dimethyl sulfoxide (2 mL) with (R)-5-fluoro-N-(pyrrolidin-3-yl)pyrimidin-2-amine (62.20 mg, 0.341 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.19.

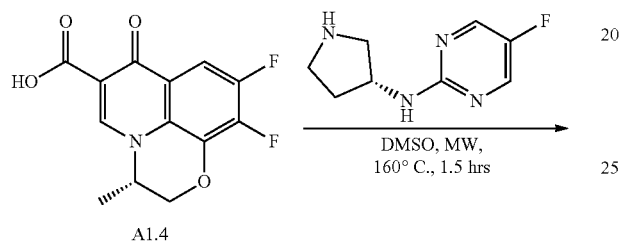

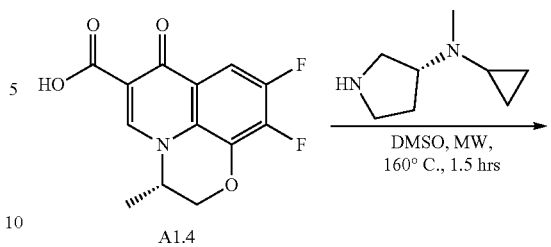

$^1$H NMR (400 MHz, DMSO-$d_6$) δ 15.42 (s, 1H), 8.89 (s, 1H), 8.40 (d, J=0.92 Hz, 2H), 7.57 (d, J=6.24 Hz, 1H), 7.54 (d, J=14.12 Hz, 1H), 4.90-4.84 (m, 1H), 4.52 (dd, J=1.47, 11.37 Hz, 1H), 4.40-4.32 (m, 1H), 4.30-4.26 (m, 1H), 4.00-3.86 (m, 2H), 3.82-3.62 (m, 2H), 2.20-1.93 (m, 2H), 1.45 (d, J=6.79 Hz, 3H); Formula $C_{21}H_{19}F_2N_5O_4$; LC-MC Retention time 3.332 min, Found 444.1 $[M-H]^+$

Synthesis of (S)-10-((R)-3-(cyclopropyl(methyl)amino)pyrrolidin-1-yl)-9-fluoro-3-methyl-7-oxo-2,3-dihydro-7H-[1,4]oxazino[2,3,4-ij]quinoline-6-carboxylic acid (KSN-82-L36/A1.20)

Compound A1.4 (48 mg, 0.170 mmol, 1 eq) was dissolved in dimethyl sulfoxide (2 mL) with Cyclopropyl-methyl-(R)-pyrrolidin-3-yl-amine (47.87 mg, 0.341 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.20.

$^1$H NMR (400 MHz, DMSO-$d_6$) δ 8.90 (s, 1H), 7.54 (d, J=14.12 Hz, 1H), 4.91-4.85 (m, 1H), 4.57-4.49 (m, 1H), 4.29-4.26 (m, 1H), 3.93-3.85 (m, 1H), 3.76-3.68 (m, 1H), 3.63 (t, J=8.80 Hz, 1H), 3.15-3.04 (m, 1H), 2.49 (s, 3H), 2.14-2.12 (In, 1H), 1.76-1.88 (m, 1H), 1.84-1.78 (m, 1H), 1.74-1.70 (m, 1H), 1.42-1.48 (m, 3H), 0.29-0.53 (m, 4H); Formula $C_{21}H_{24}FN_3O_4$; LC-MC Retention time 2.123 min, Found 402.2 $[M-H]^+$

Synthesis of (S)-9-fluoro-3-methyl-7-oxo-10-((R)-3-(3-(pyridin-2-yl)ureido)pyrrolidin-1-yl)-2,3-dihydro-7H-[1,4]oxazino[2,3,4-ij]quinoline carboxylic acid (KSN-82-L37/A1.21)

Compound A1.4 (50 mg, 0.177 mmol, 1 eq) was dissolved in dimethyl sulfoxide (2 mL) (R) (pyridin-2-yl)-3-(pyrrolidin-3-yl)urea (73.34 mg, 0.355 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.21.

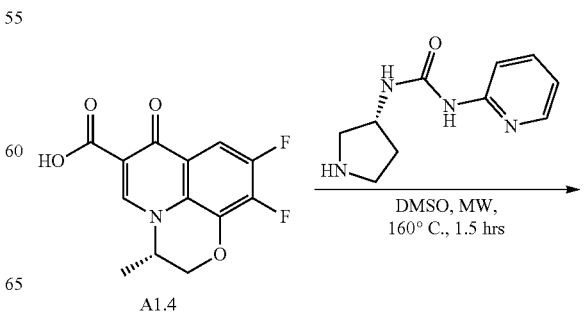

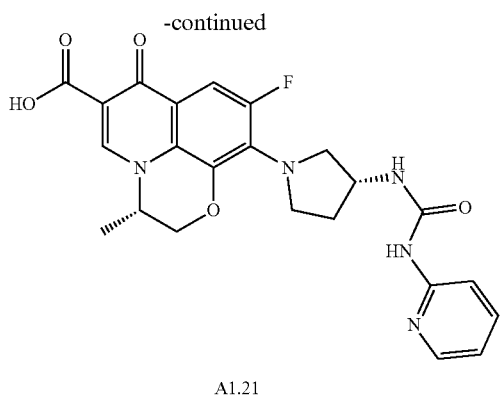

A1.21

Formula $C_{23}H_{22}FN_5O_5$; LC-MC Retention time 2.23 min, Found 468.3 $[M+H]^+$ Synthesis of (S)-8-amino-9-fluoro-3-methyl-7-oxo-10-((R)-3-(pyrimidin-2-ylamino)pyrrolidin-1-yl)-2,3-dihydro-7H-[1,4]oxazino[2,3,4-ij]quinoline-6-carboxylic acid (KSN-82-L40/A 1.22)

Compound A1.6 (34 mg, 0.114 mmol, 1 eq) was dissolved in dimethyl sulfoxide (2 mL) with (S)—N-(pyrrolidin-3-yl)pyrimidin-2-amine (37.70 mg, 0.229 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.22.

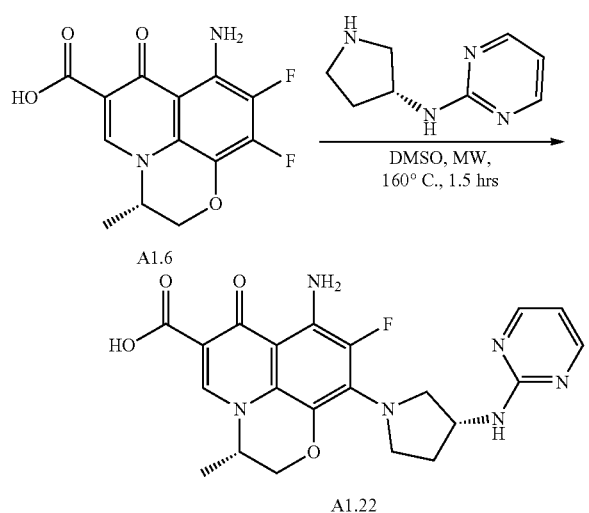

Formula $C_{21}H_{21}FN_6O_4$; LC-MC Retention time 2.47 min, Found 441.36 $[M+H]^+$ Synthesis of (S)-10-((R)-3-aminopyrrolidin-1-yl)-9-fluoro-3-methyl-7-oxo-2,3-dihydro-7H-[1,4]oxazino[2,3,4-ij]quinoline-6-carboxylic acid (KSN-82-L44-D/A1.23)

Compound A1.4 (44 mg, 0.156 mmol, 1 eq) was dissolved in dimethyl sulfoxide (2 mL) with (3S)-(−)-3-(tert-Butoxycarbonylamino)pyrrolidine (58.28 mg, 0.312 mmol, 2 eq) in a 5 mL capacity microwave vessel fitted with a magnetic stirrer bar and microwaved at 100° C. for 1 hour. The DMSO was evaporated and the compound was crystalized. The crystalized product was dissolved in methanol and 2M HCl in dioxane (2 mL) was added. Reaction was left at room temperature for 3 hours so that the boc protected group was removed. Solvent was evaporated and compound 1.22 was isolated as a free base to afford compound A1.23 (KSN-82-L44-D) was isolated as a free base.

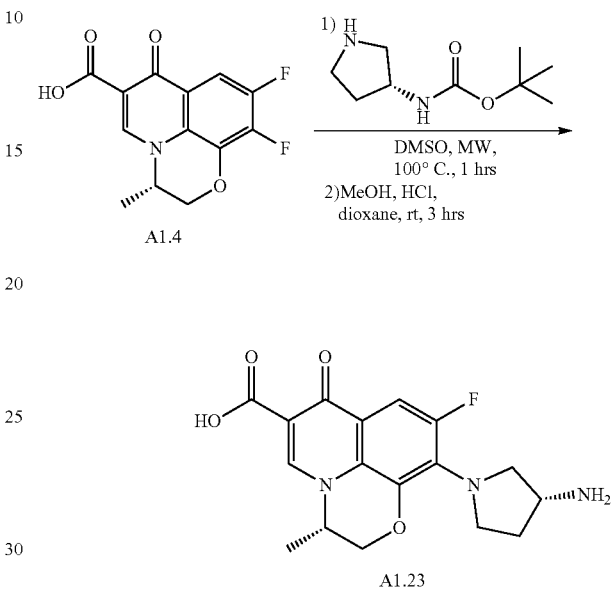

$^1$H NMR (400 MHz, DMSO-d$_6$) δ 8.89 (s, 1H), 7.54 (d, J=14.12 Hz, 1H), 4.91-4.84 (m, 1H), 4.53 (d, J=9.72 Hz, 1H), 4.28 (d, J=9.35 Hz, 1H), 4.05 (d, J=5.87 Hz, 1H), 3.92-3.76 (m, 2H), 3.76-3.64 (m, 1H), 3.53-3.46 (m, 1H), 2.09-1.98 (m, 1H), 1.89-1.74 (m, 1H), 1.45 (d, J=6.79 Hz, 3H); Formula $C_{17}H_{18}FN_3O_4$; LC-MC Retention time 1.916 min, Found 348.1 $[M+H]^+$ Synthesis of (S)-10-(((R)-1-(5-aminopyrimidin-2-yl)pyrrolidin-3-yl)amino)-9-fluoro-3-methyl-7-oxo-2,3-dihydro-7H-[1,4]oxazino[2,3,4-ij]quinoline-6-carboxylic acid (KSN-82-L46/A1.24)

(S)-9-fluoro-3-methyl-7-oxo-10-(((R)-pyrrolidin-3-yl)amino)-2,3-dihydro-7H-[1,4]oxazino[2,3,4-ij]quinoline-6-carboxylic acid (39 mg, 0.112 mmol, 1 eq) was dissolved in dimethyl sulfoxide (2 mL) 2-Chloropyrimidin-5-amine (43.64 mg, 0.336 mmol, 3 eq) in a 5 mL capacity microwave vessel fitted with a magnetic stirrer bar and microwaved at 160° C. for 1.5 hours. The DMSO was evaporated the compound was crystalized using hot ethanol to afford compound A1.24.

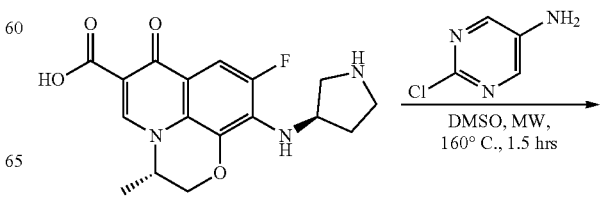

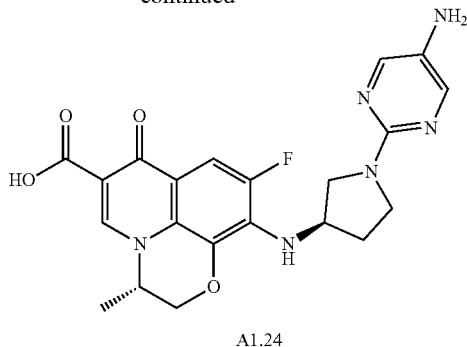

A1.24

Formula $C_{21}H_{21}FN_6O_4$; LC-MC Retention time 2.12 min, Found 441.27 [M+H]⁺

Synthesis of (S)-9-fluoro-3-methyl-10-((R)-3-((5-nitropyrimidin-2-yl)amino)pyrrolidin-1-yl)-7-oxo-2,3-dihydro-7H-[1,4]oxazino[2,3,4-ij]quinoline-6-carboxylic acid (KSN-82-L52/A1.25)

Compound A1.4 (190 mg, 0.675 mmol, 1 eq) was dissolved in dimethyl sulfoxide (2 mL) with (R)-5-nitro-N-(pyrrolidin-3-yl)pyrimidin-2-amine (282.70 mg, 1.35 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.25.

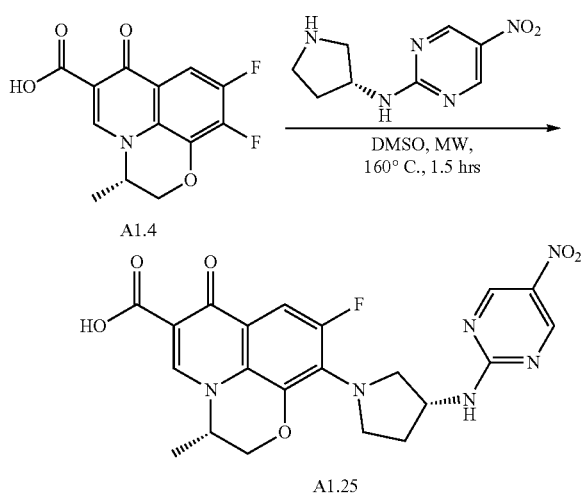

A1.4

A1.25

¹H NMR (400 MHz, DMSO-d₆) δ 9.15 (d, J=3.30 Hz, 1H), 9.08 (d, J=3.30 Hz, 1H), 8.83 (s, 1H), 7.51 (d, J=14.49 Hz, 1H), 4.86-4.78 (m, 1H), 4.61-4.54 (m, 1H), 4.51 (d, J=9.90 Hz, 1H), 4.27 (d, J=9.17 Hz, 1H), 4.04-3.85 (m, 2H), 3.78-3.61 (m, 2H), 2.35-2.32 (m, 1H), 2.25-2.20 (m, 1H), 2.09-2.03 (m, 1H), 1.43 (d, J=6.60 Hz, 3H); Formula $C_{21}H_{19}FN_6O_6$; LC-MC Retention time 3.365 min, Found 471.1 [M–H]⁺

Synthesis of (S)-9-fluoro-3-methyl-10-((S)-3-((5-nitropyrimidin-2-yl)amino)pyrrolidin-1-yl)-7-oxo-2,3-dihydro-7H-[1,4]oxazino[2,3,4-ij]quinoline-6-carboxylic acid (KSN-82-L56/A1.26)

Compound A1.4 (40 mg, 0.142 mmol, 1 eq) was dissolved in dimethyl sulfoxide (2 mL) with (S)-5-nitro-N-(pyrrolidin-3-yl)pyrimidin-2-amine (59.52 mg, 0.284 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.26.

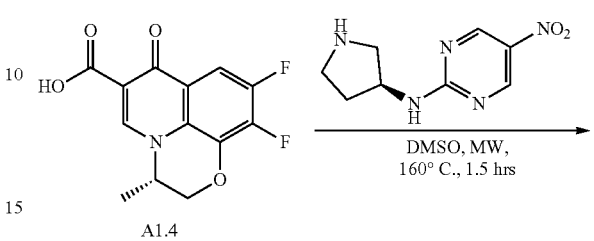

A1.4

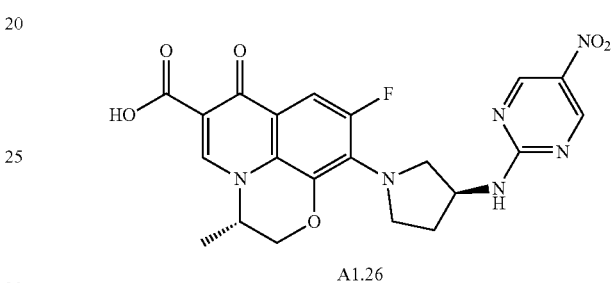

A1.26

¹H NMR (400 MHz, DMSO-d₆) δ15.39 (br. s., 1H), 9.14 (d, J=3.30 Hz, 1H), 9.08 (d, J=3.30 Hz, 1H), 8.90 (s, 1H), 7.54 (d, J=14.12 Hz, 1H), 4.90-4.85 (m, 1H), 4.62-4.48 (m, 2H), 4.32-4.24 (m, 1H), 4.05-3.89 (m, 2H), 3.82-3.68 (m, 2H), 2.27-2.19 (m, 1H), 2.08-2.01 (m, 1H), 1.45 (d, J=6.60 Hz, 3H); Formula $C_{21}H_{19}FN_6O_6$; LC-MC Retention time 3.372 min, Found 471.1 [M-1-1]+

Synthesis of (3S)-9-fluoro-3-methyl-10-(3-((5-nitropyrimidin yl)amino)pyrrolidin-1-yl)-7-oxo-2,3-dihydro-7H-[1,4]oxazino[2,3,4-ij]quinoline-6-carboxylic acid (KSN-82-L57/A1.27)

(3S)-10-(3-aminopyrrolidin-1-yl)-9-fluoro-3-methyl-7-oxo-2,3-dihydro-7H-[1,4]oxazino[2,3,4-ij]quinoline-6-carboxylic acid (40 mg, 0.115 mmol, 1 eq) was dissolved in dimethyl sulfoxide (2 mL) with 2-Chloro-5-nitropyrimidine (36.74 mg, 0.230 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.27.

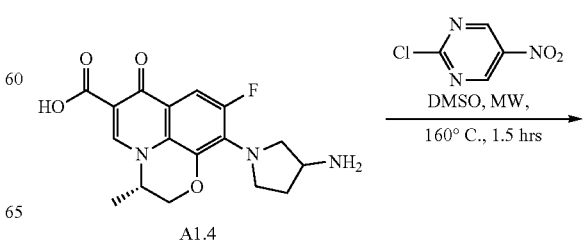

A1.4

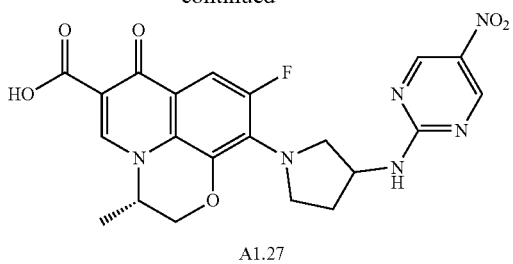

A1.27

¹H NMR (400 MHz, DMSO-d₆) δ 15.38 (br. s., 1H), 9.15 (d, J=3.30 Hz, 1H), 9.08 (d, J=3.30 Hz, 1H), 8.90 (s, 1H), 7.56 (d, J=14.12 Hz, 1H), 4.90-4.85 (m, 1H), 4.60-4.56 (m, 1H), 4.53 (d, J=11.74 Hz, 1H), 4.28 (d, J=11.19 Hz, 1H), 4.05-3.90 (m, 2H), 3.75-3.83-3.68 (m, 2H), 2.22 (td, J=6.53, 12.79 Hz, 1H), 2.05 (dd, J=6.51, 12.56 Hz, 1H), 1.45 (d, J=6.79 Hz, 3H); Formula $C_{21}H_{19}FN_6O_6$; LC-MC Retention time 3.362 min, Found 471.1 $[M+H]^+$ Synthesis of (S)-10-((S)-3-((5-aminopyrimidin-2-yl)amino)pyrrolidin-1-yl)-9-fluoro-3-methyl-7-oxo-2,3-dihydro-7H-[1,4]oxazino[2,3,4-ij]quinoline-6-carboxylic acid (KSN-82-L62/A1.28)

Compound A1.4 (50 mg, 0.177 mmol, 1 eq) was dissolved in dimethyl sulfoxide (2 mL) with (S)—N2-(pyrrolidin-3-yl)pyrimidine-2,5-diamine (47.80 mg, 0.266 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.28.

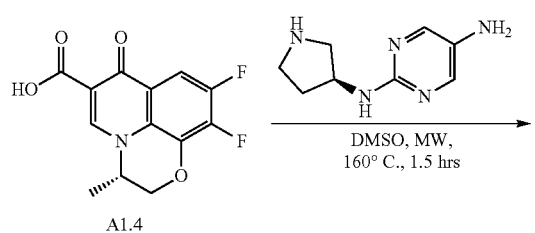

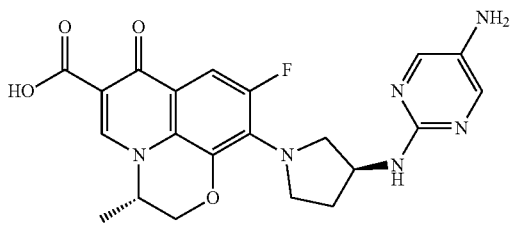

A1.28

¹H NMR (400 MHz, DMSO-d₆) δ 8.88 (s, 1H), 70.83 (s, 2H), 7.54 (d, J=14.12 Hz, 1H), 6.51 (d, J=6.42 Hz, 1H), 4.82-4.91 (m, 1H), 4.52 (d, J=9.90 Hz, 1H), 4.45 (s, 2H), 4.24-4.33 (m, 1H), 3.96-3.93 (m, 1H), 3.74-3.79-3.86 (m, 2H), 3.62-3.57 (m, 1H), 2.35 (s, 1H), 2.13 (td, J=6.19, 12.20 Hz, 1H), 1.88-1.98 (m, 1H), 1.45 (d, J=6.79 Hz, 3H); Formula $C_{21}H_{21}FN_6O_4$; LC-MC Retention time 2.357 min, Found 441.1 $[M+H]^+$ Synthesis of (S)-10-((R)-3-((5-aminopyrimidin-2-yl)amino)pyrrolidin-1-yl) fluoro-3-methyl-7-oxo-2,3-dihydro-7H-[1,4]oxazino[2,3,4-ij]quinoline carboxylic acid (KSN-82-L65/A1.29)

Compound A1.4 (40 mg, 0.142 mmol, 1 eq) was dissolved in dimethyl sulfoxide (2 mL) with (R)—N2-(pyrrolidin-3-yl)pyrimidine-2,5-diamine (38.24 mg, 0.213 mmol, 1.5 eq) in a 5 mL capacity microwave vessel fitted with a magnetic stirrer bar and microwaved at 160° C. for 1.5 hours. The DMSO was evaporated the compound was crystalized using hot ethanol to afford compound A1.29.

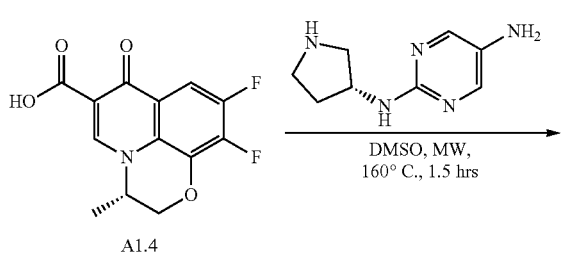

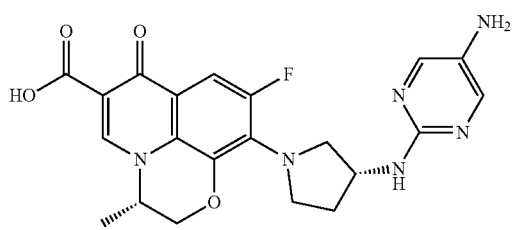

A1.29

Formula $C_{21}H_{21}FN_6O_4$; LC-MC Retention time 2.37 min, Found 441.1 $[M+H]^+$ Synthesis of (S)-9-fluoro-3-methyl-7-oxo-10-((R)-3-(pyrazin-2-ylamino)pyrrolidin-1-yl)-2,3-dihydro-7H-[1,4]oxazino[2,3,4-ij]quinoline-6-carboxylic acid (BL-1/A1.30)

Compound A1.4 (107.1 mg, 0.381 mmol, 1 eq) was dissolved in dimethyl sulfoxide (2 mL) with (R)-4-(pyrrolidin-3-yl)pyrimidine (126 mg, 0.767 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.30.

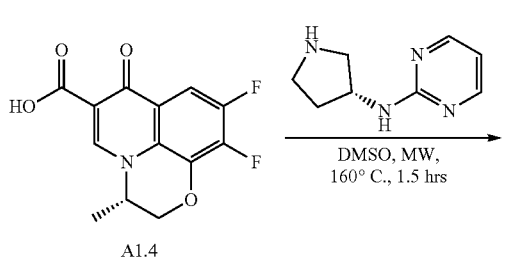

A1.4

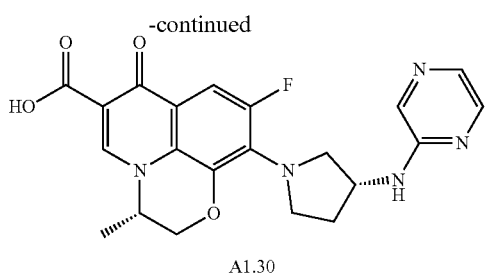

A1.30

¹H NMR (400 MHz, DMSO-d₆) δ 8.89 (s, 1H), 7.96 (s, 1H), 7.69 (d, J=2.38 Hz, 1H), 7.54 (d, J=14.12 Hz, 1H), 7.38 (d, J=6.24 Hz, 1H), 4.89-4.84 (m, 1H), 4.56-4.48 (m, 1H), 4.45-4.35 (m, 1H), 4.32-4.24 (m, 1H), 4.07-3.99 (m, 1H), 3.95-3.75 (m, 3H), 3.65-3.57 (m, 1H), 2.27-2.16 (m, 1H), 1.98-1.87 (m, 1H), 1.45 (d, J=6.79 Hz, 3H); Formula $C_{21}H_{20}FN_5O_4$; LC-MC Retention time 30.002 min, 426 Found [M–H]⁺

Synthesis of (S)-10-((3R,4S)-3-carboxy-4-(pyridin-4-yl)pyrrolidin-1-yl) fluoro-3-methyl-7-oxo-2,3-dihydro-7H-[1,4]oxazino[2,3,4-ij]quinoline-6-carboxylic acid (BL-4/A1.31)

Compound A1.4 (50 mg, 0.177 mmol, 1 eq) was dissolved in dimethyl sulfoxide (2 mL) (3R,4S)-4-(pyridin-3-yl)pyrrolidine-3-carboxylic acid (68.43 mg, 0.356 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.31.

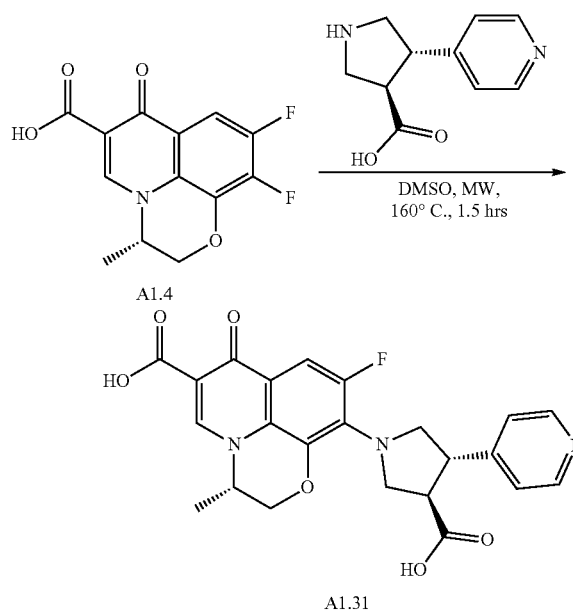

A1.31

Formula $C_{23}H_{20}FN_3O_6$; LC-MC Retention time 2.148 min, Found 451.9 [M–H]⁺

Synthesis of (S)-9-fluoro-3-methyl-7-oxo-10-((R)-3-(quinazolin-4-yl)amino)pyrrolidin-1-yl)-2,3-dihydro-7H-[1,4]oxazino[2,3,4-ij]quinoline-6-carboxylic acid (BL-5/A1.32)

Compound A1.4 (50 mg, 0.177 mmol, 1 eq) was dissolved in dimethyl sulfoxide (2 mL) (R)—N-(pyrrolidin-3-yl)quinazolin-4-amine (76.3 mg, 0.356 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.32.

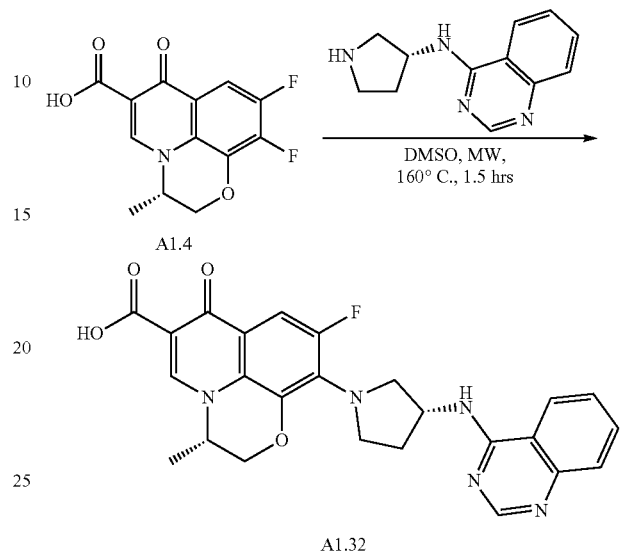

A1.32

Formula $C_{25}H_{22}FN_5O_4$; LC-MC Retention time 2.439 min, Found 476 [M+H]⁺

Synthesis of (S)-9-fluoro-3-methyl-10-((R)-3-((6-methylpyrimidin yl)amino)pyrrolidin-1-yl)-7-oxo-2,3-dihydro-7H-[1,4]oxazino[2,3,4-ij]quinoline-6-carboxylic acid (BL-6/A1.33)

Compound A1.4 (50 mg, 0.177 mmol, 1 eq) was dissolved in dimethyl sulfoxide (2 mL) (R)-6-methyl-N-(pyrrolidin-3-yl)pyrimidin-4-amine (63.45 mg, 0.356 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.33.

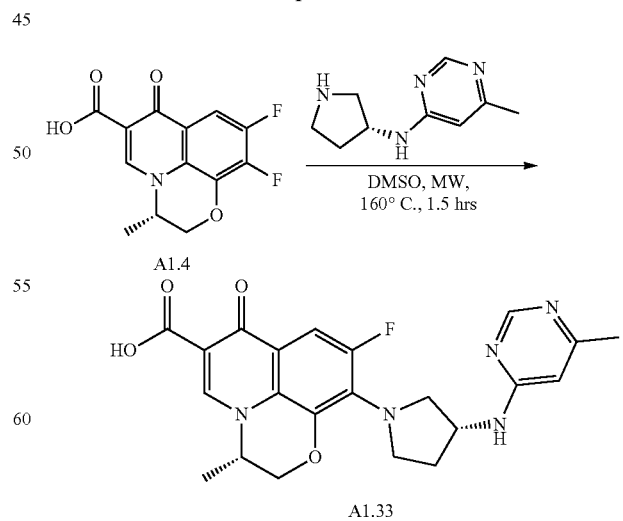

A1.33

¹H NMR (400 MHz, DMSO-d₆) δ 8.90 (s, 1H), 8.33 (s, 1H), 7.57-7.50 (m, 2H), 6.36 (br. s., 1H), 4.88 (q, J=6.91 Hz,

1H), 4.54-4.47 (m, 2H), 4.32-4.25 (m, 1H), 4.04-3.97 (m, 1H), 3.91-3.76 (m, 2H), 3.59 (dd, J=2.57, 5.50 Hz, 1H), 2.24-2.15 (m, 4H), 1.91 (dd, J=6.05, 11.92 Hz, 1H), 1.45 (d, J=6.60 Hz, 3H); Formula $C_{22}H_{22}FN_5O_4$; LC-MC Retention time 2.262 min, Found 440.1 [M+H]$^+$ Synthesis of (S)-10-((R)-3-((4,6-dimethylpyrimidin-2-yl)amino)pyrrolidin-1-yl)-9-fluoro-3-methyl-7-oxo-2,3-dihydro-7H-[1,4]oxazino[2,3,4-ij]quinoline-6-carboxylic acid (BL-7/A1.34)

Compound A1.4 (50 mg, 0.177 mmol, 1 eq) was dissolved in dimethyl sulfoxide (2 mL) (R)-4,6-dimethyl-2-(pyrrolidin-3-yl)pyrimidine (68.5 mg, 0.356 mmol, 2 eq) in a 5 mL capacity microwave vessel fitted with a magnetic stirrer bar and microwaved at 160° C. for 1.5 hours. The DMSO was evaporated the compound was crystalized using hot ethanol to afford compound A1.34.

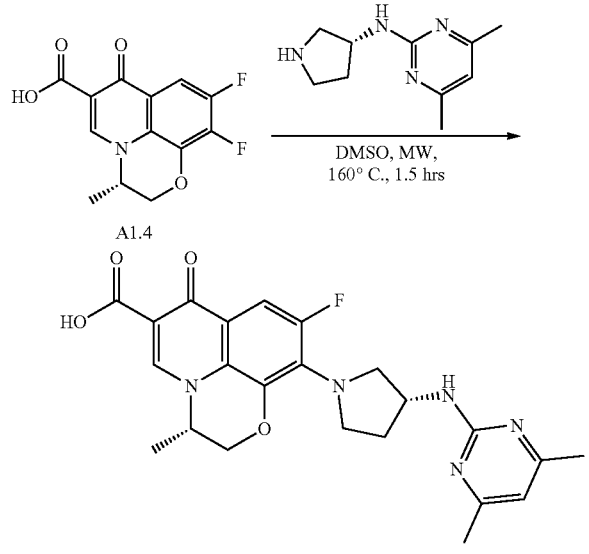

$^1$H NMR (400 MHz, DMSO-d$_6$) δ 15.43 (s, 1H), 8.89 (s, 1H), 7.54 (d, J=14.12 Hz, 1H), 7.25 (d, J=6.60 Hz, 1H), 6.39 (s, 1H), 4.87 (d, J=6.97 Hz, 1H), 4.52 (d, J=10.27 Hz, 1H), 4.49-4.41 (m, 1H), 4.28 (d, J=9.72 Hz, 1H), 3.99-3.92 (m, 1H), 3.87-3.80 (m, 2H), 3.64-3.56 (m, 1H), 2.23-2.18 (m, 6H), 2.18-2.09 (m, 1H), 2.02-1.90 (m, 1H), 1.45 (d, J=6.60 Hz, 3H); Formula $C_{23}H_{24}FN_5O_4$; LC-MC Retention time 2.686 min, Found 454.1 [M+H]$^+$ Synthesis of Parent Fluoroquinolones Synthesis of ethyl (Z)-3-(cyclopropylamino)-2-(2,4,5-trifluorobenzoyl)-acrylate (1.2)

Ethyl 2,4,5-trifluorobenzoylacetate (1.1; 1 g, 4.06 mmol, 1 eq) was dissolved in triethyl orthoformate (1.15 mL, 6.90 mmol, 1.7 eq) and heated at 140° C. for 30 minutes. Ac$_2$O (1.15 mL, 12.19 mmol, 3 eq) was added and the mixture refluxed at 140° C. for another 3 hours and monitored by TLC (90% Hex/10% EtOAc). Upon completion, the reaction was cooled to room temperature, DCM (3 mL) was added and the mixture was stirred at room temperature for 10 minutes. Then cyclopropylamine (703 µL, 10.15 mmol, 2.5 eq) was added and the reaction was stirred at room temperature until completion. The crude was concentrated under reduced pressure and the resulting solid was dissolved in DCM (2 mL) and purified by flash chromatography (50% Hex/50% EtOAc) to yield compound 1.2 (1.158 g, 91.0% yield) as a pale yellow solid.

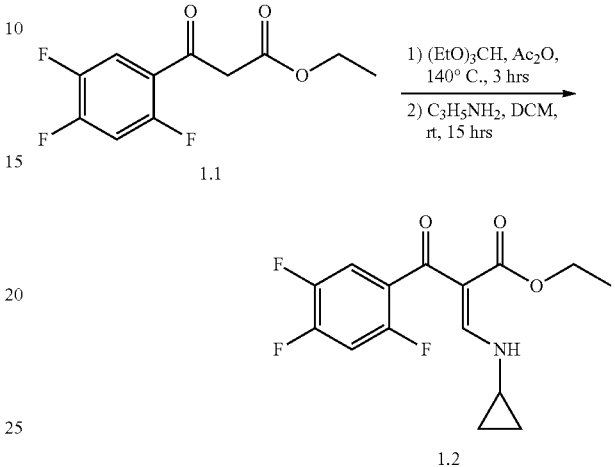

$^1$H NMR (400 MHz, CDCl$_3$) δ 10.87 (d, J=14.10 Hz, 1H), 8.14-8.22 (m, 1H), 7.18 (td, J=6.29, 9.32 Hz, 1H), 6.87 (td, J=6.29, 9.57 Hz, 1H), 4.05 (q, J=7.13 Hz, 2H), 2.97 (qt, J=3.27, 6.88 Hz, 1H), 1.08 (t, J=7.18 Hz, 3H), 0.88-0.94 (m, 2H), 0.82-0.87 (m, 2H); IR (υ$_{max}$/cm$^{-1}$) 1686, 1623, 1569, 1508, 1426, 1406, 1357, 1330, 1294, 1244, 1228, 1174, 1136, 1088, 1058, 1033, 1015, 890, 877, 809, 797, 773, 754, 734, 660, 588

Synthesis of ethyl 1-cyclopropyl-6,7-difluoro-4-oxo-1,4-dihydroquinoline-3-carboxylate (1.3)

Compound 1.2 (1 g, 3.13 mmol, 1 eq) was dissolved in DCM (7 mL). DBU (573 µL, 3.83 mmol, 1.2 eq) and LiCl (270 mg, 6.38 mmol, 2 eq) were subsequently added and the reaction was stirred at 45° C. for 2.5 hours, then at room temperature for 15 hours. Upon completion, the mixture was extracted with DCM (2×20 mL) and washed with water (15 mL) with the aqueous phase neutralized using a 1M solution of citric acid (3 mL). The combined organic phases were dried over magnesium sulphate and concentrated under reduced pressure to give the crude product 1.3 (1.022 g, >95% crude yield) as a pale yellow solid which was used in the successive reaction without further purification.

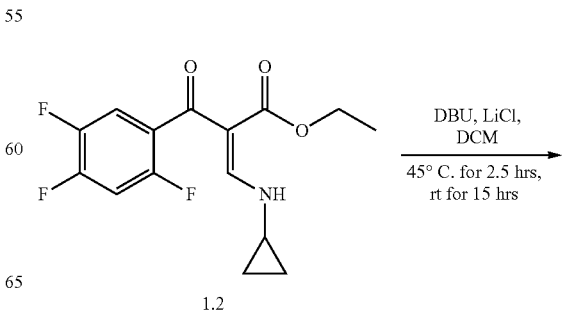

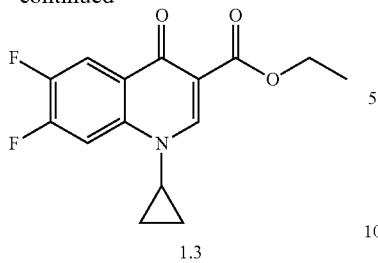

1.3

¹H NMR (400 MHz, CDCl₃) δ 8.55 (s, 1H), 8.20 (dd, J=8.69, 10.45 Hz, 1H), 7.72 (dd, J=6.29, 11.33 Hz, 1H), 4.37 (q, J=7.05 Hz, 2H), 3.42-3.48 (m, 1H), 1.40 (t, J=7.18 Hz, 3H), 1.21-1.37 (m, 2H), 1.13-1.18 (m, 2H); IR ($\upsilon_{max}$/cm⁻¹) 1723, 1617, 16.02, 1490, 1479, 1454, 1446, 1424, 1396, 1386, 1379, 1335, 1314, 1287, 1228, 1209, 1202, 1167, 1121, 1094, 1054, 1033, 1018, 899, 855, 849, 826, 802, 781, 748, 729, 717, 619, 607, 595, 548, 540; LC-MS Retention time 3.28 minutes, found 294.0 [M+H]⁺; calculated for $C_{15}H_{13}F_2NO_3$ 294.27 [M+H]⁺.

Synthesis of 1-cyclopropyl-6,7-difluoro-4-oxo-1,4-dihydroquinoline-3-carboxylic acid (1.4)

Crude compound 1.3 (700 mg, 2.39 mmol, 1 eq) was refluxed with concentrated HCl (3.5 mL) and concentrated AcOH (13 mL) for 2.5 hours. The mixture was allowed to cool to room temperature, and the resulting precipitate was filtered, washed with water (3 mL) and dried to give the crude product 1.4 (573 mg, 90.4% yield) as a white solid which was used in the successive reaction without further purification.

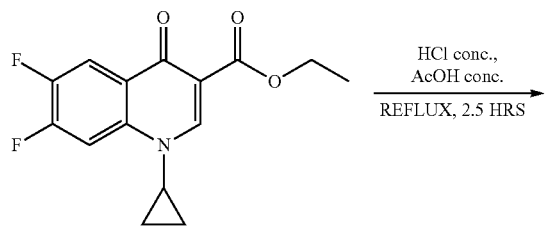

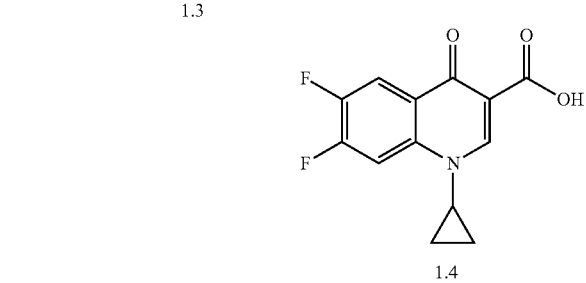

1.4

¹H NMR (400 MHz, TFA-d) δ 9.34 (d, J=3.53 Hz, 1H), 8.32-8.40 (m, 2H), 3.99-4.06 (m, 1H), 1.54-1.62 (m, 2H), 1.35 (br. s., 2H); IR ($\upsilon_{max}$/cm⁻¹) 1719, 1614, 1556, 1421, 1332, 1303, 1289, 1231, 1204, 1056, 1033, 1020, 891, 806, 778, 748, 719, 606; LC-MS Retention time 3.37 minutes, found 265.9 [M+H]⁺; calculated for $C_{13}H_9F_2NO_3$ 266.22 [M+H]⁺.

Synthesis of 7-(4-(tert-butoxycarbonyl)piperazin-1-yl)-1-cyclopropyl-6-fluoro-4-oxo-1,4-dihydroquinoline-3-carboxylic acid (1.5)

A mixture of compound 1.4 (500 mg, 1.89 mmol, 1 eq), tert-butyl piperazine-1-carboxylate (1.06 g, 5.67 mmol, 3 eq) and potassium carbonate (552 mg, 3.78 mmol, 2 eq) was stirred in DMF (18 mL) at 140° C. for 15 hours. Upon completion (as monitored by LC-MS), the mixture was extracted with DCM (2×15 mL) and washed with water (10 mL) with the aqueous layer neutralized using a 1M solution of citric acid. The combined organic layers were dried over magnesium sulfate and concentrated under reduced pressure. The crude compound was recrystallized from DMF (5 mL) to give pure compound 1.5 (285 mg, 35.0% yield) as a pale orange solid.

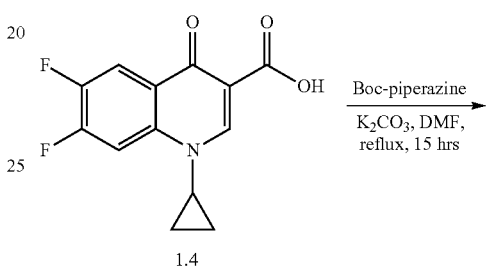

1.4

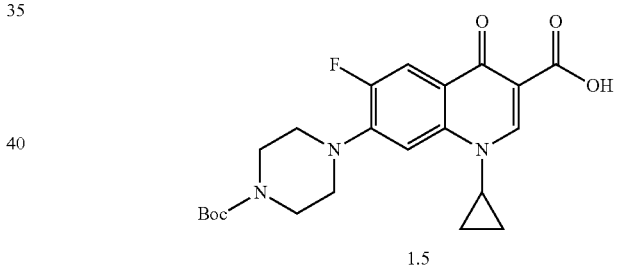

1.5

IR ($\upsilon_{max}$/cm⁻¹) 1729, 1687, 1627, 1502, 1462, 1417, 1383, 1340, 1286, 1246, 1217, 1168, 1124, 1083, 1045, 1034, 940, 891, 856, 828, 805, 782, 770, 746, 703, 667, 625; LC-MS Retention time 3.95 minutes, found 432.0 [M+H]⁺; calculated for $C_{22}H_{26}FN_3O_5$ 432.46 [M+H]⁺

Synthesis of 1-cyclopropyl-6-fluoro-4-oxo-7-(piperazin-1-yl)-1,4-dihydroquinoline-3-carboxylic acid (2.1)

Compound 1.5 (200 mg, 0.46 mmol, 1 eq) was dissolved in dry DCM (7 mL) at room temperature, then the mixture was cooled to 0° C. and TFA (710 μL, 9.27 mmol, 20 eq) added. The mixture was allowed to warm to room temperature while stirring over 2 hours. Upon completion (monitored by LC-MS), the solution was concentrated under reduced pressure and washed with toluene (4×3 mL). The crude solid was washed with EtOAc (5 mL) and MeOH (5 mL) to give pure compound 2.1 (150 mg, 98.7% yield) as a light orange solid.

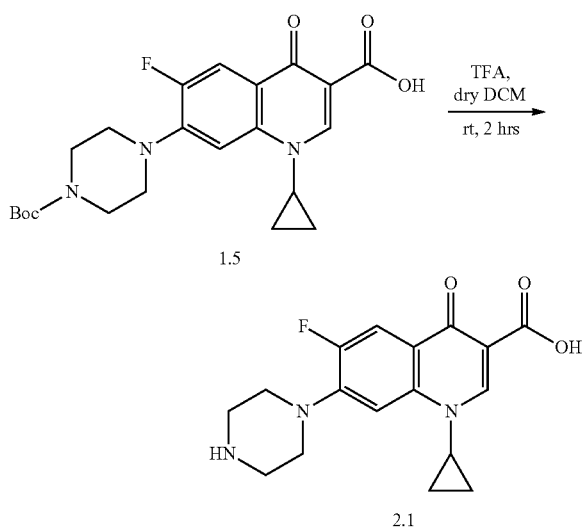

$^1$H NMR (400 MHz, TFA-d) δ 9.29 (s, 1H), 8.24 (d, J=12.34 Hz, 1H), 7.90 (d, J=6.80 Hz, 1H), 4.03-4.12 (m, 1H), 3.90-3.99 (m, 4H), 3.70-3.78 (m, 4H), 1.60-1.68 (m, 2H), 1.34-1.43 (m, 2H); IR ($\upsilon_{max}$/cm$^{-1}$) 1685, 1627, 1612, 1490, 1454, 1341, 1272, 1259, 1184, 1138, 1107, 1056, 1034, 941, 894, 886, 829, 807, 793, 785, 749, 723, 708, 665, 637, 609; LC-MS Retention time 2.48 minutes, found 332.0 [M+H]$^+$; calculated for $C_{17}H_{18}FN_3O_3$ 332.35 [M+H]$^+$.

Synthesis of 1-cyclopropyl-6-fluoro-4-oxo-7-(piperazin-1-yl)-1,4-dihydroquinoline-3-carboxylic acid hydrochloride (1.6)

Compound 2.1 (150 mg, 0.45 mmol, 1 eq) was stirred in DCM (7 mL) for 5 minutes. Then 4M HCl in dioxane (2.26 mL, 9.05 mmol, 20 eq) was added dropwise and the mixture stirred for 1 hour. Upon completion, the mixture was washed with hexane (3×1 mL) and lyophilized overnight to give compound 1.6 (>95%) as a pale brown solid.

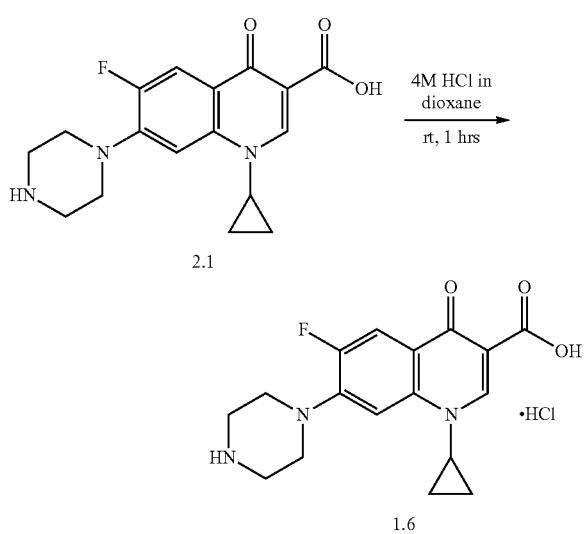

$^1$H NMR (400 MHz, DMSO-d$_6$) δ 15.20 (br. s., 1H), 9.46 (br. s., 2H), 8.67 (s, 1H), 7.94 (d, J=13.09 Hz, 1H), 7.61 (d, J=7.30 Hz, 1H), 3.86 (br. s., 1H), 3.57 (br. s., 4H), 3.31 (br. s., 4H), 1.29-1.35 (m, 2H), 1.15-1.24 (m, 3H); HRMS Observed 332.1404 [M+H]$^+$; theoretical value 332.1405 [M+H]$^+$; IR ($\upsilon_{max}$/cm$^{-1}$) 1701, 1624, 1491, 1458, 1383, 1341, 1272, 1142, 1106, 1034, 941, 909, 889, 853, 829, 804, 774, 749, 703, 665, 636, 619; LC-MS Retention time 4.70 minutes, found 332.0 [M+H]$^+$; calculated for $C_{17}H_{18}FN_3O_3$ 332.35 [M+H]$^+$.

Synthesis of ethyl (Z)-3-(ethylamino)-2-(2,4,5-trifluorobenzoyl)acrylate (1.7)

Ethyl 2,4,5-trifluorobenzoylacetate (1.1; 5 g, 20.31 mmol, 1 eq) was dissolved in triethyl orthoformate (5.74 mL, 34.53 mmol, 1.7 eq) and heated at 140° C. for 30 minutes. Ac$_2$O (5.76 mL, 60.93 mmol, 3 eq) was then added and the mixture refluxed at 140° C. for another 3 hours and monitored by TLC (90% Hex/10% EtOAc). Upon completion, the reaction was cooled, DCM (8 mL) added and the mixture stirred at room temperature for 10 minutes. Then ethylamine (20.31 mL, 40.62 mmol, 2 eq) was added and the reaction was stirred for 15 hours at room temperature. The crude was concentrated under reduced pressure and purified by flash chromatography (50% Hex/50% EtOAc) to give compound 1.7 (4.916 g, 80.3% yield) as a pale yellow solid.

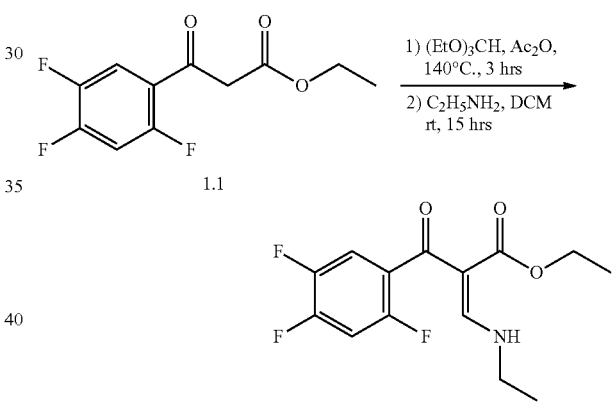

$^1$H NMR (400 MHz, CDCl$_3$) δ 10.89 (br. s., 1H), 8.13 (d, J=14.10 Hz, 1H), 7.19 (dd, J=9.32, 15.61 Hz, 1H), 6.82-6.91 (m, 1H), 4.05 (q, J=7.13 Hz, 2H), 3.46-3.54 (m, 2H), 1.36 (t, J=7.18 Hz, 3H), 1.07 (t, J=7.18 Hz, 3H); IR ($\upsilon_{max}$/cm$^{-1}$) 1678, 1622, 1560, 1510, 1428, 1415, 1380, 1364, 1330, 1310, 1283, 1244, 1219, 1175, 1156, 1136, 1092, 1050, 1036, 884, 1015, 863, 829, 800, 774.

Synthesis of ethyl 1-ethyl-6,7-difluoro-4-oxo-1,4-dihydroquinoline carboxylate (1.8)

Compound 1.7 (5 g, 16.60 mmol, 1 eq) was dissolved in DCM (35 mL). DBU (2.98 mL, 19.92 mmol, 1.2 eq) and LiCl (1.41 g, 33.20 mmol, 2 eq) were subsequently added and the reaction was stirred at 45° C. for 2.5 hours, then at room temperature for 15 hours. Upon completion, the mixture was extracted with DCM (2×15 mL) and washed with water (20 mL) with the aqueous neutralized using a 1M solution of citric acid (5 mL). The crude compound 1.8 was dried over magnesium sulphate, concentrated under reduced pressure to give a pale yellow solid (4.55 g, >95% crude yield) which was used in the successive reaction without further purification.

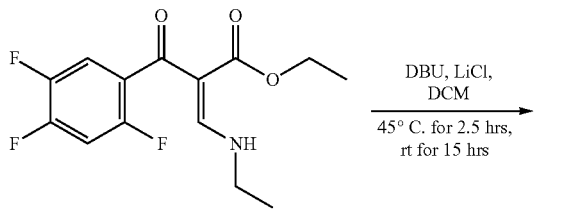

¹H NMR (400 MHz, CDCl₃) δ 8.47 (s, 1H), 8.27 (dd, J=8.81, 10.32 Hz, 1H), 7.27 (dd, J=6.17, 11.20 Hz, 1H), 4.38 (q, J=7.05 Hz, 2H), 4.21 (q, J=7.22 Hz, 2H), 1.55 (t, J=7.30 Hz, 3H), 1.40 (t, J=7.05 Hz, 3H); IR ($\upsilon m/cm^{-1}$) 1720, 1617, 1566, 1466, 1449, 1375, 1369, 1311, 1288, 1228, 1217, 1209, 1173, 1157, 1137, 1094, 1071, 1049, 1016, 902, 863, 829, 814, 802; LC-MS Retention time 3.18 minutes, Found 281.9 [M+H]⁺; calculated for $C_{14}H_{13}F_2NO_3$ 282.26 [M+H]⁺

Synthesis of 1-ethyl-6-7-difluoro-4-oxo-1,4-dihydroquinoline-3-carboxylic acid (1.9)

Crude compound 1.8 (4.5 g, 16.00 mmol, 1 eq) was refluxed in 2M NaOH (40 mL, 80.00 mmol, 5 eq) for 2 hours. The mixture was then allowed to cool to room temperature and acidified with a 1M solution of acetic acid (15 mL). The solid was filtered, washed with hexane (3×20 mL) and concentrated under reduced pressure. The solid was recrystallised from DMF (60 mL) to give pure compound 1.9 (2.964 g, 73.2% yield) as a pale yellow solid.

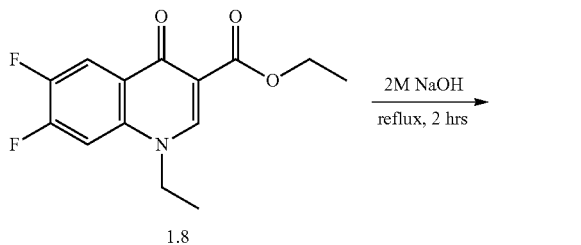

¹H NMR (400 MHz, TFA-d) δ 9.36 (s, 1H), 8.39 (t, J=8.43 Hz, 1H), 7.99 (dd, J=6.17, 9.95 Hz, 1H), 4.79 (q, J=7.13 Hz, 2H), 1.66 (t, J=7.05 Hz, 3H); IR ($\upsilon_{max}/cm^{-1}$) 1719, 1617, 1484, 1396, 1385, 1361, 1306, 1289, 1231, 1213, 1094, 1042, 948, 900, 874, 808; LC-MS Retention time 30.28 minutes, found 253.8 [M+H]⁺; calculated for $C_{12}H_9F_2NO_3$ 254.2 [M+H]⁺

Synthesis of 7-(4-(tert-butoxycarbonyl)piperazin-1-yl)-1-ethyl-6-fluoro-4-oxo-1,4-dihydroquinoline-3-carboxylic acid (1.10)

A mixture of compound 1.9 (200 mg, 0.79 mmol, 1 eq), tert-butyl piperazine-1-carboxylate (442 mg, 2.37 mmol, 3 eq) and potassium carbonate (218 mg, 1.58 mmol, 2 eq) was stirred in DMF (8 mL) at 140° C. for 20 hours. Upon completion (monitored by LC-MS), the mixture was extracted with DCM (2×15 mL) and washed with water (10 mL) with the aqueous phase neutralized using a 1M solution of citric acid (1 mL). The combined organic phases were dried over magnesium sulphate and concentrated under reduced pressure. The crude solid was recrystallized from DMF (2 mL) to give pure compound 1.10 (160 mg, 48.3% yield) as a pale brown solid.

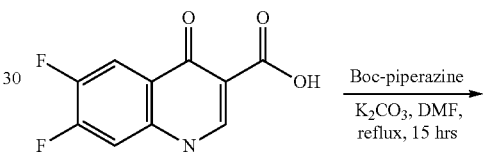

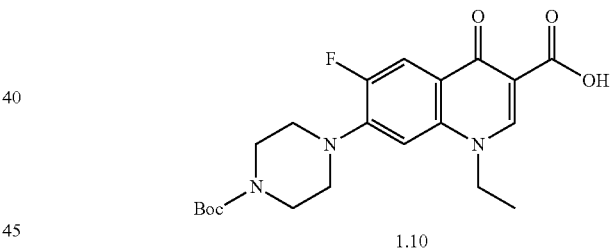

IR ($\upsilon_{max}/cm^{-1}$) 1727, 1696, 1681, 1629, 1614, 1518, 1478, 1470, 1446, 1424, 1380, 1362, 1332, 1287, 1268, 1245, 1199, 1168, 1126, 1107, 1093, 1055, 1033, 1005, 925, 906, 860, 834, 822, 803, 761; LC-MS Retention time 3.88 minutes, found 420.0 [M+H]⁺; calculated for $C_{21}H_{26}FN_3O_5$ 420.45 [M+H]⁺.

Synthesis of 1-ethyl-6-fluoro-4-oxo-7-(piperazin-1-yl)-1,4-dihydroquinoline-3-carboxylic acid (3.1)

Compound 1.10 (85 mg, 0.20 mmol, 1 eq) was dissolved in dry DCM (5 mL), then the solution cooled to 0° C. and TFA (233 μL, 3.04 mmol, 15 eq) added. The mixture was allowed to warm to room temperature while stirring over 4 hours. Upon completion (monitored by LC-MS), the mixture was concentrated under reduced pressure and washed with toluene (3×2 mL). The crude solid was recrystallised from DMF (600 μL) and washed with EtOAc (5 mL) and MeOH (5 mL) to give pure compound 3.1 (44 mg, 68.9% yield) as a pale orange solid.

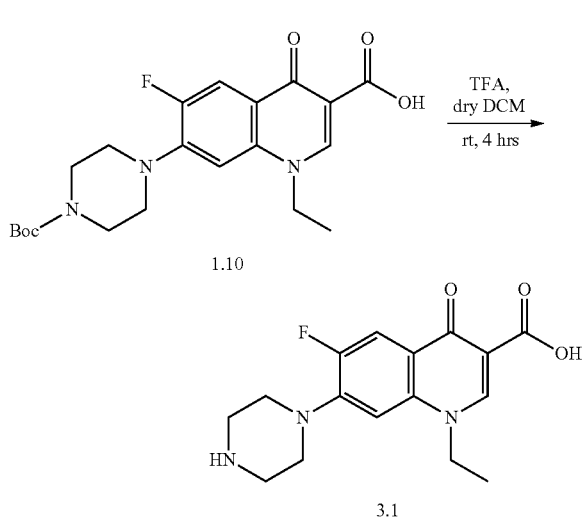

1.10

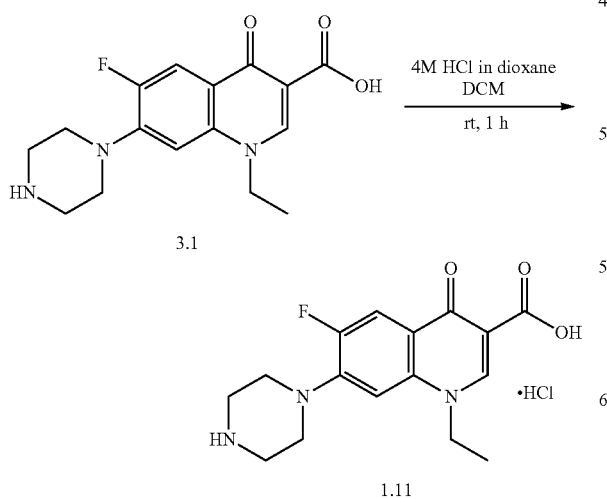

3.1

¹H NMR (400 MHz, TFA) δ 9.30 (s, 1H), 8.29 (d, J=12.09 Hz, 1H), 7.48 (d, J=6.55 Hz, 1H), 4.85 (q, J=7.22 Hz, 2H), 3.91-3.99 (m, 4H), 3.71-3.79 (m, 4H), 1.74 (t, J=7.30 Hz, 3H); IR ($\upsilon_{max}$/cm⁻¹) 1696, 1624, 1610, 1508, 1474, 1453, 1421, 1399, 1382, 1366, 1310, 1265, 1202, 1125, 1104, 1088, 1053, 1033, 990, 934, 916, 900, 828, 808, 797, 748, 720; LC-MS Retention time 2.38 minutes, found 320.0 [M+H]⁺; calculated for $C_{16}H_{18}FN_3O_3$ 320.33 [M+H]⁺.

Synthesis of 1-ethyl-6-fluoro-4-oxo-7-(piperazin-1-yl)-1,4-dihydroquinoline-3-carboxylic acid hydrochloride (1.11)

Compound 3.1 (39 mg, 0.12 mmol, 1 eq) was stirred in the minimum amount of DCM (3 mL) for 5 minutes. Then 4M HCl in dioxane (611 µL, 2.44 mmol, 20 eq) was added dropwise and the mixture stirred for 1 hour. Upon completion, the mixture was washed with hexane (3×1 mL), concentrated under reduced pressure and lyophilized overnight to give compound 1.11 (41 mg, >95% yield) as a pale orange solid.

3.1

1.11

¹H NMR (400 MHz, DMSO-d₆) δ 15.31 (br. s., 1H), 9.37 (br. s., 2H), 8.97 (s, 1H), 7.96 (d, J=13.09 Hz, 1H), 7.26 (d, J=7.30 Hz, 1H), 4.62 (q, J=7.13 Hz, 2H), 3.52-3.59 (m, 4H), 3.30 (br. s., 4H), 1.41 (t, J=7.18 Hz, 3H), 1.22 (d, J=6.55 Hz, 1H); HRMS Observed 320.1404 [M+H]⁺; theoretical value 320.1405 [M+H]⁺; Ir ($\upsilon_{max}$/cm⁻¹) 1701, 1696, 1626, 1507, 1454, 1345, 1340, 1332, 1273, 1130, 1053, 1033, 933, 899, 859, 829, 804, 746, 665; LC-MS Retention time 4.67 minutes, found 320.0 [M+H]⁺; calculated for $C_{16}H_{18}FN_3O_3$ 320.34 [M+H]⁺.

Synthesis of Ciprofloxacin-ARB Hybrid Compounds

Synthesis of 1-cyclopropyl-6-fluoro-7-(4-(naphthalen-1-ylmethyl)piperazin-1-yl)-4-oxo-1,4-dihydroquinoline-3-carboxylic acid (2.2)

Ciprofloxacin (2.1; 1 g, 3.02 mmol, 1 eq) was added to DMF (50 mL total) and stirred for 30 minutes at reflux. Then 1-(bromomethyl)naphthalene (647 mg, 2.92 mmol, 1 eq) was pre-dissolved in DMF (2 mL) at 115° C. and added via syringe. Potassium carbonate (1251 mg, 9.05 mmol, 3 eq) was subsequently added and the mixture stirred for a further 1 hour at reflux. The mixture was allowed to cool, then extracted with ethyl acetate (2×100 mL) using a 1M solution of citric acid to neutralise the aqueous phase. Combined organic fractions were washed with distilled water (100 mL) and brine (100 mL), dried over MgSO₄, filtered and concentrated in vacuo to give the crude product. Purification was achieved via flash column chromatography using ethyl acetate to afford compound 2.2 (433.27 mg, 30.4% yield) as an off white solid.

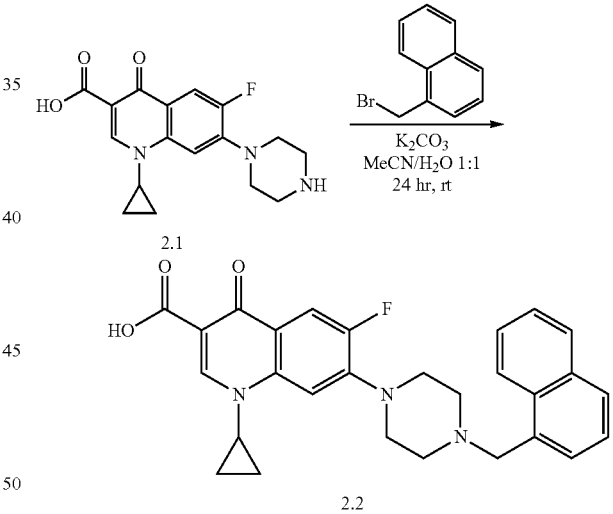

¹H NMR (400 MHz, CDCl₃) δ 15.07 (s, 1H), 8.77 (s, 1H), 8.34 (d, J=8.56 Hz, 1H), 8.03 (d, J=13.09 Hz, 1H), 7.89 (d, J=7.30 Hz, 1H), 7.83 (d, J=7.55 Hz, 1H), 7.49-7.58 (m, 2H), 7.41-7.49 (m, 2H), 7.33 (d, J=7.05 Hz, 1H), 4.02 (s, 2H), 3.49 (br. s., 1H), 3.34 (br. s., 4H), 2.76 (br. s., 4H), 1.31-1.39 (m, 2H), 1.14-1.22 (m, 2H); LC-MS Retention time 30.08 minutes, found 472.1 [M+H]⁺; calculated for $C_{28}H_{26}FN_3O_3$ 472.53 [M+H]⁺.

Synthesis of 1-cyclopropyl-6-fluoro-7-(4-(naphthalen-1-ylmethyl)piperazin-1-yl)-4-oxo-1,4-dihydroquinoline-3-carboxylic acid hydrochloride (2.3)

2.2 (780 mg, 1.65 mmol, 1 eq) was added to dichloromethane (15 mL) and stirred for 5 minutes. Then 4M HCl in dioxane (8.3 mL, 33.08 mmol, 20 eq) was added dropwise and the flask sealed and stirred for 1 hour. The mixture was then washed with hexane (3×30 mL), concentrated in vacuo and lyophilised for 24 hours to afford compound 2.3 (771.55 mg, 91.8% yield) as a pale yellow solid.

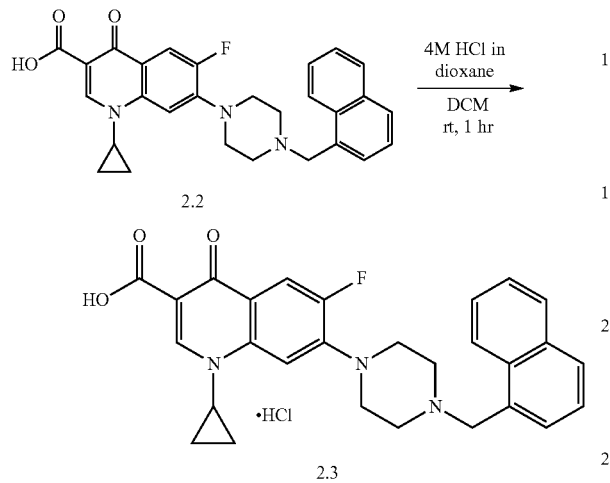

$^1$H NMR (400 MHz, TFA-d) δ 9.27 (s, 1H), 8.22 (d, J=12.09 Hz, 1H), 8.12 (d, J=8.31 Hz, 1H), 8.05 (d, J=8.06 Hz, 1H), 7.97 (d, J=80.6 Hz, 1H), 7.93 (d, J=6.55 Hz, 1H), 7.78 (d, J=7.05 Hz, 1H), 7.65-7.71 (m, 1H), 7.54-7.65 (n, 2H), 5.03 (s, 2H), 4.19 (d, J=13.09 Hz, 2H), 4.10 (br. s., 1H), 3.83-3.98 (m, 4H), 3.65 (t, J=10.95 Hz, 2H), 1.64 (d, J=5.54 Hz, 2H), 1.38 (br. s., 2H); $^{13}$C NMR (100 MHz, DMSO-d$_6$) δ 176.3, 165.8, 152.8 (C-6, $^1$J(C-F)=249 Hz), 148.2, 143.6 (C-7, $^2$J(C-F)=12 Hz), 139.0, 133.4, 132.2, 131.7, 130.4, 128.8, 127.1, 126.3, 125.6, 125.4, 124.1, 119.3, 111.2 (C-5, $^2$J(C-F)=25 HZ), 106.8, 62.8, 55.0, 50.4, 46.2, 35.9, 7.6; IR (υ$_{max}$/cm$^{-1}$) 3370, 1718, 1628, 1506, 1436, 1399, 1340, 1266, 1038, 939, 792; LC-MS Retention time 6.00 minutes, found 472.0 [M+H]$^+$; calculated for C$_{28}$H$_{26}$FN$_3$O$_3$ 472.53 [M+H]$^+$; HRMS Observed 472.2023 [M+H]$^+$; theoretical value 472.2031 [M+H]$^+$.

Synthesis of 1-cyclopropyl-6-fluoro-7-(4-(naphthalen-2-ylmethyl)piperazin-1-yl)-4-oxo-1,4-dihydroquinoline-3-carboxylic acid (2.4)

Ciprofloxacin (2.1; 200 mg, 0.60 mmol, 1 eq) was added to a 1:1 mix of acetonitrile and water (10 mL total). After stirring for 5 minutes, potassium carbonate (250 mg, 1.81 mmol, 3 eq) was added and the mixture stirred for a further 5 minutes. Once fully dissolved, 2-(bromomethyl)naphthalene (127 mg, 0.57 mmol, 0.95 eq) was added slowly over the course of 1 hour and the mixture subsequently stirred for 24 hours. Upon completion, the product was extracted with dichloromethane (2×30 mL) using a 1M solution of citric acid to neutralise the aqueous phase. Combined organic fractions were washed with distilled water (30 mL) and dried over MgSO$_4$, filtered and concentrated in vacuo to give the crude product. Purification was achieved using an SCX-2 catch and release cartridge (see Solid Phase Extraction method) to afford compound 2.4 (219.68 mg, 81.2% yield) as a pale yellow solid.

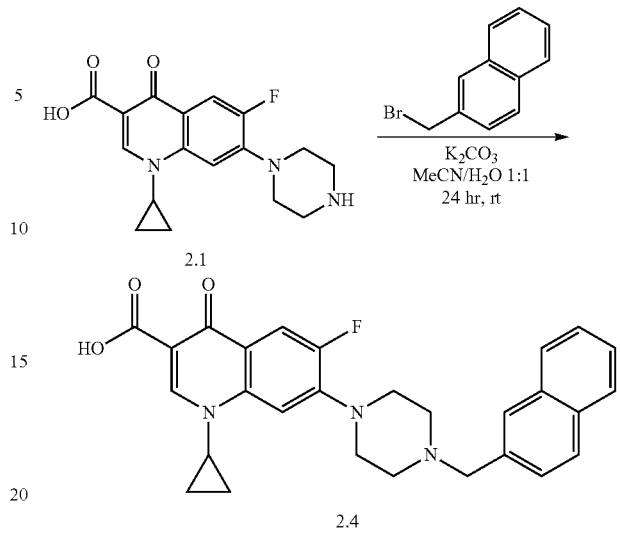

$^1$H NMR (400 MHz, CDCl$_3$) δ 15.05 (br. s., 1H), 8.72 (s, 1H), 7.96 (d, J=13.09 Hz, 1H), 7.81-7.86 (m, 3H), 7.78 (s, 1H), 7.54 (dd, J=1.64, 8.44 Hz, 1H), 7.45-7.52 (m, 2H), 7.34 (d, J=7.05 Hz, 1H), 3.77 (s, 2H), 3.52 (br. s., 1H), 3.34-3.40 (m, 4H), 2.71-2.77 (m, 4H), 10.32-1.39 (m, 2H), 1.14-1.21 (m, 2H); LC-MS Retention time 2.95 minutes, found 472.0 [M+H]$^+$; calculated for C$_{28}$H$_{26}$FN$_3$O$_3$ 472.53 [M+H]$^+$.

Synthesis of 1-cyclopropyl-6-fluoro-7-(4-(naphthalen-2-ylmethyl)piperazin-1-yl)-4-oxo-1,4-dihydroquinoline-3-carboxylic acid hydrochloride (2.5)

2.4 (30 mg, 0.063 mmol, 1 eq) was added to equal parts methanol and dioxane (60 mL total) and stirred for 10 minutes. Then 4M HCl in dioxane (32 μL, 0.126 mmol, 2 eq) was added dropwise and the flask sealed and stirred for 1 hour. The mixture was then washed with hexane (3×30 mL), concentrated in vacuo and lyophilised for 24 hours to afford compound 2.5 (22.18 mg, 68.6% yield) as a white solid.

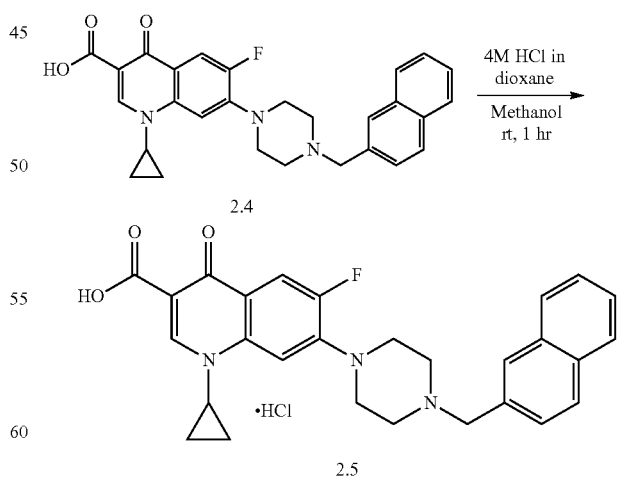

$^1$H NMR (400 MHz, TFA-d) δ 9.29-9.35 (m, 1H), 8.28 (dd, J=30.65, 12.21 Hz, 1H), 7.99-8.05 (m, 2H), 7.88-7.97 (m, 3H), 7.59-7.67 (m, 2H), 7.55 (d, J=6.04 Hz, 1H), 4.72 (br. s., 2H), 4.26 (d, J=12.34 Hz, 2H), 4.08-4.16 (m, 1H), 3.99 (d, J=11.33 Hz, 2H), 3.78 (t, J=11.08 Hz, 2H), 3.60 (t, J=11.83 Hz, 2H), 1.68 (br. s., 2H), 1.42 (br. s., 2H); IR (υm/cm$^{-1}$) 3428, 2923, 2282, 1728, 1629, 1500, 1449, 1387, 1267, 1104, 941, 804; LC-MS Retention time 5.93 minutes, found 472.1 [M+H]$^+$; calculated for $C_{28}H_{26}FN_3O_3$ 472.53 [M+H]$^+$; HRMS Observed 472.2020 [M+H]$^+$; theoretical value 472.2031 [M+H]$^+$.

Synthesis of 1-cyclopropyl-6-fluoro-7-(4-benzylpiperazin-1-yl)-4-oxo-1,4-dihydroquinoline-3-carboxylic acid (2.6)

Ciprofloxacin (2.1; 100 mg, 0.30 mmol, 1 eq) was added to a 1:1 mix of acetonitrile and water (10 mL total). After stirring for 5 minutes, potassium carbonate (125 mg, 0.91 mmol, 3 eq) was added and the mixture stirred for a further 5 minutes. Once fully dissolved, bromomethylbenzene (49 mg, 0.29 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 2.6 (112.69 mg, 93.3% yield) as a pale yellow solid.

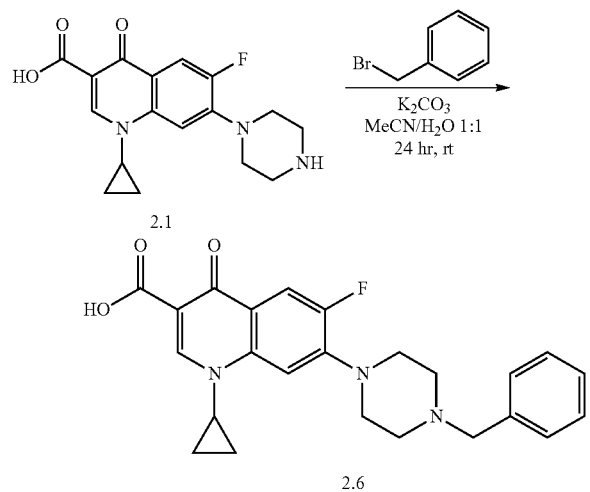

$^1$H NMR (400 MHz, CDCl$_3$) δ 15.05 (br. s., 1H), 8.76 (s, 1H), 8.00 (d, J=13.09 Hz, 1H), 7.32-7.39 (m, 5H), 7.28-7.32 (m, 1H), 3.62 (s, 2H), 3.53 (br. s., 1H), 3.32-3.40 (m, 4H), 2.65-2.73 (m, 4H), 1.38 (q, J=6.38 Hz, 2H), 1.19 (br. s., 2H); LC-MS Retention time 2.83 minutes, found 422.0 [M+H]$^+$; calculated for $C_{24}H_{24}FN_3O_3$ 422.47 [M+H]$^+$.

Synthesis of 1-cyclopropyl-6-fluoro-7-(4-benzylpiperazin-1-yl)-4-oxo-1,4-dihydroquinoline-3-carboxylic acid hydrochloride (2.7)

2.6 (30 mg, 0.07 mmol, 1 eq) was added to methanol (10 mL) and stirred for 10 minutes. Then 4M HCl in dioxane (36 μL, 0.14 mmol, 2 eq) was added dropwise and the flask sealed and stirred for 1 hour. The mixture was then washed with hexane (3×30 mL), concentrated in vacuo and lyophilised for 24 hours to afford compound 2.7 (30.68 mg (91.7% yield) as an off white solid.

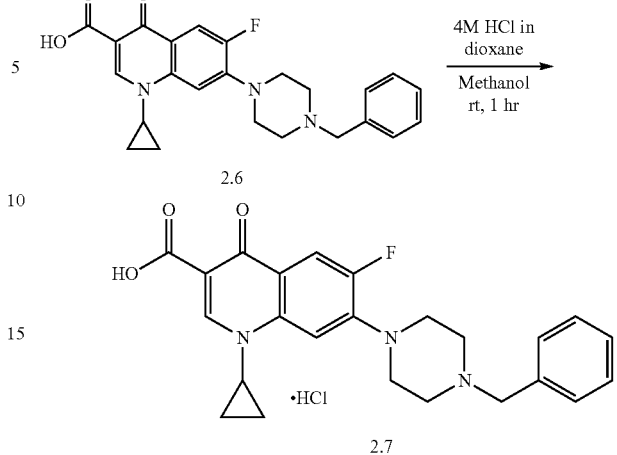

$^1$H NMR (400 MHz, DMSO-d$_6$) δ 15.13 (br. s., 1H), 11.55 (br. s., 1H), 8.68 (s, 1H), 7.96 (d, J=13.09 Hz, 1H), 7.68 (dd, J=2.77, 6.29 Hz, 2H), 7.60 (d, J=7.55 Hz, 1H), 7.46-7.51 (m, 3H), 4.42 (d, J=5.04 Hz, 2H), 3.81-3.92 (m, 3H), 3.44-3.52 (m, 4H), 3.29 (q, J=10.74 Hz, 2H), 1.28-1.35 (m, 2H), 1.15-1.21 (m, 2H); IR (υ$_{max}$/cm$^{-1}$) 2922, 2286, 1729, 1628, 1502, 1468, 1335, 1270, 1104, 941, 803, 702; LC-MS Retention time 5.38 minutes, found 422.1 [M+H]$^+$; calculated for $C_{24}H_{24}FN_3O_3$ 422.47 [M+H]$^+$; HRMS Observed 422.1864 [M+H]$^+$; theoretical value 422.1874 [M+H]$^+$.

Synthesis of 1-cyclopropyl-6-fluoro-7-(4-(benzo[d][1,3]dioxol-4-ylmethyl)-piperazin-1-yl)-4-oxo-1,4-dihydroquinoline-3-carboxylic acid (2.8)

Ciprofloxacin (2.1; 53 mg, 0.16 mmol, 1 eq) was added to a 1:1 mix of acetonitrile and water (5 mL total). After stirring for 5 minutes, potassium carbonate (66 mg, 0.48 mmol, 3 eq) was added and the mixture stirred for a further 5 minutes. Once fully dissolved, 4-(bromomethyl)benzo[d][1,3]dioxole (33 mg, 0.15 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 2.8 (47.78 mg, 67.6% yield) as an off white solid.

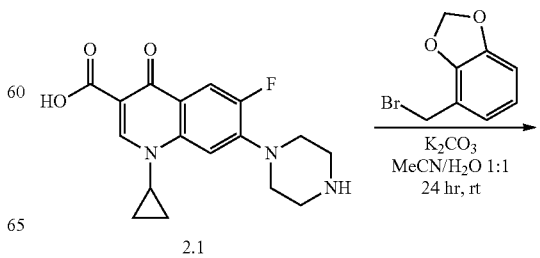

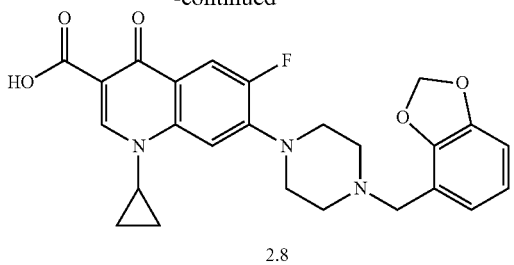

2.8

¹H NMR (400 MHz, CDCl₃) δ 15.04 (br. s., 8.76 (s, 1H), 8.01 (d, J=13.09 Hz, 1H), 7.35 (d, J=70.05 Hz, 1H), 6.76-6.88 (m, 3H), 5.98 (s, 2H), 3.63 (s, 2H), 3.53 (br. s., 1H), 3.33-3.40 (m, 4H), 2.69-2.76 (m, 4H), 1.38 (m, 2H), 1.19 (br. s., 2H); ¹³C NMR (100 MHz, CDCl₃) δ 177.1, 167.1, 155.0, 152.5, 147.4, 147.3, 146.3, 146.1, 146.0, 139.1, 123.5, 121.4, 119.8, 119.7, 118.6, 112.5, 112.3, 108.1, 107.8, 104.7, 100.8, 56.2, 52.5, 49.8, 49.8, 35.3, 8.3; LC-MS Retention time 2.87 minutes, found 466.0 [M+H]⁺; calculated for $C_{25}H_{24}FN_3O_5$ 466.48 [M+H]⁺

Synthesis of 1-cyclopropyl-6-fluoro-7-(4-(benzo[d][1,3]dioxol-4-ylmethyl)-piperazin-1-yl)-4-oxo-1,4-dihydroquinoline-3-carboxylic acid hydrochloride (2.9)

2.8 (50 mg, 0.11 mmol, 1 eq) was added to methanol (25 mL) and stirred for 10 minutes. Then 4M HCl in dioxane (54 μL, 0.21 mmol, 2 eq) was added dropwise and the flask sealed and stirred for 1 hour. The mixture was then washed with hexane (3×30 mL), concentrated in vacuo and lyophilised for 24 hours to afford compound 2.9 (38.23 mg, 70.9% yield) as a pale yellow solid.

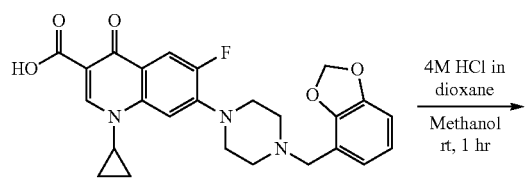

2.8

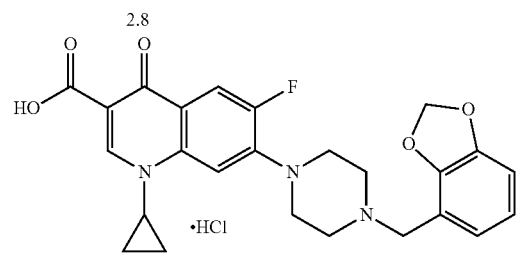

2.9

¹³C NMR (100 MHz, DMSO-d₆) δ 176.3, 165.8, 152.8 (C-6, ¹J(C-F)=254 Hz), 148.3, 147.5, 147.3, 143.6 (C-7, ²J(C-F)=15 Hz), 139.0, 125.1, 121.9, 119.3 ((C-F)=7 Hz), 111.2 (C-5, ²J(C-F)=17 HZ), 110.3, 109.9, 107.0, 106.8, 101.3, 52.7, 50.1, 46.1, 35.9, 7.6; IR ($\upsilon_{max}$/cm⁻¹) 3378, 2913, 2571, 2362, 1719, 1627, 1507, 1452, 1399, 1253, 1035, 952, 804, 725; LC-MS Retention time 5.48 minutes, found 466.1 [M+H]⁺; calculated for $C_{25}H_{24}FN_3O_5$ 466.48 [M+H]⁺; HRMS Observed 466.1762 [M+H]⁺; theoretical value 466.1773 [M+H]⁺.

Synthesis of 1-cyclopropyl-6-fluoro-7-(4-(benzo[b]thiophen-7-ylmethyl)-piperazin-1-yl)-4-oxo-1,4-dihydroquinoline-3-carboxylic acid (2.10)

Ciprofloxacin (2.1; 77 mg, 0.23 mmol, 1 eq) was added to a 1:1 mix of acetonitrile and water (5 mL total). After stirring for 5 minutes, potassium carbonate (96 mg, 0.70 mmol, 3 eq) was added and the mixture stirred for a further 5 minutes. Once fully dissolved, 7-(bromomethyl)benzo[b]thiophene (50 mg, 0.22 mmol, 0.95 eq) was added slowly over the course of 1 hour and the mixture subsequently stirred for 24 hours. Upon completion, extraction using dichloromethane (2×20 mL), using a 1M solution of citric acid to neutralise the aqueous phase, resulted in formation of a white precipitate. The precipitate was filtered, washed with distilled water (3×20 mL), re-suspended in dichloromethane (2 mL) and purified via automated column chromatography (see Flash Column Chromatography method) to afford compound 2.10 (34.67 mg, 32.9% yield) as an off white solid.

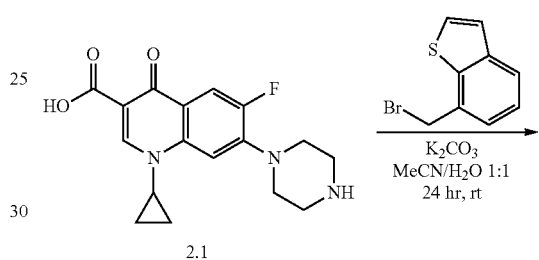

2.1

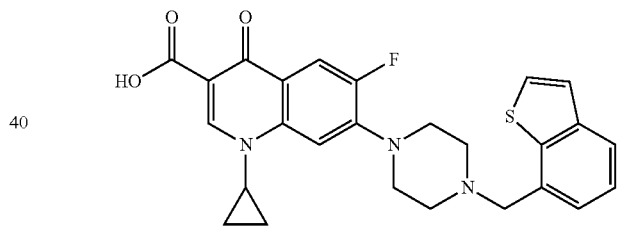

2.10

¹H NMR (400 MHz, CDCl₃) δ 15.09 (br. s., 1H), 8.78 (s, 1H), 8.03 (d, J=13.09 Hz, 1H), 7.79 (d, J=70.81 Hz, 1H), 7.47 (d, J=5.29 Hz, 1H), 7.34-7.41 (m, 3H), 7.28 (s, 1H), 3.89 (s, 2H), 3.48-3.56 (m, 1H), 3.36-3.42 (m, 4H), 2.73-2.79 (m, 4H), 1.37 (q, J=6.71 Hz, 2H), 1.17-1.23 (m, 2H); LC-MS Retention time 3.15 minutes, found 477.9 [M+H]⁺; calculated for $C_{26}H_{24}FN_3O_3S$ 478.55 [M+H]⁺.

Synthesis of 1-cyclopropyl-6-fluoro-7-(4-(benzo[b]thiophen-7-ylmethyl)piperazin-1-yl)-4-oxo-1,4-dihydroquinoline-3-carboxylic acid hydrochloride (2.11)

2.10 (20 mg, 0.042 mmol, 1 eq) was added to methanol (10 mL) and stirred for 10 minutes. Then 4M HCl in dioxane (21 μL, 0.084 mmol, 2 eq) was added dropwise and the flask sealed and stirred for 1 hour. The mixture was then washed with hexane (3×30 mL), concentrated in vacuo and lyophilised for 24 hours to afford compound 2.11 (16.35 mg, 73.3% yield) as a pale yellow solid.

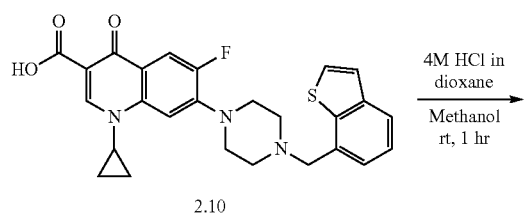

2.10

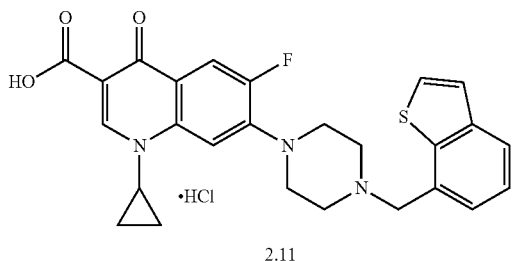

2.11

¹H NMR (400 MHz, DMSO-d₆) δ15.13 (br. s, 1H), 11.45 (br. s., 1H), 8.68 (s, 1H), 7.86-8.05 (m, 4H), 7.51-7.61 (m, 3H), 4.71 (br. s., 2H), 3.90 (br. s., 2H), 3.82 (br. s., 2H), 3.51 (br. s., 6H), 1.30 (d, J=5.79 Hz, 2H), 1.18 (d, J=4.03 Hz, 3H); IR ($\upsilon_{max}$/cm⁻¹) 3380, 1715, 1628, 1457, 1339, 1265, 1042, 943, 803; LC-MS Retention time 6.12 minutes, found 478.0 [M+H]⁺; calculated for $C_{26}H_{24}FN_3O_3S$ 478.55 [M+H]⁺; HRMS Observed 478.1584 [M+H]⁺; theoretical value 478.1595 [M+H]⁺.

Synthesis of 1-cyclopropyl-6-fluoro-7-(4-((4-fluoronaphthalen yl)methyl)piperazin-1-yl)-4-oxo-1,4-dihydroquinoline-3-carboxylic acid (2.12)

Ciprofloxacin (2.1; 100 mg, 0.30 mmol, 1 eq) was added to a 1:1 mix of acetonitrile and water (10 mL total). After stirring for 5 minutes, potassium carbonate (125 mg, 0.91 mmol, 3 eq) was added and the mixture stirred for a further 5 minutes. Once fully dissolved, 1-(bromomethyl)-4-fluoronaphthalene (69 mg, 0.29 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford compound 2.12 (74.68 mg, 53.2% yield) as a pale yellow solid.

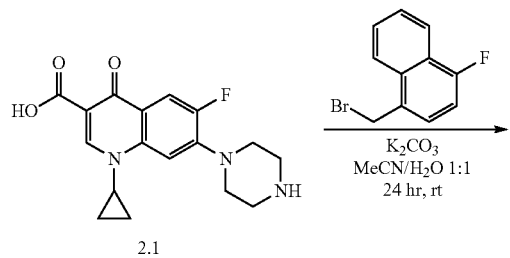

2.1

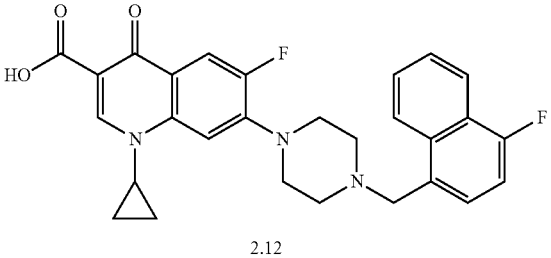

2.12

LC-MS Retention time 3.18 minutes, found 490.0 [M+H]⁺; calculated for $C_{28}H_{25}F_2N_3O_3$ 490.52 [M+H]⁺.

Synthesis of 1-cyclopropyl-6-fluoro-7-(4-((4-fluoronaphthalen-1-yl)methyl)piperazin-1-yl)-4-oxo-1,4-dihydroquinoline-3-carboxylic acid hydrochloride (2.13)

2.12 (80 mg, 0.16 mmol, 1 eq) was added to methanol (40 mL) and stirred for 10 minutes. Then 4M HCl in dioxane (82 μL, 0.33 mmol, 2 eq) was added dropwise and the flask sealed and stirred for 1 hour. The mixture was then washed with hexane (3×30 mL), concentrated in vacuo and lyophilised for 24 hours to afford compound 2.13 (75.76 mg, 88.1% yield) as a light brown solid.

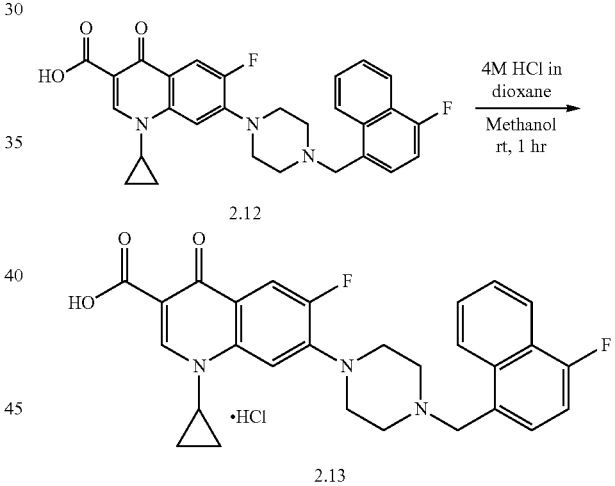

2.12

2.13

¹H NMR (400 MHz, TFA-d) δ 9.24 (d, J=3.78 Hz, 1H), 8.25 (d, J=8.56 Hz, 1H), 8.19 (d, J=13.35 Hz, 1H), 8.06 (d, J=7.55 Hz, 1H), 7.87 (br. s., 1H), 7.62-7.75 (m, 3H), 7.20 (t, J=8.44 Hz, 1H), 4.96 (br. s., 2H), 4.16 (d, J=12.34 Hz, 2H), 4.05 (br. s., 1H), 3.90 (d, J=11.58 Hz, 2H), 3.75 (t, J=11.71 Hz, 2H), 3.59 (t, J=10.95 Hz, 2H), 1.60 (br. s., 2H), 1.34 (br. s., 2H); IR ($\upsilon_{max}$/cm⁻¹) 3373, 1715, 1628, 1457, 1395, 1340, 1266, 1042, 943, 804; LC-MS Retention time 6.08 minutes, found 490.1 [M+H]⁺; calculated for $C_{28}H_{25}F_2N_3O_3$ 490.52 [M+H]⁺; HRMS Observed 490.1929 [M+H]⁺; theoretical value 490.1937 [M+H]⁺.

Synthesis of 1-cyclopropyl-6-fluoro-7-(4-(2-oxo-1,2-dihydroquinolin yl)methyl)piperazin-1-yl)-4-oxo-1,4-dihydroquinoline-3-carboxylic acid (2.14)

Ciprofloxacin (2.1; 1 g, 3.02 mmol, 1 eq) was added to a 1:1 mix of acetonitrile and water (50 mL total). After stirring for 5 minutes, potassium carbonate (1251 mg, 9.05 mmol, 3 eq) was added and the mixture stirred for a further 5 minutes. Once fully dissolved, 4-(bromomethyl)quinolin-2(1H)-one (683 mg, 2.87 mmol, 0.95 eq) was added slowly over the course of 1 hour and the mixture subsequently stirred for 24 hours. Upon completion, extraction using dichloromethane (2)(100 mL), using a 1M solution of citric acid to neutralise the aqueous phase, resulted in formation of a white precipitate. The precipitate was filtered, washed with distilled water (100 mL) and methanol (100 mL) then re-dissolved in excess DMSO. Purification was achieved using an SCX-2 catch and release cartridge (see Solid Phase Extraction method) to afford compound 2.14 (1.06 g, 75.7% yield) as a pale yellow solid.

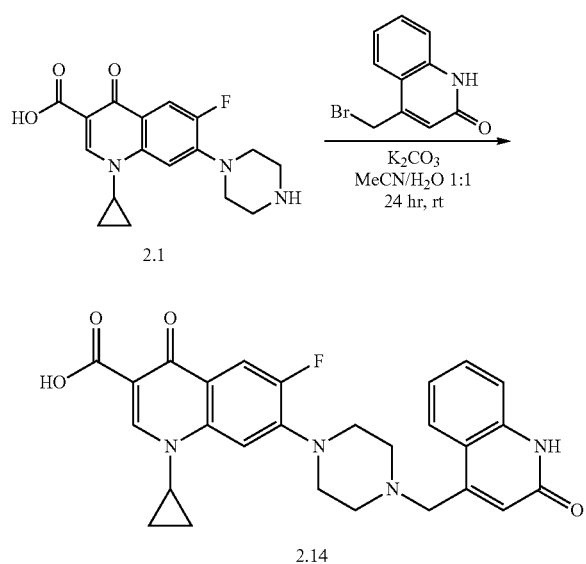 [SMILES: O=C(O)c1cn(C2CC2)c2cc(N3CCNCC3)c(F)cc2c1=O ; O=c1cc(CBr)c2ccccc2[nH]1 ; O=C(O)c1cn(C2CC2)c2cc(N3CCN(Cc4cc(=O)[nH]c5ccccc45)CC3)c(F)cc2c1=O]

LC-MS Retention time 2.92 minutes, found 489.0 [M+H]$^+$; calculated for $C_{27}H_{25}FN_4O_4$ 489.52 [M+H]$^+$.

Synthesis of 1-cyclopropyl-6-fluoro-7-(4-(2-oxo-1,2-dihydroquinolin-4-yl)methyl)piperazin-1-yl)-4-oxo-1,4-dihydroquinoline-3-carboxylic acid hydrochloride (2.15)

2.14 (50 mg, 0.10 mmol, 1 eq) was added to methanol (15 mL) and stirred for 10 minutes. Then 4M HCl in dioxane (524, 0.20 mmol, 2 eq) was added dropwise and the flask sealed and stirred for 1 hour. The mixture was then washed with hexane (3×30 mL), concentrated in vacuo and lyophilised for 24 hours to afford compound 2.15 (42.09 mg, 78.3% yield) as a white solid.

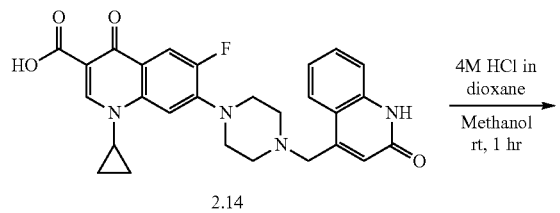

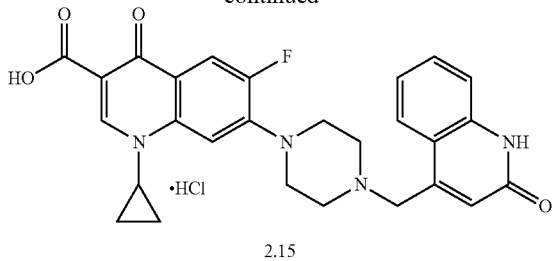

$^1$H NMR (400 MHz, TFA-d) δ 9.32 (s, 1H), 8.20-8.31 (m, 2H), 7.97-8.03 (m, 1H), 7.94 (br. s., 1H), 70.86 (d, J=8.56 Hz, 1H), 7.77 (br. s., 2H), 5.14 (br. s., 2H), 4.25 (br. s., 2H), 4.12 (br. s., 3H), 30.86 (br. s., 4H), 1.67 (br. s., 2H), 1.41 (br. s., 2H); IR ($υ_{max}$/cm$^{-1}$) 3446, 2826, 2362, 1710, 1664, 1625, 1558, 1473, 1439, 1357, 1257, 1038, 958, 887, 805, 747; LC-MS Retention time 5.67 minutes, found 489.0 [M+H]$^+$; calculated for $C_{27}H_{25}FN_4O_4$ 489.52 [M+H]$^+$; HRMS Observed 489.1924 [M+H]$^+$; theoretical value 489.1933 [M+H]$^+$.

Synthesis of 1-cyclopropyl-6-fluoro-7-(4-(quinolin-8-ylmethyl)piperazin-1-yl) oxo-1,4-dihydroquinoline-3-carboxylic acid (2.16)

Ciprofloxacin (2.1; 100 mg, 0.30 mmol, 1 eq) was added to a 1:1 mix of acetonitrile and water (10 mL total). After stirring for 5 minutes, potassium carbonate (125 mg, 0.91 mmol, 3 eq) was added and the mixture stirred for a further 5 minutes. Once fully dissolved, 8-(bromomethyl)quinoline (64 mg, 0.29 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 2.16 as a tan solid.

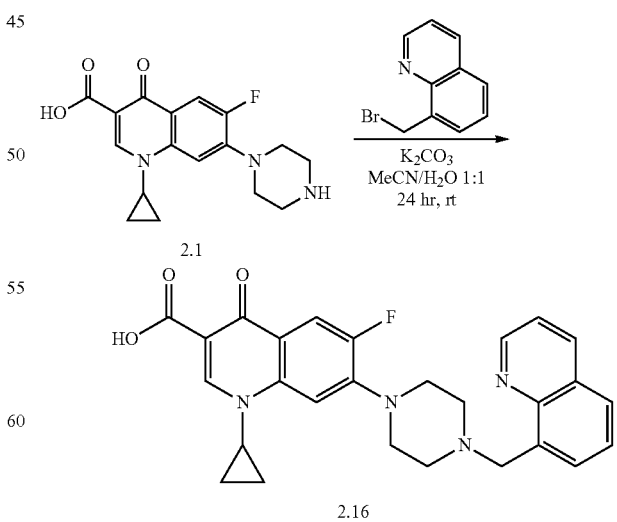

LC-MS Retention time 2.88 minutes, found 473.0 [M+H]$^+$; calculated for $C_{27}H_{25}FN_4O_3$ 473.52 [M+H]$^+$.

Synthesis of 1-cyclopropyl-6-fluoro-7-(4-(quinolin-8-ylmethyl)piperazin-1-34)-4-oxo-1,4-dihydroquinoline-3-carboxylic acid hydrochloride (2.17)

2.16 (50 mg, 0.11 mmol, 1 eq) was added to methanol (25 mL) and stirred for 10 minutes. Then 4M HCl in dioxane (53 µL, 0.21 mmol, 2 eq) was added dropwise and the flask sealed and stirred for 1 hour. The mixture was then washed with hexane (3×30 mL), concentrated in vacuo and lyophilised for 24 hours to afford compound 2.17, as a light brown solid.

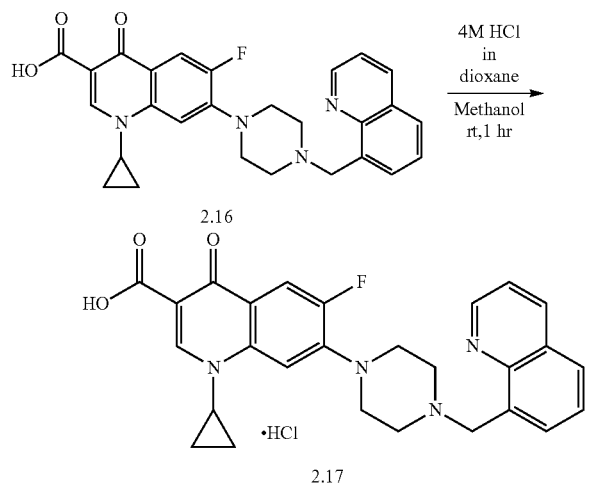

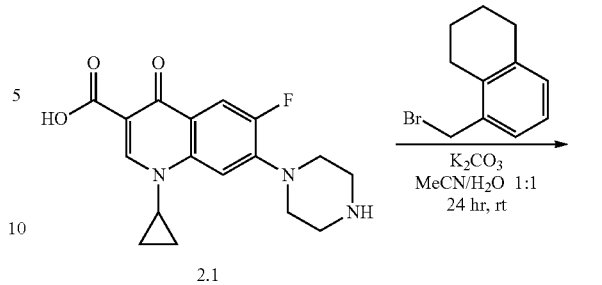

$^1$H NMR (400 MHz, TFA-d) δ 9.42 (d, J=5.29 Hz, 1H), 9.37 (s, 1H), 9.35 (d, J=8.56 Hz, 1H), 8.66 (d, J=7.55 Hz, 1H), 8.60 (d, J=8.06 Hz, 1H), 8.29-8.36 (m, 2H), 8.24 (t, J=7.30 Hz, 1H), 8.01 (d, J=5.79 Hz, 1H), 5.48 (s, 2H), 4.34 (d, J=11.83 Hz, 2H), 4.08-4.20 (m, 3H), 3.99 (t, J=10.70 Hz, 2H), 3.81-3.92 (m, 2H), 1.73 (d, J=5.04 Hz, 2H), 1.47 (br. s., 2H); IR ($v_{max}$/cm$^{-1}$) 3393, 2355, 1726, 1628, 1473, 1333, 1257, 943, 832, 804, 746; LC-MS Retention time 5.62 minutes, found 473.1 [M+H]$^+$; calculated for $C_{27}H_{25}FN_4O_3$ 473.52 [M+H]$^+$; HRMS Observed 473.1974 [M+H]$^+$; theoretical value 473.1983 [M+H]$^+$.

Synthesis of 1-cyclopropyl-6-fluoro-7-(4-((5,6,7,8-tetrahydronaphthalen-1-yl)methyl)-piperazin-1-yl)-4-oxo-1,4-dihydroquinoline-3-carboxylic acid (2.18)

Ciprofloxacin (2.1; 100 mg, 0.30 mmol, 1 eq) was added to a 1:1 mix of acetonitrile and water (10 mL total). After stirring for 5 minutes, potassium carbonate (125 mg, 0.91 mmol, 3 eq) was added and the mixture stirred for a further 5 minutes. Once fully dissolved, 5-(bromomethyl)-1,2,3,4-tetrahydronaphthalene (65 mg, 0.29 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 2.18 (96.47 mg, 70.8% yield) as a pale brown solid.

$^1$H NMR (400 MHz, CDCl$_3$) δ 15.06 (br. s., 1H), 8.75 (s, 1H), 7.98 (d, J=13.09 Hz, 1H), 7.34 (d, J=6.80 Hz, 1H), 7.02-7.14 (m, 3H), 3.52 (s, 3H), 3.31-3.37 (m, 4H), 2.79-2.88 (m, 4H), 2.66-2.71 (m, 4H), 1.76-1.88 (m, 4H), 1.34-1.41 (m, 2H), 1.20 (m, 2H); LC-MS Retention time 30.17 minutes, found 476.1 [M+H]$^+$; calculated for $C_{28}H_{30}FN_3O_3$ 476.56 [M+H]$^+$.

Synthesis of 1-cyclopropyl-6-fluoro-7-(4-((5,6,7,8-tetrahydronaphthalen-1-yl)methyl)piperazin-1-yl)-4-oxo-1,4-dihydroquinoline-3-carboxylic acid hydrochloride (2.19)

2.18 (40 mg, 0.084 mmol, 1 eq) was added to methanol (10 mL) and stirred for 10 minutes. Then 4M HCl in dioxane (42 µL, 0.17 mmol, 2 eq) was added dropwise and the flask sealed and stirred for 1 hour. The mixture was then washed with hexane (3×30 mL), concentrated in vacuo and lyophilised for 24 hours to afford compound 2.19 (259.01 mg, 98.6% yield) as a yellow solid.

In an alternative method, 2.18 (244 mg, 0.51 mmol, 1 eq) was added to dichloro-methane (5 mL) and stirred for 10 minutes. Then 4M HCl in dioxane (2.6 mL, 10.26 mmol, 20 eq) was added dropwise and the flask sealed and stirred for 2 hours. The mixture was then washed with hexane (3×30 mL), concentrated in vacuo and lyophilised for 24 hours to afford 2.19 as a yellow solid.

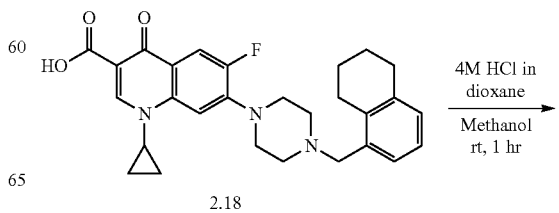

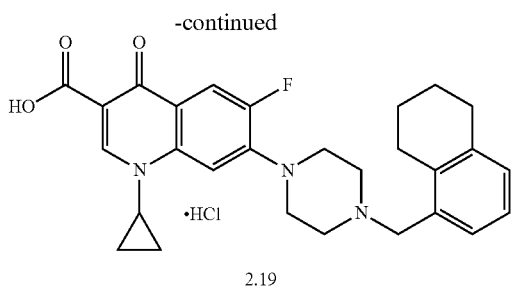

2.19

¹H NMR (400 MHz, DMSO-d₆+TFA) δ 8.69 (s, 1H), 7.97 J=13.35 Hz, 1H), 7.59 (d, J=7.30 Hz, 1H), 7.52 (d, J=6.55 Hz, 1H), 7.14-7.22 (m, 2H), 4.39 (br. s., 2H), 3.79-3.94 (m, 3H), 3.36-3.53 (m, 4H), 2.89 (t, J=5.54 Hz, 2H), 2.76 J=5.92 Hz, 2H), 1.67-1.83 (m, 4H), 1.31 (d, J=6.55 Hz, 1H), 1.19 (br. s., 2H); IR ($\upsilon_{max}$/cm⁻¹) 3382, 2928, 1716, 1628, 1452, 1388, 1265, 941, 831, 804; LC-MS Retention time 6.07 minutes, found 476.1 [M+H]⁺; calculated for $C_{28}H_{30}FN_3O_3$ 476.56 [M+H]⁺; HRMS Observed 476.2334 [M+H]⁺; theoretical value 476.2344 [M+H]⁺.

Synthesis of 1-cyclopropyl-7-(4-(4-(dimethylamino)benzyl)piperazin-1-yl)-6-fluoro-4-oxo-1,4-dihydroquinoline-3-carboxylic acid (2.20)

Ciprofloxacin (2.1; 100 mg, 0.30 mmol, 1 eq) was added to a 1:1 mix of acetonitrile and water (5 mL total). After stirring for 5 minutes, potassium carbonate (125 mg, 0.91 mmol, 3 eq) was added and the mixture stirred for a further 5 minutes. Once fully dissolved, 4-(bromomethyl)-N,N-dimethylanilene (65 mg, 0.30 mmol, 1 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford compound 2.20 (67.25 mg, 50.5% yield) as an off white solid.

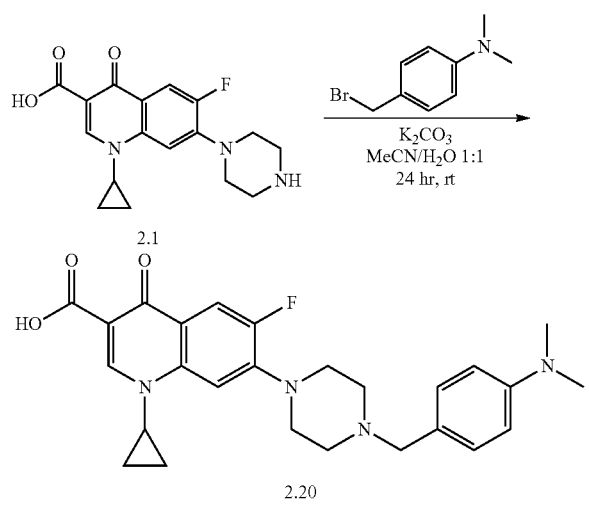

2.1

2.20

¹H NMR (400 MHz, CDCl₃) δ 15.07 (br. s., 1H), 8.77 (s, 1H), 8.02 (d, J=13.09 Hz, 1H), 7.35 (d, J=7.30 Hz, 1H), 7.19-7.23 (m, J=8.56 Hz, 2H), 6.70-6.75 (m, J=8.56 Hz, 2H), 3.52 (s, 3H), 3.31-3.37 (m, 4H), 2.96 (s, 6H), 2.64-2.70 (m, 4H), 1.34-1.40 (m, 2H), 1.16-1.22 (m, 2H); LC-MS Retention time 50.48 minutes, found 465.0 [M+H]⁺; calculated for $C_{26}H_{29}FN_4O_3$ 465.54 [M+H]⁺.

Synthesis of 1-cyclopropyl-7-(4-(4-(dimethylamino)benzyl)piperazin-1-yl) fluoro-4-oxo-1,4-dihydroquinoline-3-carboxylic acid hydrochloride (2.21)

2.20 (61.14 mg, 0.13 mmol, 1 eq) was added to dichloromethane (5 mL) and stirred for 5 minutes. Then 4M HCl in dioxane (658 µL, 2.63 mmol, 20 eq) was added dropwise and the flask sealed and stirred for 1 hour. The mixture was then washed with hexane (3×30 mL), concentrated in vacuo and lyophilised for 24 hours to afford compound 2.21 (61.72 mg, 93.6% yield) as an off white solid.

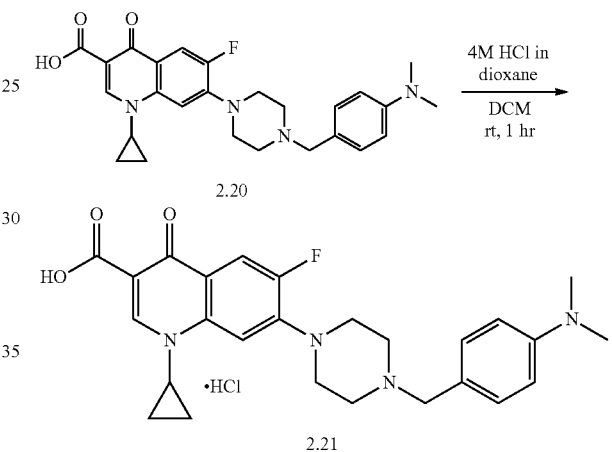

2.20

2.21

¹H NMR (400 MHz, TFA-d) δ 9.26 (d, J=3.02 Hz, 1H), 8.22 (d, J=12.09 Hz, 1H), 7.89-7.96 (m, 3H), 7.82 (d, J=5.54 Hz, 2H), 4.62 (br. s., 2H), 4.18 (d, J=13.60 Hz, 2H), 4.08 (br. s., 1H), 3.78-3.90 (m, 4H), 3.57 (t, J=11.20 Hz, 2H), 3.43 (br. s., 6H), 1.63 (br. s., 2H), 1.37 (br. s., 2H); 13C NMR (100 MHz, DMSO-d₆) δ 176.0 (C=O), 169.0 (CO₂H), 153.3 (C-6, ¹J(C-F)=250 Hz), 148.4, 144.4, 144.0 (C-7, ²J(C-F)= 10 Hz), 138.9, 133.4, 128.9, 120.7, 120.4, 118.9 ((C-F)=8 Hz), 110.7 (C-5, ²J(C-F)=23 Hz), 106.8, 1051, 59.3, 51.0, 46.3, 45.6, 36.1, 7.4; IR ($\upsilon_{max}$/cm⁻¹) 3500, 3438, 3384, 2553, 2459, 1718, 1631, 1478, 1390, 1267, 1184, 1103, 1027, 946, 894, 801, 594; LC-MS Retention time 50.53 minutes, found 465.0 [M+H]⁺; calculated for $C_{26}H_{29}FN_4O_3$ 465.54 [M+H]⁺; HRMS Observed 465.2285 [M+H]⁺; theoretical value 465.2296 [M+H]⁺.

Synthesis of tert-butyl 4-(2-(naphthalen-1-yl)ethyl)piperazine-1-carboxylate (2.23)

1-(2-bromoethyl)naphthalene (2.22; 1 g, 4.25 mmol, 1 eq), tert-butyl piperazine-1-carboxylate (1 g, 50.37 mmol, 1.25 eq) and potassium carbonate (2.23 g, 16.1 mmol, 3.8 eq) were added to a 1:1 mixture of acetonitrile and water (10 mL total) and stirred for 72 hours at room temperature. Upon completion, the mixture was extracted with dichloromethane (3×50 mL) using a 1M solution of citric acid to neutralise the aqueous phase. Combined organic fractions were washed with distilled water (50 mL) followed by brine (50 mL), dried over MgSO$_4$, filtered and concentrated in vacuo to give the crude product. Flash column chromatography (0%-3%-10% DCM/MeOH) was used to afford compound 2.23 (1.093 g, 75.5% yield) as a brown oil.

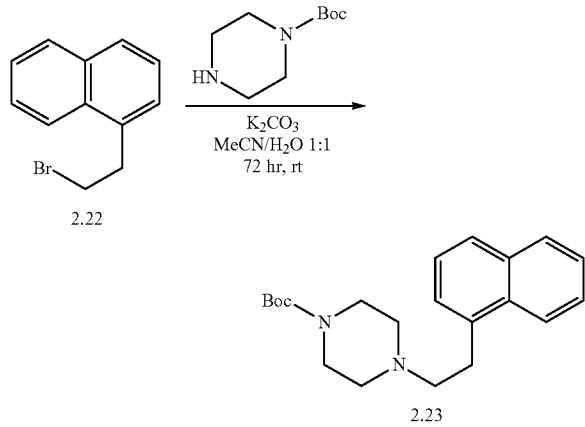

$^1$H NMR (400 MHz, CDCl$_3$) δ 8.05 (dd, J=1.13, 8.43 Hz, 1H), 7.87 (dd, J=1.26, 8.31 Hz, 1H), 7.74 (d, J=8.06 Hz, 1H), 7.46-7.55 (m, 2H), 7.34-7.43 (m, 2H), 3.49-3.54 (m, 4H), 3.26-3.32 (m, 2H), 2.71-2.77 (m, 2H), 2.52-2.59 (m, 4H), 10.49 (s, 9H); LC-MS Retention time 2.97 minutes, found 341.1 [M+H]$^+$; calculated for C$_{21}$H$_{28}$N$_2$O$_2$ 341.47 [M+H]$^+$.

Synthesis of 1-(2-(naphthalen-1-yl)ethyl)piperazine (2.24)

2.23 (1.093 g, 3.21 mmol, 1 eq) was added to dichloromethane (10 mL) followed by 4M HCl in dioxane (16 mL, 64.3 mmol, 20 eq), the flask sealed and stirred for 3 hours at room temperature. Upon completion, the mixture was extracted with dichloromethane (2×50 mL) using a saturated solution of sodium hydrogencarbonate to neutralise the aqueous phase. Combined organic fractions were washed with distilled water (50 mL) followed by brine (50 mL), dried over MgSO$_4$, filtered and concentrated in vacuo to give the crude product 2.24 as an off white solid which was used in successive reactions without further purification.

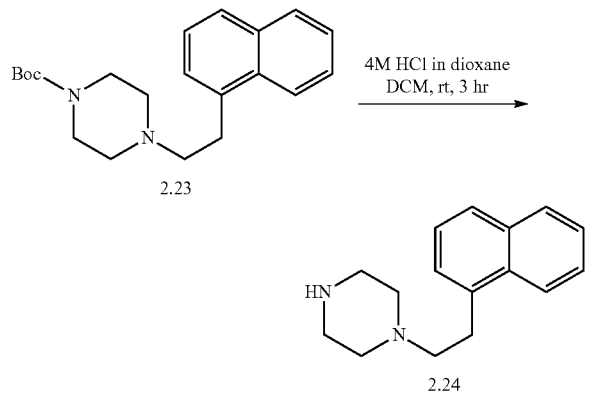

$^1$H NMR (400 MHz, CDCl$_3$) δ 7.99 (d, J=8.56 Hz, 1H), 7.78 (dd, J=1.64, 7.93 Hz, 1H), 7.65 (d, J=7.81 Hz, 1H), 7.38-7.47 (m, 2H), 7.26-7.35 (m, 2H), 3.19-3.25 (m, 2H), 2.90 (t, J=4.91 Hz, 4H), 2.62-2.67 (m, 2H), 2.52 (br. s., 4H); LC-MS Retention time 2.27 minutes, found 241.0 [M+H]$^+$; calculated for C$_{16}$H$_{20}$N$_2$ 241.35 [M+H]$^+$.

Synthesis of 1-cyclopropyl-6-fluoro-7-(4-(2-(naphthalen-1-yl)ethyl)-piperazin-1-yl)-4-oxo-1,4-dihydroquinoline-3-carboxylic acid (2.25)

1-cyclopropyl-6,7-difluoro-4-oxo-1,4-dihydroquinoline-3-carboxylic acid (1.4; 100 mg, 0.38 mmol, 1 eq) and 1-(2-(naphthalen-1-yl)ethyl)piperazine (2.24; 200 mg, 0.83 mmol, 2.2 eq) were added to DMSO (5 mL) and stirred until full dissolution of both compounds was achieved. The reaction was subsequently heated to 140° C. for one and a half hours. Upon completion, the mixture was allowed to cool, then extracted with dichloromethane (25 mL). Combined organic fractions were washed with distilled water (2×200 mL), dried over MgSO$_4$, filtered and concentrated in vacuo to remove any residual DMSO. The crude solid was purified via trituration; the crude was washed with methanol (5×10 mL), then the remaining powder collected and re-filtered using dichloromethane. This second filtrate was concentrated in vacuo to afford compound 2.25 (45 mg, 24.6% yield) as a light brown solid.

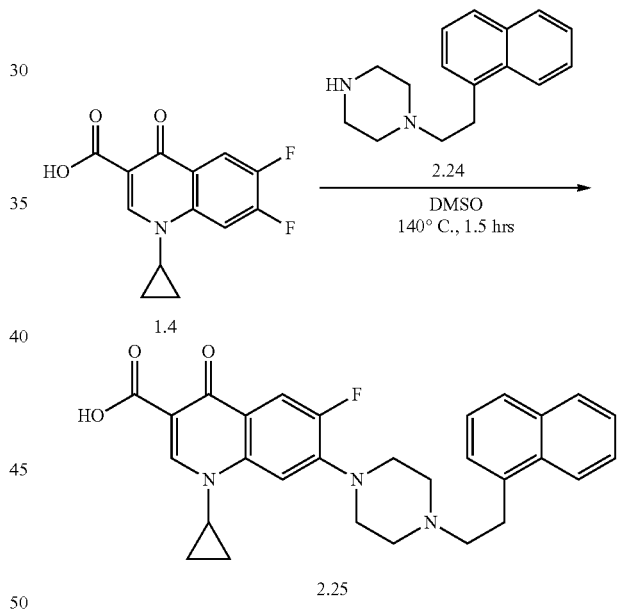

$^1$H NMR (400 MHz, CDCl$_3$) δ 15.05 (br. s., 1H), 8.79 (s, 1H), 8.08 (d, J=8.31 Hz, 1H), 8.04 (d, J=13.09 Hz, 1H), 7.88 (dd, J=1.01, 8.06 Hz, 11-1), 7.76 (d, J=7.81 Hz, 1H), 7.48-7.57 (m, 2H), 7.37-7.45 (m, 3H), 3.53-3.60 (m, 1H), 3.40-3.46 (m, 4H), 3.31-3.37 (m, 2H), 2.81-2.88 (m, 6H), 1.38-1.44 (m, 2H), 1.19-1.25 (m, 2H); $^{19}$F NMR (400 MHz, CDCl$_3$) δ −120.66; LC-MS Retention time 3.15 minutes, found 486.2 [M+H]$^+$; calculated for C$_{29}$H$_{28}$FN$_3$O$_3$ 486.56 [M+H]$^+$.

Synthesis of 1-cyclopropyl-6-fluoro-7-(4-(2-(naphthalen-1-yl)ethyl)-piperazin-1-yl)-4-oxo-1,4-dihydroquinoline-3-carboxylic acid hydrochloride (2.26)

2.25 (25.8 mg, 0.053 mmol, 1 eq) was added to dichloromethane (5 mL total) and stirred for 10 minutes. Then 4M HCl in dioxane (265 μL, 1.06 mmol, 20 eq) was added dropwise and the flask sealed and stirred for 1 hour. The mixture was then washed with hexane (3×30 mL), concentrated in vacuo and lyophilised for 24 hours to afford compound 2.26 as a light brown solid.

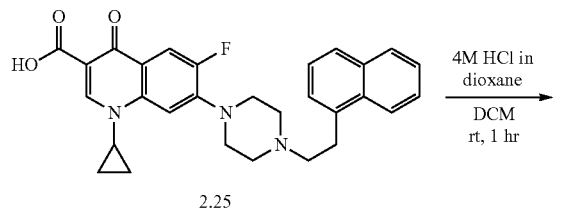

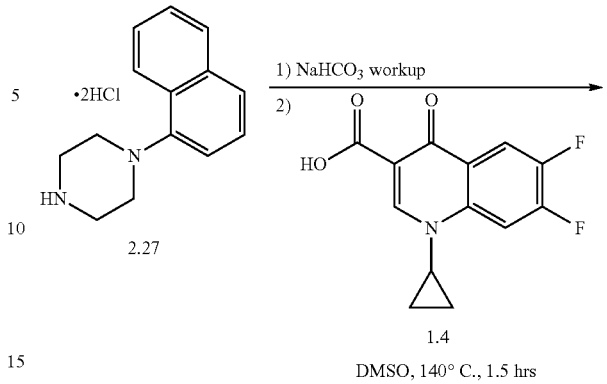

LC-MS Retention time 6.08 minutes, found 486.2 [M+H]+; calculated for $C_{29}H_{28}FN_3O_3$ 486.56 [M+H]+.

Synthesis of 1-cyclopropyl-6-fluoro-7-(4-(naphthalen-1-yl)piperazin-1-yl)-4-oxo-1,4-dihydroquinoline-3-carboxylic acid (2.28)

Firstly, 1-(naphthalen-1-yl)piperazine dihydrochloride (2.27; 100 mg, 0.35 mmol, 1 eq) was converted to its freebase form through workup with dichloromethane (3×20 mL) and water (10 mL) using a saturated solution of sodium hydrogencarbonate to neutralise the aqueous phase. Combined organic fractions were dried over MgSO4, filtered and concentrated in vacuo. Secondly, 1-(naphthalen-1-yl)piperazine freebase (74.4 mg, 0.35 mmol, 1 eq) and 1-cyclopropyl-6-7-difluoro-4-oxo-1,4-dihydroquinoline-3-carboxylic acid (1.4; 83.6 mg, 0.32 mmol, 0.9 eq) were added to DMSO (5 mL) and stirred until full dissolution of both compounds was achieved. The reaction was subsequently heated to 140° C. for one and a half hours. Upon completion, the mixture was allowed to cool and added to an SCX-2 catch and release cartridge (see Solid Phase Extraction method) to remove the DMSO solvent. The eluted crude was purified via trituration; the crude was washed with methanol (5×10 mL), then the remaining powder collected and re-filtered using dichloromethane. This second filtrate was concentrated in vacuo to afford compound 2.28 (67.05 mg, 41.8% yield) as a brown solid.

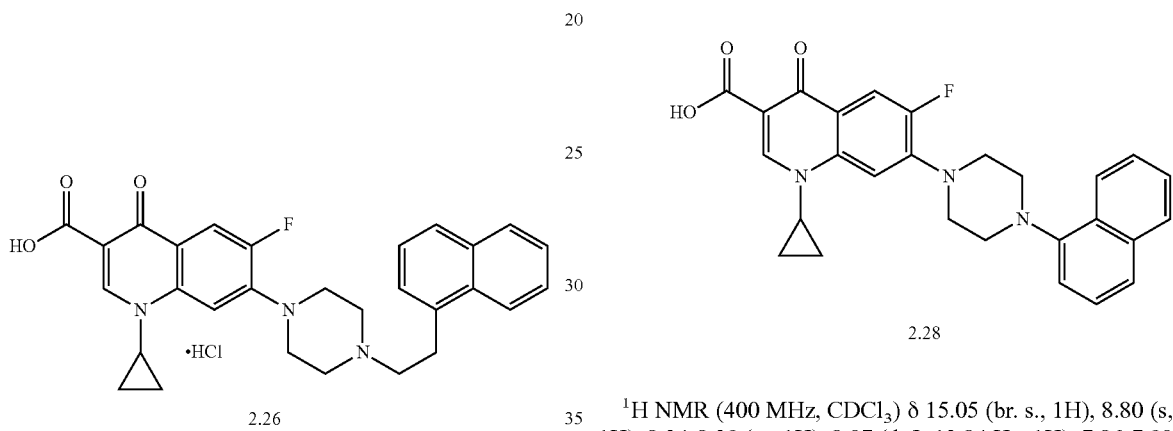

1H NMR (400 MHz, CDCl3) δ 15.05 (br. s., 1H), 8.80 (s, 1H), 8.24-8.29 (m, 1H), 8.07 (d, J=12.84 Hz, 1H), 7.86-7.90 (m, 1H), 7.63 (d, J=8.06 Hz, 1H), 7.47-7.54 (m, 3H), 7.45 (d, J=8.06 Hz, 1H), 7.19 (dd, J=0.88, 7.43 Hz, 1H), 3.63 (br. s., 4H), 3.50 (br. s., 1H), 3.37 (br. s., 4H), 1.45 (br. s., 2H), 1.26 (br. s., 2H); 19F NMR (400 MHz, CDCl3) δ −120.50; LC-MS Retention time 8.78 minutes, found 458.1 [M+H]+; calculated for $C_{27}H_{24}FN_3O_3$ 458.51 [M+H]+.

Synthesis of 1-cyclopropyl-6-fluoro-7-(4-(naphthalen-1-yl)piperazin-1-yl)-4-oxo-1,4-dihydroquinoline-3-carboxylic acid hydrochloride (2.29)

2.28 (32.94 mg, 0.072 mmol, 1 eq) was added to dichloromethane (5 mL total) and stirred for 10 minutes. Then 4M HCl in dioxane (360 μL, 1.44 mmol, 20 eq) was added dropwise and the flask sealed and stirred for 1 hour. The mixture was then washed with hexane (3×30 mL), concentrated in vacuo and lyophilised for 24 hours to afford compound 2.29. (35.27 mg, 99.2% yield) as a grey solid.

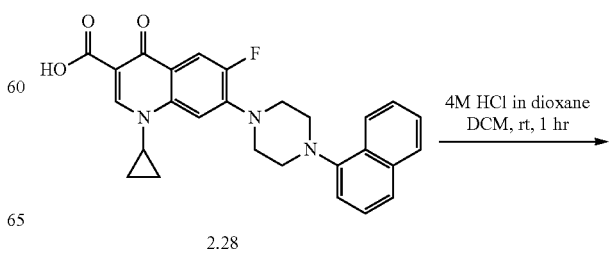

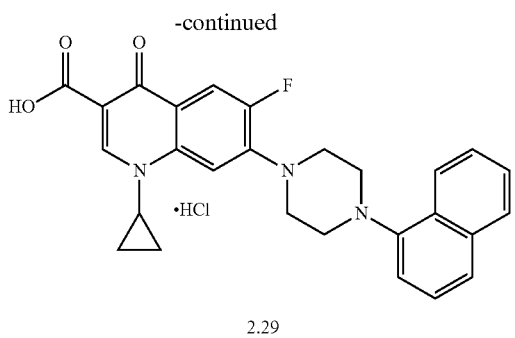

2.29

LC-MS Retention time 8.77 minutes, found 458.1 [M+H]$^+$; calculated for $C_{27}H_{24}FN_3O_3$ 458.51 [M+H]$^+$ Synthesis of 1-cyclopropyl-7-(4-(3,5-dimethylbenzyl)piperazin-1-yl)-6-fluoro oxo-1,4-dihydroquinoline-3-carboxylic acid (2.30)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, 3,5-dimethylbenzyl bromide (60 mg, 0.29 mmol, 0.95 eq) was added slowly over the course of 1 hour and the mixture subsequently stirred for 43 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford 2.30 as an off-white solid.

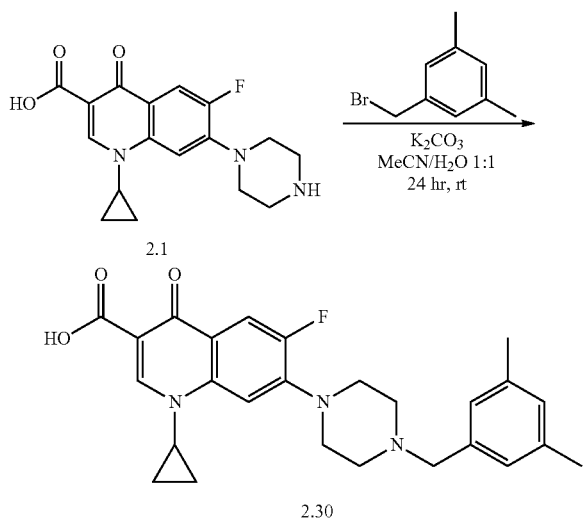

2.30

LC-MS Retention time 3.03 minutes, found 450.0 [M+H]$^+$; calculated for $C_{26}H_{28}FN_3O_3$ 450.53 [M+H]$^{-1}$.

Synthesis of 1-cyclopropyl-7-(4-(3,5-dimethylbenzyl)piperazin-1-yl)-6-fluoro-4-oxo-1,4-dihydroquinoline-3-carboxylic acid hydrochloride (2.31)

2.30 (61.14 mg, 0.13 mmol, 1 eq) was added to dichloromethane (5 mL) and stirred for 5 minutes. Then 4M HCl in dioxane (658 μL, 2.63 mmol, 20 eq) was added dropwise and the flask sealed and stirred for 1 hour. The mixture was then washed with hexane (3×30 mL), concentrated in vacuo and lyophilised for 24 hours to afford 2.31 as an off-white solid.

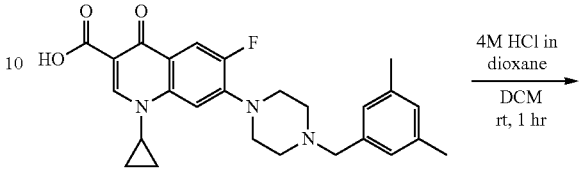

2.30

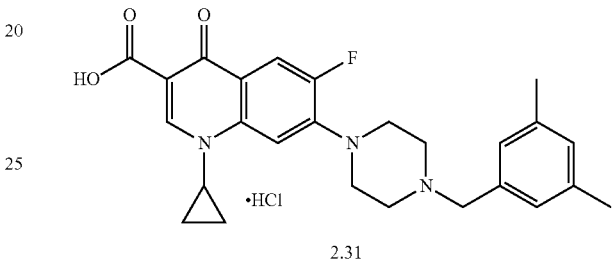

2.31

LC-MS Retention time 50.92 minutes, found 450.1 [M+H]$^+$; calculated for $C_{26}H_{28}FN_3O_3$ 450.53 [M+H]$^+$.

Synthesis of 7-(4-(4-(1H-pyrrol-1-yl)benzyl)piperazin-1-yl)-1-cyclopropyl fluoro-4-oxo-1,4-dihydroquinoline-3-carboxylic acid (2.32)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, 1-(4-(bromomethyl)phenyl)-1H-pyrrole (68 mg, 0.29 mmol, 0.95 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford 2.32 (56.90 mg, 40.8% yield) as an off-white solid.

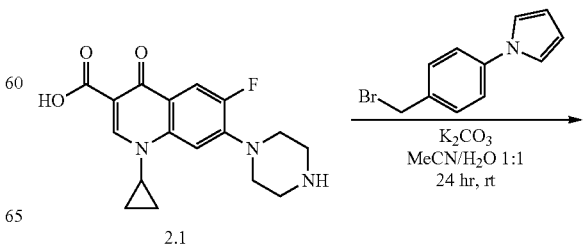

2.1

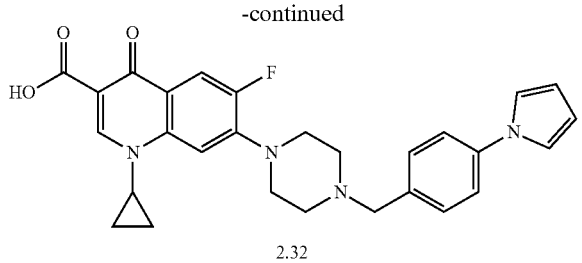

2.32

¹H NMR (400 MHz, CDCl₃) δ 14.95 (br. s., 1H), 8.71 (s, 1H), 7.94 (d, J=13.09 Hz, 1H), 7.31-7.45 (m, 5H), 7.10 (t, J=2.27 Hz, 2H), 6.36 (t, J=2.27 Hz, 2H), 3.63 (s, 2H), 3.50-3.57 (m, 1H), 3.34-3.41 (m, 4H), 2.66-2.74 (m, 4H), 1.34-1.41 (m, 2H), 1.15-1.22 (m, 2H); ¹³C NMR (100 MHz, CDCl₃) δ 177.0, 167.1, 154-9, 152.4, 147.4, 146.0, 145.9, 139.9, 139.1, 135.1, 130.3, 120.4, 119.7, 119.6, 119.3, 112.4, 112.2, 110.4, 110.1, 108.0, 104.8, 62.3, 52.7, 49.8, 35.3, 8.2; LC-MS Retention time 6.05 minutes, found 487.2 [M+H]⁺; calculated for $C_{28}H_{27}FN_4O_3$ 487.2 [M+H]⁺.

Synthesis of 7-(4-(4-(1H-pyrrol-1-yl)benzyl)piperazin-1-yl)-1-cyclopropyl-6-fluoro-4-oxo-1,4-dihydroquinoline-3-carboxylic acid hydrochloride (2.33)

2.32 (40.98 mg, 0.08 mmol, 1 eq) was added to dichloromethane (3 mL) and stirred for 5 minutes. Then 4M HCl in dioxane (421 µL, 1.68 mmol, 20 eq) was added dropwise and the flask sealed and stirred for 1 hour. The mixture was then washed with hexane (3×30 mL), concentrated in vacuo and lyophilised for 24 hours to afford 2.33 as an off-white solid.

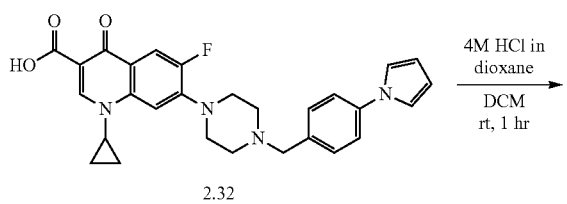

2.32

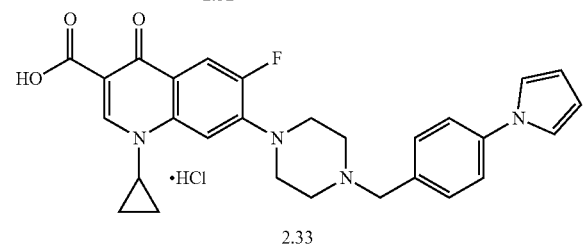

2.33

¹H NMR (400 MHz, DMSO-d₆) δ15.12 (br. s., 1H), 11.44 (s, 1H), 8.69 (s, 1H), 7.97 (d, J=12.96 Hz, 1H), 7.73 (m, 4H), 7.61 (d, J=7.41 Hz, 1H), 7-45 (t, J=2.31 Hz, 2H), 6.30 (t, J=2.21 Hz, 2H), 4.44 (d, J=5.07 Hz, 2H), 3.93-3.79 (m, 3H), 3.47 (m, 4H), 3.30 (m, 2H), 1.37-1.27 (m, 2H), 1.19 (m, 2H); LC-MS Retention time 5.97 minutes, found 487.1 [M+H]⁺; calculated for $C_{28}H_{27}FN_4O_3$ 487.2 [M+H]⁺.

Synthesis of 7-(4-(4-(1H-pyrazol-1-yl)benzyl)piperazin-1-yl)-1-cyclopropyl fluoro-4-oxo-1,4-dihydroquinoline-3-carboxylic acid (2.34)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, 1-(4-(bromomethyl)phenyl)-1H-pyrazole (68 mg, 0.29 mmol, 0.95 eq) was added slowly over the course of 1 hour and the mixture subsequently stirred for 96 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford 2.34 (131.70 mg, 94.2% yield) as an off-white solid.

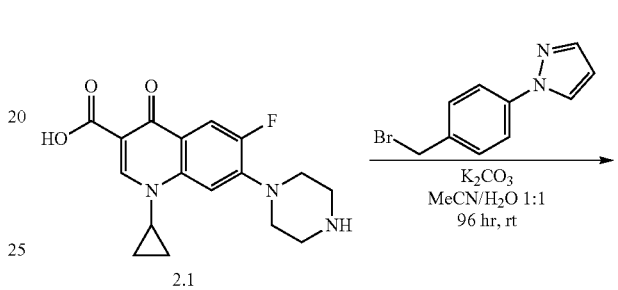

2.1

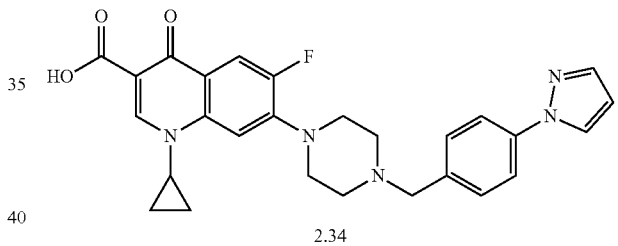

2.34

¹H NMR (400 MHz, CDCl₃) δ 15.03 (br. s., 1H), 8.75 (s, 1H), 7.99 (d, J=13.09 Hz, 1H), 7.94 (dd, J=0.50, 2.52 Hz, 1H), 7.72-7.74 (m, 1H), 7.65-7.70 (m, 2H), 7.43-7.47 (m, 2H), 7.35 (d, J=6.55 Hz, 1H), 6.46-6.50 (m, 1H), 3.64 (s, 2H), 3.54 (br. s., 1H), 3.33-3.40 (m, 4H), 2.66-2.74 (m, 4H), 1.38 (m, 2H), 1.19 (br. s., 2H); ¹³C NMR (100 MHz, CDCl₃) δ 177.1, 167.1, 147.4, 141.1, 139.4, 139.1, 136.1, 130.2 (2C), 126.7, 119.8, 119.2 (2C), 112.5, 112.3, 108.1, 107.7, 104.8, 62.3, 52.7, 49.8, 35.3, 8.2; LC-MS Retention time 2.83 minutes, found 488.1 [M+H]⁺; calculated for $C_{27}H_{26}FN_3O_3$ 488.54 [M+H]⁺.

Synthesis of 7-(4-(4-(1H-pyrazol-1-yl)benzyl)piperazin-1-yl)-1-cyclopropyl-6-fluoro-4-oxo-1,4-dihydroquinoline-3-carboxylic acid hydrochloride (2.35)

2.34 (73.78 mg, 0.15 mmol, 1 eq) was added to dichloromethane (3 mL) and stirred for 5 minutes. Then 4M HCl in dioxane (757 µL, 30.03 mmol, 20 eq) was added dropwise and the flask sealed and stirred for 1 hour. The mixture was then washed with hexane (3×30 mL), concentrated in vacuo and lyophilised for 24 hours to afford 2.35 as an off-white solid.

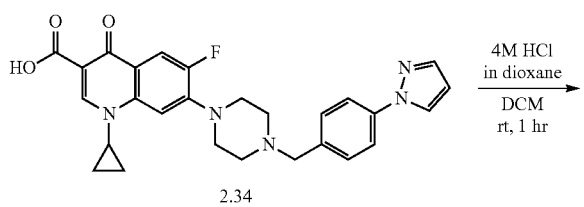

2.34

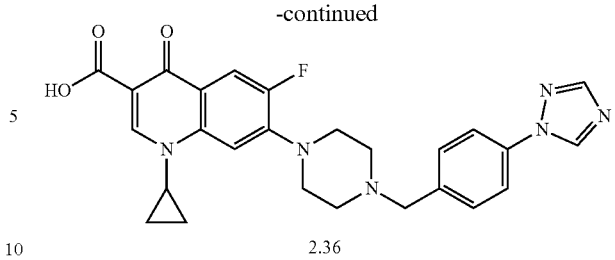

2.36

$^1$H NMR (400 MHz, CDCl$_3$) δ 15.02 (br. s., 1H), 8.72 (s, 1H), 8.56 (s, 1H), 8.11 (s, 1H), 7.95 (d, J=13.09 Hz, 1H), 7.63-7.69 (m, 2H), 7.50-7.55 (m, 2H), 7.35 (d, J=7.05 Hz, 1H), 3.67 (s, 2H), 3.50-3.57 (m, 1H), 3.33-3.40 (m, 4H), 2.67-2.75 (m, 4H), 1.34-1.41 (m, 2H), 1.16-1.22 (m, 2H); $^{13}$C NMR (1.00 MHz, CDCl$_3$) δ 177.0, 167.0, 154.9, 152.6, 152.4, 147.4, 145.9, 140.9, 139.1, 138.2, 136.2, 130.4, 120.1, 119.8, 112.5, 112.2, 108.0, 104.8, 62.1, 52.7, 49.8, 35.3, 8.2; LC-MS Retention time 2.73 minutes, found 489.0 [M+H]$^+$; calculated for C$_{26}$H$_{25}$FN$_6$O$_3$ 489.52 [M+H]$^+$.

Synthesis of 7-(4-(4-(1H-1,2,4-triazol-1-yl)benzyl)piperazin-1-yl)-1-cyclopropyl-6-fluoro-4-oxo-1,4-dihydroquinoline-3-carboxylic acid hydrochloride (2.37)

2.36 (19.76 mg, 0.04 mmol, 1 eq) was added to dichloromethane (3 mL) and stirred for 5 minutes. Then 4M HCl in dioxane (202 µL, 0.81 mmol, 20 eq) was added dropwise and the flask sealed and stirred for 18 hours. The mixture was then washed with hexane (3×30 mL), concentrated in vacuo and lyophilised for 24 hours to afford 2.37 as an off-white solid.

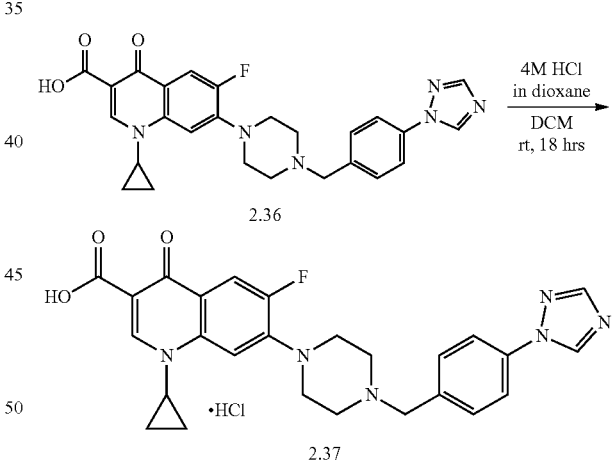

$^1$H NMR (400 MHz, DMSO-d$_6$) δ 11.76 (s, $^1$H), 9.39 (s, 1H), 8.69 (s, 1H), 8.29 (s, $^1$H), 8.04 (m, 3H), 7.91-7.84 (m, 2H), 7.61 (d, J=7.40 Hz, 1H), 4.48 (s, 2H), 3.93-3.79 (m, 3H), 3.48 (d, J=12.46 Hz, 4H), 3.32 (d, J=11.27 Hz, 2H), 1.31 (dd, J=5.49, 7.53 Hz, 2H), 1.25-1.14 (m, 2H); LC-MS Retention time 5.30 minutes, found 489.1 [M+H]$^+$; calculated for C$_{26}$H$_{23}$FN$_6$O$_3$ 489.52 [M+H]$^+$.

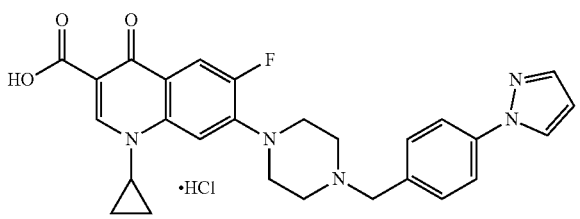

2.36

$^1$H NMR (400 MHz, DMSO-d$_6$) δ 15.11 (s, 1H), 11.73 (s, 1H), 8.67 (s, 1H), 8.58 (d, J=2.52 Hz, 1H), 8.00-7.91 (m, 3H), 7.84-7.76 (m, 3H), 7.60 (d, J=7.41 Hz, in), 6.59-6.57 (m, 1H), 4.45 (s, 2H), 3.93-3.79 (m, 3H), 3.56-3.43 (m, 4H), 3.31 (m, 2H), 1.31 (dd, J=5.51, 7.46 Hz, 2H), 1.21-1.14 (m, 2H); LC-MS Retention time 5.48 minutes, found 488.1 [M+H]$^+$; calculated for C$_{27}$H$_{26}$FN$_3$O$_3$ 488.54 [M+H]$^+$.

Synthesis of 7-(4-(4-(1H-1,2,4-triazol-1-yl)benzyl)piperazin-1-yl)-1-cyclopropyl-6-fluoro-4-oxo-1,4-dihydroquinoline-3-carboxylic acid (2.36)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, 1-(4-(bromomethyl)phenyl)-1H-1,2,4-triazole (68 mg, 0.29 mmol, 0.95 eq) was added slowly over the course of 1 hour and the mixture subsequently stirred for 116 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford 2.36 as an off-white solid.

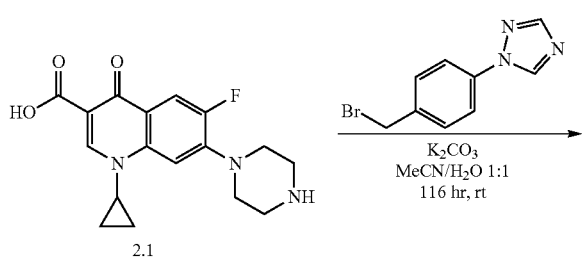

2.1

Synthesis of 7-(4-(4-(1,2,3-thiadiazol-4-yl)benzyl)piperazin-1-yl)-1-cyclopropyl-6-fluoro-4-oxo-1,4-dihydroquinoline-3-carboxylic acid (2.38)

Ciprofloxacin (2.1; 100 mg, 0.30 mmol, 1 eq) was added to a 1:1 mix of acetonitrile and distilled water (5 mL total).

After stirring for 5 minutes, potassium carbonate (125 mg, 0.91 mmol, 3 eq) was added and the mixture stirred for a further 5 minutes. Once fully dissolved, 4-(4-(bromomethyl)phenyl)-1,2,3-thiadiazole (73 mg, 0.29 mmol, 0.95 eq) was added slowly over the course of 1 hour and the mixture subsequently stirred for 42 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford 2.38 (108.9 mg, 75.1% yield) as an off-white solid.

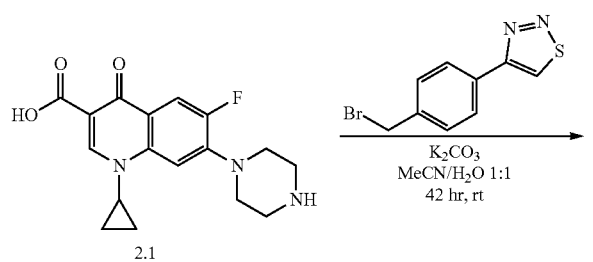

2.1

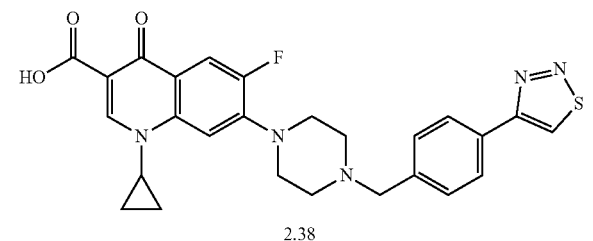

2.38

$^1$H NMR (400 MHz, CDCl$_3$) δ 15.02 (br. s., 1H), 8.76 (s, 1H), 8.67 (s, 1H), 8.03-80.6 (m, 2H), 8.01 (d, J=13.09 Hz, 1H), 7.53 (d, J=8.31 Hz, 2H), 7.36 (d, J=7.30 Hz, 1H), 3.69 (s, 2H), 3.50-3.57 (m, $^1$H), 3.35-3.41 (m, 4H), 2.71-2.76 (m, 4H), 1.35-1.41 (m, 2H), 1.17-1.23 (m, 2H); $^{13}$C NMR (100 MHz, CDCl$_3$) δ 177.1, 167.1, 162.7, 147.4, 146.0, 145.9, 139.3, 139.1, 129.9, 127.5, 112.6, 112.3, 108.1, 104.8, 62.6, 52.7, 49.9, 35.3, 8.3; LC-MS Retention time 2.87 minutes, found 506.0 [M+H]$^+$; calculated for C$_{26}$H$_{24}$FN$_5$O$_3$S 506.57 [M+H]$^+$.

Synthesis of 7-(4-(4-(1,2,3-thiadiazol-4-yl)benzyl)piperazin-1-yl)-1-cyclopropyl-6-fluoro-4-oxo-1,4-dihydroquinoline-3-carboxylic acid hydrochloride (2.39)

2.38 (32.49 mg, 0.06 mmol, 1 eq) was added to dichloromethane (3 mL) and stirred for 5 minutes. Then 4M HCl in dioxane (320 μL, 1.28 mmol, 20 eq) was added dropwise and the flask sealed and stirred for 1 hour. The mixture was then washed with hexane (3×30 mL), concentrated in vacuo and lyophilised for 24 hours to afford 2.39 as an off white solid.

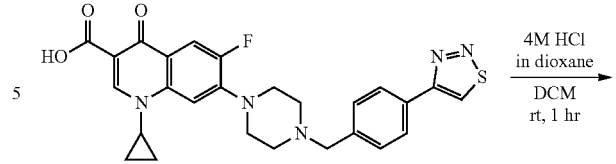

2.38

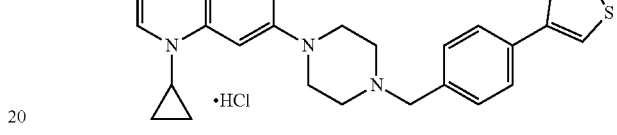

2.39

$^1$H NMR (400 MHz, DMSO-d$_6$) δ 15.12 (br. s., 11.60 (br. s., 9.73 (s, 1H), 8.68 (s, 1H), 8.24-8.28 (m, J=8.31 Hz, 2H), 7.96 (d, J=12.84 Hz, 1H), 7.83-7.88 (m, J=8.31 Hz, 2H), 7.61 (d, J=7.30 Hz, 1H), 4.50 (br. s., 2H), 3.81-3.94 (m, 3H), 3.65-3.73 (m, 1H), 3.45-3.54 (m, 5H), 1.29-1.35 (m, 2H), 1.16-1.21 (m, 2H); LC-MS Retention time 5.12 minutes, found 506.0 [M+H]$^+$; calculated for C$_{26}$H$_{24}$FN$_5$O$_3$S 506.57 [M+H]$^+$.

Synthesis of 1-cyclopropyl-6-fluoro-7-(4-(4-(5-methyl-1,2,4-oxadiazol-3-yl)benzyl)piperazin-1-yl)-4-oxo-1,4-dihydroquinoline-3-carboxylic acid (2.40)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, 3-(4-(bromomethyl)phenyl)-5-methyl-1,2,4-oxadiazole (73 mg, 0.29 mmol, 0.95 eq) was added slowly over the course of 1 hour and the mixture subsequently stirred for 96 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford (113.21 mg, 78.4% yield) 2.40 as an off white solid.

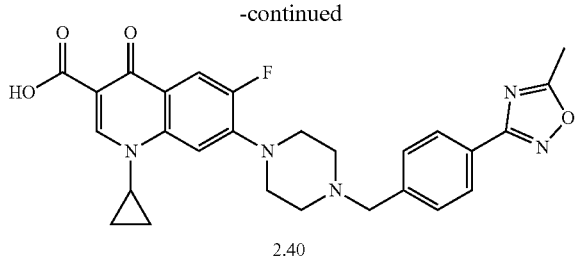

2.40

$^1$H NMR (400 MHz, CDCl$_3$) δ 15.01 (br. s., 1H), 8.73 (s, 1H), 8.01-8.06 (m, J=8.31 Hz, 2H), 7.97 (d, J=13.09 Hz, 1H), 7.46-7.51 (m, J=8.06 Hz, 2H), 7.35 (d, J=6.80 Hz, 2H), 3.66 (s, 2H), 3.54 (br. s., 1H), 3.37 (m, 4H), 2.71 (m, 4H), 2.67 (s, 3H), 1.38 (d, J=5.04 Hz, 2H), 1.19 (br. s., 2H); $^{13}$C NMR (100 MHz, CDCl$_3$) δ 177.1, 176.6, 168.2, 167.1, 147.4, 145.9, 141.2, 139.1, 129.5 (2C), 127.4 (2C), 125.9, 119.7, 112.5, 112.2, 108.1, 104.8, 62.6, 52.8, 49.9, 49.8, 35.3, 12.5, 8.2; LC-MS Retention time 2.87 minutes, Found 504.0 [M+H]$^+$; calculated for C$_{24}$H$_{26}$FN$_5$O$_4$ 504.53 [M+H]$^+$ Synthesis of 1-cyclopropyl-6-fluoro-7-(4-(4-(5-methyl-1,2,4-oxadiazol-3-yl)benzyl)piperazin-1-yl)-4-oxo-1,4-dihydroquinoline-3-carboxylic acid hydrochloride (2.41)

2.40 (93.48 mg, 0.19 mmol, 1 eq) was added to dichloromethane (3 mL) and stirred for 5 minutes. Then 4M HCl in dioxane (928 μL, 3.71 mmol, 20 eq) was added dropwise and the flask sealed and stirred for 1 hour. The mixture was then washed with hexane (3×30 mL), concentrated in vacuo and lyophilised for 24 hours to afford 2.41 as an off white solid.

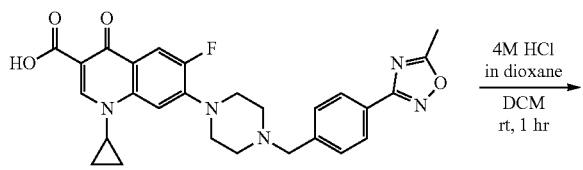

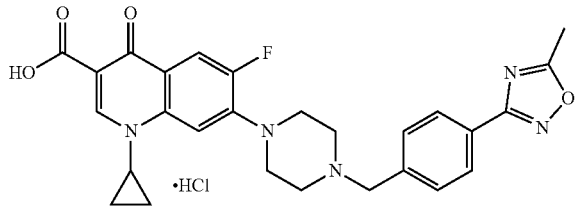

2.41

$^1$H NMR (400 MHz, DMSO-d$_6$) δ 11.99 (s, 1H), 8.67 (s, 1H), 8.08 (d, J=7.94 Hz, 2H), 7.95 (d, J=13.00 Hz, 1H), 7.89 (d, J=7.98 Hz, 2H), 7.60 (d, J=7.35 Hz, 1H), 4.51 (s, 2H), 3.93-3.81 (m, 3H), 3.60-3.42 (m, 4H), 3.33 (m, 2H), 2.69 (s, 3H), 1.36-1.27 (m, 2H), 1.25-1.13 (m, 2H); LC-MS Retention time 5.58 minutes, Found 504.2 [M+H]$^+$; calculated for C$_{27}$H$_{26}$FN$_5$O$_4$ 504.53 [M+H]$^+$ Synthesis of 7-(4-([1,1'-biphenyl]-4-ylmethyl)piperazin-1-yl)-1-cyclopropyl-6-fluoro-4-oxo-1,4-dihydroquinoline-3-carboxylic acid (2.42)

Ciprofloxacin (2.1; 100 mg, 0.30 mmol, 1 eq) was added to a 1:1 mix of acetonitrile and distilled water (5 mL total).

After stirring for 5 minutes, potassium carbonate (125 mg, 0.91 mmol, 3 eq) was added and the mixture stirred for a further 5 minutes. Once fully dissolved, 4-(bromomethyl)-1,1'-biphenyl (71 mg, 0.29 mmol, 0.95 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford (107.1 mg, 75.1% yield) 2.42, as an off white solid.

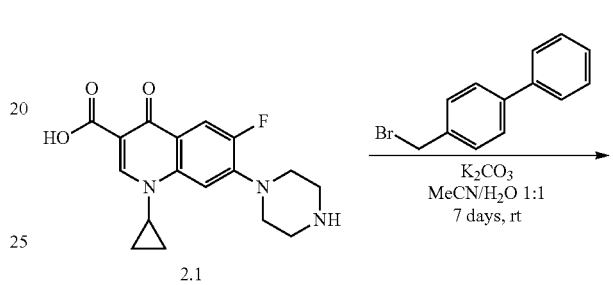

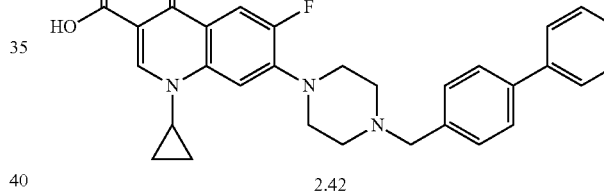

2.42

$^1$H NMR (400 MHz, CDCl$_3$) δ 15.00 (br. s., 1H), 8.75 (s, 1H), 8.00 (d, J=13.09 Hz, 1H), 7.56-7.63 (m, 4H), 7.41-7.48 (m, 4H), 7.33-7.39 (m, 2H), 3.66 (s, 2H), 3.53 (tt, J=3.75, 7.08 Hz, 1H), 3.35-3.41 (m, 4H), 2.70-2.76 (m, 4H), 1.35-1.41 (m, 2H), 1.17-1.22 (m, 2H); $^{13}$C NMR (100 MHz, CDCl$_3$) δ 177.1, 167.1, 155.0, 152.5, 147.4, 146.1, 146.0, 140.8, 140.3, 139.1, 136.7, 129.6, 128.8, 127.3, 127.1, 127.1, 119.8, 119.7, 112.5, 112.3, 108.1, 104.8, 62.6, 52.7, 49.9, 49.9, 35.3, 8.2; LC-MS Retention time 6.23 minutes, Found 498.1 [M+H]$^+$; calculated for C$_{30}$H$_{28}$FN$_3$O$_3$ 498.57 [M+H]$^+$ Synthesis of 7-(4-([1,1'-biphenyl]-4-ylmethyl)piperazin-1-yl)-1-cyclopropyl-6-fluoro-4-oxo-1,4-dihydroquinoline-3-carboxylic acid hydrochloride (2.43)

2.42 (85.37 mg, 0.17 mmol, 1 eq) was added to dichloromethane (3 mL) and stirred for 5 minutes. Then 4M HCl in dioxane (858 μL, 3.43 mmol, 20 eq) was added dropwise and the flask sealed and stirred for 1 hour. The mixture was then washed with hexane (3×30 mL), concentrated in vacuo and lyophilised for 24 hours to afford 2.43 as an off white solid.

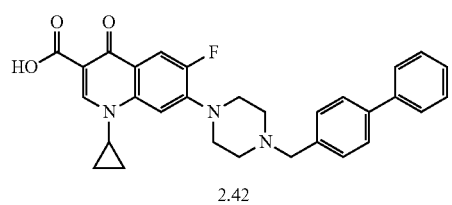

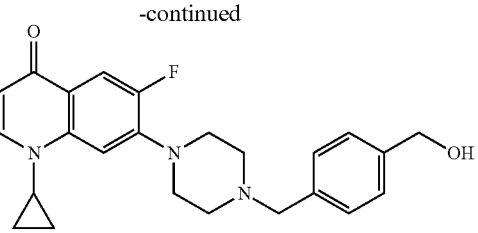

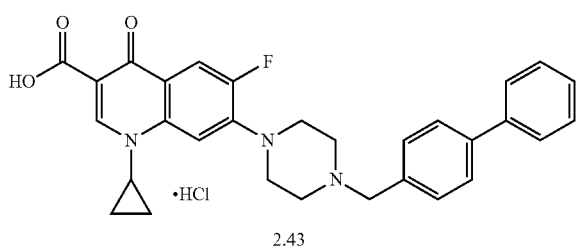

¹H NMR (400 MHz, DMSO-d₆) δ 15.13 (br. s., 1H), 11.32 (br. s., 1H), 8.69 (s, 1H), 7.97 (d, J=13.09 Hz, 1H), 7.69-7.82 (m, 6H), 7.61 (d, J=7.30 Hz, 1H), 7.47-7.53 (m, 2H), 7.38-7.43 (m, 1H), 4.47 (d, J=4.03 Hz, 2H), 3.90 (d, J=12.59 Hz, 2H), 3.81-3.86 (m, 1H), 3.42-3.54 (m, 4H), 3.32 (br. s., 2H), 1.28-1.35 (m, 2H), 1.15-1.22 (m, 2H); LC-MS Retention time 6.18 minutes, Found 498.1 [M+H]⁺; calculated for C₃₀H₂₈FN₃O₃ 498.57 [M+H]⁺

Synthesis of 1-cyclopropyl-6-fluoro-7-(4-(4-(hydroxymethyl)benzyl)piperazin yl)-4-oxo-1,4-dihydroquinoline-3-carboxylic acid (2.44)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, (4-(bromomethyl)phenyl)methanol (61 mg, 0.30 mmol, 1 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford 2.44 as an off white solid.

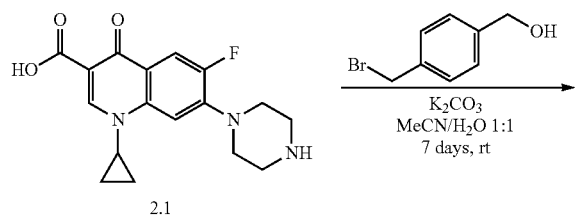

¹H NMR (400 MHz, CDCl₃) δ 15.05 (br. s., 1H), 8.75 (s, 1H), 7.99 (d, J=13.09 Hz, al), 7.36 (m, 5H), 4.71 (s, 2H), 3.61 (s, 2H), 3.50-3.56 (m, 1H), 3.32-3.38 (m, 4H), 2.65-2.71 (m, 4H), 1.34-1.40 (m, 2H), 1.16-1.22 (m, 2H) ¹³C NMR (100 MHz, CDCl₃) δ 177.1, 167.1, 155.0, 152.5, 147.4, 146.1, 146.0, 140.0, 139.1, 137.0, 129.4, 128.2, 127.1, 119.8, 119.7, 112.5, 112.3, 108.1, 104.8, 65.1, 62.6, 53.5, 52.6, 49.9, 49.8, 35.3, 8.2; LC-MS Retention time 50.03 minutes, Found 452.2 [M+H]⁺; calculated for C₂₅H₂₆FN₃O₄ 452.50 [M+H]⁺

Synthesis of 1-cyclopropyl-6-fluoro-7-(4-(4-(hydroxymethyl)benzyl)piperazin-1-yl)-4-oxo-1,4-dihydroquinoline-3-carboxylic acid hydrochloride (2.45) 2.44 (61.14 mg, 0.13 mmol, 1 eq) was added to dichloromethane (5 mL) and stirred for 5 minutes. Then 4M HCl in dioxane (658 µL, 2.63 mmol, 20 eq) was added dropwise and the flask sealed and stirred for 30 minutes. The mixture was then washed with hexane (3×30 mL), concentrated in vacuo and lyophilised for 24 hours to afford 2.45 as an off white solid.

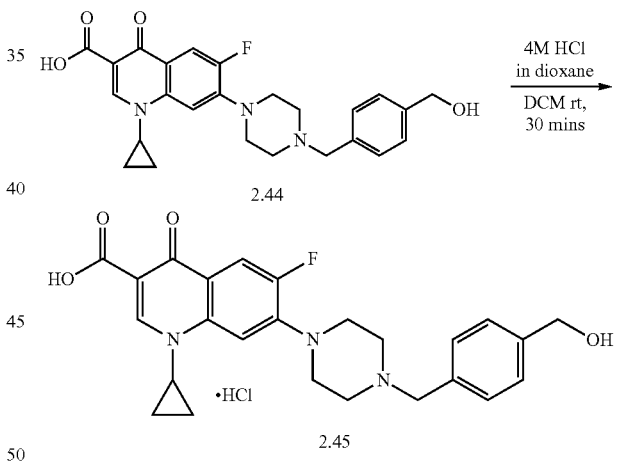

¹H NMR (400 MHz, DMSO-d₆) δ 11.66 (br. s., 1H), 8.67 (s, 1H), 70.94 (d, J=13.09 Hz, 1H), 7.63 (d, J=80.6 Hz, 2H), 7.59 (d, J=7.55 Hz, 1H), 7.41 (d, J=7.81 Hz, 2H), 4.54 (s, 2H), 4.39 (d, J=4.53 Hz, 2H), 3.81-3.91 (m, 3H), 3.39-3.54 (m, 4H), 3.21-3.33 (m, 2H), 1.28-1.35 (m, 2H), 1.15-1.20 (m, 2H); LC-MS Retention time 5.10 minutes, Found 452.1 [M+H]⁺; calculated for C₂₅H₂₆FN₃O₄ 452.50 [M+H]⁺

Synthesis of (4-(methoxymethyl)phenyl)methanol (2.47)

(4-(bromomethyl)phenyl)methanol (2.46; 306 mg, 1.52 mmol, 1 eq) was added to excess methanol (20 mL) at room temperature and stirred for 2 minutes. To the resulting brown suspension, potassium carbonate (631 mg, 4.57 mmol, 3 eq) was added and the suspension stirred for a further 5 minutes at room temperature. The mixture was then heated to reflux, with distilled water (5 mL) added during heating. After 15 minutes at reflux, complete dissolution of 2.46 furnished a yellow solution. TLC indicated reaction was complete after 15 hours; product was extracted using ethyl acetate (10 mL) washed with distilled water (3×20 mL). Combined aqueous fractions were back extracted using dichloromethane (20 mL). Combined organic fractions were then dried over MgSO$_4$, filtered and concentrated in vacuo to give the crude product. Purification was achieved via automated flash column chromatography of the crude oil (see Flash Column Chromatography method; 0%-10% DCM/ethyl acetate) to afford pure (56.95 mg, 24.6% yield) 2.47 as a yellow oil.

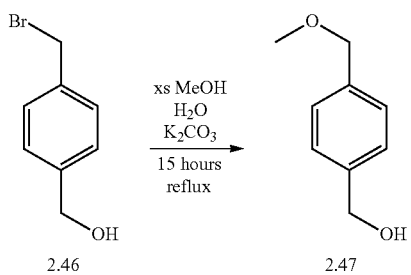

$^1$H NMR (400 MHz, CDCl$_3$) δ 7.31 (s, 4H), 4.62 (d, J=5.54 Hz, 2H), 4.44 (s, 2H), 3.37 (s, 3H), 2.60 (t, J=5.67 Hz, 1H); $^{13}$C NMR (100 MHz, CDCl$_3$) δ 140.5, 137.3, 128.0, 127.0, 74.5, 64.9, 58.1

Synthesis of 1-(chloromethyl)-4-(methoxymethyl)benzene (2.48)

(4-(methoxymethyl)phenyl)methanol (2.47; 56.95 mg, 0.37 mmol, 1 eq) was added to anhydrous dichloromethane (1 mL) and the solution cooled to 0° C. Then thionyl chloride (30 µL, 0.41 mmol, 1.1 eq) was added and the reaction stirred at 0° C. for 1 hour, then warmed to room temperature over a second hour. After 3 hours, a catalytic amount of DMF (3 drops) was added. TLC indicated reaction was complete after 20 hours; reaction was quenched by the addition of a saturated solution of NaHCO$_3$ (1 mL) dropwise, then the product was extracted using dichloromethane (10 mL) washed with distilled water (3×10 mL). TLC confirmed reaction was spot-10-spot; (43.76 mg, 68.5% yield) 2.48 as a colourless oil, 2.48 was characterised and used in subsequent reactions without further purification.

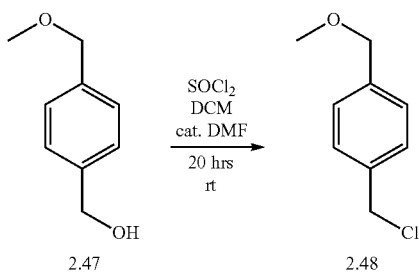

$^1$H NMR (400 MHz, CDCl$_3$) δ 7.39 (d, 2H), 7.35 (d, 2H), 4.60 (s, 2H), 4.47 (s, 2H), 3.40 (s, 3H); $^{13}$C NMR (100 MHz, CDCl$_3$) δ 138.6, 136.9, 128.7, 128.0, 74.2, 58.2, 46.1

Synthesis of 1-cyclopropyl-6-fluoro-7-(4-(4-(methoxymethyl)benzyl)piperazin-1-yl)-4-oxo-1,4-dihydroquinoline-3-carboxylic acid (2.49)

Ciprofloxacin (2.1; 29 mg, 0.09 mmol, 1 eq) was added to a 1:1 mix of acetonitrile and distilled water (2 mL total). After stirring for 5 minutes, potassium carbonate (36 mg, 0.26 mmol, 3 eq) was added and the mixture stirred for a further 5 minutes. Once fully dissolved, 1-(chloromethyl)-4-(methoxymethyl)benzene (14 mg, 0.08 mmol, 0.95 eq) was added slowly over the course of 1 hour and the mixture subsequently stirred for 17 hours. Reaction was subsequently heated to reflux and stirred for 24 hours. Upon completion, the product was extracted with dichloromethane (3×10 mL) using a 1M solution of citric acid to neutralise the aqueous phase. Combined organic fractions were washed with distilled water (10 mL) and dried over MgSO$_4$, filtered and concentrated in vacuo to give the crude product. Flash column chromatography (0%-100% DCM/acetone) was employed to afford pure (35.05 mg, 90.6% yield) 2.49 as an off white solid.

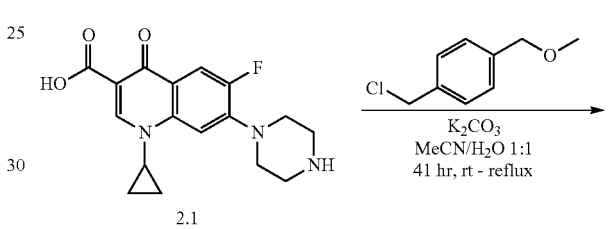

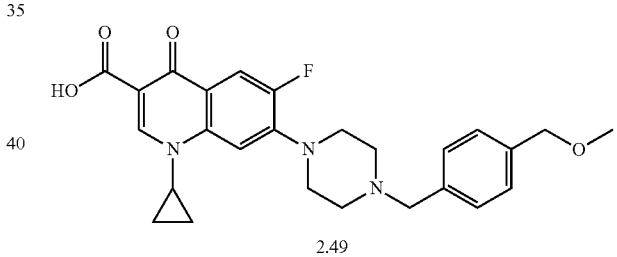

$^1$H NMR (400 MHz, CDCl$_3$) δ 15.06 (br. s., 1H), 8.76 (s, 1H), 8.00 (d, J=13.09 Hz, 1H), 7.30

7.38 (m, 5H), 4.46 (s, 2H), 3.61 (s, 2H), 3.50-3.56 (m, 1H), 3.42 (s, 3H), 3.33-3.38 (m, 4H), 2.66-2.71 (m, 4H), 1.34-1.39 (m, 2H), 1.16-1.22 (m, 2H); LC-MS Retention time 2.87 minutes, Found 466.1 [M+H]$^+$; calculated for C$_{26}$H$_{28}$FN$_3$O$_4$ 466.53 [M+H]F Synthesis of 1-cyclopropyl-6-fluoro-7-(4-(4-(methoxymethyl)benzyl)piperazin-1-yl)-4-oxo-1,4-dihydroquinoline-3-carboxylic acid hydrochloride (2.50)

2.49 (11.14 mg, 0.02 mmol, 1 eq) was added to dichloromethane (2 mL) and stirred for 5 minutes. Then 4M HCl in dioxane (120 µL, 0.48 mmol, 20 eq) was added dropwise and the flask sealed and stirred for 1 hour. The mixture was then washed with hexane (3×10 mL), concentrated in vacuo and lyophilised for 24 hours to afford 2.50 as an off white solid.

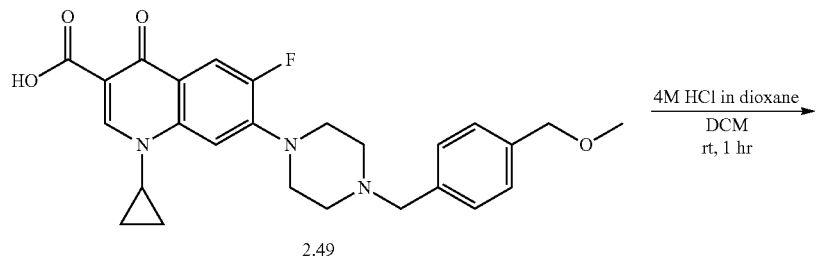

2.49

LC_MS Retention time 4.87 minutes, Found 466.2 [M+H]⁺; calculated for $C_{26}H_{28}FN_3O_4$ 466.53 [M+H]⁺

Synthesis of 1-cyclopropyl-6-fluoro-7-(4-(3-(methoxymethyl)benzyl)piperazin-1-yl)-4-oxo-1,4-dihydroquinoline-3-carboxylic acid (2.51)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, 1-(bromomethyl)-3-(methoxymethyl)benzene (62 mg, 0.29 mmol, 0.95 eq) was added slowly over the course of 1 hour and the mixture subsequently stirred for 88 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Flash column chromatography (0%-20% DCM/acetone, silica deactivated via 3% triethylamine in DCM wash) was employed to afford pure 2.51 as an off white solid.

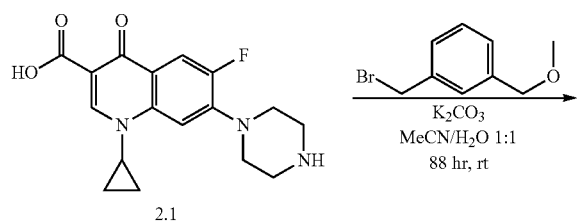

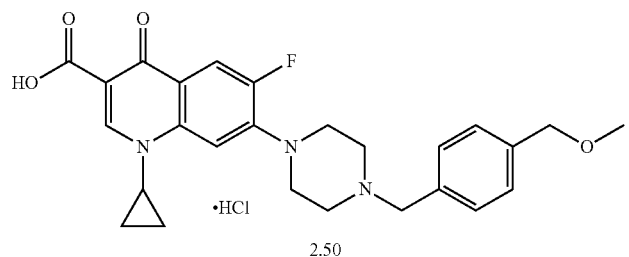

2.50

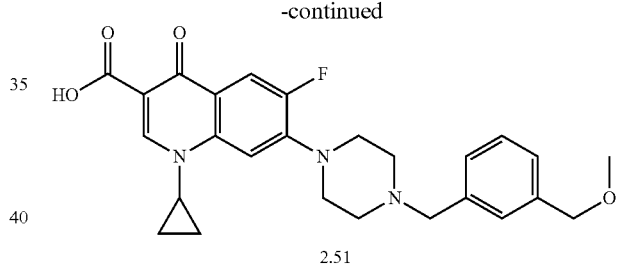

2.51

LC-MS Retention time 5.45 minutes, Found 466.1 [M+H]⁺; calculated for $C_{26}H_{28}FN_3O_4$ 466.53 [M+H]⁺

Synthesis of 1-cyclopropyl-6-fluoro-7-(4-(3-(methoxymethyl)benzyl)piperazin-1-yl)-4-oxo-1,4-dihydroquinoline-3-carboxylic acid hydrochloride (2.52)

2.51 (16 mg, 0.03 mmol, 1 eq) was added to dichloromethane (3 mL) and stirred for 5 minutes. Then 4M HCl in dioxane (172 μL, 0.69 mmol, 20 eq) was added dropwise and the flask sealed and stirred for 40 minutes. The mixture was then washed with hexane (3×20 mL), concentrated in vacuo and lyophilised for 24 hours to afford 2.52 as an off white solid.

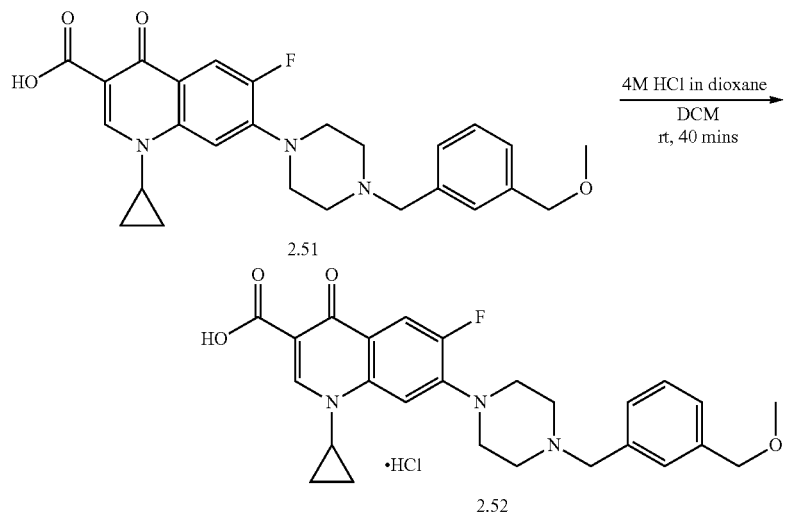

LC-MS Retention time 4.83 minutes, Found 466.2 [M+H]$^+$; calculated for $C_{26}H_{28}FN_3O_4$ 466.53 [M+H]$^+$ Synthesis of 1-cyclopropyl-6-fluoro-7-(4-(3-(methoxymethyl)benzyl)-piperazin-1-yl)-4-oxo-1,4-dihydroquinoline-3-carboxylic acid (2.53)

Ciprofloxacin (2.1; 100 mg, 0.30 mmol, 1 eq) was added to a 1:1 mix of acetonitrile and distilled water (5 mL total). After stirring for 5 minutes, potassium carbonate (125 mg, 0.91 mmol, 3 eq) was added and the mixture stirred for a further 5 minutes. Once fully dissolved, N-(2-(1H-indol-3-yl)ethyl)-4-(bromomethyl)benzenesulfonamide (119 mg, 0.30 mmol, 1 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford 2.53 as an off white solid.

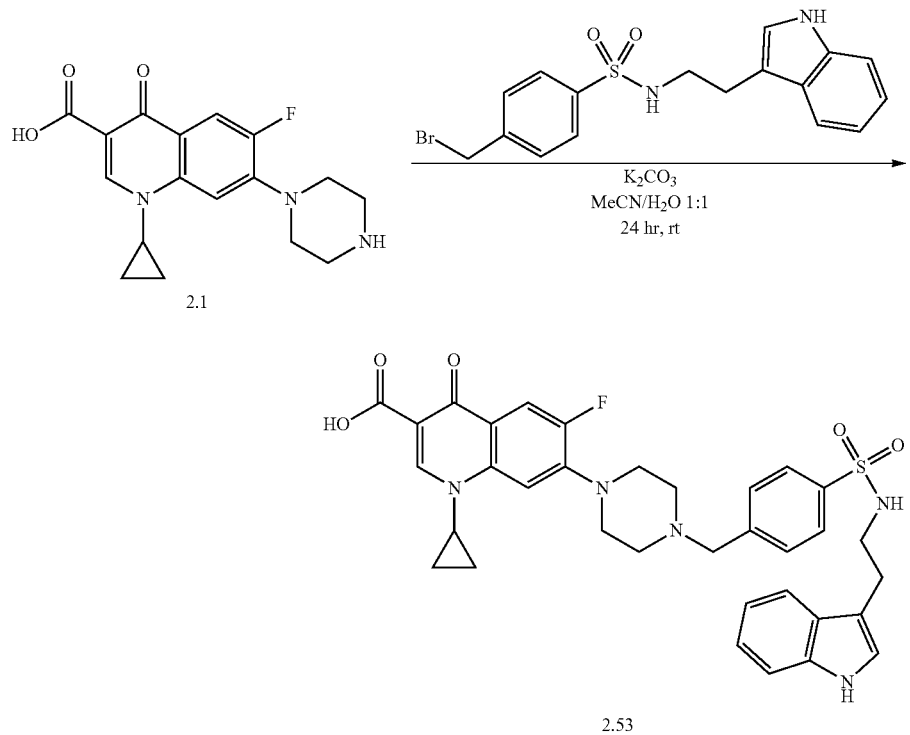 [SMILES: O=C(O)c1cn(C2CC2)c2cc(N3CCNCC3)c(F)cc2c1=O ; O=S(=O)(NCCc1c[nH]c2ccccc12)c1ccc(CBr)cc1 ; O=C(O)c1cn(C2CC2)c2cc(N3CCN(Cc4ccc(S(=O)(=O)NCCc5c[nH]c6ccccc56)cc4)CC3)c(F)cc2c1=O]

LC-MS Retention time 3.13 minutes, Found 644.0 [M+H]$^+$; calculated for $C_{34}H_{34}FN_5O_5S$ 644.73 [M+H]$^+$

Synthesis of 1-cyclopropyl-6-fluoro-7-(4-(3-(methoxymethyl)benzyl)-piperazin-1-yl)-4-oxo-1,4-dihydroquinoline-3-carboxylic acid hydrochloride (2.54)

2.53 (61.14 mg, 0.13 mmol, 1 eq) was added to dichloromethane (5 mL) and stirred for 5 minutes. Then 4M HCl in dioxane (658 µL, 2.63 mmol, 20 eq) was added dropwise and the flask sealed and stirred for 1 hour. The mixture was then washed with hexane (3×30 mL), concentrated in vacuo and lyophilised for 24 hours to afford 2.54 as an off white solid.

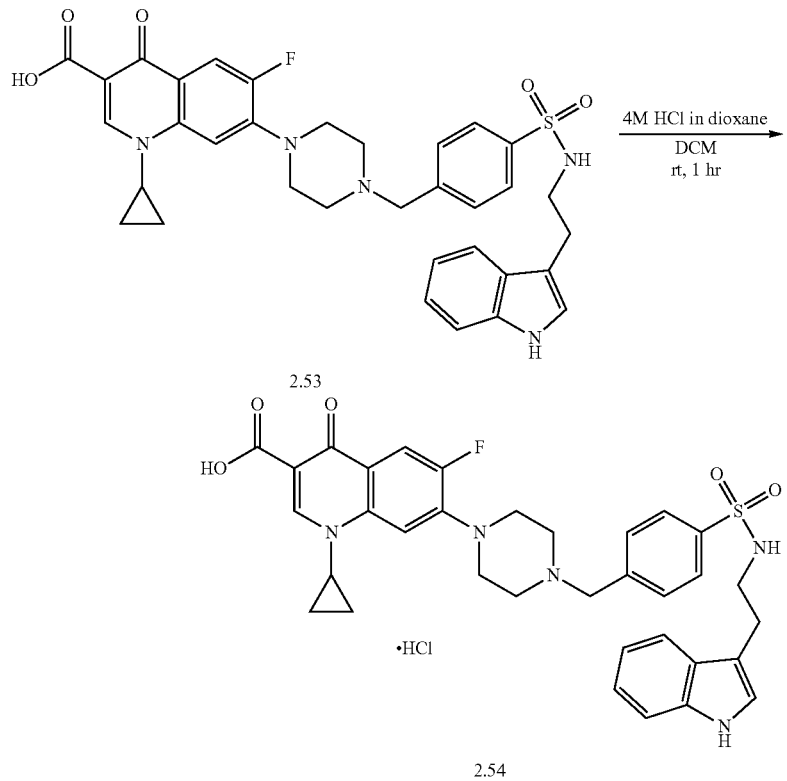

LC-MS Retention time 6.03 minutes, Found 644.2 [M+H]$^+$; calculated for $C_{34}H_{34}FN_5O_5S$ 644.73 [M+H]$^+$

Synthesis of Norfloxacin-ARB Hybrid Compounds

Synthesis of 1-ethyl-6-fluoro-7-(4-(naphthalen-1-ylmethyl)piperazin-1-yl)-4-oxo-1,4-dihydroquinoline-3-carboxylic acid (3.2)

Norfloxacin (3.1; 1 g, 3.13 mmol, 1 eq) was added to DMF (10 mL total) and stirred for 105 minutes at 115° C. Then 1-(bromomethyl)naphthalene (685 mg, 30.13 mmol, 1 eq) and potassium carbonate (1250 mg, 9.04 mmol, 2.9 eq) were added and the mixture stirred for a further 1 hour at reflux. The mixture was allowed to cool, then extracted with ethyl acetate (2×50 mL). Combined organic fractions were washed with distilled water (20 mL) and brine (20 mL), dried over MgSO$_4$, filtered and concentrated in vacuo to give the crude product. Purification was achieved using an SCX-2 catch and release cartridge (see Solid Phase Extraction method) to afford compound 3.2 (1.00 g, 69.5% yield) as a tan solid.

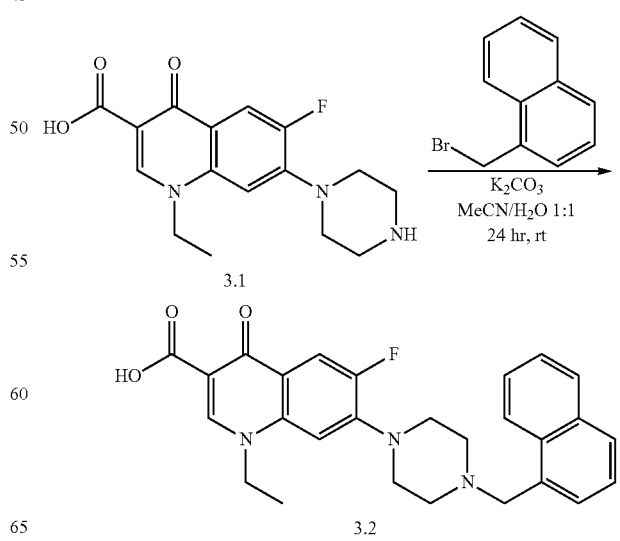

$^1$H NMR (400 MHz, CDCl$_3$) δ 15.13 (s, 1H), 8.66 (s, 1H), 8.33 (d, J=8.06 Hz, 1H), 8.07 (d, J=13.09 Hz, 1H), 7.89 (d, J=7.05 Hz, 1H), 7.82 (d, J=7.30 Hz, 1H), 7.49-7.57 (m, 2H), 7.45 (q, J=7.22 Hz, 2H), 6.81 (d, J=7.05 Hz, 1H), 4.23-4.32 (m, 2H), 4.02 (s, 2H), 3.33 (br s., 4H), 2.76 (br. s., 4H), 1.56 (t, J=6.92 Hz, 3H); LC-MS Retention time 3.05 minutes, found 460.0 [M+H]$^+$; calculated for C$_{27}$H$_{26}$FN$_3$O$_3$ 460.52 [M+H]$^+$.

Synthesis of 1-ethyl-6-fluoro-7-(4-(naphthalen-1-ylmethyl)piperazin-1-yl)-4-oxo-1,4-dihydroquinoline-3-carboxylic acid hydrochloride (3.3)

3.2 (30 mg, 0.07 mmol, 1 eq) was added to methanol (10 mL total) and stirred for 10 minutes. Then 4M HCl in dioxane (33 μL, 0.13 mmol, 2 eq) was added dropwise and the flask sealed and stirred for 1 hour. The mixture was then washed with hexane (3×30 mL), concentrated in vacuo and lyophilised for 24 hours to afford compound 3.3 (42.06 mg, 95.7% yield) as a light brown solid.

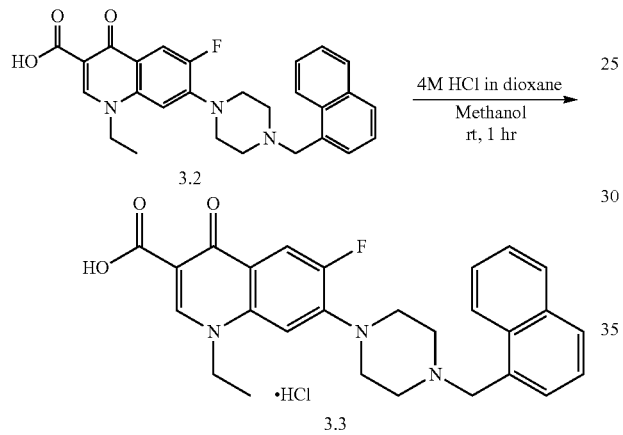

$^1$H NMR (400 MHz, DMSO-d$_6$) δ 15.25 (br. s., 1H), 11.17 (br. s., 1H), 8.96 (s, 1H), 8.49 (d, J=8.56 Hz, 1H), 80.8 (d, J=8.31 Hz, 1H), 8.04 (d, J=7.05 Hz, 2H), 7.95 (d, J=13.35 Hz, 1H), 7.68 (ddd, J=1.38, 6.86, 8.37 Hz, 1H), 7.59-7.65 (m, 2H), 7.23 (d, J=7.30 Hz, 1H), 4.93 (hr. s., 2H), 40.59 (q, J=7.05 Hz, 2H), 3.83-3.94 (m, 2H), 3.48 (br. s., 6H), 1.40 (t, J=7.18 Hz, 3H); $^{13}$C NMR (100 MHz, DMSO-d$_6$) δ 176.1 (C=O), 166.0 (CO$_2$H), 152.6 (C-6, $^1$J(C-F)=247 Hz), 148.7 (C-2), 143.8 (C-7, $^2$J(C-F)=11 Hz), 137.1, 133.4, 132.2, 131.7, 130.4, 128.8, 127.1, 126.3, 125.3, 124.1, 119.8 (C-4a, $^3$J(C-F)=8 Hz), 111.4 (C-5, $^2$J(C-F)=23 Hz), 107.1, 106.3, 54.9, 50.4, 49.1, 46.3, 30.7, 14.4; IR (υ$_{max}$/cm$^{-1}$) 3389, 2921, 1700, 1628, 1457, 1267, 1195, 1104, 937, 802; LC-MS Retention time 5.85 minutes, found 460.1 [M+H]$^+$; calculated for C$_{27}$H$_{26}$FN$_3$O$_3$ 460.52 [M+H]$^+$; HRMS Observed 460.2020 [M+H]$^+$; theoretical value 460.2031 [M+H]$^+$.

Synthesis of 1-ethyl-6-fluoro-7-(4-(naphthalen-1-ylmethyl)piperazin-1-yl)-4-oxo-1,4-dihydroquinoline-3-carboxylic acid (3.4)

Norfloxacin (3.1; 200 mg, 0.63 mmol, 1 eq) was added to a 1:1 mix of acetonitrile and water (10 mL total). After stirring for 5 minutes, potassium carbonate (260 mg, 1.88 mmol, 3 eq) was added and the mixture stirred for a further 5 minutes. Once fully dissolved, 2-(bromomethyl)naphthalene (132 mg, 0.59 mmol, 0.95 eq) was added slowly over the course of 1 hour and the mixture subsequently stirred for 24 hours. Upon completion, the product was extracted with dichloromethane (2×30 mL) using a 1M solution of citric acid to neutralise the aqueous phase. Combined organic fractions were washed with distilled water (30 mL) and dried over MgSO$_4$, filtered and concentrated in vacuo to give the crude product. Purification was achieved using an SCX-2 catch and release cartridge (see Solid Phase Extraction method) to afford compound 3.4 (126.00 mg, 46.1% yield) as a pale yellow solid.

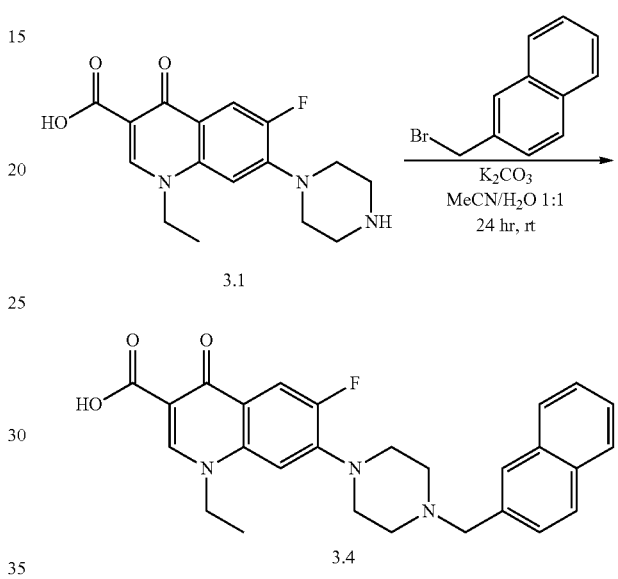

$^1$H NMR (400 MHz, CDCl$_3$) δ 15.16 (br. s., 1H), 8.64 (s, 1H), 8.00 (d, J=13.09 Hz, 1H), 7.80-7.86 (m, 3H), 7.77 (s, 1H), 7.53 (dd, J=1.64, 8.44 Hz, 1H), 7.45-7.51 (m, 2H), 6.81 (d, J=6.80 Hz, 1H), 4.29 (q, J=7.05 Hz, 2H), 3.77 (s, 2H), 3.32-3.39 (m, 4H), 2.69-2.77 (m, 4H), 1.55 (t, J=7.18 Hz, 3H); LC-MS Retention time 2.95 minutes, found 460.1 [M+H]$^+$; calculated for C$_{27}$H$_{26}$FN$_3$O$_3$ 460.52 [M+H]$^+$.

Synthesis of 1-ethyl-6-fluoro-7-(4-(naphthalen-1-ylmethyl)piperazin-1-yl)-4-oxo-1,4-dihydroquinoline-3-carboxylic acid hydrochloride (3.5)

3.4 (30 mg, 0.065 mmol, 1 eq) was added to equal parts methanol and dioxane (40 mL total) and stirred for 10 minutes. Then 4M HCl in dioxane (33 μL, 0.131 mmol, 2 eq) was added dropwise and the flask sealed and stirred for 1 hour. The mixture was then washed with hexane (3×30 mL), concentrated in vacuo and lyophilised for 24 hours to afford compound 3.5 (23.95 mg, 74.0% yield) as an off white solid.

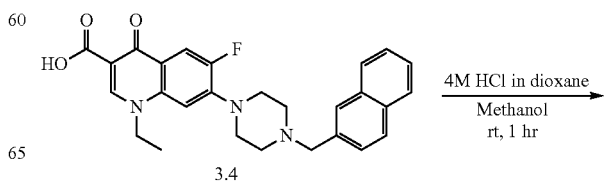

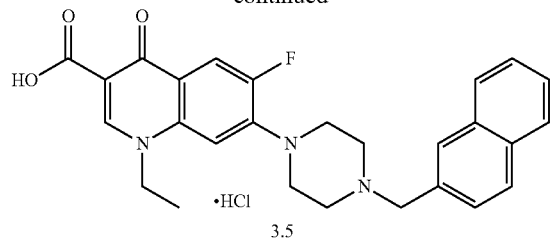

3.5

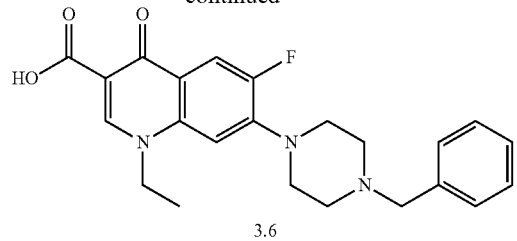

3.6

$^1$H NMR (400 MHz, DMSO-d$_6$) δ 15.28 (br. s., 1H), 11.52 (br. s., 1H), 8.97 (s, 1H), 8.17 (s, 1H), 8.03 (d, J=8.56 Hz, 1H), 7.93-8.01 (m, 3H), 7.84 (d, J=7.05 Hz, 1H), 7.60 (m, 2H), 7.26 (d, J=7.05 Hz, 1H), 4.56-4.65 (m, 4H), 3.88 (d, J=12.34 Hz, 2H), 3.44-3.54 (m, 4H), 3.27-3.32 (m, 2H), 1.40 (t, J=7.18 Hz, 3H); $^{13}$C NMR (100 MHz, DMSO-d$_6$) δ 176.2, 166.0, 152.6 (C-6, $^1$J(C-F)=248 Hz), 148.7, 137.1, 133.1, 132.5, 131.3, 128.4, 128.2, 128.0, 127.7, 127.1, 127.0, 126.7, 119.9, 115.6, 111.4 (C-5, $^2$J(C-F)=24 Hz), 107.2, 106.5, 58.8, 50.2, 49.1, 46.3, 14.4; IR (υ$_{max}$/cm$^{-1}$) 2922, 2500, 2399) 1718, 1627, 1516, 1456, 1414, 1279, 1099 961, 802, 746; LC-MS Retention time 5.95 minutes, found 460.1 [M+H]$^+$; calculated for C$_{27}$H$_{26}$FN$_3$O$_3$ 460.52 [M+H]$^+$; HRMS Observed 460.2019 [M+H]$^+$; theoretical value 460.2031 [M+H]$^+$.

Synthesis of 1-ethyl-6-fluoro-7-(4-benzylpiperazin-1-yl)-4-oxo-1,4-dihydroquinoline-3-carboxylic acid (3.6)

Norfloxacin (3.1; 100 mg, 0.31 mmol, 1 eq) was added to a 1:1 mix of acetonitrile and water (10 mL total). After stirring for 5 minutes, potassium carbonate (130 mg, 0.94 mmol, 3 eq) was added and the mixture stirred for a further 5 minutes. Once fully dissolved, bromomethylbenzene (51 mg, 0.30 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 3.6 (770.00 mg, 63.2% yield) as an off white solid.

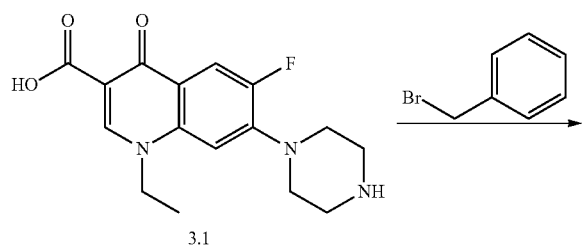

3.1

$^1$H NMR (400 MHz, CDCl$_3$) δ 15.14 (br. s., 1H), 8.66 (s, 1H), 8.02 (d, J=13.09 Hz, 1H), 7.32-7.38 (m, 4H), 7.28-7.32 (m, 1H), 6.82 (d, J=6.80 Hz, 1H), 4.31 (q, J=7.05 Hz, 2H), 3.61 (s, 2H), 3.31-3.37 (m, 4H), 2.66-2.72 (m, 4H), 1.57 (t, J=6.92 Hz, 3H); LC-MS Retention time 2.95 minutes, found 410.0 [M+H]$^+$; calculated for C$_{23}$H$_{24}$FN$_3$O$_3$ 410.46 [M+H]$^+$.

Synthesis of 1-ethyl-6-fluoro-7-(4-benzylpiperazin-1-yl)-4-oxo-1,4-dihydroquinoline-3-carboxylic acid hydrochloride (3.7)

3.6 (30 mg, 0.073 mmol, 1 eq) was added to methanol (25 mL) and stirred for 10 minutes. Then 4M HCl in dioxane (37 μL, 0.15 mmol, 2 eq) was added dropwise and the flask sealed and stirred for 1 hour. The mixture was then washed with hexane (3×30 mL), concentrated in vacuo and lyophilised for 24 hours to afford compound 3.7 as a yellow solid.

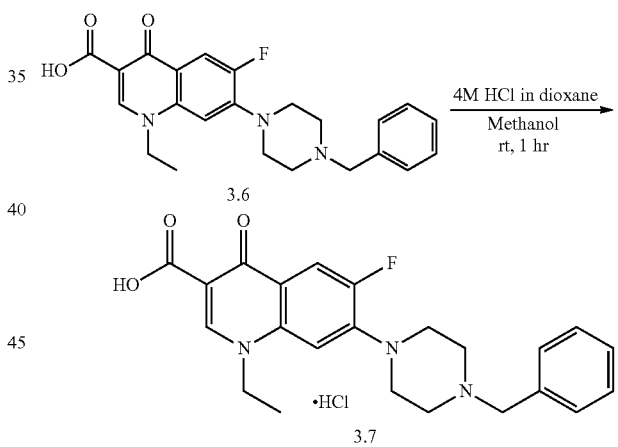

$^1$H NMR (400 MHz, TFA) δ 9.21 (s, 1H), 8.22 (d, J=12.59 Hz, 1H), 7.43-7.53 (m, 3H), 7.37-7.43 (m, 3H), 4.77 (q, J=7.47 Hz, 2H), 4.45 (s, 2H), 4.14 (d, J=13.60 Hz, 2H), 3.82 (d, J=12.09 Hz, 2H), 3.56-3.66 (m, 2H), 3.38-3.48 (m, 2H), 1.67 (t, J=7.18 Hz, 3H); IR (υ$_{max}$/cm$^{-1}$) 3390, 2358, 1700, 1628, 1457, 1420, 1271, 1104, 961, 804, 747, 699; LC-MS Retention time 5.37 minutes, found 410.0 [M+H]$^+$; calculated for C$_{23}$H$_{24}$FN$_3$O$_3$ 410.46 [M+H]$^+$; HRMS Observed 410.1863 [M+H]$^+$; theoretical value 410.1874 [M+H]$^+$.

Synthesis of 1-ethyl-6-fluoro-7-(4-(benzo[d][1,3] dioxol-4-ylmethyl)piperazin-1-yl)-4-oxo-1,4-dihydroquinoline-3-carboxylic acid (3.8)

Norfloxacin (3.1; 157 mg, 0.49 mmol, 1 eq) was added to a 1:1 mix of acetonitrile and water (10 mL total). After stirring for 5 minutes, potassium carbonate (203 mg, 1.47 mmol, 3 eq) was added and the mixture stirred for a further 5 minutes. Once fully dissolved, 4-(bromomethyl)benzo[d][1,3]dioxole (100 mg, 0.47 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 3.8 (178.48 mg, 84.3% yield) as a white solid.

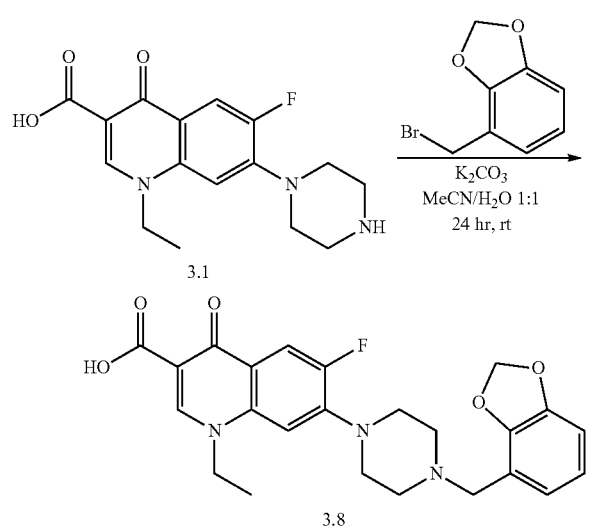

$^1$H NMR (400 MHz, CDCl$_3$) δ 15.13 (br. s., 1H), 8.66 (s, 1H), 8.03 (d, J=13.35 Hz, 1H), 6.76-6.87 (m, 4H), 5.98 (s, 2H), 4.27-4.35 (m, 2H), 3.63 (s, 2H), 3.32-3.38 (m, 4H), 2.69-2.75 (m, 4H), 1.57 (t, J=6.80 Hz, 3H); LC-MS Retention time 2.87 minutes, found 454.1 [M+H]$^+$; calculated for C$_{24}$H$_{24}$FN$_3$O$_5$ 454.47 [M+H]$^+$.

Synthesis of 1-ethyl-6-fluoro-7-(4-(benzo[d][1,3]dioxol-4-ylmethyl)-piperazin-1-yl)-4-oxo-1,4-dihydroquinoline-3-carboxylic acid hydrochloride (3.9)

3.8 (20 mg, 0.044 mmol, 1 eq) was added to equal parts methanol and dioxane (60 mL total) and stirred for 10 minutes. Then 4M HCl in dioxane (22 µL, 0.088 mmol, 2 eq) was added dropwise and the flask sealed and stirred for 1 hour. The mixture was then washed with hexane (3×30 mL), concentrated in vacuo and lyophilised for 24 hours to afford compound 3.9 (15.58 mg, 70.4% yield) as a white solid.

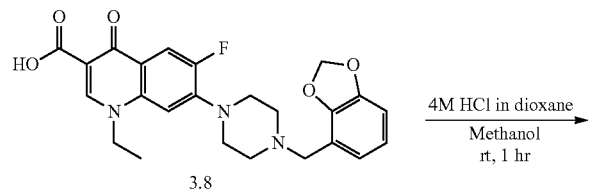

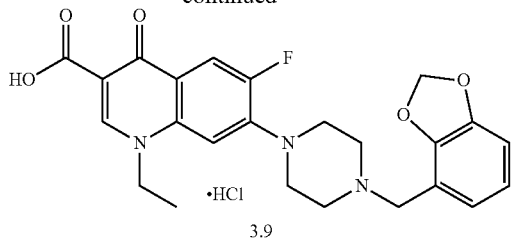

$^1$H NMR (400 MHz, DMSO-d$_6$) δ 15.27 (br. s., 1H), 11.47 (br. s., 1H), 8.98 (s, 1H), 7.96 (d, J=13.35 Hz, 1H), 7.26 (d, J=7.30 Hz, 1H), 7.18 (d, J=7.55 Hz, 1H), 7.03 (d, J=7.81 Hz, 1H), 6.94 (t, J=7.93 Hz, 1H), 6.11 (s, 2H), 4.62 (q, J=7.22 Hz, 2H), 4.36 (br. s., 2H), 3.89 (d, J=12.59 Hz, 2H), 3.44-3.56 (m, 4H), 3.22-3.34 (m, 2H), 1.40 (t, J=7.18 Hz, 3H); $^{13}$C NMR (100 MHz, DMSO-d$_6$) δ 176.1, 166.0, 151.4, 147.5, 147.3, 137.1, 125.0, 121.9, 120.0, 119.9, 111.5, 111.3, 110.3, 109.8, 107.2, 106.5, 101.3, 52.5, 50.1, 49.1, 46.3, 14.4; IR 2906, 2358, 1700, 1628, 1464, 1378, 1251, 1051, 958, 807, 725; LC-MS Retention time 5.48 minutes, found 454.0 [M+H]$^+$; calculated for C$_{24}$H$_{24}$FN$_3$O$_5$ 454.47 [M+H]$^+$; HRMS Observed 4540.1763 [M+H]$^+$; theoretical value 4540.1773 [M+H]$^+$.

Synthesis of 1-ethyl-6-fluoro-7-(4-(benzo[b]thiophen-7-ylmethyl)piperazin yl)-4-oxo-1,4-dihydroquinoline-3-carboxylic acid (3.10)

Norfloxacin (3.1; 174 mg, 0.54 mmol, 1 eq) was added to a 1:1 mix of acetonitrile and water (5 mL total). After stirring for 5 minutes, potassium carbonate (226 mg, 1.63 mmol, 3 eq) was added and the mixture stirred for a further 5 minutes. Once fully dissolved, 7-(bromomethyl)benzo[b]thiophene (118 mg, 0.52 mmol, 0.95 eq) was added slowly over the course of 1 hour and the mixture subsequently stirred for 24 hours. Upon completion, extraction using dichloromethane (2×30 mL), using a 1M solution of citric acid to neutralise the aqueous phase, resulted in formation of a white precipitate. The precipitate was filtered, washed with distilled water (3×20 mL), re-suspended in dichloromethane (2 mL) and purified via automated column chromatography (see Flash Column Chromatography method) to afford compound 3.10 (84.50 mg, 35.1% yield) as a yellow solid.

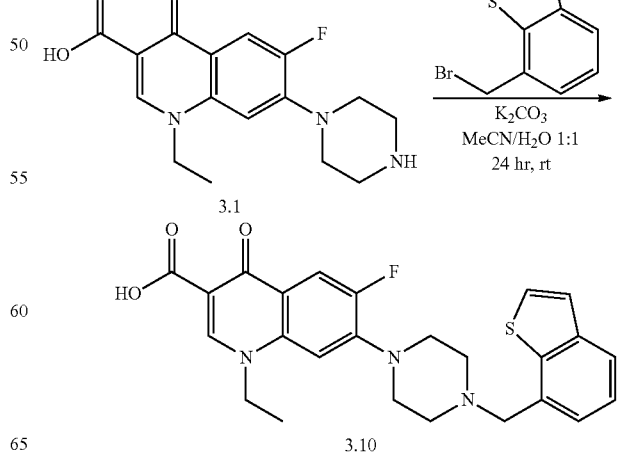

LC-MS Retention time 3.13 minutes, found 466.0 [M+H]+; calculated for $C_{25}H_{24}FN_3O_3S$ 466.54 [M+H]+.

Synthesis of 1-ethyl-6-fluoro-7-(4-(benzo[b]thiophen-7-ylmethyl)piperazin-1-yl)-4-oxo-1,4-dihydroquinoline-3-carboxylic acid hydrochloride (3.11)

3.10 (20 mg, 0.043 mmol, 1 eq) was added to methanol (10 mL) and stirred for 10 minutes. Then 4M HCl in dioxane (21 µL, 0.086 mmol, 2 eq) was added dropwise and the flask sealed and stirred for 1 hour. The mixture was then washed with hexane (3×30 mL), concentrated in vacuo and lyophilised for 24 hours to afford compound 3.11 (11.19 mg, 76.9% yield) as a pale yellow solid.

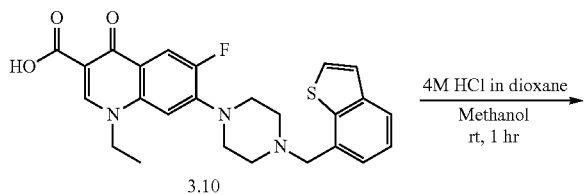

IR ($\upsilon_{max}$/cm$^{-1}$) 3394, 1718, 1624, 1457, 1257, 943, 803; LC-MS Retention time 6.03 minutes, found 466.0 [M+I-1]+; calculated for $C_{25}H_{24}FN_3O_3S$ 466.54 [M+H]+; HRMS Observed 466.1584 [M+H]+; theoretical value 466.1595 [M+H]+.

Synthesis of 1-ethyl-6-fluoro-7-(4-((4-fluoronaphthalen-1-yl)methyl)-piperazin-1-yl)-4-oxo-1,4-dihydroquinoline-3-carboxylic acid (3.12)

Norfloxacin (3.1; 100 mg, 0.31 mmol, 1 eq) was added to a 1:1 mix of acetonitrile and water (5 mL total). After stirring for 5 minutes, potassium carbonate (130 mg, 0.94 mmol, 3 eq) was added and the mixture stirred for a further 5 minutes. Once fully dissolved, 1-(bromomethyl)-4-fluoronaphthalene (71 mg, 0.30 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 3.12 (64.91 mg, 45.7% yield) as a white solid.

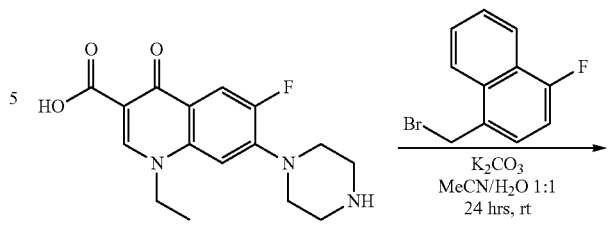

$^1$H NMR (400 MHz, CDCl$_3$) δ 15.13 (s, 1H), 8.65 (s, 1H), 8.31-8.35 (m, 1H), 8.12-8.17 (m, 1H), 8.04 (d, J=13.09 Hz, 1H), 7.55-7.62 (m, 2H), 7.38 (dd, J=5.41, 7.68 Hz, 1H), 7.09 (dd, J=7.81, 10.32 Hz, 1H), 6.80 (d, J=7.05 Hz, 1H), 4.28 (q, J=7.05 Hz, 2H), 3.97 (s, 2H), 3.29-3.34 (m, 4H), 2.71-2.76 (m, 4H), 1.55 (t, J=7.05 Hz, 3H); IR Retention time 3.13 minutes, found 478.0 [M+H]+; calculated for $C_{27}H_{23}F_2N_3O_3$ 478.51 [M+H]+.

Synthesis of 1-ethyl-6-fluoro-7-(4-((4(4-fluoronaphthalen-1-yl)methyl)-piperazin-1-yl)-4-oxo-1,4-dihydroquinoline-3-carboxylic acid hydrochloride (3.13)

3.12 (50 mg, 0.10 mmol, 1 eq) was added to methanol (25 mL) and stirred for to minutes. Then 4M HCl in dioxane (52 µL, 0.21 mmol, 2 eq) was added dropwise and the flask sealed and stirred for 1 hour. The mixture was then washed with hexane (3×30 mL), concentrated in vacuo and lyophilised for 24 hours to afford compound 3.13 (43.22 mg, 77.5% yield) as a white solid.

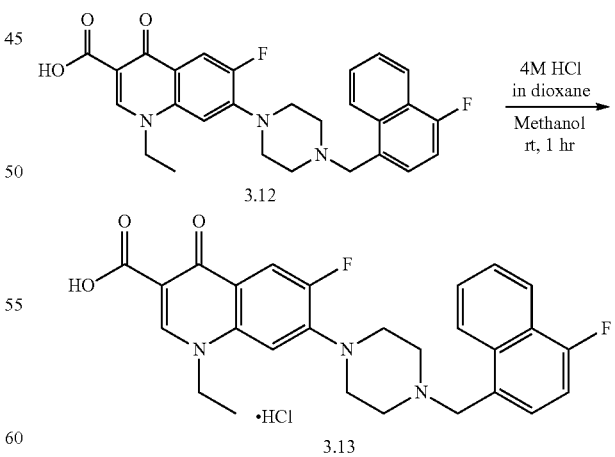

$^1$H NMR (400 MHz, DMSO-d$_6$+TFA) δ 8.98 (s, 1H), 8.55 (d, J=7.55 Hz, 1H), 8.17 (d, J=8.56 Hz, 1H), 7.95-8.03 (m, 2H), 7.72-7.83 (m, 2H), 7.48-7.55 (m, 1H), 7.24 (d, J=7.55 Hz, 1H), 4.89-4.94 (m, 2H), 4.60 (q, J=6.88 Hz, 2H), 3.90 (d, J=11.58 Hz, 2H), 3.51 (br. s., 4H), 3.39 (br. s., 2H), 1.40

(t, J=7.05 Hz, 3H); IR ($v_{max}$/cm$^{-1}$) 3385, 2928, 1715, 1628, 1457, 1387, 1266, 1044, 942, 805; LC-MS Retention time 6.07 minutes, found 478.1 [M+H]$^+$; calculated for $C_{27}H_{23}F_2N_3O_3$ 478.51 [M+H]$^+$; HRMS Observed 478.1925 [M+H]$^+$; theoretical value 478.1937 [M+H]$^+$.

Synthesis of 1-ethyl-6-fluoro-7-(4-((2-oxo-1,2-dihydroquinolin-4-yl)-methyl)piperazin-1-yl)-4-oxo-1,4-dihydroquinoline-3-carboxylic acid (3.14)

Norfloxacin (3.1; 1 g, 3.13 mmol, 1 eq) was added to a 1:1 mix of acetonitrile and water (50 mL total). After stirring for 5 minutes, potassium carbonate (1298 mg, 9.39 mmol, 3 eq) was added and the mixture stirred for a further 5 minutes. Once fully dissolved, 4-(bromomethyl)quinolin-2(1H)-one (708 mg, 2.97 mmol, 0.95 eq) was added slowly over the course of 1 hour and the mixture subsequently stirred for 24 hours. Upon completion, extraction using dichloromethane (2×100 mL), using a 1M solution of citric acid to neutralise the aqueous phase, resulted in formation of a white precipitate. The precipitate was filtered, washed with distilled water (100 mL) and methanol (100 mL) then re-dissolved in excess DMSO. Purification was achieved using an SCX-2 catch and release cartridge (see Solid Phase Extraction method) to afford compound 3.14 (1.26 g, 88.9% yield) as an off white solid.

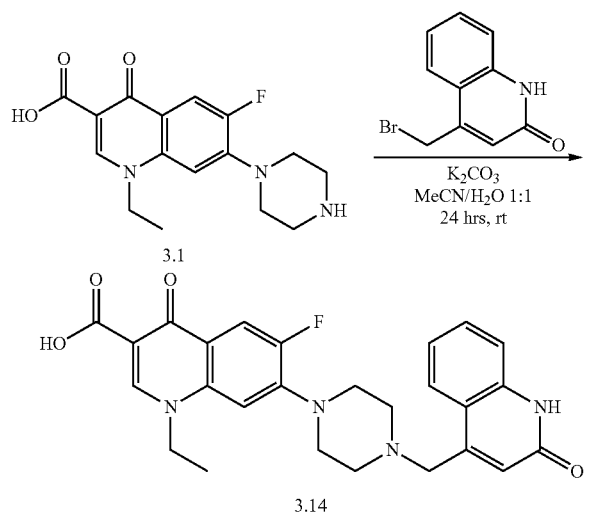

LC-MS Retention time 2.87 minutes, found 477.0 [M+H]$^+$; calculated for $C_{26}H_{25}FN_4O_4$ 477.51 [M+H]$^+$.

Synthesis of 1-ethyl-6-fluoro-7-(4-((2-oxo-1,2-dihydroquinolin-4-yl)-methyl)piperazin-1-yl)-4-oxo-1,4-dihydroquinoline-3-carboxylic acid hydrochloride (3.15)

3.14 (too mg, 0.21 mmol, 1 eq) was added to methanol (25 mL) and stirred for to minutes. Then 4M HCl in dioxane (105 µL, 0.42 mmol, 2 eq) was added dropwise and the flask sealed and stirred for 1 hour. The mixture was then washed with hexane (3×30 mL), concentrated in vacuo and lyophilised for 24 hours to afford compound 3.15 (94.53 mg, 87.8% yield) as an off white solid.

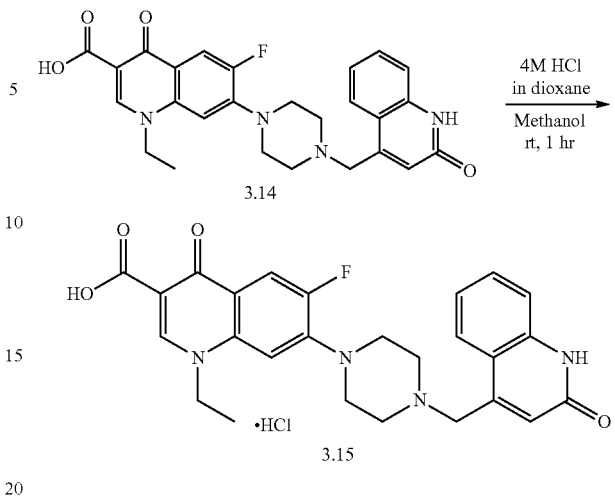

$^1$H NMR (400 MHz, TFA-d) δ 9.23 (s, 1H), 8.23 (d, J=12.84 Hz, 1H), 8.19 (d, J=7.55 Hz, 1H), 7.89-7.95 (m, 1H), 7.77 (d, J=7.30 Hz, 1H), 7.69 (br. s., 2H), 7.45 (br. s., 1H), 5.05 (br. s., 2H), 4.79 (br. s., 2H), 4.16 (d, J=9.06 Hz, 2H), 4.00-4.10 (m, 2H), 3.70-3.89 (m, 4H), 1.68 (t, J=6.04 Hz, 3H); IR ($v_{max}$/cm$^{-1}$) 2975, 2365, 1700, 1663, 1628, 1517, 1477, 1437, 1374, 1273, 957, 805; LC-MS Retention time 5.52 minutes, found 477.0 [M+H]$^+$; calculated for $C_{26}H_{25}FN_4O_4$ 477.51 [M+H]$^+$; HRMS Observed 477.1923 [M+H]$^+$; theoretical value 477.1933 [M+H]$^+$.

Synthesis of 1-ethyl-6-fluoro-7-(4-(quinolin-8-ylmethyl)piperazin-1-yl)-4-oxo-1,4-dihydroquinoline-3-carboxylic acid (3.16)

Norfloxacin (3.1; 100 mg, 0.31 mmol, 1 eq) was added to a 1:1 mix of acetonitrile and water (10 mL total). After stirring for 5 minutes, potassium carbonate (130 mg, 0.94 mmol, 3 eq) was added and the mixture stirred for a further 5 minutes. Once fully dissolved, 8-(bromomethyl)quinoline (66 mg, 0.30 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 3.16 (67.52 mg, 49.3% yield) as an off white solid.

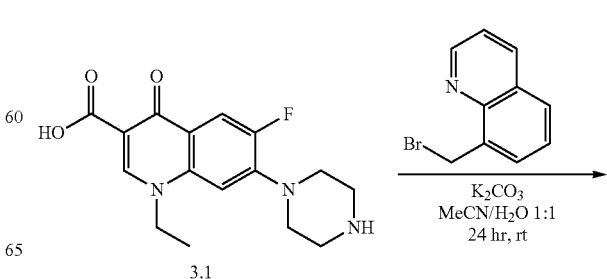

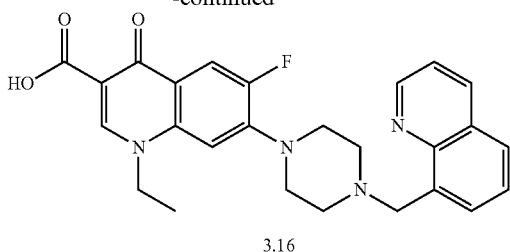

3.16

$^1$H NMR (400 MHz, CDCl$_3$) δ 15.15 (br. s., 1H), 8.96 (dd, J=1.76, 4.28 Hz, 1H), 8.67 (s, 1H), 8.19 (dd, J=1.76, 8.31 Hz, 1H), 8.06 (d, J=13.35 Hz, 1H), 7.90 (d, J=7.05 Hz, 1H), 7.78 (dd, J=1.26, 8.06 Hz, 1H), 7.57 (dd, J=7.05, 80.6 Hz, 1H), 7.44 (dd, J=4.15, 8.18 Hz, 1H), 6.84 (d, J=6.80 Hz, 1H), 4.40 (s, 2H), 4.31 (q, J=7.55 Hz, 2H), 3.38-3.44 (m, 4H), 2.84-2.90 (m, 4H), 1.58 (t, J=7.18 Hz, 3H); LC-MS Retention time 2.85 minutes, found 461.0 [M+H]$^+$; calculated for C$_{26}$H$_{25}$FN$_4$O$_3$ 461.51 [M+H]$^+$.

Synthesis of 1-ethyl-6-fluoro-7-(4-(quinolin-8-ylmethyl)piperazin-1-yl)-4-oxo-1,4-dihydroquinoline-3-carboxylic acid hydrochloride (3.17)

3.16 (50 mg, 0.11 mmol, 1 eq) was added to methanol (25 mL) and stirred for 10 minutes. Then 4M HCl in dioxane (54 μL, 0.22 mmol, 2 eq) was added dropwise and the flask sealed and stirred for 1 hour. The mixture was then washed with hexane (3×30 mL), concentrated in vacuo and lyophilised for 24 hours to afford compound 3.17 as a brown solid.

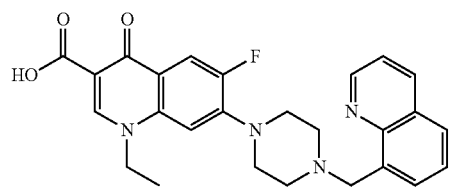 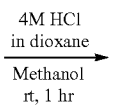

3.16

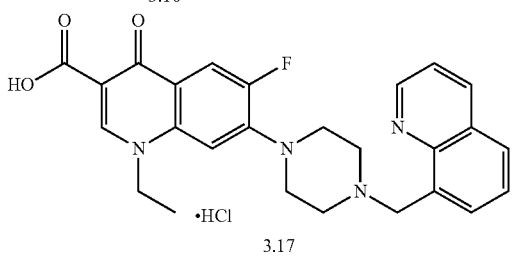

3.17

$^1$H NMR (400 MHz, TFA-d) δ 9.31 (d, J=4.78 Hz, 1H), 9.21-9.27 (m, 2H), 8.55 (d, J=7.30 Hz, 1H), 8.49 (d, J=80.6 Hz, 1H), 8.18-8.29 (m, 2H), 8.13 (t, J=7.55 Hz, 1H), 7.44-7.51 (m, 1H), 5.37 (br. s., 2H), 4.76-4.86 (m, 2H), 4.21 (d, J=11.58 Hz, 2H), 3.96-4.05 (m, 2H), 3.88 (t, J=10.32 Hz, $^2$H), 3.77 (t, J=13.09 Hz, 2H), 1.70 (t, J=6.42 Hz, 3H); IR (υ$_{max}$/cm$^{-1}$) 3393, 2377, 1700, 1624, 1457, 1388, 1270, 1195, 953, 935, 834, 805, 750; LC-MS Retention time 5.48 minutes, found 461.0 [M+H]$^+$; calculated for C$_{26}$H$_{25}$FN$_4$O$_3$ 461.51 [M+H]$^+$; HRMS Observed 461.1973 [M+H]$^+$; theoretical value 461.1973 [M+H]$^+$.

Synthesis of 1-ethyl-6-fluoro-7-(4-((5,6,7,8-tetrahydronaphthalen-1-yl)methyl)piperazin-1-yl)-4-oxo-1,4-dihydroquinoline-3-carboxylic acid (3.18)

Norfloxacin (3.1; 100 mg, 0.31 mmol, 1 eq) was added to a 1:1 mix of acetonitrile and water (10 mL total). After stirring for 5 minutes, potassium carbonate (130 mg, 0.94 mmol, 3 eq) was added and the mixture stirred for a further 5 minutes. Once fully dissolved, 5-(bromomethyl)-1,2,3,4-tetrahydronaphthalene (67 mg, 0.30 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford compound 3.18 (59.70 mg, 43.2% yield) as a pale brown solid.

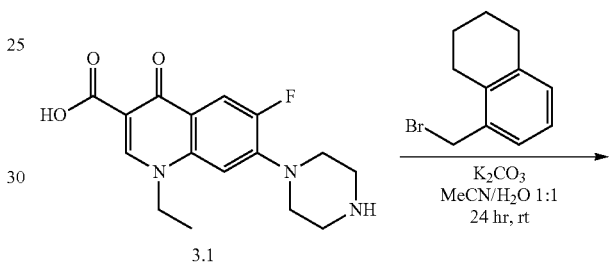

3.1

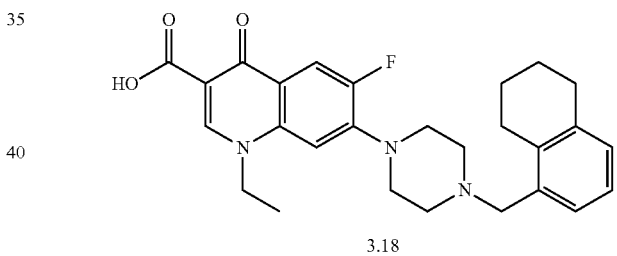

3.18

$^1$H NMR (400 MHz, CDCl$_3$) δ 15.15 (br. s., 1H), 8.67 (s, 1H), 8.04 (d, J=13.09 Hz, 1H), 7.01-7.14 (m, 3H), 6.83 (d, J=6.29 Hz, 1H), 4.31 (d, J=6.80 Hz, 2H), 3.52 (s, 2H), 3.28-3.35 (m, 4H), 2.78-2.87 (m, 4H), 2.65-2.71 (m, 4H), 1.75-1.87 (m, 4H), 1.58 (t, J=6.55 Hz, 3H); LC-MS Retention time 3.18 minutes, found 4640.1 [M+H]$^+$; calculated for C$_{27}$H$_{30}$FN$_3$O$_3$ 464.55 [M+H]$^+$.

Synthesis of 1-ethyl-6-fluoro-7-(4-((5,6,7,8-tetrahydronaphthalen yl)methyl)piperazin-1-yl)-4-oxo-1,4-dihydroquinoline-3-carboxylic acid hydrochloride (3.19)

3.18 (30 mg, 0.065 mmol, 1 eq) was added to methanol (10 mL) and stirred for 10 minutes. Then 4M HCl in dioxane (32 μL, 0.13 mmol, 2 eq) was added dropwise and the flask sealed and stirred for 1 hour. The mixture was then washed with hexane (3×30 mL), concentrated in vacuo and lyophilised for 24 hours to afford compound 3.19 (32.57 mg, 100% yield) as a pale brown solid.

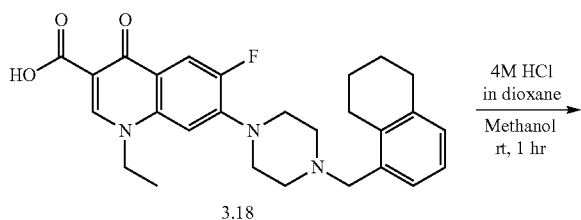

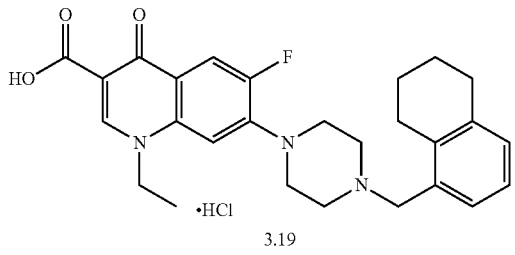

13C NMR (100 MHz, DMSO-d$_6$) δ 176.1, 166.0, 148.8, 137.9, 137.4, 137.1, 130.6, 129.7, 127.8, 125.3, 107.2, 55.7, 50.5, 49.1, 46.2, 29.5, 25.8, 22.6, 22.0, 14.4; IR ($\upsilon_{max}$/cm$^{-1}$) 2929, 2363, 1718, 1700, 1628, 1473, 1261, 1043, 1007, 946, 891, 804, 750; LC-MS Retention time 6.00 minutes, found 4640.0 [M+H]$^+$; calculated for C$_{27}$H$_{30}$FN$_3$O$_3$ 464.55 [M+H]$^+$; HRMS Observed 464.2333 [M+H]$^+$; theoretical value 464.2344 [M+H]$^+$.

Synthesis of 7-(4-(4-(dimethylamino)benzyl)piper-azin-1-yl)-1-ethyl-6-fluoro-4-oxo-1,4-dihydroquino-line-3-carboxylic acid (3.20)

Norfloxacin (3.1; 100 mg, 0.31 mmol, 1 eq) was added to a 1:1 mix of acetonitrile and water (5 mL total). After stirring for 5 minutes, potassium carbonate (130 mg, 0.94 mmol, 3 eq) was added and the mixture stirred for a further 5 minutes. Once fully dissolved, 4-(bromomethyl)-N,N-dimethyl-anilene (64 mg, 0.30 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product.

Purification was achieved using an SCX-2 catch and release cartridge (see Solid Phase Extraction method) to afford compound 3.20 (75.04 mg, 55.7% yield) as a yellow solid.

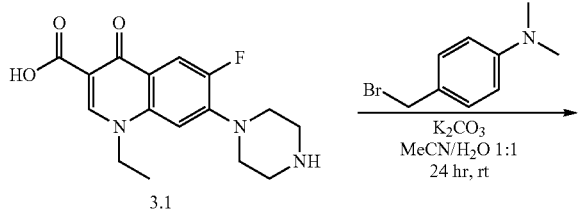

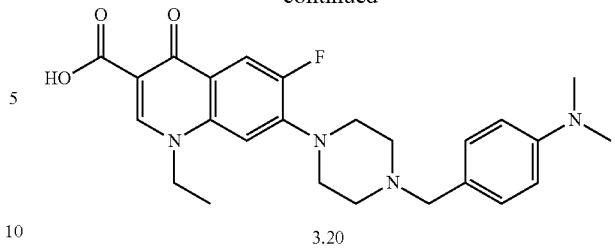

$^1$H NMR (400 MHz, CDCl$_3$) δ 15.14 (br. s., 1H), 8.67 (s, 1H), 8.05 (d, J=13.09 Hz, 1H), 7.19-7.23 (m, 2H), 6.82 (d, J=7.05 Hz, 1H), 6.70-6.74 (m, 2H), 4.31 (q, J=6.88 Hz, 2H), 3.52 (s, 2H), 3.29-3.37 (m, 4H), 2.96 (s, 6H), 2.63-2.70 (m, 4H), 1.57 (t, J=6.80 Hz, 3H); LC-MS Retention time 5.43 minutes, found 453.1 [M+H]$^+$; calculated for C$_{25}$H$_{29}$FN$_4$O$_3$ 453.53 [M+H]$^+$.

Synthesis of 7-(4-(4-(dimethylamino)benzyl)piper-azin-1-yl)-1-ethyl-6-fluoro oxo-1,4-dihydroquino-line-3-carboxylic acid hydrochloride (3.21)

3.20 (56.26 mg, 0.12 mmol, 1 eq) was added to dichloromethane (5 mL) and stirred for 5 minutes. Then 4M HCl in dioxane (622 µL, 2.49 mmol, 20 eq) was added dropwise and the flask sealed and stirred for 1 hour. The mixture was then washed with hexane (3×30 mL), concentrated in vacuo and lyophilised for 24 hours to afford compound 3.21 (59.94 mg, 98.6% yield) as a yellow solid.

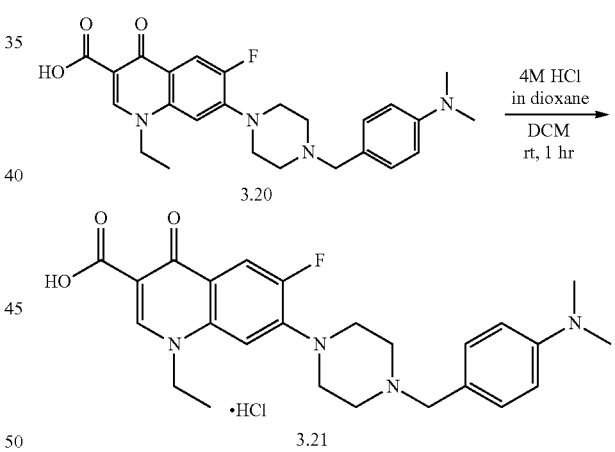

$^1$H NMR (400 MHz, DMSO-d$_6$+TFA) δ 8.94 (s, 1H), 7.92 (d, J=13.09 Hz, 1H), 7.72-7.77 (m, J=8.56 Hz, 2H), 7.45-7.51 (m, J=8.31 Hz, 2H), 7.25 (d, J=7.30 Hz, 1H), 4.60 (q, J=6.97 Hz, 2H), 4.40 (s, 2H), 3.86 (d, J=11.33 Hz, 2H), 3.53 (br. s., 2H), 3.35-3.42 (m, 2H), 3.25 (br. s., 2H), 3.06 (s, 6H), 1.35-1.42 (m, 3H); 13C NMR (100 MHz, DMSO-d$_6$) δ 176.1, 166.0, 152.6 (C-6, $^1$J(C-F)=248 Hz), 148.6, 146.9, 143.9 (C-7, $^2$J(C-F)=10 Hz), 137.1, 132.9, 119.9 ((C-F)=8 Hz), 117.8, 111.4 (C-5, $^2$J(C-F)=23 Hz), 107.1, 106.4, 66.3, 57.8, 49.8, 49.1, 46.2, 43.2, 14.4; IR ($\upsilon$m/cm$^{-1}$) 3411, 2507, 2433, 1718, 1627, 1517, 1472, 1417, 1276, 1100, 961, 897, 803, 746, 591; LC-MS Retention time 5.50 minutes, found 453.1 [M+H]$^+$; calculated for C$_{25}$H$_{29}$FN$_4$O$_3$ 453.53 [M+H]$^+$; HRMS Observed 453.2286 [M+H]$^+$; theoretical value 4530.2296 [M+H]$^+$.

Synthesis of 1-ethyl-6-fluoro-7-(4-(2-(naphthalen-1-yl)ethyl)piperazin-1-yl)-4-oxo-1,4-dihydroquinoline-3-carboxylic acid (3.22)

1-ethyl-6,7-difluoro-4-oxo-1,4-dihydroquinoline-3-carboxylic acid (1.9; 100 mg, 0.39 mmol, 1 eq) and 1-(2-(naphthalen-1-yl)ethyl)piperazine (2.24; 190 mg, 0.79 mmol, 2 eq) were added to DMSO (5 mL) and stirred until full dissolution of both compounds was achieved. The reaction was subsequently heated to 140° C. for one and a half hours. Upon completion, the mixture was allowed to cool for 10 minutes and formation of a precipitate was observed.

The crude precipitate was purified via trituration; the crude was filtered, then washed with methanol (5×10 mL), then the remaining powder collected and re-filtered using dichloromethane. This second filtrate was concentrated in vacuo to afford compound 3.22 (75 mg, 40.1% yield) as a light brown solid.

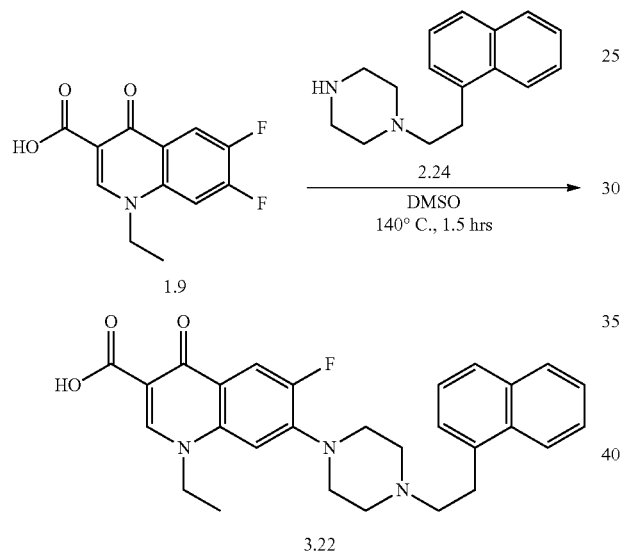

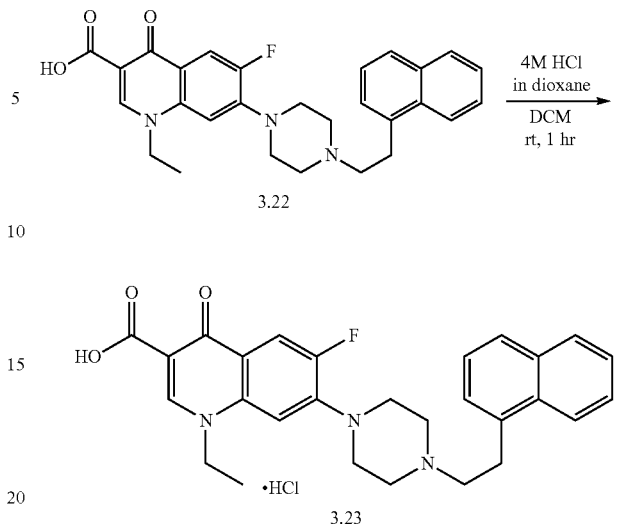

$^1$H NMR (400 MHz, CDCl$_3$) δ 15.12 (br. s., 1H), 8.69 (s, 1H), 8.05-8.11 (m, 2H), 7.86-7.90 (m, 1H), 7.76 (d, J=7.55 Hz, 1H), 7.48-7.58 (m, 2H), 7.37-7.45 (m, 2H), 6.86 (d, J=7.05 Hz, 1H), 4.34 (q, J=7.30 Hz, 2H), 3.37-3.44 (m, 4H), 3.31-3.37 (m, 2H), 2.81-2.88 (m, 6H), 1.61 (t, J=7.30 Hz, 3H); $^{19}$F NMR (400 MHz, CDCl$_3$) δ −120.46; LC-MS Retention time 6.05 minutes, found 474.1 [M+H]$^+$; calculated for C$_{28}$H$_{28}$FN$_3$O$_3$ 474.55 [M+M]$^+$.

Synthesis of 1-ethyl-6-fluoro-7-(4-(2-(naphthalen-1-yl)ethyl)piperazin-1-yl)-4-oxo-1,4-dihydroquinoline-3-carboxylic acid hydrochloride (3.23)

3.22 (40.28 mg, 0.085 mmol, 1 eq) was added to dichloromethane (5 mL total) and stirred for 10 minutes. Then 4M HCl in dioxane (425 µL, 1.70 mmol, 20 eq) was added dropwise and the flask sealed and stirred for 1 hour. The mixture was then washed with hexane (3×30 mL), concentrated in vacuo and lyophilised for 24 hours to afford compound 3.23, as a light brown solid.

LC-MS Retention time 6.15 minutes, found 474.1 [M+H]$^+$; calculated for C$_{28}$H$_{28}$FN$_3$O$_3$ 474.55 [M+H]$^+$.

Synthesis of 1-ethyl-6-fluoro-7-(4-(naphthalen-1-yl)piperazin-1-yl)-4-oxo-1,4-dihydroquinoline-3-carboxylic acid (3.24)

Firstly, 1-(naphthalen-1-yl)piperazine dihydrochloride (2.27; 1 g, 3.51 mmol, 1 eq) was converted to its freebase form through workup with dichloromethane (3×50 mL) and water (50 mL) using a saturated solution of sodium hydrogencarbonate to neutralise the aqueous phase. Combined organic fractions were dried over MgSO$_4$, filtered and concentrated in vacuo. Secondly, 1-(naphthalen-1-yl)piperazine freebase (115.3 mg, 0.54 mmol, 1 eq) and 1-ethyl-6-7-difluoro-4-oxo-1,4-dihydroquinoline-3-carboxylic acid (1.9; 124.0 mg, 0.49 mmol, 0.9 eq) were added to DMSO (5 mL) and stirred until full dissolution of both compounds was achieved. The reaction was subsequently heated to 140° C. for one and a half hours. Upon completion, the mixture was allowed to cool for to minutes and formation of a precipitate was observed. The crude precipitate was purified via trituration; the crude was washed with methanol (5×10 mL), then the remaining powder collected and re-filtered using dichloromethane. This second filtrate was concentrated in vacuo to afford compound 3.24 (145.09 mg, 60.0% yield) as a yellow solid.

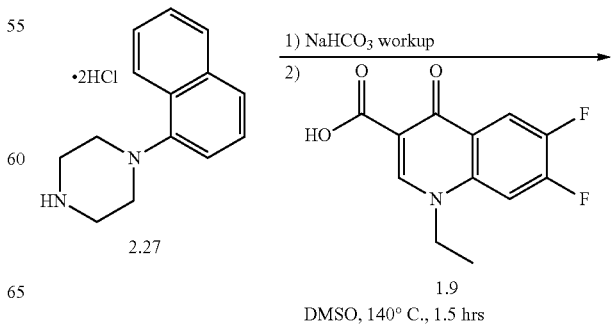

187

-continued

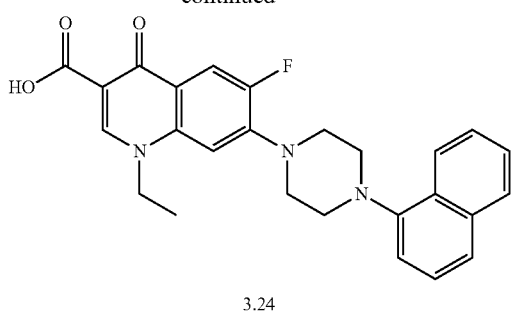

3.24

¹H NMR (400 MHz, CDCl₃) δ 15.13 (s, 1H), 8.71 (s, 1H), 8.24-8.28 (m, 1H), 8.11 (d, J=13.09 Hz, 1H), 7.85-7.90 (m, 1H), 7.63 (d, J=80.6 Hz, 1H), 7.49-7.55 (m, 2H), 7.44-7.49 (m, 1H), 7.19 (dd, J=1.01, 7.30 Hz, 1H), 6.97 (d, J=6.80 Hz, 1H), 4.37 (q, J=7.30 Hz, 2H), 3.62 (br. s., 4H), 3.37 (br. s., 4H), 1.65 (t, J=7.30 Hz, 3H); ¹⁹F NMR (400 MHz, CDCl₃) δ −120.32; LC-MS Retention time 8.75 minutes, found 446.2 [M+H]⁺; calculated for $C_{26}H_{24}FN_3O_3$ 446.49 [M+H]⁺.

Synthesis of 1-ethyl-6-fluoro-7-(4-(naphthalen-1-yl)piperazin-1-yl)-4-oxo-1,4-dihydroquinoline-3-carboxylic acid hydrochloride (3.25)

3.24 (61.14 mg, 0.137 mmol, 1 eq) was added to dichloromethane (5 mL total) and stirred for 10 minutes. Then 4M HCl in dioxane (686 µL, 2.74 mmol, 20 eq) was added dropwise and the flask sealed and stirred for 1 hour. The mixture was then washed with hexane (3×30 mL), concentrated in vacuo and lyophilised for 24 hours to afford compound 3.25 (67.50 mg, 98.0% yield) as an off white solid.

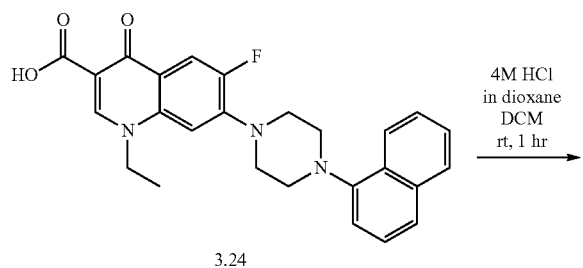

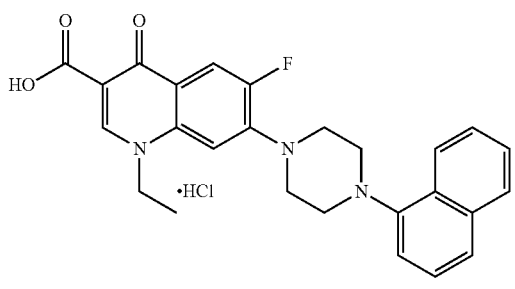

3.25

LC-MS Retention time 8.75 minutes, found 446.1 [M+H]⁺; calculated for $C_{26}H_{24}FN_3O_3$ 446.49 [M+H]⁺.

188

Synthesis of 7-(4-(3,5-dimethylbenzyl)piperazin-1-yl)-1-ethyl-6-fluoro-4-oxo-1,4-dihydroquinoline-3-carboxylic acid (3.26)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 1-(bromomethyl)-3,5-dimethylbenzene (62 mg, 0.31 mmol, 1 eq) was added slowly over the course of 1 hour and the mixture subsequently stirred for 42 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford 3.26 as an off white solid.

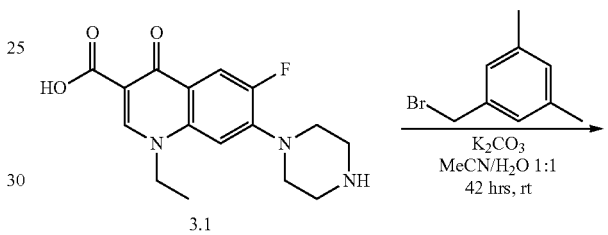

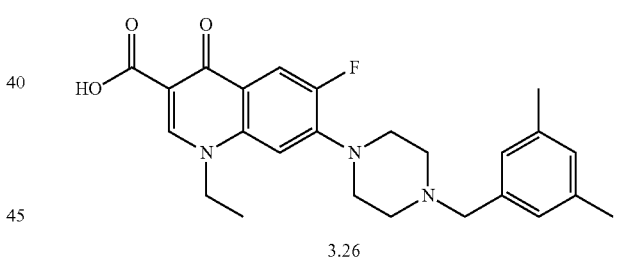

3.26

¹H NMR (400 MHz, CDCl₃) δ 15.12 (br. s., 1H), 8.67 (s, 1H), 8.06 (d, J=13.35 Hz, 1H), 6.97 (s, 2H), 6.94 (s, 1H), 6.83 (d, J=7.30 Hz, 1H), 4.27-4.36 (m, 2H), 3.55 (s, 2H), 3.36 (br. s., 4H), 2.69 (br. s., 4H), 2.33 (s, 6H), 1.58 (t, J=6.92 Hz, 3H); LC-MS Retention time 3.05 minutes, Found 438.0 [M+H]⁺; calculated for $C_{25}H_{28}FN_3O_3$ 438.52 [M+H]⁺

Synthesis of 7-(4-(3,5-dimethylbenzyl)piperazin-1-yl)-1-ethyl-6-fluoro-4-oxo-1,4-dihydroquinoline-3-carboxylic acid hydrochloride (3.27)

3.26 (61.14 mg, 0.13 mmol, 1 eq) was added to dichloromethane (5 mL) and stirred for 5 minutes. Then 4M HCl in dioxane (658 µL, 2.63 mmol, 20 eq) was added dropwise and the flask sealed and stirred for 1 hour. The mixture was then washed with hexane (3×30 mL), concentrated in vacuo and lyophilised for 24 hours to afford 30.27 as an off white solid.

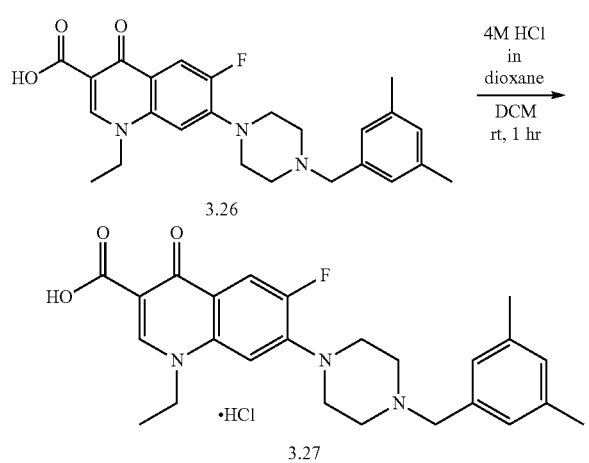

LC-MS Retention time 5.88 minutes, Found 438.2 [M+H]⁺; calculated for $C_{25}H_{28}FN_3O_3$ 438.52 [M+H]⁺

Synthesis of 7-(4-(4-(1H-pyrrol-1-yl)benzyl)piperazin-1-yl)-1-ethyl-6-fluoro oxo-1-4-dihydroquinoline-3-carboxylic acid (3.28)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 1-(4-(bromomethyl)phenyl)-1H-pyrrole (70 mg, 0.30 mmol, 0.95 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford (470.20 mg, 34.7% yield) 3.28 as an off white solid.

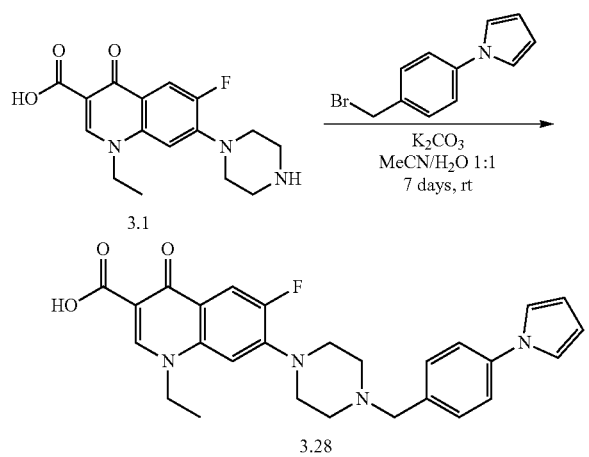

¹H NMR (400 MHz, CDCl₃) δ 15.10 (br. s., 1H), 8.68 (s, 1H), 8.08 (d, J=13.09 Hz, 1H), 7.33-7.44 (m, 4H), 7.10 (t, J=2.14 Hz, 2H), 6.84 (d, J=6.80 Hz, 1H), 6.37 (t, J=2.14 Hz, 2H), 4.31 (q, J=7.22 Hz, 2H), 3.63 (s, 2H), 3.33-3.38 (m, 4H), 2.68-2.74 (m, 4H), 1.55-1.59 (m, 3H); LC-MS Retention time 50.92 minutes, and 475.1 [M+H]⁺; calculated for $C_{27}H_{27}FN_4O_3$ 475.54 [M+H]⁺

Synthesis of 7-(4-(4-(1H-pyrrol-1-yl)benzyl)piperazin-1-yl)-1-ethyl-6-fluoro-4-oxo-1,4-dihydroquinoline-3-carboxylic acid hydrochloride (3.29)

3.28 (42.96 mg, 0.09 mmol, 1 eq) was added to dichloromethane (3 mL) and stirred for 5 minutes. Then 4M HCl in dioxane (453 µL, 1.81 mmol, 20 eq) was added dropwise and the flask sealed and stirred for 1 hour. The mixture was then washed with hexane (3×30 mL), concentrated in vacuo and lyophilised for 24 hours to afford 30.29 as an off white solid.

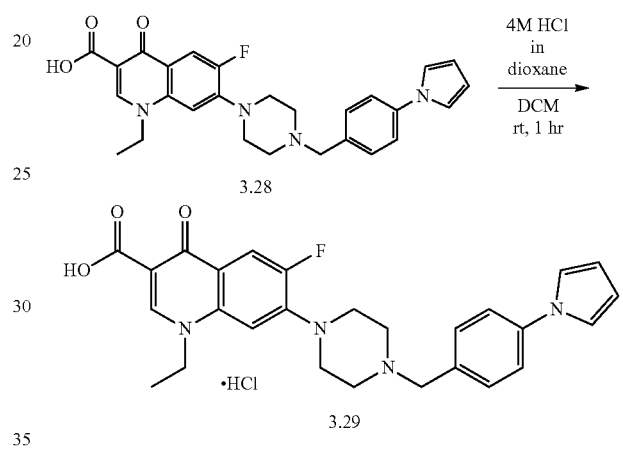

¹H NMR (400 MHz, DMSO-d₆) δ 15.29 (br. s., 1H), 11.45 (s, 1H), 8.98 (s, 1H), 7.98 (d, J=13.07 Hz, 1H), 7.79-7.66 (m, 4H), 7.46 (t, J=2.23 Hz, 2H), 7.28 (d, J=7.22 Hz, 1H), 6.30 (t, J=2.20 Hz, 2H), 4.62 (q, J=7.05 Hz, 2H), 4.47-4.40 (m, 2H), 3.90 (d, J=13.31 Hz, 2H), 3.55-3.42 (m, 4H), 3.34-3.22 (m, 2H), 1.41 (t, J=7.10 Hz, 3H); LC-MS Retention time 5.95 minutes, Found 4750.1 [M+H]⁺; calculated for $C_{27}H_{27}FN_4O_3$ 475.54 [M+H]⁺

Synthesis of 7-(4-(4-(1H-pyrazol-1-yl)benzyl)piperazin-1-yl)-1-ethyl-6-fluoro oxo-1-4-dihydroquinoline-3-carboxylic acid (3.30)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 1-(4-(bromomethyl)phenyl)-1H-pyrazole (71 mg, 0.30 mmol, 0.95 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford 30.30 as an off white solid.

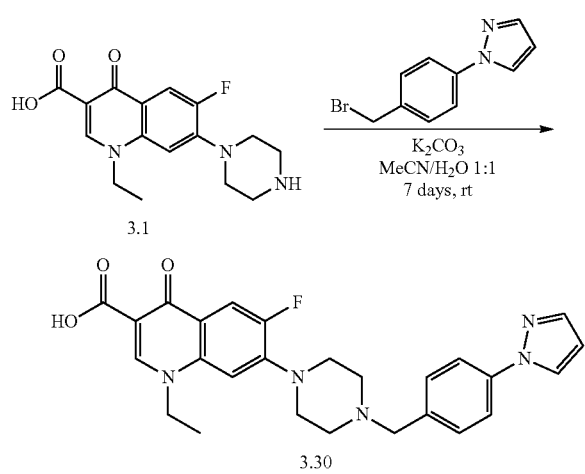

<sup>1</sup>H NMR (400 MHz, CDCl₃) δ 15.12 (br. s., 1H), 8.65 (s, 1H), 8.03 (d, J=13.09 Hz, 1H), 7.93 (d, J=2.27 Hz, 1H), 7.73 (d, J=1.76 Hz, 1H), 7.67 (d, J=8.31 Hz, 2H), 7.45 (d, J=8.56 Hz, 2H), 6.83 (d, J=6.80 Hz, 1H), 6.45-6.50 (m, 1H), 4.31 (q, J=7.22 Hz, 2H), 3.64 (s, 2H), 3.31-3.38 (m, 4H), 2.66-2.73 (m, 4H), 1.57 (t, J=7.30 Hz, 3H); $^{13}$C NMR (100 MHz, CDCl₃) δ 177.0, 167.3, 154.8, 152.3, 147.1, 146.2, 146.1, 141.1, 139.4, 137.1, 136.0, 130.2, 126.8, 120.5, 120.4, 119.2, 112.8, 112.6, 108.3, 107.7, 103.8, 62.2, 52.7, 49.9, 49.9, 49.8, 14.5; LC-MS Retention time 2.85 minutes, Found 476.0 [M+H]$^+$; calculated for C$_{26}$H$_{26}$FN$_5$O$_3$ 476.52 [M+H]$^+$ Synthesis of 7-(4-(4-(1H-pyrazol-1-yl)benzyl)piper-azin-1-yl)-1-ethyl-6-fluoro-4-oxo-1,4-dihydroquino-line-3-carboxylic acid hydrochloride (3.31)

3.30 (37.21 mg, 0.08 mmol, 1 eq) was added to dichloromethane (3 mL) and stirred for 5 minutes. Then 4M HCl in dioxane (391 μL, 1.57 mmol, 20 eq) was added dropwise and the flask sealed and stirred for 1 hour. The mixture was then washed with hexane (3×30 mL), concentrated in vacuo and lyophilised for 24 hours to afford 3.31 as an off white solid.

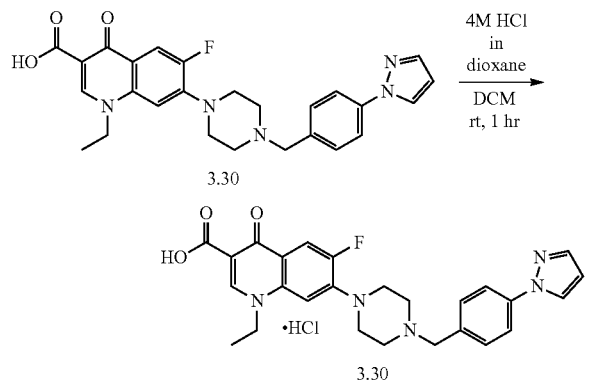

LC-MS Retention time 50.53 minutes, Found 476.1 [M+H]$^+$; calculated for C$_{26}$H$_{26}$FN$_5$O$_3$ 476.52 [M+H]$^+$ Synthesis of 7-(4-(4-(1H-1,2,4-triazol-1-yl)benzyl) piperazin-1-yl)-1-ethyl-6-fluoro-4-oxo-1,4-dihydro-quinoline-3-carboxylic acid (3.32)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 1-(4-(bromomethyl) phenyl)-1H-1,2,4-triazole (71 mg, 0.30 mmol, 0.95 eq) was added slowly over the course of 1 hour and the mixture subsequently stirred for 116 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford 3.32 as an off white solid.

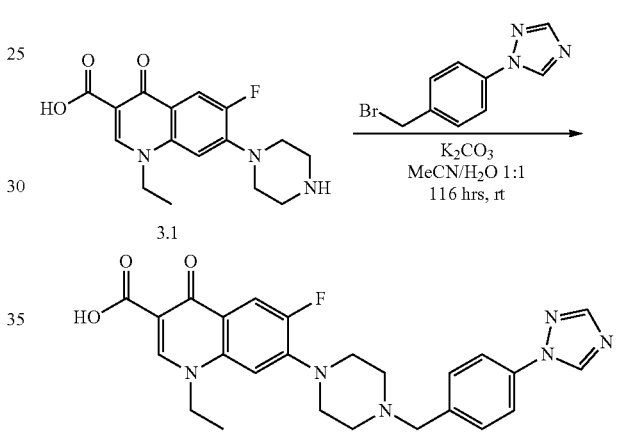

<sup>1</sup>H NMR (400 MHz, CDCl₃) δ 15.11 (br. s., 8.65 (s, 1H), 8.57 (s, 1H), 8.11 (s, 1H), 8.00 (d, J=13.09 Hz, 1H), 7.63-7.68 (m, J=8.56 Hz, 2H), 7.49-7.54 (m, J=8.56 Hz, 2H), 6.83 (d, J=6.80 Hz, 1H), 4.32 (q, J=7.22 Hz, 2H), 3.66 (s, 2H), 3.31-3.38 (m, 4H), 2.65-2.74 (m, 4H), 1.57 (t, J=7.30 Hz, 3H); $^{13}$C NMR (100 MHz, CDCl₃) δ 17.0, 167.2, 154.8, 152.6, 152.3, 147.1, 146.2, 146.1, 140.9, 138.2, 137.1, 136.1, 130.4, 120.5, 120.4, 120.1, 112.8, 112.6, 108.3, 103.8, 62.1, 52.7, 49.9, 49.8, 14.5; LC-MS Retention time 2.68 minutes, Found 477.0 [M+H]$^+$; calculated for C$_{25}$H$_{25}$FN$_{16}$O$_3$ 477.51 [M+H]$^+$ Synthesis of 7-(4-(4-(1H-1,2,4-triazol-1-yl)benzyl) piperazin-1-yl)-1-ethyl fluoro-4-oxo-1,4-dihydroqui-noline-3-carboxylic acid (3.33)

3.32 (28.07 mg, 0.06 mmol, 1 eq) was added to dichloromethane (3 mL) and stirred for 5 minutes. Then 4M HCl in dioxane (295 μL, 1.18 mmol, 20 eq) was added dropwise and the flask sealed and stirred for 17 hours. The mixture was then washed with hexane (3×30 mL), concentrated in vacuo and lyophilised for 24 hours to afford 3.33 as an off white solid.

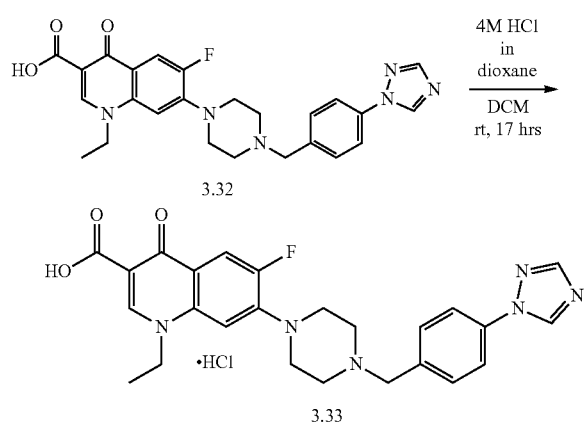

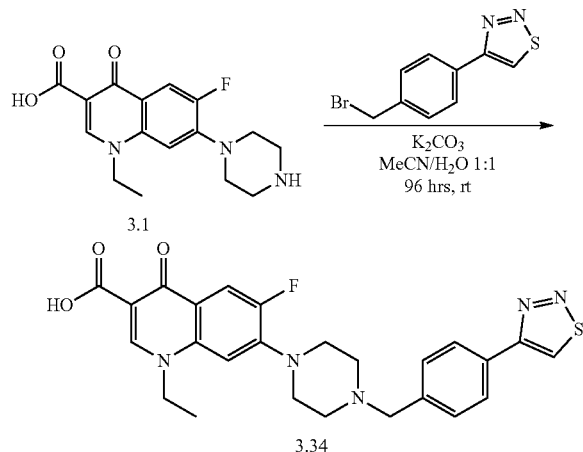

¹H NMR (400 MHz, DMSO-d₆) δ 11.75 (s, 1H), 9.39 (s, 1H), 8.98 (s, 1H), 8.29 (s, 1H), 8.03-7.93 (m, 3H), 7.93-7.84 (m, 2H), 7.27 (d, J=7.28 Hz, 1H), 4.62 (q, J=7.09 Hz, 2H), 4.48 (d, J=4.57 Hz, 2H), 3.88 (d, J=13.28 Hz, 2H), 3.58-3.40 (m, 4H), 3.29 (d, J=11.35 Hz, 2H), 1.40 (t, J=7.09 Hz, 3H); LC-MS Retention time 50.20 minutes, Found 4770.1 [M+H]⁺; calculated for $C_{25}H_{25}FN_6O_3$ 477.51 [M+H]⁺

Synthesis of 7-(4-(4-(1,2,3-thiadiazol-4-yl)benzyl)piperazin-1-yl)-1-ethyl-6-fluoro-4-oxo-1,4-dihydroquinoline-3-carboxylic acid (3.34)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 4-(4-(bromomethyl)phenyl)-1,2,3-thiadiazole (76 mg, 0.30 mmol, 0.95 eq) was added slowly over the course of 1 hour and the mixture subsequently stirred for 96 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford (117.85 mg, 80.3% yield) 3.34 as an off white solid.

LC-MS Retention time 2.92 minutes, Found 494.0 [M+H]⁺; calculated for $C_{25}H_{24}FN_5O_3S$ 494.56 [M+H]⁺

Synthesis of 7-(4-(4-(1,2,3-thiadiazol-4-yl)benzyl)piperazin-1-yl)-1-ethyl fluoro-4-oxo-1,4-dihydroquinoline-3-carboxylic acid hydrochloride (3.35)

3.34 (90 mg, 0.18 mmol, 1 eq) was added to dichloromethane (3 mL) and stirred for 5 minutes. Then 4M HCl in dioxane (912 µL, 3.65 mmol, 20 eq) was added dropwise and the flask sealed and stirred for 1 hour. The mixture was then washed with hexane (3×30 mL), concentrated in vacuo and lyophilised for 24 hours to afford 3.35 as an off white solid.

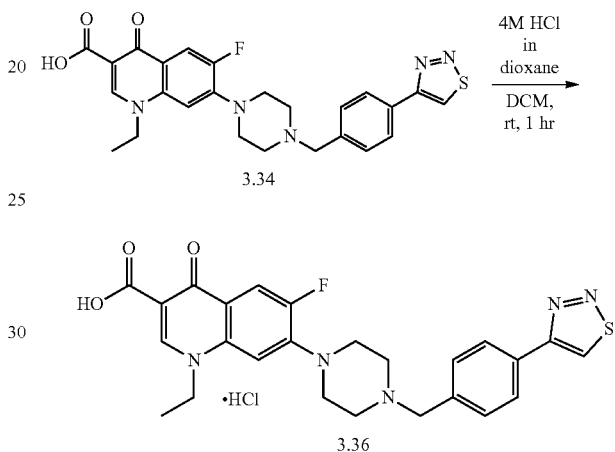

¹H NMR (400 MHz, DMSO-d₆) δ 15.26 (s, 1H), 11.77 (s, 1H), 9.73 (s, 1H), 8.97 (s, 1H), 8.25 (d, J=8.34 Hz, 2H), 7.96 (d, J=13.08 Hz, 1H), 7.87 (d, J=8.20 Hz, 2H), 7.27 (d, J=7.25 Hz, 1H), 4.61 (q, J=7.10 Hz, 2H), 4.50 (d, J=4.74 Hz, 2H), 3.89 (d, J=13.31 Hz, 2H), 3.62-3.43 (m, 4H), 3.37-3.26 (m, 2H), 1.41 (t, J=7.08 Hz, 3H); LC-MS Retention time 5.62 minutes, Found 4940.1 [M+H]⁺; calculated for $C_{25}H_{24}FN_5O_{38}$ 494.56 [M+H]⁺

Synthesis of 1-ethyl-6-fluoro-7-(4-(4-(5-methyl-1,2,4-oxadiazol-3-yl)-benzyl)piperazin-1-yl)-4-oxo-1,4-dihydroquinone-3-carboxylic acid (3.36)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 3-(4-(bromomethyl)phenyl)-5-methyl-1,2,4-oxadiazole (75 mg, 0.30 mmol, 0.95 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford 3.36 as an off white solid.

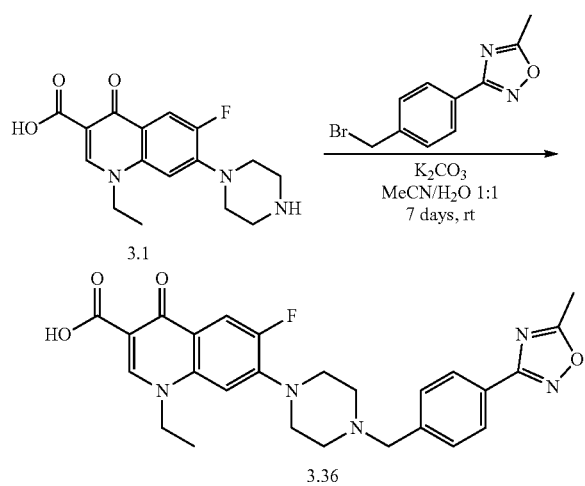

<sup>1</sup>H NMR (400 MHz, CDCl₃) δ 15.13 (br. s., 1H), 8.63 (s, 1H), 8.02 (d, J=8.31 Hz, 2H), 7.98 (d, J=13.09 Hz, 1H), 7.48 (d, J=80.6 Hz, 2H), 6.82 (d, J=6.80 Hz, 1H), 4.31 (q, =7.05 Hz, 2H), 3.65 (s, 2H), 3.32-3.38 (m, 4H), 2.67-2.73 (m, 4H), 2.66 (s, 3H) 1.56 (t, J=7.18 Hz, 3H); ¹³C NMR (too MHz, CDCl₃) δ 176.9, 176.6, 168.2, 167.2, 152.3, 147.1, 146.2, 146.1, 141.1, 137.1, 129.5 (2C), 127.4 (2C), 125.9, 120.4, 120.3, 112.7, 112.5, 108.2, 103.8, 62.5, 52.7 (2C), 49.9, 49.9, 49.8, 14.4, 12.4; LC-MS Retention time 2.88 minutes, Found 492.0 [M+H]⁺; calculated for C₂₆H₂₆FN₅O₄ 492.52 [M+1-1]

Synthesis of 1-ethyl-6-fluoro-7-(4-(4-(5-methyl-1,2,4-oxadiazol yl)benzyl)piperazin-1-yl)-4-oxo-1,4-dihydroquinoline-3-carboxylic acid hydrochloride (3.37)

3.36 (17.34 mg, 0.04 mmol, 1 eq) was added to dichloromethane (3 mL) and stirred for 5 minutes. Then 4M HCl in dioxane (176 µL, 0.71 mmol, 20 eq) was added dropwise and the flask sealed and stirred for 17 hours. The mixture was then washed with hexane (3×20 mL), concentrated in vacuo and lyophilised for 24 hours to afford 3.37 as an off white solid.

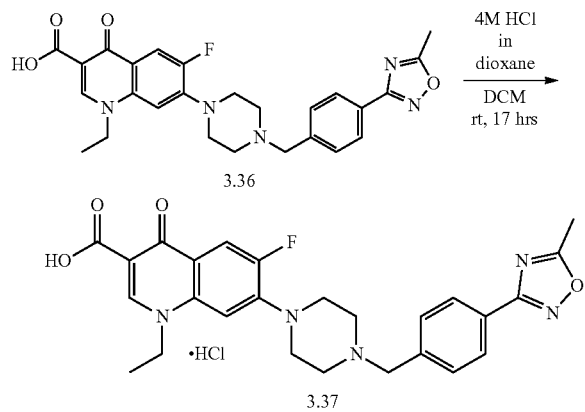

<sup>1</sup>H NMR (400 MHz, DMSO-d₆) δ 11.54 (s, 1H), 8.98 (s, 1H), 8.12-8.06 (m, 2H), 7.98 (d, J=13.06 Hz, 1H), 7.89-7.82 (m, 2H), 7.27 (d, J=7.23 Hz, 1H), 4.62 (q, J=7.07 Hz, 2H), 4.50 (s, 2H), 3.89 (d, J=13.27 Hz, 2H), 3.48 (m, 4H), 3.31 (d, J=11.54 Hz, 2H), 1.40 (t, J=7.07 Hz, 3H); LC-MS Retention time 5.58 minutes, Found 492.1 [M+H]⁺; calculated for C₂₆H₂₆FN₅O₄ 492.52 [M+H]⁺

Synthesis of 7-(4-([1,1'-biphenyl]-4-ylmethyl)piperazin-1-yl)-1-ethyl-6-fluoro-4-oxo-1,4-dihydroquinoline-3-carboxylic acid (3.38)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 4-(bromomethyl)-1,1'-biphenyl (74 mg, 0.30 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved using an SCX-2 catch and release cartridge (see Solid Phase Extraction method) to afford (123.74 mg, 85.7% yield) 3.38 as an off white solid.

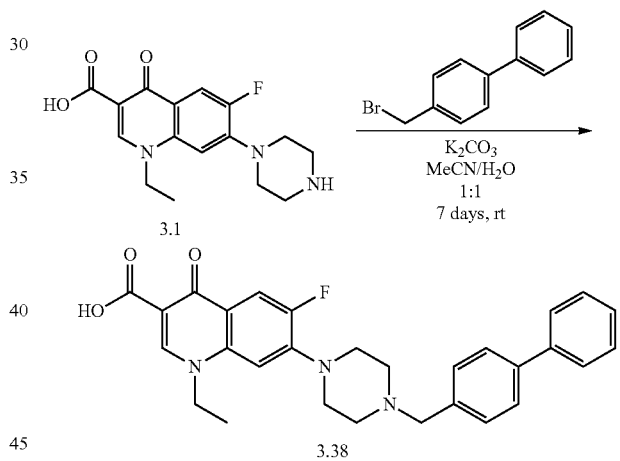

<sup>1</sup>H NMR (400 MHz, CDCl₃) δ 15.12 (br. s., 1H), 8.66 (s, 1H), 8.04 (d, J=13.09 Hz, 1H), 7.56-7.63 (m, 4H), 7.41-7.48 (m, 4H), 7.33-7.39 (m, 1H), 6.83 (d, J=6.29 Hz, 1H), 4.26-4.37 (m, 2H), 3.66 (s, 2H), 3.37 (br. s., 4H), 2.73 (br. s., 4H), 1.58 (t, J=6.17 Hz, 3H); LC-MS Retention time 6.18 minutes, Found 486.2 [M+H]⁺; calculated for C₂₉H₂₈FN₃O₃ 486.56 [M+H]⁺

Synthesis of 7-(4-([1,1'-biphenyl]-4-ylmethyl)piperazin-1-yl)-1-ethyl-6-fluoro-4-oxo-1-4-dihydroquinoline-3-carboxylic acid hydrochloride (3.39)

3.38 (123.74 mg, 0.25 mmol, 1 eq) was added to dichloromethane (5 mL) and stirred for 5 minutes. Then 4M HCl in dioxane (1.27 mL, 5.10 mmol, 20 eq) was added dropwise and the flask sealed and stirred for 1 hour. The mixture was then washed with hexane (3×30 mL), concentrated in vacuo and lyophilised for 24 hours to afford 3.39 as an off white solid.

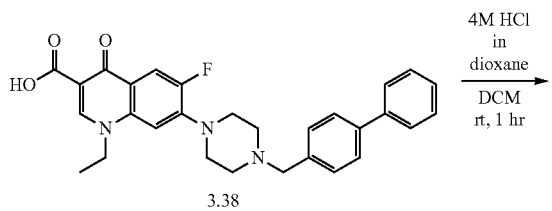

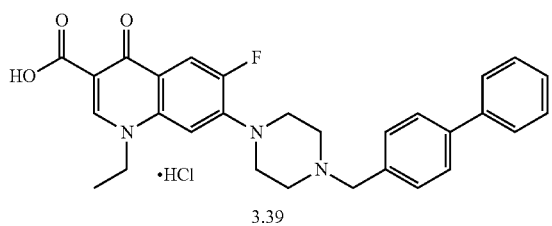

<sup>1</sup>H NMR (400 MHz, DMSO-d$_6$) δ 15.27 (br. s., 1H), 11.43 (br. s., 1H), 8.98 (s, 1H), 7.97 (d, J=13.09 Hz, 1H), 7.73-7.81 (m, 4H), 7.69-7.73 (m, 2H), 7.47-7.52 (m, 2H), 7.38-7.43 (m, 1H), 7.27 (d, J=7.55 Hz, 1H), 4.62 (q, J=6.88 Hz, 2H), 4.44-4.49 (m, 2H), 3.90 (d, J=12.59 Hz, 2H), 3.44-3.54 (m, 4H), 3.24-3.32 (m, 2H), 1.41 (t, J=7.05 Hz, 3H); <sup>13</sup>C NMR (100 MHz, CDCl$_3$) δ 177.0, 167.3, 154.8, 152.3, 147.1, 146.3, 146.2, 140.8, 140.3, 137.1, 136.7, 129.6, 128.8, 127.3, 127.1, 127.1, 120.5, 120.4, 112.9, 112.6, 108.3, 103.8, 62.6, 52.7, 50.0, 49.9, 49.8, 49.8, 14.5; LC-MS Retention time 6.17 minutes, Found 486.1 [M+H]$^+$; calculated for C$_{29}$H$_{28}$FN$_3$O$_3$ 486.56 [M+H]$^+$ Synthesis of 1-ethyl-6-fluoro-7-(4-(4-(hydroxymethyl)benzyl)piperazin-1-yl)-4-oxo-1,4-dihydroquinoline-3-carboxylic acid (3.40)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, (4-(bromomethyl)phenyl)methanol (63 mg, 0.31 mmol, 1 eq) was added slowly over the course of 1 hour and the mixture subsequently stirred for 7 days. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford (133.70 mg, 97.1% yield) 3.40 as an off white solid.

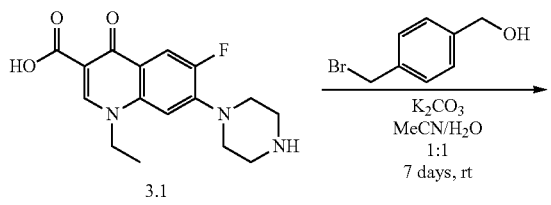

<sup>1</sup>H NMR (400 MHz, CDCl$_3$) δ 15.13 (br. s., 1H), 8.64 (s, 1H), 7.98 (d, J=13.09 Hz, 1H), 7.35 (s, 4H), 6.82 (d, J=6.80 Hz, 1H), 4.70 (s, 2H), 4.31 (q, J=7.13 Hz, 2H), 3.59 (s, 2H), 3.30-3.36 (m, 4H), 2.64-2.70 (m, 4H), 1.56 (t, J=7.18 Hz, 3H); <sup>13</sup>C NMR (100 MHz, CDCl$_3$) δ 176.9, 167.3, 152.3, 147.1, 146.3, 146.2, 140.1, 137.1, 136.9, 129.4 (2C), 127.1 (2C), 120.4, 120.3, 112.7, 112.5, 108.2, 103.8, 65.0, 62.6, 53.5, 52.6 (2C), 49.9, 49.8, 14.4; LC-MS Retention time 50.03 minutes, Found 440.1 [M+H]$^+$; calculated for C$_{24}$H$_{26}$FN$_3$O$_4$ 440.49 [M+H]$^+$ Synthesis of 1-ethyl-6-fluoro-7-(4-(4-(hydroxymethyl)benzyl)piperazin-1-yl)-4-oxo-1,4-dihydroquinoline-3-carboxylic acid hydrochloride (3.41)

3.40 (35.61 mg, 0.8 mmol, 1 eq) was added to dichloromethane (3 mL) and stirred for 5 minutes. Then 4M HCl in dioxane (405 µL, 1.62 mmol, 20 eq) was added dropwise and the flask sealed and stirred for 30 minutes. The mixture was then washed with hexane (3×30 mL), concentrated in vacuo and lyophilised for 24 hours to afford 3.41 as an off white solid.

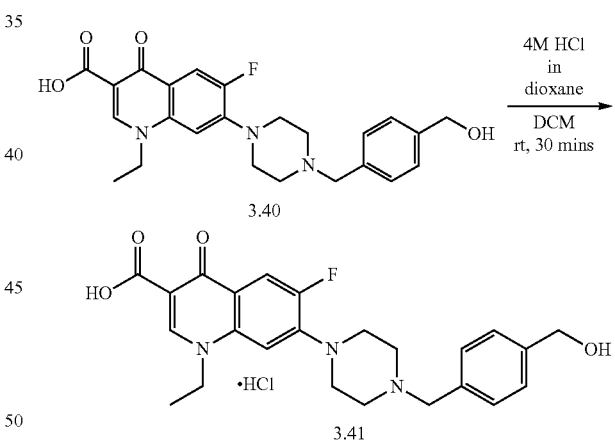

1H NMR (400 MHz, DMSO-d$_6$) δ 15.26 (s, 1H), 11.32 (s, 1H), 8.98 (s, 1H), 7.98 (d, J=13.07 Hz, 1H), 7.61 (d, J=8.06 Hz, 2H), 7.42 (d, J=7.83 Hz, 2H), 7.27 (d, J=7.23 Hz, 1H), 4.62 (q, J=7.09 Hz, 2H), 4.55 (s, 2H), 4.40 (d, J=5.09 Hz, 2H), 3.88 (d, J=13.30 Hz, 2H), 3.53-3.41 (m, 4H), 3.33-3.19 (m, 2H), 1.41 (t, J=7.07 Hz, 3H); LC-MS Retention time 5.15 minutes, Found 440.0 [M+H]$^+$; calculated for C$_{24}$H$_{26}$FN$_3$O$_4$ 440.49 [M+H]+

Synthesis of 1-ethyl-6-fluoro-7-(4-(4-(methoxymethyl)benzyl)piperazin-1-yl)-4-oxo-1,4-dihydroquinoline-3-carboxylic acid (3.42)

Norfloxacin (3.1; 28 mg, 0.09 mmol, 1 eq) was added to a 1:1 mix of acetonitrile and distilled water (2 mL total).

After stirring for 5 minutes, potassium carbonate (36 mg, 0.26 mmol, 3 eq) was added and the mixture stirred for a further 5 minutes. Once fully dissolved, 1-(chloromethyl)-4-(methoxymethyl)benzene (14 mg, 0.08 mmol, 0.95 eq) was added slowly over the course of 1 hour and the mixture subsequently heated to reflux and stirred for 24 hours. Upon completion, the product was extracted with dichloromethane (2×10 mL) using a 1M solution of citric acid to neutralise the aqueous phase. Combined organic fractions were washed with distilled water (10 mL) and dried over MgSO₄, filtered and concentrated in vacuo to give the crude product. Flash column chromatography (0%-100% DCM/acetone) was employed to afford pure 3.42.

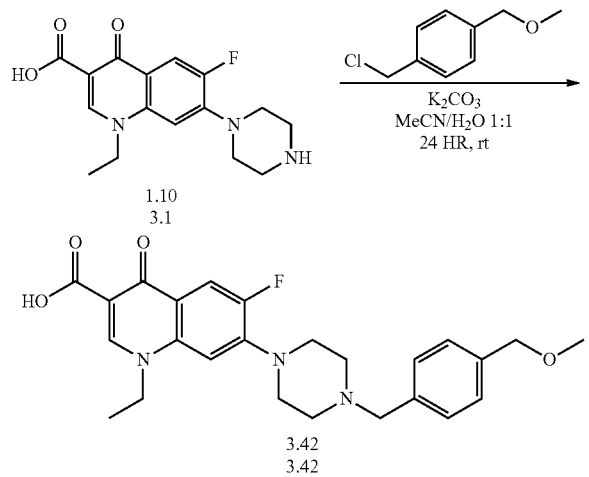

| 3.42 Off white solid | $^1$H NMR | $^1$H NMR (400 MHz, CDCl$_3$) δ 15.14 (br. s., 1H), 8.67 (s, 1H), 8.04 (d, J = 13.09 Hz, 1H), 7.30-7.38 (m, 4H), 6.82 (d, J = 6.80 Hz, 1H), 4.46 (s, 2H), 4.31 (q, J = 7.30 Hz, 2H), 3.61 (s, 2H), 3.42 (s, 3H), 3.31-3.36 (m, 4H), 2.66-2.71 (m, 4H), 1.58 (t, J = 7.18 Hz, 3H) |
|---|---|---|
| | $^{13}$C NMR | $^{13}$C NMR (100 MHz, CDCl$_3$) δ 177.0, 167.3, 154.8, 152.3, 147.1, 146.3, 146.2, 137.4, 137.1, 137.0, 129.3, 127.9, 120.5, 120.5, 112.9, 112.6, 108.3, 103.7, 74.5, 62.6, 58.3, 52.6, 49.9, 49.9, 49.8, 14.4 |
| | Yield | 23.31 mg (61.7% yield) |

Synthesis of 1-ethyl-6-fluoro-7-(4-(4-(methoxymethyl)benzyl)piperazin-1-yl)-4-oxo-1,4-dihydroquinoline-3-carboxylic acid hydrochloride (3.43)

3.42 (12.01 mg, 0.03 mmol, 1 eq) was added to dichloromethane (2 mL) and stirred for 5 minutes. Then 4M HCl in dioxane (1324, 0.53 mmol, 20 eq) was added dropwise and the flask sealed and stirred for 1 hour. The mixture was then washed with hexane (3×20 mL), concentrated in vacuo and lyophilised for 24 hours to afford 3.43.

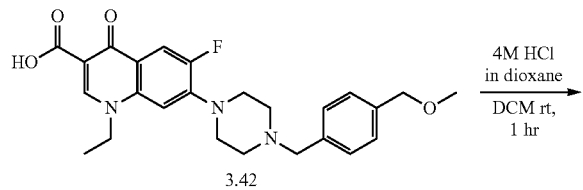

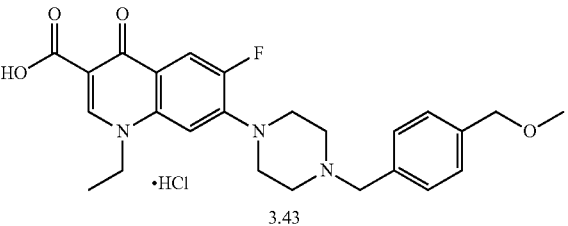

| 3.43 Off white solid | LC-MS | Retention time 4.79 minutes |
|---|---|---|
| | | Found 454.2 [M + H]$^+$; calculated for C$_{25}$H$_{28}$FN$_3$O$_4$ 454.51 [M + H]$^+$ |

Synthesis of 1-ethyl-6-fluoro-7-(4-(3-(methoxymethyl)benzyl)piperazin-1-yl)-4-oxo-1,4-dihydroquinoline-3-carboxylic acid (3.44)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, 1-(bromomethyl)-3-(methoxymethyl)benzene (64 mg, 0.30 mmol, 0.95 eq) was added slowly over the course of 1 hour and the mixture subsequently stirred for 88 hours. Upon completion, the product was extracted with dichloromethane (2×20 mL) using a 1M solution of citric acid to neutralise the aqueous phase. Combined organic fractions were washed with distilled water (20 mL) and dried over MgSO₄, filtered and concentrated in vacuo to give the crude product. Purification was achieved via automated flash column chromatography of the crude solid (see Flash Column Chromatography method; 0%-30% DCM/acetone) to afford pure 3.44.

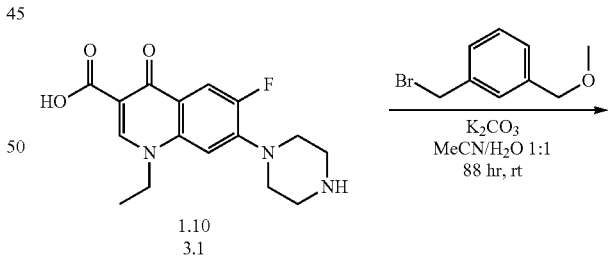

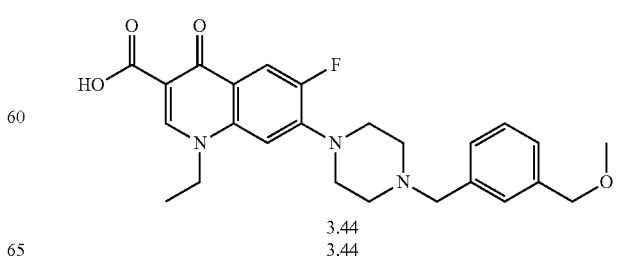

| 3.44 | LC-MS | Retention time 5.33 minutes |
| Off white solid | | Found 454.1 [M + H]$^+$; calculated for $C_{25}H_{28}FN_3O_4$ 454.51 [M + H]$^+$ |
| | Yield | 119.00 mg (88.2% yield) |

Synthesis of 1-ethyl-6-fluoro-7-(4-(3-(methoxymethyl)benzyl)piperazin-1-yl)-4-oxo-1,4-dihydroquinoline-3-carboxylic acid hydrochloride (3.45)

3.44 (36.59 mg, 0.09 mmol, 1 eq) was added to dichloromethane (3 mL) and stirred for 5 minutes. Then 4M HCl in dioxane (403 µL, 1.61 mmol, 20 eq) was added dropwise and the flask sealed and stirred for 40 minutes. The mixture was then washed with hexane (3×30 mL), concentrated in vacuo and lyophilised for 24 hours to afford 3.45.

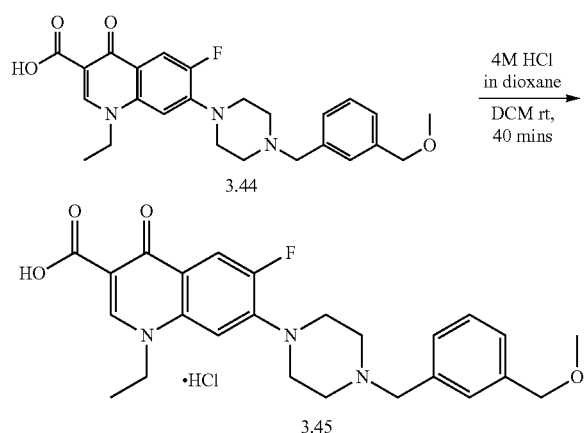

| 3.45 | LC-MS | Retention time 4.78 minutes |
| Off white solid | | Found 454.2 [M + H]$^+$; calculated for $C_{25}H_{28}FN_3O_4$ 454.51 [M + H]$^+$ |

Synthesis of 1-ethyl-6-fluoro-7-(4-(3-(methoxymethyl)benzyl)piperazin-1-yl)-4-oxo-1,4-dihydroquinoline-3-carboxylic acid (3.46)

Norfloxacin (3.1; 100 mg, 0.31 mmol, 1 eq) was added to a 1:1 mix of acetonitrile and distilled water (5 mL total). After stirring for 5 minutes, potassium carbonate (130 mg, 0.94 mmol, 3 eq) was added and the mixture stirred for a further 5 minutes. Once fully dissolved, N-(2-(1H-indol-3-yl)ethyl)-4-(bromomethyl)benzenesulfonamide (123 mg, 0.31 mmol, 1 eq) was added slowly over the course of 1 hour and the mixture subsequently stirred for 42 hours. Upon completion, the product was extracted with dichloromethane (2×20 mL) using a 1M solution of citric acid to neutralise the aqueous phase. Combined organic fractions were washed with distilled water (20 mL) and dried over $MgSO_4$, filtered and concentrated in vacuo to give the crude product. Purification was achieved using an SCX-2 catch and release cartridge (see 1.1.8 Solid Phase Extraction) to afford 3.46.

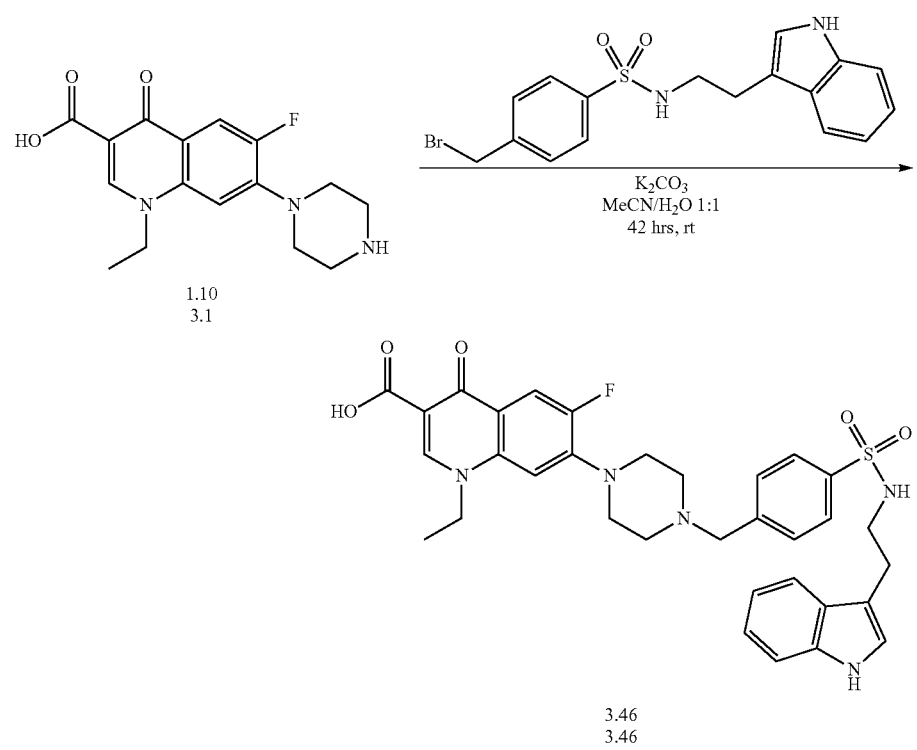

| | | |
|---|---|---|
| 3.46 Off white solid | LC-MS | Retention time 3.12 minutes Found 632.1 [M + H]⁺; calculated for $C_{33}H_{34}FN_5O_5S$ 632.72 [M + H]⁺ |

Synthesis of 1-ethyl-6-fluoro-7-(4-(3-(methoxymethyl)benzyl)piperazin-1-yl)-4-oxo-1,4-dihydroquinoline-3-carboxylic acid hydrochloride (3.47)

3.46 (61.14 mg, 0.13 mmol, 1 eq) was added to dichloromethane (5 mL) and stirred for 5 minutes. Then 4M HCl in dioxane (658 μL, 2.63 mmol, 20 eq) was added dropwise and the flask sealed and stirred for 1 hour. The mixture was then washed with hexane (3×30 mL), concentrated in vacuo and lyophilised for 24 hours to afford 3.47.

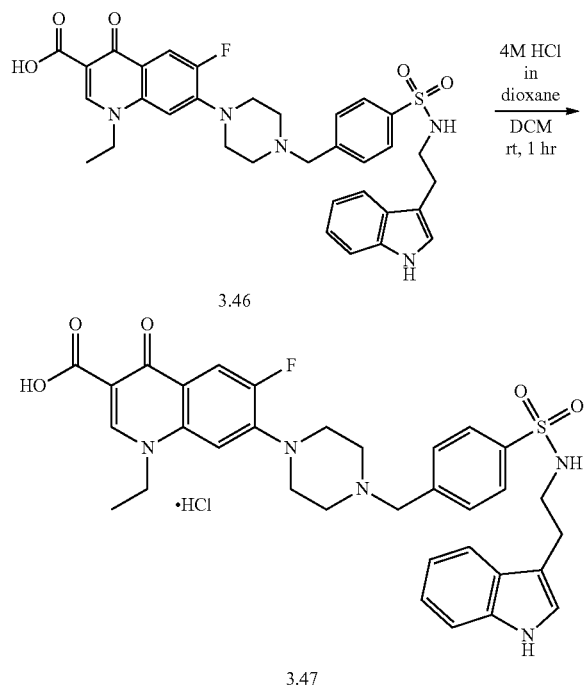

| | | |
|---|---|---|
| 3.47 Off white solid | LC-MS | Retention time 6.07 minutes Found 632.2 [M + H]⁺; calculated for $C_{33}H_{34}FN_5O_5S$ 632.72 [M + H]⁺ |

Synthesis of Enoxacin-ARB Hybrid Compounds

Synthesis of 1-cyclopropyl-6-fluoro-7-(4-(naphthalen-1-ylmethyl)piperazin-1-yl)-4-oxo-1,4-dihydro-1,8-naphthyridine-3-carboxylic acid (4.2)

Enoxacin (4.1; 250 mg, 0.78 mmol, 1 eq) was added to DMF (15 mL) and stirred for 20 minutes at 120° C. Then 1-(bromomethyl)naphthalene (173 mg, 0.78 mmol, 1 eq) and potassium carbonate (324 mg, 2.34 mmol, 3 eq) were added and the mixture stirred for a further 30 minutes at reflux. The mixture was allowed to cool, then extracted with dichloromethane (2×50 mL) using a 1M solution of citric acid to neutralise the aqueous phase. Combined organic fractions were washed with distilled water (50 mL) followed by brine (50 mL), dried over MgSO₄, filtered and concentrated in vacuo to give the crude product. Purification was achieved using an SCX-2 catch and release cartridge (see Solid Phase Extraction method) to afford compound 4.2 (113.86 mg, 79.2% yield) as a pale brown solid.

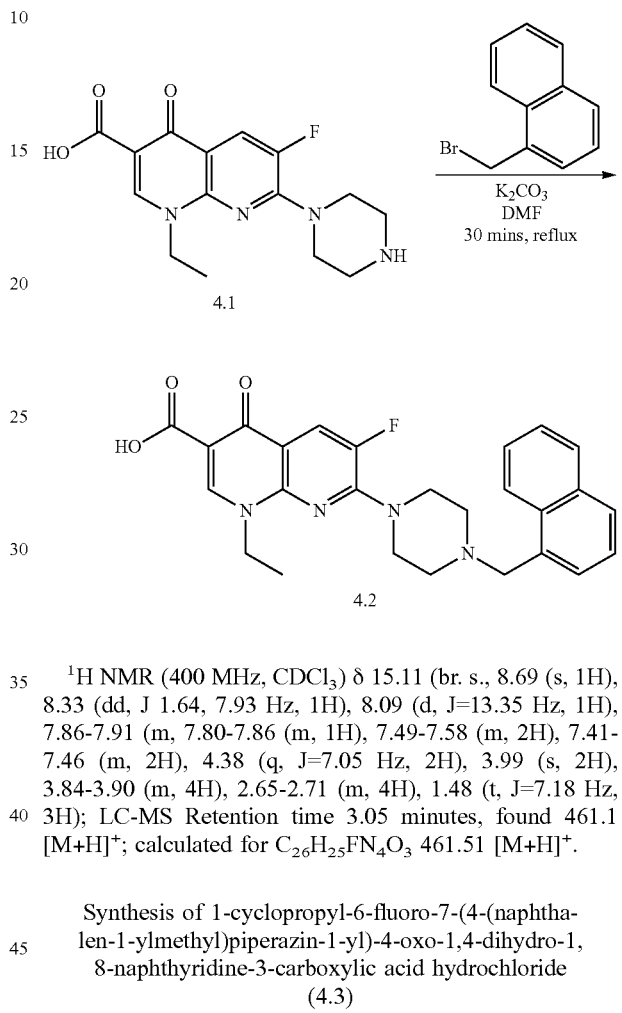

¹H NMR (400 MHz, CDCl₃) δ 15.11 (br. s., 8.69 (s, 1H), 8.33 (dd, J 1.64, 7.93 Hz, 1H), 8.09 (d, J=13.35 Hz, 1H), 7.86-7.91 (m, 7.80-7.86 (m, 1H), 7.49-7.58 (m, 2H), 7.41-7.46 (m, 2H), 4.38 (q, J=7.05 Hz, 2H), 3.99 (s, 2H), 3.84-3.90 (m, 4H), 2.65-2.71 (m, 4H), 1.48 (t, J=7.18 Hz, 3H); LC-MS Retention time 3.05 minutes, found 461.1 [M+H]⁺; calculated for $C_{26}H_{25}FN_4O_3$ 461.51 [M+H]⁺.

Synthesis of 1-cyclopropyl-6-fluoro-7-(4-(naphthalen-1-ylmethyl)piperazin-1-yl)-4-oxo-1,4-dihydro-1,8-naphthyridine-3-carboxylic acid hydrochloride (4.3)

4.2 (30 mg, 0.07 mmol, 1 eq) was added to methanol (10 mL) and stirred for 10 minutes. Then 4M HCl in dioxane (33 μL, 0.13 mmol, 2 eq) was added dropwise and the flask sealed and stirred for 1 hour. The mixture was then washed with hexane (3×30 mL), concentrated in vacuo and lyophilised for 24 hours to afford compound 4.3 (18.64 mg, 86.4% yield) as a pale brown solid.

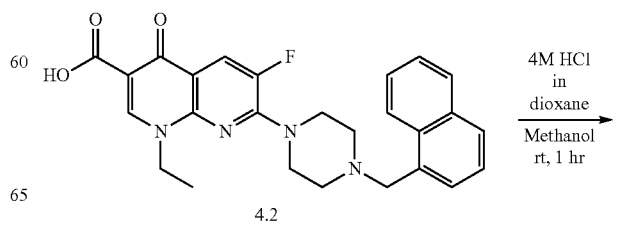

-continued

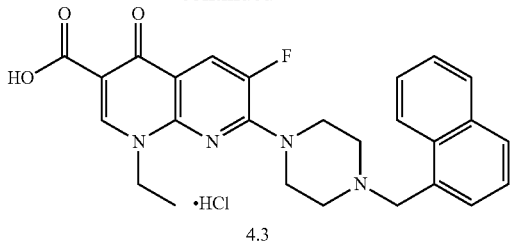

4.3

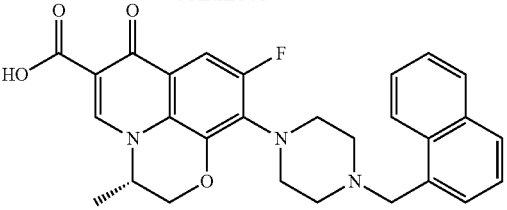

5.2

$^1$H NMR (400 MHz, DMSO-d$_6$) δ 15.21 (br. s., 1H), 11.07 (br. s., 1H), 9.03 (s, 1H), 8.41 (d, J=8.31 Hz, 1H), 8.21 (d, J=12.84 Hz, 1H), 8.08 (d, J=8.56 Hz, 1H), 8.04 (d, J=80.6 Hz, 1H), 7.97 (d, J=7.30 Hz, 1H), 7.59-7.69 (m, 3H), 4.87 (br. s., 2H), 4.58 (d, J=12.84 Hz, 2H), 4.51 (q, J=6.88 Hz, 2H), 3.66 (t, J=12.09 Hz, 2H), 3.47 (br. s., 4H), 1.37 (t, J=7.05 Hz, 3H); IR (υ$_{max}$/cm$^{-1}$) 3388, 1715, 1628, 1457, 1396, 1340, 1265, 1042, 943, 804; LC-MS Retention time 5.85 minutes, found 461.1 [M+H]$^+$; calculated for C$_{26}$H$_{25}$FN$_4$O$_3$ 461.51 [M+H]$^+$; HRMS Observed 461.1974 [M+H]$^+$; theoretical value 461.1983 [M+H]$^+$.

Synthesis of Levofloxacin-ARB Hybrid Compounds

Synthesis of (S)-9-fluoro-3-methyl-10-(4-(naphthalen-1-ylmethyl)piperazin-1-yl)-7-oxo-2,3-dihydro-7H-[1,4]oxazino[2,3,4-ij]quinoline-6-carboxylic acid (5.2)

(S)-9,10-difluoro-3-methyl-7-oxo-2,3-dihydro-7H-[1,4]oxazino[2,3,4-ij]quinolone carboxylic acid (A1.4, 5.1; 100 mg, 0.36 mmol, 1 eq) and 1-(naphthalen-1-ylmethyl)piperazine (322 mg, 1.42 mmol, 4 eq) were added to DMSO (5 mL) and stirred until full dissolution of both compounds was achieved. The reaction was subsequently heated to 100° C. for 1 hour, then 140° C. for another hour. The mixture was allowed to cool, then extracted with dichloromethane (2×20 mL). Combined organic fractions were washed with distilled water (3×100 mL), dried over MgSO$_4$, filtered and concentrated in vacuo to remove any residual DMSO. The crude solid was purified via trituration; the crude was washed with methanol (5×10 mL), then the remaining powder collected and re-filtered using dichloromethane. This second filtrate was concentrated in vacuo to afford compound 5.2 (75 mg, 43.3% yield) as a pale yellow solid.

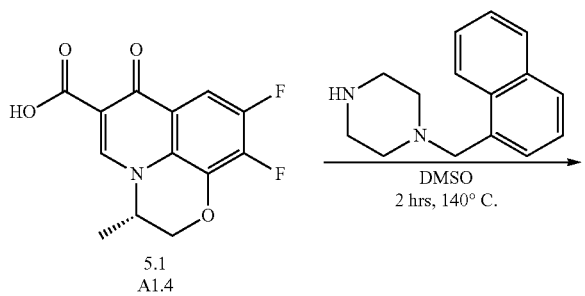

5.1
A1.4

$^1$H NMR (400 MHz, CDCl$_3$) δ 14.73 (s, 1H), 13.16 (br. s., 1H), 8.62 (s, 1H), 8.20 (d, J=6.55 Hz, 1H), 8.16 (d, J=80.6 Hz, 1H), 8.01 (d, J=8.06 Hz, 1H), 7.97 (d, J=8.06 Hz, 1H), 7.57-7.74 (m, 4H), 4.79 (br. s., 2H), 4.48-4.53 (m, 1H), 4.45 (d, J=11.83 Hz, 1H), 4.33 (d, J=12.59 Hz, 1H), 4.17-4.29 (m, 2H), 3.49 (br. S., 2H), 3.41 (d, J=12.84 Hz, 2H), 3.10 (br. s., 2H), 1.59 (d, J=6.55 Hz, 3H); $^{19}$F NMR (400 MHz, CDCl$_3$) δ −106.9, −119.5; LC-MS Retention time 3.00 minutes, found 488.1 [M+H]$^+$; calculated for C$_{28}$H$_{26}$FN$_3$O$_4$ 488.53 [M+H]$^+$.

Synthesis of (S)-9-fluoro-3-methyl-10-(4-(naphthalen-1-ylmethyl)piperazin-1-yl)-7-oxo-2,3-dihydro-7H-[1,4]oxazino[2,3,4-ij]quinoline-6-carboxylic acid hydrochloride (5.3)

5.2 (20 mg, 0.04 mmol, 1 eq) was added to dichloromethane (2 mL) and stirred for 10 minutes. Then 4M HCl in dioxane (205 μL, 0.82 mmol, 20 eq) was added dropwise and the flask sealed and stirred for 1 hour. The mixture was then washed with hexane (3×30 mL), concentrated in vacuo and lyophilised for 24 hours to afford compound 5.3 (18 mg, 83.7% yield) as a yellow solid.

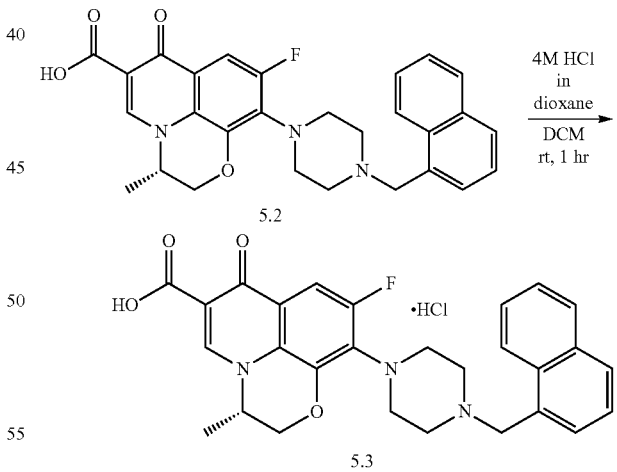

$^1$H NMR (400 MHz, DMSO-d$_6$) δ 10.92 (br. s., 1H), 9.00 (s, 1H), 8.50 (d, J=8.31 Hz, 1H), 8.08 (d, J=8.31 Hz, 1H), 8.04 (dd, J=4.66, 7.43 Hz, 2H), 7.66-7.71 (m, 1H), 7.59-7.66 (m, 3H), 4.90-4.97 (m, 3H), 4.56-4.61 (m, 1H), 4.36-4.41 (m, 1H), 3.63-3.74 (m, 2H), 3.49-3.57 (m, 2H), 3.41 (br. s., 4H), 1.44 (d, J=6.55 Hz, 3H); $^{19}$F NMR (400 MHz, CDCl$_3$) δ −106.9, −120.5; LC-MS Retention time 5.92 minutes, found 488.1 [M+H]$^+$; calculated for C$_{28}$H$_{26}$FN$_3$O$_4$ 488.53 [M+H]$^+$.

Synthesis of (S)-9-fluoro-10-(4-(2-isopropyl-6-methylpyrimidin-4-yl)piperazin-1-yl)-3-methyl-7-oxo-2,3-dihydro-7H-[1,4]oxazino[2,3,4-ij]quinoline-6-carboxylic acid (5.4)

(S)-9,10-difluoro-3-methyl-7-oxo-2,3-dihydro-7H-[1,4]oxazino[2,3,4-ij]quinolone-6-carboxylic acid (A1.4, 5.1; 128 mg, 0.45 mmol, 1 eq) and 2-isopropyl-4-methyl-6-(piperazin-1-yl)pyrimidine (100 mg, 0.45 mmol, 1 eq) were added to DMF (3 mL) and stirred at 140° C. for 1.5 hours. The mixture was allowed to cool and the crude concentrated in vacuo, then re-suspended in 3:1 distilled water:MeOH (20 mL) and filtered hot. Purification was achieved via automated flash column chromatography of the crude solid (see Flash Column Chromatography method); 0%-50%-100% DCM/Acetone) to afford compound 5.4 (22 mg, 10.0%) as a pale yellow solid.

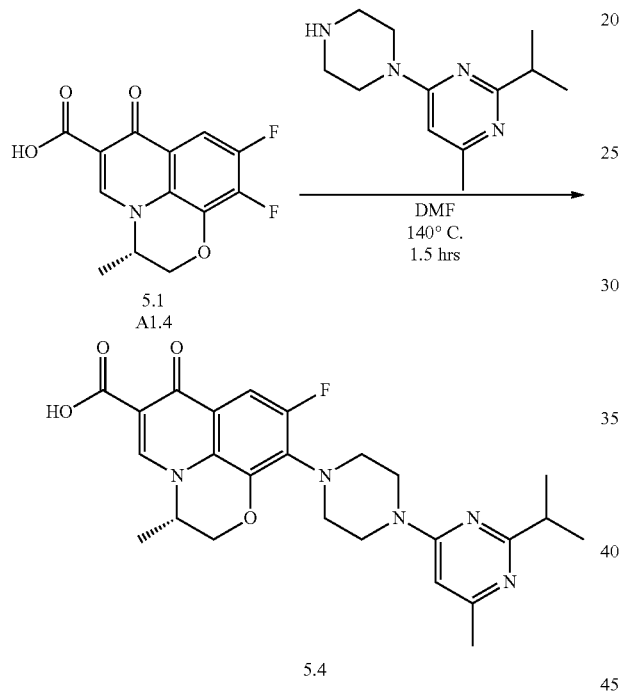

$^1$H NMR (400 MHz, CDCl$_3$) δ 14.92 (br. s., 1H), 8.64 (s, 1H), 7.76 (d, J=12.09 Hz, 1H), 6.26 (s, 1H), 4.53 (d, J=5.54 Hz, 1H), 4.49 (d, J=11.33 Hz, 1H), 4.36-4.43 (m, 1H), 3.85 (br. s., 4H), 3.45 (td, J=5.07, 9.76 Hz, 4H), 3.04-3.13 (m, 1H), 2.41 (s, 3H), 1.64 (d, J=6.55 Hz, 3H), 1.29 (d, J=7.05 Hz, 6H); $^{19}$F NMR (400 MHz, CDCl$_3$) δ –106.9, –119.2; LC-MS Retention time 3.07 minutes, found 482.0 [M+H]$^+$; calculated for C$_{25}$H$_{28}$FN$_5$O$_4$ 482.53 [M+H]$^+$.

Synthesis of (S)-9-fluoro-10-(4-(2-isopropyl-6-methylpyrimidin-4-yl)piperazin-1-yl)-3-methyl-7-oxo-2,3-dihydro-7H-[1,4]oxazino[2,3,4-ij]quinoline carboxylic acid hydrochloride (5.5)

5.4 (22 mg, 0.05 mmol, 1 eq) was added to dichloromethane (2 mL) and stirred for 2 minutes. Then 4M HCl in dioxane (228 µL, 0.91 mmol, 20 eq) was added dropwise and the flask sealed and stirred for 15.5 hours. The mixture was then washed with hexane (3×10 mL), concentrated in vacuo and lyophilised for 24 hours to afford compound 5.5 as a pale yellow solid.

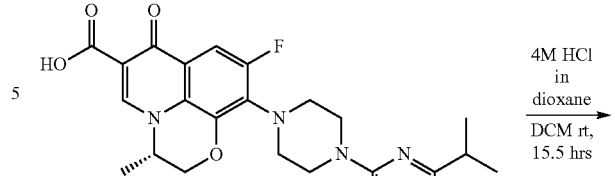

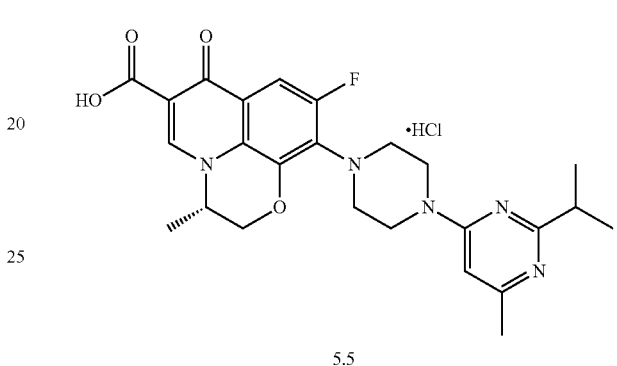

LC-MS Retention time 5.92 minutes, found 482.1 [M+H]$^+$; calculated for C$_{23}$H$_{28}$FN$_3$O$_4$ 482.53 [M+H]$^+$.

Synthesis of (S)-9-fluoro-3-methyl-7-oxo-10-(4-(pyrimidin-4-yl)piperazin-1-yl)-2,3-dihydro-7H-[1,4]oxazino[2,3,4-ij]quinoline-6-carboxylic acid (5.6)

(S)-9,10-difluoro-3-methyl-7-oxo-2,3-dihydro-7H-[1,4]oxazino[2,3,4-ij]quinolone-6-carboxylic acid (A1.4, 5.1; 1.37 g, 4.87 mmol, 1 eq) and 4-(piperazin-1-yl)pyrimidine (1 g, 6.09 mmol, 1.25 eq) were added to DMF (20 mL) and stirred at 140° C. for 90 hours. The mixture was allowed to cool, then DMF removed using a 10 g SCX-2 catch and release cartridge (see Solid Phase Extraction method) followed by extraction with dichloromethane (2×50 mL, washed with 100 mL distilled water, 100 mL brine). Purification was achieved via flash column chromatography (gradient elution; 0-100% DCM/acetonitrile, then 1% water in acetonitrile, then 100% NH$_3$ in MeOH) to afford compound 5.6 (234.4 mg, 11.3% yield) as a pale yellow solid.

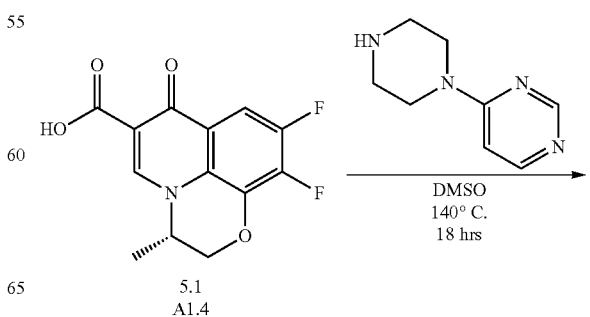

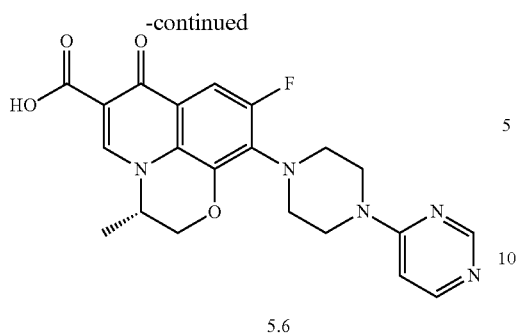

5.6

LC-MS Retention time 2.72 minutes, found 425.9 [M+H]⁺; calculated for $C_{21}H_{20}FN_5O_4$ 426.42 [M+H]⁺.

Synthesis of (S)-9-fluoro-3-methyl-7-oxo-10-(4-(pyrimidin-4-yl)piperazin-1-yl)-2,3-dihydro-7H-[1,4]oxazino[2,3,4-ij]quinoline-6-carboxylic acid hydrochloride (5.7)

5.6 (5.07 mg, 0.01 mmol, 1 eq) was added to dichloromethane (1 mL) and stirred for 2 minutes. Then 4M HCl in dioxane (60 μL, 0.24 mmol, 20 eq) was added dropwise and the flask sealed and stirred for 1 hour. The mixture was then washed with hexane (3×10 mL), concentrated in vacuo and lyophilised for 24 hours to afford compound 5.7 as a pale yellow solid.

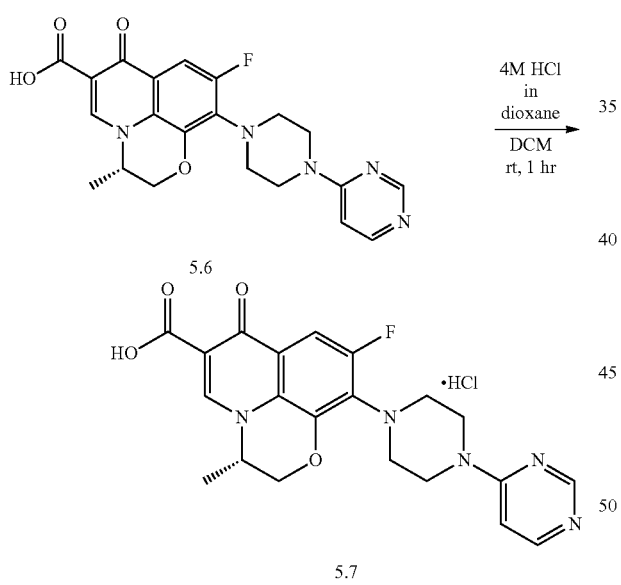

5.6

5.7

LC-MS Retention time 5.25 minutes, found 426.0 [M+H]⁺; calculated for $C_{21}H_{20}FN_5O_4$ 426.42 [M+H]⁺.

Synthesis of (S)-9-fluoro-3-methyl-7-oxo-w-(4-(pyridin-2-yl)piperazin-1-yl)-2,3-dihydro-7H-[1,4]oxazino[2,3,4-ij]quinoline-6-carboxylic acid (5.8)

(S)-9,10-difluoro-3-methyl-7-oxo-2,3-dihydro-7H-[1,4]oxazino[2,3,4-ij]quinolone-6-carboxylic acid (A1.4, 5.1; 100 mg, 0.36 mmol, 1 eq) and 1-(pyridin-2-yl)piperazine (108 μL, 0.71 mmol, 2 eq) were added to DMSO (3 mL) and stirred at 140° C. for 2 hours. The mixture was allowed to cool, then DMSO removed using a 1 g SCX-2 catch and release cartridge (see Solid Phase Extraction method). Trace solvent was subsequently removed by extraction with dichloromethane (20 mL) and washing with saturated brine (3×100 mL). Combined organic fractions were dried over $MgSO_4$, filtered and concentrated in vacuo. Purification was achieved via automated flash column chromatography (see Flash Column Chromatography method; 0%-5%-10%-20%-50% DCM/Acetone) to afford compound 5.8 (69.19 mg, 45.8% yield) as a yellow solid.

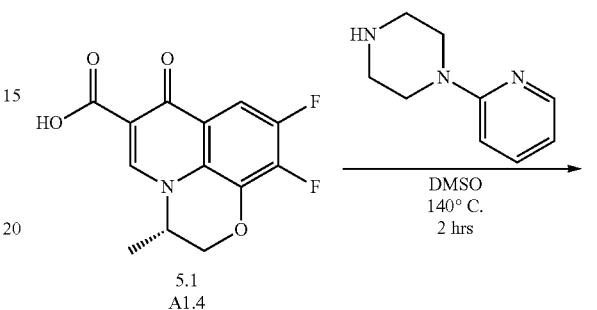

5.1
A1.4

5.8

¹H NMR (400 MHz, CDCl₃) δ 14.99 (s, 1H), 8.64 (s, 1H), 8.23 (dd, J=1.64, 4.91 Hz, 1H), 7.74 (d, J=12.09 Hz, 1H), 7.52-7.58 (m, 1H), 6.73 (d, J=8.81 Hz, 1H), 6.69 (dd, J=50.04, 6.80 Hz, 1H), 4.51-4.57 (m, 1H), 4.48 (dd, J=2.14, 11.46 Hz, 1H), 4.39 (dd, J=2.39, 11.46 Hz, 1H), 3.72 (br. s., 4H), 3.43-3.56 (m, 4H), 1.64 (d, J=6.80 Hz, 3H); ¹⁹F NMR (400 MHz, CDCl₃) δ −107.0, −134.8; LC-MS Retention time 5.43 minutes, found 425.0 [M+H]⁺; calculated for $C_{22}H_{21}FN_4O_4$ 425.43 [M+H]⁺.

Synthesis of (S)-9-fluoro-3-methyl-7-oxo-10-(4-(pyridin-2-yl)piperazin-1-yl)-2,3-dihydro-7H-[1,4]oxazino[2,3,4-ij]quinoline-6-carboxylic acid hydrochloride (5.9)

5.8 (20.27 mg, 0.05 mmol, 1 eq) was added to dichloromethane (2 mL) and stirred for 2 minutes. Then 4M HCl in dioxane (239 μL, 0.96 mmol, 20 eq) was added dropwise and the flask sealed and stirred for 1.5 hours. The mixture was then washed with hexane (3×10 mL), concentrated in vacuo and lyophilised for 24 hours to afford compound 5.9 as a pale yellow solid.

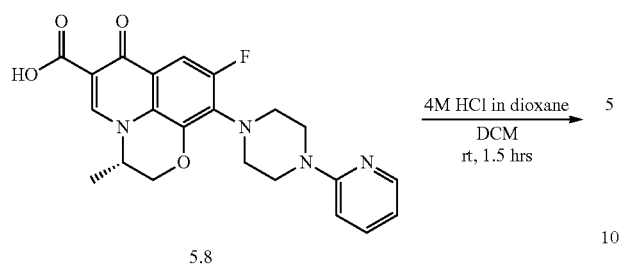

5.8

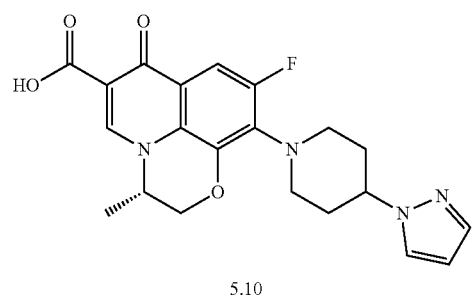

5.10

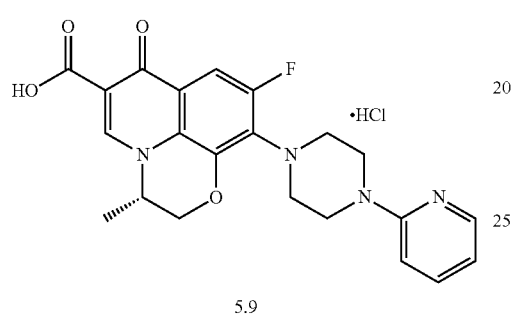

5.9

LC-MS Retention time 50.33 minutes, found 425.0 [M+H]$^+$; calculated for $C_{22}H_{21}FN_4O_4$ 425.43 [M+H]$^+$.

Synthesis of (S)-10-(4-(1H-pyrazol-1-yl)piperidin-1-yl)-9-fluoro-3-methyl-7-oxo-2,3-dihydro-7H-[1,4]oxazino[2,3,4-ij]quinoline-6-carboxylic acid (5.10)

(S)-9,10-difluoro-3-methyl-7-oxo-2,3-dihydro-7H-[1,4]oxazino[2,3,4-ij]quinolone-6-carboxylic acid (A1.4, 5.1; 100 mg, 0.36 mmol, 1 eq) and 4-(1H-pyrazol-1-yl)piperidine (108 mg, 0.71 mmol, 2 eq) were added to DMF (3 mL) and stirred at 140° C. for 95 hours. The mixture was allowed to cool, then concentrated in vacuo. The crude was then dissolved in minimal 1:1 DCM/methanol (3 mL) and added dropwise to 200 mL of ice water. Following stirring for 10 minutes, the brown bottom layer was pipetted out and concentrated in vacuo. Purification was achieved via automated flash column chromatography (see Flash Column Chromatography method; 0%-100% DCM/acetone) to afford 5.10.

| 5.10 White solid | $^1$H NMR | $^1$H NMR (400 MHz, CDCl$_3$) δ 15.01 (s, 1H), 8.64 (s, 1H), 7.73 (d, J = 12.09 Hz, 1H), 7.54-7.57 (m, 1H), 7.51 (d, J = 2.27 Hz, 1H), 6.30 (t, J = 1.76 Hz, 1H), 4.51-4.58 (m, 1H), 4.46-4.51 (m, 1H), 4.39 (dd, J = 2.27, 11.58 Hz, 1H), 4.31-4.37 (m, 1H), 3.61 (d, J = 13.35 Hz, 2H), 3.32-3.47 (m, 2H), 2.16-2.29 (m, 4H), 1.63 (d, J = 6.80 Hz, 3H) |
|---|---|---|
| | $^{19}$F NMR | $^{19}$F NMR (400 MHz, CDCl$_3$) δ −119.1 |
| | LC-MS | Retention time 3.53 minutes Found 413.0 [M + H]$^+$; calculated for $C_{21}H_{21}FN_4O_4$ 413.42 [M + H]$^+$ |

Synthesis of (S)-10-(4-(1H-pyrazol-1-yl)piperidin-1-yl)-9-fluoro-3-methyl-7-oxo-2,3-dihydro-7H-[1,4]oxazino[2,3,4-ij]quinoline-6-carboxylic acid hydrochloride (5.11)

5.10 (13.30 mg, 0.03 mmol, 1 eq) was added to dichloromethane (3 mL) and stirred for 2 minutes. Then 4M HCl in dioxane (161 μL, 0.64 mmol, 20 eq) was added dropwise and the flask sealed and stirred for 1 hour. The mixture was then washed with hexane (3×20 mL), concentrated in vacuo and lyophilised for 24 hours to afford 5.11.

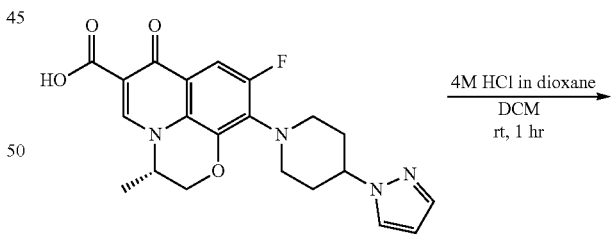

5.10

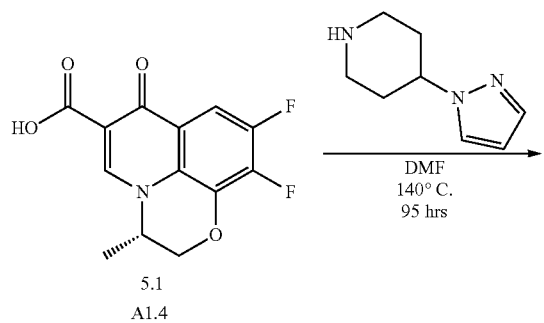

5.1
A1.4

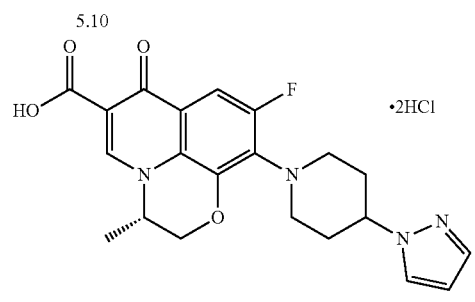

5.11

| 5.11 | LC-MS | Retention time 7.11 minutes |
| --- | --- | --- |
| White solid | | Found 413.2 [M + H]$^+$; calculated for C$_{21}$H$_{21}$FN$_4$O$_4$ 413.42 [M + H]$^+$ |

Synthesis of (S)-9-fluoro-3-methyl-7-oxo-10-(piperazin-1-yl)-2,3-dihydro-7H-[1,4]oxazino[2,3,4-ij]quinoline-6-carboxylic acid (5.12)

(S)-9,10-difluoro-3-methyl-7-oxo-2,3-dihydro-7H-[1,4]oxazino[2,3,4-ij]quinolone-6-carboxylic acid (A1.4, 5.1; 1 g, 3.56 mmol, 1 eq) and piperazine (613 mg, 7.11 mmol, 2 eq) were added to DMSO (5 mL) and stirred at 125° C. for 16 hours. The mixture was allowed to cool, then ice cold acetone (50 mL) was added. The resulting brown precipitate was filtered and triturated with further cold acetone (5×10 mL), air dried for 30 minutes then dried under vacuum for a further 1 hour. This cycle of trituration and drying was then repeated once more to afford 5.12.

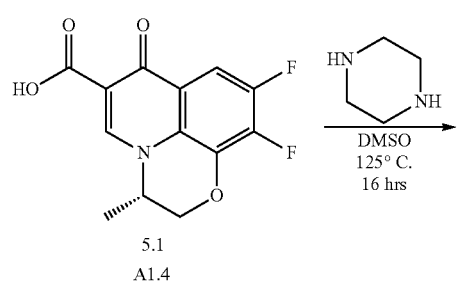

| 5.12 | LC-MS | Retention time 1.86 minutes |
| --- | --- | --- |
| Light brown solid | | Found 348.1 [M + H]$^+$; calculated for C$_{17}$H$_{18}$FN$_3$O$_4$ 348.35 [M + H]$^+$ |
| | Yield | 931.63 mg (75.4 % yield) |

Synthesis of (S)-9-fluoro-3-methyl-7-oxo-10-(piperazin-1-yl)-2,3-dihydro-7H-[1,4]oxazino[2,3,4-ij]quinoline-6-carboxylic acid hydrochloride (5.13)

5.12 (147.42 mg, 0.42 mmol, 1 eq) was added to dichloromethane (5 mL) and stirred for 2 minutes. Then 4M HCl in dioxane (2.12 mL, 8.49 mmol, 20 eq) was added dropwise and the flask sealed and stirred for 1 hour. The mixture was then washed with hexane (3×30 mL), concentrated in vacuo and lyophilised for 24 hours to afford 5.13.

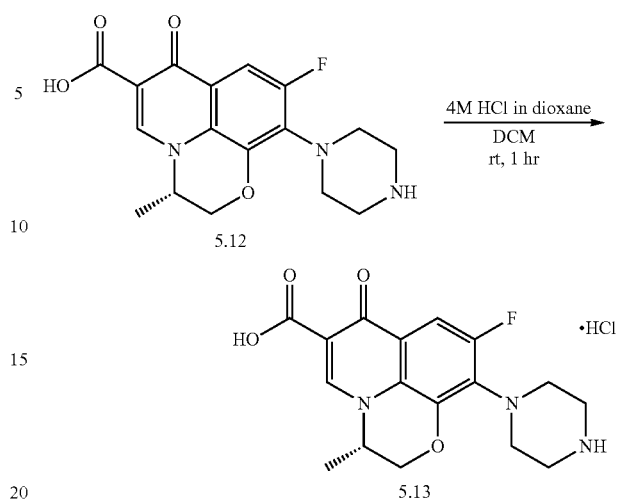

| 5.13 | LC-MS | Retention time 3.14 minutes |
| --- | --- | --- |
| solid White | | Found 348.1 [M + H]$^+$; calculated for C$_{17}$H$_{18}$FN$_3$O$_4$ 348.35 [M + H]$^+$ |

Synthesis of (3S)-9-fluoro-3-methyl-7-oxo-10-(3-(pyrimidin-2-ylamino)-pyrrolidin-1-yl)-2,3-dihydro-7H-[1,4]oxazino[2,3,4-ij]quinoline-6-carboxylic acid (5.14)

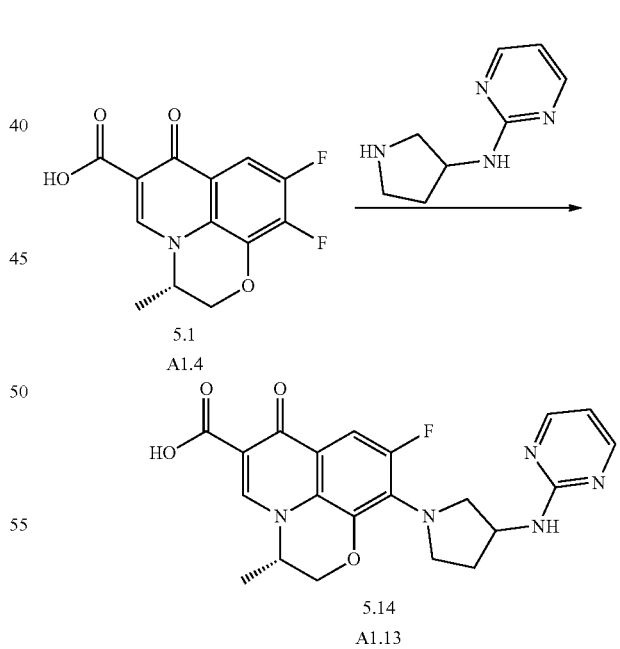

| 5.14 | LC-MS | Retention time 3.28 minutes |
| --- | --- | --- |
| White solid | | Found 426.2 [M + H]$^+$; calculated for C$_{21}$H$_{20}$FN$_5$O$_4$ 426.42 [M + H]$^+$ |

Synthesis of (3S)-9-fluoro-3-methyl-7-oxo-10-(3-(pyrimidin-2-ylamino)-pyrrolidin-1-yl)-2,3-dihydro-7H-[1,4]oxazino[2,3,4-ij]quinoline-6-carboxylic acid hydrochloride (5.15)

5.14 (6.81 mg, 0.02 mmol 1 eq) was added to dichloromethane (1 mL) and methanol (1 mL) and stirred for 2 minutes. Then 4M HCl in dioxane (80 µL, 0.32 mmol, 20 eq) was added dropwise and the flask sealed and stirred for 1 hour. The mixture was then washed with hexane (3×10 mL), concentrated in vacuo and lyophilised for 24 hours to afford 5.15.

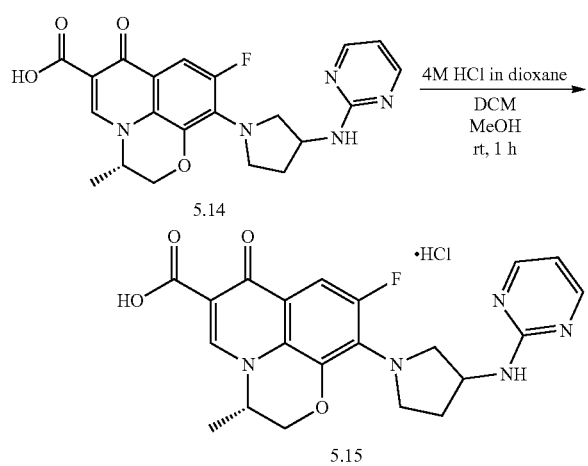

| 5.15 | LC-MS | Retention time 6.32 minutes |
| White solid | | Found 426.2 [M + H]$^+$; calculated for $C_{21}H_{20}FN_5O_4$ 426.42 [M + H]$^+$ |

Synthesis of (S)-9-fluoro-3-methyl-7-oxo-10-(4-(pyrazin-2-yl)-1,4-diazepan-1-yl)-2,3-dihydro-7H-[1,4]oxazino[2,3,4-ij]quinoline-6-carboxylic acid (5.16)

(S)-9,10-difluoro-3-methyl-7-oxo-2,3-dihydro-7H-[1,4]oxazino[2,3,4-ij]quinolone carboxylic acid (5.1; 80 mg, 0.284 mmol, 1 eq) and 1-(pyrazin-2-yl)-1,4-diazepane (101.41 mg, 0.568 mmol, 2 eq) were added to DMSO (3 mL) and stirred at 140° C. for 18 hours. The mixture was allowed to cool, then added dropwise to ice cold water. The resulting precipitate was filtered and dried in vacuo to produce pure 5.16.

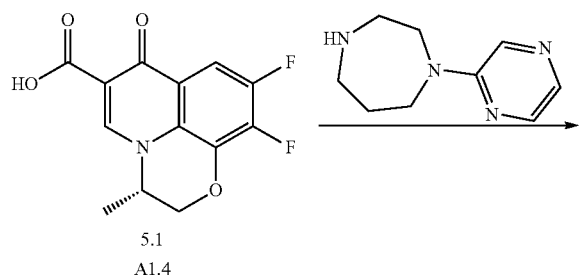

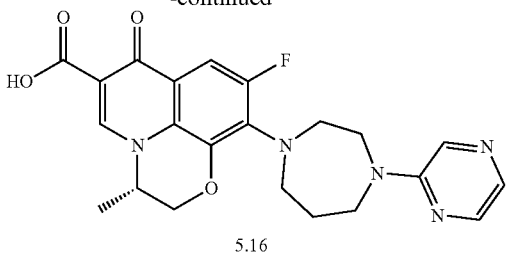

| 5-16 | LC-MS | Retention time 3.57 minutes |
| White solid | | Found 440.2 [M + H]$^+$; calculated for $C_{22}H_{22}FN_5O_4$ 440.45 [M + H]$^+$ |
| | Yield | 84 mg (68%) |

Synthesis of (S)-9-fluoro-3-methyl-7-oxo-10-(4-(pyrazin-2-yl)-1,4-diazepan-1-yl)-2,3-dihydro-7H-[1,4]oxazino[2,3,4-ij]quinoline-6-carboxylic acid hydrochloride (5.17)

5.16 (20.29 mg, 0.05 mmol, 1 eq) was added to dichloromethane (2 mL) and methanol (2 mL) and stirred for 2 minutes. Then 4M HCl in dioxane (231 µL, 0.92 mmol, 20 eq) was added dropwise and the flask sealed and stirred for 1 hour. The mixture was then washed with hexane (3×10 mL), concentrated in vacuo and lyophilised for 24 hours to afford 5.17.

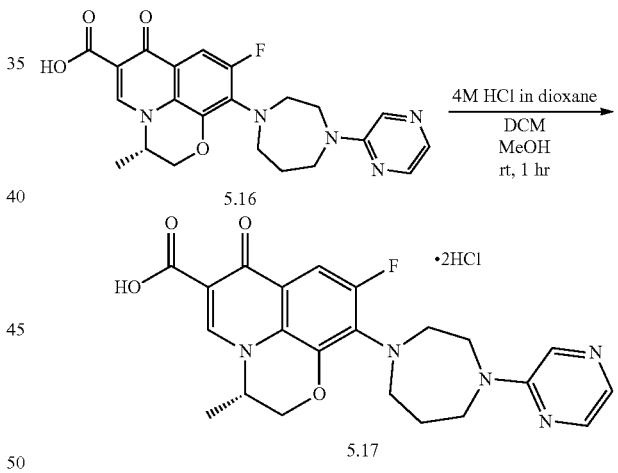

| 5-17 | LC-MS | Retention time 7.00 minutes |
| White solid | | Found 440.2 [M + H]$^+$; calculated for $C_{22}H_{22}FN_5O_4$ 440.45 [M + H]$^+$ |

Synthesis of Moxifloxacin-ARB Hybrid Compounds

Synthesis of 1-cyclopropyl-6-fluoro-8-methoxy-7-((4aS-7aS)-1-(naphthalen-1-ylmethyl)octahydro-6H-pyrrolo[3,4-b]pyridine-6-yl)-4-oxo-1,4-dihydroquinoline-3-carboxylic acid (6.2)

Moxifloxacin hydrochloride (6.1; 100 mg, 0.23 mmol, 1 eq) was added to a 1:1 mix of acetonitrile and distilled water (10 mL total). After stirring for 5 minutes, potassium carbonate (95 mg, 0.69 mmol, 3 eq) was added and the mixture stirred for a further 5 minutes. Once fully dissolved, 1-(bromomethyl)naphthalene (48 mg, 0.22 mmol, 0.95 eq) was added slowly over the course of 1 hour and the mixture subsequently stirred for 24 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the crude product. Purification was achieved using an SCX-2 catch and release cartridge (see Solid Phase Extraction method) to afford 6.2.

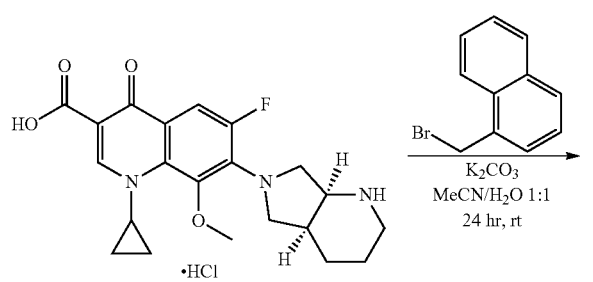

6.1

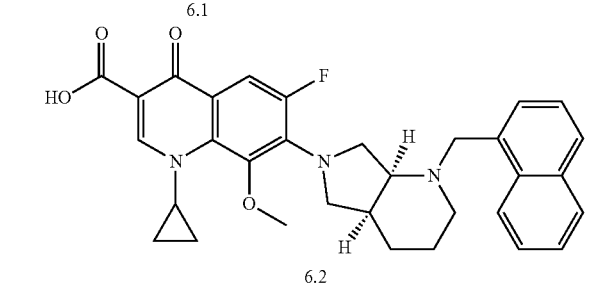

6.2

| 6.2 Pale yellow solid | LC-MS | Retention time 3.23 minutes Found 542.1 [M + H]$^+$; calculated for C$_{32}$H$_{32}$FN$_3$O$_4$ 542.62 [M + H]$^+$ |
| --- | --- | --- |
| | Yield | 104.65 mg (84.6 % yield) |

Synthesis of 1-cyclopropyl-6-fluoro-8-methoxy-7-((4aS,7aS)-1-(naphthalen-1-ylmethyl)octahydro-6H-pyrrolo[3,4-b]pyridine-6-yl)-4-oxo-1,4-dihydroquinoline-3-carboxylic acid hydrochloride (6.3)

6.2 (30.65 mg, 0.06 mmol, 1 eq) was added to methanol (25 mL) and stirred for 10 minutes. Then 4M HCl in dioxane (28 µL, 0.11 mmol, 2 eq) was added dropwise and the flask sealed and stirred for 6 hours. The mixture was then washed with hexane (3×30 mL), concentrated in vacuo and lyophilised for 24 hours to afford 6.3.

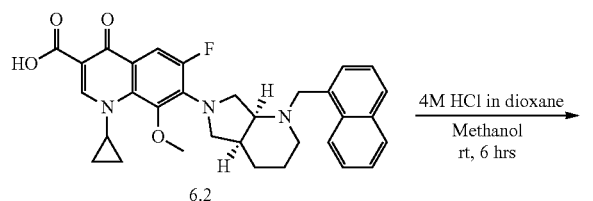

6.2

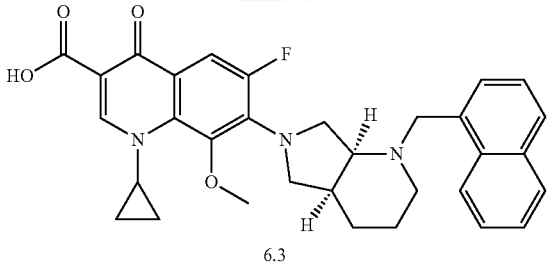

6.3

| 6.3 Yellow solid | LC-MS | Retention time 6.30 minutes Found 542.1 [M + H]$^+$; calculated for C$_{32}$H$_{32}$FN$_3$O$_4$ 542.62 [M + H]$^+$ |
| --- | --- | --- |
| | Yield | 18.30 mg (57.2 % yield) |

Synthesis of 7-((4aS,7aS)-1-benzyloctahydro-6H-pyrrolo[3,4-b]pyridin-6-yl)-1-cyclopropyl-6-fluoro-8-methoxy-4-oxo-1,4-dihydroquinoline-3-carboxylic acid (6.4)

Moxifloxacin hydrochloride (6.1; 80 mg, 0.199 mmol, 1 eq) was added to a 1:1 mix of acetonitrile and distilled water (5 mL total). After stirring for 5 minutes, potassium carbonate (82.63 mg, 0.58 mmol, 3 eq) was added and the mixture stirred for a further 5 minutes. Once fully dissolved, bromomethylbenzene (30.68 mg, ° AB mmol, 0.90 eq) was added slowly over the course of 1 hour and the mixture subsequently stirred for 18 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the pure product 6.4.

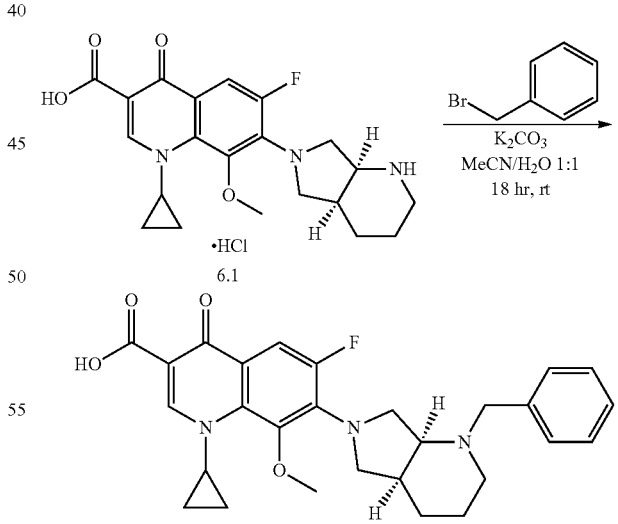

6.1

6.4

| 6.4 Brown solid | LC-MS | Retention time 2.90 minutes Found 492.0 [M + H]$^+$; calculated for C$_{32}$H$_{32}$FN$_3$O$_4$ 492.56 [M + H]$^+$ |
| --- | --- | --- |

Synthesis of 1-cyclopropyl-6-fluoro-7-((4aS-7aS)-1-(4-(hydroxymethyl)benzyl)octahydro-6H-pyrrolo[3,4-b]pyridin-6-yl)-8-methoxy-4-oxo-1,4-dihydroquinoline-3-carboxylic acid (6.6)

Moxifloxacin hydrochloride (6.1; 80 mg, 0.199 mmol, 1 eq) was added to a 1:1 mix of acetonitrile and distilled water (5 mL total). After stirring for 5 minutes, potassium carbonate (82.63 mg, 0.58 mmol, 3 eq) was added and the mixture stirred for a further 5 minutes. Once fully dissolved, ((4-(bromomethyl)phenyl)methanol (36.06 mg, 0.18 mmol, 0.90 eq) was added slowly over the course of 1 hour and the mixture subsequently stirred for 18 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the pure product 6.6.

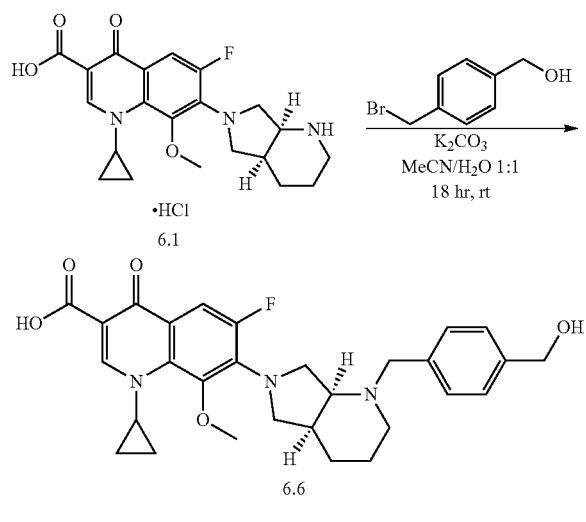

| 6.6 | LC-MS | Retention time 2.85 minutes |
| --- | --- | --- |
| Brown solid | | Found 522.1 [M + H]$^+$; calculated for C$_{32}$H$_{32}$FN$_3$O$_4$ 522.59 [M + H]$^+$ |

Synthesis of 1-cyclopropyl-6-fluoro-8-methoxy-4-oxo-7-((4aS,7aS)-1-(4-(pyrrolidin-1-yl)benzyl)octahydro-6H-pyrrolo[3,4-b]pyridin-6-yl)-1,4-dihydroquinoline-3-carboxylic acid (6.8)

Moxifloxacin hydrochloride (6.1; 80 mg, 0.199 mmol, 1 eq) was added to a 1:1 mix of acetonitrile and distilled water (5 mL total). After stirring for 5 minutes, potassium carbonate (82.63 mg, 0.58 mmol, 3 eq) was added and the mixture stirred for a further 5 minutes. Once fully dissolved, 1-(4-(bromomethyl)phenyl)pyrrolidine (43 mg, 0.18 mmol, 0.90 eq) was added slowly over the course of 1 hour and the mixture subsequently stirred for 18 hours. Upon completion, the product was extracted with dichloromethane (2×20 mL) using a 1M solution of citric acid to neutralise the aqueous phase. Combined organic fractions were washed with distilled water (20 mL) and dried over MgSO$_4$, filtered and concentrated in vacuo to give the pure product 6.8.

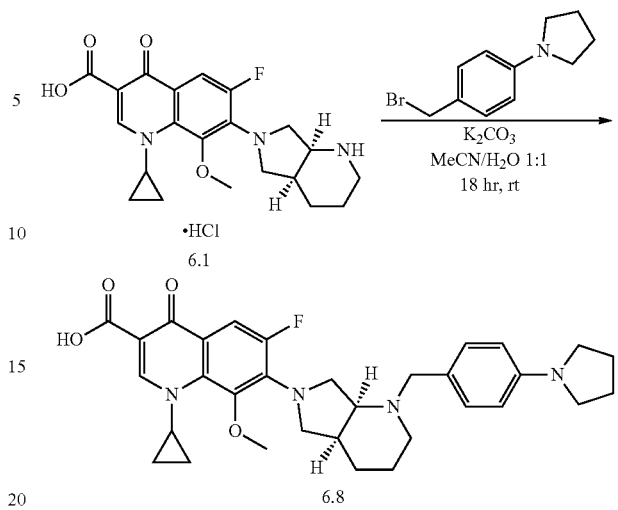

| 6.8 | LC-MS | Retention time 6.30 minutes |
| --- | --- | --- |
| Yellow solid | | Found 558.0 [M − H]$^+$; calculated for C$_{32}$H$_{32}$FN$_3$O$_4$ 559.67 [M − H]$^+$ |

Biological Testing

Minimum Inhibitory Concentration Protocol

Minimal inhibitory concentrations (MICs) were determined using the microdilution broth method. Briefly, compounds were added to the first two columns of a 96-well plate and diluted two-fold down the plate in tryptic soy broth (TSB). Overnight cultures of bacteria were then adjusted to an optical density (OD) of 0.01 in TSB, which is equivalent to 1×10$^6$ CFU/mL, and added to each well. Untreated controls and blank wells were included. Compounds were initially dissolved in DMSO prior to dilution in water and in broth. Equivalent concentrations of solvent had no effect on bacterial growth. The MIC was defined as the lowest concentration of compound which resulted in no visible growth at an optical density of 600 nm after 20 hours incubation at 37° C.

Reserpine Assay

A simple plate based method was used as described by Beyer et al. (24). The compound was added at a final concentration of 0.25×MIC (made up at 1×MIC in water, 50 μL/well). Reserpine was added at a final concentration of 10 μg/mL (made up at 40 μg/mL in TSB, 50 μL per well). The bacteria were added at an OD of 0.01 in TSB (100 μL/well). The plate was a normal clear plate as used for MICs. OD was read every 30 minutes for 9 hours (the literature states 7 hours, but this is strain-dependent). Blanks of TSB and water were added to ensure no infections were present.

Galleria Assay

Wax moth larvae (*Galleria mellonella*) were purchased from Livefood UK Ltd (Rooks Bridge, Somerset, UK) and were maintained on wood chips in the dark at 15° C. until used. Bacteria from overnight cultures were adjusted to a known concentration in PBS and a Hamilton syringe was used to inject 10 μL aliquots of this suspension into *G. mellonella* larvae. Injections were performed into haemocoel of 10 larvae per bacterial strain via the foremost leg proleg. Control larvae were either injected with 10 μL PBS in order to measure any potential lethal effects of the injection process, or not injected to measure the effects of the incubation procedure. After injection, larvae were incubated statically at 37° C. inside petri dishes and the number of dead larvae was scored periodically. Larvae were considered dead when they displayed no movement in response to gentle prodding with a pipette tip. All experiments were carried out at least in triplicate. Data were analysed using the Mantel-Cox method using Prism Software Version 6 109 (Graphpad, San Diego, Calif., USA).

Computational Modelling

Homology Modelling

A 3D structure for the *Staphylococcus aureus* NorA efflux pump protein was generated by homology modelling through its corresponding amino acid sequence (FASTA format) through use of the I-TASSER web server. PDB crystal structure 3WDO was used as the template. A C-score (confidence score; an estimate of the quality of models predicted by I-TASSER) of 1.27 was obtained for the model generated. C-scores are typically in the range of −5 to 2, with higher C-scores indicating higher quality models. Compound structures were generated using Chem3D 15.0 software and minimised using both the AMBER 12 package program and SYBYL software.

Molecular Docking

Molecular docking protocols were used in order to predict compound binding sites and affinities. The relationship between the binding affinity of the compounds under study and the docking score was used for comparison of the binding energies and affinities of the ligands for NorA. Molecular docking was performed to generate several distinct binding orientations and binding affinities for each binding mode. Subsequently, the binding modes that showed the lowest binding free energy were considered as the most favorable binding mode for each compound.

In the first step, AutoDock SMINA was used for molecular docking of the compounds to the efflux pump structure for finding the best binding pocket by exploring all probable binding cavities in the proteins. All the parameters were set in their default values. Then GOLD molecular docking was applied for docking of the compounds into the SMINA-located best binding site for performing flexible molecular docking and determining more precise and evaluated energies and scores. Based on the fitness function scores and ligand binding position, the best-docked poses for each ligand were selected; the pose with the smallest fitness function score and highest GOLD fitness energy was considered the best-docked pose for each system.

Genetic algorithm (GA) is used in GOLD ligand docking to thoroughly examine the ligand conformational flexibility along with partial flexibility of the protein. The maximum number of runs was set to 20 for each compound and the default parameters were selected (100 population size, 5 for the number of islands, 100,000 number of operations and 2 for the niche size). Default cutoff values of 2.5 Å (dH-X) for hydrogen bonds and 4.0 Å for van-der-Waals distance were employed. When the top solutions attained the RMSD values within 1.5 A°, the GA docking was terminated.

Molecular Hydrophobicity Potential (MHP)

Molecular Hydrophobicity Potential (MHP) was performed for the compounds in free form and complex states with NorA by using the Protein-Ligand Attractions Investigation Numerically (PLATINUM) web server. Molecular Hydrophobicity Potential (MHP) parameters for rescoring results of GOLD were set as follows: dotdensity=High, MHPoffset=0.03, MHPshift-lig=0.5, MHPshift-rec=0.5. After docking and hydrophobic complementarity calculations, the part of ligand responsible for non-optimal hydrophobic or hydrophilic contact was investigated and the overall distribution of ligand hydrophobicity analysed. To this end, visualization of hydrophobic/hydrophilic properties and their complementarity between ligand and receptor molecules was performed by Jmol.

Modelling Experiment

Two example fragments, see ML-77-005 and ML-77-076 entries in Table 1, interact with the MFS-type pumps that operate in many clinical isolates of methicillin-resistant *Staphylococcus aureus* (MRSA), vancomycin-resistant enterococci (VRE), and a large number of pathogens that are resistant to ciprofloxacin (20,21). The resistance in MRSA and VRE is commonly mediated by up-regulation of the NorA efflux pump (22,23) and this also contributes to subsequent mutations giving high level resistance to ciprofloxacin (e.g. gyrA, parC).

Figure 2:
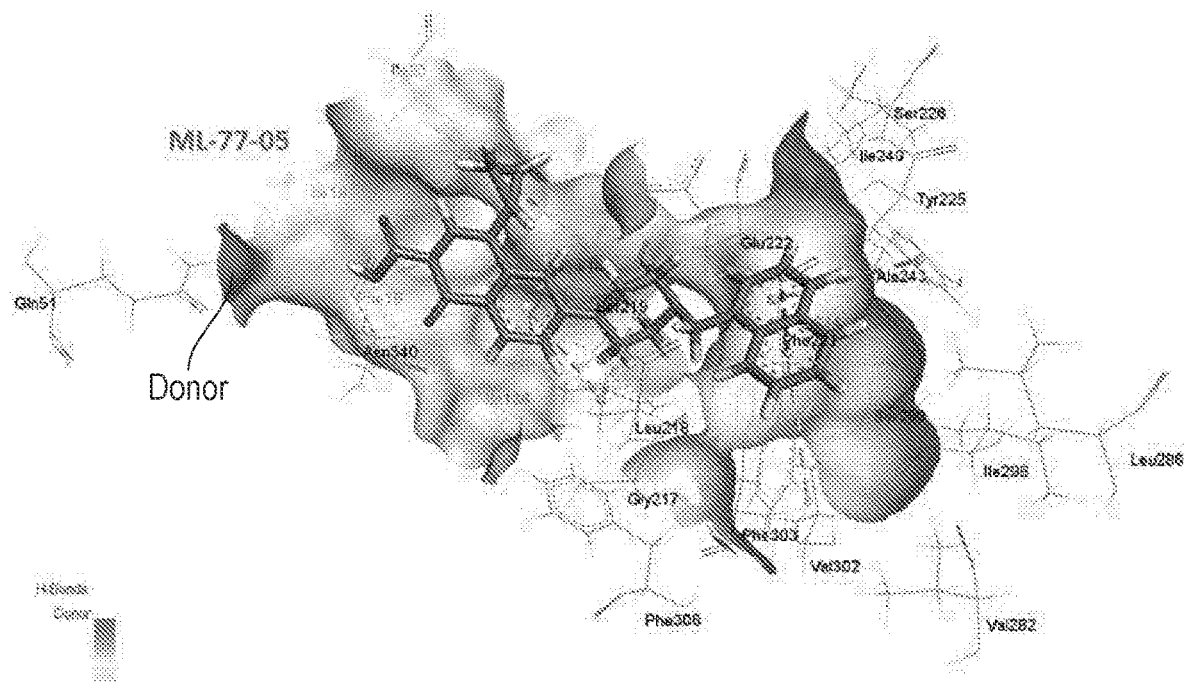
FIG. 2 shows a molecular model showing the key interactions of ARB-Ciprofloxacin (ML-77-05) with DNA gyrase.
Figure 3:
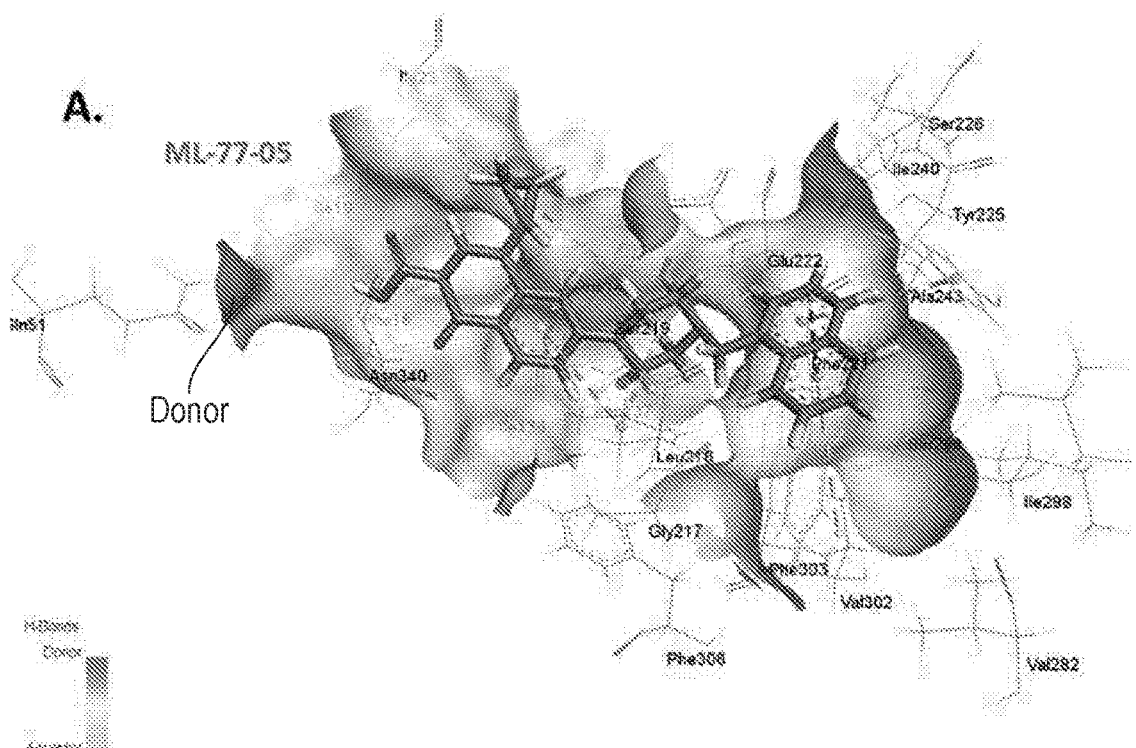
FIG. 3 shows a molecular model showing the key interactions of ARB-Ciprofloxacin (ML-77-05) with the NorA efflux pump.
Figure 4:
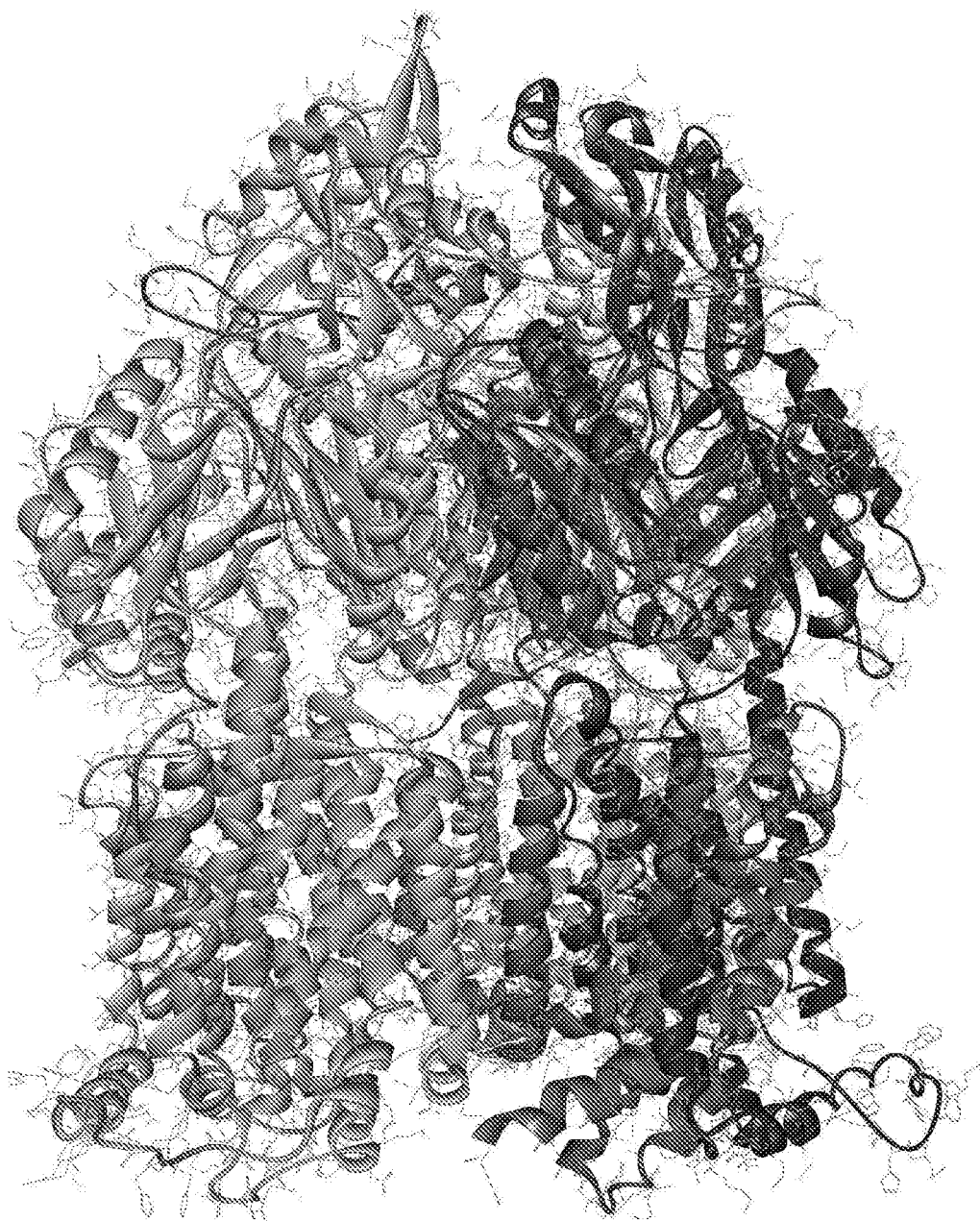
FIG. 4 shows a molecular model of AdeB efflux pump in *Acientobacter baumanii*
Figure 4:
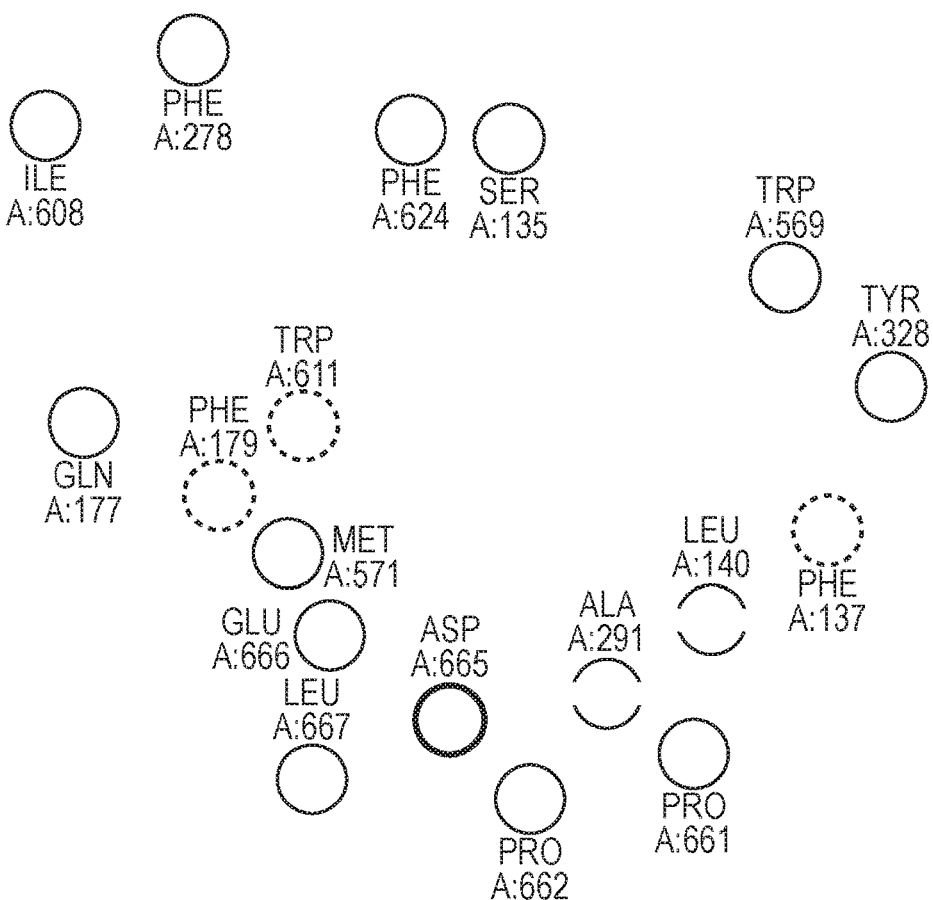
Figure 4:
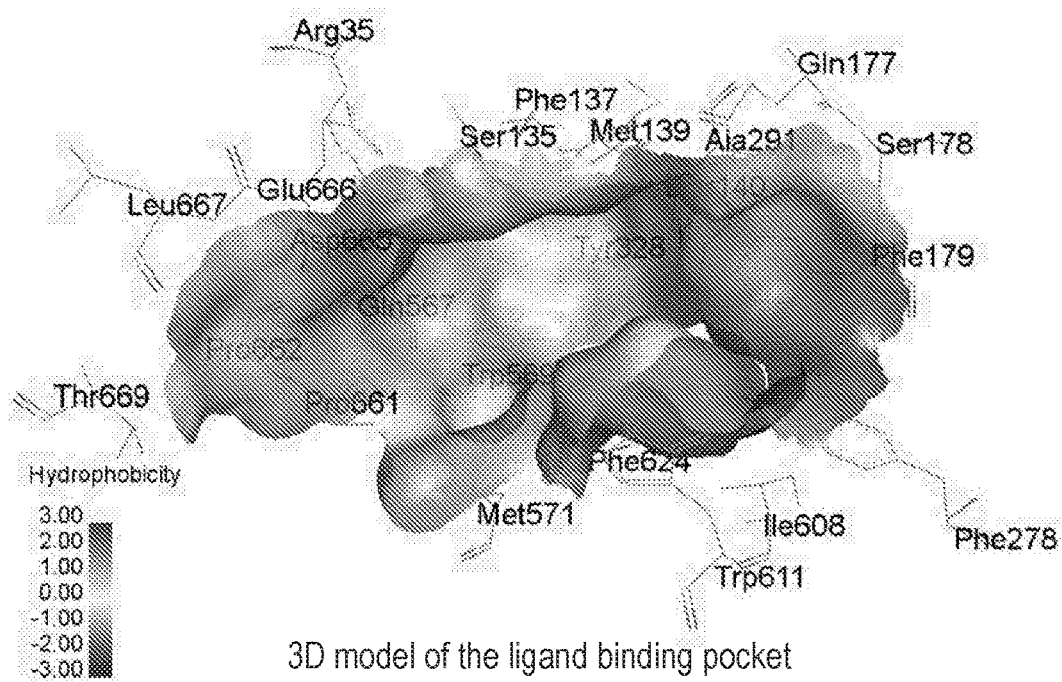
Figure 5:
FIG. 5 shows a molecular model of NorM efflux pump in *Acientobacter baumanii*
Figure 5:
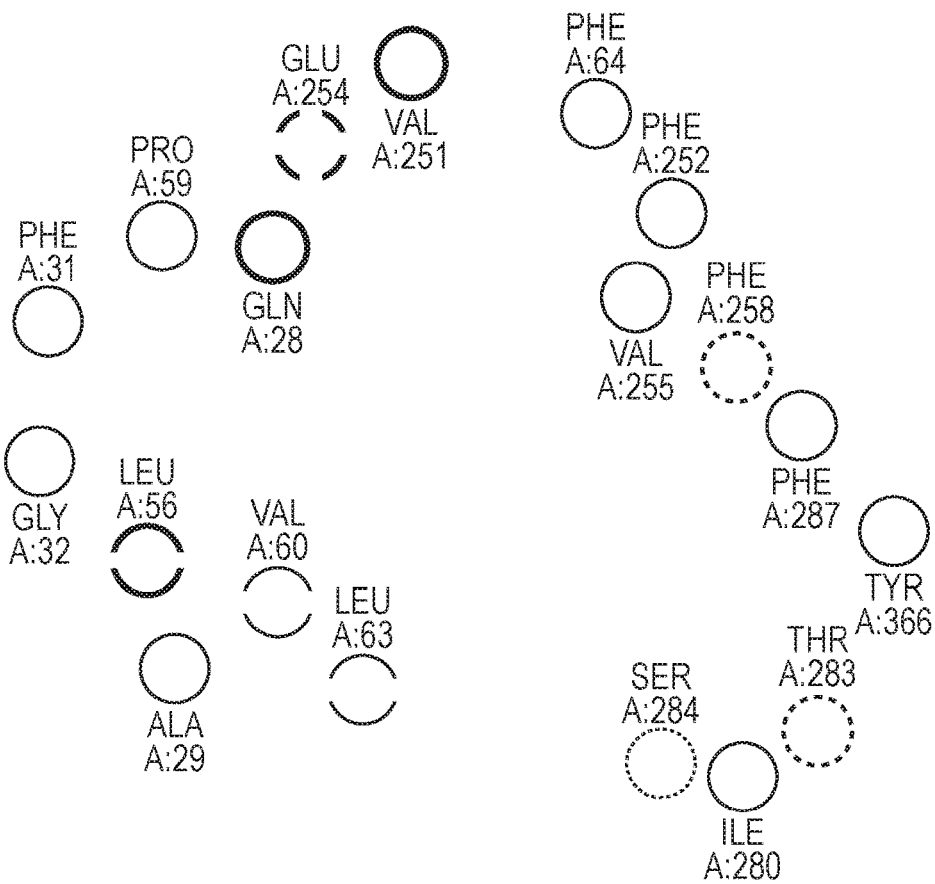
Figure 5:
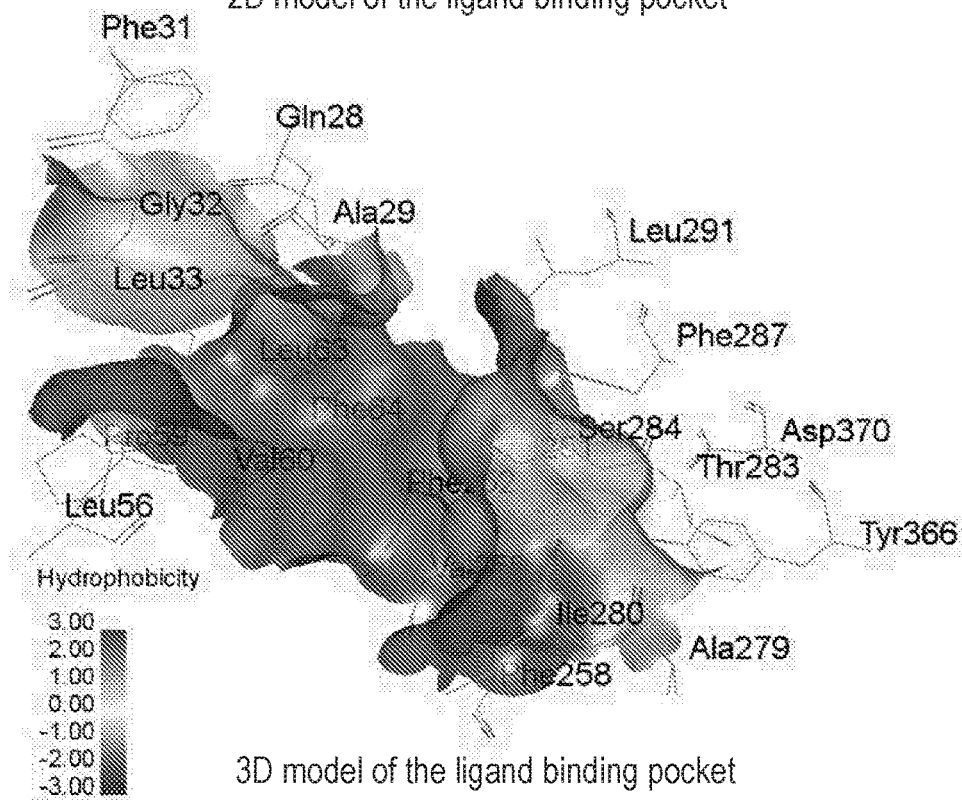
Figure 6:
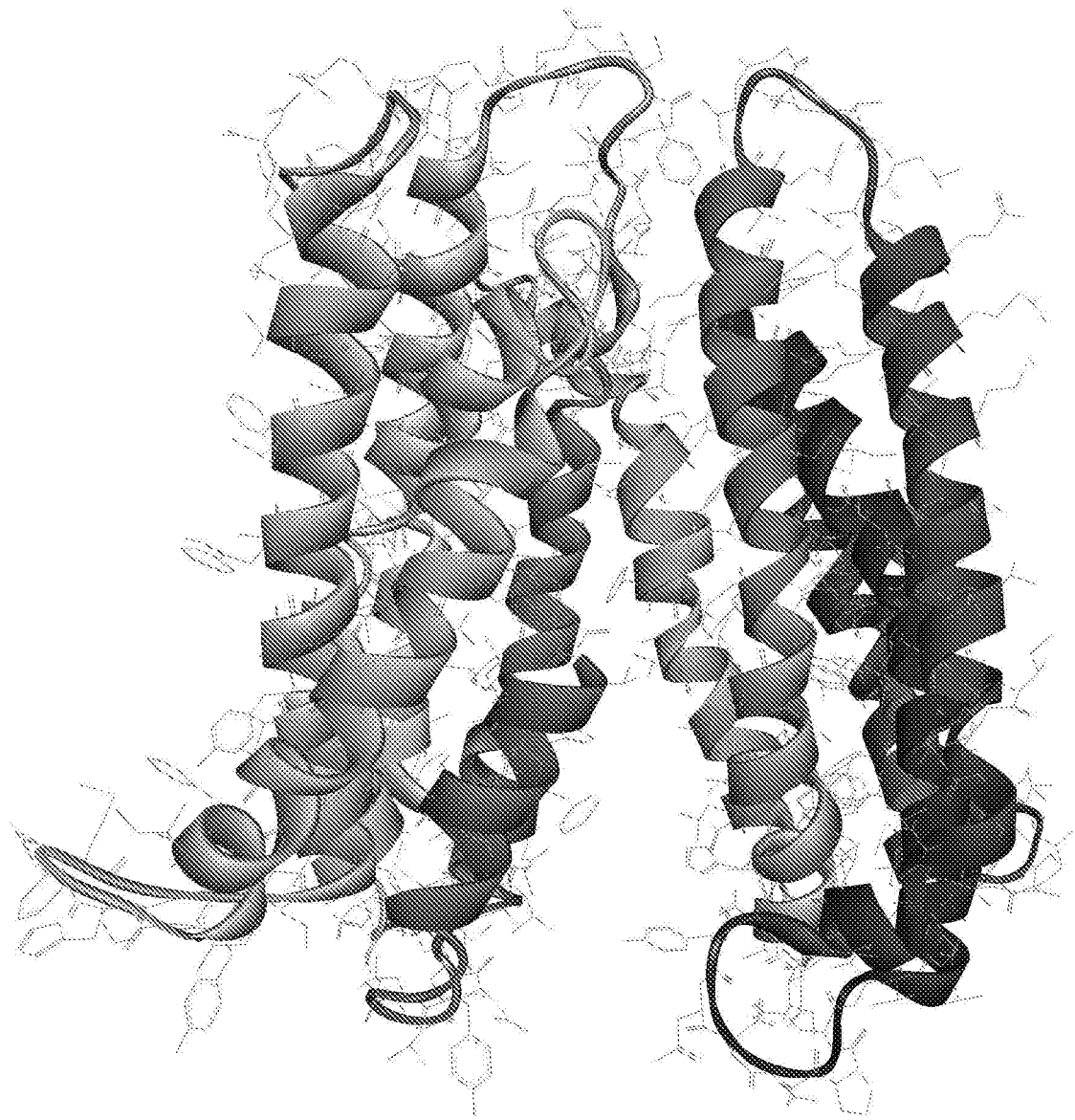
FIG. 6 shows a molecular model of MdtK efflux pump in *Escherichia coli*
Figure 6:
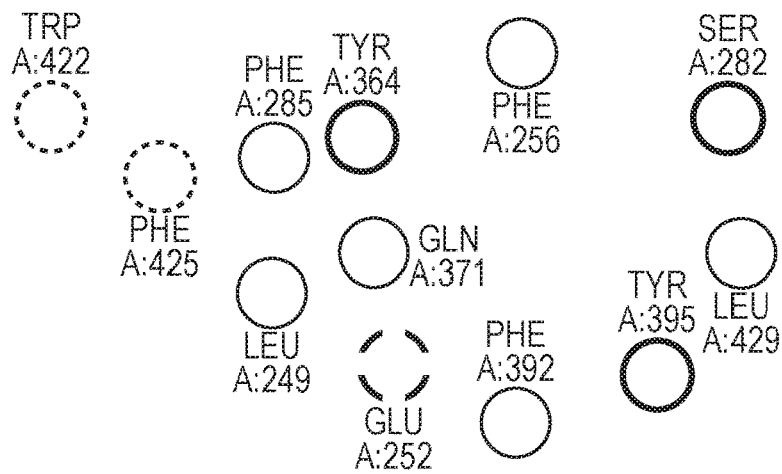
Figure 6:
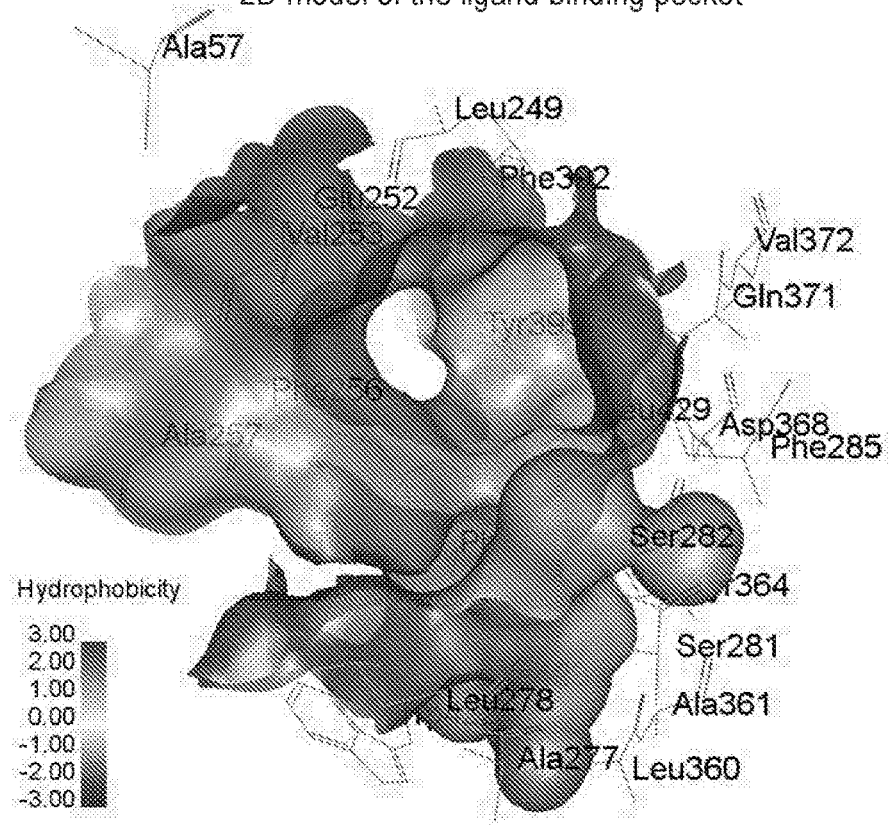
Figure 7:
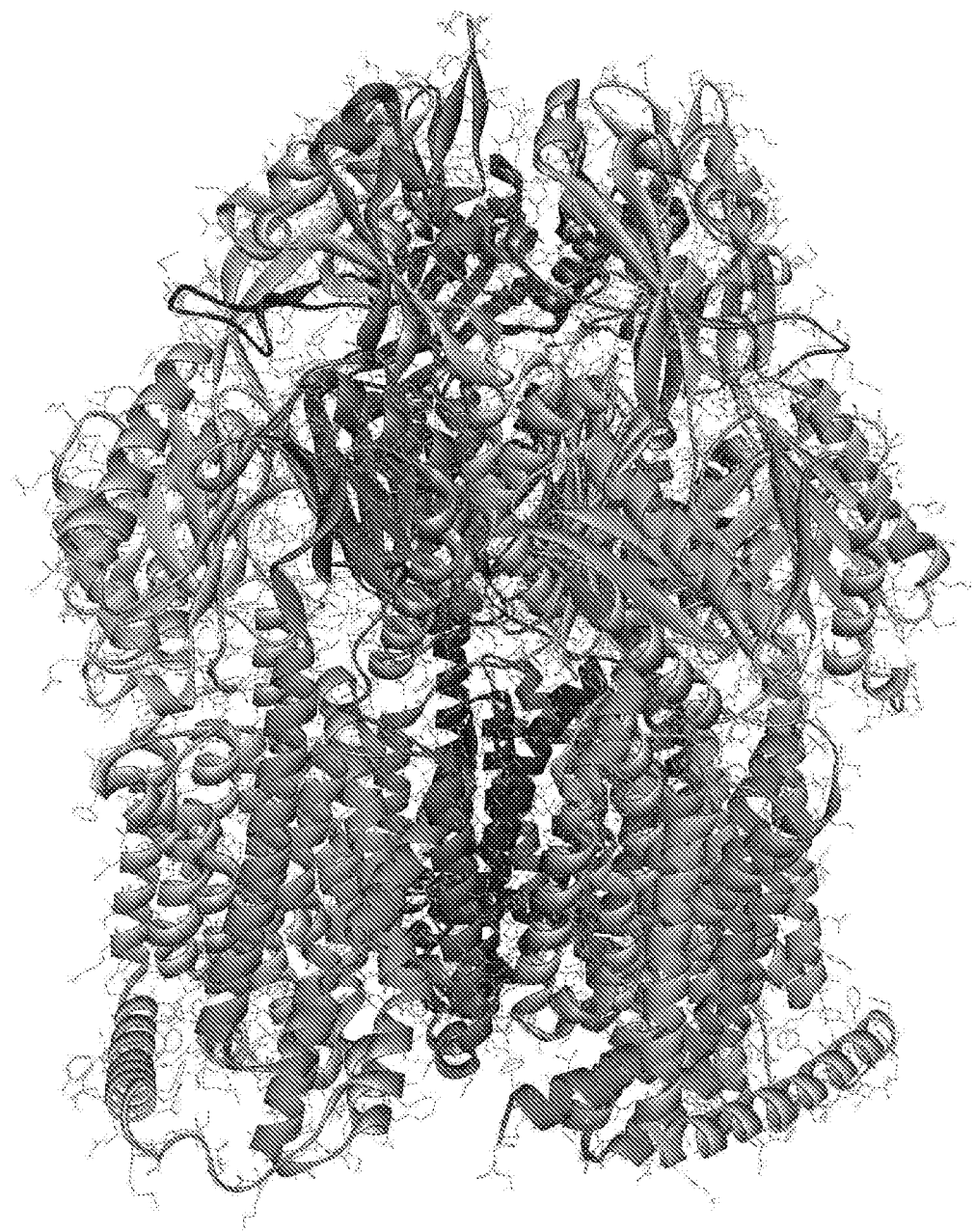
FIG. 7 shows a molecular model of AcrB efflux pump in *Escherichia coli*
Figure 7:
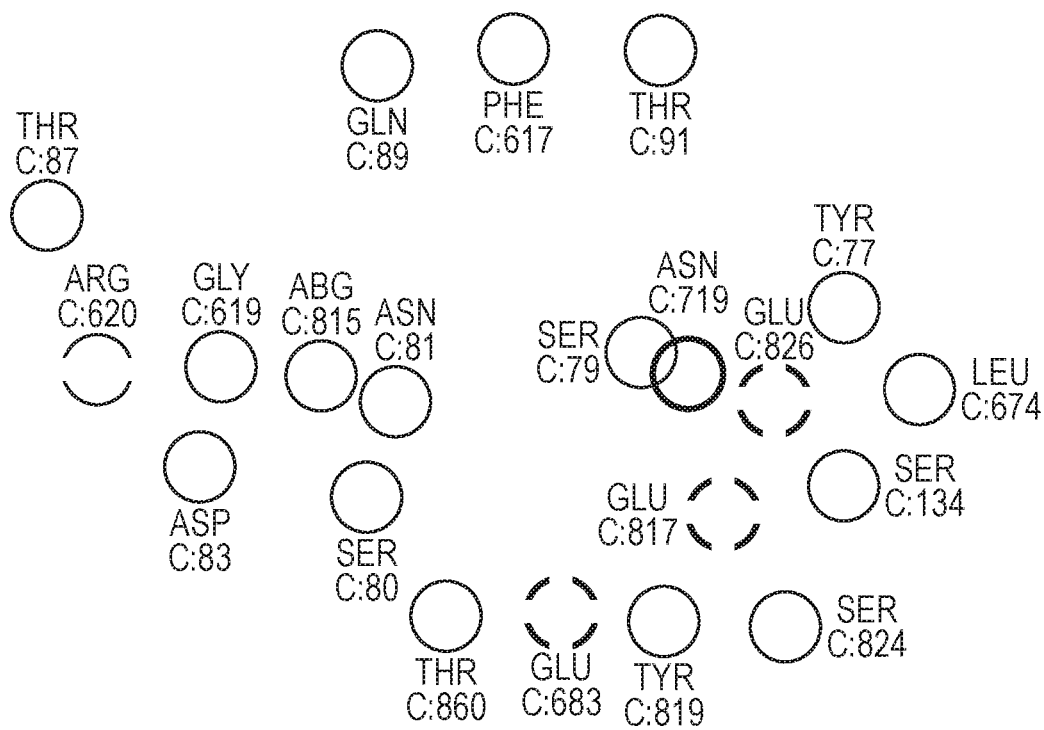
Figure 7:
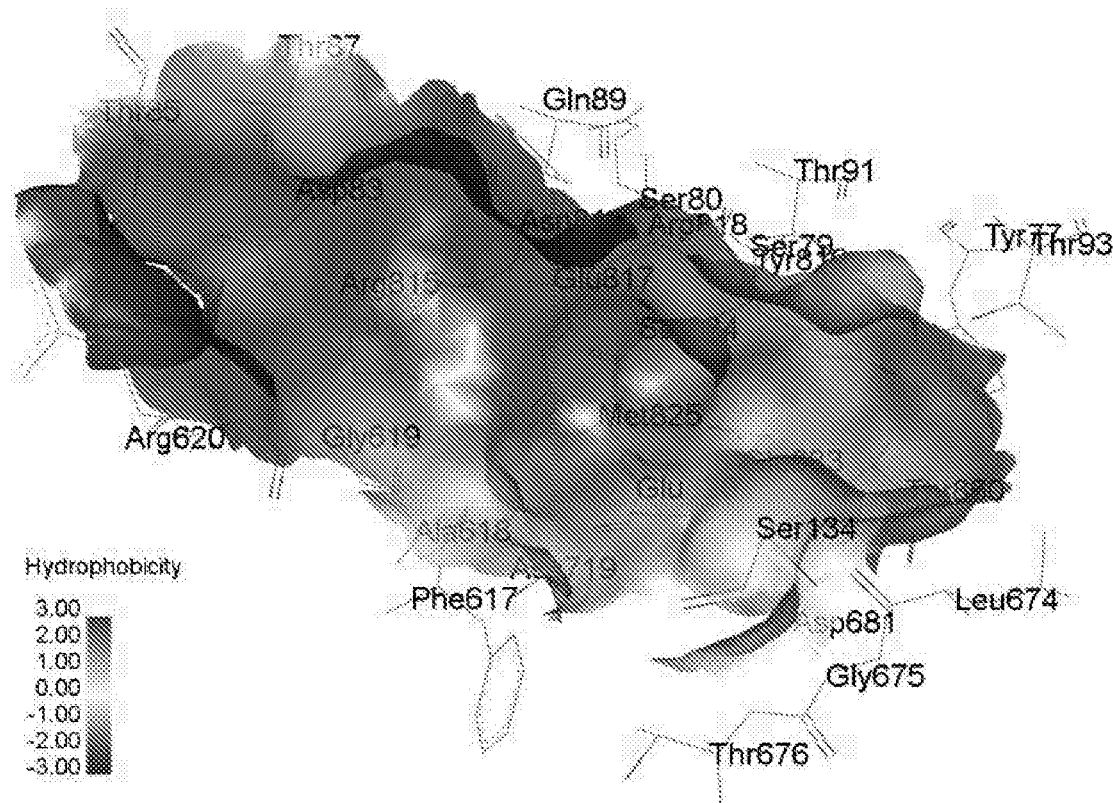
Figure 8:
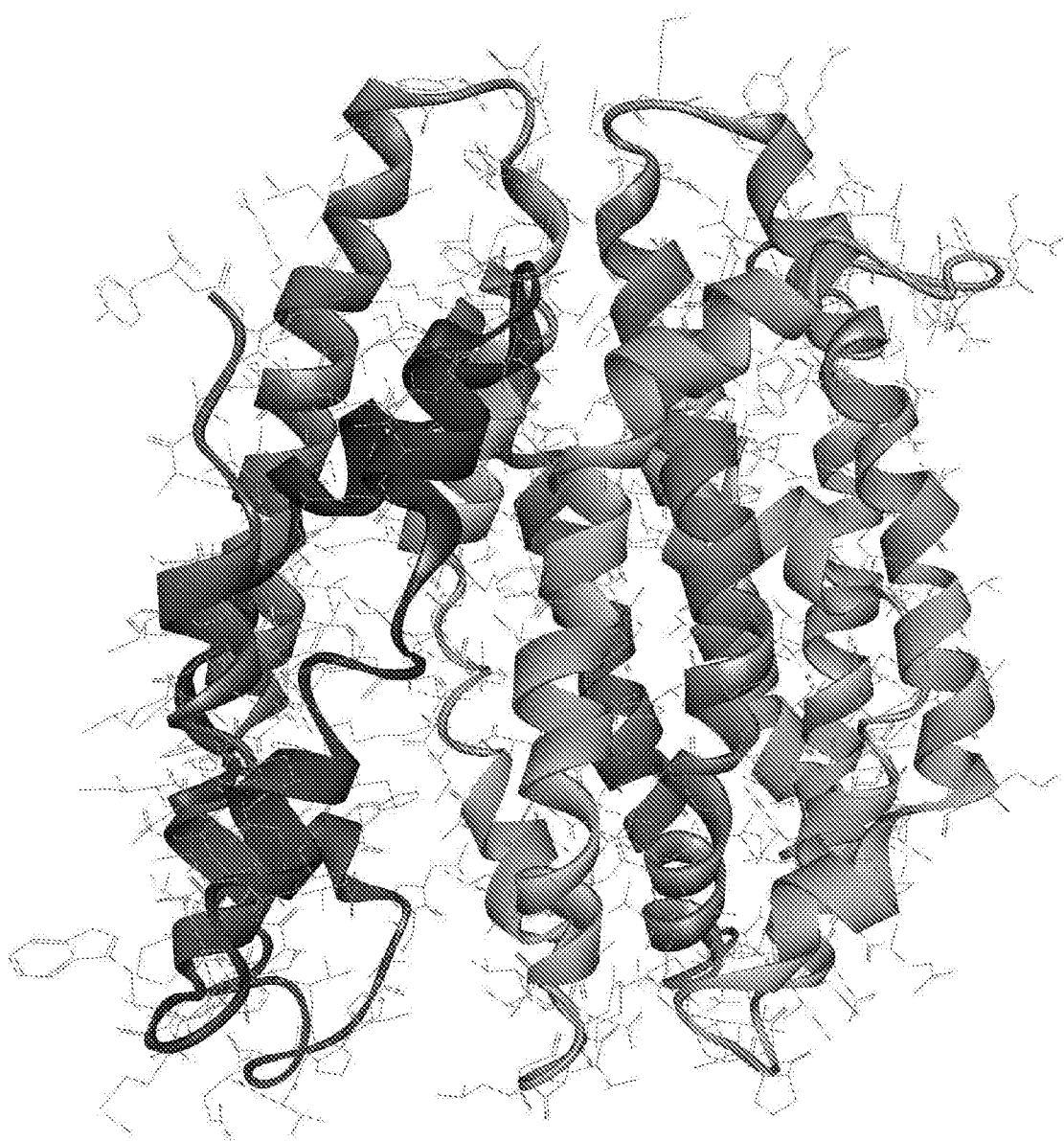
FIG. 8 shows a molecular model of EfmE efflux pump in *Enterococcus faecium*
Figure 8:
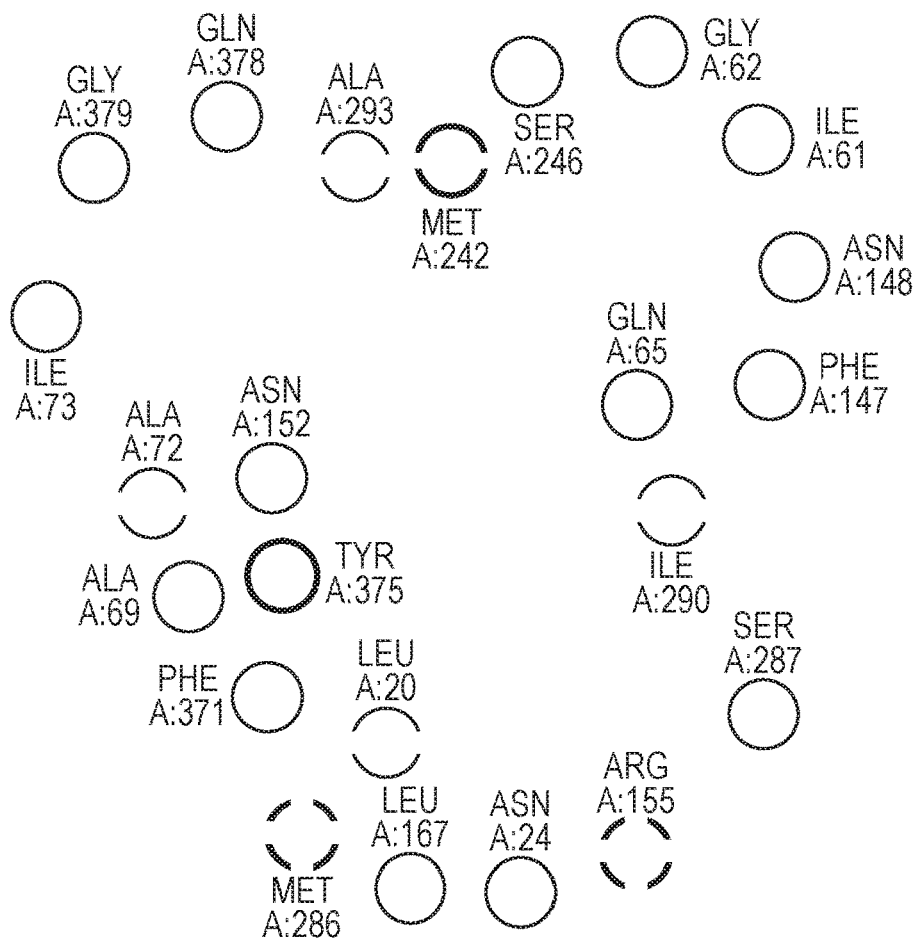
Figure 8:
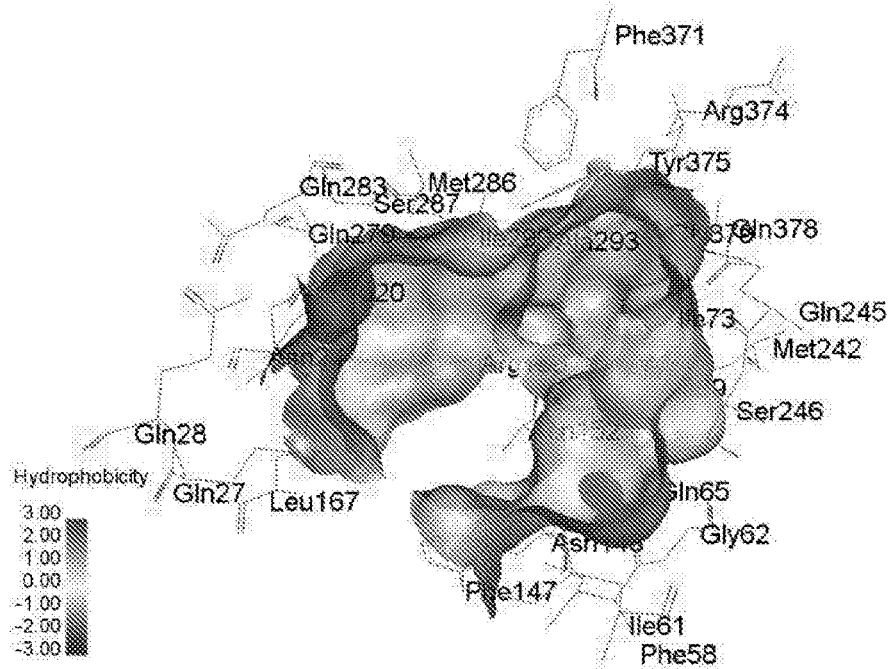
Figure 9:
FIG. 9 shows a molecular model of EfmE efflux pump in *Enterococcus faecalis*
Figure 9:
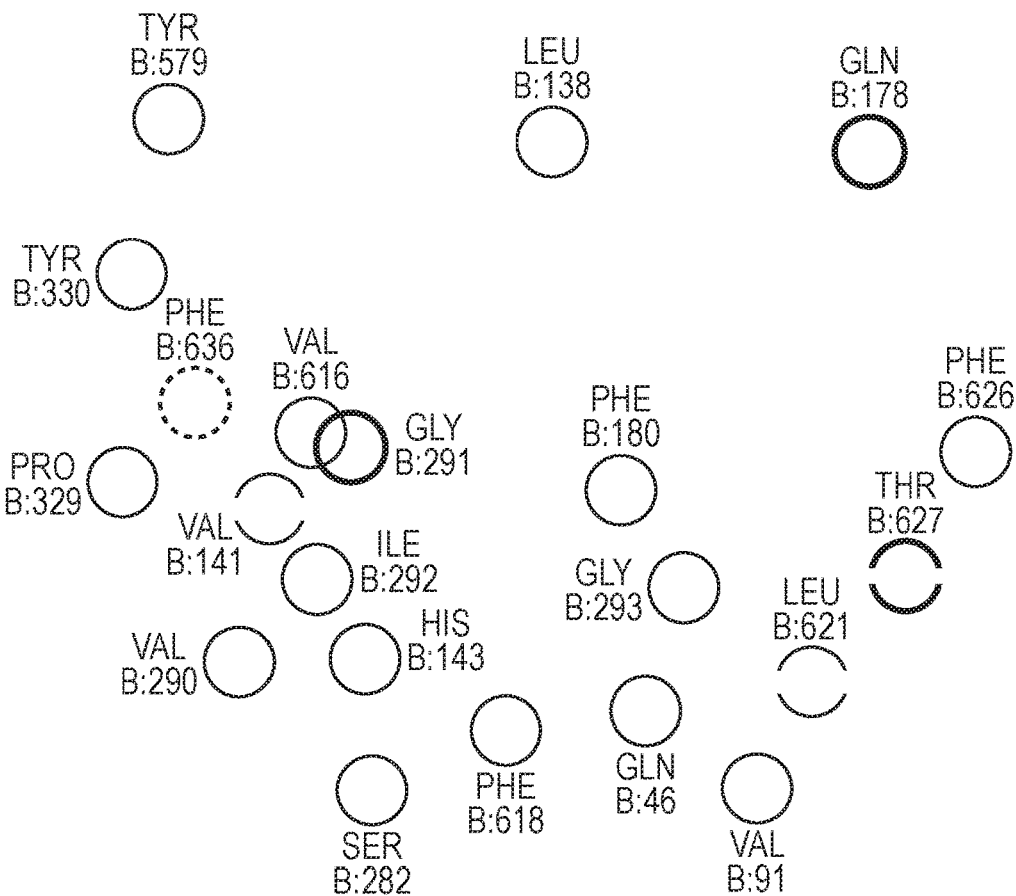
Figure 9:
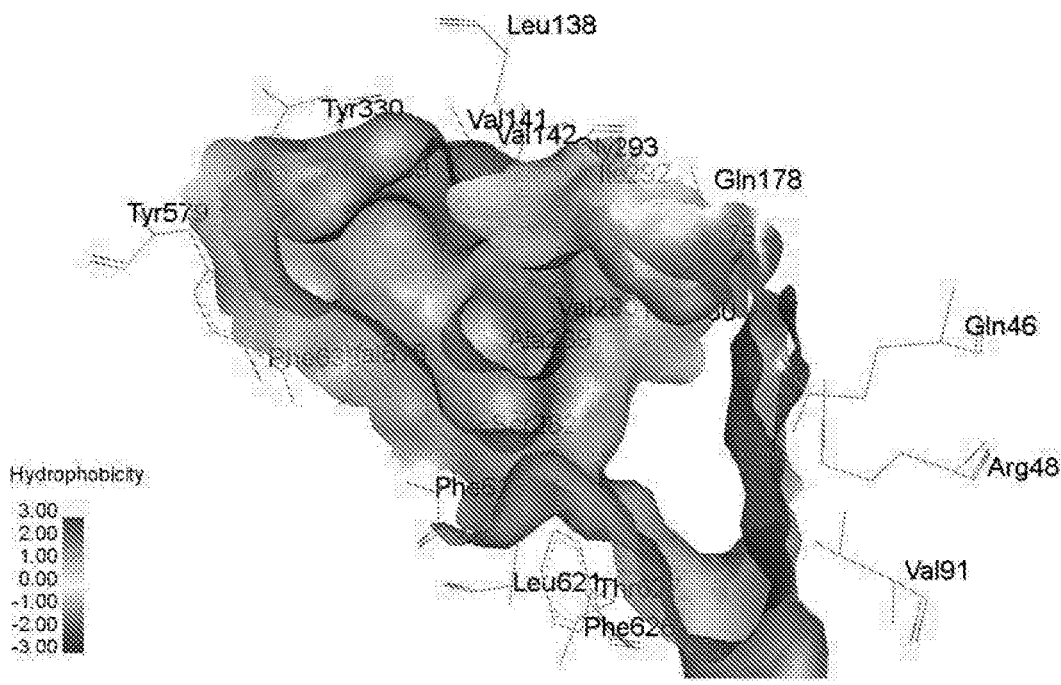
Figure 10:
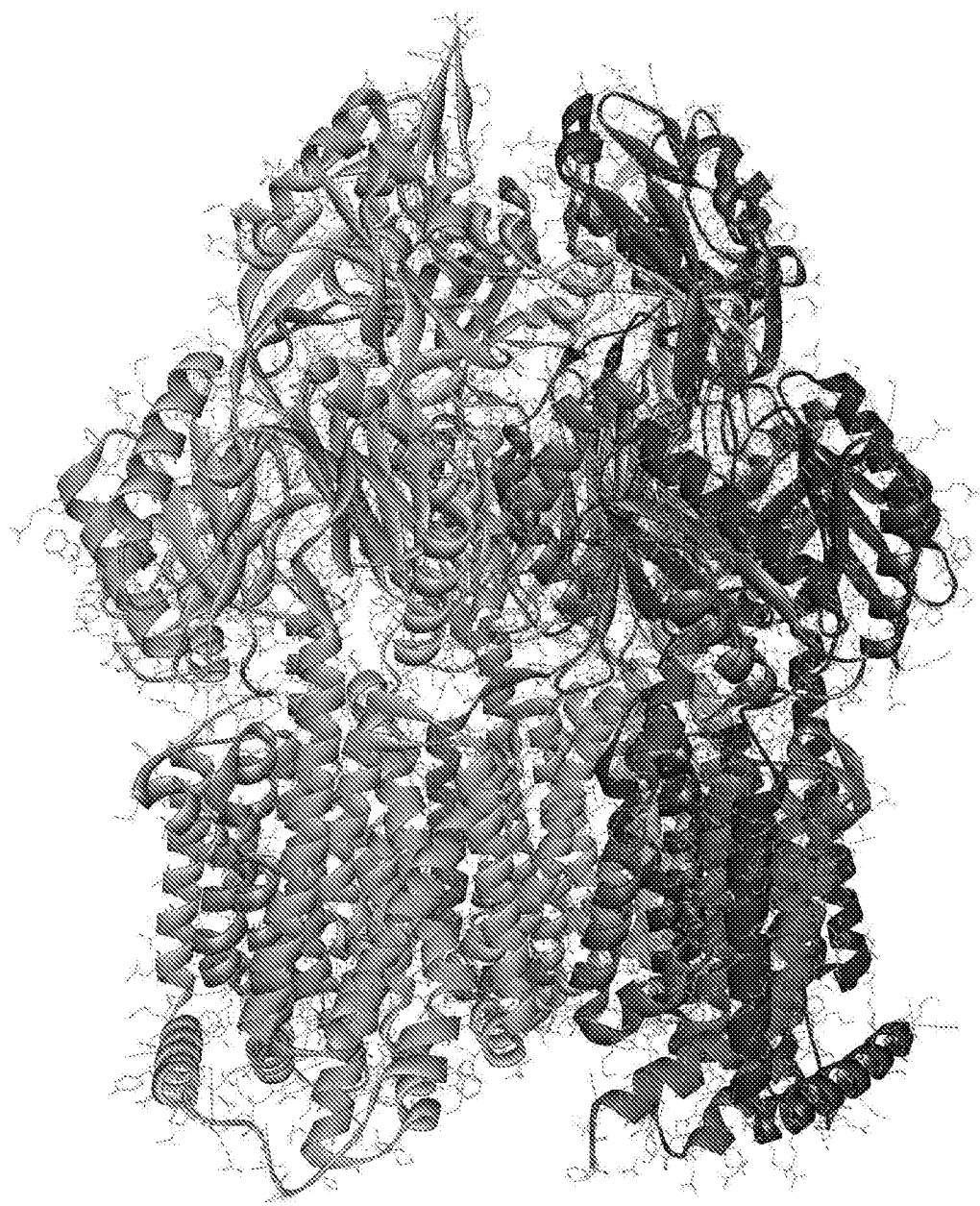
FIG. 10 shows a molecular model of AcrB efflux pump in *Klebsiella pneumoniae*
Figure 10:
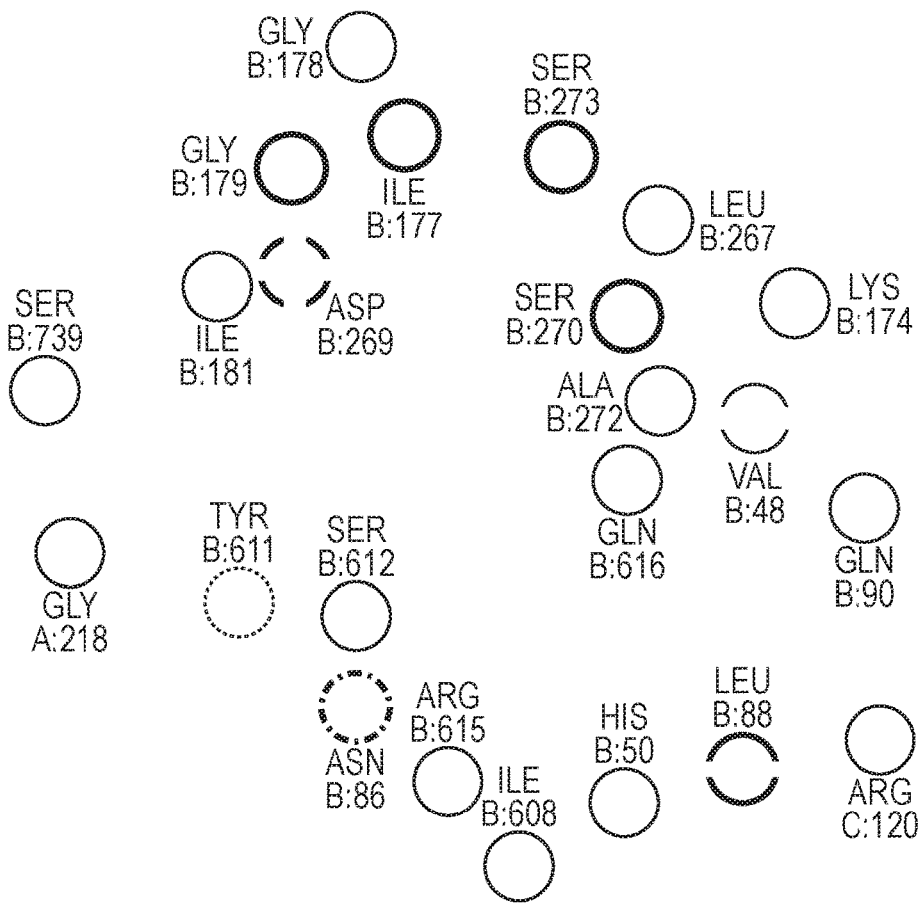
Figure 10:
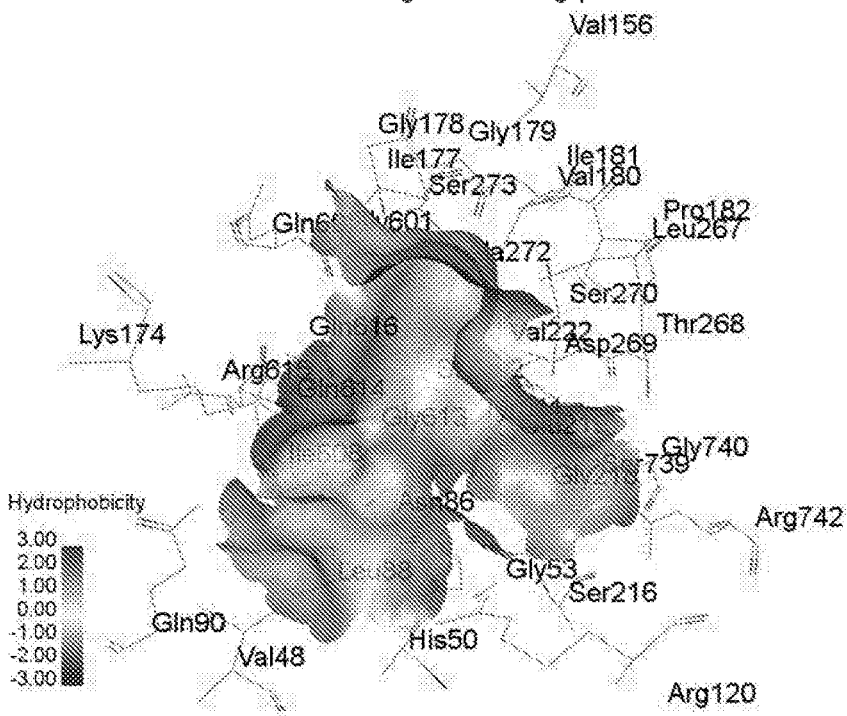
Figure 11:
FIG. 11 shows a molecular model of MdtK efflux pump in *Klebsiella pneumoniae*
Figure 11:
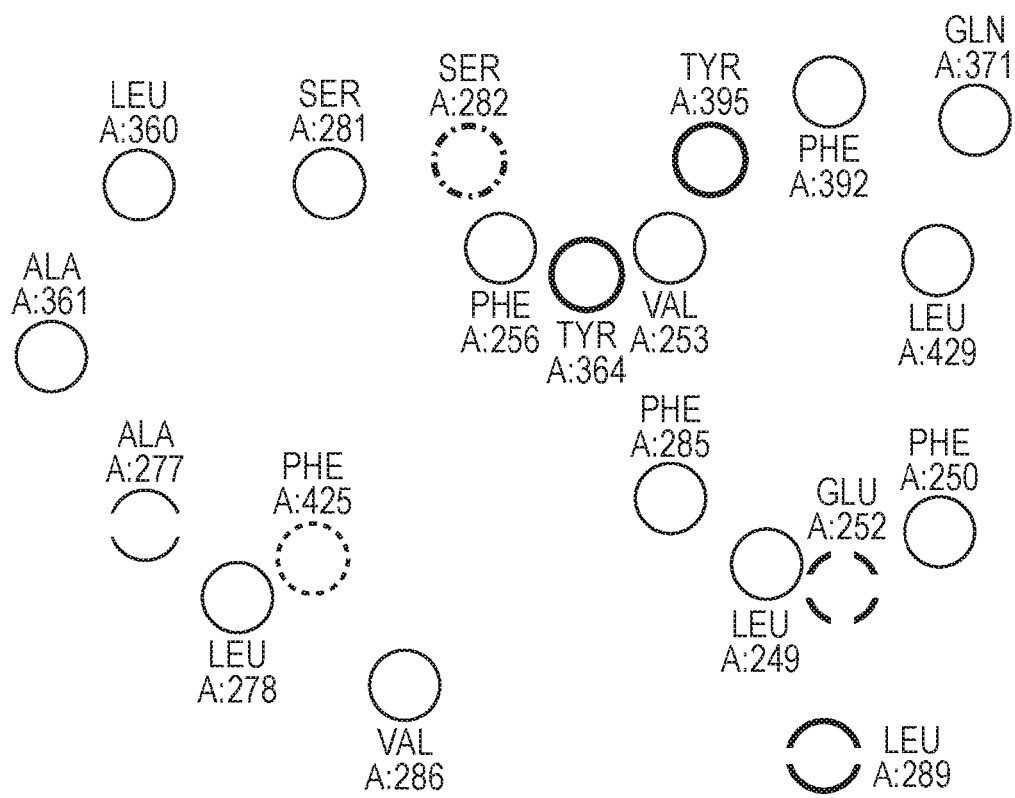
Figure 11:
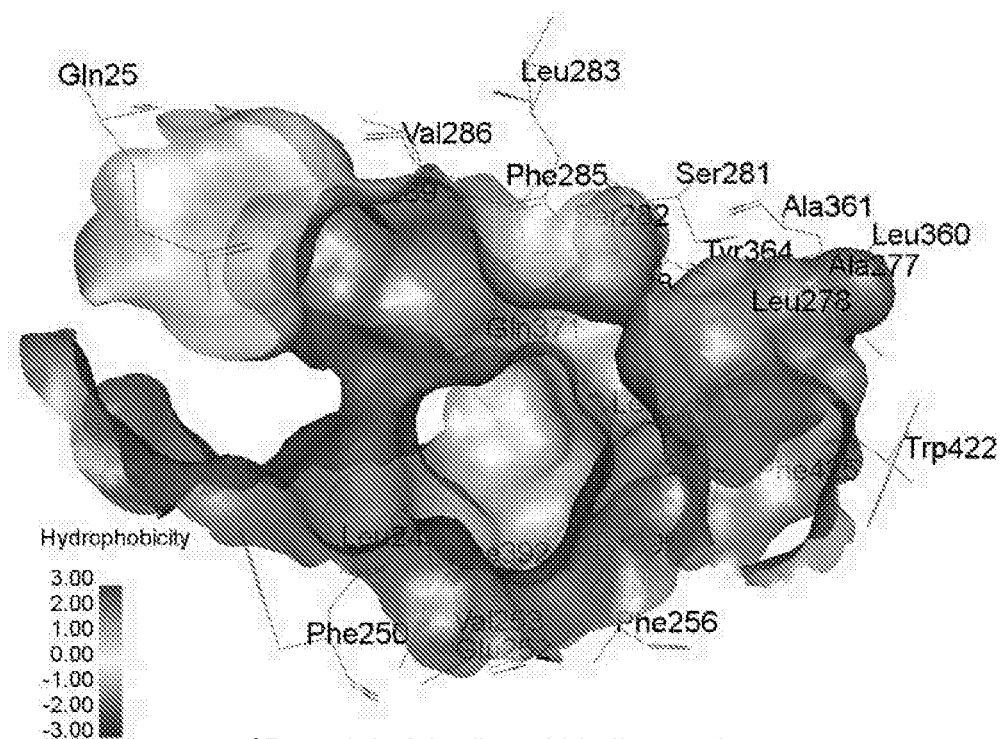
Figure 12:
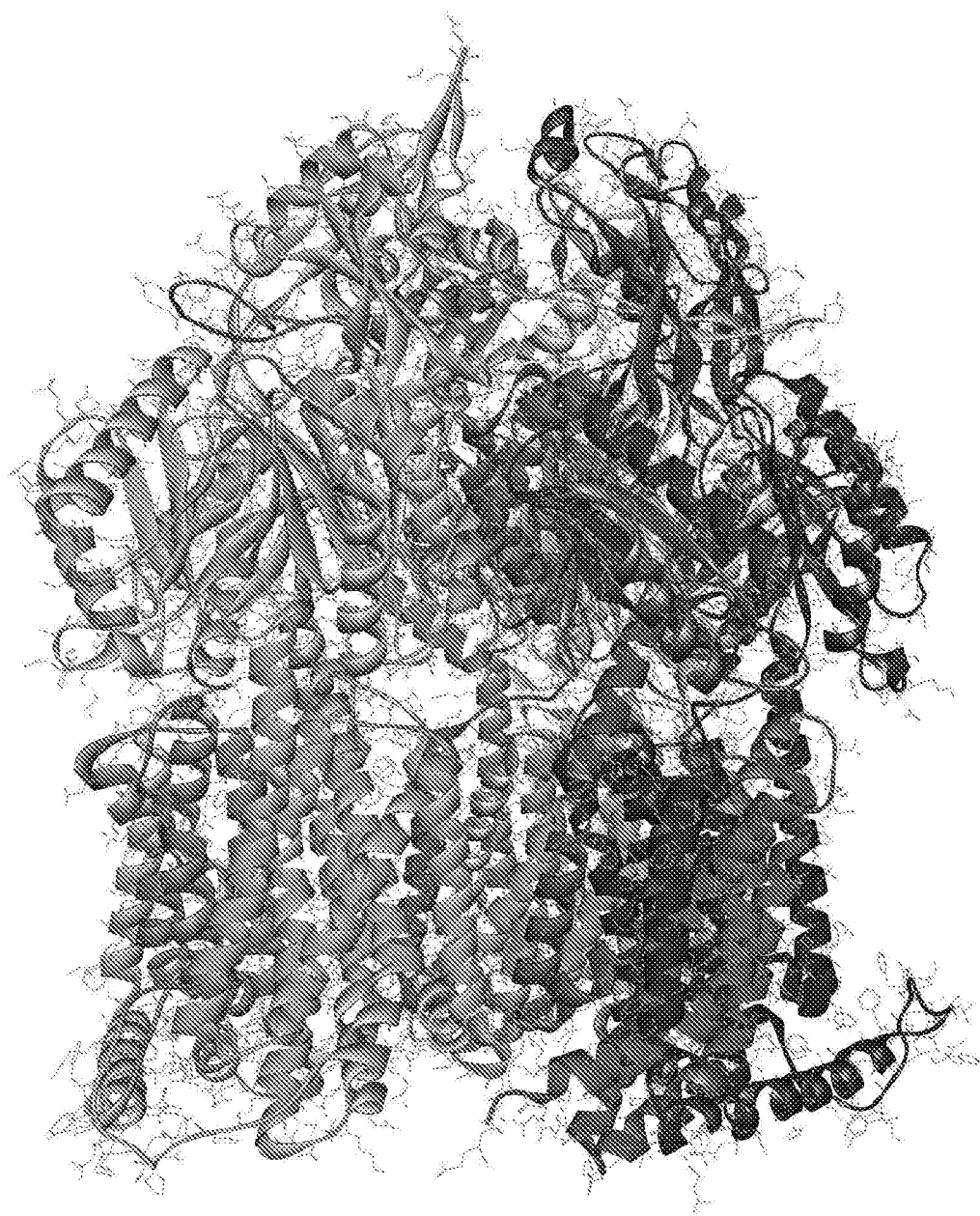
FIG. 12 shows a molecular model of MexF efflux pump in *Pseudomonas aeruginosa*
Figure 12:
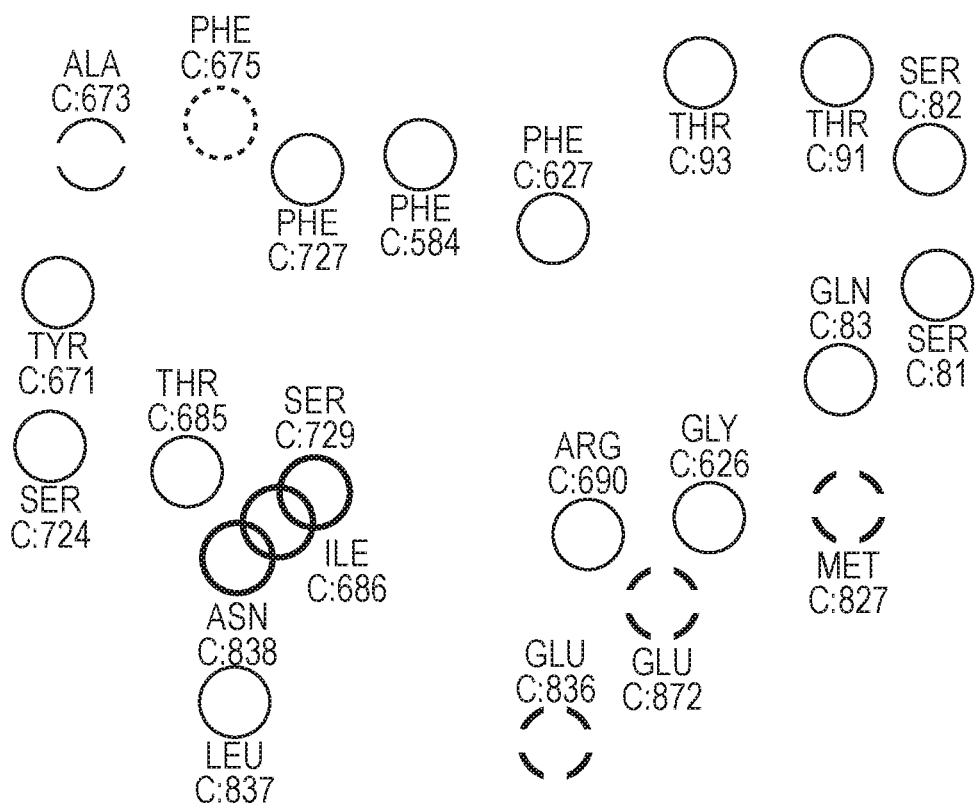
Figure 12:
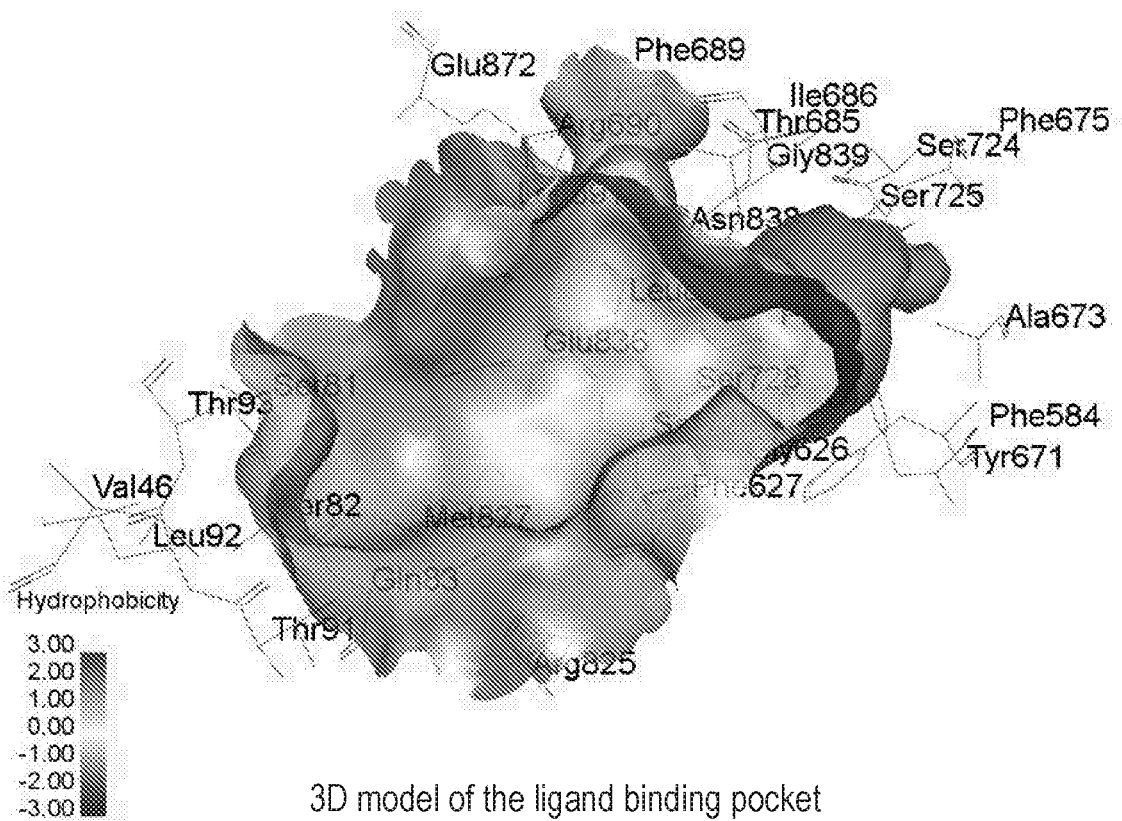
Figure 13:
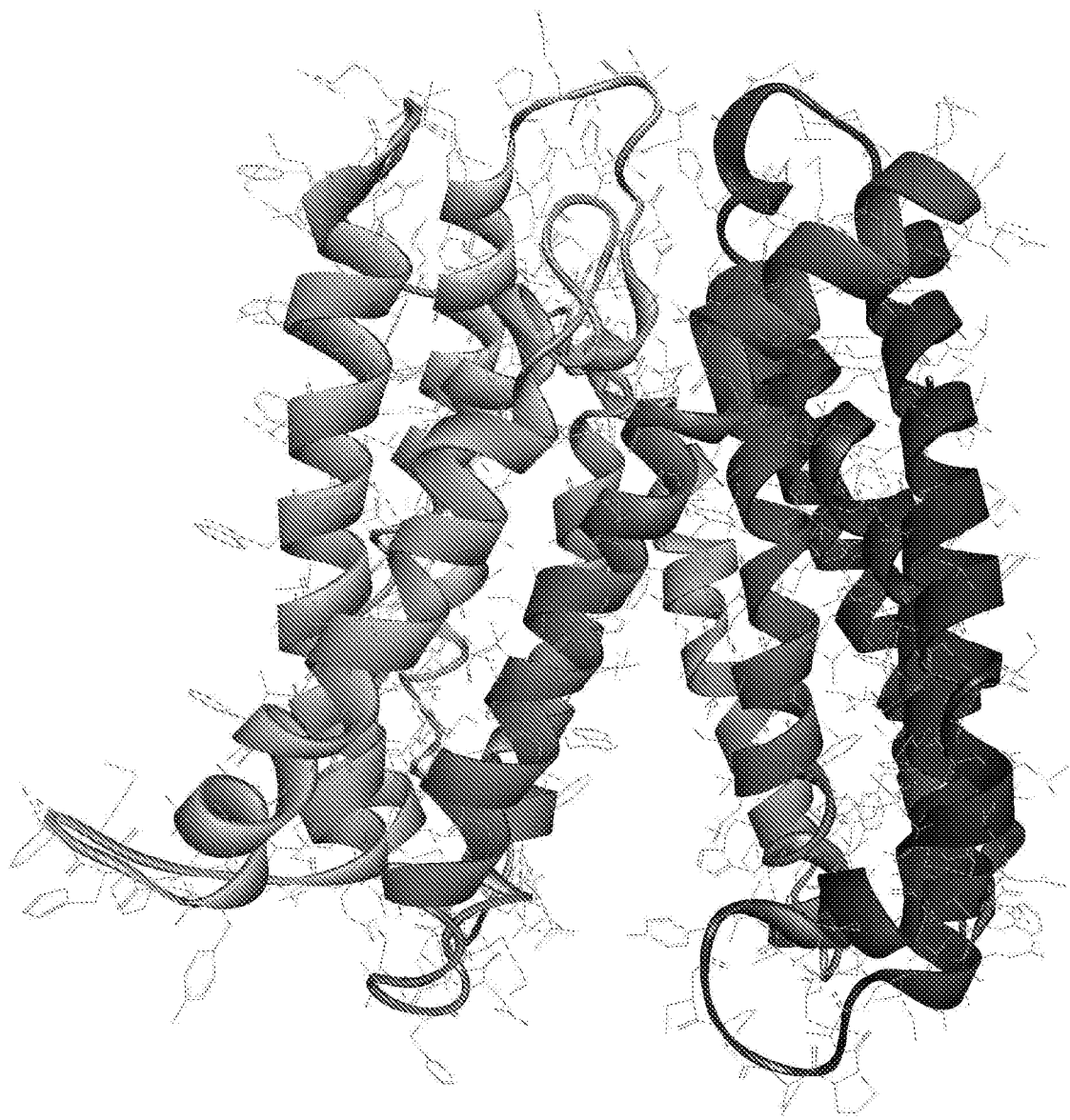
FIG. 13 shows a molecular model of PmpM efflux pump in *Pseudomonas aeruginosa*
Figure 13:
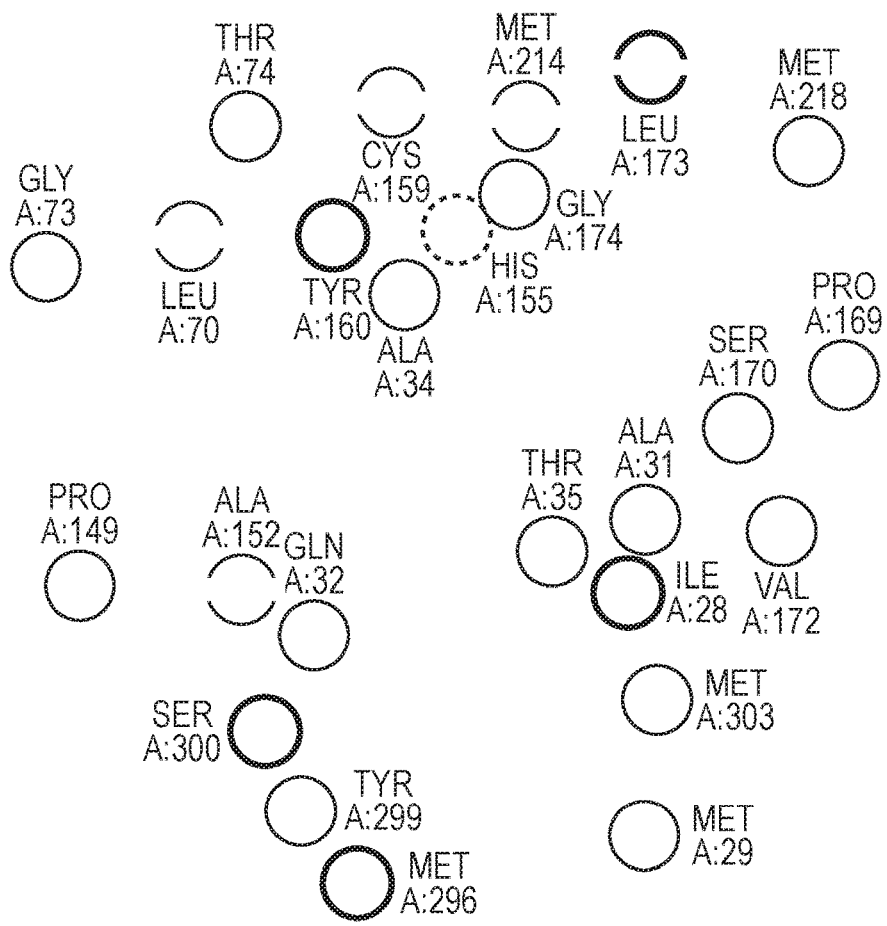
Figure 13:
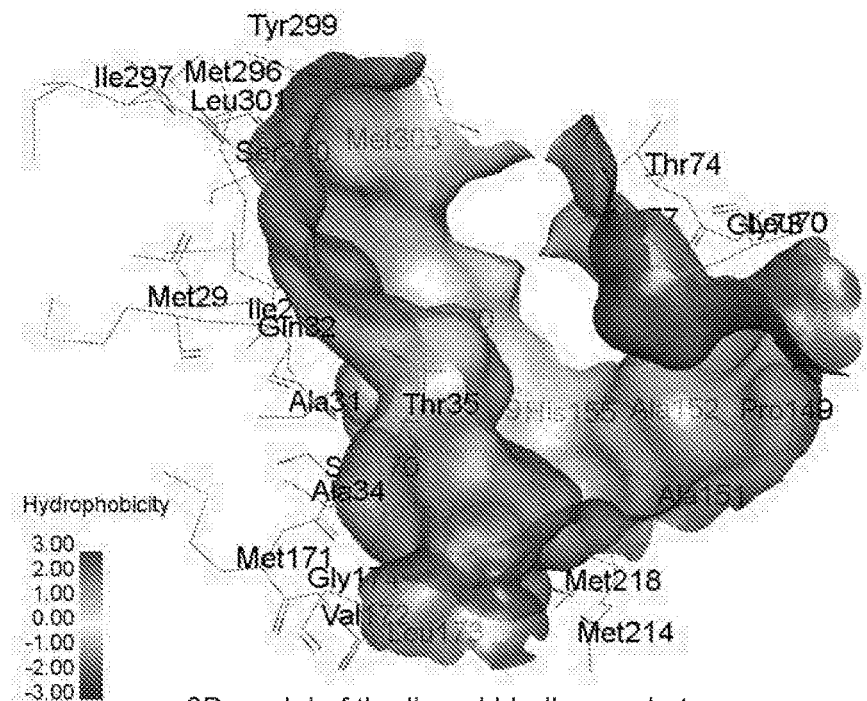
Figure 14:
FIG. 14 shows a molecular model of MexB efflux pump in *Pseudomonas aeruginosa*
Figure 14:
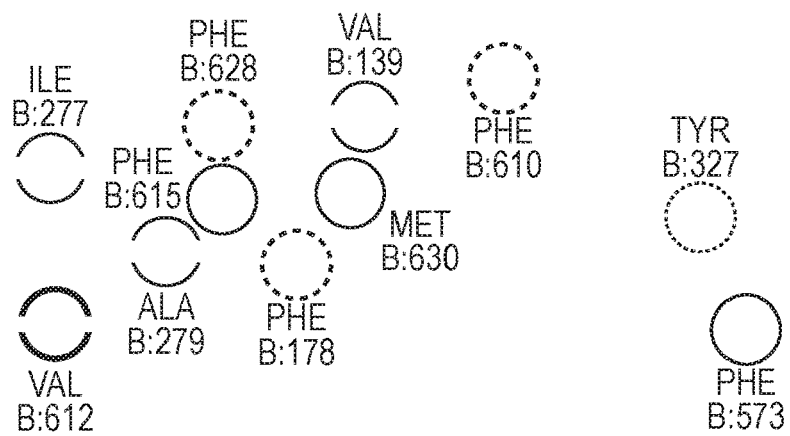
Figure 14:
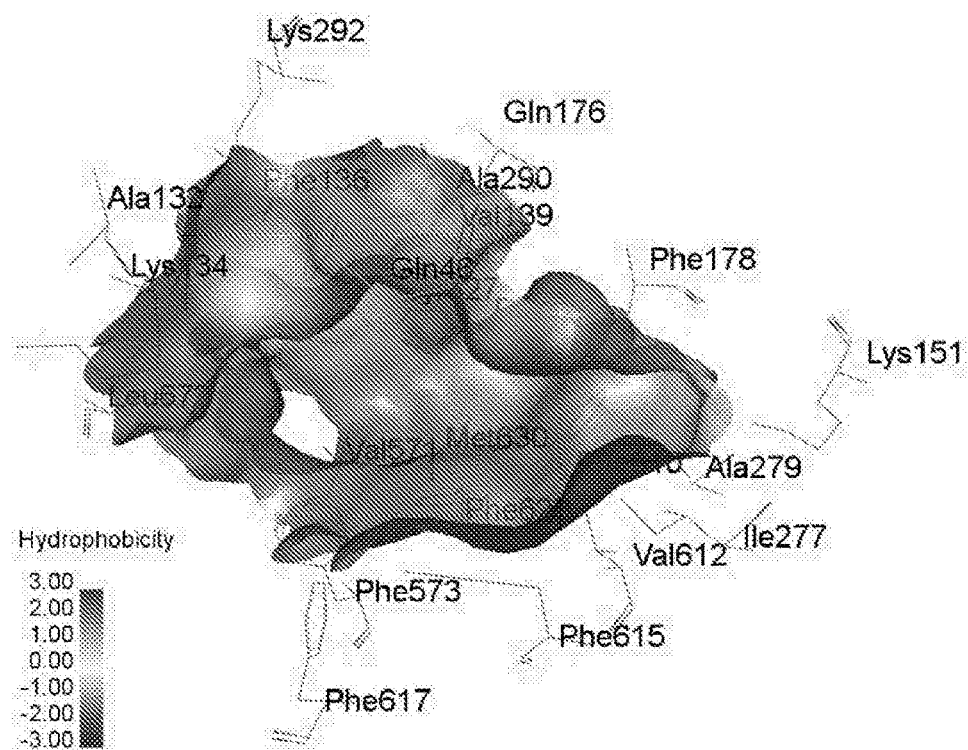
Figure 15:
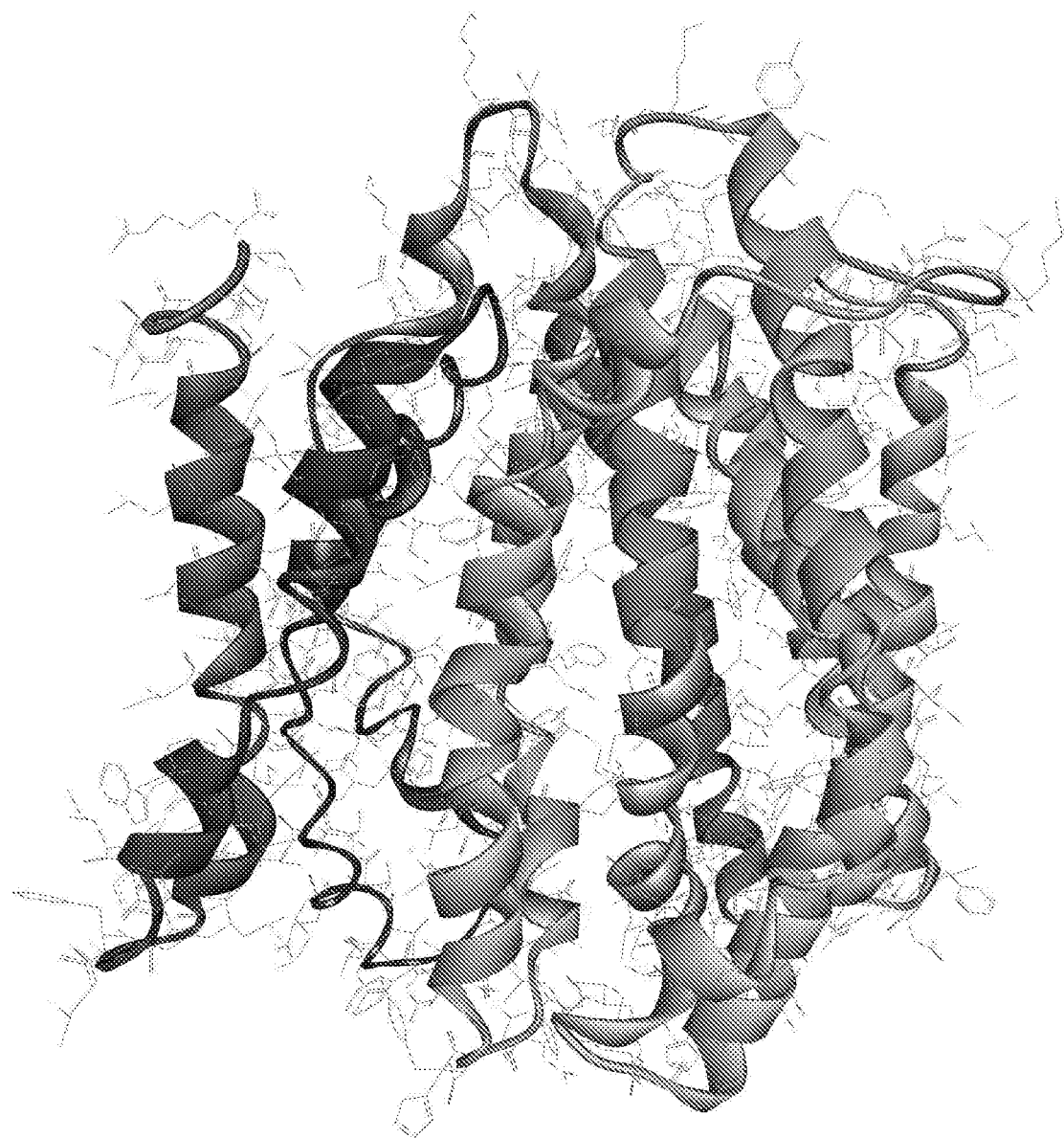
FIG. 15 shows a molecular model of MepA efflux pump in *Staphylococcus aureus*
Figure 15:
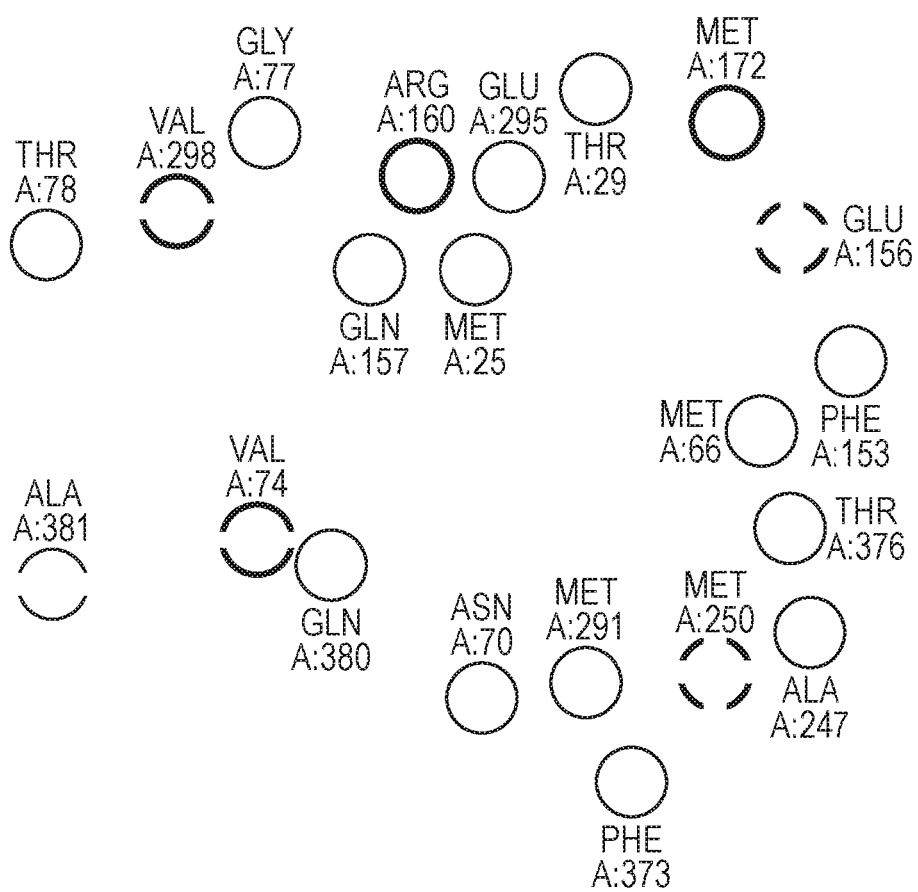
Figure 15:
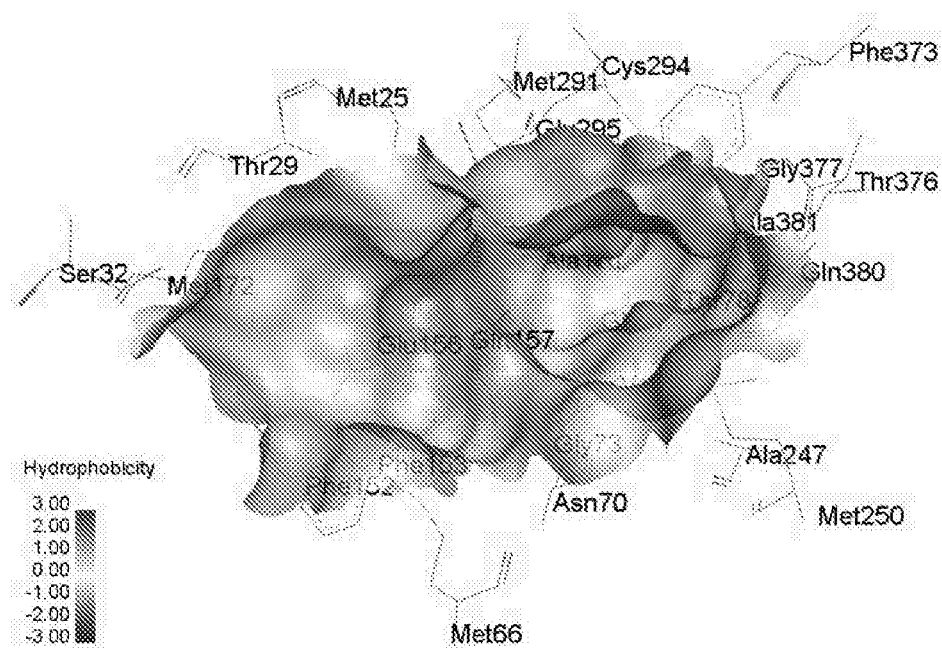
Figure 16:
FIG. 16 shows a molecular model of NorA efflux pump in *Staphylococcus aureus*
Figure 16:
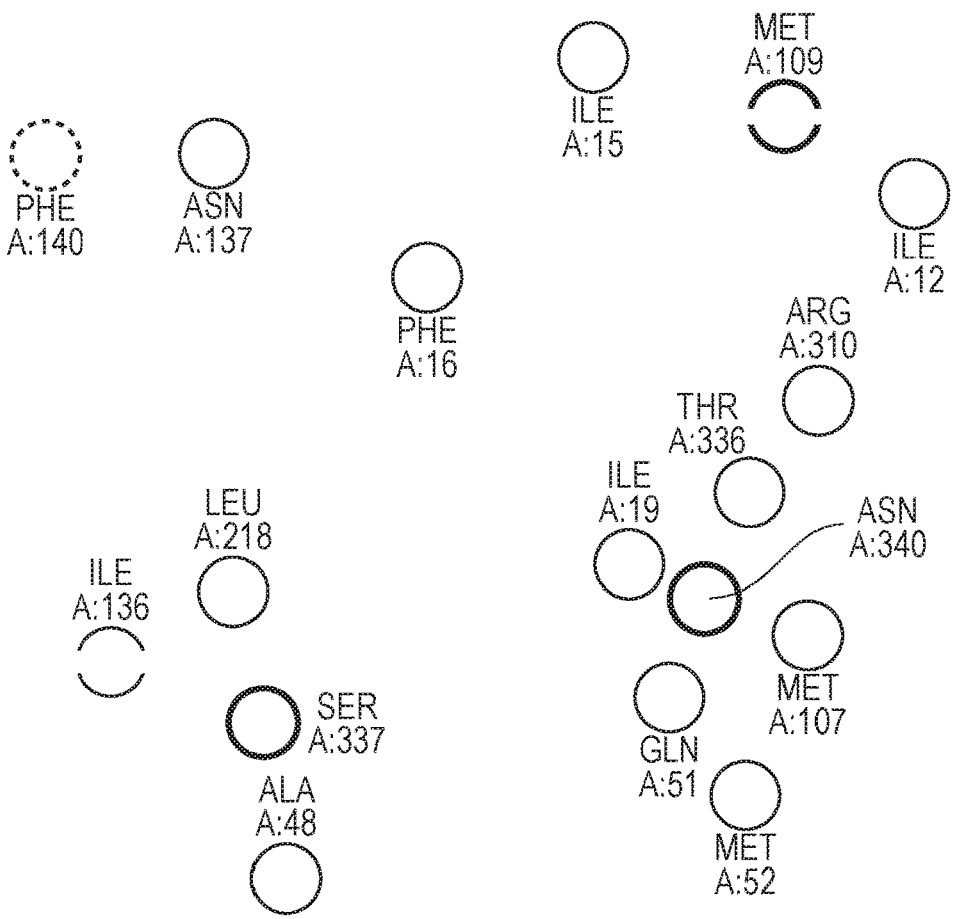
Figure 16:
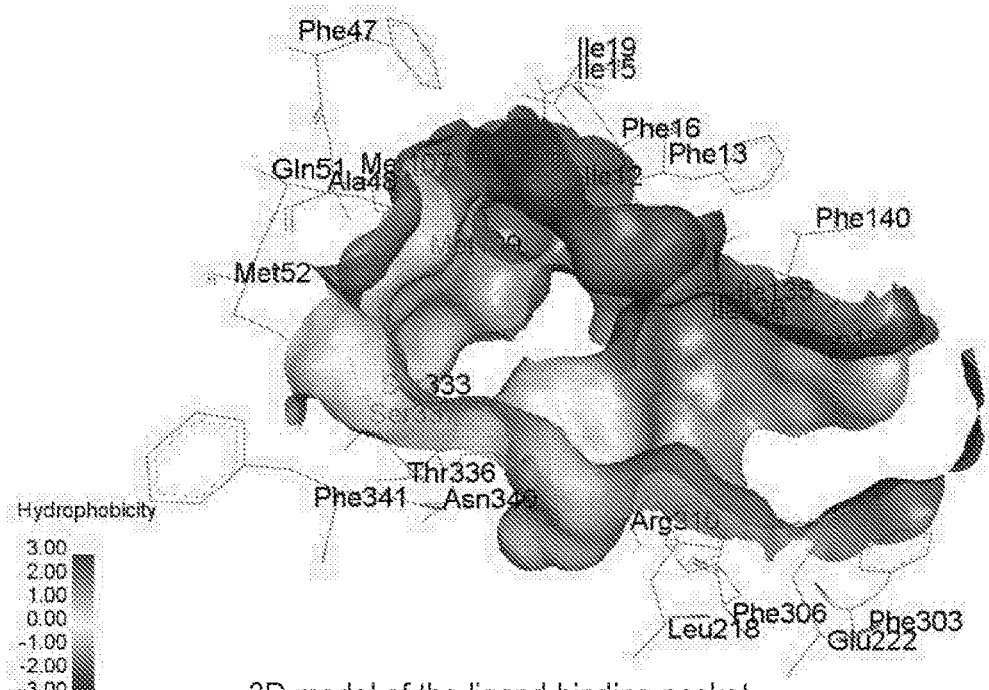
Figure 17:
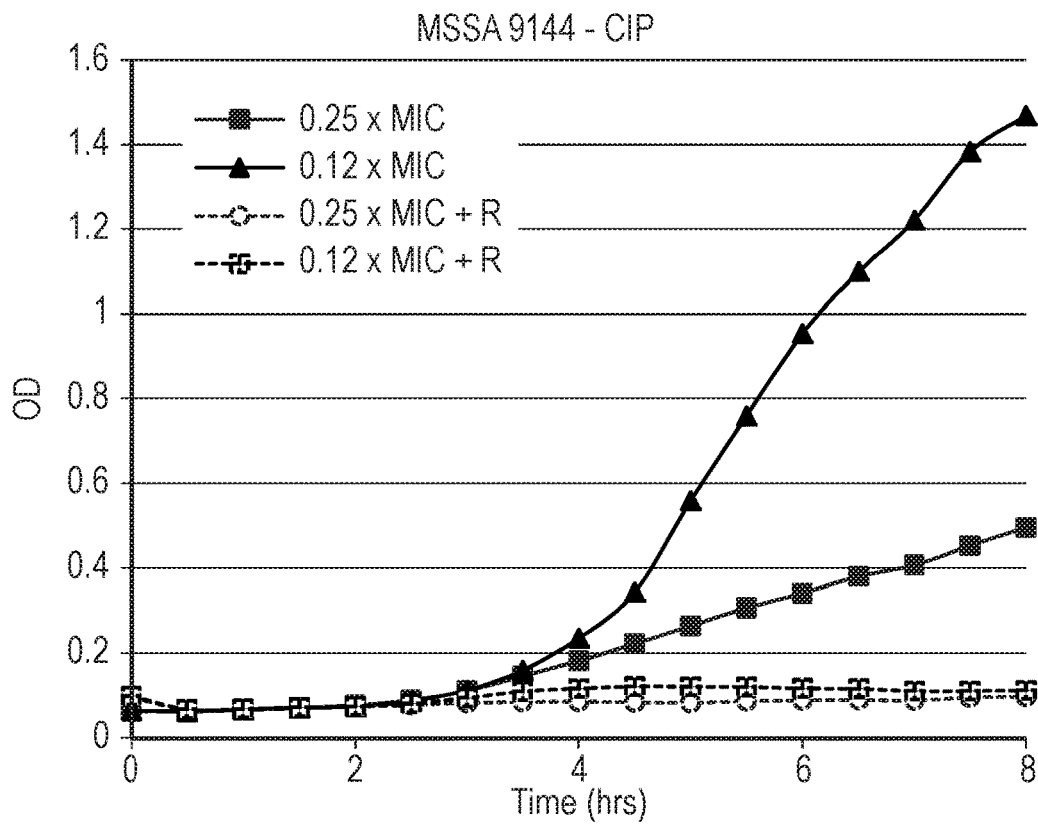
FIG. 17 show the results for the reserpine assay using ciprofloxacin (CIP) which shows that it is effluxed by the multidrug-resistant MSSA 9144 strain.
Figure 18:
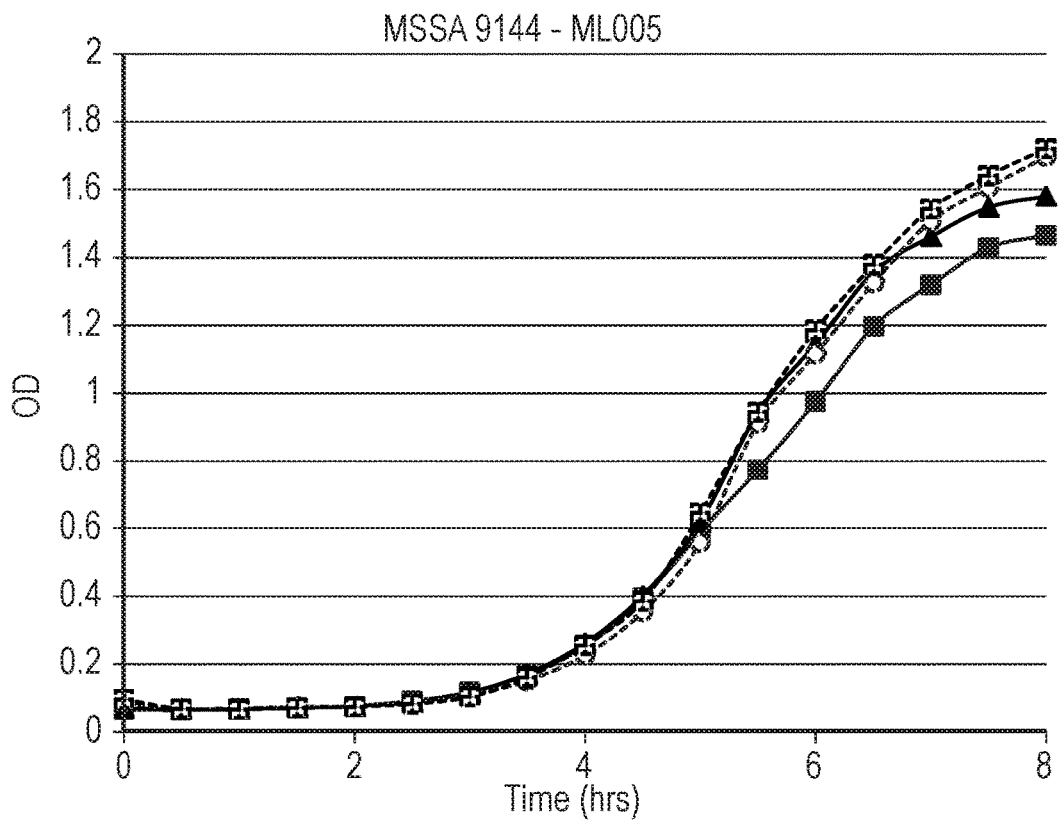
FIG. 18 shows the results for the reserpine assay using napthyl-linked ciprofloxacin (ML-77-005 referred to as ML005) which shows that it is not effluxed by the multidrug-resistant MSSA 9144 strain.
Figure 19:
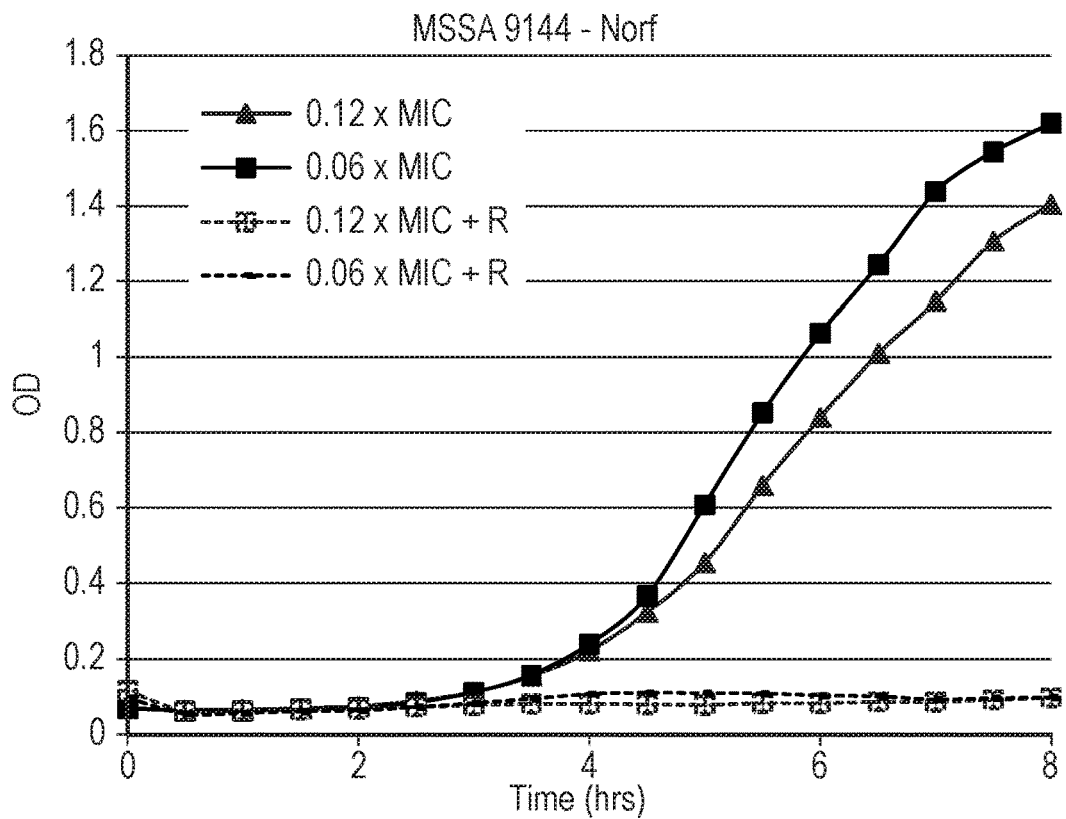
FIG. 19 shows the results for the reserpine assay using norfloxacin (Norf) which shows that it is effluxed by the multidrug-resistant MSSA 9144 strain.
Figure 20:
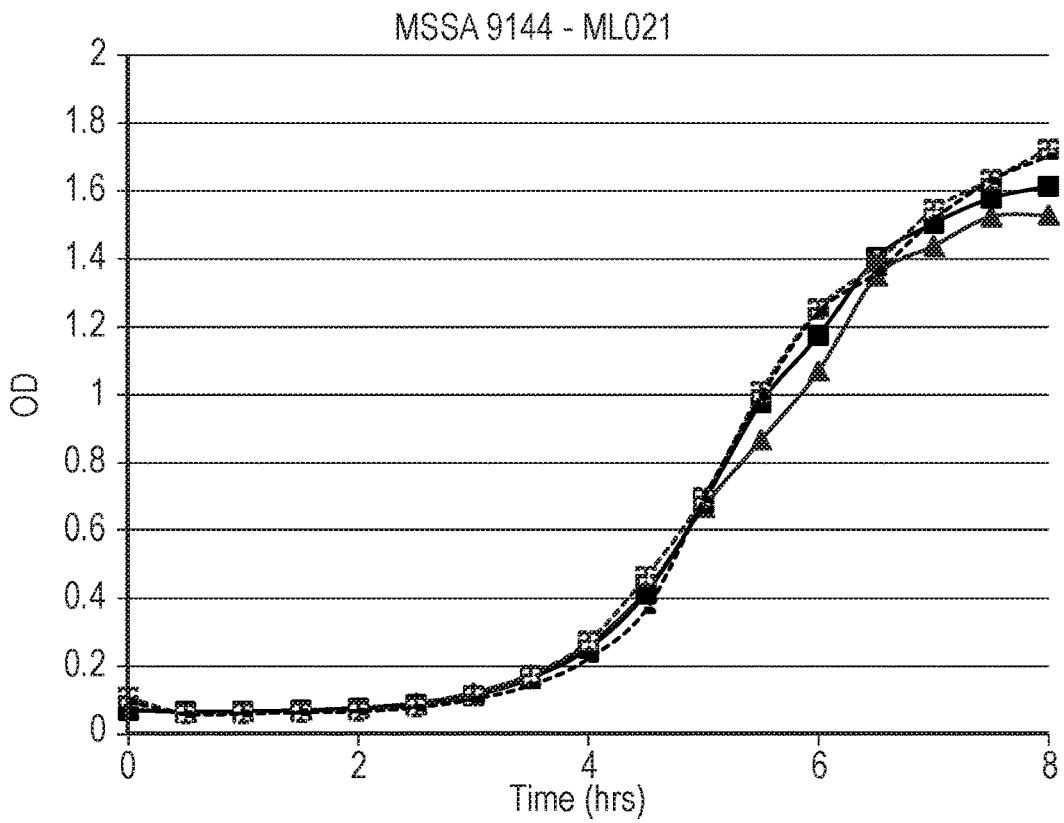
FIG. 20 shows the results for the reserpine assay using napthyl-linked norfloxacin (ML-77-021 referred to as ML021 in the figures) which shows that it is not effluxed by the multidrug-resistant MSSA 9144 strain.
Figure 21:
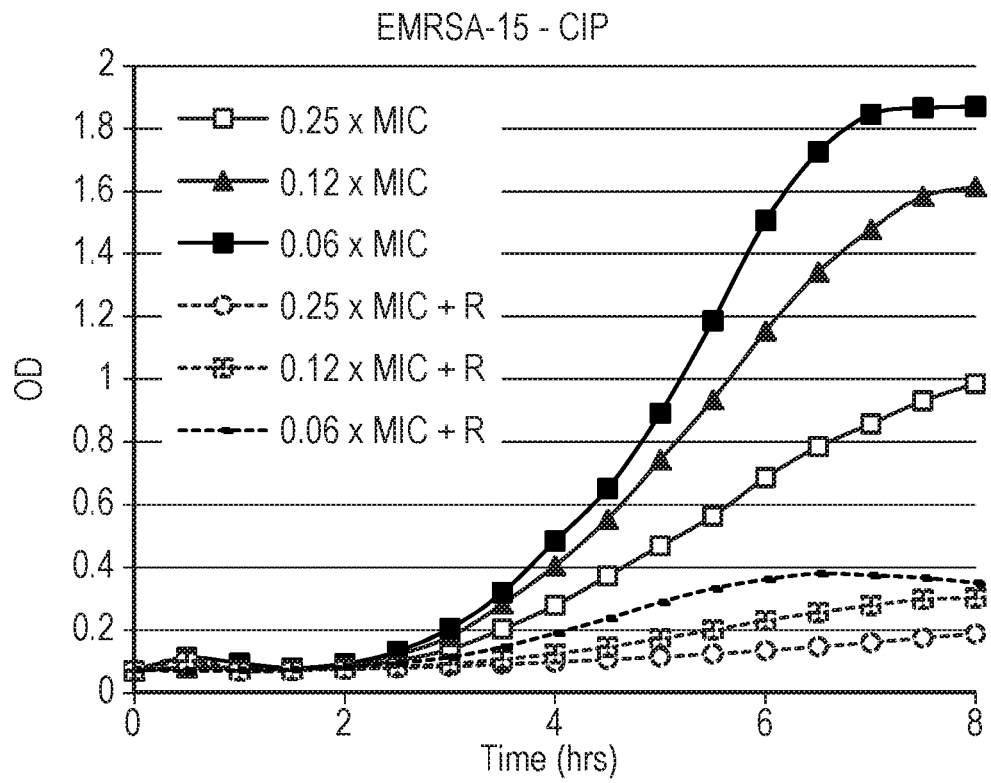
FIG. 21 show the results for the reserpine assay using ciprofloxacin (CIP) which shows that it is effluxed by the multidrug-resistant EMRSA 15 strain.
Figure 22:
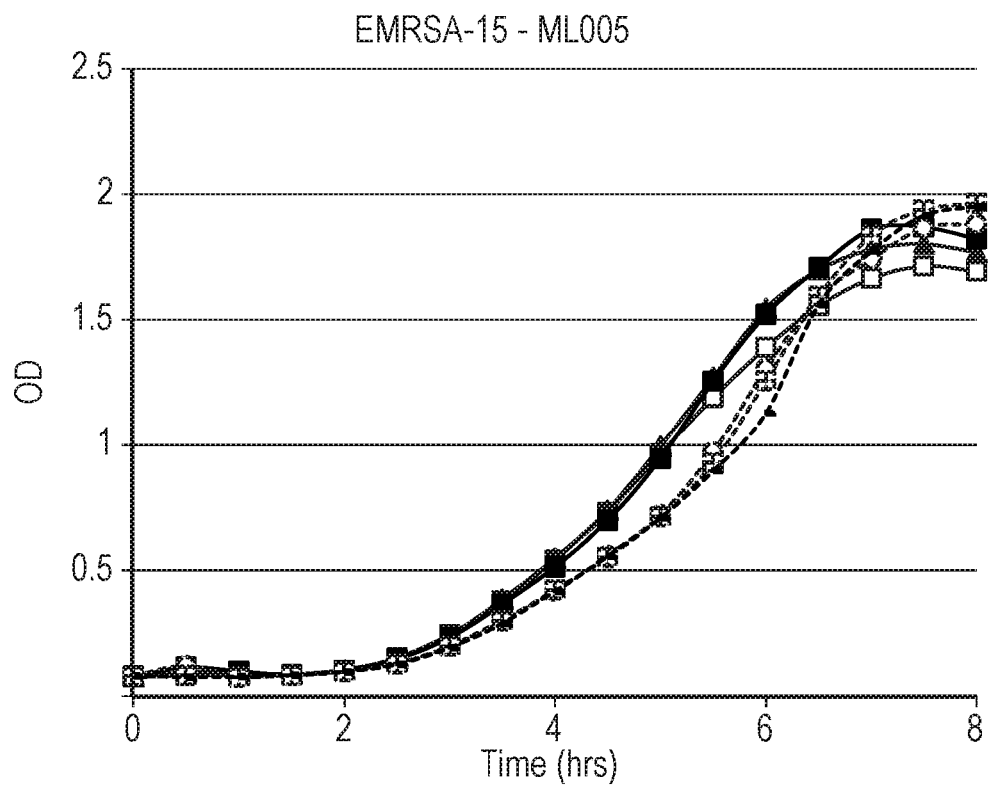
FIG. 22 shows the results for the reserpine assay using napthyl-linked ciprofloxacin ML-77-005 (labelled ML005 in the figure) which shows that it is not effluxed by the multidrug-resistant EMRSA 15 strain.
Figure 23:
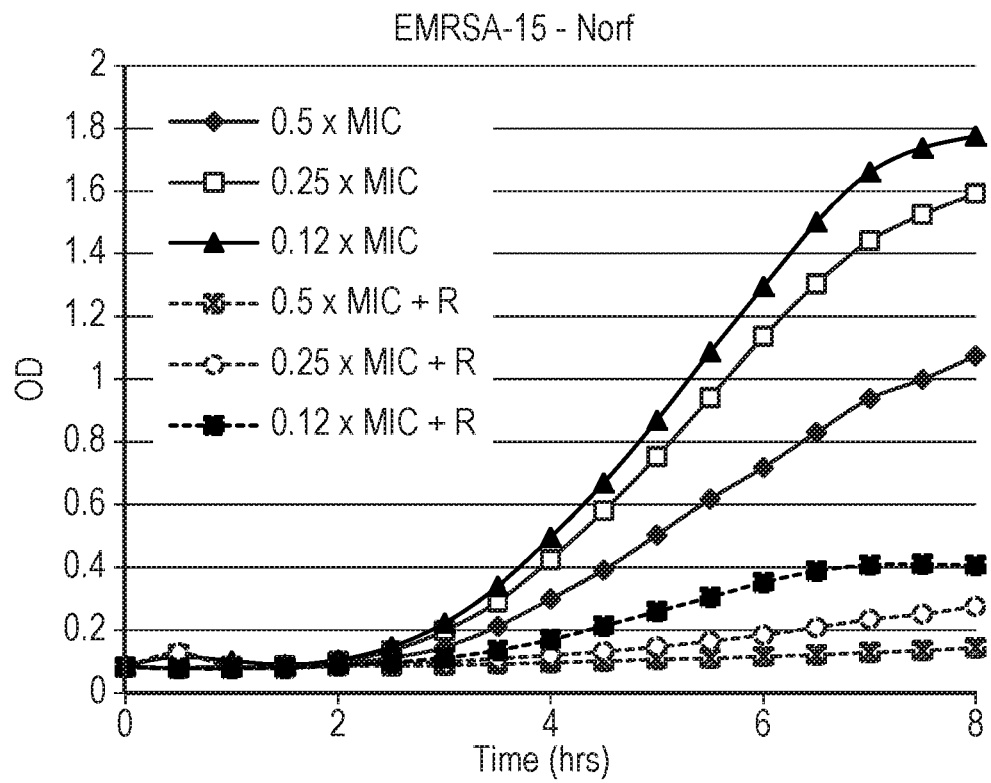
FIG. 23 show the results for the reserpine assay using norfloxacin (Norf) which shows that it is effluxed by the multidrug-resistant EMRSA 15 strain.
Figure 24:
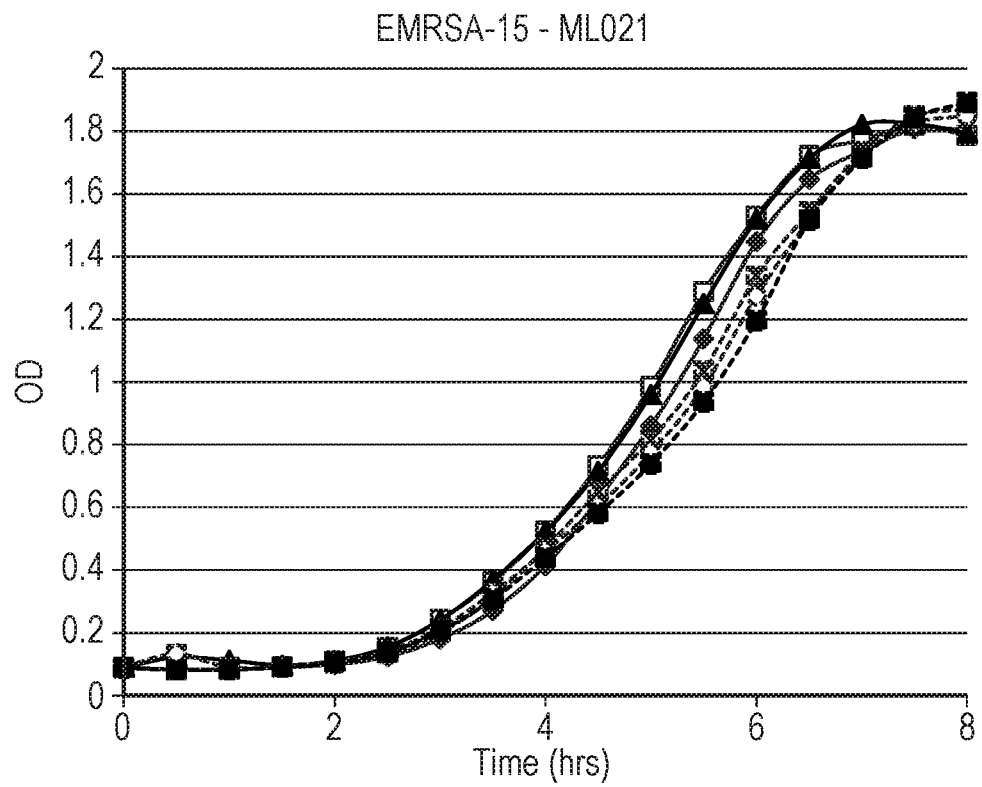
FIG. 24 shows the results for the reserpine assay using napthyl-linked norfloxacin which shows that it is not effluxed by the multidrug-resistant EMRSA 15 strain.

The identified ARB-fragment was linked to the fluoroquinolone (initially ciprofloxacin was used as the model fluoroquinolone) and advanced MD simulations were carried out to ensure the ARB-linked fluoroquinolone still occupied the same binding domain of DNA gyrase (FIG. 2). However, only ML-77-05 was able to interact with the EPI binding domain of the NorA efflux pump, ciprofloxacin was not able to interact with this binding domain (FIG. 3).

Molecular Models of Key Efflux Pumps in ESKAPE Pathogens and Binding Pockets of Ligands that were Utilized to Identify the ARB Fragments Gram-Negative Species:

*Acinetobacter baumannii* AYE, NCTC13424
*Klebsiella pneumoniae* MGH78578, NTUH K2044
*Pseudomonas aeruginosa* PAO1, PA14
*Escherichia coli*

Gram-Positive Species:

*Enterococcus faecalis* (*Streptococcus faecalis*)
*Enterococcus faecium* (*Streptococcus faecium*)
*Staphylococcus aureus*

TABLE 1

Details of multidrug efflux pumps in ESKAPE pathogens utilized to identify the ARB fragments

| Species | Strain | Multidrug Efflux Pump | Type | Template |
|---|---|---|---|---|
| *Acinetobacter* | AYE | AdeB | RND | 3aoa |
| *baumannii* | — | NorM | MATE | 3mkt |
| *Klebsiella* | MGH 78578 | AcrB | RND | 2j8s |
| *pneumoniae* | MGH 78578 | MdtK | MATE | 3mku |
| *Pseudomonas* | PAO1 | MexB | RND | 3w9i |
| *aeruginosa* | PAO1 | PmpM | MATE | 3mku |
|  | PA14 | MexB | RND | 3w9i |
|  | PA14 | MexF | RND | 3w9j |
| *Escherichia coli* | K12 | AcrB | RND | 3aoc |
|  | GM4792 | MdtK | MATE | 3mku |
| *Enterococcus* | — | EmeA | MFS | 3wdo |
| *faecalis* | — | OqxD | RND | 2v5o |
| (*Streptococcus faecalis*) | — | EfrB | ABC | 3qf4 |
| *Enterococcus* | — | EfmA | MFS | 1pw4 |
| *faecium* | E980 | EfmE | MATE | 5c6o |
| (*Streptococcus faecium*) |  |  |  |  |
| *Staphylococcus* | N315 | SdrM | MFS | 4w6v |
| *aureus* | N315 | MepA | MATE | 4lz6 |
|  | NCTC 8325 | MepA | MATE | 3wbn |
|  | — | QacA | MFS | 4zpo |
|  | — | NorA | MFS | 3wdo |

Molecular models of various of the above key efflux pumps in ESKAPE pathogens and binding pockets of ligands that were utilized to identify the ARB fragments are shown in FIGS. 4 to 16.

Biological Data
NorA-Targeting Series
MIC Data

With regard to the Gram positive bacteria in Table 1, MSSA 9144 is methicillin sensitive *S. aureus* ATTC 9144 (NCTC 6571); EMRSA15 is a strain endemic to UK hospitals (NCTC 13616, HO 5096 0412); EMRSA16 is a representative of the epidemic EMRSA16 lineage endemic in UK hospitals (NCTC 13277, MRSA252); VSE 775 is *E. faecalis* VSE NCTC 775; VRE 12201 is *E. faecalis* VRE NCTC 12201 and VRE 12204 is *E. faecium* VRE NCTC 12204.

MIC Tests

The synthesized conjugate ML-77-005 was tested against MDR Gram-positive strains that over-express NorA efflux pump. ML-77-005 showed a 128 to 64 fold reduction in MIC compared to ciprofloxacin in EMRSA-15 and EMRSA-16. This is highly surprising as compositions comprising combinations of an efflux pump inhibitors and an antibiotic usually result in 2-8 fold potentiation of MIC without any significant effect of antimicrobial resistance. Retention of activity in strains which are susceptible to fluoroquinolones (e.g. Ab17978, VSE/VRE strains) suggests that the molecule is fully functional. This is a very significant observation as for the first time an efflux pump-targeting ARB has re-sensitised resistant bacteria to an antibacterial agent (see MIC data in Table 2).

A range of further ARB-linked ciprofloxacin compounds were prepared and tested. It was possible to establish a well-defined SAR profile and the hydrophobicity of the ARB-linked fluoroquinolones played an important role in reversing the multiple drug resistance and re-sensitising the bacteria (see Table 2).

The complete structure of the ciprofloxacin derivatives shown in Table 2 are arrived at by replacing the hydrogen of the NH in ciprofloxacin with the bond indicated by the zig-zag line to the fragment structure. The complete structure of the fragment ML-77-005 can also be seen, for example, as compound (2.2) in the organic synthesis section, and the complete structure of the HCl salt ML-77-023 can be seen as compound (2.3).

TABLE 2

MIC Data for Ciprofloxacin and Ciprofloxacin Derivatives

| Freebase Code<br>HCl Salt Code | Ciprofloxacin | | ML-77-005 (2.2)<br>ML-77-023 (2.3) | | ML-77-036 (2.4)<br>ML-77-044 (2.5) | ML-77-048 (2.12)<br>ML-77-061 (2.13) |
|---|---|---|---|---|---|---|
| Structure | (ciprofloxacin structure) | | (naphthyl structure) | | (naphthyl structure) | (fluoronaphthyl structure) |
| | Normal | | | +PMBN | | |
| Gram Negative | | | | | | |
| KP13368 | 0.5 | | >128 | 2 | 64-128 | 128 |
| M6 | 0.125 | | 32-64 | 0.5 | 4-32 | 64 |
| AYE | >128 | | >128 | 32 | >128 | >128 |
| Ab17978 | 0.25 | | 4 | –.12-0.25 | 8 | 8 |
| PA01 | 0.25 | | >128 | <0.12-0.25 | 128 | 128 |
| PA13437 | 64 | | 128 | 32 | >128 | >128 |
| Gram Positive | | | | | | |
| MSSA9144 | 0.25 | | | 0.25-8 | 0.12 | 4 |
| EMRSA15 | 128 | | | 2 | 2 | 4 |
| EMRSA16 | 128 | | | 2 | 2 | 8 |
| VSE775 | 1 | | | 0.5 | 0.5-2 | 8 |
| VRE12201 | 0.5 | | | 2 | 0.5 | 8 |
| VRE12204 | 1 | | | | 2 | N/A |

TABLE 2-continued

MIC Data for Ciprofloxacin and Ciprofloxacin Derivatives

| Freebase Code<br>HCl Salt Code | ML-77-052 (2.16)<br>ML-77-063 (2.17) | ML-77-058 (2.14)<br>ML-77-089 (2.15) | ML-77-171 (2.25)<br>ML-77-177 (2.26) | ML-77-168 (2.28)<br>ML-77-175 (2.29) | ML-77-078 (2.10)<br>ML-77-090 (2.11) | ML-77-032 (2.8)<br>ML-77-038 (2.9) |
|---|---|---|---|---|---|---|
| Structure | | | | | | |
| Gram Negative | | | | | | |
| KP13368 | 32 | 32 | N/A | N/A | 64-128 | 32 |
| M6 | 4 | 4-32 | N/A | N/A | 32 | 2 |
| AYE | 128 | >32 | N/A | N/A | >128 | 64 |
| Ab17978 | 0.25 | >32 | N/A | N/A | 4-8 | 0.25 |
| PA01 | 32 | 32 | N/A | N/A | 128 | 16 |
| PA13437 | >128 | >32 | N/A | N/A | >128 | >128 |
| Gram Positive | | | | | | |
| MSSA9144 | 0.5 | 0.25-1 | 0.5 | 1 | <0.12 | 0.25-1 |
| EMRSA15 | 64 | >32 | 2-4 | 1-2 | 2 | 64 |
| EMRSA16 | 128 | >32 | 4 | 1 | 2 | 64 |
| VSE775 | 4 | 32 | 4 | 2 | 2-4 | 2 |
| VRE12201 | 2 | 0.5-4 | 2 | 0.25-0.5 | 0.5 | 1 |
| VRE12204 | N/A | 32 | 4 | 1 | 1-2 | N/A |

TABLE 2-continued
MIC Data for Ciprofloxacin and Ciprofloxacin Derivatives
| Freebase Code / HCl Salt Code | ML-77-076 (2.18) / ML-77-083 (2.19) | ML-77-046 (2.6) / ML-77-054 (2.7) | | ML-77-149 (2.30) / ML-77-155 (2.31) | ML-77-112 (2.20) / ML-77-119 (2.21) | ML-77-135 (2.32) / ML-77-145 (2.33) |
|---|---|---|---|---|---|---|
| Structure | 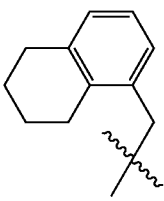 | 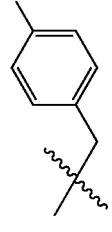 | 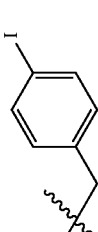 | 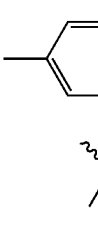 | 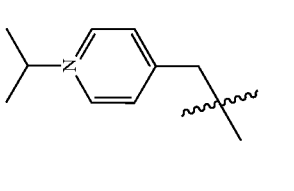 | 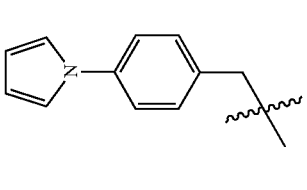 |
| Gram Negative | | | | | | |
| KP13368 | 128 | 16 | N/A | 31-64 | 16 | N/A |
| M6 | 8 | 2 | N/A | 4-8 | 1-2 | N/A |
| AYE | >128 | 64-128 | N/A | >128 | >128 | N/A |
| Ab17978 | 128 | 0.25 | N/A | 4 | 0.5-1 | N/A |
| PA01 | 128 | 16-32 | N/A | 32 | 8 | N/A |
| PA13437 | >128 | >128 | N/A | 128 | >128 | N/A |
| Gram Positive | | | | | | |
| MSSA9144 | 0.25 | 0.12-0.25 | 0.12-0.25 | 0.25 | 0.0625-0.125 | 0.5 |
| EMRSA15 | 1 | 16-32 | 4 | 4-8 | 8-16 | 16 |
| EMRSA16 | 1-2 | 32 | 4 | 8 | 16-32 | 16 |
| VSE775 | 2 | 2-4 | 2 | 2-4 | 0.25-1 | 4-8 |
| VRE12201 | 1-2 | 1-2 | 1-2 | 1 | 0.125-0.5 | 2 |
| VRE12204 | 1-2 | 4-8 | 4 | 8 | 1 | 16 |

TABLE 2-continued

MIC Data for Ciprofloxacin and Ciprofloxacin Derivatives

| Freebase Code<br>HCl Salt Code | ML-77-162 (2.34)<br>ML-77-165 (2.35) | (2.36)<br>ML-83-006 (2.37) | ML-77-157 (2.38)<br>ML-77-160 (2.39) | ML-77-163 (2.40)<br>ML-77-166 (2.41) | ML-77-133 (2.42)<br>ML-77-141 (2.43) |
|---|---|---|---|---|---|
| Structure | pyrrole-phenyl | triazole-phenyl | thiadiazole-phenyl | methyl-oxadiazole-phenyl | biphenyl |
| Gram Negative | | | | | |
| KP13368 | 4-8 | N/A | 16 | 16-64 | 8 |
| M6 | 0.5-1 | N/A | 1 | 2 | 1 |
| AYE | 128 | N/A | >128 | 128->128 | >128 |
| Ab17978 | 0.5 | N/A | 0.25-0.5 | 0.5-1 | 2 |
| PA01 | 16-32 | N/A | 16 | 32 | 4 |
| PA13437 | 128 | N/A | >128 | 128 | |
| Gram Positive | | | | | >128 |
| MSSA9144 | ≤0.12 | 0.12 | <0.12 | ≤0.12 | 1 |
| EMRSA15 | 16 | 16-32 | 4 | 16 | 2 |
| EMRSA16 | 32 | 16 | 8 | 32 | 2 |
| VSE775 | 1-2 | 1 | 0.5 | 1-2 | 2 |
| VRE12201 | 1 | 0.5 | 0.5 | 1 | 4 |
| VRE12204 | 16 | 8 | 4-8 | 16 | 2 |

The same ARB-fragment as ML-77-005 was covalently linked to norfloxacin (see ML-77-021 in Table 3), another 4-fluoroquinolone antibiotic, as norfloxacin suffers from the same efflux-mediated resistance. Again, the ARB-linked norfloxacin was able to re-sensitise the resistant EMRSA-15 and EMRSA-16 strains without any loss of activity against sensitive strains. A range of further ARB-linked norfloxacin compounds were prepared and tested and the results are also give in Table 3. The complete structure of the norfloxacin derivatives shown in Table 3 are arrived at by replacing the hydrogen of the NH in norfloxacin with the bond indicated by the zig-zag line to the fragment structure.

TABLE 3

MIC Data for Norfloxacin and Norfloxacin Derivatives

| Freebase Code | Norfloxacin | ML-77-021 (3.2) ML-77-024 (3.3) | | ML-77-031 (3.4) ML-77-037 (3.5) | ML-77-049 (3.12) ML-77-062 (3.13) |
|---|---|---|---|---|---|
| HCl Salt Code | | | | | |
| Structure | | | | | |
| | | Normal | +PMBN | | |
| Gram Negative | | | | | |
| KP13368 | 4 | >32 | 4-8 | 128 | >128 |
| M6 | 0.25 | 32 | 1-4 | 16-32 | 128 |
| AYE | >128 | >32 | >32 | >128 | >128 |
| Ab17978 | 4 | 32 | 0.5 | 128 | 128 |
| PA01 | 2 | >32 | 0.06-0.25 | >128 | 128 |
| PA13437 | 128 | >32 | >32 | >128 | >128 |
| Gram Positive | | | | | |
| MSSA9144 | 2 | 1 | | 0.25 | 8 |
| EMRSA15 | >128 | 2 | | 4 | 8 |
| EMRSA16 | >128 | 2 | | 4 | 8 |
| VSE775 | 8 | 4 | | 4 | 8 |
| VRE12201 | 4 | 2 | | 4 | 16 |
| VRE12204 | 4 | | | 2 | N/A |

TABLE 3-continued

MIC Data for Norfloxacin and Norfloxacin Derivatives

| Freebase Code / HCl Salt Code | ML-77-053 (3.16) ML-77-064 (3.17) | ML-77-059 (3.14) ML-77-082 (3.15) | ML-77-173 (3.22) ML-77-178 (3.23) | ML-77-169 (3.24) ML-77-176 (3.25) | ML-77-079 (3.10) ML-77-091 (3.11) | ML-77-035 (3.8) ML-77-043 (3.9) |
|---|---|---|---|---|---|---|
| Structure | (quinoline) | (2-oxo-quinoline) | (naphthyl-propyl) | (naphthyl-methyl) | (benzothiophene) | (benzodioxole) |
| Gram Negative | | | | | | |
| KP13368 | 64 | >32 | N/A | N/A | 128 | 128 |
| M6 | 8 | 16 | N/A | N/A | 32 | 8-16 |
| AYE | >128 | >32 | N/A | N/A | 128 | >128 |
| Ab17978 | 4 | 32 | N/A | N/A | 128 | 2-4 |
| PA01 | 64 | >32 | N/A | N/A | 128 | 64-128 |
| PA13437 | 128 | >32 | N/A | N/A | 128 | >128 |
| Gram Positive | | | | | | |
| MSSA9144 | 1 | 16-32 | 2-4 | 2 | 0.25 | 0.5 |
| EMRSA15 | 128 | >32 | 4 | 1-2 | 2 | >32 |
| EMRSA16 | 128 | >32 | 4-8 | 1 | 2 | >32 |
| VSE775 | 16 | >32 | 4-8 | 2 | 4 | 8 |
| VRE12201 | 8 | >32 | 4 | 2 | 0.5-2 | 4 |
| VRE12204 | N/A | >32 | 4 | 1 | 1-2 | 8 |

TABLE 3-continued

MIC Data for Norfloxacin and Norfloxacin Derivatives

| Freebase Code HCl Salt Code | ML-77-077 (3.18) ML-77-084 (3.19) | ML-77-047 (3.6) ML-77-055 (3.7) | ML-77-150 (3.26) ML-77-156 (3.27) | ML-77-113 (3.20) ML-77-120 (3.21) | ML-77-136 (3.28) ML-77-151 (3.29) | (3.30) ML-83-004 (3.31) |
|---|---|---|---|---|---|---|
| Structure | | | | | | |
| Gram Negative | | | | | | |
| KP13368 | 128 | 32 | >128 | 32 | 64-128 | N/A |
| M6 | 64 | 4 | 32-64 | 4-16 | 8-32 | N/A |
| AYE | >128 | 128 | >128 | >128 | >128 | N/A |
| Ab17978 | 32-128 | 1-16 | 16 | 2 | 16-32 | N/A |
| PA01 | 128 | 32 | 128 | 16-32 | 64-128 | N/A |
| PA13437 | >128 | >128 | 128 | >128 | >128 | N/A |
| Gram Positive | | | | | | |
| MSSA9144 | 1 | 0.25 | 0.5-1 | 0.125-0.25 | 0.25-0.5 | 0.5 |
| EMRSA15 | 2 | 16 | 4-8 | 16-32 | 8 | 16-32 |
| EMRSA16 | 2 | 16-32 | 4-8 | >32 | 8-16 | 32 |
| VSE775 | 2 | 4 | 8 | 4-8 | 4-8 | 8 |
| VRE12201 | 2 | 2 | 2 | 2 | 4-8 | 4-8 |
| VRE12204 | 1-2 | 4 | 4-8 | 0.25 | 4-8 | 16 |

TABLE 3-continued
MIC Data for Norfloxacin and Norfloxacin Derivatives
| Freebase Code | (3.32) | ML-77-161 (3.34) | (3.36) | ML-77-134 (3.38) |
|---|---|---|---|---|
| HCl Salt Code | ML-83-007 (3.33) | ML-77-164 (3.35) | ML-83-005 (3.37) | ML-77-142 (3.39) |
| Structure | 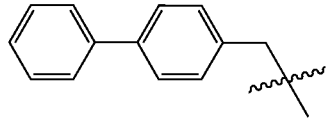 | 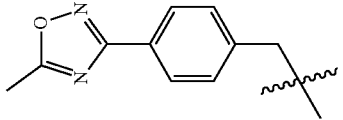 | 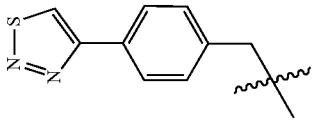 | 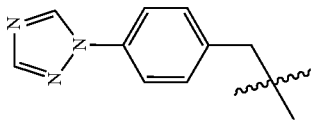 |
| Gram Negative | | | | |
| KP13368 | N/A | 64 | N/A | >128 |
| M6 | N/A | 4-8 | N/A | 64 |
| AYE | N/A | 128->128 | N/A | >128 |
| Ab17978 | N/A | 2 | N/A | 128 |
| PA01 | N/A | 64 | N/A | >128 |
| PA13437 | N/A | 128 | N/A | >128 |
| Gram Positive | | | | |
| MSSA9144 | 1 | <0.12 | 0.25 | 2 |
| EMRSA15 | 128 | 8 | 16-32 | 2 |
| EMRSA16 | 128 | 16 | 32 | 4 |
| VSE775 | 8 | 8 | 8 | 2 |
| VRE12201 | 8 | 4 | 4 | 4 |
| VRE12204 | 16 | 16 | 8 | 2 |

The same ARB-fragment as used for (ML-77-005) was linked to enoxacin, which is another 4-fluoroquinolone antibiotic hampered by efflux-mediated resistance, and testing against the same panel of bacteria. The ARB-linked enoxacin (ML-77-025) similarly re-sensitised the resistant EMRSA strains with 64-128 fold potentiation of MIC (see Table 4). The complete structure of the enoxacin derivatives shown in Table 3 are arrived at by replacing the hydrogen of the NH in enoxacin with the bond indicated by the zig-zag line to the fragment structure.

TABLE 4

MIC Data for Enoxacin and a Enoxacin Derivative

| Freebase Code | Enoxacin | ML-77-025 (4.2) |
|---|---|---|
| HCl Salt Code | | ML-77-034 (4.3) |
| Structure | 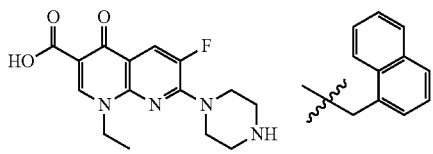 | 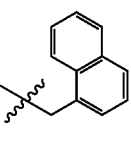 [SMILES: *Cc1cccc2ccccc12] |
| MSSA9144 | 2 | 0.5-1 |
| EMRSA15 | >128 | 2-8 |
| EMRSA16 | 128 | 2-4 |
| VSE775 | 16 | 16 |
| VRE12201 | 8 | 8 |
| VRE12204 | 4-8 | 4 |

The same ARB-fragment as used for (ML-77-005) was linked to levofloxacin, which is another 4-fluoroquinolone antibiotic, and testing against the same panel of bacteria. The ARB-linked levofloxacin (ML-77-140) similarly re-sensitised the resistant EMRSA strains (see Table 5). The complete structure of the levofloxacin derivatives shown in Table 3 are arrived at by replacing the methyl group of the N—CH$_3$ in enoxacin with the bond indicated by the zig-zag line to the fragment structure.

TABLE 5

MIC Data for Levofloxacin and a Levofloxacin Derivative

| Freebase Code | Levofloxacin | ML-77-140 (5.2) |
|---|---|---|
| HCl Salt Code | | ML-77-144 (5.3) |
| Structure | 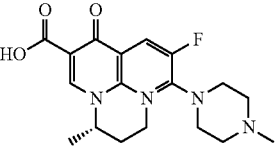 | 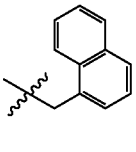 [SMILES: *Cc1cccc2ccccc12] |
| MSSA9144 | 0.125 | 0.125-1 |
| EMRSA15 | 16 | 4 |
| EMRSA16 | 16 | 2-4 |
| VSE775 | 1 | 1-2 |
| VRE12201 | 0.5-1 | 0.5-1 |
| VRE12204 | 1-2 | 1-2 |

ARB-linked ciprofloxacin (ML-77-05) and ARB-linked norfloxacin (ML-7-021) were subsequently tested against a wider panel of 4-fluoroquinolone-resistant *Streptococcus* and *Enterococcus* strains. Both conjugate compounds were able to re-sensitise resistant bacterial strains including cases where resistance is due to mutations in DNA gyrases (Table 6). This was surprising and suggests that reversing efflux-mediated resistance can also reverse other associated resistance mechanisms including mutations due to the presence of high intracellular concentrations of ARB-linked antibiotic.

TABLE 6

ML-77-005/023 and ML-77-021/024 Extended Gram-positive MIC Panel

| Species | Strain | Chromosomal mutations | CIP | ML-77-005 (2.2) | Fold decrease | NOR | ML-77-021 (3-2) | Fold decrease |
|---|---|---|---|---|---|---|---|---|
| S. epidermidis | SE1 | N/A | 0.5-1 | 0.25-2 | 0.25-4 | 1-4 | 1 | 1-4 |
| S. aureus | SA1 | gyrA, 84:S => L; grlA, 80:S => F | 64-128 | 2 | 32-63 | >128 | 4 | ≥32 |
| S. aureus | SA2 | N/A | 1 | 0.5 | 0.5 | 8-64 | 1 | 8-64 |
| S. aureus | SA3 | gyrA, 84:S => L; grlA, 80:S => F | 32 | 2 | 16 | 64 | 2 | 32 |
| S. haemolyticus | SH1 | N/A | 16 | 4 | 4 | 128 | 4 | 32 |
| S. aureus | SA4 | gyrA, 84:S => L; grlA, 80:S => F | 16 | 2 | 8 | 64 | 2 | 32 |
| S. aureus | SA5 | gyrA, 84:S => L; grlA, 80:S => F | 32-64 | 2 | 16-32 | >128 | 2 | ≥64 |
| S. aureus | SA6 | gyrA, 84:S => V; grlA, 80:S => F | 128 | 2 | 64 | >128 | 2 | ≥64 |
| E. faecalis | EF1 | N/A | 64 | 2 | 32 | >128 | 4 | ≥32 |
| E. faecium | EF2 | N/A | 128 | 2 | 64 | >128 | 2-4 | ≥32 |
| S. aureus | SA7 | gyrA, 84:S => L; grlA, 80:S => F | 64 | 2 | 32 | >128 | 2 | ≥64 |
| S. aureus | SA8 | gyrA, 84:S => L; grlA, 80:S => F | 64 | 2 | 32 | 128 | 2 | 64 |
| S. aureus | SA9 | gyrA, 84:S => L; grlA, 80:S => F | 128 | 2 | 64 | >128 | 2 | ≥64 |
| S. aureus | SA10 | gyrA, 84:S => L; grlA, 80:S => F | 32-64 | 2 | 16-32 | 128 | 2 | 64 |

AdeB-Targeting Series

MIC Data

Further ciprofloxacin linked compounds ML-77-147 and ML-77-138 were prepared and tested against a wider panel of bacteria. The results for these two compounds are provided below in Table 7.

TABLE 7

MIC Data for Ciprofloxacin and Ciprofloxacin Derivatives Against AdeB-targeting Series

| Freebase Code<br>HCl Salt Code | Ciprofloxacin | ML-77-147 (2.44)<br>ML-77-158 (2.45) | ML-77-138 (2.53)<br>ML-77-153 (2.54) | |
|---|---|---|---|---|
| Structure | (ciprofloxacin structure) | (4-hydroxymethylbenzyl structure) | (sulfonamide-indole structure) | |
| Gram Negative | | | Normal | +PMBN |
| KP13368 | 0.5 | 4-8 | 128 | 128 |
| M6 | 0.125 | 0.5-1 | 32-128 | 1 |
| AYE | >128 | 16-32 | 128 | >128 |
| Ab17978 | 0.25 | 0.25-0.5 | 64 | 1 |
| PA01 | 0.25 | 4 | 128 | ≤0.12 |
| PA13437 | 64 | ≥128 | 128 | 128 |
| EC12923 | N/A | N/A | N/A | N/A |
| Gram Positive | | | | |
| MSSA9144 | 0.25 | <0.12 | 0.25-0.5 | |
| EMRSA15 | >128 | 8 | >128 | |
| EMRSA16 | >128 | 8 | >128 | |
| VSE775 | 1 | 1 | 128 | |
| VRE12201 | 0.5 | 0.5 | 128 | |
| VRE12204 | 1 | 4 | >128 | |

| Freebase Code<br>HCl Salt Code | ML-83-050 (2.49)<br>ML-83-056 (2.50) | ML-83-036 (2.51)<br>ML-83-043 (2.52) |
|---|---|---|
| Structure | (4-methoxymethylbenzyl structure) | (3-methoxymethylbenzyl structure) |
| Gram Negative | | |
| KP13368 | 32 | 64 |
| M6 | 2 | 8 |
| AYE | 128 | 128 |
| Ab17978 | 1 | 2 |
| PA01 | 32-64 | 64 |
| PA13437 | >128 | >128 |
| EC12923 | 1 | 4 |
| Gram Positive | | |
| MSSA9144 | 0.25 | 0.5 |
| EMRSA15 | 16-32 | 64 |
| EMRSA16 | 32-64 | 128 |
| VSE775 | 1-2 | 2-4 |
| VRE12201 | 1 | 2-4 |
| VRE122041 | 16 | 16 |

Further norfloxacin linked compounds ML-77-148 and ML-77-146 were prepared and tested against a wider panel of bacteria. The results for these two compounds are provided below in Table 8.

TABLE 8

MIC Data for Norfloxacin and Norfloxacin Derivatives Against AdeB-targeting Series

| Freebase Code | Norfloxacin | ML-77-148 (3.40) | ML-77-146 (3.46) | |
|---|---|---|---|---|
| HCl Salt Code | | ML-77-159 (3.41) | ML-77-154 (3.47) | |
| Structure | (norfloxacin structure) | (4-benzyl-OH structure) | (sulfonamide-indole structure) | |
| | | | Normal | +PMBN |
| Gram Negative | | | | |
| KP13368 | 4 | 32 | >128 | 128 |
| M6 | 0.25 | 4 | 128 | 128 |
| AYE | >128 | 128 | 128 | >128 |
| Ab17978 | 4 | 2 | 128 | 4 |
| PA01 | 2 | 32 | 128 | 0.25 |
| PA13437 | 128 | >128 | 128 | >128 |
| EC12923 | N/A | N/A | N/A | N/A |
| Gram Positive | | | | |
| MSSA9144 | 2 | 0.5 | 8 | |
| EMRSA15 | >128 | 32 | 128 | |
| EMRSA16 | >128 | 32 | >128 | |
| VSE775 | 8 | 4-8 | 128 | |
| VRE12201 | 4 | 4 | 128 | |
| VRE12204 | 4 | 8 | >128 | |

| Freebase Code | ML-83-052 (3.42) | ML-83-037 (3.44) |
|---|---|---|
| HCl Salt Code | ML-83-075 (3.43) | ML-83-044 (3.45) |
| Structure | (4-benzyl-OMe) | (3-benzyl-OMe) |
| Gram Negative | | |
| KP13368 | 64 | 64-128 |
| M6 | 8-16 | 32 |
| AYE | >128 | >128 |
| Ab17978 | 4 | 8 |
| PA01 | 128 | 128 |
| PA13437 | >128 | >128 |
| EC12923 | 4 | 16 |
| Gram Positive | | |
| MSSA9144 | 0.5-1 | 1 |
| EMRSA15 | 64-128 | 64-128 |
| EMRSA16 | 64 | 64 |
| VSE775 | 8-16 | 16 |
| VRE12201 | 8 | 8 |
| VRE12204 | 16 | 16 |

The HCl salt ciprofloxacin linked compound ML-77-158 (structure shown in table 7 above) was also tested against an extended *A. baumannii* panel of bacteria. The results for this panel are provided below in Table 9.

TABLE 9

ML-77-147/158 *A. baumannii* Extended MIC Panel

| Species | Strain | CIP | ML-77-158 | Fold decrease |
|---|---|---|---|---|
| A. baumannii | W1 | 128 | 32 | 4 |
| A. baumannii | OXA23.1 | 128 | 64 | 2 |
| A. baumannii | UKA7 | >512 | 64 | >8 |
| A. baumannii | UKA10 | 256 | 128 | 2 |
| A. baumannii | UKA12 | 512 | 32 | 16 |
| A. baumannii | UKA16 | 128 | 32 | 8 |
| A. baumannii | 13423 | 256 | 128 | 2 |
| A. baumannii | UKA13 | 512 | 32 | 16 |
| A. baumannii | 13302 | 128 | 64 | 2 |
| A. baumannii | UKA1 | 32 | 16 | 2 |
| A. baumannii | A601 | 32 | 8 | 4 |
| A. baumannii | 12156 | 1 | 0.5 | 2 |

MexB-Targeting Series

Two further levofloxacin-linked compounds were prepared and tested against a wider panel of bacteria. The results for these compounds against this wider panel of bacteria are shown in Table 10 below.

TABLE 10

MIC Data for Levofloxacin and Levofloxacin Derivatives Against MexB-targeting Series

| Freebase Code | Levofloxacin | ML-83-019 | ML-83-0018 (5.8) | ML-83-001 (5.6) | ML-83-011 (5.4) |
|---|---|---|---|---|---|
| HCl Salt Code | | | ML-83-025 (5.9) | ML-83-009 (5.7) | ML-83-012 (5.5) |

Structure

| Gram Negative | | | | Normal | +PMBN | |
|---|---|---|---|---|---|---|
| KP13368 | 1-2 | 128 | 32 | 64 | 4 | 64 |
| M6 | 0.125 | 64 | 8 | 8 | 0.5 | 16-64 |
| AYE | 8 | >128 | 128 | 128 | 64 | 128 |
| Ab17978 | 0.125 | 64 | 2 | 4 | 1 | 16 |
| PA01 | 1-4 | 128 | 64 | 32 | 1 | 128 |
| PA13437 | 64-128 | >128 | >128 | >128 | 32 | 128 |
| EC12923 | N/A | 32 | 2-4 | 1-4 | N/A | 1-8 |
| Gram-Positive | | | | | | |
| MSSA9144 | 0.125 | 64 | ≤0.12 | | 0.06 | 0.25 |
| EMRSA15 | 16 | >128 | 4 | | 4 | 16 |
| EMRSA16 | 16 | >128 | 8 | | 4 | 16 |
| VSE775 | 1 | 128 | 0.25-0.5 | | 0.25 | 1 |
| VRE12201 | 0.5-1 | 128 | 0.25 | | 0.25 | 0.5-1 |
| VRE12204 | 1-2 | >128 | 2 | | 2 | 8 |

| Freebase Code | ML-83-032 | ML-83-041 (5.10) | 82-KSN-L6 | 82-KSN-L7 (5.14) | 82-KSN-L8 |
|---|---|---|---|---|---|
| HCl Salt Code | | ML-83-054 (5.11) | | ML-83-073 (5.15) | |

Structure

| Gram Negative | | | | | |
|---|---|---|---|---|---|
| KP13368 | 32 | 32 | 64 | 16 | 32 |
| M6 | 4 | 4 | 32 | 2-4 | 4 |
| AYE | >128 | >128 | >128 | 64 | 128 |
| Ab17978 | 2 | 4-8 | 16 | 1 | 2 |
| PA01 | 32 | 64 | 64 | 16 | 32 |
| PA13437 | >128 | >128 | >128 | 128 | 128 |
| EC12923 | 4 | 2 | 2 | 1 | 4 |

TABLE 10-continued

MIC Data for Levofloxacin and Levofloxacin Derivatives Against MexB-targeting Series Gram-Positive

| Strain | | | | | |
|---|---|---|---|---|---|
| MSSA9144 | ≤0.12 | 2 | 2 | ≤0.125-4 | ≤0.12 |
| EMRSA15 | 4 | >128 | >128 | 4 | 8 |
| EMRSA16 | 4 | >128 | >128 | 4 | 16 |
| VSE775 | 0.5 | 8 | 8 | 1-2 | 4 |
| VRE12201 | 0.5 | 8 | 8 | 0.5 | 2 |
| VRE12204 | 4 | 16 | 16 | 4 | 4 |

| | | | |
|---|---|---|---|
| Freebase Code | ML-83-032 | ML-83-041 (5.16) | 82-KSN-L6 |
| HCl Salt Code | | ML-83-054 (5.17) | |

Structure (shown as chemical diagrams)

Gram Negative

| Strain | | | |
|---|---|---|---|
| KP13368 | 8 | 16-32 | 16 |
| M6 | 1 | 2 | 8 |
| AYE | 16 | 64-128 | 128 |
| Ab17978 | 0.25-0.5 | 1 | 1 |
| PA01 | 8 | 16-32 | 16 |
| PA13437 | 128 | >128 | >128 |
| EC12923 | 0.5 | 1-2 | 1 |

Gram-Positive

| Strain | | | |
|---|---|---|---|
| MSSA9144 | 0.5 | ≤0.125 | ≤0.12 |
| EMRSA15 | 32 | 4-8 | 8 |
| EMRSA16 | 16 | 8 | 16 |
| VSE775 | 2 | 1 | 1 |
| VRE12201 | 2 | 0.5-1 | 0.5-1 |
| VRE12204 | 4 | 4 | 4 |

TABLE 11

Evidence of reversal of efflux mediated resistance observed using ARB technology in fluoroquinolones

| Species | Strain Name | Levofloxacin | Ciprofloxacin | KSN-L22 | Chromosomal mutations (quinolones) | Fold change |
|---|---|---|---|---|---|---|
| S. aureus | SA238 | 32 | >64 | 1 | gyrA, 84:S => L; grlA, 80:S => F | 32-64 |
| S. aureus | SA215 | 32 | 64-128 | 1 | gyrA, 84:S => L; grlA, 80:S => F | 32-128 |
| S. aureus | SA454 | 8 | >64 | 1 | gyrA, 84:S => L; grlA, 80:S => F | 8-64 |
| S. aureus | SA282 | 16 | >64 | 1 | gyrA, 84:S => L; grlA, 80:S => F | 16-64 |
| S. aureus | SA275 | 8 | 128 | 1 | gyrA, 84:S => V; grlA, 80:S => F | 8-128 |
| S. aureus | SA046 | 16 | >64 | 1 | gyrA, 84:S => L; grlA, 80:S => F | 16-64 |

TABLE 11-continued

Evidence of reversal of efflux mediated resistance observed using ARB technology in fluoroquinolones

| Species | Strain Name | Levofloxacin | Ciprofloxacin | KSN-L22 | Chromosomal mutations (quinolones) | Fold change |
|---|---|---|---|---|---|---|
| S. aureus | SA275 | 16 | 128 | 1 | gyrA, 84:S => L; grlA, 80:S => F | 16-128 |
| S. aureus | EMRSA15 | 16 | 128 | 0.5-1 | gyrA, 84:S => L; grlA, 80:S => F | 32-256 |
| S. aureus | EMRSA16 | 16 | 128 | 1 | gyrA, 84:S => L; grlA, 80:S => F | 16-128 |

Using a unique approach of antibiotic resistance breakers, that has never been adopted or tested by researchers working in the field, has resulted in surprising potentiation of the modified antibiotic by up to 128 fold which has never been observed before. A traditional approach of combining an efflux pump inhibitors with antibiotics typically result in 4-8 fold potentiation, which is not enough to reverse efflux mediated resistance. We have been able to use this unique approach to reverse efflux mediated resistance in a number of multiple drug resistance pathogens with multiple target mutations using fluoroquinolones as model antibiotics (Table 11). The ability of these molecules to reverse efflux mediated resistance was studied using MIC testing against MDR pathogens, and the inability of bacteria to efflux these molecules was tested using a reserpine growth assay.

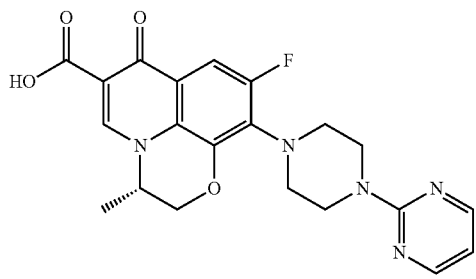

Linear molecule with less flexibility
ML-83-009

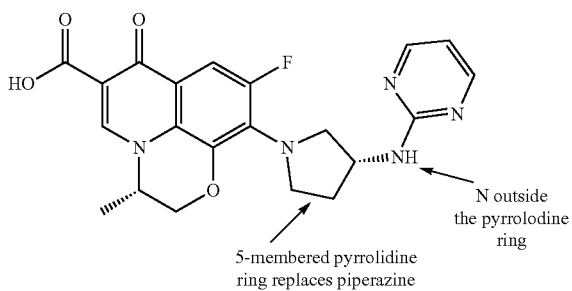

5-membered pyrrolidine ring replaces piperazine

Flexible ARB unit due to exocyclic amine
KSN-L-22

Modification of ML-83-009 with six membered piperazine ring to 5-membered pyrrolidine ring to develop ARB s.

Figure 26:
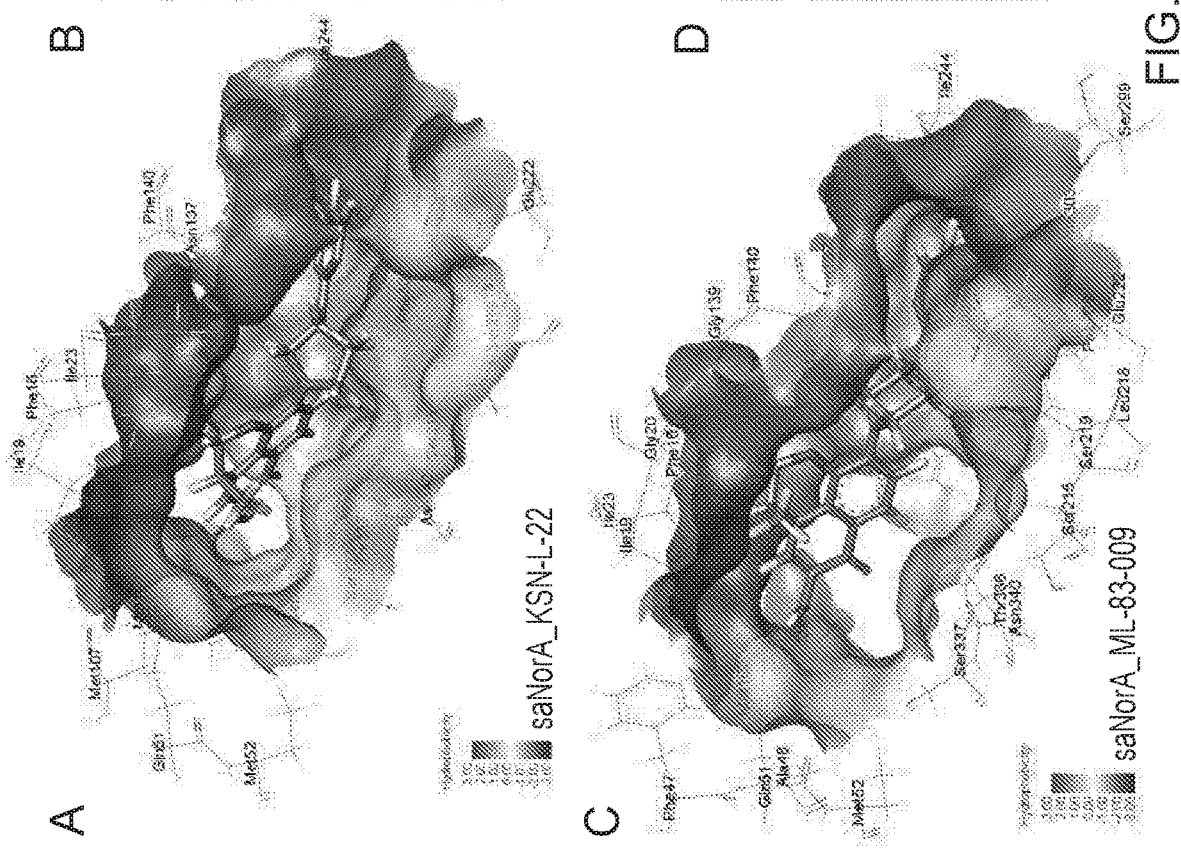
FIG. 26A-26D shows A: compound (KSN-L22) in interaction with the key residues in NorA, B: the five membered pyrrolidine with excocyclic amine group provides additional flexibility and curvature, C: & D: relatively linear structure of six membered piperazine ring containing ML-83-009 doesn't interact efficiently with the key residues.

One of the identified ARB fragments contained a six-membered piperazine ring connected directly to a pyrimidine ring via N—C coupling. This first generation ARB-modified ML-83-009 was weakly inhibiting efflux. Further MD simulations revealed its contact with the key residues were not sufficiently strong to prevent its efflux. Molecular modelling revealed that the molecule cannot fit snugly within the binding pocket and interact with key residues due to its linear shape and relative rigidity of the piperazine ring containing ARB. This information was used to convert the 6-membered piperazine ring to a 5-membered pyrrolodine ring, and take the second nitrogen outside the ring. Finally, the pyrimidine ring was connected with the amine group that was placed outside the ring. This provided additional flexibility to the ARB fragment and allowed the terminal pyrimidine ring to form to rotate and form curved structure that allowed optimum contact with the key residues which was not possible with the rigid linear six-membered piperzine ring linked ARB fragment. This has been illustrated below with NorA efflux pump in S. aureus as an example (FIG. 26). NorA is overexpressed in MRSA and is responsible for efflux mediated resistance.

This flexibility of the terminal ARB fragment with the key residues were only observed when the amine group was placed outside the five membered ring, as the molecule with a seven membered diazepine ring did not provide adequate contact due to relatively linear and inflexible nature of the molecule.

TABLE 12

Superiority of 5-member pyrrolidine ring with exocyclic amine as part of ARB fragment.

| | ML-83-009<br>6-member ring | KSN-L22<br>5-member ring with<br>exocyclic amine | ML-83-034<br>7-member ring |
|---|---|---|---|
| | MIC (µg/mL) | | |
| Staphylococcus aureus (EMRSA15) | 4 | 0.5-1 | 8 |
| Staphylococcus aureus (EMRSA16) | 4 | 1 | 16 |

Figure 27E:
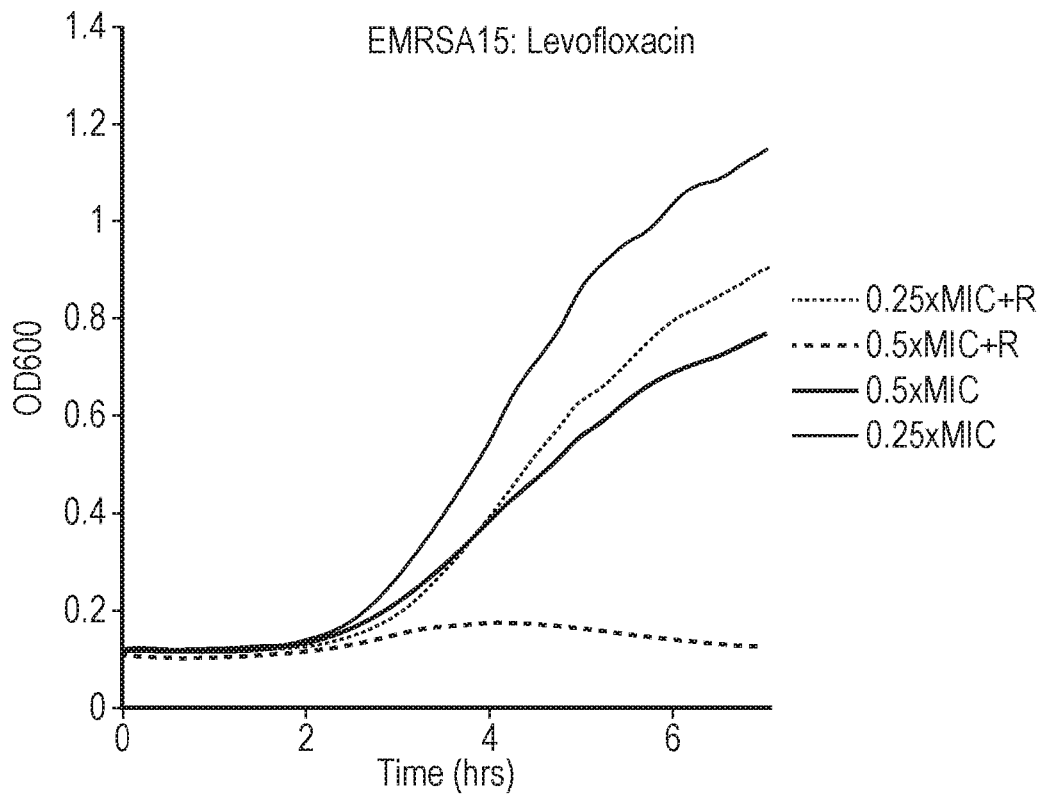
Figure 27F:
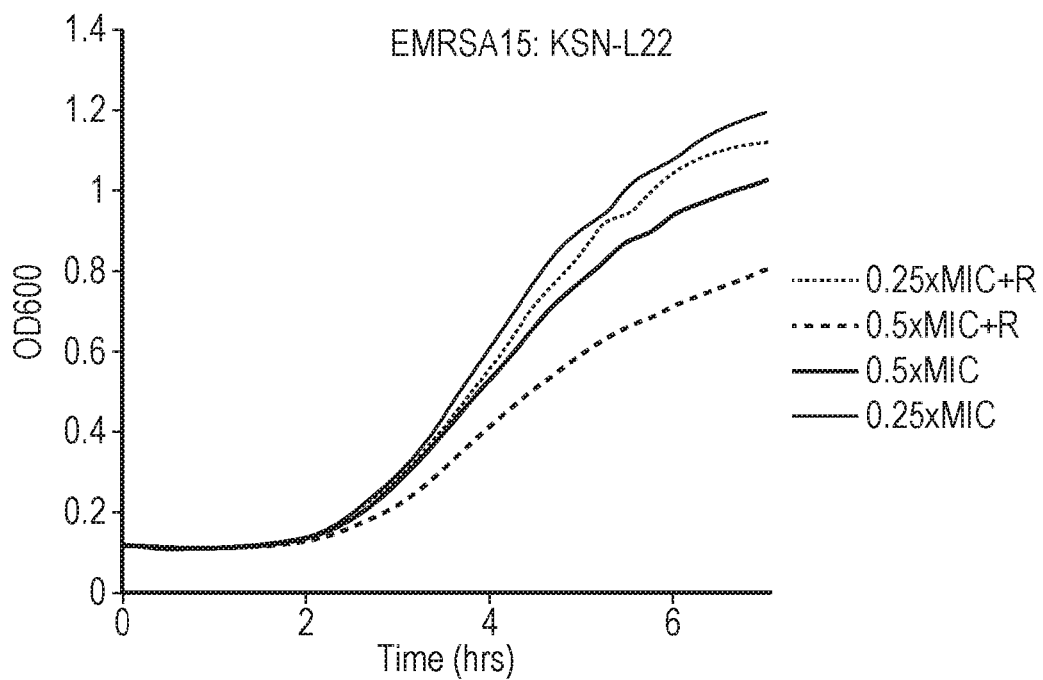
Figure 27G:
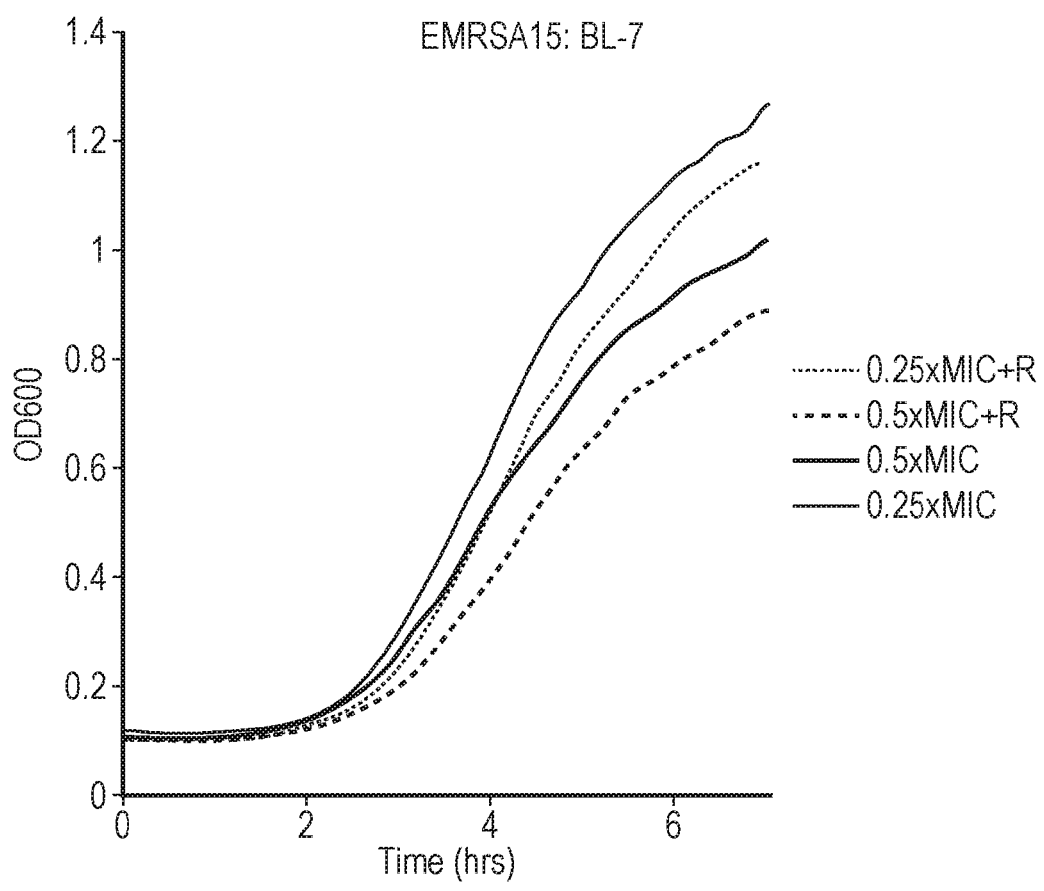

This flexible ARB fragment which can adopt different curvature, helped to obtain the critical and stable contact with the key residues within the binding pocket (FIG. 26). The resulting ARB-fluoroquinolone KSN-L22 showed significantly greater potency against MDR strains compared to the piperazine ring containing ML-83-009 (FIG. 27A) and Levofloxacin (FIGS. 27B & 27E). The reserpine growth assay showed KSN-L22 show reduced efflux from the bacteria (FIGS. 27C & 27F) as compared to ML-83-009 or levofloxacin. Similarly, the 5-membered pyrrolidine ring with exocyclic amine containing ARB fragment KSN-BL7 (FIGS. 27C & 27G) show reduced efflux from the bacteria from the bacteria as compared to ML-83-009 or levofloxacin This was further evident when the 6-member ring containing ML-83-009 was tested against an extended MDR panel with known multiple target mutations (Table 13). The compound did show 4-8 fold potentiation but was significantly less active than KSN-L22 which showed between 16 to 266 fold potentiation (Table 13) due to the superiority of the ARB fragment.

TABLE 13

Activity of ML-83-009 and KSN-L22 against extended panel of MDR strains.

| Strain name | Species | ML83-009 | Levofloxacin | KSN-L22 | Mutations | Fold decrease ML83-009 v Levo | Fold decrease KSN-L22 v Levo |
|---|---|---|---|---|---|---|---|
| SA 215 | S. aureus | 4 | 16 | 1 | gyrA, 84:S => L; grlA, 80:S => F | 4 | 16 |
| SA 105 | S. aureus | 4 | 8-16 | 1 | gyrA, 84:S => L; grlA, 80:S => F | 2-4 | 16 |
| SA 275 | S. aureus | 4 | 32 | 1 | gyrA, 84:S => V; grlA, 80:S => F | 8 | 32 |
| SA 046 | S. aureus | 4 | 16 | 1 | gyrA, 84:S => L; grlA, 80:S => F | 4 | 16 |
| SA 318 | S. aureus | 4 | 16 | 1 | gyrA, 84:S => L; grlA, 80:S => F | 4 | 16 |
| SA 388 | S. aureus | 4 | 16 | 1 | gyrA, 84:S => L; grlA, 80:S => F | 4 | 16 |
| EF 205 | E. faecium | 16-32 | >32 | 0.12 | Not done | >2 | 266 |
| EF 602 | E. faecalis | 16 | >32 | 0.25 | Not done | >2 | 64 |

Figure 28:
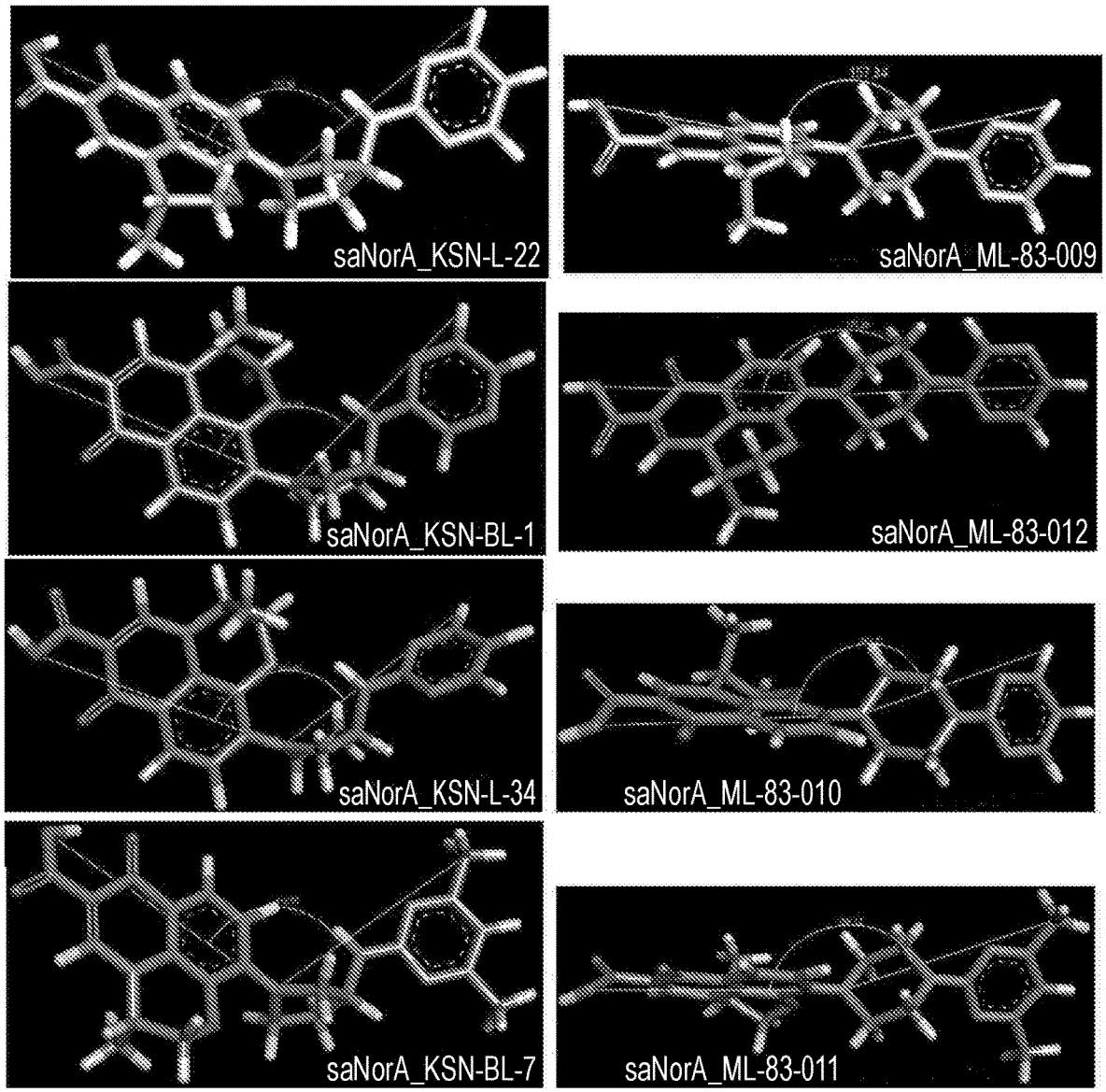
FIG. 28 shows side by side comparison of flexibility and curvature of 4-pair of compounds adopted within the NorA binding site. The left side panels show the five-membered pyrrolidine ring with exocyclic amine group, and the right side panels show the six-membered piperazine ring containing compounds.

Four pairs of molecules were synthesized to rationalise the observation and demonstrate the flexibility of the ARB units, and in each case the 5-membered pyrrolidine ring with exocyclic amine containing ARB-Fluoroquinolone showed superior MIC against efflux resistant MDR strains with multiple target mutations compared to corresponding six-membered or seven-membered analogues (see below and FIG. 28 and Table 13). The compounds also showed superior MIC against other MDR pathogens (both Gram-positive and Gram-negative) bacteria due to their ability to maintain high intracellular concentration within the bacteria (Table 14).

KSN-L-22

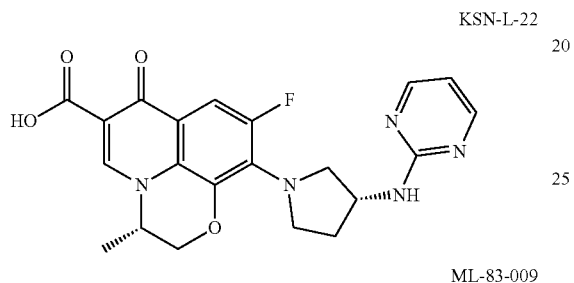

ML-83-009

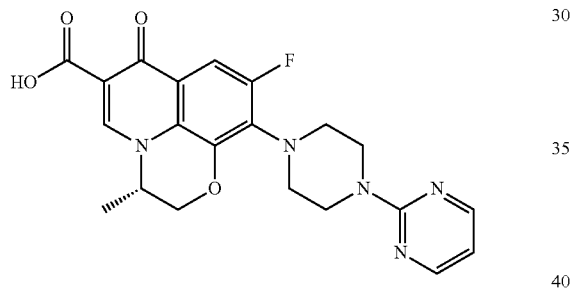

KSN-BL-1

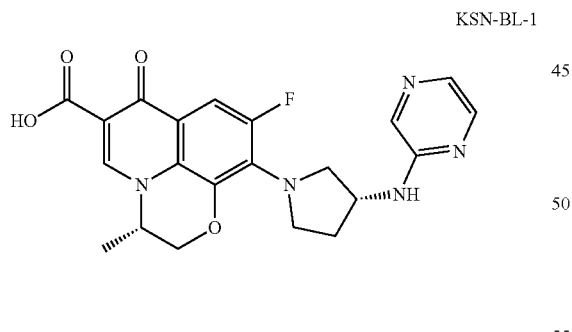

ML-83-012

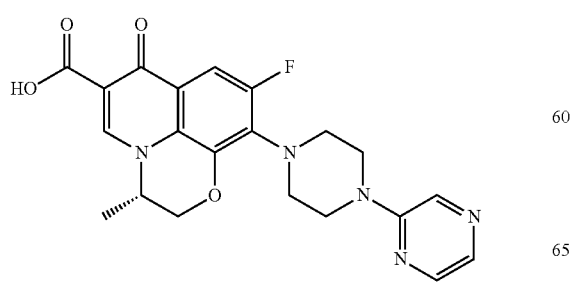

KSN-L-34

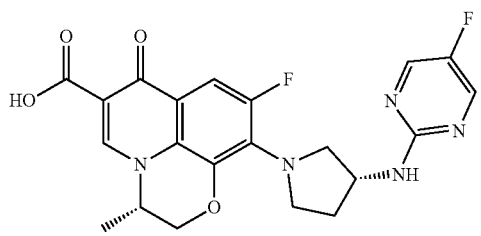

ML-83-010

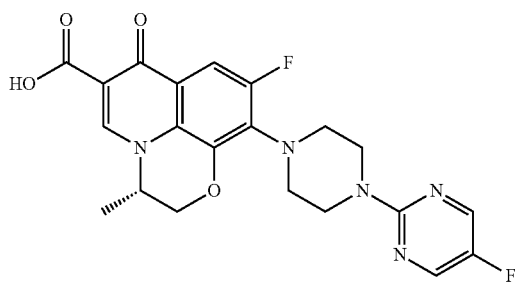

KSN-BL-7

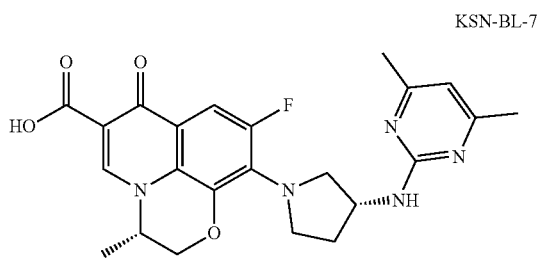

ML-83-011

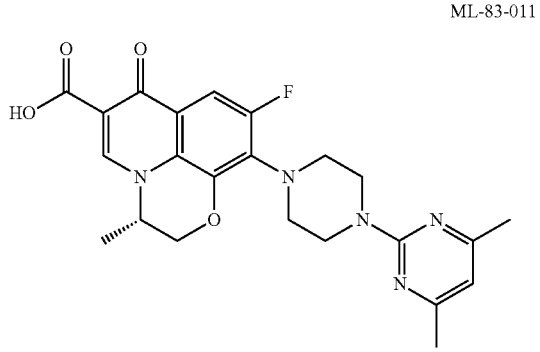

Four pair of compounds as shown above were synthesized to show the superiority of ARB fragments with five membered pyrrolidine ring with an exocyclic amine group compared to six membered piperazine ring containing ARB fragments.

TABLE 14

MIC comparison of compounds (KSN-coded) containing 5-membered pyrrolidine ring with exocyclic amino group with 6-membered piperazine ring containing compounds (ML-coded).

| | KSN-L22 | ML-83-009 | KSN-BL1 | ML-83-012 | KSN-L34 | ML-83-010 | KSN-BL7 | ML-83-011 |
|---|---|---|---|---|---|---|---|---|
| | | | | MIC (µg/mL) | | | | |
| Gram-Negative | | | | | | | | |
| *Klebsiella pneumoniae* (KP13368) | 4 | 64 | 8 | 64 | 32 | 32 | 16 | 64 |
| *Klebsiella pneumoniae* (M6) | 1 | 8 | 0-5 | 16 | 2 | 4 | 2 | 16-64 |
| *Acinetobacter baumannii* (AYE) | 4 | 128 | 8 | 128 | 4 | 128 | 8 | 128 |
| *Acinetobacter baumannii* (AB17978) | 0.125 | 4 | 0.25 | 8 | ≤0.125 | 2 | ≤0.125 | 16 |
| *Pseudomonas aeruginosa* (PA01) | 4 | 32 | 4 | 32 | 4 | 64 | 8 | 128 |
| *Escherichia coli* (EC12923) | 0.5 | 1-4 | 0.25 | 4 | 0.125 | 2 | 1 | 1-8 |
| Gram-Positive | | | | | | | | |
| *Staphylococcus aureus* (MSSA9144) | ≤0.03 | 0.125 | ≤0.125 | 0.25 | ≤0.125 | ≤0.125 | ≤0.0039 | 0.25 |
| *Staphylococcus aureus* (EMRSA15) | 0.5 | 4 | 1 | 2 | 0.5 | 2 | 0.125 | 16 |
| *Staphylococcus aureus* (EMRSA16) | 1 | 4 | 1 | 2 | 1 | 2 | 0.25 | 16 |
| *Enterococcus* (VRE775) | 0.06 | 0.25 | ≤0.125 | 0-5 | ≤0.125 | 0.5 | 0.06 | 1 |
| *Enterococcus* (VRE12201) | 0.06 | 0.25 | ≤0.125 | ≤0.125 | ≤0.125 | ≤0.125 | 0.03 | 0.5-1 |

TABLE 15

MIC comparison of KSN-BL-7 containing a 5-membered pyrrolidine ring with three known antibiotics against an extended bacterial panel

| | | | | | | MIC, µg/ml | | | |
|---|---|---|---|---|---|---|---|---|---|
| No. | Batch No. | Assay # | Species | Strain ID | Resistance | PT#1218400 KSN-BL-7 | Linezolid | Tigecycline | Vancomycin |
| 1 | 421779 | 602050 | *Enterococcus faecalis* | ATCC 29212 | — | 0.25 | | 0.125 | |
| 2 | 421780 | 602100 | *Enterococcus faecalis* | ATCC 51575 | VanB | 0.25 | | 0.125 | |
| 3 | 421781 | 602200 | *Enterococcus faecalis* | ATCC 51299 | VanB | 0.125 | | 0.0625 | |
| 4 | 421782 | 602201 | *Enterococcus faecalis* | CCUG 47775 | Van A | 0.5 | | 0.125 | |
| 5 | 421783 | 602202 | *Enterococcus faecalis* | ATCC 700802 | VanB | 0.125 | | 0.125 | |
| 12 | 421790 | 602374 | *Enterococcus faecium* | TUH44-29, CCUG 59167 | Van A | 1 | | 0.0625 | |
| 13 | 421791 | 602380 | *Enterococcus gallinarum* | ATCC 49608 | VanC | 0.25 | | 0.125 | |
| 14 | 421792 | 603100 | *Streptococcus agalactiae* | ATCC 12386 | — | 0.25 | | | 0.5 |
| 15 | 421793 | 603200 | *Streptococcus oralis* | ATCC 9811 | — | 0.25 | | | 0.5 |
| 16 | 421794 | 603900 | *Streptococcus pneumoniae* | ATCC 6301 | — | 0.125 | | | 0.25 |
| 17 | 421795 | 603910 | *Streptococcus pneumoniae* | S. Africa 6B-8, ATCC 700675 | — | 0.0625 | | | 0.25 |
| 18 | 421796 | 603920 | *Streptococcus pneumoniae* | ATCC 49619 | — | 0.125 | | | 0.25 |

TABLE 15-continued

MIC comparison of KSN-BL-7 containing a 5-membered
pyrrolidine ring with three known antibiotics against an extended bacterial panel

| | | | | | | MIC, µg/ml | | | |
|---|---|---|---|---|---|---|---|---|---|
| No. | Batch No. | Assay # | Species | Strain ID | Resistance | PT#1218400 KSN-BL-7 | Linezolid | Tigecycline | Vancomycin |
| 19 | 421797 | 603930 | Streptococcus pneumoniae | Tenessee 23F, ATCC 51916 | MDR | 0.125 | | | 0.25 |
| 20 | 421798 | 603940 | Streptococcus pneumoniae | CSR 14-10, ATCC 700677 | PRSP | 0.0625 | | | 0.25 |
| 21 | 421799 | 603941 | Streptococcus pneumoniae | SP264, ATCC 700669 | ST 23F | 0.0625 | | | 0.25 |
| 22 | 421800 | 603942 | Streptococcus pneumoniae | Hungary 19A, ATCC 700673 | MDR | 0.0625 | | | 0.25 |
| 23 | 421801 | 603943 | Streptococcus pneumonia | England ST14-9 ATCC 700676 | ERY-R | 0.125 | | | 0.25 |
| 24 | 421802 | 603950 | Strepotococcus pyogenes | ATCC 14289 | — | 0.125 | | | 0.25 |
| 25 | 421803 | 603960 | Strepotococcus pyogenes | ATCC 19615 | — | 0.125 | | | 0.25 |
| 26 | 421804 | 604000 | Staphylococcus aureus | 6538P | — | ≤0.03125 | | | 0.125 |
| 27 | 421805 | 604010 | Staphylococcus aureus | ATCC 33592 | MRSA | ≤0.03125 | | | 0.5 |
| 28 | 421806 | 604020 | Staphylococcus aureus | ATCC 33594 | — | ≤0.03125 | | | 0.5 |
| 29 | 421807 | 604030 | Staphylococcus aureus | ATCC 27660 | — | ≤0.03125 | | | 0.5 |
| 30 | 421808 | 604035 | Staphylococcus aureus | MW2, BAA-1707 | USA400 MRSA | ≤0.03125 | | | 0.5 |
| 31 | 421809 | 604040 | Staphylococcus aureus | Mu50, ATCC 700699 | MRSA/VISA | 2 | 2 | | |
| 32 | 421810 | 604045 | Staphylococcus aureus | TCH1516, BAA-1717 | USA300 MRSA | ≤0.03125 | | | 0.5 |
| 33 | 421811 | 604050 | Staphylococcus aureus | ATCC 13709 | MRSA | ≤0.03125 | | | 0.5 |
| 34 | 421812 | 604055 | Staphylococcus aureus | FPR3757, BAA-1556 | USA300 MRSA | 0.5 | | | 0.5 |
| 35 | 421813 | 604060 | Staphylococcus aureus | ATCC 49230 | — | ≤0.03125 | | | 0.5 |
| 36 | 421814 | 604070 | Staphylococcus aureus | R136 | MRSA | 0.5 | | | 0.5 |
| 37 | 421815 | 604100 | Staphylococcus aureus | ATCC 10390 | — | ≤0.03125 | | | 1 |
| 38 | 421816 | 604110 | Staphylococcus aureus | ATCC 29213 | — | ≤0.03125 | | | 0.5 |
| 39 | 421817 | 604111 | Staphylococcus aureus | ATCC 29213 with 50% human serum | — | 1 | | | 1 |
| 40 | 421818 | 604112 | Staphylococcus aureus | ECL 2963621 | MRSA DAP-NS | 0.25 | | | 1 |
| 41 | 421819 | 604113 | Staphylococcus aureus | ECL 2963646 | VRSA | 0.5 | 2 | | |
| 42 | 421820 | 604114 | Staphylococcus aureus | ECL 2963666 | MRSA DAP-NS | 1 | 1 | | |
| 43 | 421821 | 604115 | Staphylococcus aureus | ECL 2963667 | MRSA DAP-NS | 1 | | | 1 |
| 44 | 421822 | 604116 | Staphylococcus aureus | ECL 2963743 | MRSA DAP-NS | 0.5 | | | 1 |
| 45 | 421823 | 604117 | Staphylococcus aureus | COL, NRS100 | MRSA | ≤0.03125 | 2 | | |
| 46 | 421824 | 604118 | Staphylococcus epidermidis | NRS101 | — | ≤0.03125 | | | 1 |
| 47 | 421825 | 604119 | Staphylococcus aureus | NRS119 | MRSA LZD-NS | 1 | | | 1 |
| 48 | 421826 | 604120 | Staphylococcus aureus | NRS12 | VISA | 0.0625 | 4 | | |
| 49 | 421827 | 604121 | Staphylococcus aureus | NRS123 | USA400 MRSA | ≤0.03125 | | | 0.5 |
| 50 | 421828 | 604122 | Staphylococcus aureus | NRS127 | MRSA LZD-NS | 4 | | | 1 |
| 51 | 421829 | 604123 | Staphylococcus aureus | NRS157 | — | ≤0.03125 | | | 0.5 |
| 52 | 421830 | 604124 | Staphylococcus aureus | NRS17 | MRSA/VISA | 1 | 2 | | |
| 53 | 421831 | 604126 | Staphylococcus aureus | NRS22 | USA600 MRSA/VISA | 4 | 4 | | |

TABLE 15-continued

MIC comparison of KSN-BL-7 containing a 5-membered
pyrrolidine ring with three known antibiotics against an extended bacterial panel

| | | | | | | MIC, µg/ml | | | |
|---|---|---|---|---|---|---|---|---|---|
| No. | Batch No. | Assay # | Species | Strain ID | Resistance | PT#1218400 KSN-BL-7 | Linezolid | Tigecycline | Vancomycin |
| 54 | 421832 | 604127 | *Staphylococcus aureus* | NRS269 | MRSA TGC-NS | 2 | 2 | | |
| 55 | 421833 | 604128 | *Staphylococcus aureus* | E-MRSA 15, NRS271 | MRSA LZD-NS | 0.5 | | | 0.5 |
| 56 | 421834 | 604129 | *Staphylococcus aureus* | NRS3 | MRSA/VISA | 0.5 | 1 | | |
| 57 | 421835 | 604130 | *Staphylococcus aureus* | NRS382 | USA100 MRSA | 0.5 | | | 1 |
| 58 | 421836 | 604131 | *Staphylococcus aureus* | NRS383 | USA200 MRSA TIG-NS | 1 | | | 0.5 |
| 59 | 421837 | 604132 | *Staphylococcus aureus* | NRS384 | USA300 MRSA | ≤0.03125 | | | 0.5 |
| 60 | 421838 | 604133 | *Staphylococcus aureus* | NRS385 | USA500 MRSA | 0.5 | | | 0.5 |
| 61 | 421839 | 604134 | *Staphylococcus aureus* | NRS386 | USA700 MRSA | 0.25 | | | 0.5 |
| 62 | 421840 | 604135 | *Staphylococcus aureus* | NRS387 | USA800 MRSA | ≤0.03125 | | | 1 |
| 63 | 421841 | 604136 | *Staphylococcus aureus* | NRS402 | MRSA/VISA DAP-NS | 1 | 1 | | |
| 64 | 421842 | 604137 | *Staphylococcus aureus* | NRS483 | USA1000 MRSA | ≤0.03125 | | | 0.5 |
| 65 | 421843 | 604138 | *Staphylococcus aureus* | NRS484 | USA1100 MRSA | ≤0.03125 | | | 1 |
| 66 | 421844 | 604139 | *Staphylococcus aureus* | NRS56 | MRSA/VISA | 1 | 2 | | |
| 67 | 421845 | 604140 | *Staphylococcus epidermidis* | NRS60 | VISE | 0.0625 | 2 | | |
| 68 | 421846 | 604141 | *Staphylococcus epidermidis* | NRS7 | VISE | 0.5 | 4 | | |
| 69 | 421847 | 604142 | *Staphylococcus aureus* | NRS71 | MRSA | 1 | | | 0.25 |
| 70 | 421848 | 604143 | *Staphylococcus aureus* | Sanger-476, NRS72 | — | ≤0.03125 | | | 0.5 |
| 71 | 421849 | 604144 | *Staphylococcus epidermidis* | NRS8 | VISE | 1 | 2 | | |
| 72 | 421850 | 604145 | *Staphylococcus aureus* | VRS1 | VanA MRSA/VRSA | 1 | 2 | | |
| 73 | 421851 | 604146 | *Staphylococcus aureus* | VRS11b | VanA MRSA/VRSA | 2 | 2 | | |
| 74 | 421852 | 604147 | *Staphylococcus aureus* | VRS2 | VanA MRSA/VRSA | 0.5 | 2 | | |
| 75 | 421853 | 604148 | *Staphylococcus aureus* | VRS3a | VanA MRSA/VRSA | 0.5 | 4 | | |
| 76 | 421854 | 604149 | *Staphylococcus aureus* | FDA-CDC AR-BANK# 0215 | MRSA/VISA | 16 | 4 | | |
| 77 | 421855 | 604150 | *Staphylococcus aureus* | FDA-CDC AR-BANK# 0216 | MRSA/VISA | 0.5 | 2 | | |
| 78 | 421856 | 604151 | *Staphylococcus aureus* | FDA-CDC AR-BANK# 0217 | MRSA/VISA | 1 | 1 | | |
| 79 | 421857 | 604152 | *Staphylococcus aureus* | FDA-CDC AR-BANK# 0218 | MRSA/VISA Mupirocin-R | 1 | 1 | | |
| 80 | 421858 | 604153 | *Staphylococcus aureus* | FDA-CDC AR-BANK# 0219 | MRSA/VISA | 4 | 2 | | |
| 81 | 421859 | 604154 | *Staphylococcus aureus* | FDA-CDC AR-BANK# 0220 | MRSA/VISA | 1 | 2 | | |
| 82 | 421860 | 604155 | *Staphylococcus aureus* | FDA-CDC AR-BANK# 0221 | MRSA/VISA | 0.5 | 2 | | |
| 83 | 421861 | 604156 | *Staphylococcus aureus* | FDA-CDC AR-BANK# 0222 | VISA | ≤0.03125 | 2 | | |
| 84 | 421862 | 604157 | *Staphylococcus aureus* | FDA-CDC AR-BANK# 0223 | MRSA/VISA | 1 | 2 | | |
| 85 | 421863 | 604158 | *Staphylococcus aureus* | FDA-CDC AR-BANK# 0224 | MRSA/VISA Mupirocin-R | 1 | 4 | | |
| 86 | 421864 | 604159 | *Staphylococcus aureus* | FDA-CDC AR-BANK# 0225 | MRSA/VISA | 1 | 2 | | |
| 87 | 421865 | 604160 | *Staphylococcus aureus* | FDA-CDC AR-BANK# 0226 | MRSA/VISA | ≤0.03125 | 2 | | |
| 88 | 421866 | 604161 | *Staphylococcus aureus* | FDA-CDC AR-BANK# 0227 | MRSA/VISA | 1 | 4 | | |

TABLE 15-continued

MIC comparison of KSN-BL-7 containing a 5-membered pyrrolidine ring with three known antibiotics against an extended bacterial panel

| | | | | | | MIC, µg/ml | | | |
|---|---|---|---|---|---|---|---|---|---|
| No. | Batch No. | Assay # | Species | Strain ID | Resistance | PT#1218400 KSN-BL-7 | Linezolid | Tigecycline | Vancomycin |
| 89 | 421867 | 604162 | Staphylococcus aureus | FDA-CDC AR-BANK# 0228 | MRSA/VISA Mupirocin-R | 8 | 2 | | |
| 90 | 421868 | 604250 | Staphylococcus intermedius | ATCC 29663 | — | ≤0.03125 | | | 1 |
| 91 | 421869 | 604300 | Staphylococcus epidermidis | ATCC 12228 | — | ≤0.03125 | | | 0.5 |
| 92 | 421870 | 604310 | Staphylococcus epidermidis | CCF 15990, ATCC 51625 | — | ≤0.03125 | | | 1 |
| 93 | 421871 | 604400 | Staphylococcus haemolyticus | ATCC 29970 | — | ≤0.03125 | | | 1 |
| 94 | 421872 | 604450 | Staphylococcus saprophyticus | ATCC 15305 | — | 0.0625 | | | 0.5 |
| 95 | 421873 | 604500 | Streptococcus mutans | ATCC 25175 | — | ≤0.03125 | | | 2 |
| 96 | 421874 | 604600 | Streptococcus salivarius | ATCC 13419 | — | 0.25 | | | 0.5 |
| 97 | 421875 | 604700 | Streptococcus sanguinis | ATCC 10556 | — | 0.25 | | | 0.5 |
| 98 | 421876 | 605000 | Staphylococcus aureus | ATCC 33591 | MRSA | ≤0.03125 | | | 0.5 |
| 99 | 421877 | 606000 | Staphylococcus aureus | Smith, ATCC 19636 | — | ≤0.03125 | | | 0.5 |
| 100 | 421878 | 661000 | Streptococcus pneumoniae | TM532 | PRSP | 0.0625 | | | 0.25 |

The role of the ARB fragment in reversing efflux mediated resistance was further studied using a SAR study, and the absence of the terminal pyrimidine, which provides critical contact, showed no potentiation in KSN-L44 against EMRSA-15 and EMRSA-16, in which NorA efflux pump is upregulated (Table 16). Similarly, removing the complete ARB fragment also resulted in loss of activity against MDR strains, showing the importance of the ARB fragment in conferring activity against MDR strains and reversing efflux mediated resistance.

TABLE 16

Role of the terminal pyrimidine ring in reversing resistance against resistance strains.

| | EMRSA15 | EMRSA16 |
|---|---|---|
| KSN-L22 [structure] | 0.5-1 | 1 |
| KSN-L44 [structure] | 32 | 32 |

TABLE 16-continued

Role of the terminal pyrimidine ring in reversing resistance against resistance strains.

| Compound | Structure | EMRSA15 | EMRSA16 |
|---|---|---|---|
| KSN-L34 | [structure] | 0.5 | 1 |
| KSN-BL1 | [structure] | 1 | 1 |
| KSN-BL6 | [structure] | 2 | 1 |
| KSN-BL7 | [structure] | 0.125-0.25 | 0.25-0.5 |

Figure 29A:
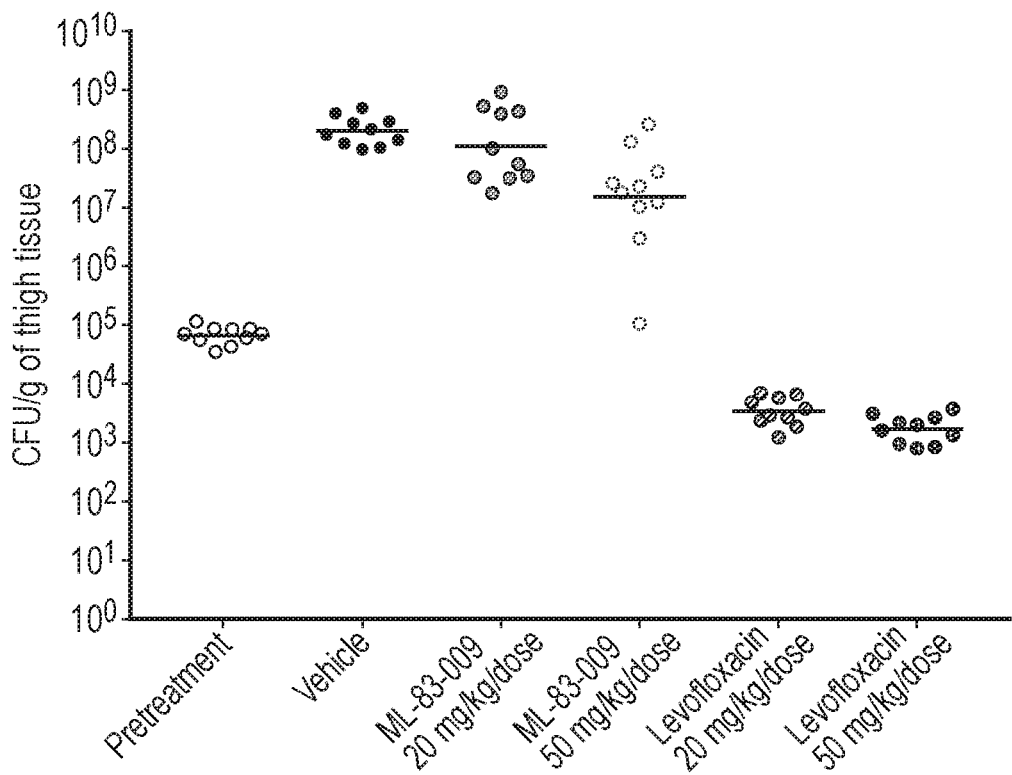
FIG. 29A shows in vivo thigh infection efficacy data for ML-83-009.
Figure 29B:
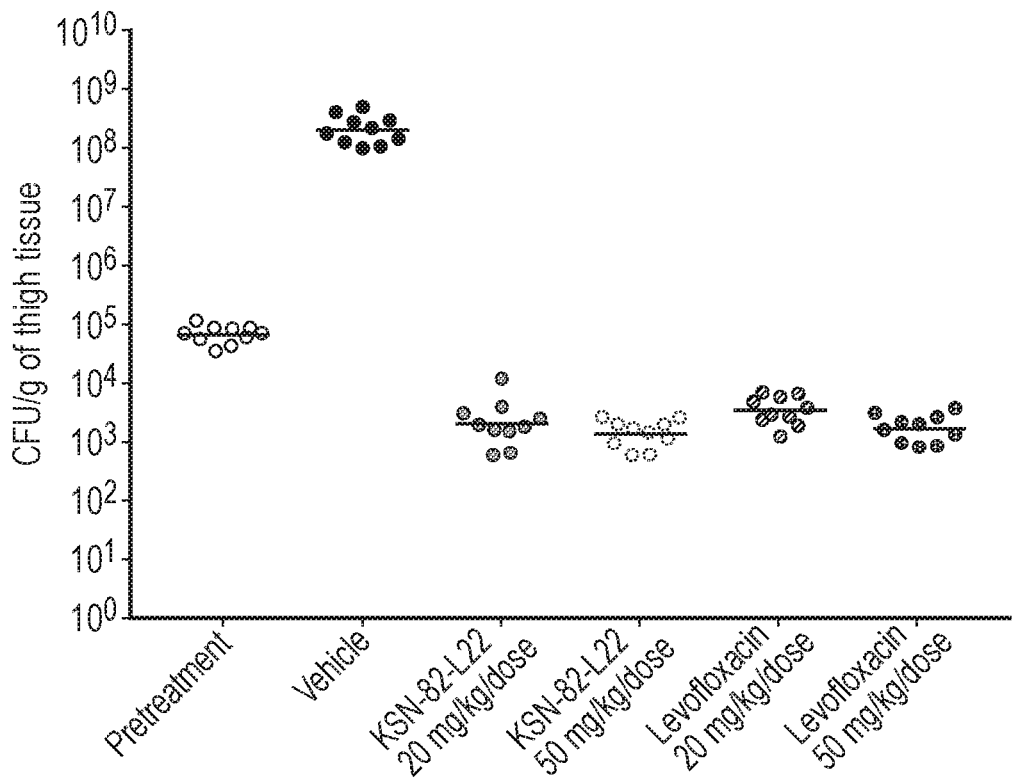
FIG. 29B shows in vivo thigh infection efficacy data for KSN-82-L22.

Finally, the superiority of the five-membered pyrrolidine ring with exocyclic amine group containing ARB was further demonstrated in the in vivo thigh infection model in which KSN-L22 showed statistically significant reduction of bacterial load while six-membered piperazine ring containing ML-83-009 wasn't able to reduce the bacterial load significantly. Treatment with ML-83-009 at 20 or 50 mg/kg/dose slightly decreased bacterial burden, by 0.26 and 1.12 $\log_{10}$ CFU/g compared to vehicle group, respectively, which was not statistically significant (FIG. 29A). KSN-82-L22 at 20 mg/kg and 50 mg/kg decreased significantly the bacteria burden in comparison to the vehicle by 5 and 5.16 $\log_{10}$ CFU/g respectively (FIG. 29B), similarly to the levofloxacin treated group. Moreover KSN-82-L22 at the two doses decreased significantly the bacteria burden in comparison to the pre-treatment group by about 1.6 $\log_{10}$ CFU/g.

The current patent application covers these 5-member pyrrolidine ring with exocyclic amine containing ARB-fragment linked antibiotics, which have not been synthesized before using this approach or any other synthetic approach.

Reserpine Assay Experiments

The ability of a napthyl-linked ciprofloxacin (ML-77-005 referred to as ML005 in the figures) and napthyl-linked norfloxacin (ML-77-021 referred to as ML021 in the figures) to prevent efflux was investigated through a reserpine growth assay (see FIGS. 17-24). Reserpine is a competitive efflux pump inhibitor which has been shown to inhibit a multitude of efflux pumps in Gram-positive species including Bmr (*Bacillus subtilis*) and NorA (*S. aureus*). The mechanism of inhibition for reserpine involves direct binding to and competitive inhibition of the efflux pump during drug/H$^+$ antiport. This assay was validated as a method for testing active efflux of fluoroquinolones in *Staphylococcus* strains by Beyer et al. (24). The results show that both ciprofloxacin (CIP) and norfloxacin (Norf) are effluxed by multidrug-resistant MSSA strains (see FIGS. 17 and 19) multidrug-resistant EMRSA strains (see FIGS. 21 and 23) while napthyl-linked ciprofloxacin and napthyl-linked norfloxacin cannot be effluxed by multidrug-resistant MSSA strains (see FIGS. 18 and 20) and multidrug-resistant EMRSA strains (see FIGS. 22 and 24), making them susceptible to these ARB-linked antibiotics.

*Galleria mellonella* Challenge Model

Figure 25A:
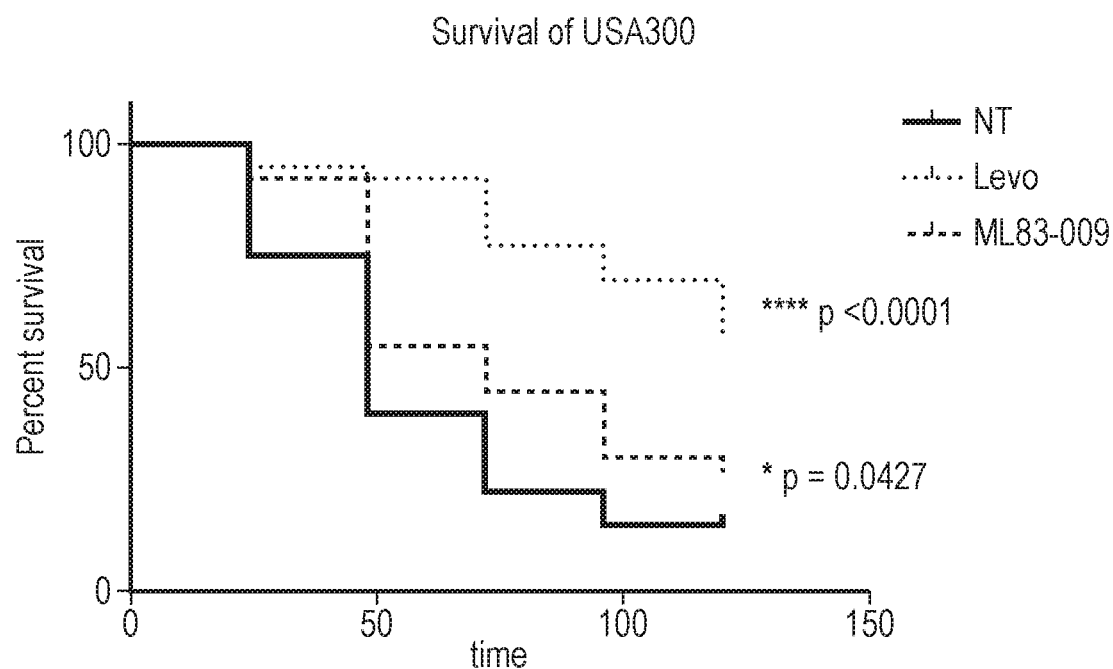
FIG. 25A shows the results for a *Galleria mellonella* challenge model when *G. mellonella* larvae were challenged with *S. aureus* strains USA300.
Figure 25B:
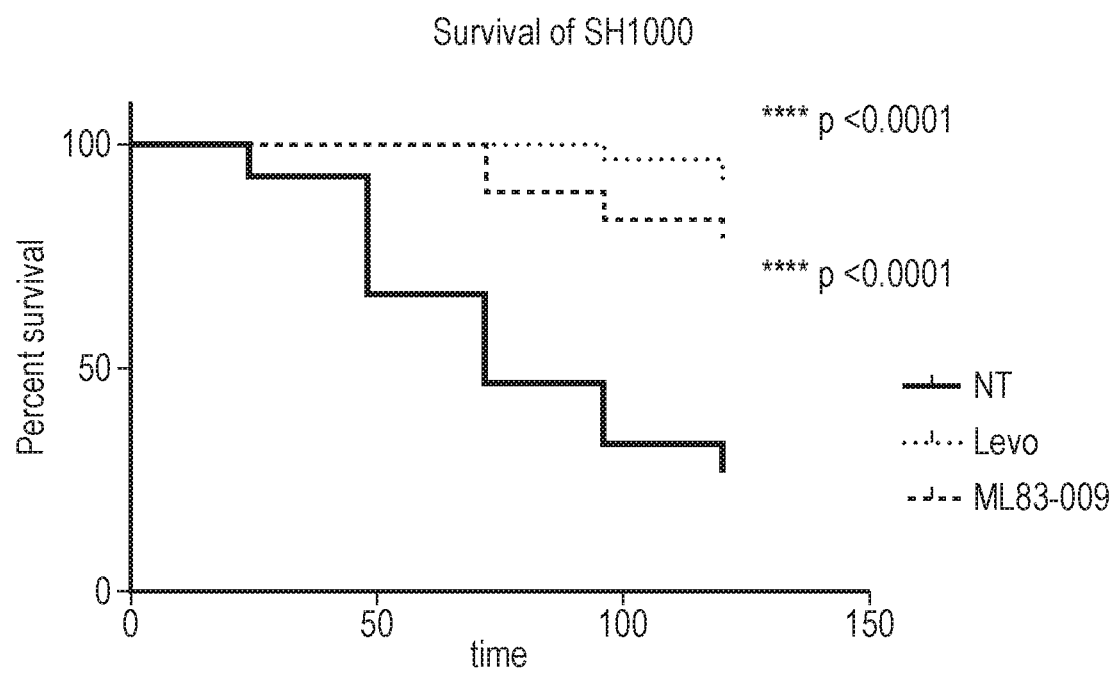
FIG. 25B shows the results for a *Galleria mellonella* challenge model when *G. mellonella* larvae were challenged with *S. aureus* strains SH1000.

*G. mellonella* larvae were challenged with 107 colony forming units of either *S. aureus* strains USA300 (FIG. 25A) or *S. aureus* strains SH1000 (FIG. 25B). After 30 minutes ML-83-009 or levofloxacin at a dose of 50 mg/kg was injected. Larval survival was monitored up to 100 hours post bacterial challenge. Non-treated (NT) larvae were given PBS only after the initial *S. aureus* challenge. ML-83-009 showed significant levels of protection in both challenge models. The strains used in this study are both classified as being levofloxacin-resistant with USA300 having a MIC of 8 µg/ml for levofloxacin and with SH1000 having a MIC of 2-4 µg/ml for levofloxacin.

The data is the average of 3 independent experiments each with 10 larvae.

Pharmacokinetic Study of KSN-L22

Mouse Strain

ICR breed Mice (CD-1® IGS mice) were used in these studies and was supplied by Charles River (Margate UK) and. The mice were allowed to acclimatise for at least 7 days before starting the study.

Animal Housing

Mice were housed in sterilised individual ventilated cages that expose the mice at all times to HEPA filtered sterile air. Mice had free access to food and water (sterile) and will have aspen chip bedding.

The room temperature was 22° C.+/−1° C., with a relative humidity of 60% and maximum background noise of 56 dB. Mice was exposed to 12 hour light/dark cycles.

WP1: Single Dose Pharmacokinetics Study

Treatments was administered by oral route or intravenous route according to the table below.

For the PK study, 12 mice for each compound for oral route and 12 mice per compound for the intravenous route was treated.

Mice was sequentially bled from a caudal vein into a 20 µL capillary (by agreement containing an anticoagulant) at different time as indicated in table below and a terminal bleed by cardiac puncture at 8 h after administration. Samples collected by capillary was directly transferred into a 96 well and mixed with 20 µl, of water, then frozen and store at −80° C. until bioanalysis.

Mice for urine collection was housed singly in metabolic cages and urine collected at 0-1, 1-2, 2-4 h and 4-8 h post administration. Urine removed from the collection vessels in the metabolic cages and were frozen and store at −80° C. until bioanalysis. 12 mice were used for urine collection.

WP2: Bio-Analysis and Determination of PK Parameters

Analysis of up to 39 blood samples and up to 30 urine samples per test compound. A compound specific LC-MS/MS method was developed for each test compound and samples was quantified using matrix matched calibrators. Samples was prepared for bio-analysis via protein precipitation.

Concentration vs time data and non-compartmental analysis was utilised to determine relevant PK parameters e.g. CL, Vss, $t_{1/2}$, $AUC_{inf}$ AUCo-t, Cmax, tmax, % F, % dose in urine and CLR. Levofloxacin was used as a control in all cases for comparison purpose.

TABLE 18

Result of IV PK Study with key parameters

| PK Parameter (iv) | KSN-L-22 Composite Mean | Levofloxacin Composite Mean |
|---|---|---|
| Dose (mg/kg) | 5.0 | 5.0 |
| Dose (µmol/kg) | 11.8 | 13.8 |
| $C_o/C_{max}$ (ng/mL) | 9389 | 3890 |
| $C_o/C_{max}$ (nM) | 22071 | 10764 |
| $T_{max}$ (h) | — | — |
| T½ (h) | 0.6 | 0.5 |
| MRT (h) | 1.8 | 30 |
| Vdss (L/kg) | 1-4 | 4-5 |
| Blood CL (ml/min/kg) | 12.5 | 25.2 |
| CL_F (ml/min/kg) | — | — |
| Liver Blood Flow (%) | 10.4% | 21.0% |
| $AUG_{inf}$ (ng.hr/mL) | 6691 | 3313 |
| $AUC_{inf}$ (nM.hr) | 15728 | 9186 |
| $AUC_{o,t}$ (ng.hr/mL) | 6425 | 3091 |
| $AUC_{o,t}$ (nM.hr) | 15103 | 8553 |
| Fraction Absorbed | — | — |
| $C_{last}$ (ng/mL) | 286 | 281.6 |
| Bioavailability (%) Using $AUC_{inf}$ | — | — |
| Bioavailability (%) Using $AUC_{o,t}$ | — | — |

Figure 30:
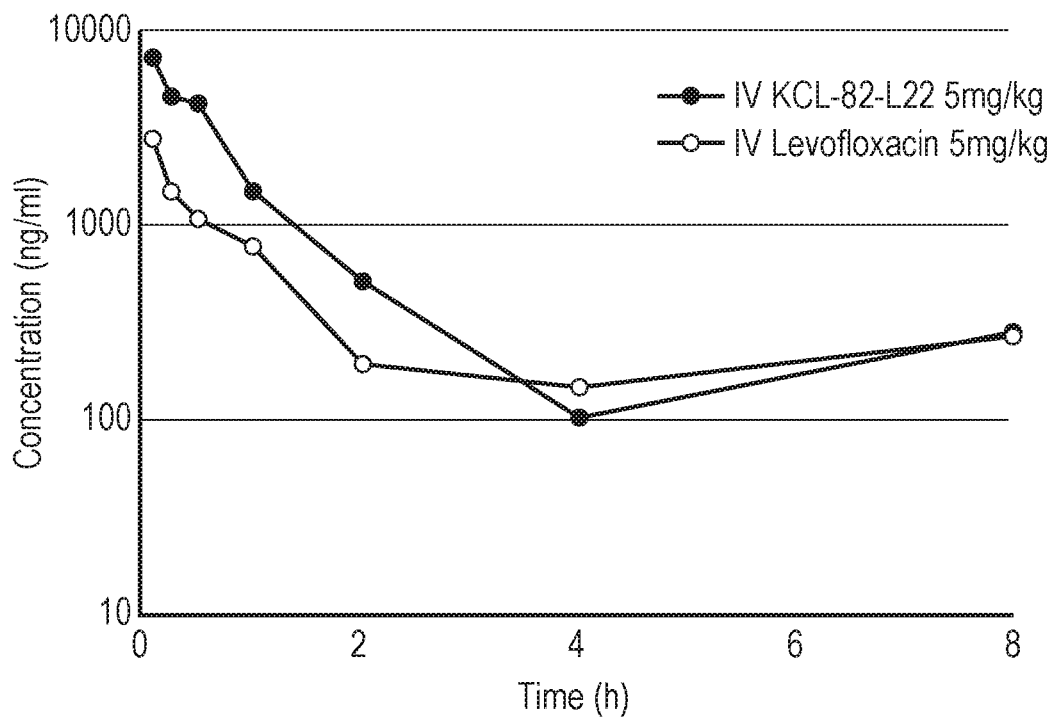
FIG. 30 shows the mean total blood concentrations of KSN-82-L22 and Levofloxacin following i.v. admistration to Male $CD_1$ Mouse at 5 mg/kg.

A graph showing the mean total blood concentrations of KSN-82-L22 and Levofloxacin following iv administration to Male CD1 mouse at 5 mg/kg is shown in FIG. 30.

TABLE 17

Summary of treatments

| Gp. No. | Treatment | Dose (mg/kg) | Route | Blood Collection (h after administration) | No Mice per group | Urine collection | No Mice per group |
|---|---|---|---|---|---|---|---|
| 1 | KSN-82-L22 | 20 | PO | 0.25, 0.5, 1, 2, 4 and 8 h | 3 | 0-1 h, 1-2 h, 2-4 h, 4-8 h, 8-24 h | 3 |
| 2 | KSN-82-L22 | 5 | IV | 0.083, 0.25, 0.5, 1, 2, 4 and 8 h | 6[b] | 0-1 h, 1-2 h, 2-4 h, 4-8 h, 8-24 h | 3 |
| 3 | Levofloxacin | 20 | PO | 0.25, 0.5, 1, 2, 4 and 8 h | 3 | 0-1 h, 1-2 h, 2-4 h, 4-8 h, 8-24 h | 3 |
| 4 | Levofloxacin | 5 | IV | 0.083, 0.25, 0.5, 1, 2, 4 and 8 h | 6[b] | 0-1 h, 1-2 h, 2-4 h, 4-8 h, 8-24 h | 3 |

[a]Total number of mice: 30 mice
[b]Only 3 mice per time point was bleed
[c]Samples for bioanalysis 69 per test article - 39 plasma and 30 urine, 138 in total for 2 test articles

TABLE 19

Result of Oral PK Study with key parameters

| PK Parameter (PO) | KSN-L-22 Mean/Median ($T_{max}$) | Levofloxacin Mean/Median ($T_{max}$) |
|---|---|---|
| Dose (mg/kg) | 20.0 | 20.0 |
| Dose (µmol/kg) | 47·0 | 55·3 |
| $C_o/C_{max}$ (ng/mL) | 2965 | 2947 |
| $C_o/C_{max}$ (nM) | 4007 | 8156 |
| $T_{max}$ (h) | 1.00 | 0.50 |
| $T^{1/2}$ (h) | 5·1 | 5·7 |
| MRT (h) | — | — |
| Vdss (L/kg) | — | — |
| Blood CL (ml/min/kg) | — | — |
| CL_F (ml/min/kg) | 26.4 | 65.4 |
| Liver Blood Flow (%) | — | — |
| $AUC_{inf}$ (ng.hr/mL) | 13203 | 5388 |
| $AUC_{inf}$ (nM.hr) | 31036 | 14909 |
| $AUC_{o.t}$ (ng.hr/mL) | 8231 | 4264 |
| $AUC_{o.t}$ (nM.hr) | 19347 | 11800 |
| Fraction Absorbed | — | — |
| $C_{last}$ (ng/mL) | 628 | 115 |
| Bioavailability (%) Using $AUC_{inf}$ | 49·3% | 40.7% |
| Bioavailability (%) Using $AUC_{o.t}$ | 32.0% | 34·5% |

Figure 31:
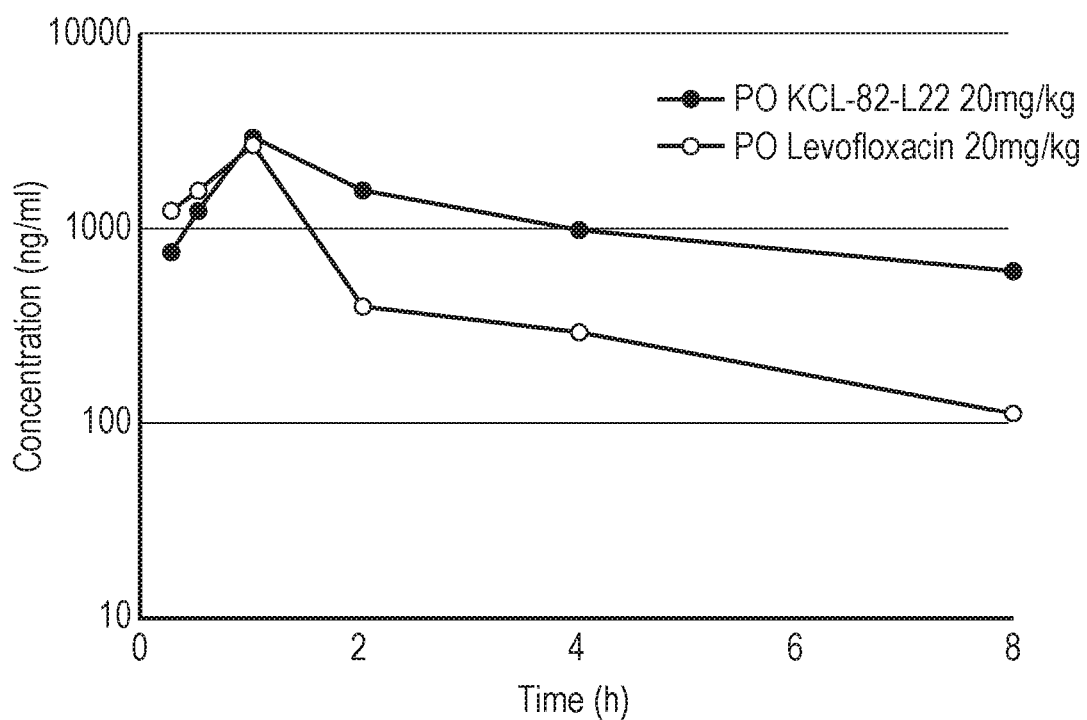
FIG. 31 shows mean total blood concentrations of KSN-82-L22 and Levofloxacin following PO admistration to Male $CD_1$ Mouse at 5 mg/kg.

A graph showing the mean total blood concentrations of KSN-82-L22 and Levofloxacin following PO administration to Male CD1 mouse at 20 mg/kg is shown in FIG. 31.

In Vivo Efficacy Data of KSN-L22 and ML-83-009

KSN-L22 which has the ARB Fragment Containing the 5-Members Pyrrolodine Ring Showed Notably Superior Activity Compared to Six-Member Piperazine Ring Containing ML-83-009.

Executive Summary

The aim of the study was to assess the efficacy of ML-83-009 and KSN-82-L22 at 20 mg/kg and 50 mg/kg in murine model of thigh infection with *Staphylococcus aureus* (*S. aureus*) ATCC29213 in comparison to levofloxacin as reference at the same dose. At 18 h post infection, after dosing at 2 h, 8 h and 14 h post infection, bacterial burden was unchanged by ML-83-009 treatment at 20 and 50 mg/kg. However, KSN-82-L22 at 20 and 50 mg/kg significantly decreased bacterial burden in comparison to vehicle and to pre-treatment group demonstrating bactericidal activity. This efficacy was similar to the Levofloxacin Study Aim The aim of the study was to assess the efficacy of two test articles in murine thigh infection model with *S. aureus* ATCC29213, 26 h post infection. The primary objectives was to assess the efficacy at 2 doses for each articles at 26 h, after dosing 2 h, 8 h and 14 h post infection. Moreover their efficacy were compared to the Levofloxacin efficacy with same doses and same regimen.

Methods

Regulatory

The experiment was performed under UK Home Office Licences and with local ethical committee clearance. The experiment was performed by technicians that have completed parts A, B and C of the Home Office Personal License course and hold a current personal license. The experiment was performed in dedicated Biohazard 2 facilities.

Animal Strain and Housing

40 Male mice used in these study were supplied by Charles River UK and were specific pathogen free. The strain of mouse used was Hsd:ICR (CD-1®), which is a well characterized outbred strain. Mice were 11-15 g on receipt at Evotec's facility and were allowed to acclimatize for minimum of 7 days prior to infection. Mice were approximately 28 g at the start of the study. Mice were housed in sterile individual ventilated cages exposing animals at all times to HEPA filtered sterile air. Mice had free access to food and water (sterile) and had sterile aspen chip bedding. The room temperature was 22° C.±1° C., with a relative humidity of 50-60% and maximum background noise of 56 dB. Mice were exposed to 12 hour light/dark cycles with dawn/dusk phases.

Immunosuppression

All mice were rendered neutropenic by immunosuppression with cyclophosphamide at 150 mg/kg 4 days before infection and then 100 mg/kg 1 day before infection administered by intraperitoneal injection. The immunosuppression regime leads to neutropenia starting 24 hours post administration of the first injection, which continues throughout the study. Mice were infected approximately 24 hours after the second dose of immunosuppressive agent.

Preparation of Organism and Infection

*Staphylococcus aureus* ATCC29213 was used for the study. Mice were infected with an inoculum prepared from a frozen stock diluted with phosphate buffered saline (PBS) to obtain 105 CFU/mL. 50 µL of this solution was injected to administer $5 \times 10^3$ CFU/thigh. The actual concentration of organism was $2.65 \times 10^5$ CFU/mL corresponding to $1.33 \times 10^4$ CFU/thigh.

Mice were infected by intramuscular injection of 50 µL inoculum into both lateral thigh muscles under inhaled anaesthesia using 2.5% isofluorane in 97.5% oxygen. Whilst still under anaesthesia mice were administered a single dose of buprenorphine (0.03 mg/kg) subcutaneously for pain relief.

Preparation of Test Articles

Test articles and comparator were prepared in stock solutions at 10× concentration as described in Table 20. The stock solutions were prepared in aliquots (i aliquot per time of dosing) and frozen at −20° C. The solutions were thawed and then diluted in water just before dosing to obtain the appropriate concentration of 5 mg/mL or 2 mg/mL for oral administration at 10 mL/kg of the dose of 50 mg/kg or 20 mg/kg respectively (Table 20). 10% DMSO in water was used as the vehicle

TABLE 20 test article stock solutions

| Test article | Quantity (mg) | Correction factor | Quantity of active molecule (mg) | Stock solution 50 mg/mL | Stock solution 20 mg/mL |
|---|---|---|---|---|---|
| ML-83-009 | 40 | 1 | 40 | 0.8 mL of DMSO added | 0.21 mL of 50 mg/mL stock solution + 0.31 mL DMSO |
| KSN-82-L22 | 41·30 | 1·17 | 41·30 | 0826 mL of DMSO added | 0.21 mL of 50 mg/mL stock solution + 0.31 mL DMSO |
| Levofloxacin (Sigma ref 28266) | 45 | 1 | 45 | 0.9 mL of DMSO added | 0.21 mL of 50 mg/mL stock solution + 0.31 mL DMSO |

Study Design and Schedule

Figure 32:
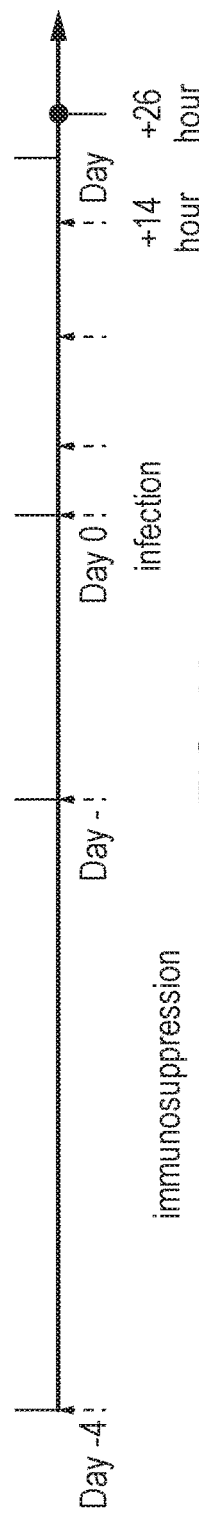
FIG. 32 shows a study design.

Two hour post infection animals from the pre-treatment groups were euthanised and the remainder of animals were treated at 2 h, 8 h and 14 h post infection. Eighteen hours post infection, vehicle group displayed clinical signs of infection beyond the ethical limit, and thus the experiment was stopped and all remaining animals were euthanised. The study schedule is summarised in FIG. 32 and Table 21.

aureus ATCC29213, 26 h post infection. 2 doses for each articles were assesses with dosing 2 h, 8 h and 14 h post infection. Moreover their efficacy was compared to the one of levofloxacin with same doses and same regimen.

Body Weights

Figure 33:
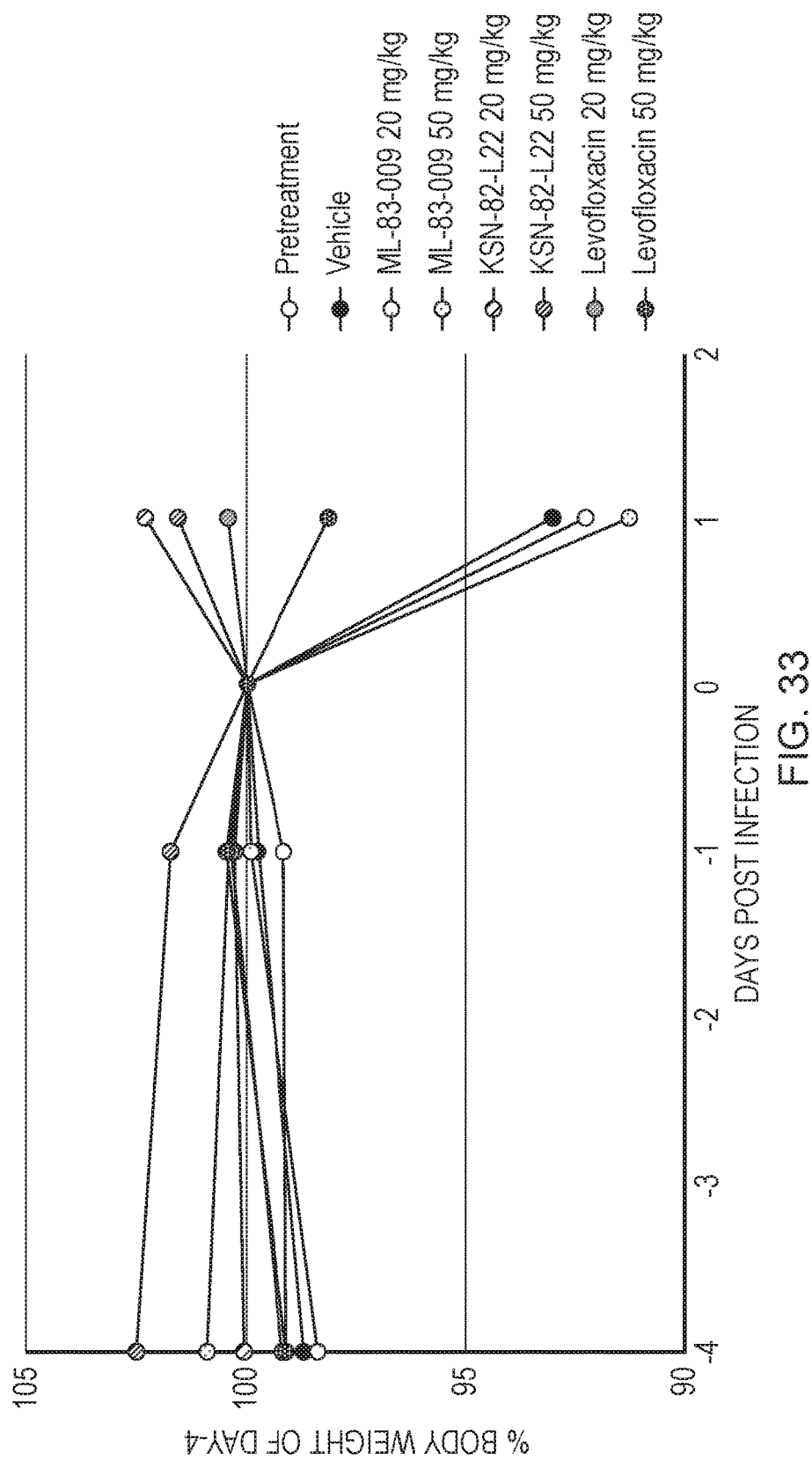
FIG. 33 shows the average body weight of groups relative to weight on day of infection.
Figure 34:
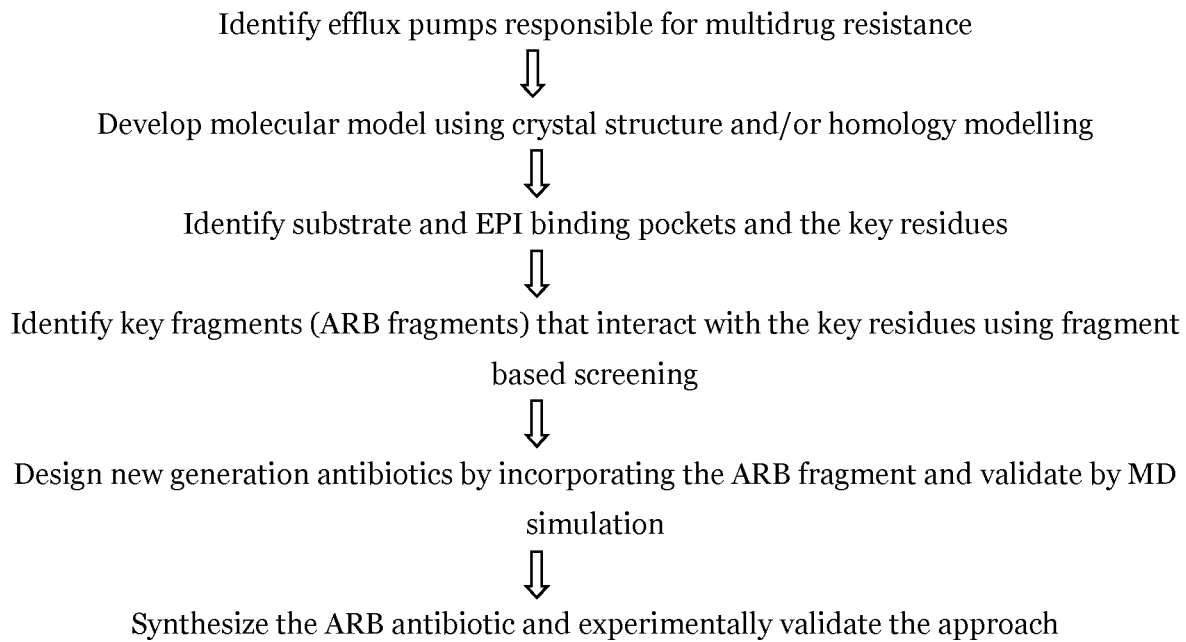
FIG. 34 shows the experimental approach for identifying a suitable ARB fragment, covalently linking them to core antibiotic chemical scaffold, developing ARB-linked antibiotic and validation of the concept.

Animal weights as group averages throughout the study are shown in FIG. 33. Animal weights are shown relative to

TABLE 21

Study design

| Group # | Test Article | Concentration (mg/mL) | Dose per Treatment (mg/kg) | Total Dose (mg/kg) | Route of admin. | Treatments (h post-infection) | End of Experiment (h post infection) |
|---|---|---|---|---|---|---|---|
| 1 | Pre-Treatment | | NA | NA | NA | NA | 2 h |
| 2 | Vehicle | — | — | — | PO | 2 h, 8 h, 14 h | 18 h |
| 3 | ML-83-009 | 2 | 20 | 60 | PO | 2 h, 8 h, 14 h | 18 h |
| 4 | ML-83-009 | 5 | 50 | 150 | PO | 2 h, 8 h, 14 h | 18 h |
| 5 | KSN-82-L7 | 2 | 20 | 60 | PO | 2 h, 8 h, 14 h | 18 h |
| 6 | KSN-82-L7 | 5 | 50 | 150 | PO | 2 h, 8 h, 14 h | 18 h |
| 7 | Levofloxacin | 2 | 20 | 60 | PO | 2 h, 8 h, 14 h | 18 h |
| 8 | Levofloxacin | 5 | 50 | 150 | PO | 2 h, 8 h, 14 h | 18 h |

For all of the above groups the No. mice was 5

For all of the above groups 2 to 8 the dose volume was 10 mL/kg. For the pre-treatment (group 1) the dose volume is not applicable.

General Health Monitoring

General health of animal were monitored in particular after 14 h post infection. Where the clinical deterioration of mice exceeded the ethically agreed limits, they were immediately euthanized using a pentobarbitone overdose. Once animals from the vehicle group exceeded ethical limits all animals in the experiment were euthanized.

Endpoints

After sacrifice of animal, both posterior thighs were removed, weighed, then homogenised in 2 mL PBS using a Precellys bead beater and the homogenates individually quantitatively cultured on CLED agar to determine the bacterial burdens.

Statistics

The data from the culture burdens were analysed using appropriate non-parametric statistical models (Kruskal-Wallis using Conover-Inman to make all pairwise comparisons between groups) with StatsDirect software v. 2.7.8., and compared to pre-treatment and vehicle controls.

Results

The aim of the study was to assess the efficacy of two client's test articles in murine thigh infection model with S.

the weight on the day of infection (day 0). Individual mouse weights throughout the study are detailed in Table 24.

Following infection, Vehicle and ML-83-009 treated animals lost weight. The body weights of animals of treated groups with levofloxacin were unchanged and slightly increased for the animals of the KSN-82-L22 treated groups.

Clinical Observations

The experiment was terminated at 18 h post infection due to vehicle treated animals reaching the clinical end point for the model. No adverse effect of treatment was observed in treated groups.

Thigh Bacteria Burden

The infection was well established with the bacterial burden increasing by about 3.5 $\log_{10}$ CFU/g between 2 h and 18 h post infection. (Table 22 and FIG. 29). The burden in the vehicle group reached $2\times10^8$ CFU/g 18 h post infection.

Levofloxacin administered at 20 and 50 mg/kg/dose reduced thigh bacterial burden by ~5 $\log_{10}$ cfu/g (P<0.0001).

Treatment with ML-83-009 at 20 or 50 mg/kg/dose slightly decreased bacterial burden, by 0.26 and 1.12 $\log_{10}$ CFU/g compared to vehicle group, respectively, which was not statistically significant (FIG. 29A). KSN-82-L22 at 20 mg/kg and 50 mg/kg decreased significantly the bacteria burden in comparison to the vehicle by 5 and 5.16 $\log_{10}$ CFU/g respectively (FIG. 29B), similarly to the levofloxacin treated group. Moreover KSN-82-L22 at the two doses decreased significantly the bacteria burden in comparison to the pre-treatment group by about 1.6 $\log_{10}$ CFU/g.

TABLE 22

Thigh bacterial burden

| Group No | Treatment | Group Geometric mean (cfu/g) | Standard Deviation (cfu/g) | $\log_{10}$ Group Geometric mean (cfu/g) | $\log_{10}$ reduction from vehicle control | n |
|---|---|---|---|---|---|---|
| 1 | Pre-treatment | $6.67 \times 10^4$ | $2.36 \times 10^4$ | 4.82 | | 5 |
| 2 | Vehicle | $2.01 \times 10^8$ | $1.33 \times 10^8$ | 8.30 | — | 5 |
| 3 | ML-83-009 20 mg/kg | $1.11 \times 10^8$ | $3.06 \times 10^8$ | 8.05 | 0.26 | 5 |
| 4 | ML-83-009 50 mg/kg | $1.51 \times 10^7$ | $8.29 \times 10^7$ | 7.18 | 1.12 | 5 |
| 5 | KSN-82-L22 20 mg/kg | $2.01 \times 10^3$ | $3.27 \times 10^3$ | 3.30 | 5.00 | 5 |
| 6 | KSN-82-L22 50 mg/kg | $1.37 \times 10^3$ | $7.50 \times 10^2$ | 3.14 | 5.16 | 5 |

TABLE 22-continued

| | | Thigh bacterial burden | | | | |
|---|---|---|---|---|---|---|
| Group No | Treatment | Group Geometric mean (cfu/g) | Standard Deviation (cfu/g) | $Log_{10}$ Group Geometric mean (cfu/g) | $Log_{10}$ reduction from vehicle control | n |
| 7 | Levofloxacin 20 mg/kg | $3.39 \times 10^3$ | $2.02 \times 10^3$ | 3.53 | 4.77 | 5 |
| 8 | Levofloxacin 50 mg/kg | $1.68 \times 10^3$ | $1.00 \times 10^3$ | 3.23 | 5.08 | 5 |

TABLE 23

| | Statistic analysis | | | | | | |
|---|---|---|---|---|---|---|---|
| | Vehicle | ML-83-009 20 mg/kg | ML-83-009 50 mg/kg | KSN-82-L22 20 mg/kg | KSN-82-L22 50 mg/kg | Levofloxacin 20 mg/kg | Levofloxacin 50 mg/kg |
| Pre treatment | P = 0.0153 | P = 0.0359 | NS | P = 0.0139 | P = 0.0026 | NS | P = 0.0084 |
| Vehicle | | NS | NS | P < 0.0001 | P < 0.0001 | P < 0.0001 | P < 0.0001 |
| ML-83-009 20 mg/kg | | | NS | P < 0.0001 | P < 0.0001 | P = 0.0003 | P < 0.0001 |
| ML-83-009 50 mg/kg | | | | P = 0.0002 | P < 0.0001 | P = 0.0058 | P < 0.0001 |
| KSN-82-L22 20 mg/kg | | | | | NS | NS | NS |
| KSN-82-L22 50 mg/kg | | | | | | NS | NS |
| Levofloxacin 20 mg/kg | | | | | | | NS |

Summary

A robust infection of *S. aureus* ATCC29213 was achieved in the thigh of ICR mice with ~4.5 $log_{10}$ CFU/g of tissue increase between pre-treatment group and vehicle group and the vehicle group reaching a terminal burden of $2 \times 10^8$ CFU/g ML-83-009 at 20 and 50 mg/kg reduced thigh burden by 0.26 and 1.12 $log_{10}$ CFU/g compared to vehicle treated animals, respectively, which was not statistically significant.

KSN-82-L22 at 20 and 50 mg/kg significantly decreased bacterial burden by >5 $Log_{10}$ CFU/g compared to vehicle group level and by >1.6 $log_{10}$ CFU/g compared to the pre-treatment group suggesting bactericidal activity.

The efficacy of KS-82-L22 at 20 and 50 mg/kg was similar to groups treated with Levofloxacin at 20 and 50 mg/kg.

Raw Data

TABLE 24

| | Bodyweight raw data | | | | | |
|---|---|---|---|---|---|---|
| Group No. | Treatment | Mouse No. | −4 | −1 | 0 | 1 |
| 1 | Pretreatment | 1 | 26.9 | 26.3 | 26.4 | |
| | | 2 | 27.9 | 28.2 | 28.7 | |
| | | 3 | 29.1 | 28.6 | 28.8 | |
| | | 4 | 28.1 | 28.4 | 28.5 | |
| | | 5 | 27.9 | 28.4 | 28.7 | |
| 2 | Vehicle | 6 | 29.4 | 30 | 31 | 29.2 |
| | | 7 | 31.3 | 31.4 | 29.9 | 28.9 |
| | | 8 | 31.0 | 30.9 | 30.9 | 29.2 |
| | | 9 | 25.8 | 26.7 | 31.4 | 24 |
| | | 10 | 29.7 | 29.8 | 26.6 | 27.5 |
| 3 | ML-83-009 20 mg/kg | 11 | 29.4 | 29.6 | 29.7 | 27.4 |
| | | 12 | 25.4 | 25.9 | 25.9 | 23.3 |
| | | 13 | 25.7 | 25.9 | 26.1 | 23.8 |
| | | 14 | 29.1 | 30.0 | 29.7 | 27.4 |
| | | 15 | 27.2 | 27.6 | 27.6 | 26.4 |
| 4 | ML-83-009 50 mg/kg | 16 | 27.9 | 27.6 | 27 | 24.4 |
| | | 17 | 27.5 | 27.4 | 27.9 | 25.5 |

TABLE 24-continued

| | Bodyweight raw data | | | | | |
|---|---|---|---|---|---|---|
| Group No. | Treatment | Mouse No. | −4 | −1 | 0 | 1 |
| | | 18 | 30.1 | 30.3 | 30.7 | 28.1 |
| | | 19 | 26.5 | 26.8 | 26.2 | 23.6 |
| | | 20 | 28.7 | 27.9 | 27.7 | 25.8 |
| 5 | KSN-82-L22 20 mg/kg | 21 | 28.7 | 29.1 | 28.4 | 29.3 |
| | | 22 | 30.2 | 29.2 | 29.4 | 29.5 |
| | | 23 | 26.9 | 27-3 | 27.2 | 27.5 |
| | | 24 | 29.8 | 30.2 | 30.5 | 31.3 |
| | | 25 | 29.7 | 29.8 | 29.7 | 31.0 |
| 6 | KSN-82-L22 50 mg/kg | 26 | 27.8 | 27.9 | 28.2 | 29 |
| | | 27 | 29.2 | 29.5 | 27.8 | 28.1 |
| | | 28 | 28.9 | 29.1 | 29.3 | 30.1 |
| | | 29 | 27.0 | 26.5 | 26.6 | 26.1 |
| | | 30 | 27.9 | 26.8 | 25.6 | 26.4 |
| 7 | Levofloxacin 20 mg/kg | 31 | 30.2 | 30.5 | 30.1 | 29.1 |
| | | 32 | 27.8 | 28.2 | 28.2 | 28.9 |
| | | 33 | 28.9 | 29.2 | 29.3 | 29.5 |
| | | 34 | 29.3 | 30.0 | 29.4 | 29.7 |
| | | 35 | 29.9 | 30.0 | 30.3 | 30.7 |
| 8 | Levofloxacin 50 mg/kg | 36 | 27.1 | 28.1 | 27.5 | 27 |
| | | 37 | 27.7 | 27.5 | 27.1 | 27.2 |
| | | 38 | 29.5 | 30.2 | 30.3 | 29.8 |
| | | 39 | 31.2 | 30.7 | 30.9 | 30.2 |
| | | 40 | 28.5 | 29.5 | 29.6 | 28.4 |

TABLE 25

Bacterial burden data

| Pretreatment | Vehicle | ML-83-009 20 mg/kg | ML-83-009 50 mg/kg | KSN-82-L7 20 mg/kg | KSN-82-L7 50 mg/kg | Levofloxacin 20 mg/kg | Levofloxacin 50 mg/kg |
|---|---|---|---|---|---|---|---|
| 8.67E+04 | 2.72E+08 | 9.25E+08 | 1.25E+07 | 2.48E+03 | 2.58E+03 | 5.82E+03 | 1.32E+03 |
| 8.39E+04 | 4.93E+08 | 1.01E+08 | 2.30E+07 | 3.92E+03 | 1.98E+03 | 6.89E+03 | 1.59E+03 |
| 1.15E+05 | 4.01E+08 | 3.48E+07 | 2.62E+08 | 5.78E+02 | 5.78E+02 | 1.86E+03 | 8.41E+02 |
| 7.04E+04 | 1.75E+08 | 3.27E+07 | 1.82E+07 | 1.80E+03 | 1.70E+03 | 3.76E+03 | 2.19E+03 |
| 4.28E+04 | 1.05E+08 | 1.77E+07 | 1.33E+08 | 6.42E+02 | 5.94E+02 | 2.36E+03 | 9.47E+02 |
| 5.55E+04 | 1.24E+08 | 5.48E+07 | 4.12E+07 | 1.94E+03 | 2.63E+03 | 2.68E+03 | 3.73E+03 |
| 6.94E+04 | 2.90E+08 | 3.93E+08 | 2.96E+06 | 1.60E+03 | 2.00E+03 | 1.23E+03 | 3.09E+03 |
| 8.68E+04 | 2.15E+08 | 3.15E+07 | 1.05E+05 | 3.05E+03 | 1.44E+03 | 4.80E+03 | 2.01E+03 |
| 5.94E+04 | 9.82E+07 | 4.35E+07 | 2.60E+07 | 1.51E+03 | 9.34E+02 | 2.90E+03 | 2.64E+03 |
| 3.49E+04 | 1.42E+08 | 5.32E+08 | 1.04E+07 | 1.18E+04 | 1.14E+03 | 6.60E+03 | 7.99E+02 |

TABLE 26

Interaction of the lead compound KSN-L22 with cytochrome P450 enzymes at 10 µM concentration

| ASSAY NUMBER | ASSAY NAME | STUDY NUMBER | CLIENT COMPOUND ID | % inhibition |
|---|---|---|---|---|
| 1770 | CYP3A inhibition (HLM, midazolam substrate) | US034-0002914 | KSN-82-L22 | 25.1969 |
| 4481 | CYP2C8 inhibition (HLM, amodiaquine substrate) | US034-0002914 | KSN-82-L22 | 3.05344 |
| 1769 | CYP3A inhibition (HLM, testosterone substrate) | US034-0002914 | KSN-82-L22 | 6.52493 |
| 2065 | CYP2B6 inhibition (HLM, bupropion substrate) | US034-0002914 | KSN-82-L22 | −1.31579 |
| 1838 | CYP2D6 inhibition (HLM, dextromethorphan substrate) | US034-0002914 | KSN-82-L22 | 0 |
| 2066 | CYP2C9 inhibition (HLM, diclofenac substrate) | US034-0002914 | KSN-82-L22 | 12.8205 |
| 2064 | CYPiA inhibition (HLM, phenacetin substrate) | US034-0002914 | KSN-82-L22 | 9.55985 |
| 1772 | CYP2C19 inhibition (HLM, omeprazole substrate) | US034-0002914 | KSN-82-L22 | 0.631579 |

TABLE 27

Safetyscreen44 data for the lead compound KSN-L22: This assay tests potential off target toxicity.

| ASSAY NUMBER | ASSAY NAME | STUDY NUMBER | CLIENT COMPOUND ID | % inhibition |
|---|---|---|---|---|
| 933 | AR (h) (agonist radioligand) | FR095-0004874 | KSN-82-L22 | 4.24138 |
| 39 | CCK1 (CCKA) (h) (agonist radioligand) | FR095-0004874 | KSN-82-L22 | −2.03813 |
| 18 | beta 1 (h) (agonist radioligand) | FR095-0004874 | KSN-82-L22 | 1.92061 |
| 469 | GR (h) (agonist radioligand) | FR095-0004874 | KSN-82-L22 | 3.45577 |
| 118 | mu (MOP) (h) (agonist radioligand) | FR095-0004874 | KSN-82-L22 | 6.53465 |
| 471 | 5-HT2A (h) (agonist radioligand) | FR095-0004874 | KSN-82-L22 | −8.88055 |
| 132 | 5-HT1B (antagonist radioligand) | FR095-0004874 | KSN-82-L22 | −16.7063 |
| 4173 | COX1 (h) | FR095-0004874 | KSN-82-L22 | 30.3185 |
| 439 | 5-HT transporter (h) (antagonist radioligand) | FR095-0004874 | KSN-82-L22 | −16.9663 |
| 2338 | alpha 1A (h) (antagonist radioligand) | FR095-0004874 | KSN-82-L22 | 11.5312 |
| 131 | 5-HT1A(h) (agonist radioligand) | FR095-0004874 | KSN-82-L22 | −3.77016 |
| 93 | M2 (h) (antagonist radioligand) | FR095-0004874 | KSN-82-L22 | 1.06575 |
| 4 | A2A (h) (agonist radioligand) | FR095-0004874 | KSN-82-L22 | 53.628 |
| 54 | ETA (h) (agonist radioligand) | FR095-0004874 | KSN-82-L22 | −5.23641 |

TABLE 27-continued

Safetyscreen44 data for the lead compound KSN-L22: This assay tests potential off target toxicity.

| ASSAY NUMBER | ASSAY NAME | STUDY NUMBER | CLIENT COMPOUND ID | % inhibition |
|---|---|---|---|---|
| 1208 | H2 (h) (antagonist radioligand) | FR095-0004874 | KSN-82-L22 | −40.1709 |
| 166 | KV channel (antagonist radioligand) | FR095-0004874 | KSN-82-L22 | −4-64385 |
| 28 | BZD (central) (agonist radioligand) | FR095-0004874 | KSN-82-L22 | −44.8289 |
| 1322 | D2S (h) (agonist radioligand) | FR095-0004874 | KSN-82-L22 | −7.80669 |
| 20 | beta 2 (h) (antagonist radioligand) | FR095-0004874 | KSN-82-L22 | 11.3086 |
| 52 | dopamine transporter (h) (antagonist radioligand) | FR095-0004874 | KSN-82-L22 | 10.0257 |
| 13 | alpha 2A (h) (antagonist radioligand) | FR095-0004874 | KSN-82-L22 | 4-4791 |
| 4186 | COX2(h) | FR095-0004874 | KSN-82-L22 | 8.11129 |
| 1971 | kappa (KOP) (agonist radioligand) | FR095-0004874 | KSN-82-L22 | 27.3513 |
| 95 | M3 (h) (antagonist radioligand) | FR095-0004874 | KSN-82-L22 | 2.27343 |
| 114 | delta (DOP) (h) (agonist radioligand) | FR095-0004874 | KSN-82-L22 | 2.15892 |
| 37 | CB2 (h) (agonist radioligand) | FR095-0004874 | KSN-82-L22 | 0 |
| 161 | Ca2+ channel (L, dihydropyridine site) (antagonist radioligand) | FR095-0004874 | KSN-82-L22 | 6.04874 |
| 159 | V1a (h) (agonist radioligand) | FR095-0004874 | KSN-82-L22 | −12.5662 |
| 1333 | 5-HT2B (h) (agonist radioligand) | FR095-0004874 | KSN-82-L22 | 5.37361 |
| 4077 | PDE4D2 (h) | FR095-0004874 | KSN-82-L22 | 14.8003 |
| 44 | D1 (h) (antagonist radioligand) | FR095-0004874 | KSN-82-L22 | −154033 |
| 870 | H1 (h) (antagonist radioligand) | FR095-0004874 | KSN-82-L22 | 5.56418 |
| 3029 | N neuronal alpha 4beta 2 (h) (agonist radioligand) | FR095-0004874 | KSN-82-L22 | −41.8108 |
| 66 | NMDA (antagonist radioligand) | FR095-0004874 | KSN-82-L22 | 12.6124 |
| 443 | MAO-A (antagonist radioligand) | FR095-0004874 | KSN-82-L22 | −9.12972 |
| 4072 | PDE3A (h) | FR095-0004874 | KSN-82-L22 | 7.50221 |
| 2906 | Lck kinase (h) | FR095-0004874 | KSN-82-L22 | −2.89115 |
| 4094 | Potassium Channel hERG (human)-[3H] Dofetilide | FR095-0004874 | KSN-82-L22 | −0.246078 |
| 169 | Na+ channel (site 2) (antagonist radioligand) | FR095-0004874 | KSN-82-L22 | 23.6539 |
| 363 | acetylcholinesterase (h) | FR095-0004874 | KSN-82-L22 | 32.9861 |
| 411 | 5-HT3 (h) (antagonist radioligand) | FR095-0004874 | KSN-82-L22 | −4.70826 |
| 36 | CB1 (h) (agonist radioligand) | FR095-0004874 | KSN-82-L22 | 1.85658 |
| 355 | norepinephrine transporter (h) (antagonist radioligand) | FR095-0004874 | KSN-82-L22 | −6.47059 |
| 91 | M1 (h) (antagonist radioligand) | FR095-0004874 | KSN-82-L22 | 3.12943 |

TABLE 28

MIC Data of ARB compounds against ESKAPE panel of pathogens

| Freebase Code Code in patent document | Levofloxacin Commercial | ML-83-009 1-9 | ML-83-011 1.11 | ML-83-010 1.10 | ML-83-012 1.6 |
|---|---|---|---|---|---|
| KP13368 | 1-2 | 64 | 64 | 32 | 64 |
| M6 | 0.125 | 8 | 16-64 | 4 | 16 |
| AYE | 8 | 128 | 128 | 128->128 | 128 |
| Ab17978 | 0.125 | 4 | 16 | 2 | 8 |
| PA01 | 1-4 | 32 | 128 | 64 | 32 |
| PA13437 | 64-128 | >128 | 128 | >128 | >128 |
| EC12923 | N/A | 1-4 | 1-8 | 2 | 4 |
| MSSA9144 | 0.125 | 0.06 | 0.25 | 2 0.125 | 0.25 |
| EMRSA15 | 16 | 4 | 16 | 2 | 16 |
| EMRSA16 | 16 | 4 | 16 | 2 | 16 |
| VSE775 | 1 | 0.25 | 1 | < 0.125 - 0.5 | 1 |

TABLE 28-continued

MIC Data of ARB compounds against ESKAPE panel of pathogens

| | | | | | | | |
|---|---|---|---|---|---|---|---|
| VRE12201 | 0.5-1 | | 0.25 | 0.5-1 | 2 | 0.125 | 0.5-1 |
| VRE12204 | 1-2 | | 2 | 8 | 1-4 | | 8 |

| Freebase Code | KSN-L7 | KSN-L14 | KSN-L19 | KSN-L21 | KSN-L22 | KSN-L31 | KSN-L33 | KSN-L34 |
|---|---|---|---|---|---|---|---|---|
| Code in patent document | 1.12 | | 1.13 | 1.14 | 1.15 | 1.16 | 1.17 | 1.18 |

Gram-negative

| | | | | | | | | |
|---|---|---|---|---|---|---|---|---|
| KP13368 | 16 | 16 | >32 | >32 | 4 | 64 | 32 | 32 |
| M6 | 4-8 | 2 | 4 | 16 | 1 | 4 | 8 | 2 |
| AYE | 16-32 | >32 | >32 | >32 | 4 | >128 | 128 | 4 |
| Ab17978 | 0.5 | 0.5 | 4 | 2 | 0.125 | 4 | 2 | ≤0.125 |
| PA01 | 8-32 | 32 | >32 | >32 | 4 | 64 | 32-64 | 4 |
| PA13437 | >32 | >32 | >32 | >32 | >32 | >128 | 128 | >32 |
| EC12923 | 1 | 1 | 4 | 0.5 | 0.5 | 2 | 2 | 0.125 |

Gram-positive

| | | | | | | | | |
|---|---|---|---|---|---|---|---|---|
| MSSA9144 | 0.06 | 0.125 | 0.25 | 0.5 | ≤0.03 | 0.5-1 | 0.25 | ≤0.125 |
| EMRSA15 | 4 | 8 | 8 | 32 | 0.5 | 64 | 16 | 0.5 |
| EMRSA16 | 4 | 8-32 | 8 | >32 | 1 | 64 | 16-32 | 1 |
| VSE775 | 0.5 | 1 | 2 | 4 | 0.06 | 4 | 4 | ≤0.125 |
| VRE12201 | 0.5 | 0.5 | 1 | 1 | 0.06 | 2 | 2 | ≤0.125 |
| VRE12204 | 4 | 4 | 4 | 16 | 1 | 8 | 4 | 1 |

| Freebase Code | KSN-L36 | KSN-L44-D | KSN-L62 | KSN-L65 |
|---|---|---|---|---|
| Figure Number | 1-19 | 1.22 | 1.27 | 1.28 |

Gram Negative

| | | | | |
|---|---|---|---|---|
| KP13368 | 32 | 4 | 16 | |
| M6 | 2-4 | ≤0.125 | 1 | |
| AYE | 64 | 128 | 4 | |
| Ab17978 | 0.5-1 | 2 | 0.25 | |
| PA01 | 16 | 0.25-0.5 | 8 | |
| PA13437 | >64 | 32 | 128 | |
| EC12923 | 0.5-1 | ≤0.125 | 1 | |

Gram Positive

| | | | | |
|---|---|---|---|---|
| MSSA9144 | 0.25-0.5 | 0.25 | ≤0.125 | |
| EMRSA15 | 32 | 32 | 1 | |
| EMRSA16 | 32 | 32 | 4 | |
| VSE775 | 4 | 1-4 | ≤0.125 | |
| VRE12201 | 2 | 0.5-1 | ≤0.125 | |
| VRE12204 | 8 | 1 | 1 | |

| Freebase Code | KSN-BL-1 | KSN-BL-3 | KSN-BL-6 | KSN-BL-7 |
|---|---|---|---|---|
| Figure Number | 1.29 | 1-34 | 1.32 | 1.33 |

Gram-negative

| | | | | |
|---|---|---|---|---|
| KP13368 | 8 | 8 | 16 | 16 |
| M6 | 0.5 | 1-4 | 1-4 | 2 |
| AYE | 8 | 32 | 16 | 8 |
| A17978 | 0.25 | 0.25 | 0.5 | ≤0.125 |
| PA01 | 4 | 8 | 8 | 8 |
| PA13437 | >128 | >128 | >128 | >128 |
| EC12923 | 0.25-0.5 | 0.5 | 0.5 | 1 |

Gram-positive

| | | | | |
|---|---|---|---|---|
| MSSA9144 | ≤0.125 | 0.0156 | 0.0156 | ≤0.0039 |
| EMRSA15 | 1 | 0.5 | 2 | 0.125- |
| EMRSA16 | 1 | 0.5 | 1 | 0.25 |
| VSE775 | ≤0.125 | ≤0.125 | 0.0625-0.25 | 0.0625 |
| VRE12201 | ≤0.125 | 0.0625 | 0.0625 | 0.0313 |
| VRE12204 | 0.5 | 1 | 1 | 1 |

The ARB compound KSN-82-L22 was tested against a broad spectrum of *Neisseria gonorrhoeae* strains and the MIC data was determined (see Table 29).

TABLE 29

MIC Data of ARB compound KSN-82-L22 against a broad spectrum of Neisseria gonorrhoeae strains

| No. | Assay # | Strain ID | Resistance | MIC, µg/ml PT #1218401 KSN-82-L22 |
|---|---|---|---|---|
| 1 | 612500 | ATCC 49226 | PEN-I TET-I | <0.03125 |
| 2 | 612501 | ATCC 700825 | | 50.03125 |
| 3 | 612502 | CCUG 57595 | | 50.03125 |
| 4 | 612503 | CCUG 57596 | CIP-I PEN-I TET-R | 0.125 |
| 5 | 612504 | CCUG 57597 | FEP-NS FOX-I CAZ-NS CIP-R OFX-R PEN-R TET-R | 2 |
| 6 | 612505 | CCUG 57598 | FOX-R CAZ-NS CRO-NS CIP-R OFX-R PEN-R TET-R | 2 |
| 7 | 612506 | CCUG 57599 | CIP-R OFX-R PEN-R TET-R | 0-5 |
| 8 | 612507 | CCUG 57600 | CIP-R OFX-R PEN-R TET-R | 1 |
| 9 | 612508 | CCUG 57601 | PEN-R TET-R | <0.03125 |
| 10 | 612509 | CCUG 57602 | PEN-I TET-I | 0.0625 |
| 11 | 612568 | NCTC 13817 | PEN-R TET-I | 0-5 |
| 12 | 612569 | NCTC 13818 | CIP-R OFX-R PEN-R TET-R | 2 |
| 13 | 612570 | NCTC 13819 | FEP-NS CAZ-NS CIP-R OFX-R PEN-R TET-I | 2 |
| 14 | 612571 | NCTC 13820 | FEP-NS CFM-NS CAZ-NS CRO-NS CIP-R OFX-R PEN-R TET-R | 2 |
| 15 | 612572 | NCTC 13821 | FEP-NS CFM-NS CAZ-NS CRO-NS CIP-R PEN-I TET-I | 2 |
| 16 | 612573 | NCTC 13822 | FEP-NS CFM-NS CAZ-NS CIP-R OFX-R PEN-R TET-I | 2 |
| 17 | 612510 | BAA-1833 | PEN-I TET-I | 50.03125 |
| 18 | 612511 | BAA-1838 | | 50.03125 |
| 19 | 612512 | TCDC-NG08107 | PEN-R CFM-R CPD-R CIP-R | 2 |
| 20 | 612513 | 2007NG046 | PEN-R CFM-R CPD-R CIP-R | 4 |
| 21 | 612514 | 2008NG057 | PEN-R CFM-R CPD-R CIP-R | 2 |
| 22 | 612515 | 2008NG097 | PEN-R CFM-R CPD-R CIP-R | 2 |
| 23 | 612516 | 2009NG514 | PEN-R CPD-R CIP-R | 2 |
| 24 | 612517 | 2010NG122 | PEN-R CFM-R CIP-R | 2 |
| 25 | 612518 | FDA-CDC AR-BANK#0165 | CIP-R PEN-I TET-R | 2 |
| 26 | 612519 | FDA-CDC AR-BANK#0166 | CIP-R PEN-I TET-R | 2 |
| 27 | 612520 | FDA-CDC AR-BANK#0167 | CIP-S PEN-S TET-I | <0.03125 |
| 28 | 612521 | FDA-CDC AR-BANK#0168 | CIP-R PEN-I TET-R | 1 |
| 29 | 612522 | FDA-CDC AR-BANK#0169 | CIP-R PEN-I TET-R | 2 |
| 30 | 612523 | FDA-CDC AR-BANK#0170 | CIP-R PEN-I TET-R | 2 |
| 31 | 612524 | FDA-CDC AR-BANK#0171 | CIP-R PEN-I TET-R | 1 |
| 32 | 612525 | FDA-CDC AR-BANK#0172 | CIP-R PEN-R TET-R | 1 |
| 33 | 612526 | FDA-CDC AR-BANK#0173 | CIP-R PEN-R TET-R | 2 |
| 34 | 612527 | FDA-CDC AR-BANK#0174 | CIP-R PEN-R TET-R | 2 |
| 35 | 612528 | FDA-CDC AR-BANK#0175 | CIP-S PEN-I TET-I | <0.03125 |
| 36 | 612529 | FDA-CDC AR-BANK#0176 | CIP-R PEN-R TET-R | 2 |
| 37 | 612530 | FDA-CDC AR-BANK#0177 | CIP-S PEN-I TET-R | <0.03125 |
| 38 | 612531 | FDA-CDC AR-BANK#0178 | CIP-R PEN-R TET-R | 2 |
| 39 | 612532 | FDA-CDC AR-BANK#0179 | CIP-S PEN-S TET-I | <0.03125 |
| 40 | 612533 | FDA-CDC AR-BANK#0180 | CIP-R PEN-I TET-R | 2 |
| 41 | 612534 | FDA-CDC AR-BANK#0181 | CIP-S PEN-I TET-R | <0.03125 |
| 42 | 612535 | FDA-CDC AR-BANK#0182 | CIP-R PEN-I TET-R | 2 |
| 43 | 612536 | FDA-CDC AR-BANK#0183 | CIP-R PEN-R TET-R | 2 |
| 44 | 612537 | FDA-CDC AR-BANK#0184 | CIP-R PEN-R TET-R | 2 |
| 45 | 612538 | FDA-CDC AR-BANK#0185 | CIP-R PEN-I TET-R | 2 |
| 46 | 612539 | FDA-CDC AR-BANK#0186 | CIP-R PEN-R TET-R | 1 |
| 47 | 612540 | FDA-CDC AR-BANK#0187 | CIP-R PEN-I TET-R | 2 |
| 48 | 612541 | FDA-CDC AR-BANK#0188 | CIP-R PEN-I TET-R | 1 |
| 49 | 612542 | FDA-CDC AR-BANK#0189 | CIP-R PEN-R TET-R | 2 |
| 50 | 612543 | FDA-CDC AR-BANK#0190 | CIP-R PEN-R TET-R | 2 |
| 51 | 612544 | FDA-CDC AR-BANK#0191 | CIP-R PEN-R TET-R | 2 |
| 52 | 612545 | FDA-CDC AR-BANK#0192 | CIP-R PEN-R TET-R | 2 |
| 53 | 612546 | FDA-CDC AR-BANK#0193 | CIP-S PEN-R TET-R | <0.03125 |
| 54 | 612547 | FDA-CDC AR-BANK#0194 | CRO-NS CIP-S PEN-I TET-R | <0.03125 |
| 55 | 612548 | FDA-CDC AR-BANK#0195 | CIP-R PEN-I TET-R | 2 |
| 56 | 612549 | FDA-CDC AR-BANK#0196 | CIP-R PEN-R TET-R | 2 |
| 57 | 612550 | FDA-CDC AR-BANK#0197 | CIP-R PEN-I TET-I | 2 |
| 58 | 612551 | FDA-CDC AR-BANK#0198 | CIP-R PEN-I TET-R | 2 |
| 59 | 612552 | FDA-CDC AR-BANK#0199 | CIP-S PEN-R TET-R | <0.03125 |
| 60 | 612553 | FDA-CDC AR-BANK#0200 | CIP-R PEN-R TET-R | 2 |
| 61 | 612554 | FDA-CDC AR-BANK#0201 | CIP-R PEN-R TET-R | 2 |
| 62 | 612555 | FDA-CDC AR-BANK#0202 | CIP-S PEN-S TET-I | <0.03125 |
| 63 | 612556 | FDA-CDC AR-BANK#0203 | CIP-R PEN-R TET-R | 2 |
| 64 | 612557 | FDA-CDC AR-BANK#0204 | CIP-R PEN-I TET-R | 2 |
| 65 | 612558 | FDA-CDC AR-BANK#0205 | CIP-R PEN-R TET-R | 2 |

TABLE 29-continued

MIC Data of ARB compound KSN-82-L22 against a broad spectrum of Neisseria gonorrhoeae strains

| No. | Assay # | Strain ID | Resistance | MIC, µg/ml PT #1218401 KSN-82-L22 |
|---|---|---|---|---|
| 66 | 612559 | FDA-CDC AR-BANK#0206 | CIP-R PEN-R TET-R | 2 |
| 67 | 612560 | FDA-CDC AR-BANK#0207 | CIP-R PEN-R TET-R | 2 |
| 68 | 612561 | FDA-CDC AR-BANK#0208 | CIP-R PEN-I TET-R | 2 |
| 69 | 612562 | FDA-CDC AR-BANK#0209 | CIP-R PEN-I TET-R | 2 |
| 70 | 612563 | FDA-CDC AR-BANK#0210 | CIP-R PEN-I TET-I | 2 |
| 71 | 612564 | FDA-CDC AR-BANK#0211 | CIP-R PEN-R TET-R | 2 |
| 72 | 612565 | FDA-CDC AR-BANK#0212 | CIP-R PEN-I TET-R | 2 |
| 73 | 612566 | FDA-CDC AR-BANK#0213 | CIP-R PEN-I TET-I | 1 |
| 74 | 612567 | FDA-CDC AR-BANK#0214 | CIP-R PEN-R TET-R | 2 |

All publications mentioned in the above specification are herein incorporated by reference. Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

REFERENCES

1. *Antimicrobial Resistance: Tackling a crisis for the health and wealth of nations*, HM Government, London, 2014.
2. L. L. Silver, *Clin. Microbiol. Rev.*, 2011, 24, 71-109.
3. M. A. Fischbach and C. T. Walsh, *Science*, 2009, 325, 1089-1093.
4. K. Lewis, *Nat Rev Drug Discov*, 2013, 12, 371-387.
5. K. K. Kumarasamy, M. A. Toleman, T. R. Walsh, J. Bagaria, F. Butt, R. Balakrishnan, U. Chaudhary, M. Doumith, C. G. Giske, S. Irfan, P. Krishnan, A. V. Kumar, S. Maharjan, S. Mushtaq, T. Noorie, D. L. Paterson, A. Pearson, C. Perry, R. Pike, B. Rao, U. Ray, J. B. Sarma, M. Sharma, E. Sheridan, M. a. Thirunarayan, J. Turton, S. Upadhyay, M. Warner, W. Welfare, D. M. Livermore and N. Woodford, *Lancet Infect. Dis.*, 2010, 10, 597-602.
6. M. L. Cristina, A. M. Spagnolo, P. Orlando, F. Perdelli, *Rev. Med. Microbiol.*, 2013, 24, 104-112.
7. L. L. Maragakis and T. M. Perl, *Clin. Infect. Dis.*, 2008, 46, 1254-1263.
8. D. E. Karageorgopoulos and M. E. Falagas, *Lancet Infect. Dis.*, 2008, 8, 751-762.
9. D. Brown, *Nat Rev Drug Discov*, 2015, 14, 821-32.
10. M. A. Webber and L. J. V. Piddock, *J. Antimicrob. Chemother.*, 2003, 51, 9-11.
11. A. A. Neyfakh, V. E. Bidnenko and L. B. Chen, *Proc. Natl. Acad. Sci.*, 1991, 88, 4781-4785.
12. F. R. Stermitz, P. Lorenz, J. N. Tawara, L. a Zenewicz and K. Lewis, *Proc. Natl. Acad. Sci. U.S.A*, 2000, 97, 1433-1437.
13. M. Stavri, L. J. V Piddock and S. Gibbons, *J. Antimicrob. Chemother.*, 2007, 59, 1247-60.
14. T. E. Renau, R. Leger, E. M. Flamme, J. Sangalang, M. W. She, and R. Yen, *J. Med Chem.*, 1999, 42, 4928-31.
15. S. Mullin, N. Mani and T. H. Grossman, *J. Antimicrob. Agents Chemother.*, 2004, 48, 4171-4176.
16. A. M. Bailey, I. T. Paulsen and L. J. V Piddock, *Antimicrob. Agents Chemother.*, 2008, 52, 3604-3611.
17. A. Mahamoud, J. Chevalier, A. Davin-Regli, J. Barbe and J. M. Pages, *Curr. Drug Targets*, 2006, 7, 843-847.
18. D. Du, H. W. van Veen, and B. F. Luisi, *Trends Microbiol.*, 2015, 23, 311-319.
19. J.-M. M. Pages, L. Amaral, and S. Fanning, *Curr. Med. Chem.*, 2011, 18, 2969-2980.
20. H. M. Blumberg, D. Rimland, D. J. Carroll, P. Terry, and I. K. Wachsmuth, *J. Infect. Dis.*, 1991, 163, 1279-1285.
21. A. Dalhoff, *Interdiscip. Perspect. Infect. Dis.*, 2012, 2012, 976273.
22. L. Piddock, *Nature Rev. Microbiol.*, 2006, 4, 629-636.
23. K. Poole, *Antimicrob. Agents Chemother.*, 2000, 44, 2595-2599.
24. R. Beyer, E. Pestova, J. J. Millichap, V. Stosor, G. A. Noskin, and L. R. Peterson, *Antimicrob. Agents Chemother.*, 2000, 44, 798-801.
25. J. F. Turton, et al. *J. Clin Microbiol*, 2005, 43, 3074-3082.
26. J. F. Turton. et al. *Clin Microbiol Infect*, 2007, 13, 807-815.
27. K. Smith, et al. *Antimicrob Agents Chemother*, 2010, 54, 380-387.

What is claimed is:

1. An antibiotic compound of formula (A1):

or a pharmaceutically acceptable salt, solvate, tautomer, or combination thereof, wherein:

$X_1$ is C—$R_B$, and $R_A$ and $R_B$ together with the atoms to which they are attached form a 6-membered ring wherein from $R_A$ to $R_B$ is a —CH(CH$_3$)—CH$_2$—O— linking group;

R* is H or NH$_2$;

either $Z_1$ is CH and X* is —NR'—; or $Z_1$ is N and X* is absent;

$L_1$ is —NH— or —N(CH$_3$)—;

n is 1;

Z is N or C—H;

R'$_1$ is H, C$_{1-6}$ alkyl or —(CH$_2$)$_t$—C(=O)—OR';

R₁ is Ar₁;

Ar₁ is a six-membered ring; and the Ar₁ group may be optionally substituted with 1, 2 or 3 substituents selected from the group consisting of —C₁₋₆ alkyl, -halo, —(CH₂)ₜ—OR', —(CH₂)ᵣ C(=O)—OR', oxo, —(CH₂)ₜ—NR'R", —NO₂, —NR'-(cyclopropyl), -(cyclopropyl), —NR'—(CH₂)ₜ—NR'R", —C(=NR')—NR'R", —(CH₂)ₜ—NR'—C(=NR')—NR'R", —CH₂—CH=CH₂, —CH=CH—(C₁₋₆ alkyl), —CH=CH—CN, —SO₂—NR'R" and —SO₂NR'—(CH₂)ₜ—Ar₂;

each t is independently 0, 1, 2, 3, 4 or 5;

each Ar₂ is independently C₅₋₉ heteroaryl; and each R' and R" is independently H or C₁₋₆ alkyl.

2. The compound of claim 1, wherein the compound is a compound of formula (A2);

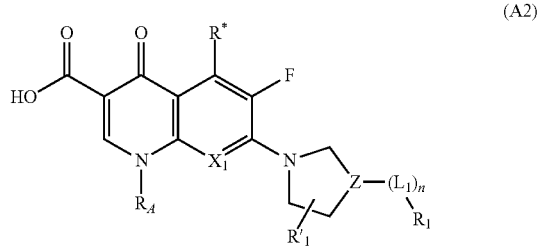

(A2)

or a pharmaceutically acceptable salt, solvate, tautomer, or combination thereof.

3. The compound of claim 1, wherein Ar₁ is a ring structure selected from the group consisting of cyclohexyl; morpholinyl; phenyl; piperazinyl; piperidinyl; pyrazinyl; pyridinyl; pyrimidinyl; thiomorpholinyl; and triazinyl.

4. The compound of claim 1, wherein Ar₁ is a ring structure selected from the group consisting of morpholinyl; piperazinyl; pyrazinyl; pyridinyl; pyrimidinyl; thiomorpholinyl; and triazinyl; wherein the ring structure is optionally substituted with 1, 2 or 3 substituents selected from the group consisting of —C₁₋₆ alkyl, -halo, —(CH₂)ₜ—OR', —(CH₂)ₜ—C(=O)—OR', oxo, —(CH₂)ₜ—NR'R", —NO₂, —NR'-(cyclopropyl), -(cyclopropyl), —NR'—(CH₂)ₜ—NR'R", —C(=NR')—NR'R", —(CH₂)ₜ—NR'—C(=NR')—NR'R", —CH₂—CH=CH₂, —CH=CH—(C₁₋₆ alkyl), —CH=CH—CN, —SO₂—NR'R" and —SO₂NR'—(CH₂)ₜ—Ar₂.

5. The compound of claim 1, wherein the structure:

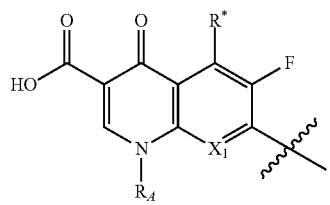

is:

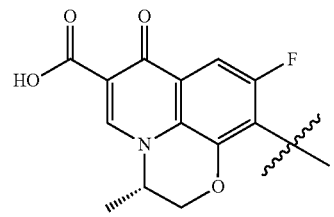 [SMILES: *c1c(F)cc2c(=O)c(C(=O)O)cn3c2c1OC[C@@H]3C]

or

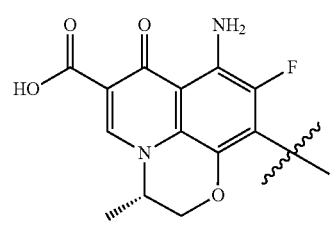

6. The compound of claim 1, wherein the compound is selected from the group consisting of:

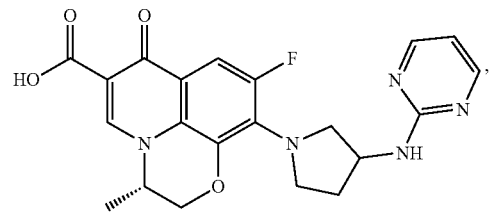

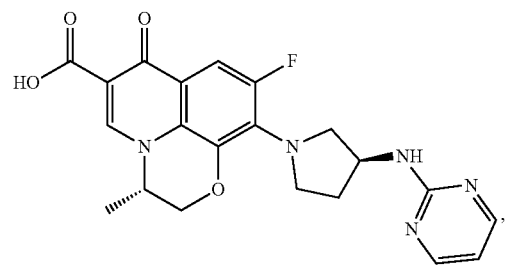

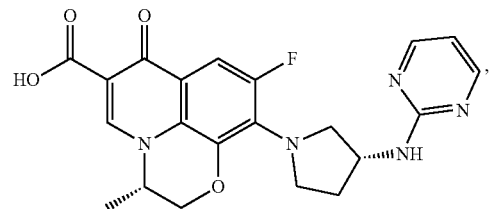

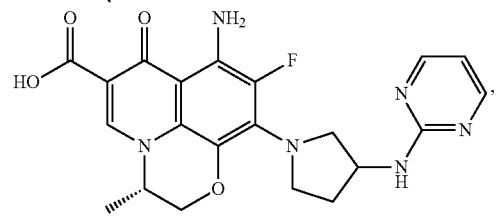

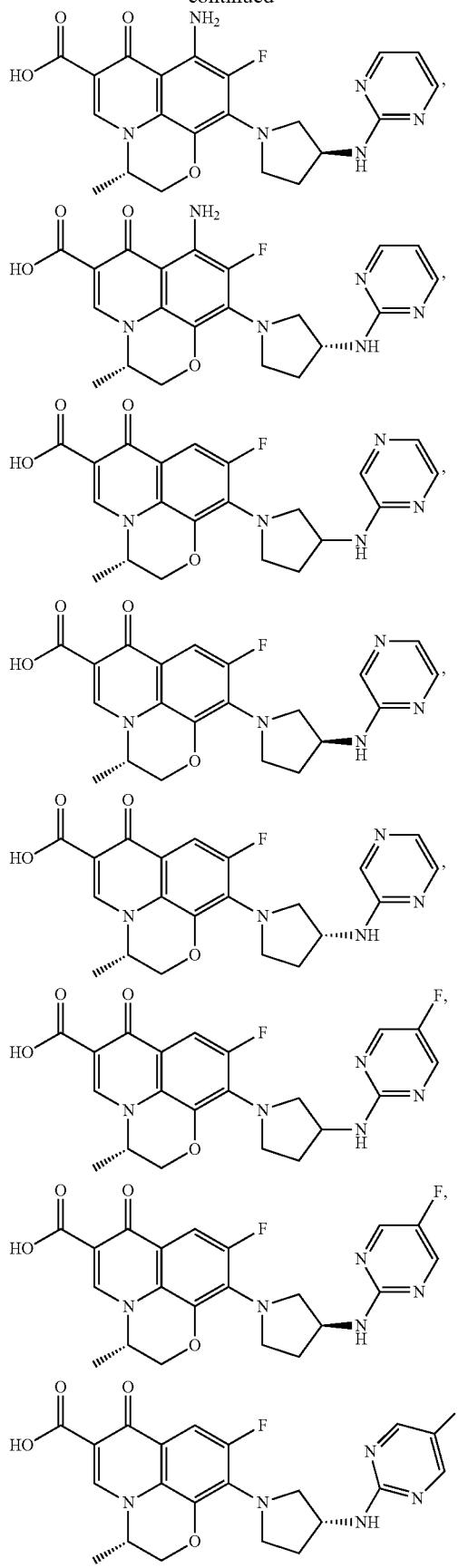
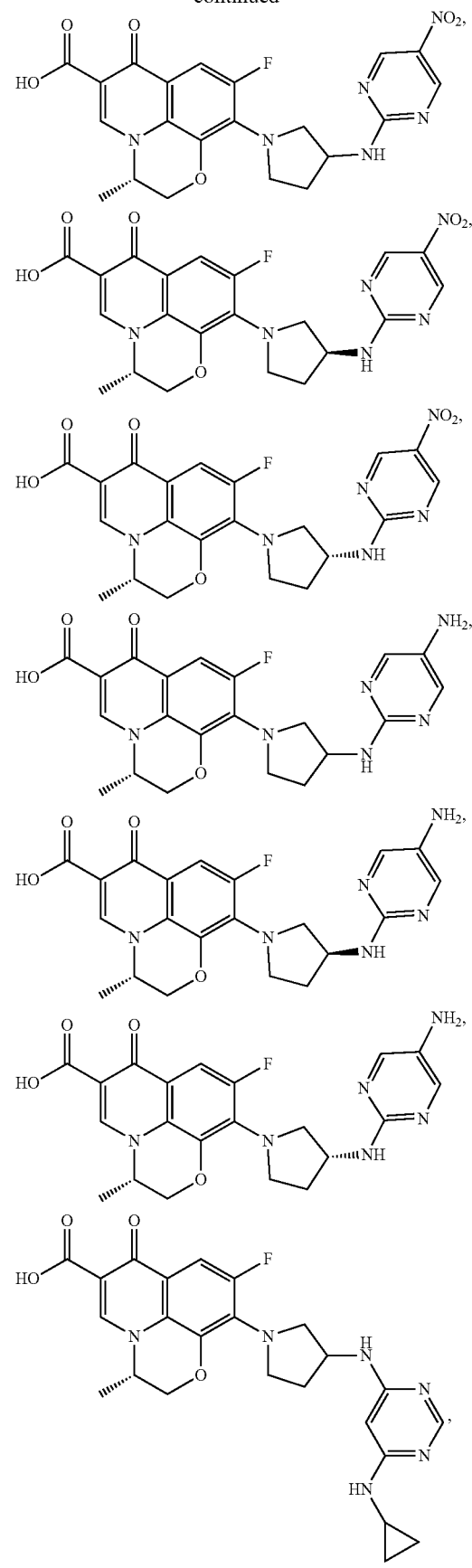

291
-continued

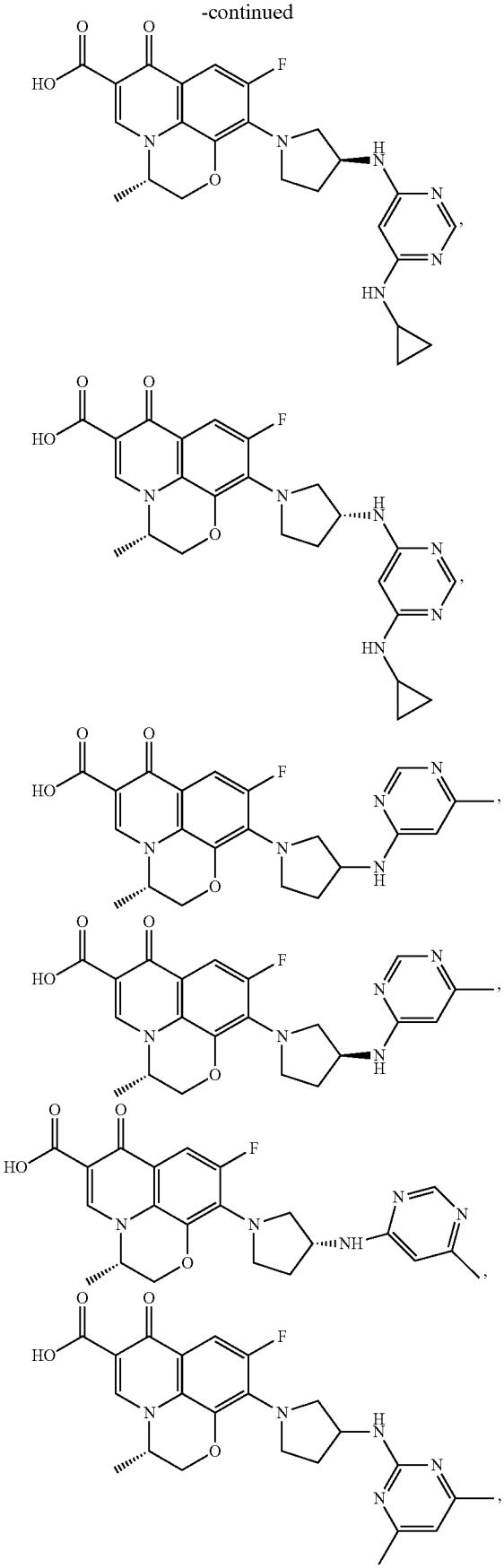

292
-continued

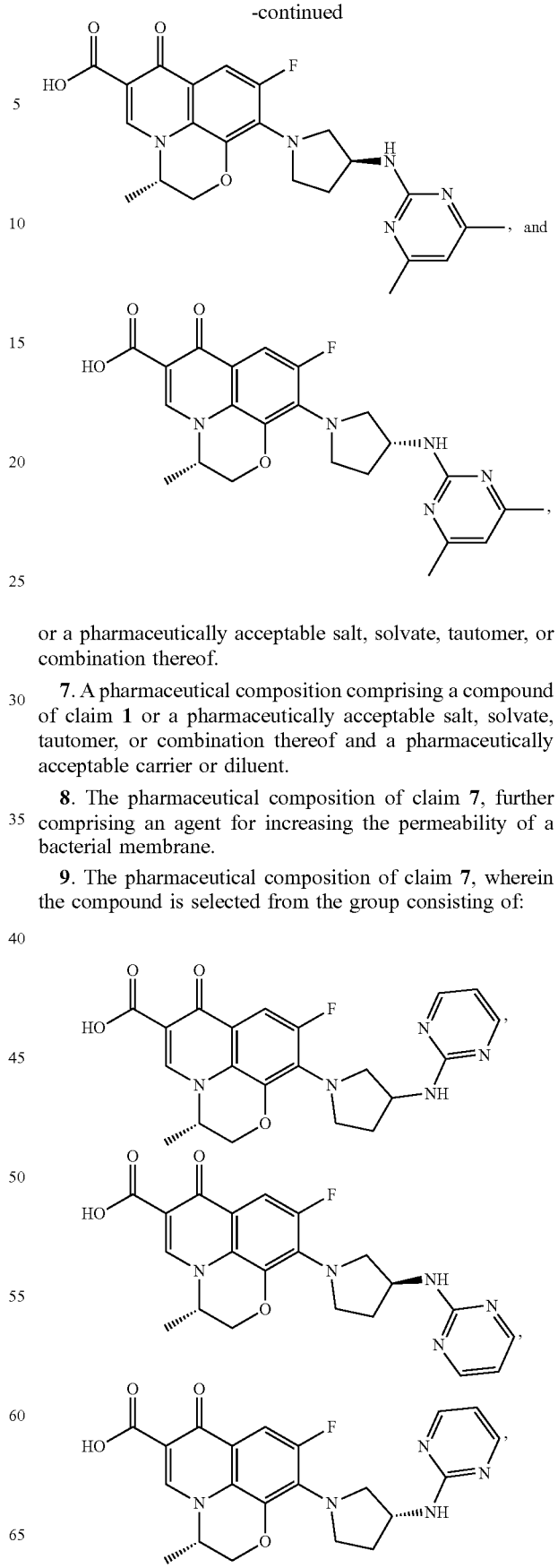

or a pharmaceutically acceptable salt, solvate, tautomer, or combination thereof.

7. A pharmaceutical composition comprising a compound of claim 1 or a pharmaceutically acceptable salt, solvate, tautomer, or combination thereof and a pharmaceutically acceptable carrier or diluent.

8. The pharmaceutical composition of claim 7, further comprising an agent for increasing the permeability of a bacterial membrane.

9. The pharmaceutical composition of claim 7, wherein the compound is selected from the group consisting of:

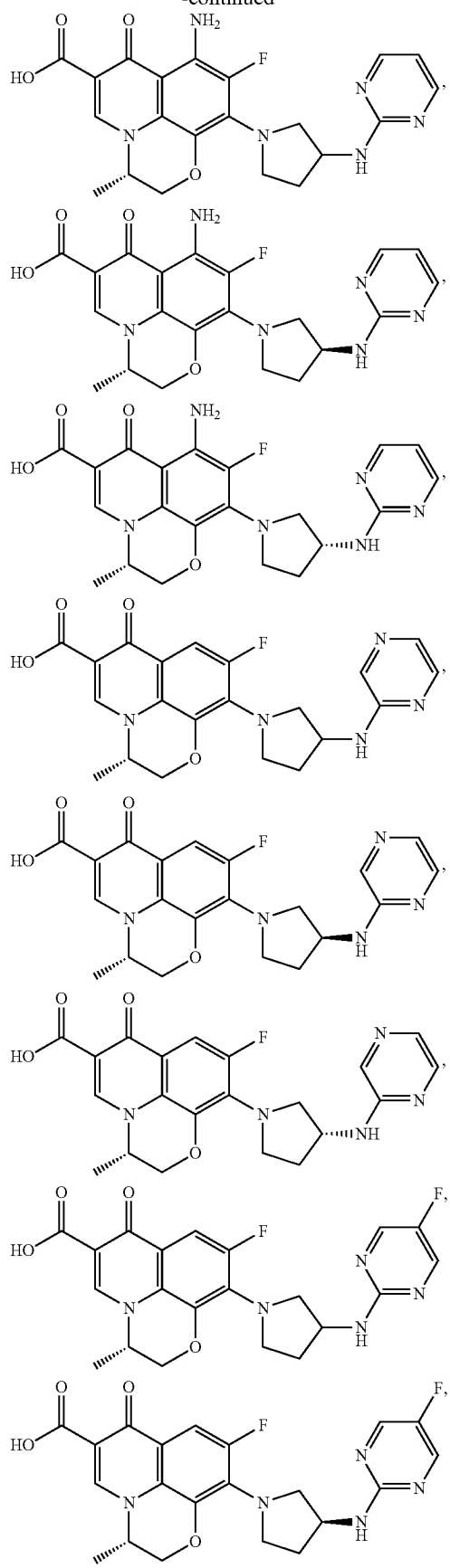
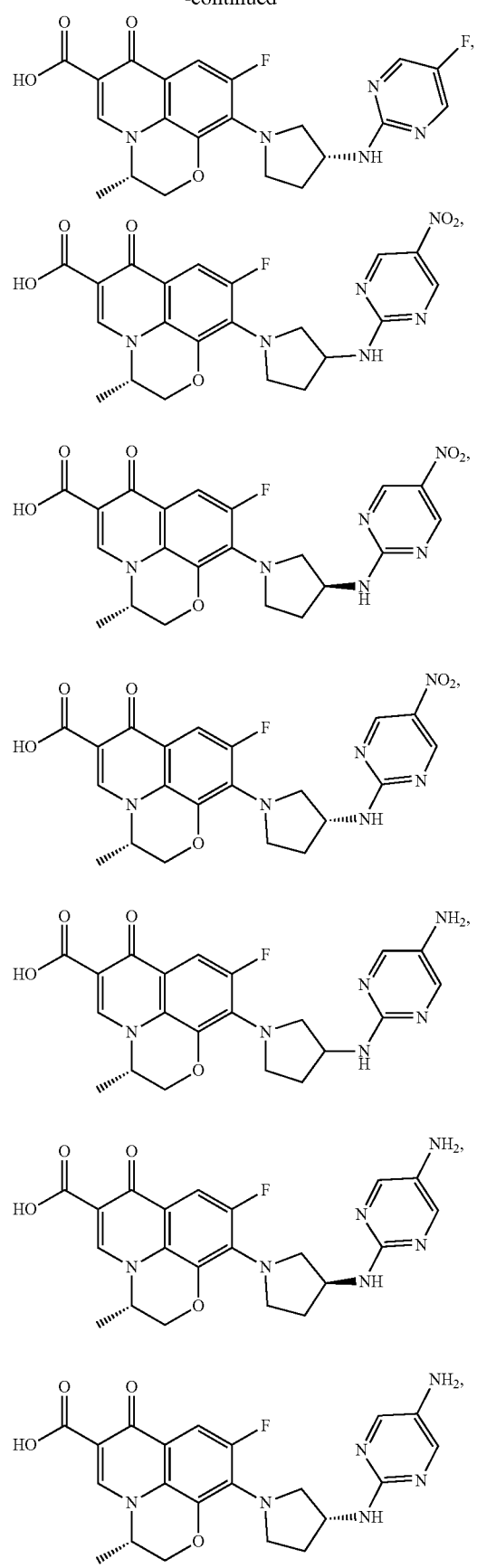

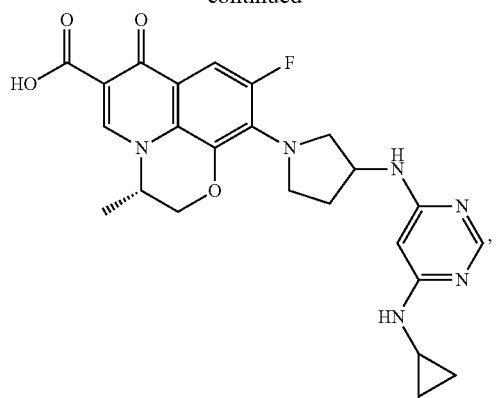

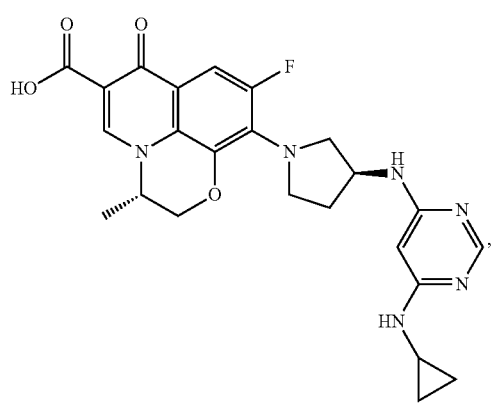

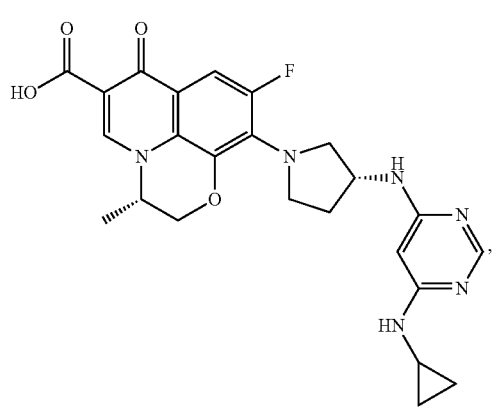

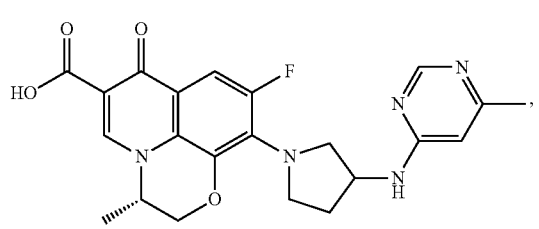

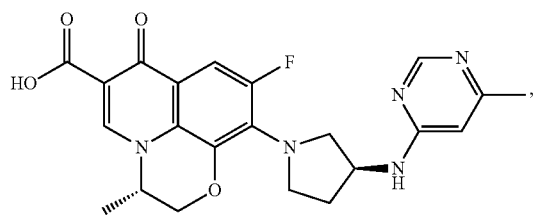

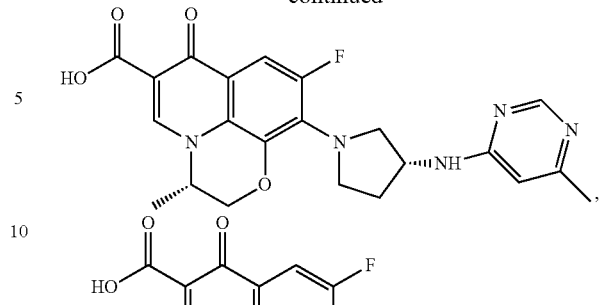

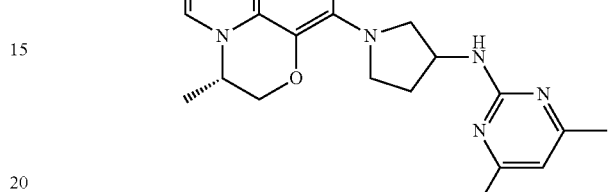

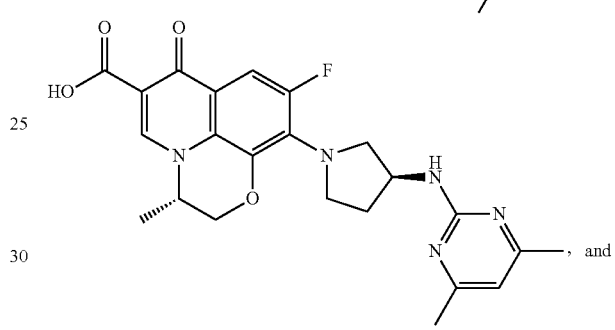

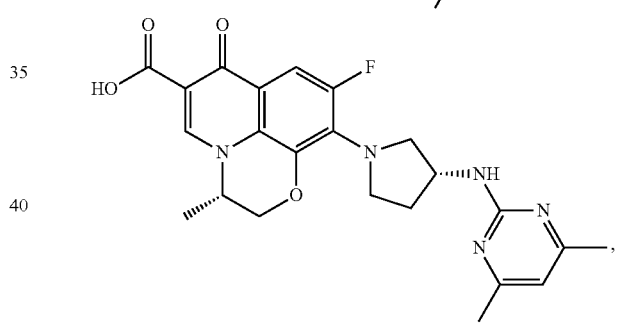

or a pharmaceutically acceptable salt, solvate, tautomer, or combination thereof.

10. A kit comprising:
   (i) a compound of claim 1, or a pharmaceutically acceptable salt, solvate, tautomer, or combination thereof, and at least one of:
   an agent for increasing permeability of a bacterial membrane; and an efflux pump inhibitor.

11. The kit of claim 10, wherein the compound is selected from the group consisting of:

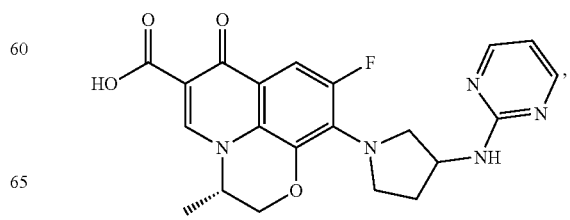

-continued
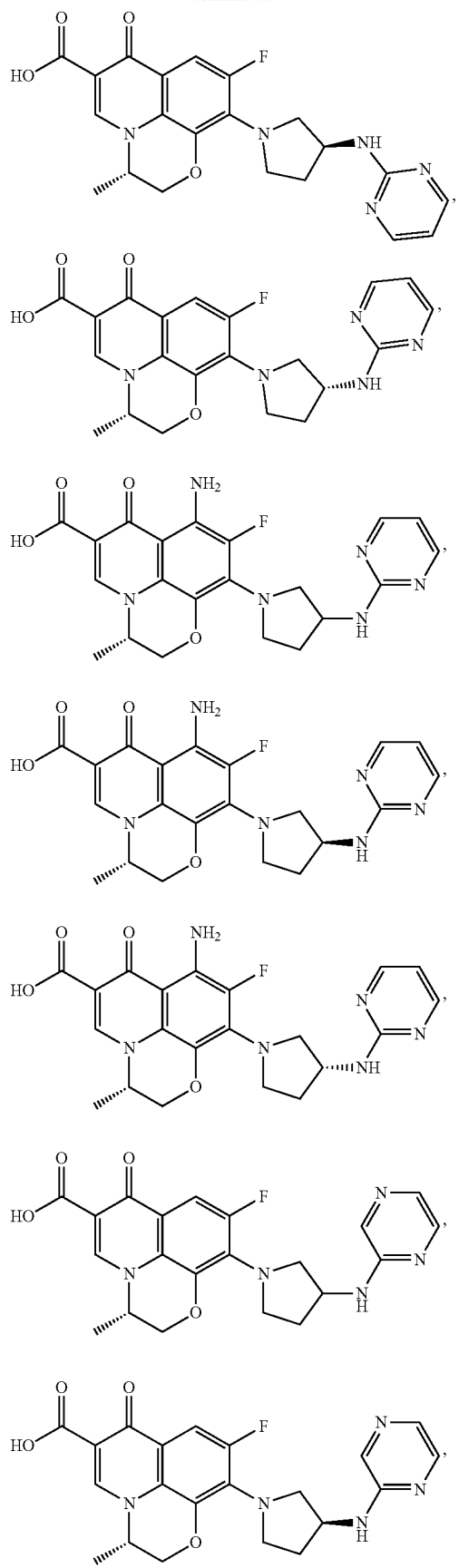
-continued
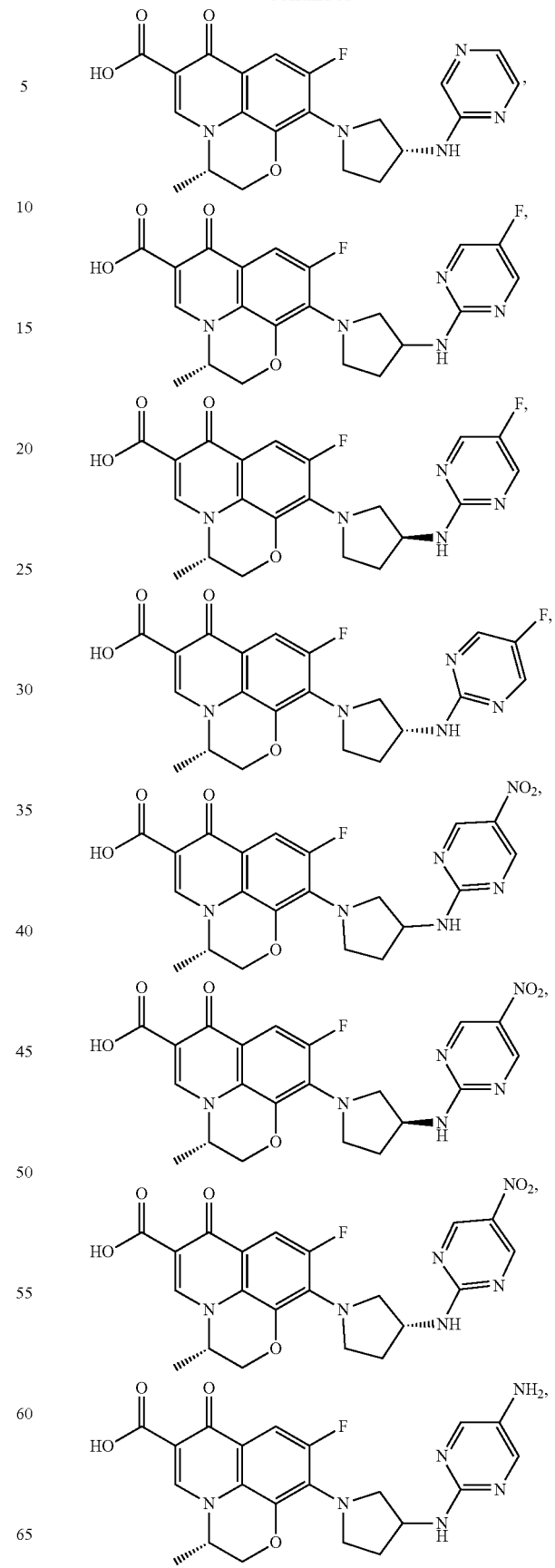

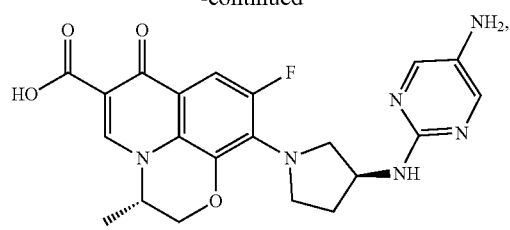
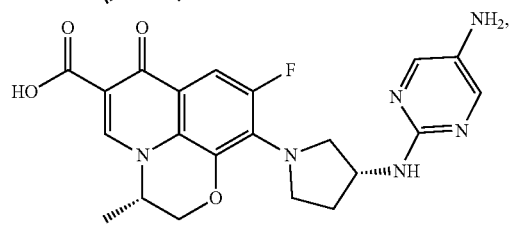
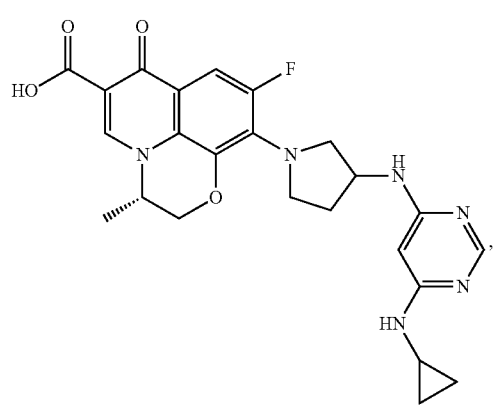
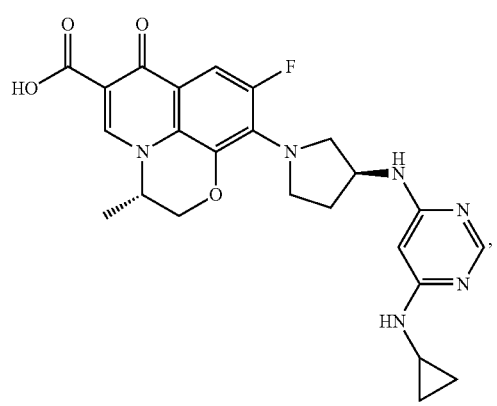
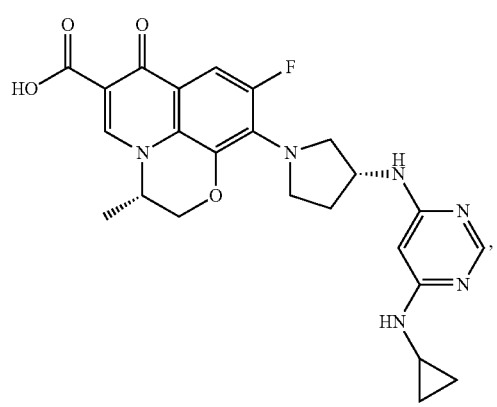
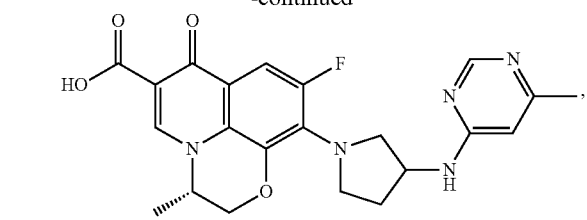
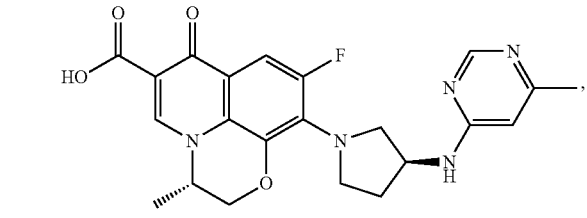
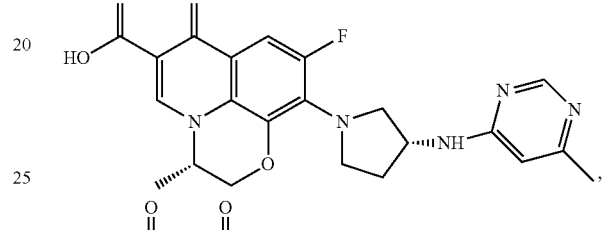
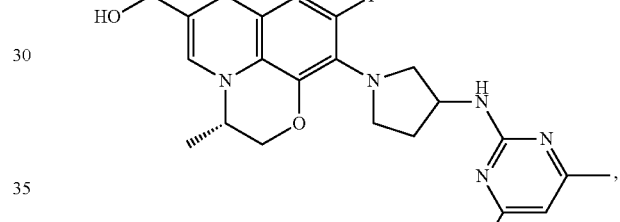
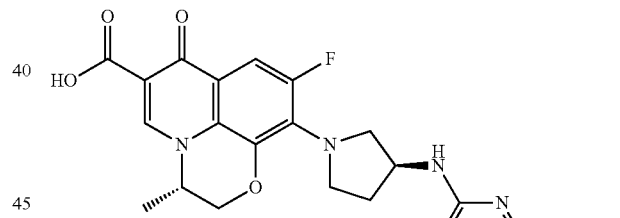
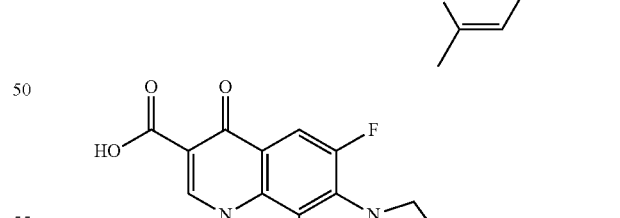
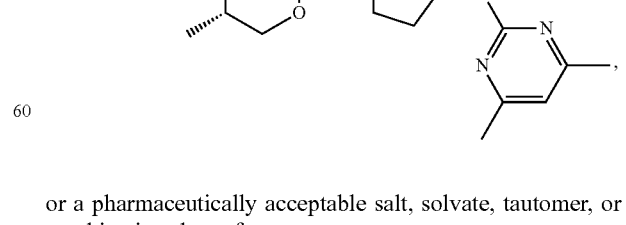
or a pharmaceutically acceptable salt, solvate, tautomer, or combination thereof.
12. A method of treating a bacterial infection in a patient, the method comprising a step of administering to the patient a therapeutically effective amount of a compound of claim 1 or a pharmaceutically acceptable salt, solvate, tautomer, or combination thereof.

13. The method of claim 12, wherein the bacterial infection is caused by at least one bacterium of a genera selected from the group consisting of *Acinetobacter, Bacillus, Brucella, Burkholderia, Campylobacter, Coxiella, Enterococcus, Enterobacter, Escherichia, Francisella, Klebsiella, Neisseria, Pseudomonas, Staphylococcus, Streptococcus* and *Yersina*.

14. The method of claim 12, wherein the bacterial infection is a caused by at least one bacterium selected from the group consisting of *Campylobacter jejuni, Neisseria gonorrhoea, Enterococcus faecalis, Enterococcus faecium, Staphylococcus aureus, Staphylococcus epidermidis, Streptococcus pneumoniae, Klebsiella pneumoniae, Acinetobacter baumannii, Pseudomonas aeruginosa, Enterobacter cloacae* and *Escherichia coli*; or at least one bacterium selected from *Bacillus anthracis, Burkholderia mallei, Burkholderia pseudomallei, Brucella melitensis, Coxiella bumettii, Francisella tularensis, Proteus mirabilis* and *Yersinia pestis*.

15. The method of claim 12, wherein the bacterial infection is anthrax, bronchitis, pneumonia, prostatitis, pyelonephritis, sinusitis, skin and skin structure infections, sexually transmitted disease or urinary tract infections.

16. The method of claim 12, wherein the bacterial infection is a multi-drug resistant bacterial infection.

17. The method of claim 12, wherein the compound is selected from the group consisting of:

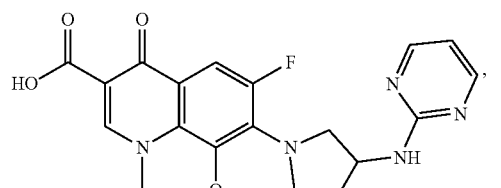

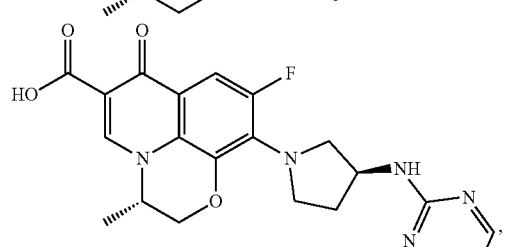

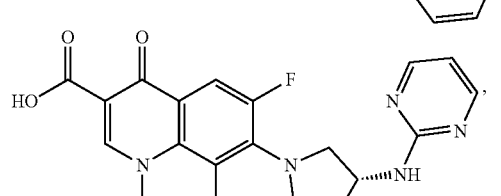

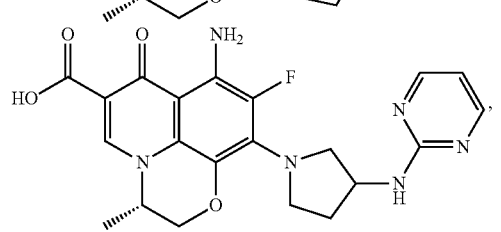

-continued

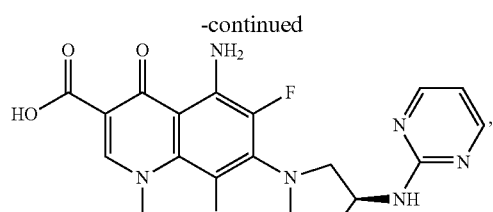

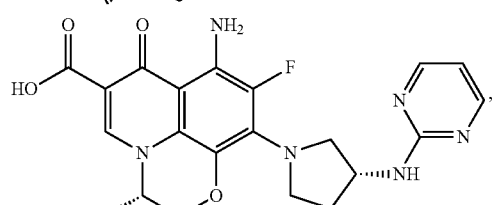

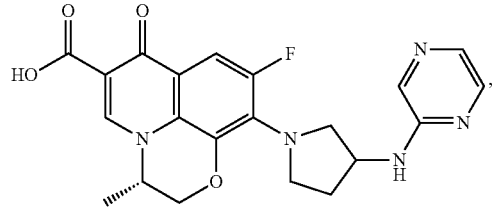

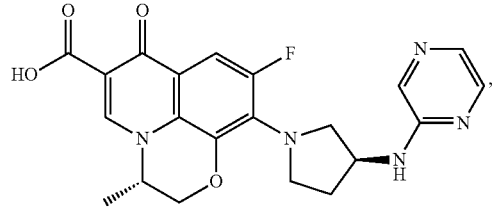

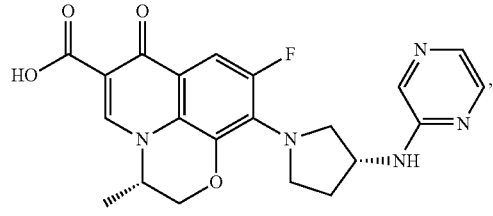

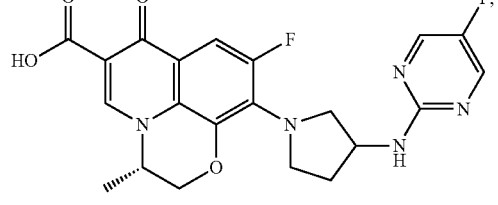

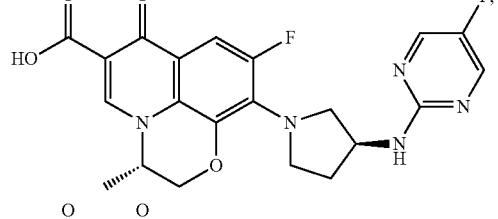

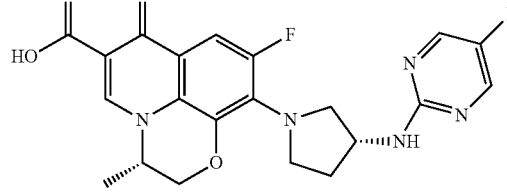

-continued
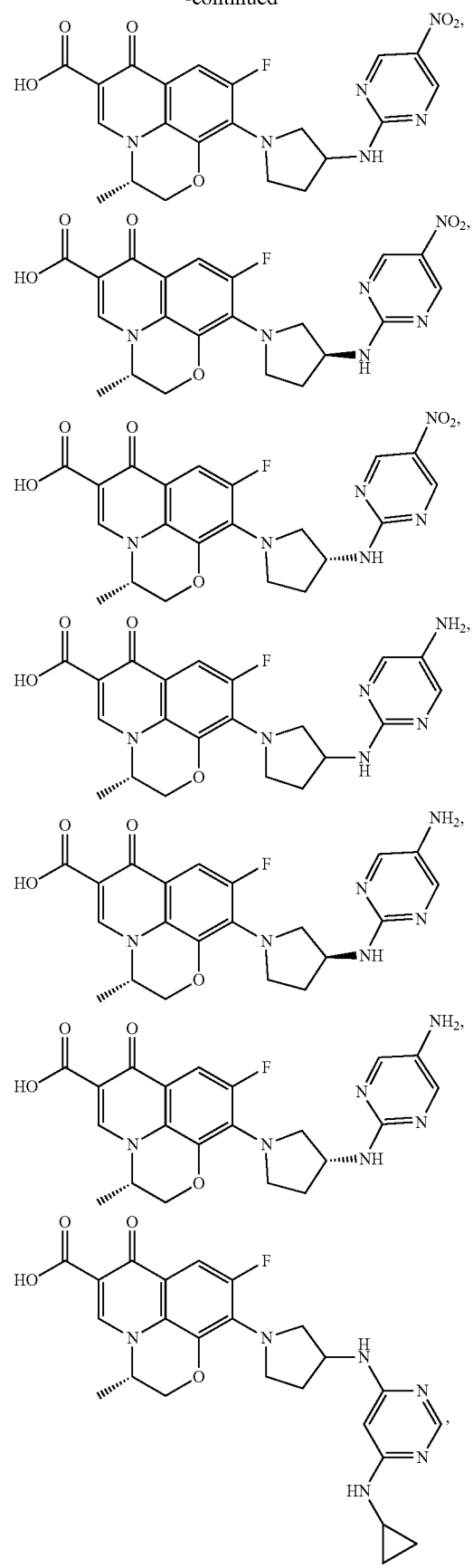
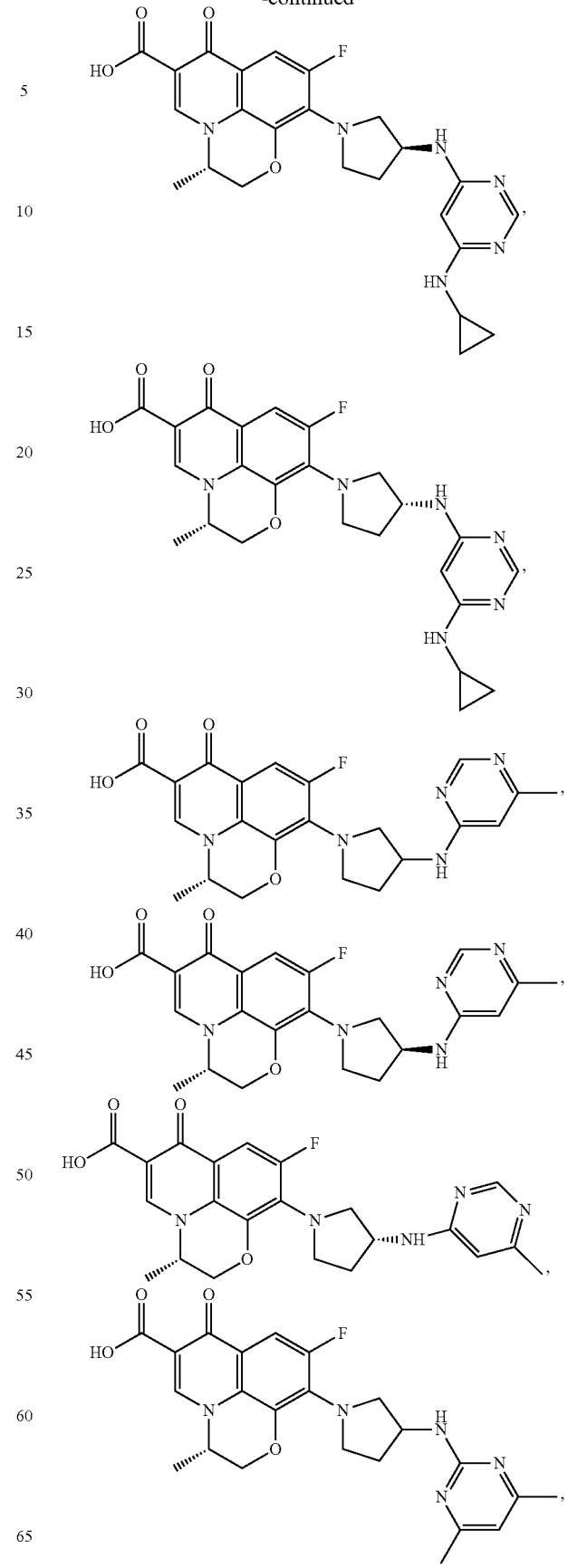

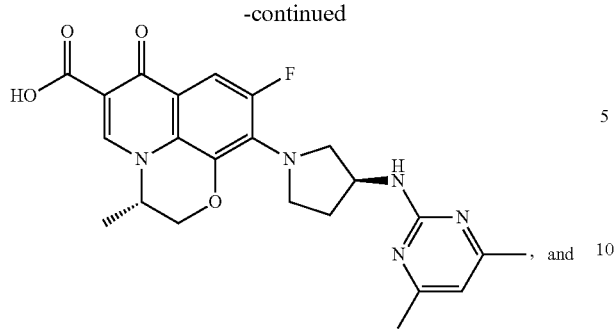
, and
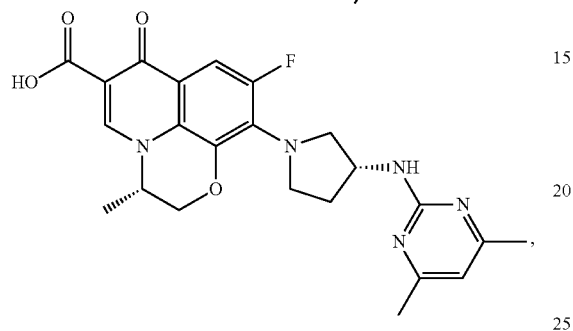
,
or a pharmaceutically acceptable salt, solvate, tautomer, or combination thereof.
* * * * *